US008987551B2

(12) United States Patent
Roberts et al.

(10) Patent No.: US 8,987,551 B2

(45) Date of Patent: Mar. 24, 2015

(54) MODIFIED OIL ENCAPSULATING PROTEINS AND USES THEREOF

(75) Inventors: Nicholas John Roberts, Feilding (NZ); Richard William Scott, Palmerston North (NZ); Somrutai Winichayakul, Palmerston North (NZ); Marissa Roldan, Palmerston North (NZ)

(73) Assignee: Agresearch Limited, East Street Hamilton (NZ)

( * ) Notice: Subject to any disclaimer, the term of this patent is extended or adjusted under 35 U.S.C. 154(b) by 395 days.

(21) Appl. No.: 13/460,464

(22) Filed: Apr. 30, 2012

(65) Prior Publication Data

US 2012/0278951 A1 Nov. 1, 2012

Related U.S. Application Data

(63) Continuation-in-part of application No. PCT/NZ2010/000218, filed on Oct. 29, 2010.

(60) Provisional application No. 61/256,689, filed on Oct. 30, 2009, provisional application No. 61/515,610, filed on Aug. 5, 2011.

(51) Int. Cl.

| | |
|---|---|
| ***A01H 1/00*** | (2006.01) |
| ***A01H 5/10*** | (2006.01) |
| ***C12N 15/82*** | (2006.01) |
| ***C12N 5/04*** | (2006.01) |
| ***C07H 21/04*** | (2006.01) |
| ***A61K 36/00*** | (2006.01) |
| ***C07K 14/415*** | (2006.01) |
| ***C12P 7/64*** | (2006.01) |

(52) U.S. Cl.

CPC .......... *C07K 14/415* (2013.01); *C12N 15/8243* (2013.01); *C12N 15/8245* (2013.01); *C12N 15/8247* (2013.01); *C12N 15/8257* (2013.01); *C12N 15/8261* (2013.01); *C12N 15/8269* (2013.01); *C12N 15/8271* (2013.01); *C12N 15/8273* (2013.01); *C07K 2319/00* (2013.01); *C07K 2319/21* (2013.01); *C12P 7/6463* (2013.01)

USPC ........ 800/278; 800/298; 435/419; 435/320.1; 536/23.4; 536/23.6; 530/370; 530/377

(58) Field of Classification Search

CPC .. C12N 15/29; C12N 9/1029; C12N 15/8247; C12N 15/102; C12N 15/82; C12N 15/8201; C07K 14/415; C07K 2319/00

See application file for complete search history.

(56) References Cited

U.S. PATENT DOCUMENTS

| | | | |
|---|---|---|---|
| 4,943,674 | A | 7/1990 | Houck et al. |
| 5,086,169 | A | 2/1992 | Mascarenhas |
| 5,412,085 | A | 5/1995 | Allen et al. |
| 5,536,653 | A | 7/1996 | Barry et al. |
| 5,545,546 | A | 8/1996 | Allen et al. |
| 5,608,150 | A | 3/1997 | Conner |
| 5,639,952 | A | 6/1997 | Quail et al. |
| 5,656,496 | A | 8/1997 | Quail et al. |
| 5,750,385 | A | 5/1998 | Shewmaker et al. |
| 5,837,848 | A | 11/1998 | Ely et al. |
| 6,127,179 | A | 10/2000 | DellaPenna et al. |
| 6,184,443 | B1 | 2/2001 | Pedersen et al. |
| 6,228,643 | B1 | 5/2001 | Greenland et al. |
| 6,229,067 | B1 | 5/2001 | Sonnewald et al. |
| 6,342,657 | B1 | 1/2002 | Thomas et al. |
| 6,448,048 | B1 | 9/2002 | Tomono et al. |
| 6,582,710 | B2 | 6/2003 | Deckers et al. |
| 7,081,565 | B2 | 7/2006 | Ohlrogge et al. |
| 7,141,424 | B2 | 11/2006 | Shin et al. |
| 7,153,953 | B2 | 12/2006 | Marraccini et al. |
| 7,371,928 | B2 | 5/2008 | Suh et al. |

(Continued)

FOREIGN PATENT DOCUMENTS

| | | |
|---|---|---|
| TW | I250466 | 3/2006 |
| WO | 02/26788 | 4/2002 |

(Continued)

OTHER PUBLICATIONS

Search Report, dated Feb. 14, 2011, corresponding to International Application No. PCT/NZ2010/000218 (filed Oct. 29, 2010), parent of the present application, 6 pp.

European Search Report and Supplemental Search Report, dated Mar. 20, 2013, corresponding to European Application No. 10827209.7 (filed Oct. 29, 2010), 7 pp.

Abell et al. (2004) "Membrane Topology and Sequence Requirements for Oil Body Targeting of Oleosin," Plant J. 37:461-470.

Altschul et al. (1997) "Gapped BLAST and PSI-BLAST: a New Generation of Protein Database Search Programs," Nucleic Acids Res 25(17):3389-3402.

Andrianov et al. (2010) "Tobacco as a Production Platform for Biofuel: Overexpression of Arabidopsis DGAT and LEC2 Genes Increases Accumulation and Shifts the Composition of Lipids in Green Biomass," Plant Biotechnol J. 8(3):277-287.

(Continued)

*Primary Examiner* — Eileen B O Hara

(74) *Attorney, Agent, or Firm* — Lathrop & Gage LLP

(57) ABSTRACT

The invention provides modified oleosins, including at least one artificially introduced cysteine, and methods and compositions for producing the modified oleosins. Also provided are polynucleotides encoding the modified oleosins, constructs and host cells comprising the polynucleotides, methods for producing oil bodies comprising the modified oleosins, in vivo and in vitro, and methods for producing oil in host cells and plants. The invention also provides methods for increasing the rate of $CO_2$ assimilation in photosynthetic cells and plants, and involves reducing or preventing lipid recycling, and/or expressing modified oleosins with artificially introduced cysteine residues in the photosynthetic cells and plants. Also provided are methods for increasing oil production in plants, via expression of modified oleosins in the non-photosynthetic tissues/organs of plants. The method also optionally includes the step of extracting the oil from the non-photosynthetic tissues/organs of the plant, or processing the oil rich non-photosynthetic tissues/organs into animal or biofuel feedstocks.

54 Claims, 79 Drawing Sheets

(56) References Cited

U.S. PATENT DOCUMENTS

| | | | | |
|---|---|---|---|---|
| 7,405,345 | B2 | 7/2008 | Ohlrogge et al. | |
| 7,629,454 | B2 | 12/2009 | Chan et al. | |
| 7,642,346 | B2 | 1/2010 | Chaudhary et al. | |
| 7,667,097 | B2 | 2/2010 | Scheirlinck et al. | |
| 7,745,697 | B2 | 6/2010 | Perez et al. | |
| 2001/0047525 | A1 | 11/2001 | Bruce et al. | |
| 2004/0067506 | A1 | 4/2004 | Scheres et al. | |
| 2007/0118927 | A1 | 5/2007 | Bryan et al. | |
| 2014/0105818 | A1* | 4/2014 | Hammer et al. | 424/1.21 |

FOREIGN PATENT DOCUMENTS

| | | |
|---|---|---|
| WO | 2004/076673 | 9/2004 |
| WO | 2007/045019 | 4/2007 |
| WO | 2008/130248 | 10/2008 |
| WO | 2011/053169 | 5/2011 |

OTHER PUBLICATIONS

Bao et al. (2000) "Understand in vivo Carbon Precursor Supply for Fatty Acid Synthesis in Leaf Tissue," Plant J. 22(1):39-50.

Bari et al. (2009) "A Glycolate Dehydrogenase in the Mitochondria of *Arabidopsis thaliana,*" J. Exp. Bot. 55(397):623-630.

Birch, R. G. (1997) "Plant Transformation: Problems and Strategies for Practical Application," Ann Rev Plant Phys Plant Mol Biol 48:297-326.

Bock et al. (2004) "Taming Plastids for a Green Future," Trends in Biotech 22(6):311-318.

Bolton et al. (1962) "A General Method for the Isolation of RNA Complementary to DNA," PNAS 48:1390-1397.

Bouvier-Nave et al. (2000) "Expression in Yeast and Tobacco of Plant cDNAs Encoding Acyl CoA:Diacylglycerol Acyltransferase," Eur. J. Biochem. 267:85-96.

Bowie et al. (1990) "Deciphering the Message in Protein Sequences: Tolerance to Amino Acid Substitutions," Science 247:1306-1310.

Capuano et al. (2007) "Properties and Exploitation of Oleosins," Biotechnol Adv 25:203-206.

Chen et al. (1999) "Cloning and Secondary Structure Analysis of Caleosin, a Unique Calcium-Binding Protein in Oil Bodies of Plant Seeds," Plant Cell Physiol 40(10):1079-1086.

Chen et al. (2004) "Constitution of Stable Artificial Oil Bodies with Triacylglycerol, Phospholipid, and Caleosin," J Agric Food Chem 52:3982-3987.

Chiang et al. (2005) "Efficient System of Artificial Oil Bodies for Functional Expression and Purification of Recombinant Nattokinase in *Escherichia coli,*" J Agric Food Chem 53:4799-4804.

Chiang et al. (2007) "One-Step Purification of Insoluble Hydantoinase Overproduced in *Escherichia coli,*" Protein Expr Purif 52:14-18.

Chisti, Y. (2007) "Biodiesel from Microalgae," Biotech. Adv. 25:294-306.

Colman et al. (1974) "A Study of the Control of Glycolate Excretion in Chlorella," Plant Phys 53:395-397.

Dahlqvist et al. (2000) "Phospholipid:Diacylglycerol Acyltransferase: An Enzyme that Catalyzes the Acyl-CoA-Independent Formation of Triacylglycerol in Yeast and Plants," PNAS 97(12):6487-6492.

Demeyer et al. (1999) "Targets and Procedures for Altering Ruminant Meat and Milk Lipids," Proc Nutr Soc. 58(3):593-607.

Durrett et al. (2008) "Plant Triacylglycerols as Feedstocks for the Production of Biofuels," Plant J 54:593-607.

Falquet et al. (2002) "The PROSITE Database, Its Status in 2002," Nucleic Acids Res 30(1):235-238.

Feng et al. (1987) "Progressive Sequence Alignment as a Prerequisite to Correct Phylogenetic Trees," J. Mol. Evol. 25:351-360.

Firkins et al. (2006) "Integration of Ruminal Metabolism in Dairy Cattle," J Dairy Sci. 89(E. Suppl.):E31-51. American Dairy Science Association.

Frandsen et al. (2001) "Oil Bodies and Their Associated Proteins, Oleosin and Caleosin," Physiologia Plantarum 112(3):301-307.

Frohman, M. (1993) "Rapid Amplification of Complementary DNA Ends for Generation of Full-Length Complementary DNAs: Thermal RACE," Methods Enzymol 218: 340-356.

Giesen et al. (1998) "A Formula for Thermal Stability ($T_m$) Prediction of PNA/DNA Duplexes," Nucleic Acids Res 26(21):5004-5006.

Giordano et al. (2005) "$CO_2$ Concentrating Mechanisms in Algae: Mechanisms, Environmental Modulation, and Evolution," Ann. Rev. Pl. Biol. 56:99-131.

Greenspan et al. (1985) "Nile Red" A Selective Fluorescent Stain for Intracellular Lipid Droplets, J Cell Biology 100:965-973.

Halford et al. (1998) "SNF1-related protein kinases: global regulators of carbon metabolism in plants?," Plant Mol Bio. 37:735-748.

Hellens et al. (2000) "pGreen: a Versatile and Flexible Binary Ti Vector for *Agrobacterium*-Mediated Plant Transformation," Plant Mol Biol 42:819-832.

Hellens et al. (2005) "Transient Expression Vectors for Functional Genomics, Quantification of Promoter Activity and RNA Silencing in Plants," Plant Meth 1:1-14.

Herrera-Estrella et al. (1993) "Expression of Chimaeric Genes Transferred into Plant Cells Using a Ti-Plasmid-Derived Vector," Nature 303:209-213.

Hofmann et al. (1999) "The PROSITE Database, Its Status in 1999," Nucleic Acids Res 27(1):215-219.

Hou et al. (2003) "Increase of Viability of Entrapped Cells of *Lactobacillus delbrueckii* ssp. *bulgaricus* in Artificial Sesame Oil Emulsions," J Dairy Sci 86:424-428.

Huang, A. (1992) "Oil Bodies and Oleosins in Seeds," Ann. Rev. Plant Physiol. Plant Mol. Biol. 43:177-200.

Huang, X. (1994) "On Global Sequence Alignment," Computer Applications in the Biosciences 10(3):227-235.

Jang et al. (2006) "Functional Classification, Genomic Organization, Putatively cis-Acting Regulatory Elements, and Relationship to Quantitative Trait Loci, of Sorghum Genes with Rhizome-Enriched Expression," Plant Physiology 142:1148-1159.

Jeanmougin et al. (1998) "Multiple Sequence Alignment with Clustal X," Trends Biochem. Sci. 23:403-405.

Jenkins et al. (2006) "Major Advances in Nutrition: Impact on Milk Composition," J Dairy Sci. 89(4):1302-1310. Review.

Jenkins et al. (2007) "Protection of Fatty Acids Against Ruminal Biohydrogenation in Cattle," Eur. J. Lipid Sci. Technol. 109:778-789.

Kaup et al. (2002) "A Role for Diacylglycerol Acyltransferase during Leaf Senescence," Plant Physiol 129(4):1616-1626.

Kebeish et al. (2007) "Chloroplastic Photorespiratory Bypass Increases Photosynthesis and Biomass Production in *Arabidopsis thaliana,*" Nature Biotech 25(5):593-599.

Kozaki et al. (1996) "Photorespiration Protects C3 Plants from Photooxidation," Nature 384:557-560.

Kyte et al. (1982) "A Simple Method for Displaying the Hydropathic Character of a Protein," J. Mol. Biol. 157:105-132.

Lanfranco L. (2003) "Engineering Crops, a Deserving Venture," Riv Biol 96(1):31-54.

Lardizabal et al. (2001) "DGAT2 Is a New Diacylglycerol Acyltransferase Gene Family," J. Biological Chemistry 276(42):38862-38869.

Leprince et al. (1998) "Oleosins Prevent Oil-Body Coalescence During Seed Imbibition as Suggested by a Low-Temperature Scanning Electron Microscope Study of Desiccation-Tolerant and -Sensitive Oilseeds," Planta 204:109-119.

Lin et al. (2004) "Two Distinct Steroleosins are Present in Seed Oil Bodies," Plant Physiology and Biochemistry 42:601-608.

Liu et al. (2009) "Stability of Artificial Oil Bodies Constituted with Recombinant Caleosins," J Agric Food Chem 57:2308:2313.

Lock et al. (2004) "Modifying Milk Fat Composition of Dairy Cows to Enhance Fatty Acids Beneficial to Human Health," Lipids 39(12):1197-1206.

Loer et al. (1993) "Cotranslational Integration of Soybean (*Glycine max*) Oil Body Membrane Protein Oleosin into Microsomal Membranes," Plant Physiol 101(3):993-998.

Mekhedov et al. (2000) "Toward a Functional Catalog of the Plant Genome. A Survey of Genes for Lipid Biosynthesis," Plant Physiol 122(2):389-401.

(56) References Cited

OTHER PUBLICATIONS

Moroney et al. (2007) "Proposed Carbon Dioxide Concentrating Mechanism in *Chlamydomonas reinhardtii*," Eukaryotic Cell 6(8):1251-1259.
Murphy, D.J. (1993) "Structure, Function and Biogenesis of Storage Lipid Bodies and Oleosins in Plants," Prog. Lipid Res. 32(3):247-280.
Nakamura et al. (2005) "Disruption of the Glycolate Dehydrogenase Gene in the High-CO2-Requiring Mutant HCR89 of *Chlamydomonas reinhardtii*," Can. J. Bot. 83:820-833.
Naot et al. (1995) "Induction of a Gene Encoding an Oleosin Homologue in Cultured Citrus Cells Exposed to Salt Stress," Gene 161:171-173.
Needleman et al. (1970) "A General Method Applicable to the Search for Similarities in the Amino Acid Sequence of Two Proteins," J. Mol. Biol. 48:443-453.
Nielsen et al. (1991) "Sequence-Selective Recognition of DNA by Strand Displacement with a Thymine-Substituted Polyamide," Science 254(5037):1497-1500.
Notredame et al. (2000) "T-Coffee: A Novel Method for Fast and Accurate Multiple Sequence Alignment," J. Mol. Biol. 302:205-217.
Ohlrogge et al. (1997) "Regulation of Fatty Acid Synthesis," Annu Rev Plant Physiol Plant Mol Biol. 48:109-136.
Papapostolou et al. (2009) "Engineering and exploiting protein assemblies in synthetic biology," Mol Biosyst. 5(7):723-732.
Parry et al. (2003) "Manipulation of Rubisco: the Amount, Activity, Function and Regulation," J. Exp. Bot. 54(386):1321-1333.
Peng et al. (2004) "A System for Purification of Recombinant Proteins in *Escherichia coli* via Artificial Oil Bodies Constituted with Their Oleosin-Fused Polypeptides," J Biotechnol 111:51-57.
Potrykus et al., Eds. (1995) "Gene Transfer to Plants," Springer-Verlag, Berlin.
Purkrtova et al. (2007) "Structural Properties of Caleosin: A MS and CD study," Archives of Biochemistry and Biophysics 464:335-343.
Purkrtova et al. (2008) "Structure and Function of Seed Lipid Body-Associated Proteins," C.R. Biologies 331:746-754.
Rachmilevitch et al. (2004) "Nitrate Assimilation in Plant Shoots Depends on Photorespiration," PNAS 101(31):11506-11510.
Roberts et al. (2008) "Recent Biotechnological Applications Using Oleosins," The Open Biotechnology Journal 2:13-21.
Roux et al. (2004) "Oleosins of *Arabidopsis thaliana*: Expression in *Escherichia coli*, Purification, and Functional Properties," J Agric Food Chem. 52(16):5245-5249.
Saha et al. (2006) "Cytosolic Triacylglycerol Biosynthetic Pathway in Oilseeds. Molecular Cloning and Expression of Peanut Cytosolic Diacylglycerol Acyltransferase," Plant Physiol. 141(4):1533-1543.
Sarmiento et al. (1997) "Expression and Subcellular Targeting of a Soybean Oleosin in Transgenic Rapeseed. Implications for the Mechanism of Oil-Body Formation in Seeds," Plant J. 11(4):783-796.
Scott et al. (2010) "Elevation of Oil Body Integrity and Emulsion Stability by Polyoleosins, Multiple Oleosin Units Joined in Tandem Head-To-Tail Fusions," Plant Biotechnology J 8:912-927.
Shimada et al. (2008) "A Novel Role for Oleosins in Freezing Tolerance of Oilseeds in *Arabidopsis thaliana*," Plant J. 55(5):798-809.
Shockey et al. (2006) "Tung Tree DGAT1 and DGAT2 have Nonredundant Functions in Triacylglycerol Biosynthesis and Are Localized to Different Subdomains of the Endoplasmic Reticulum," Plant Cell 18:2294-2313.
Siloto et al. (2006) "The Accumulation of Oleosins Determines the Size of Seed Oilbodies in *Arabidopsis*," Plant Cell 18(8):1961-1974.
Slack et al. (1980) "Some Studies on the Composition and Surface Properties of Oil Bodies from the Seed Cotyledons of Safflower (*Carthamus tinctorius*) and Linseed (*Linum ustatissimum*)," Biochem J. 190(3):551-561.
Slocombe et al. (2009) "Oil Accumulation in Leaves Directed by Modification of Fatty Acid Breakdown and Lipid Synthesis Pathways," Plant Biotechnol J. 7(7):694-703.
Smeets, et al. (1997) "Developmental Regulation of Lectin and Alliinase Synthesis in Garlic Bulbs and Leaves," Plant Physiol 113:765-771.
Stahl et al. (2004) "Cloning and Functional Characterization of a Phospholipid:Diacylglycerol Acyltransferase from *Arabidopsis*," Plant Physiology 135:1324-1335.
Tadege et al. (2005) "Insertional Mutagenesis: a Swiss Army Knife for Functional Genomics of *Medicago truncatula*," Trends Plant Sci. 10(5):229-235.
Thompson et al. (1994) "Clustal W: Improving the Sensitivity of Progressive Multiple Sequence Alignment through Sequence Weighting, Position-Specific Gap Penalties and Weight Matrix Choice," Nucleic Acids Research 22(22):4673-4680.
Ting et al. (1997) "Oleosin of Plant Seed Oil Bodies Is Correctly Targeted to the Lipid Bodies in Transformed Yeast," J Biol Chem. 272(6):3699-3706.
Tolbert et al. (1983) "Aminooxyacetate Stimulation of Glycolate Formation and Excretion by *Chiamydomonas*," Pl. Physiol. 72:1075-1083.
Tolbert, N.E. (1997) "The $C_2$ Oxidative Photosynthetic Carbon Cycle," Ann. Rev. Pl. Phys. Pl. Molec. Biol. 48:1-25.
Triglia et al. (1988) "A procedure for In Vitro Amplification of DNA Segments that Lie Outside the Boundaries of Known Sequences," Nucleic Acids Res 16(16):8186.
Tzen et al. (1992) "Characterization of the Charged Components and Their Topology on the Surface of Plant Seed Oil Bodies," J. Biol. Chem. 267(22):15626-15634.
Tzen et al. (1997) "A New Method for Seed Oil Body Purification and Examination of Oil Body Integrity Following Germination," J Biochem. 121(4):762-768.
Tzen et al. (2003) "Seed Oil Body Proteins: Oleosin, Caleosin, and Steroleosin," Current Topics in Biochemical Research 5:133-139.
Voisey et al. (1994) "*Agrobacterium*-Mediated Transformation of White Clover Using Direct Shoot Organogenesis," Plant Cell Reports 13:309-314.
Winichayakul et al. (2008) "Delivery of Grasses with High Levels of Unsaturated, Protected Fatty Acids," Proc. NZGA, 70:211-216.
Xu et al. (2005) "Mutation of the TGD1 Chloroplast Envelope Protein Affects Phosphatidate Metabolism in *Arabidopsis*," Plant Cell 17(11):3094-3110.
Zou et al. (1999) "The *Arabidopsis thaliana* TAG1 Mutant has a Mutation in a Diacylglycerol Acyltransferase Gene," Plant J. 19(6):645-653.
Zou et al. (2008) "Cloning and Characterization of an acyl-CoA-Dependent diacylglycerol acyltransferase 1 (DGAT1) Gene from *Tropaeolum majus*, and a Study of the Functional Motifs of the DGAT Protein Using Site-Directed Mutagenesis to Modify Enzyme Activity and Oil Content," Plant Biotech. J. 6(8):799-818.

* cited by examiner

CaMV 35S

T CGA CGA ATT AAT TCC AAT CCC ACA AAA ATC

CaMV 35S

TGA GCT TAA CAG CAC AGT TGC TCC TCT CAG AGC AGA ATC GGG TAT TCA ACA CCC TCA TAT

CaMV 35S

CAA CTA CTA CGT TGT GTA TAA CGG TCC ACA TGC CGG TAT ATA CGA TGA CTG GGG TTG TAC

CaMV 35S

AAA GGC GGC AAC AAA CGG CGT TCC CGG AGT TGC ACA CAA GAA ATT TGC CAC TAT TAC AGA

CaMV 35S

GGC AAG AGC AGC AGC TGA CGC GTA CAC AAC AAG TCA GCA AAC AGA CAG GTT GAA CTT CAT

CaMV 35S

CCC CAA AGG AGA AGC TCA ACT CAA GCC CAA GAG CTT TGC TAA GGC CCT AAC AAG CCC ACC

CaMV 35S

AAA GCA AAA AGC CCA CTG GCT CAC GCT AGG AAC CAA AAG GCC CAG CAG TGA TCC AGC CCC

CaMV 35S

AAA AGA GAT CTC CTT TGC CCC GGA GAT TAC AAT GGA CGA TTT CCT CTA TCT TTA CGA TCT

CaMV 35S

AGG AAG GAA GTT CGA AGG TGA AGG TGA CGA CAC TAT GTT CAC CAC TGA TAA TGA GAA GGT

CaMV 35S

TAG CCT CTT CAA TTT CAG AAA GAA TGC TGA CCC ACA GAT GGT TAG AGA GGC CTA CGC AGC

CaMV 35S

AGG TCT CAT CAA GAC GAT CTA CCC GAG TAA CAA TCT CCA GGA GAT CAA ATA CCT TCC CAA

CaMV 35S

GAA GGT TAA AGA TGC AGT CAA AAG ATT CAG GAC TAA TTG CAT CAA GAA CAC AGA GAA AGA

CaMV 35S

CAT ATT TCT CAA GAT CAG AAG TAC TAT TCC AGT ATG GAC GAT TCA AGG CTT GCT TCA TAA

CaMV 35S

ACC AAG GCA AGT AAT AGA GAT TGG AGT CTC TAA AAA GGT AGT TCC TAC TGA ATC TAA GGC

CaMV 35S

CAT GCA TGG AGT CTA AGA TTC AAA TCG AGG ATC TAA CAG AAC TCG CCG TGA AGA CTG GCG

Figure 1

```
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~~
AAC AGT TCA TAC AGA GTC TTT TAC GAC TCA ATG ACA AGA AGA AAA TCT TCG TCA ACA TGG
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~~
TGG AGC ACG ACA CTC TGG TCT ACT CCA AAA ATG TCA AAG ATA CAG TCT CAG AAG ACC AAA
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~~
GGG CTA TTG AGA CTT TTC AAC AAA GGA TAA TTT CGG GAA ACC TCC TCG GAT TCC ATT GCC
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~~
CAG CTA TCT GTC ACT TCA TCG AAA GGA CAG TAG AAA AGG AAG GTG GCT CCT ACA AAT GCC
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~~
ATC ATT GCG ATA AAG GAA AGG CTA TCA TTC AAG ATC TCT CTG CCG ACA GTG GTC CCA AAG
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~~
ATG GAC CCC CAC CCA CGA GGA GCA TCG TGG AAA AAG AAG ACG TTC CAA CCA CGT CTT CAA
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~~
AGC AAG TGG ATT GAT GTG ACA TCT CCA CTG ACG TAA GGG ATG ACG CAC AAT CCC ACT ATC
                       CaMV 35S
~~~~~~~~~~~~~~~~~~~~~~~~~~~~~~~~~~~~~~~~~~~~~~~~~~~~~~~~~~~~~~~~~~~~~~~~~~
CTT CGC AAG ACC CTT CCT CTA TAT AAG GAA GTT CAT TTC ATT TGG AGA GGA CAC GCT CGA
                                 attB1
                         ~~~~~~~~~~~~~~~~~~~~~~~~~~~~
GGA ATT CGG TAC CCC ATC ACA AGT TTG TAC AAA AAA GCA GGC TGC GGC CGC TTG CTC CCT
                                 5' Oleo_0-0
              ~~~~~~~~~~~~~~~~~~~~~~~~~~~~~~~~~~~~~~~~~~~~~~~~~~~~~~~~~~~~~~~~~
             NcoI
            ~~~~~~~~
              M   A   E   H   Y   G   Q   Q   Q   Q   T   R   A   P   H   L   Q
TAA AAA AAA CCA TGG CAG AGC ATT ACG GAC AAC AGC AAC AGA CTA GAG CAC CTC ATC TTC
                 5' Oleo_0-0
~~~~~~~~~~~~~~~~~~~~~~~~~~~~~~~~~~~~~~~~~~~~~~~~~~~~~~~~~~~~~~~~~~~~~~
                                                                     UBQ10
                                                                   ~~~~~~~~~~~
 · L   Q   P   R   A   Q   R   V   V   K   A   A   T   A   V   T  (SEQ ID NO:113)
AGC TTC AAC CTA GAG CAC AGA GAG TTG TGA AGG CTG CTA CTG CTG TTA CTG TAA ATT TCT
                          UBQ10
~~~~~~~~~~~~~~~~~~~~~~~~~~~~~~~~~~~~~~~~~~~~~~~~~~~~~~~~~~~~~~~~~~~~~~~~~~~~~~~~
GTG TTC CTT ATT CTC TCA AAA TCT TCG ATT TTG TTT TCG TTC GAT CCC AAT TTC GTA TAT
                          UBQ10
~~~~~~~~~~~~~~~~~~~~~~~~~~~~~~~~~~~~~~~~~~~~~~~~~~~~~~~~~~~~~~~~~~~~~~~~~~~~~~~~
GTT CTT TGG TTT AGA TTC TGT TAA TCT TAG ATC GAA GAC GAT TTT CTG GGT TTG ATC GTT
```

Figure 1 cont.

```
                               UBQ10
~~~~~~~~~~~~~~~~~~~~~~~~~~~~~~~~~~~~~~~~~~~~~~~~~~~~~~~~~~~~~~~~~~~~~~~~~~~~~~~
AGA TAT CAT CTT AAT TCT CGA TTA GGG TTT CAT AGA TAT CAT CCG ATT TGT TCA AAT AAT
                               UBQ10
~~~~~~~~~~~~~~~~~~~~~~~~~~~~~~~~~~~~~~~~~~~~~~~~~~~~~~~~~~~~~~~~~~~~~~~~~~~~~~~
TTG AGT TTT GTC GAA TAA TTA CTC TTC GAT TTG TGA TTT CTA TCT AGA TCT GGT GTT AGT
                                                                     3'Oleo_0-0
                                                                        ~~~~~~~
                            UBQ10
~~~~~~~~~~~~~~~~~~~~~~~~~~~~~~~~~~~~~~~~~~~~~~~~~~~~~~~~~~~~~~~~~~~~~~~~
                                                                     A   G
TTC TAG TTT GTG CGA TCG AAT TTG TCG ATT AAT CTG AGT TTT TCT GAT TAA CAG GCT GGA
                        3' Oleo_0-0
~~~~~~~~~~~~~~~~~~~~~~~~~~~~~~~~~~~~~~~~~~~~~~~~~~~~~~~~~~~~~~~~~~~~~~~~~~~~~~~
 G   S   L   L   V   L   S   G   L   T   L   A   G   T   V   I   A   L   T   I
GGA TCT CTT CTT GTT CTC TCT GGA CTT ACT CTC GCT GGA ACT GTT ATC GCT CTC ACT ATC
                        3' Oleo_0-0
~~~~~~~~~~~~~~~~~~~~~~~~~~~~~~~~~~~~~~~~~~~~~~~~~~~~~~~~~~~~~~~~~~~~~~~~~~~~~~~
 A   T   P   L   L   V   I   F   S   P   V   L   V   P   A   V   I   T   I   F
GCT ACA CCT CTT CTC GTT ATC TTC TCT CCT GTT CTC GTT CCT GCT GTG ATC ACT ATC TTC
                        3' Oleo_0-0
~~~~~~~~~~~~~~~~~~~~~~~~~~~~~~~~~~~~~~~~~~~~~~~~~~~~~~~~~~~~~~~~~~~~~~~~~~~~~~~
 L   L   G   A   G   F   L   A   S   G   G   F   G   V   A   A   L   S   V   L
CTT CTC GGA GCT GGA TTT CTT GCT TCT GGT GGA TTT GGA GTT GCT GCT CTC TCT GTT CTC
                        3' Oleo_0-0
~~~~~~~~~~~~~~~~~~~~~~~~~~~~~~~~~~~~~~~~~~~~~~~~~~~~~~~~~~~~~~~~~~~~~~~~~~~~~~~
 S   W   I   Y   R   Y   L   T   G   K   H   P   P   G   A   D   Q   L   E   S
TCT TGG ATC TAC AGA TAC CTC ACT GGA AAA CAT CCT CCA GGT GCT GAT CAA CTT GAG TCT
                        3' Oleo_0-0
~~~~~~~~~~~~~~~~~~~~~~~~~~~~~~~~~~~~~~~~~~~~~~~~~~~~~~~~~~~~~~~~~~~~~~~~~~~~~~~
 A   K   T   K   L   A   S   K   A   R   E   M   K   D   R   A   E   Q   F   S
GCT AAG ACT AAG CTC GCT TCT AAG GCT AGA GAG ATG AAG GAT AGA GCA GAG CAA TTC TCT
            3' Oleo_0-0                                 OCS terminator
~~~~~~~~~~~~~~~~~~~~~~~~~~~~~~~~~~~~~~~~~~~~~~~~         ~~~~~~~~~~~~~~~~~~~~~~
 Q   Q   P   V   A   G   S   Q   T   S  (SEQ ID NO:114)
CAA CAG CCT GTT GCT GGA TCT CAG ACT TCT TAA TGA ACA TAT GGT CCT GCT TTA ATG AGA
                       OCS terminator
~~~~~~~~~~~~~~~~~~~~~~~~~~~~~~~~~~~~~~~~~~~~~~~~~~~~~~~~~~~~~~~~~~~~~~~~~~~~~~~
TAT GCG AGA CGC CTA TGA TCG CAT GAT ATT TGC TTT CAA TTC TGT TGT GCA CGT TGT AAA
                       OCS terminator
~~~~~~~~~~~~~~~~~~~~~~~~~~~~~~~~~~~~~~~~~~~~~~~~~~~~~~~~~~~~~~~~~~~~~~~~~~~~~~~
AAA CCT GAG CAT GTG TAG CTC AGA TCC TTA CCG CCG GTT TCG GTT CAT TCT AAT GAA TAT
                       OCS terminator
~~~~~~~~~~~~~~~~~~~~~~~~~~~~~~~~~~~~~~~~~~~~~~~~~~~~~~~~~~~~~~~~~~~~~~~~~~~~~~~
ATC ACC CGT TAC TAT CGT ATT TTT ATG AAT AAT ATT CTC CGT TCA ATT TAC TGA TTG TAC
```

Figure 1 cont.

```
                       OCS terminator
~~~~~~~~~~~~~~~~~~~~~~~~~~~~~~~~~~~~~~~~~~~~~~~~~~~~~~~~~~~~~~~~~~~~~~~~~~~~~~~~
CCT ACT ACT TAT ATG TAC AAT ATT AAA ATG AAA ACA ATA TAT TGT GCT GAA TAG GTT TAT
                       OCS terminator
~~~~~~~~~~~~~~~~~~~~~~~~~~~~~~~~~~~~~~~~~~~~~~~~~~~~~~~~~~~~~~~~~~~~~~~~~~~~~~~~
AGC GAC ATC TAT GAT AGA GCG CCA CAA TAA CAA ACA ATT GCG TTT TAT TAT TAC AAA TCC
                       OCS terminator
~~~~~~~~~~~~~~~~~~~~~~~~~~~~~~~~~~~~~~~~~~~~~~~~~~~~~~~~~~~~~~~~~~~~~~~~~~~~~~~~
AAT TTT AAA AAA AGC GGC AGA ACC GGT CAA ACC TAA AAG ACT GAT TAC ATA AAT CTT ATT
                       OCS terminator
~~~~~~~~~~~~~~~~~~~~~~~~~~~~~~~~~~~~~~~~~~~~~~~~~~~~~~~~~~~~~~~~~~~~~~~~~~~~~~~~
CAA ATT TCA AAA GGC CCC AGG GGC TAG TAT CTA CGA CAC ACC GAG CGG CGA ACT AAT AAC
                       OCS terminator
~~~~~~~~~~~~~~~~~~~~~~~~~~~~~~~~~~~~~~~~~~~~~~~~~~~~~~~~~~~~~~~~~~~~~~~~~~~~~~~~
GTT CAC TGA AGG GAA CTC CGG TTC CCC GCC GGC GCG CAT GGG TGA GAT TCC TTG AAG TTG
                       OCS terminator
~~~~~~~~~~~~~~~~~~~~~~~~~~~~~~~~~~~~~~~~~~~~~~~~~~~~~~~~~~~~~~~~~~~~~~~~~~~~~~~~
AGT ATT GGC CGT CCG CTC TAC CGA AAG TTA CGG GCA CCA TTC AAC CCG GTC CAG CAC GGC
                       OCS terminator
~~~~~~~~~~~~~~~~~~~~~~~~~~~~~~~~~~~~~~~~~~~~~~~~~~~~~~~~~~~~~~~~~~~~~~~~~~~~~~~~
GGC CGG GTA ACC GAC TTG CTG CCC CGA GAA TTA TGC AGC ATT TTT TTG GTG TAT GTG GGC
                       OCS terminator
~~~~~~~~~~~~~~~~~~~~~~~~~~~~~~~~~~~~~~~~~~~~~~~~~~~~~~~~~~~~~~~~~~~~~~~~~~~~~~~~
CCC AAA TGA AGT GCA GGT CAA ACC TTG ACA GTG ACG ACA AAT CGT TGG GCG GGT CCA GGG
                       OCS terminator
~~~~~~~~~~~~~~~~~~~~~~~~~~~~~~~~~~~~~~~~~~~~~~~~~~~~~~~~~~~~~~~~~~~~~~~~~~~~~~~~
CGA ATT TTG CGA CAA CAT GTC GAG GCT CAG CAG GAC CTG CAG GCA TGC AAG CTA GCT TAC
          OCS terminator
~~~~~~~~~~~~~~~~~~~~~~~~~~~~~~~~~~~~~~~~~~~~~
                                                    CaMV35S
                                        ~~~~~~~~~~~~~~~~~~~~~~~~~~~~~~~~~~~~~~~~
TAG TGA TGC ATA TTC TAT AGT GTC ACC TAA ATC TTC GAC GAA TTA ATT CCA ATC CCA CAA
                          CaMV35S
~~~~~~~~~~~~~~~~~~~~~~~~~~~~~~~~~~~~~~~~~~~~~~~~~~~~~~~~~~~~~~~~~~~~~~~~~~~~~~~~
AAA TCT GAG CTT AAC AGC ACA GTT GCT CCT CTC AGA GCA GAA TCG GGT ATT CAA CAC CCT
                          CaMV35S
~~~~~~~~~~~~~~~~~~~~~~~~~~~~~~~~~~~~~~~~~~~~~~~~~~~~~~~~~~~~~~~~~~~~~~~~~~~~~~~~
CAT ATC AAC TAC TAC GTT GTG TAT AAC GGT CCA CAT GCC GGT ATA TAC GAT GAC TGG GGT
                          CaMV35S
~~~~~~~~~~~~~~~~~~~~~~~~~~~~~~~~~~~~~~~~~~~~~~~~~~~~~~~~~~~~~~~~~~~~~~~~~~~~~~~~
TGT ACA AAG GCG GCA ACA AAC GGC GTT CCC GGA GTT GCA CAC AAG AAA TTT GCC ACT ATT
                          CaMV35S
~~~~~~~~~~~~~~~~~~~~~~~~~~~~~~~~~~~~~~~~~~~~~~~~~~~~~~~~~~~~~~~~~~~~~~~~~~~~~~~~
ACA GAG GCA AGA GCA GCA GCT GAC GCG TAC ACA ACA AGT CAG CAA ACA GAC AGG TTG AAC
                          CaMV35S
```

~~~~~~~~~~~~~~~~~~~~~~~~~~~~~~~~~~~~~~~~~~~~~~~~~~~~~~~~~~~~~~~~~~~~~~~~~~~~

TTC ATC CCC AAA GGA GAA GCT CAA CTC AAG CCC AAG AGC TTT GCT AAG GCC CTA ACA AGC

CaMV35S

~~~~~~~~~~~~~~~~~~~~~~~~~~~~~~~~~~~~~~~~~~~~~~~~~~~~~~~~~~~~~~~~~~~~~~~~~~~~

CCA CCA AAG CAA AAA GCC CAC TGG CTC ACG CTA GGA ACC AAA AGG CCC AGC AGT GAT CCA

CaMV35S

~~~~~~~~~~~~~~~~~~~~~~~~~~~~~~~~~~~~~~~~~~~~~~~~~~~~~~~~~~~~~~~~~~~~~~~~~~~~

GCC CCA AAA GAG ATC TCC TTT GCC CCG GAG ATT ACA ATG GAC GAT TTC CTC TAT CTT TAC

CaMV35S

~~~~~~~~~~~~~~~~~~~~~~~~~~~~~~~~~~~~~~~~~~~~~~~~~~~~~~~~~~~~~~~~~~~~~~~~~~~~

GAT CTA GGA AGG AAG TTC GAA GGT GAA GGT GAC GAC ACT ATG TTC ACC ACT GAT AAT GAG

CaMV35S

~~~~~~~~~~~~~~~~~~~~~~~~~~~~~~~~~~~~~~~~~~~~~~~~~~~~~~~~~~~~~~~~~~~~~~~~~~~~

AAG GTT AGC CTC TTC AAT TTC AGA AAG AAT GCT GAC CCA CAG ATG GTT AGA GAG GCC TAC

CaMV35S

~~~~~~~~~~~~~~~~~~~~~~~~~~~~~~~~~~~~~~~~~~~~~~~~~~~~~~~~~~~~~~~~~~~~~~~~~~~~

GCA GCA GGT CTC ATC AAG ACG ATC TAC CCG AGT AAC AAT CTC CAG GAG ATC AAA TAC CTT

CaMV35S

~~~~~~~~~~~~~~~~~~~~~~~~~~~~~~~~~~~~~~~~~~~~~~~~~~~~~~~~~~~~~~~~~~~~~~~~~~~~

CCC AAG AAG GTT AAA GAT GCA GTC AAA AGA TTC AGG ACT AAT TGC ATC AAG AAC ACA GAG

CaMV35S

~~~~~~~~~~~~~~~~~~~~~~~~~~~~~~~~~~~~~~~~~~~~~~~~~~~~~~~~~~~~~~~~~~~~~~~~~~~~

AAA GAC ATA TTT CTC AAG ATC AGA AGT ACT ATT CCA GTA TGG ACG ATT CAA GGC TTG CTT

CaMV35S

~~~~~~~~~~~~~~~~~~~~~~~~~~~~~~~~~~~~~~~~~~~~~~~~~~~~~~~~~~~~~~~~~~~~~~~~~~~~

CAT AAA CCA AGG CAA GTA ATA GAG ATT GGA GTC TCT AAA AAG GTA GTT CCT ACT GAA TCT

CaMV35S

~~~~~~~~~~~~~~~~~~~~~~~~~~~~~~~~~~~~~~~~~~~~~~~~~~~~~~~~~~~~~~~~~~~~~~~~~~~~

AAG GCC ATG CAT GGA GTC TAA GAT TCA AAT CGA GGA TCT AAC AGA ACT CGC CGT GAA GAC

CaMV35S

~~~~~~~~~~~~~~~~~~~~~~~~~~~~~~~~~~~~~~~~~~~~~~~~~~~~~~~~~~~~~~~~~~~~~~~~~~~~

TGG CGA ACA GTT CAT ACA GAG TCT TTT ACG ACT CAA TGA CAA GAA GAA AAT CTT CGT CAA

CaMV35S

~~~~~~~~~~~~~~~~~~~~~~~~~~~~~~~~~~~~~~~~~~~~~~~~~~~~~~~~~~~~~~~~~~~~~~~~~~~~

CAT GGT GGA GCA CGA CAC TCT CGT CTA CTC CAA AAA TGT CAA AGA TAC AGT CTC AGA AGA

CaMV35S

~~~~~~~~~~~~~~~~~~~~~~~~~~~~~~~~~~~~~~~~~~~~~~~~~~~~~~~~~~~~~~~~~~~~~~~~~~~~

CCA AAG GGC TAT TGA GAC TTT TCA ACA AAG GAT AAT TTC GGG AAA CCT CCT CGG ATT CCA

CaMV35S

~~~~~~~~~~~~~~~~~~~~~~~~~~~~~~~~~~~~~~~~~~~~~~~~~~~~~~~~~~~~~~~~~~~~~~~~~~~~

TTG CCC AGC TAT CTG TCA CTT CAT CGA AAG GAC AGT AGA AAA GGA AGG TGG CTC CTA CAA

CaMV35S

~~~~~~~~~~~~~~~~~~~~~~~~~~~~~~~~~~~~~~~~~~~~~~~~~~~~~~~~~~~~~~~~~~~~~~~~~~~~

ATG CCA TCA TTG CGA TAA AGG AAA GGC TAT CAT TCA AGA TCT CTC TGC CGA CAG TGG TCC

CaMV35S

Figure 1 cont.
~~~~~~~~~~~~~~~~~~~~~~~~~~~~~~~~~~~~~~~~~~~~~~~~~~~~~~~~~~~~~~~~~~~~~~~~~~~~

```
~~~~~~~~~~~~~~~~~~~~~~~~~~~~~~~~~~~~~~~~~~~~~~~~~~~~~~~~~~~~~~~~~~~~~~~~~~~~~~~
CAA AGA TGG ACC CCC ACC CAC GAG GAG CAT CGT GGA AAA AGA AGA CGT TCC AAC CAC GTC
                          CaMV35S
~~~~~~~~~~~~~~~~~~~~~~~~~~~~~~~~~~~~~~~~~~~~~~~~~~~~~~~~~~~~~~~~~~~~~~~~~~~~~~~
TTC AAA GCA AGT GGA TTG ATG TGA CAT CTC CAC TGA CGT AAG GGA TGA CGC ACA ATC CCA
                          CaMV35S
~~~~~~~~~~~~~~~~~~~~~~~~~~~~~~~~~~~~~~~~~~~~~~~~~~~~~~~~~~~~~~~~~~~~~~~~~~~~~~~
CTA TCC TTC GCA AGA CCC TTC CTC TAT ATA AGG AAG TTC ATT TCA TTT GGA GAG GAC ACG
                                          5' DGAT1 (S205A)
                                  ~~~~~~~~~~~~~~~~~~~~~~~~~~~~~~~~~~~~~~~~~~~~~
                                 NcoI
                                ~~~~~~~~
                                  M   A   I   L   D   S   A   G   V   T   T   V
GGA TCC TTG CTC CGT TAA AAA AAA CCA TGG CTA TCC TCG ATT CTG CTG GTG TTA CTA CTG
                      5' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 ·  T   E   N   G   G   G   E   F   V   D   L   D   R   L   R   R   R   K   S   R
TGA CTG AGA ATG GTG GTG GAG AGT TCG TTG ATC TCG ATA GAC TCA GAA GAA GAA AGT CTA
5' DGAT1 (S205A)
~~~~~~
                              UBQ10
      ~~~~~~~~~~~~~~~~~~~~~~~~~~~~~~~~~~~~~~~~~~~~~~~~~~~~~~~~~~~~~~~~~~~~~~~~~
 ·  S  (SEQ ID NO:115)
GAT CTG TAA ATT TCT GTG TTC CTT ATT CTC TCA AAA TCT TCG ATT TTG TTT TCG TTC GAT
                           UBQ10
~~~~~~~~~~~~~~~~~~~~~~~~~~~~~~~~~~~~~~~~~~~~~~~~~~~~~~~~~~~~~~~~~~~~~~~~~~~~~~~
CCC AAT TTC GTA TAT GTT CTT TGG TTT AGA TTC TGT TAA TCT TAG ATC GAA GAC GAT TTT
                           UBQ10
~~~~~~~~~~~~~~~~~~~~~~~~~~~~~~~~~~~~~~~~~~~~~~~~~~~~~~~~~~~~~~~~~~~~~~~~~~~~~~~
CTG GGT TTG ATC GTT AGA TAT CAT CTT AAT TCT CGA TTA GGG TTT CAT AGA TAT CAT CCG
                           UBQ10
~~~~~~~~~~~~~~~~~~~~~~~~~~~~~~~~~~~~~~~~~~~~~~~~~~~~~~~~~~~~~~~~~~~~~~~~~~~~~~~
ATT TGT TCA AAT AAT TTG AGT TTT GTC GAA TAA TTA CTC TTC GAT TTG TGA TTT CTA TCT
                           UBQ10
~~~~~~~~~~~~~~~~~~~~~~~~~~~~~~~~~~~~~~~~~~~~~~~~~~~~~~~~~~~~~~~~~~~~~~~~~~~~~~~
AGA TCT GGT GTT AGT TTC TAG TTT GTG CGA TCG AAT TTG TCG ATT AAT CTG AGT TTT TCT
  UBQ10
~~~~~~~~~~~~
                             3' DGAT1 (S205A)
            ~~~~~~~~~~~~~~~~~~~~~~~~~~~~~~~~~~~~~~~~~~~~~~~~~~~~~~~~~~~~~~~~~~~
             D   S   S   N   G   L   L   L   S   G   S   D   N   N   S   P   S
GAT TAA CAG GAT TCT TCT AAC GGA CTT CTC CTC TCT GGA TCT GAT AAC AAC TCT CCT TCT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 D   D   V   G   A   P   A   D   V   R   D   R   I   D   S   V   V   N   D   D
```

Figure 1 cont.

```
GAT GAT GTT GGT GCT CCT GCT GAT GTG AGA GAT AGA ATC GAT TCT GTG GTG AAC GAT GAT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 A   Q   G   T   A   N   L   A   G   D   N   N   G   G   G   D   N   N   G   G
GCT CAA GGT ACT GCT AAC CTC GCT GGT GAT AAT AAC GGT GGA GGT GAT AAC AAT GGT GGA
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 G   R   G   G   G   E   G   R   G   N   A   D   A   T   F   T   Y   R   P   S
GGA AGA GGT GGA GGT GAA GGT AGA GGA AAC GCT GAT GCT ACT TTC ACT TAC AGA CCA TCT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 V   P   A   H   R   R   A   R   E   S   P   L   S   S   D   A   I   F   K   Q
GTG CCT GCT CAT AGA AGA GCT AGA GAG TCT CCT CTC TCT TCT GAT GCT ATC TTC AAG CAG
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 S   H   A   G   L   F   N   L   C   V   V   V   L   I   A   V   N   S   R   L
TCT CAC GCT GGA CTT TTC AAC CTC TGT GTG GTG GTT CTT ATC GCT GTG AAC TCT AGA CTC
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 I   I   E   N   L   M   K   Y   G   W   L   I   R   T   D   F   W   F   S   S
ATC ATC GAG AAC CTC ATG AAG TAC GGA TGG CTC ATC AGA ACT GAT TTC TGG TTC TCT TCT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 R   S   L   R   D   W   P   L   F   M   C   C   I   S   L   S   I   F   P   L
AGA TCT CTC AGA GAT TGG CCT CTT TTC ATG TGC TGC ATC TCA CTC TCA ATC TTC CCT CTC
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 A   A   F   T   V   E   K   L   V   L   Q   K   Y   I   A   E   P   V   V   I
GCT GCT TTT ACT GTT GAG AAG CTC GTG CTC CAG AAG TAT ATC GCT GAA CCT GTG GTG ATC
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 F   L   H   I   I   I   T   M   T   E   V   L   Y   P   V   Y   V   T   L   R
TTC CTC CAC ATC ATC ATC ACT ATG ACT GAG GTT CTC TAC CCT GTT TAC GTG ACT CTC AGA
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 C   D   S   A   F   L   S   G   V   T   L   M   L   L   T   C   I   V   W   L
TGC GAT TCT GCT TTC CTC TCT GGT GTT ACT CTT ATG CTC CTC ACT TGC ATT GTG TGG CTT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 K   L   V   S   Y   A   H   T   S   Y   D   I   R   S   L   A   N   A   A   D
AAG CTC GTG TCT TAC GCT CAC ACT TCT TAC GAT ATC AGA TCT CTC GCT AAC GCT GCT GAT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 K   A   N   P   E   V   S   Y   Y   V   S   L   K   S   L   A   Y   F   M   V
AAG GCT AAC CCT GAA GTG TCT TAC TAC GTG TCT CTC AAG TCT CTC GCT TAC TTC ATG GTT
```

Figure 1 cont.

3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
A P T L C Y Q P S Y P R S A C I R K G W
GCT CCT ACA CTT TGT TAC CAG CCA TCT TAC CCT AGA TCT GCT TGC ATT AGA AAG GGA TGG
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
V A R Q F A K L V I F T G F M G F I I E
GTG GCA AGA CAA TTC GCT AAG TTG GTG ATC TTC ACT GGA TTC ATG GGA TTC ATC ATC GAG
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
Q Y I N P I V R N S K H P L K G D L L Y
CAG TAC ATC AAC CCT ATT GTG AGA AAC TCT AAG CAC CCT CTC AAG GGT GAT CTT CTC TAC
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
A I E R V L K L S V P N L Y V W L C M F
GCT ATC GAG AGA GTT CTT AAG CTC TCT GTG CCT AAC CTT TAT GTG TGG CTC TGC ATG TTC
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
Y C F F H L W L N I L A E L L C F G D R
TAC TGT TTC TTC CAC CTC TGG CTT AAC ATC CTT GCT GAG TTG CTT TGC TTC GGA GAT AGA
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
E F Y K D W W N A K S V G D Y W R M W N
GAG TTC TAC AAG GAT TGG TGG AAC GCT AAG TCT GTT GGA GAT TAT TGG AGA ATG TGG AAC
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
M P V H K W M V R H I Y F P C L R S K I
ATG CCT GTG CAT AAG TGG ATG GTG CGT CAC ATC TAC TTC CCT TGC CTC AGA TCT AAG ATC
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
P K T L A I I I A F L V S A V F H E L C
CCT AAG ACT CTC GCT ATC ATT ATC GCT TTC CTC GTG TCT GCT GTT TTC CAT GAG TTG TGT
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
I A V P C R L F K L W A F L G I M F Q V
ATC GCT GTT CCT TGC AGA CTT TTC AAG CTT TGG GCT TTC CTC GGA ATC ATG TTC CAG GTT
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
P L V F I T N Y L Q E R F G S T V G N M
CCA CTC GTG TTC ATC ACT AAC TAC CTC CAA GAG AGA TTC GGA TCT ACT GTT GGA AAC ATG
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
I F W F I F C I F G Q P M C V L L Y Y H
ATT TTC TGG TTC ATT TTC TGC ATC TTC GGA CAG CCT ATG TGC GTT CTC CTC TAC TAC CAC
3' DGAT1 (S205A)

Figure 1 cont.
~~~~~~~~~~~~~~~~~~~~~~~~~~~~~~~~~~~~~~~~~~~~~~~~~~~~~~~~~~~~~~~~~~~~~~~~~~~~~~

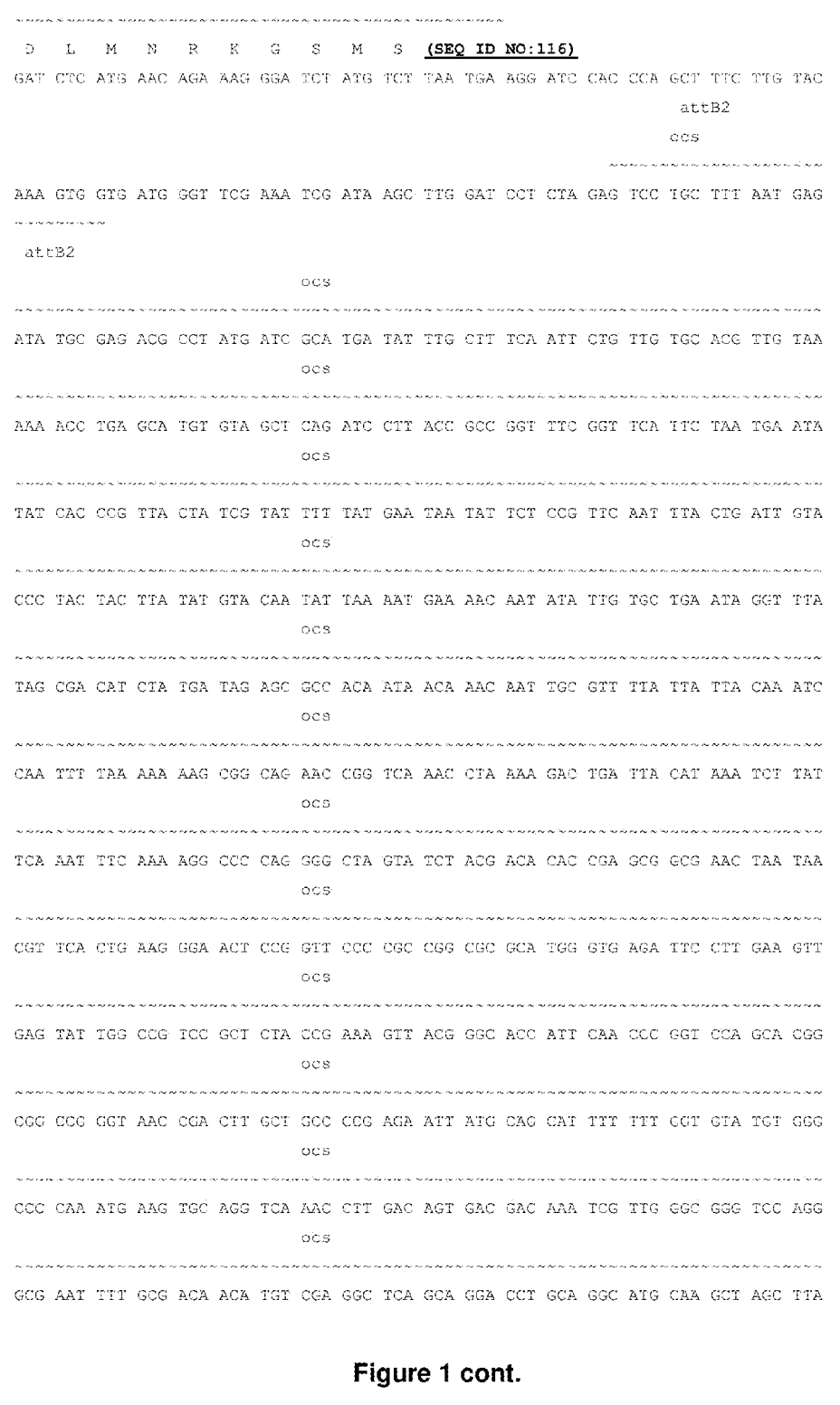

D L M N R K G S M S (SEQ ID NO:116)

GAT CTC ATG AAC AGA AAG GGA TCT ATG TCT TAA TGA AGG ATC CAC CCA GCT TTC TTG TAC attB2 ocs

AAA GTG GTG ATG GGT TCG AAA TCG ATA AGC TTG GAT CCT CTA GAG TCC TGC TTT AAT GAG attB2 ocs

ATA TGC GAG ACG CCT ATG ATC GCA TGA TAT TTG CTT TCA ATT CTG TTG TGC ACG TTG TAA ocs

AAA ACC TGA GCA TGT GTA GCT CAG ATC CTT ACC GCC GGT TTC GGT TCA TTC TAA TGA ATA ocs

TAT CAC CCG TTA CTA TCG TAT TTT TAT GAA TAA TAT TCT CCG TTC AAT TTA CTG ATT GTA ocs

CCC TAC TAC TTA TAT GTA CAA TAT TAA AAT GAA AAC AAT ATA TTG TGC TGA ATA GGT TTA ocs

TAG CGA CAT CTA TGA TAG AGC GCC ACA ATA ACA AAC AAT TGC GTT TTA TTA TTA CAA ATC ocs

CAA TTT TAA AAA AAG CGG CAG AAC CGG TCA AAC CTA AAA GAC TGA TTA CAT AAA TCT TAT ocs

TCA AAT TTC AAA AGG CCC CAG GGG CTA GTA TCT ACG ACA CAC CGA GCG GCG AAC TAA TAA ocs

CGT TCA CTG AAG GGA ACT CCG GTT CCC CGC CGG CGC GCA TGG GTG AGA TTC CTT GAA GTT ocs

GAG TAT TGG CCG TCC GCT CTA CCG AAA GTT ACG GGC ACC ATT CAA CCC GGT CCA GCA CGG ocs

CGG CCG GGT AAC CGA CTT GCT GCC CCG AGA ATT ATG CAG CAT TTT TTT GGT GTA TGT GGG ocs

CCC CAA ATG AAG TGC AGG TCA AAC CTT GAC AGT GAC GAC AAA TCG TTG GGC GGG TCC AGG ocs

GCG AAT TTT GCG ACA ACA TGT CGA GGC TCA GCA GGA CCT GCA GGC ATG CAA GCT AGC TTA

Figure 1 cont.

```
                ocs
~~~~~~~~~~~~~~~~~~~~~~~~~~~~~~~~~~~~~~~~~~~~~~
CTA GTG ATG CAT ATT CTA TAG TGT CAC CTA AAT CT (SEQ ID NO:112)
```

Figure 1 cont.

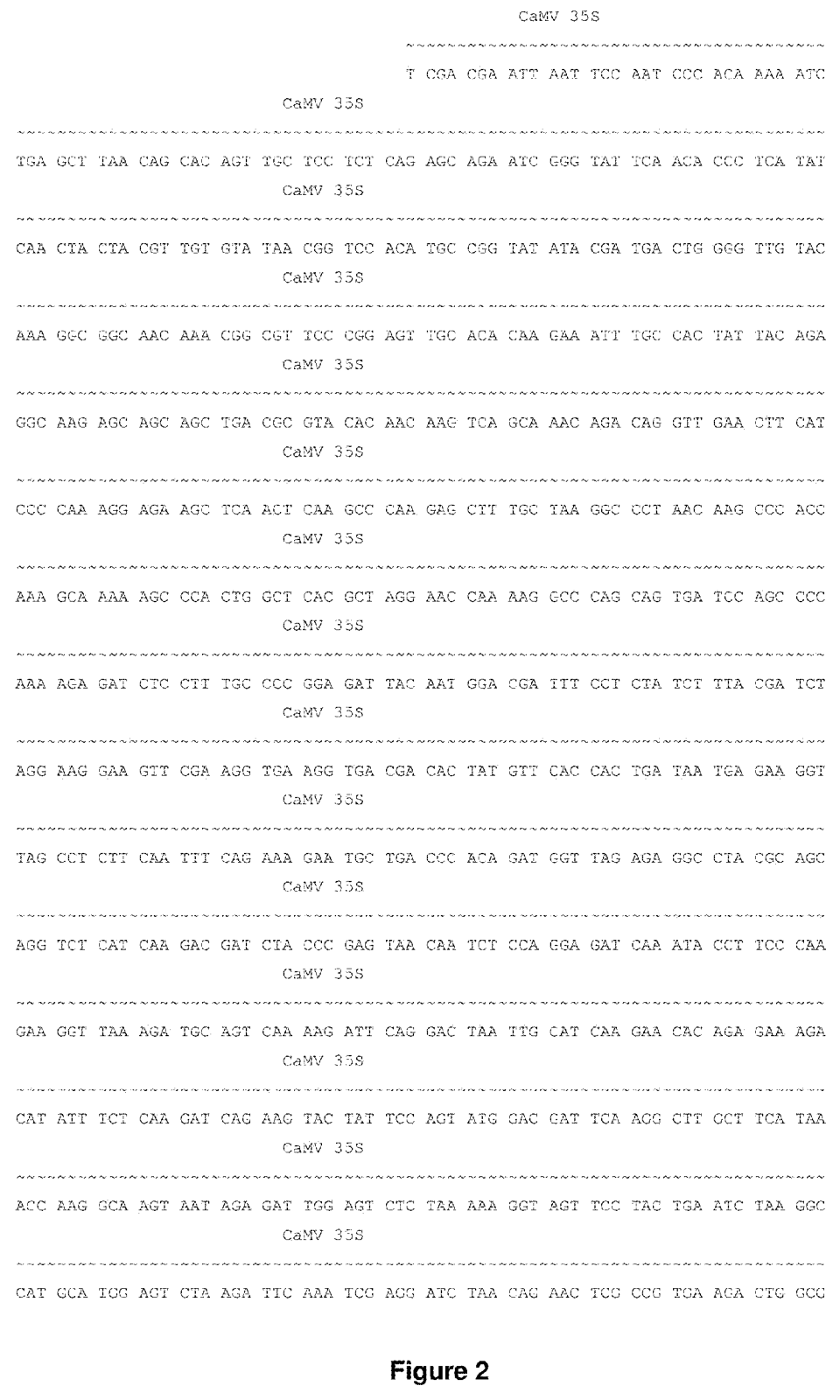

CaMV 35S

T CGA CGA ATT AAT TCC AAT CCC ACA AAA ATC

CaMV 35S

TGA GCT TAA CAG CAC AGT TGC TCC TCT CAG AGC AGA ATC GGG TAT TCA ACA CCC TCA TAT

CaMV 35S

CAA CTA CTA CGT TGT GTA TAA CGG TCC ACA TGC CGG TAT ATA CGA TGA CTG GGG TTG TAC

CaMV 35S

AAA GGC GGC AAC AAA CGG CGT TCC CGG AGT TGC ACA CAA GAA ATT TGC CAC TAT TAC AGA

CaMV 35S

GGC AAG AGC AGC AGC TGA CGC GTA CAC AAC AAG TCA GCA AAC AGA CAG GTT GAA CTT CAT

CaMV 35S

CCC CAA AGG AGA AGC TCA ACT CAA GCC CAA GAG CTT TGC TAA GGC CCT AAC AAG CCC ACC

CaMV 35S

AAA GCA AAA AGC CCA CTG GCT CAC GCT AGG AAC CAA AAG GCC CAG CAG TGA TCC AGC CCC

CaMV 35S

AAA AGA GAT CTC CTT TGC CCC GGA GAT TAC AAT GGA CGA TTT CCT CTA TCT TTA CGA TCT

CaMV 35S

AGG AAG GAA GTT CGA AGG TGA AGG TGA CGA CAC TAT GTT CAC CAC TGA TAA TGA GAA GGT

CaMV 35S

TAG CCT CTT CAA TTT CAG AAA GAA TGC TGA CCC ACA GAT GGT TAG AGA GGC CTA CGC AGC

CaMV 35S

AGG TCT CAT CAA GAC GAT CTA CCC GAG TAA CAA TCT CCA GGA GAT CAA ATA CCT TCC CAA

CaMV 35S

GAA GGT TAA AGA TGC AGT CAA AAG ATT CAG GAC TAA TTG CAT CAA GAA CAC AGA GAA AGA

CaMV 35S

CAT ATT TCT CAA GAT CAG AAG TAC TAT TCC AGT ATG GAC GAT TCA AGG CTT GCT TCA TAA

CaMV 35S

ACC AAG GCA AGT AAT AGA GAT TGG AGT CTC TAA AAA GGT AGT TCC TAC TGA ATC TAA GGC

CaMV 35S

CAT GCA TGG AGT CTA AGA TTC AAA TCG AGG ATC TAA CAG AAC TCG CCG TGA AGA CTG GCC

Figure 2

CaMV 35S

AAC AGT TCA TAC AGA GTC TTT TAC GAC TCA ATG ACA AGA AGA AAA TCT TCG TCA ACA TGG

CaMV 35S

TGG AGC ACG ACA CTC TGG TCT ACT CCA AAA ATG TCA AAG ATA CAG TCT CAG AAG ACC AAA

CaMV 35S

GGG CTA TTG AGA CTT TTC AAC AAA GGA TAA TTT CGG GAA ACC TCC TCG GAT TCC ATT GCC

CaMV 35S

CAG CTA TCT GTC ACT TCA TCG AAA GGA CAG TAG AAA AGG AAG GTG GCT CCT ACA AAT GCC

CaMV 35S

ATC ATT GCG ATA AAG GAA AGG CTA TCA TTC AAG ATC TCT CTG CCG ACA GTG GTC CCA AAG

CaMV 35S

ATG GAC CCC CAC CCA CGA GGA GCA TCG TGG AAA AAG AAG ACG TTC CAA CCA CGT CTT CAA

CaMV 35S

AGC AAG TGG ATT GAT GTG ACA TCT CCA CTG ACG TAA GGG ATG ACG CAC AAT CCC ACT ATC

CaMV 35S

CTT CGC AAG ACC CTT CCT CTA TAT AAG GAA GTT CAT TTC ATT TGG AGA GGA CAC GCT CGA attB1

GGA ATT CGG TAC CCC ATC ACA AGT TTG TAC AAA AAA GCA GGC TGC GGC CGC TTG CTC CCT

5' Oleo_1-1

NcoI

M A C H Y G Q Q Q Q T R A P H L Q

TAA AAA AAA CCA TGG CAT GTC ATT ACG GAC AAC AGC AAC AGA CTA GAG CAC CTC ATC TTC

5' Oleo_1-1

UBQ10

· L Q P R A Q R V V K A A T A V T (SEQ ID NO:118)

AGC TTC AAC CTA GAG CAC AGA GAG TTG TGA AGG CTG CTA CTG CTG TTA CTG TAA ATT TCT

UBQ10

GTG TTC CTT ATT CTC TCA AAA TCT TCG ATT TTG TTT TCG TTC GAT CCC AAT TTC GTA TAT

UBQ10

GTT CTT TGG TTT AGA TTC TGT TAA TCT TAG ATC GAA GAC GAT TTT CTG GGT TTG

Figure 2 cont.

```
                    UBQ10
~~~~~~~~~~~~~~~~~~~~~~~~~~~~~~~~~~~~~~~~~~~~~~~~~~~~~~~~~~~~~~~~~~~~~~~~~~~~~~~
AGA TAT CAT CTT AAT TCT CGA TTA GGG TTT CAT AGA TAT CAT CCG ATT TGT TCA AAT AAT
                    UBQ10
~~~~~~~~~~~~~~~~~~~~~~~~~~~~~~~~~~~~~~~~~~~~~~~~~~~~~~~~~~~~~~~~~~~~~~~~~~~~~~~
TTG AGT TTT GTC GAA TAA TTA CTC TTC GAT TTG TGA TTT CTA TCT AGA TCT GGT GTT AGT
                                                                     3'Oleo_1-1
                                                                        ~~~~~~~
                 UBQ10
~~~~~~~~~~~~~~~~~~~~~~~~~~~~~~~~~~~~~~~~~~~~~~~~~~~~~~~~~~~~~~~~~~~~~~~~
                                                                         A   G
TTC TAG TTT GTG CGA TCG AAT TTG TCG ATT AAT CTG AGT TTT TCT GAT TAA CAG GCT GGA
                 3' Oleo_1-1
~~~~~~~~~~~~~~~~~~~~~~~~~~~~~~~~~~~~~~~~~~~~~~~~~~~~~~~~~~~~~~~~~~~~~~~~~~~~~~~
 G   S   L   L   V   L   S   G   L   T   L   A   G   T   V   I   A   L   T   I
GGA TCT CTT CTT GTT CTC TCT GGA CTT ACT CTC GCT GGA ACT GTT ATC GCT CTC ACT ATC
                 3' Oleo_1-1
~~~~~~~~~~~~~~~~~~~~~~~~~~~~~~~~~~~~~~~~~~~~~~~~~~~~~~~~~~~~~~~~~~~~~~~~~~~~~~~
 A   T   P   L   L   V   I   F   S   P   V   L   V   P   A   V   I   T   I   F
GCT ACA CCT CTT CTC GTT ATC TTC TCT CCT GTT CTC GTT CCT GCT GTG ATC ACT ATC TTC
                 3' Oleo_1-1
~~~~~~~~~~~~~~~~~~~~~~~~~~~~~~~~~~~~~~~~~~~~~~~~~~~~~~~~~~~~~~~~~~~~~~~~~~~~~~~
 L   L   G   A   G   F   L   A   S   G   G   F   G   V   A   A   L   S   V   L
CTT CTC GGA GCT GGA TTT CTT GCT TCT GGT GGA TTT GGA GTT GCT GCT CTC TCT GTT CTC
                 3' Oleo_1-1
~~~~~~~~~~~~~~~~~~~~~~~~~~~~~~~~~~~~~~~~~~~~~~~~~~~~~~~~~~~~~~~~~~~~~~~~~~~~~~~
 S   W   I   Y   R   Y   L   T   G   K   H   P   P   G   A   D   Q   L   E   S
TCT TGG ATC TAC AGA TAC CTC ACT GGA AAA CAT CCT CCA GGT GCT GAT CAA CTT GAG TCT
                 3' Oleo_1-1
~~~~~~~~~~~~~~~~~~~~~~~~~~~~~~~~~~~~~~~~~~~~~~~~~~~~~~~~~~~~~~~~~~~~~~~~~~~~~~~
 A   K   T   K   L   A   S   K   A   R   E   M   K   D   R   A   E   Q   F   S
GCT AAG ACT AAG CTC GCT TCT AAG GCT AGA GAG ATG AAG GAT AGA GCA GAG CAA TTC TCT
       3' Oleo_1-1                                  OCS terminator
~~~~~~~~~~~~~~~~~~~~~~~~~~~~~~~~~~~~~~~~~~~~~~~~~   ~~~~~~~~~~~~~~~~~~~~~~~~~~~~
 C   Q   P   V   A   G   S   Q   T   S  (SEQ ID NO:119)
TGT CAG CCT GTT GCT GGA TCT CAG ACT TCT TAA TGA ACA TAT GGT CCT GCT TTA ATG AGA
                OCS terminator
~~~~~~~~~~~~~~~~~~~~~~~~~~~~~~~~~~~~~~~~~~~~~~~~~~~~~~~~~~~~~~~~~~~~~~~~~~~~~~~
TAT GCG AGA CGC CTA TGA TCG CAT GAT ATT TGC TTT CAA TTC TGT TGT GCA CGT TGT AAA
                OCS terminator
~~~~~~~~~~~~~~~~~~~~~~~~~~~~~~~~~~~~~~~~~~~~~~~~~~~~~~~~~~~~~~~~~~~~~~~~~~~~~~~
AAA CCT GAG CAT GTG TAG CTC AGA TCC TTA CCG CCG GTT TCG GTT CAT TCT AAT GAA TAT
                OCS terminator
~~~~~~~~~~~~~~~~~~~~~~~~~~~~~~~~~~~~~~~~~~~~~~~~~~~~~~~~~~~~~~~~~~~~~~~~~~~~~~~
ATC ACC CGT TAC TAT CGT ATT TTT ATG AAT AAT ATT CTC CGT TCA ATT TAC TGA TTG TAC
```

Figure 2 cont.

```
                                    OCS terminator
~~~~~~~~~~~~~~~~~~~~~~~~~~~~~~~~~~~~~~~~~~~~~~~~~~~~~~~~~~~~~~~~~~~~~~~~~~~~~
CCT ACT ACT TAT ATG TAC AAT ATT AAA ATG AAA ACA ATA TAT TGT GCT GAA TAG GTT TAT
                                    OCS terminator
~~~~~~~~~~~~~~~~~~~~~~~~~~~~~~~~~~~~~~~~~~~~~~~~~~~~~~~~~~~~~~~~~~~~~~~~~~~~~
AGC GAC ATC TAT GAT AGA GCG CCA CAA TAA CAA ACA ATT GCG TTT TAT TAT TAC AAA TCC
                                    OCS terminator
~~~~~~~~~~~~~~~~~~~~~~~~~~~~~~~~~~~~~~~~~~~~~~~~~~~~~~~~~~~~~~~~~~~~~~~~~~~~~
AAT TTT AAA AAA AGC GGC AGA ACC GGT CAA ACC TAA AAG ACT GAT TAC ATA AAT CTT ATT
                                    OCS terminator
~~~~~~~~~~~~~~~~~~~~~~~~~~~~~~~~~~~~~~~~~~~~~~~~~~~~~~~~~~~~~~~~~~~~~~~~~~~~~
CAA ATT TCA AAA GGC CCC AGG GGC TAG TAT CTA CGA CAC ACC GAG CGG CGA ACT AAT AAC
                                    OCS terminator
~~~~~~~~~~~~~~~~~~~~~~~~~~~~~~~~~~~~~~~~~~~~~~~~~~~~~~~~~~~~~~~~~~~~~~~~~~~~~
GTT CAC TGA AGG GAA CTC CGG TTC CCC GCC GGC GCG CAT GGG TGA GAT TCC TTG AAG TTG
                                    OCS terminator
~~~~~~~~~~~~~~~~~~~~~~~~~~~~~~~~~~~~~~~~~~~~~~~~~~~~~~~~~~~~~~~~~~~~~~~~~~~~~
AGT ATT GGC CGT CCG CTC TAC CGA AAG TTA CGG GCA CCA TTC AAC CCG GTC CAG CAC GGC
                                    OCS terminator
~~~~~~~~~~~~~~~~~~~~~~~~~~~~~~~~~~~~~~~~~~~~~~~~~~~~~~~~~~~~~~~~~~~~~~~~~~~~~
GGC CGG GTA ACC GAC TTG CTG CCC CGA GAA TTA TGC AGC ATT TTT TTG GTG TAT GTG GGC
                                    OCS terminator
~~~~~~~~~~~~~~~~~~~~~~~~~~~~~~~~~~~~~~~~~~~~~~~~~~~~~~~~~~~~~~~~~~~~~~~~~~~~~
CCC AAA TGA AGT GCA GGT CAA ACC TTG ACA GTG ACG ACA AAT CGT TGG GCG GGT CCA GGG
                                    OCS terminator
~~~~~~~~~~~~~~~~~~~~~~~~~~~~~~~~~~~~~~~~~~~~~~~~~~~~~~~~~~~~~~~~~~~~~~~~~~~~~
CGA ATT TTG CGA CAA CAT GTC GAG GCT CAC CAG GAC CTG CAC GCA TCC AAG CTA GCT TAC
                OCS terminator
~~~~~~~~~~~~~~~~~~~~~~~~~~~~~~~~~~~~~
                                    CaMV35S
                            ~~~~~~~~~~~~~~~~~~~~~~~~~~~~~~~~~~~~~~~~~~~
TAG TGA TGC ATA TTC TAT AGT GTC ACC TAA ATC TTC GAC GAA TTA ATT CCA ATC CCA CAA
                            CaMV35S
~~~~~~~~~~~~~~~~~~~~~~~~~~~~~~~~~~~~~~~~~~~~~~~~~~~~~~~~~~~~~~~~~~~~~~~~~~~~~
AAA TCT GAG CTT AAC AGC ACA GTT GCT CCT CTC AGA GCA GAA TCG GGT ATT CAA CAC CCT
                            CaMV35S
~~~~~~~~~~~~~~~~~~~~~~~~~~~~~~~~~~~~~~~~~~~~~~~~~~~~~~~~~~~~~~~~~~~~~~~~~~~~~
CAT ATC AAC TAC TAC GTT GTG TAT AAC GGT CCA CAT GCC GGT ATA TAC GAT GAC TGG GGT
                            CaMV35S
~~~~~~~~~~~~~~~~~~~~~~~~~~~~~~~~~~~~~~~~~~~~~~~~~~~~~~~~~~~~~~~~~~~~~~~~~~~~~
TGT ACA AAG GCG GCA ACA AAC GGC GTT CCC GGA GTT GCA CAC AAG AAA TTT GCC ACT ATT
                            CaMV35S
~~~~~~~~~~~~~~~~~~~~~~~~~~~~~~~~~~~~~~~~~~~~~~~~~~~~~~~~~~~~~~~~~~~~~~~~~~~~~
ACA GAG GCA AGA GCA GCA GCT GAC GCG TAC ACA ACA AGT CAG CAA ACA GAC AGG TTG AAC
                            CaMV35S
```

Figure 2 cont.

~~~~~~~~~~~~~~~~~~~~~~~~~~~~~~~~~~~~~~~~~~~~~~~~~~~~~~~~~~~~~~~~~~~~~~~~~~~~~~~~
TTC ATC CCC AAA GGA GAA GCT CAA CTC AAG CCC AAG AGC TTT GCT AAG GCC CTA ACA AGC
CaMV35S

~~~~~~~~~~~~~~~~~~~~~~~~~~~~~~~~~~~~~~~~~~~~~~~~~~~~~~~~~~~~~~~~~~~~~~~~~~~~~~~~
CCA CCA AAG CAA AAA GCC CAC TGG CTC ACG CTA GGA ACC AAA AGG CCC AGC AGT GAT CCA
CaMV35S

~~~~~~~~~~~~~~~~~~~~~~~~~~~~~~~~~~~~~~~~~~~~~~~~~~~~~~~~~~~~~~~~~~~~~~~~~~~~~~~~
GCC CCA AAA GAG ATC TCC TTT GCC CCG GAG ATT ACA ATG GAC GAT TTC CTC TAT CTT TAC
CaMV35S

~~~~~~~~~~~~~~~~~~~~~~~~~~~~~~~~~~~~~~~~~~~~~~~~~~~~~~~~~~~~~~~~~~~~~~~~~~~~~~~~
GAT CTA GGA AGG AAG TTC GAA GGT GAA GGT GAC GAC ACT ATG TTC ACC ACT GAT AAT GAG
CaMV35S

~~~~~~~~~~~~~~~~~~~~~~~~~~~~~~~~~~~~~~~~~~~~~~~~~~~~~~~~~~~~~~~~~~~~~~~~~~~~~~~~
AAG GTT AGC CTC TTC AAT TTC AGA AAG AAT GCT GAC CCA CAG ATG GTT AGA GAG GCC TAC
CaMV35S

~~~~~~~~~~~~~~~~~~~~~~~~~~~~~~~~~~~~~~~~~~~~~~~~~~~~~~~~~~~~~~~~~~~~~~~~~~~~~~~~
GCA GCA GGT CTC ATC AAG ACG ATC TAC CCG AGT AAC AAT CTC CAG GAG ATC AAA TAC CTT
CaMV35S

~~~~~~~~~~~~~~~~~~~~~~~~~~~~~~~~~~~~~~~~~~~~~~~~~~~~~~~~~~~~~~~~~~~~~~~~~~~~~~~~
CCC AAG AAG GTT AAA GAT GCA GTC AAA AGA TTC AGG ACT AAT TGC ATC AAG AAC ACA GAG
CaMV35S

~~~~~~~~~~~~~~~~~~~~~~~~~~~~~~~~~~~~~~~~~~~~~~~~~~~~~~~~~~~~~~~~~~~~~~~~~~~~~~~~
AAA GAC ATA TTT CTC AAG ATC AGA AGT ACT ATT CCA GTA TGG ACG ATT CAA GGC TTG CTT
CaMV35S

~~~~~~~~~~~~~~~~~~~~~~~~~~~~~~~~~~~~~~~~~~~~~~~~~~~~~~~~~~~~~~~~~~~~~~~~~~~~~~~~
CAT AAA CCA AGG CAA GTA ATA GAG ATT GGA GTC TCT AAA AAG GTA GTT CCT ACT GAA TCT
CaMV35S

~~~~~~~~~~~~~~~~~~~~~~~~~~~~~~~~~~~~~~~~~~~~~~~~~~~~~~~~~~~~~~~~~~~~~~~~~~~~~~~~
AAG GCC ATG CAT GGA GTC TAA GAT TCA AAT CGA GGA TCT AAC AGA ACT CGC CGT GAA GAC
CaMV35S

~~~~~~~~~~~~~~~~~~~~~~~~~~~~~~~~~~~~~~~~~~~~~~~~~~~~~~~~~~~~~~~~~~~~~~~~~~~~~~~~
TGG CGA ACA GTT CAT ACA GAG TCT TTT ACG ACT CAA TGA CAA GAA GAA AAT CTT CGT CAA
CaMV35S

~~~~~~~~~~~~~~~~~~~~~~~~~~~~~~~~~~~~~~~~~~~~~~~~~~~~~~~~~~~~~~~~~~~~~~~~~~~~~~~~
CAT GGT GGA GCA CGA CAC TCT GGT CTA CTC CAA AAA TGT CAA AGA TAC AGT CTC AGA AGA
CaMV35S

~~~~~~~~~~~~~~~~~~~~~~~~~~~~~~~~~~~~~~~~~~~~~~~~~~~~~~~~~~~~~~~~~~~~~~~~~~~~~~~~
CCA AAG GGC TAT TGA GAC TTT TCA ACA AAG GAT AAT TTC GGG AAA CCT CCT CGG ATT CCA
CaMV35S

~~~~~~~~~~~~~~~~~~~~~~~~~~~~~~~~~~~~~~~~~~~~~~~~~~~~~~~~~~~~~~~~~~~~~~~~~~~~~~~~
TTG CCC AGC TAT CTG TCA CTT CAT CGA AAG GAC AGT AGA AAA GGA AGG TGG CTC CTA CAA
CaMV35S

~~~~~~~~~~~~~~~~~~~~~~~~~~~~~~~~~~~~~~~~~~~~~~~~~~~~~~~~~~~~~~~~~~~~~~~~~~~~~~~~
ATG CCA TCA TTG CGA TAA AGG AAA GGC TAT CAT TCA AGA TCT CTC TGC CGA CAG TGG TCC
CaMV35S

Figure 2 cont.
~~~~~~~~~~~~~~~~~~~~~~~~~~~~~~~~~~~~~~~~~~~~~~~~~~~~~~~~~~~~~~~~~~~~~~~~~~~~~~~~

```
~~~~~~~~~~~~~~~~~~~~~~~~~~~~~~~~~~~~~~~~~~~~~~~~~~~~~~~~~~~~~~~~~~~~~~~~~~~~~~~~
CAA AGA TGG ACC CCC ACC CAC GAG GAG CAT CGT GGA AAA AGA AGA CGT TCC AAC CAC GTC
                          CaMV35S
~~~~~~~~~~~~~~~~~~~~~~~~~~~~~~~~~~~~~~~~~~~~~~~~~~~~~~~~~~~~~~~~~~~~~~~~~~~~~~~~
TTC AAA GCA AGT GGA TTG ATG TGA CAT CTC CAC TGA CGT AAG GGA TGA CGC ACA ATC CCA
                          CaMV35S
~~~~~~~~~~~~~~~~~~~~~~~~~~~~~~~~~~~~~~~~~~~~~~~~~~~~~~~~~~~~~~~~~~~~~~~~~~~~~~~~
CTA TCC TTC GCA AGA CCC TTC CTC TAT ATA AGG AAG TTC ATT TCA TTT GGA GAG GAC ACG
                                          5' DGAT1 (S205A)
                                  ~~~~~~~~~~~~~~~~~~~~~~~~~~~~~~~~~~~~~~~~~~~~~~
                                 NcoI
                                ~~~~~~~~
                                  M   A   I   L   D   S   A   G   V   T   T   V
GGA TCC TTG CTC CGT TAA AAA AAA CCA TGG CTA TCC TCG ATT CTG CTG GTG TTA CTA CTG
                      5' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
·  T   E   N   G   G   G   E   F   V   D   L   D   R   L   R   R   R   K   S   R
TGA CTG ACA ATG GTG GTG GAG AGT TCG TTG ATC TCG ATA GAC TCA GAA GAA GAA ACT CTA
5' DGAT1 (S205A)
~~~~~~
                               UBQ10
      ~~~~~~~~~~~~~~~~~~~~~~~~~~~~~~~~~~~~~~~~~~~~~~~~~~~~~~~~~~~~~~~~~~~~~~~~~~
·  S  (SEQ ID NO:115)
GAT CTG TAA ATT TCT GTG TTC CTT ATT CTC TCA AAA TCT TCG ATT TTG TTT TCG TTC GAT
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
CCC AAT TTC GTA TAT GTT CTT TGG TTT AGA TTC TGT TAA TCT TAG ATC GAA GAC GAT TTT
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
CTG GGT TTG ATC GTT AGA TAT CAT CTT AAT TCT CGA TTA GGG TTT CAT AGA TAT CAT CCG
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
ATT TGT TCA AAT AAT TTG AGT TTT GTC GAA TAA TTA CTC TTC GAT TTG TGA TTT CTA TCT
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
AGA TCT GGT GTT AGT TTC TAG TTT GTG CGA TCG AAT TTG TCG ATT AAT CTG AGT TTT TCT
  UBQ10
~~~~~~~~~~~~
                             3' DGAT1 (S205A)
            ~~~~~~~~~~~~~~~~~~~~~~~~~~~~~~~~~~~~~~~~~~~~~~~~~~~~~~~~~~~~~~~~~~~~
             D   S   S   N   G   L   L   L   S   G   S   D   N   N   S   P   S
GAT TAA CAG GAT TCT TCT AAC GGA CTT CTC CTC TCT GGA TCT GAT AAC AAC TCT CCT TCT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
 D   D   V   G   A   P   A   D   V   R   D   R   I   D   S   V   V   N   D   D
```

Figure 2 cont.

```
GAT GAT GTT GGT GCT CCT GCT GAT GTG AGA GAT AGA ATC GAT TCT GTG GTG AAC GAT GAT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 A   Q   G   T   A   N   L   A   G   D   N   N   G   G   G   D   N   N   G   G
GCT CAA GGT ACT GCT AAC CTC GCT GGT GAT AAT AAC GGT GGA GGT GAT AAC AAT GGT GGA
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 G   R   G   G   G   E   G   R   G   N   A   D   A   T   F   T   Y   R   P   S
GGA AGA GGT GGA GGT GAA GGT AGA GGA AAC GCT GAT GCT ACT TTC ACT TAC AGA CCA TCT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 V   P   A   H   R   R   A   R   E   S   P   L   S   S   D   A   I   F   K   Q
GTG CCT GCT CAT AGA AGA GCT AGA GAG TCT CCT CTC TCT TCT GAT GCT ATC TTC AAG CAG
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 S   H   A   G   L   F   N   L   C   V   V   V   L   I   A   V   N   S   R   L
TCT CAC GCT GGA CTT TTC AAC CTC TGT GTG GTG GTT CTT ATC GCT GTG AAC TCT AGA CTC
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 I   I   E   N   L   M   K   Y   G   W   L   I   R   T   D   F   W   F   S   S
ATC ATC GAG AAC CTC ATG AAG TAC GGA TGG CTC ATC AGA ACT GAT TTC TGG TTC TCT TCT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 R   S   L   R   D   W   P   L   F   M   C   C   I   S   L   S   I   F   P   L
AGA TCT CTC AGA GAT TGG CCT CTT TTC ATG TGC TGC ATC TCA CTC TCA ATC TTC CCT CTC
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 A   A   F   T   V   E   K   L   V   L   Q   K   Y   I   A   E   P   V   V   I
GCT GCT TTT ACT GTT GAG AAG CTC GTG CTC CAG AAG TAT ATC GCT GAA CCT GTG GTG ATC
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 F   L   H   I   I   I   T   M   T   E   V   L   Y   P   V   Y   V   T   L   R
TTC CTC CAC ATC ATC ATC ACT ATG ACT GAG GTT CTC TAC CCT GTT TAC GTG ACT CTC AGA
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 C   D   S   A   F   L   S   G   V   T   L   M   L   L   T   C   I   V   W   L
TGC GAT TCT GCT TTC CTC TCT GGT GTT ACT CTT ATG CTC CTC ACT TGC ATT GTG TGG CTT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 K   L   V   S   Y   A   H   T   S   Y   D   I   R   S   L   A   N   A   A   D
AAG CTC GTG TCT TAC GCT CAC ACT TCT TAC GAT ATC AGA TCT CTC GCT AAC GCT GCT GAT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 K   A   N   P   E   V   S   Y   Y   V   S   L   K   S   L   A   Y   F   M   V
AAG GCT AAC CCT GAA GTG TCT TAC TAC GTG TCT CTC AAG TCT CTC GCT TAC TTC ATG GTT
```

Figure 2 cont.

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

A P T L C Y Q P S Y P R S A C I R K G W

GCT CCT ACA CTT TGT TAC CAG CCA TCT TAC CCT AGA TCT GCT TGC ATT AGA AAG GGA TGG

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

V A R Q F A K L V I F T G F M G F I I E

GTG GCA AGA CAA TTC GCT AAG TTG GTG ATC TTC ACT GGA TTC ATG GGA TTC ATC ATC GAG

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

Q Y I N P I V R N S K H P L K G D L L Y

CAG TAC ATC AAC CCT ATT GTG AGA AAC TCT AAG CAC CCT CTC AAG GGT GAT CTT CTC TAC

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

A I E R V L K L S V P N L Y V W L C M F

GCT ATC GAG AGA GTT CTT AAG CTC TCT GTG CCT AAC CTT TAT GTG TGG CTC TGC ATG TTC

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

Y C F F H L W L N I L A E L L C F G D R

TAC TGT TTC TTC CAC CTC TGG CTT AAC ATC CTT GCT GAG TTG CTT TGC TTC GGA GAT AGA

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

E F Y K D W W N A K S V G D Y W R M W N

GAG TTC TAC AAG GAT TGG TGG AAC GCT AAG TCT GTT GGA GAT TAT TGG AGA ATG TGG AAC

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

M P V H K W M V R H I Y F P C L R S K I

ATG CCT GTG CAT AAG TGG ATG GTG CGT CAC ATC TAC TTC CCT TGC CTC AGA TCT AAG ATC

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

P K T L A I I I A F L V S A V F H E L C

CCT AAG ACT CTC GCT ATC ATT ATC GCT TTC CTC GTG TCT GCT GTT TTC CAT GAG TTG TGT

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

I A V P C R L F K L W A F L G I M F Q V

ATC GCT GTT CCT TGC AGA CTT TTC AAG CTT TGG GCT TTC CTC GGA ATC ATG TTC CAG GTT

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

P L V F I T N Y L Q E R F G S T V G N M

CCA CTC GTG TTC ATC ACT AAC TAC CTC CAA GAG AGA TTC GGA TCT ACT GTT GGA AAC ATG

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

I F W F I F C I F G Q P M C V L L Y Y H

ATT TTC TGG TTC ATT TTC TGC ATC TTC GGA CAG CCT ATG TGC GTT CTC CTC TAC TAC CAC

3' DGAT1 (S205A)

Figure 2 cont.
~~~~~~~~~~~~~~~~~~~~~~~~~~~~~~~~~~~~~~~~~~~~~~~~~~~~~~~~~~~~~~~~~~~~~~~~~~~~~~~~

```
~~~~~~~~~~~~~~~~~~~~~~~~~~~~~~~~~~~~~~~~~~~~~~~~
 D   L   M   N   R   K   G   S   M   S   (SEQ ID NO:116)
GAT CTC ATG AAC AGA AAG GGA TCT ATG TCT TAA TGA AGG ATC CAC CCA GCT TTC TTG TAC
                                                                  attB2
                                                                 ocs
                                                             ~~~~~~~~~~~~~~~~~~~~~
AAA GTG GTG ATG GGT TCG AAA TCG ATA AGC TTG GAT CCT CTA GAG TCC TGC TTT AAT GAG
~~~~~~~~~
 attB2
                            ocs
~~~~~~~~~~~~~~~~~~~~~~~~~~~~~~~~~~~~~~~~~~~~~~~~~~~~~~~~~~~~~~~~~~~~~~~~~~~~~~~
ATA TGC GAG ACG CCT ATG ATC GCA TGA TAT TTG CTT TCA ATT CTG TTG TGC ACG TTG TAA
                            ocs
~~~~~~~~~~~~~~~~~~~~~~~~~~~~~~~~~~~~~~~~~~~~~~~~~~~~~~~~~~~~~~~~~~~~~~~~~~~~~~~
AAA ACC TGA GCA TGT GTA GCT CAG ATC CTT ACC GCC GGT TTC GGT TCA TTC TAA TGA ATA
                            ocs
~~~~~~~~~~~~~~~~~~~~~~~~~~~~~~~~~~~~~~~~~~~~~~~~~~~~~~~~~~~~~~~~~~~~~~~~~~~~~~~
TAT CAC CCG TTA CTA TCG TAT TTT TAT GAA TAA TAT TCT CCG TTC AAT TTA CTG ATT GTA
                            ocs
~~~~~~~~~~~~~~~~~~~~~~~~~~~~~~~~~~~~~~~~~~~~~~~~~~~~~~~~~~~~~~~~~~~~~~~~~~~~~~~
CCC TAC TAC TTA TAT GTA CAA TAT TAA AAT GAA AAC AAT ATA TTG TGC TGA ATA GGT TTA
                            ocs
~~~~~~~~~~~~~~~~~~~~~~~~~~~~~~~~~~~~~~~~~~~~~~~~~~~~~~~~~~~~~~~~~~~~~~~~~~~~~~~
TAG CGA CAT CTA TGA TAG AGC GCC ACA ATA ACA AAC AAT TGC GTT TTA TTA TTA CAA ATC
                            ocs
~~~~~~~~~~~~~~~~~~~~~~~~~~~~~~~~~~~~~~~~~~~~~~~~~~~~~~~~~~~~~~~~~~~~~~~~~~~~~~~
CAA TTT TAA AAA AAG CGG CAG AAC CGG TCA AAC CTA AAA GAC TGA TTA CAT AAA TCT TAT
                            ocs
~~~~~~~~~~~~~~~~~~~~~~~~~~~~~~~~~~~~~~~~~~~~~~~~~~~~~~~~~~~~~~~~~~~~~~~~~~~~~~~
TCA AAT TTC AAA AGG CCC CAG GGG CTA GTA TCT ACG ACA CAC CGA GCG GCG AAC TAA TAA
                            ocs
~~~~~~~~~~~~~~~~~~~~~~~~~~~~~~~~~~~~~~~~~~~~~~~~~~~~~~~~~~~~~~~~~~~~~~~~~~~~~~~
CGT TCA CTG AAG GGA ACT CCG GTT CCC CGC CGG CGC GCA TGG GTG AGA TTC CTT GAA GTT
                            ocs
~~~~~~~~~~~~~~~~~~~~~~~~~~~~~~~~~~~~~~~~~~~~~~~~~~~~~~~~~~~~~~~~~~~~~~~~~~~~~~~
GAG TAT TGG CCG TCC GCT CTA CCG AAA GTT ACG GGC ACC ATT CAA CCC GGT CCA GCA CGG
                            ocs
~~~~~~~~~~~~~~~~~~~~~~~~~~~~~~~~~~~~~~~~~~~~~~~~~~~~~~~~~~~~~~~~~~~~~~~~~~~~~~~
CGG CCG GGT AAC CGA CTT GCT GCC CCG AGA ATT ATG CAG CAT TTT TTT GGT GTA TGT GGG
                            ocs
~~~~~~~~~~~~~~~~~~~~~~~~~~~~~~~~~~~~~~~~~~~~~~~~~~~~~~~~~~~~~~~~~~~~~~~~~~~~~~~
CCC CAA ATG AAG TGC AGG TCA AAC CTT GAC AGT GAC GAC AAA TCG TTG GGC GGG TCC AGG
                            ocs
~~~~~~~~~~~~~~~~~~~~~~~~~~~~~~~~~~~~~~~~~~~~~~~~~~~~~~~~~~~~~~~~~~~~~~~~~~~~~~~
GCG AAT TTT GCG ACA ACA TGT CGA GGC TCA GCA GGA CCT GCA GGC ATG CAA GCT AGC TTA
```

Figure 2 cont.

OCS

~~~~~~~~~~~~~~~~~~~~~~~~~~~~~~~~~~~~~~~~~~~~~~~~~~~~

CTA GTG ATG CAT ATT CTA TAG TGT CAC CTA AAT CT (SEQ ID NO:117)

Figure 2 cont.
~~~~~~~~~~~~~~~~~~~~~~~~~~~~~~~~~~~~~~~~~~~~~~~~~~~~

```
                                                        CaMV 35S
                                          ~~~~~~~~~~~~~~~~~~~~~~~~~~~~~~~~~~~~~~~~~
                                          T CGA CGA ATT AAT TCC AAT CCC ACA AAA ATC
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
TGA GCT TAA CAG CAC AGT TGC TCC TCT CAG AGC AGA ATC GGG TAT TCA ACA CCC TCA TAT
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
CAA CTA CTA CGT TGT GTA TAA CGG TCC ACA TGC CGG TAT ATA CGA TGA CTG GGG TTG TAC
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
AAA GGC GGC AAC AAA CGG CGT TCC CGG AGT TGC ACA CAA GAA ATT TGC CAC TAT TAC AGA
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
GGC AAG AGC AGC AGC TGA CGC GTA CAC AAC AAG TCA GCA AAC AGA CAG GTT GAA CTT CAT
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
CCC CAA AGG AGA AGC TCA ACT CAA GCC CAA GAG CTT TGC TAA GGC CCT AAC AAG CCC ACC
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
AAA GCA AAA AGC CCA CTG GCT CAC GCT AGG AAC CAA AAG GCC CAG CAG TGA TCC AGC CCC
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
AAA AGA GAT CTC CTT TGC CCC GGA GAT TAC AAT GGA CGA TTT CCT CTA TCT TTA CGA TCT
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
AGG AAG GAA GTT CGA AGG TGA AGG TGA CGA CAC TAT GTT CAC CAC TGA TAA TGA GAA GGT
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
TAG CCT CTT CAA TTT CAG AAA GAA TGC TCA CCC ACA GAT GGT TAG AGA GGC CTA CGC AGC
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
AGG TCT CAT CAA GAC GAT CTA CCC GAG TAA CAA TCT CCA GGA GAT CAA ATA CCT TCC CAA
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
GAA GGT TAA AGA TGC AGT CAA AAG ATT CAG GAC TAA TTG CAT CAA GAA CAC AGA GAA AGA
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
CAT ATT TCT CAA GAT CAG AAG TAC TAT TCC AGT ATG GAC GAT TCA AGG CTT GCT TCA TAA
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
ACC AAG GCA AGT AAT AGA GAT TGG AGT CTC TAA AAA GGT AGT TCC TAC TGA ATC TAA GGC
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
CAT GCA TGG AGT CTA AGA TTC AAA TCG AGG ATC TAA CAG AAC TCG CCG TGA AGA CTG GCG
```

Figure 3

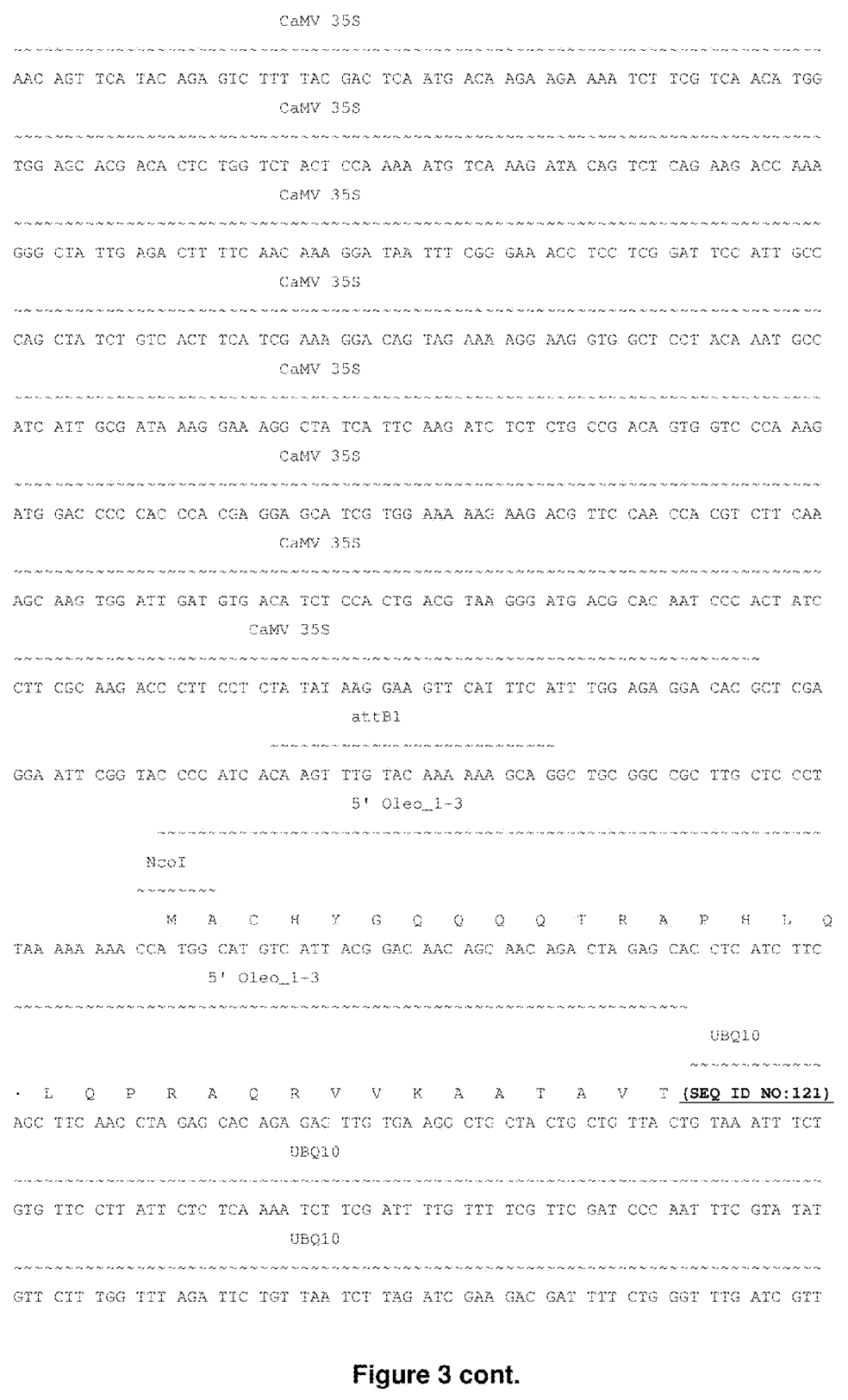

CaMV 35S
AAC AGT TCA TAC AGA GTC TTT TAC GAC TCA ATG ACA AGA AGA AAA TCT TCG TCA ACA TGG
CaMV 35S
TGG AGC ACG ACA CTC TGG TCT ACT CCA AAA ATG TCA AAG ATA CAG TCT CAG AAG ACC AAA
CaMV 35S
GGG CTA TTG AGA CTT TTC AAC AAA GGA TAA TTT CGG GAA ACC TCC TCG GAT TCC ATT GCC
CaMV 35S
CAG CTA TCT GTC ACT TCA TCG AAA GGA CAG TAG AAA AGG AAG GTG GCT CCT ACA AAT GCC
CaMV 35S
ATC ATT GCG ATA AAG GAA AGG CTA TCA TTC AAG ATC TCT CTG CCG ACA GTG GTC CCA AAG
CaMV 35S
ATG GAC CCC CAC CCA CGA GGA GCA TCG TGG AAA AAG AAG ACG TTC CAA CCA CGT CTT CAA
CaMV 35S
AGC AAG TGG ATT GAT GTG ACA TCT CCA CTG ACG TAA GGG ATG ACG CAC AAT CCC ACT ATC
CaMV 35S
CTT CGC AAG ACC CTT CCT CTA TAT AAG GAA GTT CAT TTC ATT TGG AGA GGA CAC GCT CGA
attB1
GGA ATT CGG TAC CCC ATC ACA AGT TTG TAC AAA AAA GCA GGC TGC GGC CGC TTG CTC CCT
5' Oleo_1-3
NcoI
M A C H Y G Q Q Q Q T R A P H L Q
TAA AAA AAA CCA TGG CAT GTC ATT ACG GAC AAC AGC AAC AGA CTA GAG CAC CTC ATC TTC
5' Oleo_1-3
UBQ10
· L Q P R A Q R V V K A A T A V T (SEQ ID NO:121)
AGC TTC AAC CTA GAG CAC AGA GAC TTG TGA AGG CTG CTA CTG CTG TTA CTG TAA ATT TCT
UBQ10
GTG TTC CTT ATT CTC TCA AAA TCT TCG ATT TTG TTT TCG TTC GAT CCC AAT TTC GTA TAT
UBQ10
GTT CTT TGG TTT AGA TTC TGT TAA TCT TAG ATC GAA GAC GAT TTT CTG GGT TTG ATC GTT

Figure 3 cont.

```
                           UBQ10
~~~~~~~~~~~~~~~~~~~~~~~~~~~~~~~~~~~~~~~~~~~~~~~~~~~~~~~~~~~~~~~~~~~~~~~~~~~~~~~
AGA TAT CAT CTT AAT TCT CGA TTA GGG TTT CAT AGA TAT CAT CCG ATT TGT TCA AAT AAT
                           UBQ10
~~~~~~~~~~~~~~~~~~~~~~~~~~~~~~~~~~~~~~~~~~~~~~~~~~~~~~~~~~~~~~~~~~~~~~~~~~~~~~~
TTG AGT TTT GTC GAA TAA TTA CTC TTC GAT TTG TGA TTT CTA TCT AGA TCT GGT GTT AGT
                                                                       3'Oleo_1-3
                                                                        ~~~~~~~
                        UBQ10
~~~~~~~~~~~~~~~~~~~~~~~~~~~~~~~~~~~~~~~~~~~~~~~~~~~~~~~~~~~~~~~~~~~~~~~~
                                                                        A   G
TTC TAG TTT GTG CGA TCG AAT TTG TCG ATT AAT CTG AGT TTT TCT GAT TAA CAG GCT GGA
                        3' Oleo_1-3
~~~~~~~~~~~~~~~~~~~~~~~~~~~~~~~~~~~~~~~~~~~~~~~~~~~~~~~~~~~~~~~~~~~~~~~~~~~~~~~
 G   S   L   L   V   L   S   G   L   T   L   A   G   T   V   I   A   L   T   I
GGA TCT CTT CTT GTT CTC TCT GGA CTT ACT CTC GCT GGA ACT GTT ATC GCT CTC ACT ATC
                        3' Oleo_1-3
~~~~~~~~~~~~~~~~~~~~~~~~~~~~~~~~~~~~~~~~~~~~~~~~~~~~~~~~~~~~~~~~~~~~~~~~~~~~~~~
 A   T   P   L   L   V   I   F   S   P   V   L   V   P   A   V   I   T   I   F
GCT ACA CCT CTT CTC GTT ATC TTC TCT CCT GTT CTC GTT CCT GCT GTG ATC ACT ATC TTC
                        3' Oleo_1-3
~~~~~~~~~~~~~~~~~~~~~~~~~~~~~~~~~~~~~~~~~~~~~~~~~~~~~~~~~~~~~~~~~~~~~~~~~~~~~~~
 L   L   G   A   G   F   L   A   S   G   G   F   G   V   A   A   L   S   V   L
CTT CTC GGA GCT GGA TTT CTT GCT TCT GGT GGA TTT GGA GTT GCT GCT CTC TCT GTT CTC
                        3' Oleo_1-3
~~~~~~~~~~~~~~~~~~~~~~~~~~~~~~~~~~~~~~~~~~~~~~~~~~~~~~~~~~~~~~~~~~~~~~~~~~~~~~~
 S   W   I   Y   R   Y   L   T   G   K   H   P   P   G   A   D   C   L   E   S
TCT TGG ATC TAC AGA TAC CTC ACT GGA AAA CAT CCT CCA GGT GCT GAT TGT CTT GAG TCT
                        3' Oleo_1-3
~~~~~~~~~~~~~~~~~~~~~~~~~~~~~~~~~~~~~~~~~~~~~~~~~~~~~~~~~~~~~~~~~~~~~~~~~~~~~~~
 A   K   T   K   L   A   S   C   A   R   E   M   K   D   R   A   E   Q   F   S
GCT AAG ACT AAG CTC GCT TCT TGT GCT AGA GAG ATG AAG GAT AGA GCA GAG CAA TTC TCT
             3' Oleo_1-3                                     OCS terminator
~~~~~~~~~~~~~~~~~~~~~~~~~~~~~~~~~~~~~~~~~~~~~~~~~         ~~~~~~~~~~~~~~~~~~~~~
 C   Q   P   V   A   G   S   Q   T   S   (SEQ ID NO:122)
TGT CAG CCT GTT GCT GGA TCT CAG ACT TCT TAA TGA ACA TAT GGT CCT GCT TTA ATG AGA
                       OCS terminator
~~~~~~~~~~~~~~~~~~~~~~~~~~~~~~~~~~~~~~~~~~~~~~~~~~~~~~~~~~~~~~~~~~~~~~~~~~~~~~~
TAT GCG AGA CGC CTA TCA TCG CAT GAT ATT TGC TTT CAA TTC TGT TGT GCA CGT TGT AAA
                       OCS terminator
~~~~~~~~~~~~~~~~~~~~~~~~~~~~~~~~~~~~~~~~~~~~~~~~~~~~~~~~~~~~~~~~~~~~~~~~~~~~~~~
AAA CCT GAG CAT GTG TAG CTC AGA TCC TTA CCG CCG GTT TCG GTT CAT TCT AAT GAA TAT
                       OCS terminator
~~~~~~~~~~~~~~~~~~~~~~~~~~~~~~~~~~~~~~~~~~~~~~~~~~~~~~~~~~~~~~~~~~~~~~~~~~~~~~~
ATC ACC CGT TAC TAT CGT ATT TTT ATG AAT AAT ATT CTC CGT TCA ATT TAC TGA TTG TAC
```

Figure 3 cont.

```
                      OCS terminator
~~~~~~~~~~~~~~~~~~~~~~~~~~~~~~~~~~~~~~~~~~~~~~~~~~~~~~~~~~~~~~~~~~~~~~~~~~~~~~~
CCT ACT ACT TAT ATG TAC AAT ATT AAA ATG AAA ACA ATA TAT TGT GCT GAA TAG GTT TAT
                      OCS terminator
~~~~~~~~~~~~~~~~~~~~~~~~~~~~~~~~~~~~~~~~~~~~~~~~~~~~~~~~~~~~~~~~~~~~~~~~~~~~~~~
AGC GAC ATC TAT GAT AGA GCG CCA CAA TAA CAA ACA ATT GCG TTT TAT TAT TAC AAA TCC
                      OCS terminator
~~~~~~~~~~~~~~~~~~~~~~~~~~~~~~~~~~~~~~~~~~~~~~~~~~~~~~~~~~~~~~~~~~~~~~~~~~~~~~~
AAT TTT AAA AAA AGC GGC AGA ACC GGT CAA ACC TAA AAG ACT GAT TAC ATA AAT CTT ATT
                      OCS terminator
~~~~~~~~~~~~~~~~~~~~~~~~~~~~~~~~~~~~~~~~~~~~~~~~~~~~~~~~~~~~~~~~~~~~~~~~~~~~~~~
CAA ATT TCA AAA GGC CCC AGG GGC TAG TAT CTA CGA CAC ACC GAG CGG CGA ACT AAT AAC
                      OCS terminator
~~~~~~~~~~~~~~~~~~~~~~~~~~~~~~~~~~~~~~~~~~~~~~~~~~~~~~~~~~~~~~~~~~~~~~~~~~~~~~~
GTT CAC TGA AGG GAA CTC CGG TTC CCC GCC GGC GCG CAT GGG TGA GAT TCC TTG AAG TTG
                      OCS terminator
~~~~~~~~~~~~~~~~~~~~~~~~~~~~~~~~~~~~~~~~~~~~~~~~~~~~~~~~~~~~~~~~~~~~~~~~~~~~~~~
AGT ATT GGC CGT CCG CTC TAC CGA AAG TTA CGG GCA CCA TTC AAC CCG GTC CAG CAC GGC
                      OCS terminator
~~~~~~~~~~~~~~~~~~~~~~~~~~~~~~~~~~~~~~~~~~~~~~~~~~~~~~~~~~~~~~~~~~~~~~~~~~~~~~~
GGC CGG GTA ACC GAC TTG CTG CCC CGA GAA TTA TGC AGC ATT TTT TTG GTG TAT GTG GGC
                      OCS terminator
~~~~~~~~~~~~~~~~~~~~~~~~~~~~~~~~~~~~~~~~~~~~~~~~~~~~~~~~~~~~~~~~~~~~~~~~~~~~~~~
CCC AAA TGA AGT GCA GGT CAA ACC TTG ACA GTG ACG ACA AAT CGT TGG GCG GGT CCA GGG
                      OCS terminator
~~~~~~~~~~~~~~~~~~~~~~~~~~~~~~~~~~~~~~~~~~~~~~~~~~~~~~~~~~~~~~~~~~~~~~~~~~~~~~~
CGA ATT TTG CGA CAA CAT GTC GAG GCT CAG CAG GAC CTG CAG GCA TGC AAG CTA GCT TAC
         OCS terminator
~~~~~~~~~~~~~~~~~~~~~~~~~~~~~~~~~~~~~~~~~~~~~
                                                          CaMV35S
                                             ~~~~~~~~~~~~~~~~~~~~~~~~~~~~~~~~~~
TAG TGA TGC ATA TTC TAT AGT GTC ACC TAA ATC TTC GAC GAA TTA ATT CCA ATC CCA CAA
                         CaMV35S
~~~~~~~~~~~~~~~~~~~~~~~~~~~~~~~~~~~~~~~~~~~~~~~~~~~~~~~~~~~~~~~~~~~~~~~~~~~~~~~
AAA TCT GAG CTT AAC AGC ACA GTT GCT CCT CTC AGA GCA GAA TCG GGT ATT CAA CAC CCT
                         CaMV35S
~~~~~~~~~~~~~~~~~~~~~~~~~~~~~~~~~~~~~~~~~~~~~~~~~~~~~~~~~~~~~~~~~~~~~~~~~~~~~~~
CAT ATC AAC TAC TAC GTT GTG TAT AAC GGT CCA CAT GCC GGT ATA TAC GAT GAC TGG GGT
                         CaMV35S
~~~~~~~~~~~~~~~~~~~~~~~~~~~~~~~~~~~~~~~~~~~~~~~~~~~~~~~~~~~~~~~~~~~~~~~~~~~~~~~
TGT ACA AAG GCG GCA ACA AAC GGC GTT CCC GGA GTT GCA CAC AAG AAA TTT GCC ACT ATT
                         CaMV35S
~~~~~~~~~~~~~~~~~~~~~~~~~~~~~~~~~~~~~~~~~~~~~~~~~~~~~~~~~~~~~~~~~~~~~~~~~~~~~~~
ACA GAG GCA AGA GCA GCA GCT GAC GCG TAC ACA ACA AGT CAG CAA ACA GAC AGG TTG AAC
                         CaMV35S
```

Figure 3 cont.

~~~~~~~~~~~~~~~~~~~~~~~~~~~~~~~~~~~~~~~~~~~~~~~~~~~~~~~~~~~~~~~~~~~~~~~~~~~~~~
TTC ATC CCC AAA GGA GAA GCT CAA CTC AAG CCC AAG AGC TTT GCT AAG GCC CTA ACA AGC
CaMV35S
~~~~~~~~~~~~~~~~~~~~~~~~~~~~~~~~~~~~~~~~~~~~~~~~~~~~~~~~~~~~~~~~~~~~~~~~~~~~~~
CCA CCA AAG CAA AAA GCC CAC TGG CTC ACG CTA GGA ACC AAA AGG CCC AGC AGT GAT CCA
CaMV35S
~~~~~~~~~~~~~~~~~~~~~~~~~~~~~~~~~~~~~~~~~~~~~~~~~~~~~~~~~~~~~~~~~~~~~~~~~~~~~~
GCC CCA AAA GAG ATC TCC TTT GCC CCG GAG ATT ACA ATG GAC GAT TTC CTC TAT CTT TAC
CaMV35S
~~~~~~~~~~~~~~~~~~~~~~~~~~~~~~~~~~~~~~~~~~~~~~~~~~~~~~~~~~~~~~~~~~~~~~~~~~~~~~
GAT CTA GGA AGG AAG TTC GAA GGT GAA GGT GAC GAC ACT ATG TTC ACC ACT GAT AAT GAG
CaMV35S
~~~~~~~~~~~~~~~~~~~~~~~~~~~~~~~~~~~~~~~~~~~~~~~~~~~~~~~~~~~~~~~~~~~~~~~~~~~~~~
AAG GTT AGC CTC TTC AAT TTC AGA AAG AAT GCT GAC CCA CAG ATG GTT AGA GAG GCC TAC
CaMV35S
~~~~~~~~~~~~~~~~~~~~~~~~~~~~~~~~~~~~~~~~~~~~~~~~~~~~~~~~~~~~~~~~~~~~~~~~~~~~~~
GCA GCA GGT CTC ATC AAG ACG ATC TAC CCG AGT AAC AAT CTC CAG GAG ATC AAA TAC CTT
CaMV35S
~~~~~~~~~~~~~~~~~~~~~~~~~~~~~~~~~~~~~~~~~~~~~~~~~~~~~~~~~~~~~~~~~~~~~~~~~~~~~~
CCC AAG AAG GTT AAA GAT GCA GTC AAA AGA TTC AGG ACT AAT TGC ATC AAG AAC ACA GAG
CaMV35S
~~~~~~~~~~~~~~~~~~~~~~~~~~~~~~~~~~~~~~~~~~~~~~~~~~~~~~~~~~~~~~~~~~~~~~~~~~~~~~
AAA GAC ATA TTT CTC AAG ATC AGA AGT ACT ATT CCA GTA TGG ACG ATT CAA GGC TTG CTT
CaMV35S
~~~~~~~~~~~~~~~~~~~~~~~~~~~~~~~~~~~~~~~~~~~~~~~~~~~~~~~~~~~~~~~~~~~~~~~~~~~~~~
CAT AAA CCA AGG CAA GTA ATA GAG ATT GGA GTC TCT AAA AAG GTA GTT CCT ACT GAA TCT
CaMV35S
~~~~~~~~~~~~~~~~~~~~~~~~~~~~~~~~~~~~~~~~~~~~~~~~~~~~~~~~~~~~~~~~~~~~~~~~~~~~~~
AAG GCC ATG CAT GGA GTC TAA GAT TCA AAT CGA GGA TCT AAC AGA ACT CGC CGT GAA GAC
CaMV35S
~~~~~~~~~~~~~~~~~~~~~~~~~~~~~~~~~~~~~~~~~~~~~~~~~~~~~~~~~~~~~~~~~~~~~~~~~~~~~~
TGG CGA ACA GTT CAT ACA GAG TCT TTT ACG ACT CAA TGA CAA GAA GAA AAT CTT CGT CAA
CaMV35S
~~~~~~~~~~~~~~~~~~~~~~~~~~~~~~~~~~~~~~~~~~~~~~~~~~~~~~~~~~~~~~~~~~~~~~~~~~~~~~
CAT GGT GGA GCA CGA CAC TCT GGT CTA CTC CAA AAA TGT CAA AGA TAC AGT CTC AGA AGA
CaMV35S
~~~~~~~~~~~~~~~~~~~~~~~~~~~~~~~~~~~~~~~~~~~~~~~~~~~~~~~~~~~~~~~~~~~~~~~~~~~~~~
CCA AAG GGC TAT TGA GAC TTT TCA ACA AAG GAT AAT TTC GGG AAA CCT CCT CGG ATT CCA
CaMV35S
~~~~~~~~~~~~~~~~~~~~~~~~~~~~~~~~~~~~~~~~~~~~~~~~~~~~~~~~~~~~~~~~~~~~~~~~~~~~~~
TTG CCC AGC TAT CTG TCA CTT CAT CGA AAG GAC AGT AGA AAA GGA AGG TGG CTC CTA CAA
CaMV35S
~~~~~~~~~~~~~~~~~~~~~~~~~~~~~~~~~~~~~~~~~~~~~~~~~~~~~~~~~~~~~~~~~~~~~~~~~~~~~~
ATG CCA TCA TTG CGA TAA AGG AAA GGC TAT CAT TCA AGA TCT CTC TGC CGA CAG TGG TCC
CaMV35S

Figure 3 cont.
~~~~~~~~~~~~~~~~~~~~~~~~~~~~~~~~~~~~~~~~~~~~~~~~~~~~~~~~~~~~~~~~~~~~~~~~~~~~~~

```
~~~~~~~~~~~~~~~~~~~~~~~~~~~~~~~~~~~~~~~~~~~~~~~~~~~~~~~~~~~~~~~~~~~~~~~~~~~~~~~~
CAA AGA TGG ACC CCC ACC CAC GAG GAG CAT CGT GGA AAA AGA AGA CGT TCC AAC CAC GTC
                          CaMV35S
~~~~~~~~~~~~~~~~~~~~~~~~~~~~~~~~~~~~~~~~~~~~~~~~~~~~~~~~~~~~~~~~~~~~~~~~~~~~~~~~
TTC AAA GCA AGT GGA TTG ATG TGA CAT CTC CAC TGA CGT AAG GGA TGA CGC ACA ATC CCA
                          CaMV35S
~~~~~~~~~~~~~~~~~~~~~~~~~~~~~~~~~~~~~~~~~~~~~~~~~~~~~~~~~~~~~~~~~~~~~~~~~~~~~~~~
CTA TCC TTC GCA AGA CCC TTC CTC TAT ATA AGG AAG TTC ATT TCA TTT GGA GAG GAC ACG
                                           5' DGAT1 (S205A)
                                        ~~~~~~~~~~~~~~~~~~~~~~~~~~~~~~~~~~~~~~~~
                              NcoI
                             ~~~~~~~~
                               M   A   I   L   D   S   A   G   V   T   T   V
GGA TCC TTG CTC CGT TAA AAA AAA CCA TGG CTA TCC TCG ATT CTG CTG GTG TTA CTA CTG
                      5' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
·  T   E   N   G   G   G   E   F   V   D   L   D   R   L   R   R   R   K   S   R
TGA CTG AGA ATG GTG GTG GAG AGT TCG TTG ATC TCG ATA GAC TCA GAA GAA GAA AGT CTA
5' DGAT1 (S205A)
~~~~~~
                             UBQ10
      ~~~~~~~~~~~~~~~~~~~~~~~~~~~~~~~~~~~~~~~~~~~~~~~~~~~~~~~~~~~~~~~~~~~~~~~~~~
·  S  (SEQ ID NO:115)
GAT CTG TAA ATT TCT GTG TTC CTT ATT CTC TCA AAA TCT TCG ATT TTG TTT TCG TTC GAT
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
CCC AAT TTC GTA TAT GTT CTT TGG TTT AGA TTC TGT TAA TCT TAG ATC GAA GAC GAT TTT
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
CTG GGT TTG ATC GTT AGA TAT CAT CTT AAT TCT CGA TTA GGG TTT CAT AGA TAT CAT CCG
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
ATT TGT TCA AAT AAT TTG AGT TTT GTC GAA TAA TTA CTC TTC GAT TTG TGA TTT CTA TCT
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
AGA TCT GGT GTT AGT TTC TAG TTT GTG CGA TCG AAT TTG TCG ATT AAT CTG AGT TTT TCT
  UBQ10
~~~~~~~~~~~~
                            3' DGAT1 (S205A)
            ~~~~~~~~~~~~~~~~~~~~~~~~~~~~~~~~~~~~~~~~~~~~~~~~~~~~~~~~~~~~~~~~~~~~
             D   S   S   N   G   L   L   L   S   G   S   D   N   N   S   P   S
GAT TAA CAG CAT TCT TCT AAC GGA CTT CTC CTC TCT GGA TCT GAT AAC AAC TCT CCT TCT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
 D   D   V   G   A   P   A   D   V   R   D   R   I   D   S   V   V   N   D   D
```

Figure 3 cont.

GAT GAT GTT GGT GCT CCT GCT GAT GTG AGA GAT AGA ATC GAT TCT GTG GTG AAC GAT GAT
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
A Q G T A N L A G D N N G G G D N N G G
GCT CAA GGT ACT GCT AAC CTC GCT GGT GAT AAT AAC GGT GGA GGT GAT AAC AAT GGT GGA
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
G R G G G E G R G N A D A T F T Y R P S
GGA AGA GGT GGA GGT GAA GGT AGA GGA AAC GCT GAT GCT ACT TTC ACT TAC AGA CCA TCT
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
V P A H R R A R E S P L S S D A I F K Q
GTG CCT GCT CAT AGA AGA GCT AGA GAG TCT CCT CTC TCT TCT GAT GCT ATC TTC AAG CAG
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
S H A G L F N L C V V V L I A V N S R L
TCT CAC GCT GGA CTT TTC AAC CTC TGT GTG GTG GTT CTT ATC GCT GTG AAC TCT AGA CTC
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
I I E N L M K Y G W L I R T D F W F S S
ATC ATC GAG AAC CTC ATG AAG TAC GGA TGG CTC ATC AGA ACT GAT TTC TGG TTC TCT TCT
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
R S L R D W P L F M C C I S L S I F P L
AGA TCT CTC AGA GAT TGG CCT CTT TTC ATG TGC TGC ATC TCA CTC TCA ATC TTC CCT CTC
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
A A F T V E K L V L Q K Y I A E P V V I
GCT GCT TTT ACT GTT GAG AAG CTC GTG CTC CAG AAG TAT ATC GCT GAA CCT GTG GTG ATC
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
F L H I I I T M T E V L Y P V Y V T L R
TTC CTC CAC ATC ATC ATC ACT ATG ACT GAG GTT CTC TAC CCT GTT TAC GTG ACT CTC AGA
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
C D S A F L S G V T L M L L T C I V W L
TGC GAT TCT GCT TTC CTC TCT GGT GTT ACT CTT ATG CTC CTC ACT TGC ATT GTG TGG CTT
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
K L V S Y A H T S Y D I R S L A N A A D
AAG CTC GTG TCT TAC GCT CAC ACT TCT TAC GAT ATC AGA TCT CTC GCT AAC GCT GCT GAT
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
K A N P E V S Y Y V S L K S L A Y F M V
AAG GCT AAC CCT GAA GTG TCT TAC TAC GTG TCT CTC AAG TCT CTC GCT TAC TTC ATG GTT

Figure 3 cont.
~~~~~~~~~~~~~~~~~~~~~~~~~~~~~~~~~~~~~~~~~~~~~~~~~~~~~~~~~~~~~~~~~~~~~~~~~~~~~~~

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

A P T L C Y Q P S Y P R S A C I R K G W

GCT CCT ACA CTT TGT TAC CAG CCA TCT TAC CCT AGA TCT GCT TGC ATT AGA AAG GGA TGG

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

V A R Q F A K L V I F T G F M G F I I E

GTG GCA AGA CAA TTC GCT AAG TTG GTG ATC TTC ACT GGA TTC ATG GGA TTC ATC ATC GAG

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

Q Y I N P I V R N S K H P L K G D L L Y

CAG TAC ATC AAC CCT ATT GTG AGA AAC TCT AAG CAC CCT CTC AAG GGT GAT CTT CTC TAC

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

A I E R V L K L S V P N L Y V W L C M F

GCT ATC GAG AGA GTT CTT AAG CTC TCT GTG CCT AAC CTT TAT GTG TGG CTC TGC ATG TTC

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

Y C F F H L W L N I L A E L L C F G D R

TAC TGT TTC TTC CAC CTC TGG CTT AAC ATC CTT GCT GAG TTG CTT TGC TTC GGA GAT AGA

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

E F Y K D W W N A K S V G D Y W R M W N

GAG TTC TAC AAG GAT TGG TGG AAC GCT AAG TCT GTT GGA GAT TAT TGG AGA ATG TGG AAC

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

M P V H K W M V R H I Y F P C L R S K I

ATG CCT GTG CAT AAG TGG ATG GTG CGT CAC ATC TAC TTC CCT TGC CTC AGA TCT AAG ATC

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

P K T L A I I I A F L V S A V F H E L C

CCT AAG ACT CTC GCT ATC ATT ATC GCT TTC CTC GTG TCT GCT GTT TTC CAT GAG TTG TGT

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

I A V P C R L F K L W A F L G I M F Q V

ATC GCT GTT CCT TGC AGA CTT TTC AAG CTT TGG GCT TTC CTC GGA ATC ATG TTC CAG GTT

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

P L V F I T N Y L Q E R F G S T V G N M

CCA CTC GTG TTC ATC ACT AAC TAC CTC CAA GAG AGA TTC GGA TCT ACT GTT GGA AAC ATG

3' DGAT1 (S205A)

~~~~~~~~~~~~~~~~~~~~~~~~~~~~~~~~~~~~~~~~~~~~~~~~~~~~~~~~~~~~~~~~~~~~~~~~~~~~~~~~

I F W F I F C I F G Q P M C V L L Y Y H

ATT TTC TGG TTC ATT TTC TGC ATC TTC GGA CAG CCT ATG TGC GTT CTC CTC TAC TAC CAC

3' DGAT1 (S205A)

Figure 3 cont.
~~~~~~~~~~~~~~~~~~~~~~~~~~~~~~~~~~~~~~~~~~~~~~~~~~~~~~~~~~~~~~~~~~~~~~~~~~~~~~~~

```
~~~~~~~~~~~~~~~~~~~~~~~~~~~~~~~~~~~~~~~~~~~~~~~~
 D   L   M   N   R   K   G   S   M   S   (SEQ ID NO:116)
GAT CTC ATG AAC AGA AAG GGA TCT ATG TCT TAA TGA AGG ATC CAC CCA GCT TTC TTG TAC
                                                                 attB2
                                                                ocs
                                                          ~~~~~~~~~~~~~~~~~~~~~
AAA GTG GTG ATG GGT TCG AAA TCG ATA AGC TTG GAT CCT CTA GAG TCC TGC TTT AAT GAG
~~~~~~~~~
 attB2
                            ocs
~~~~~~~~~~~~~~~~~~~~~~~~~~~~~~~~~~~~~~~~~~~~~~~~~~~~~~~~~~~~~~~~~~~~~~~~~~~~~~~
ATA TGC GAG ACG CCT ATG ATC GCA TGA TAT TTG CTT TCA ATT CTG TTG TGC ACG TTG TAA
                            ocs
~~~~~~~~~~~~~~~~~~~~~~~~~~~~~~~~~~~~~~~~~~~~~~~~~~~~~~~~~~~~~~~~~~~~~~~~~~~~~~~
AAA ACC TGA GCA TGT GTA GCT CAG ATC CTT ACC GCC GGT TTC GGT TCA TTC TAA TGA ATA
                            ocs
~~~~~~~~~~~~~~~~~~~~~~~~~~~~~~~~~~~~~~~~~~~~~~~~~~~~~~~~~~~~~~~~~~~~~~~~~~~~~~~
TAT CAC CCG TTA CTA TCG TAT TTT TAT GAA TAA TAT TCT CCG TTC AAT TTA CTG ATT GTA
                            ocs
~~~~~~~~~~~~~~~~~~~~~~~~~~~~~~~~~~~~~~~~~~~~~~~~~~~~~~~~~~~~~~~~~~~~~~~~~~~~~~~
CCC TAC TAC TTA TAT GTA CAA TAT TAA AAT GAA AAC AAT ATA TTG TGC TGA ATA GGT TTA
                            ocs
~~~~~~~~~~~~~~~~~~~~~~~~~~~~~~~~~~~~~~~~~~~~~~~~~~~~~~~~~~~~~~~~~~~~~~~~~~~~~~~
TAG CGA CAT CTA TGA TAG AGC GCC ACA ATA ACA AAC AAT TGC GTT TTA TTA TTA CAA ATC
                            ocs
~~~~~~~~~~~~~~~~~~~~~~~~~~~~~~~~~~~~~~~~~~~~~~~~~~~~~~~~~~~~~~~~~~~~~~~~~~~~~~~
CAA TTT TAA AAA AAG CGG CAG AAC CGG TCA AAC CTA AAA GAC TGA TTA CAT AAA TCT TAT
                            ocs
~~~~~~~~~~~~~~~~~~~~~~~~~~~~~~~~~~~~~~~~~~~~~~~~~~~~~~~~~~~~~~~~~~~~~~~~~~~~~~~
TCA AAT TTC AAA AGG CCC CAG GGG CTA GTA TCT ACG ACA CAC CGA GCG GCG AAC TAA TAA
                            ocs
~~~~~~~~~~~~~~~~~~~~~~~~~~~~~~~~~~~~~~~~~~~~~~~~~~~~~~~~~~~~~~~~~~~~~~~~~~~~~~~
CGT TCA CTG AAG GGA ACT CCG GTT CCC CGC CGG CGC GCA TGG GTG AGA TTC CTT GAA GTT
                            ocs
~~~~~~~~~~~~~~~~~~~~~~~~~~~~~~~~~~~~~~~~~~~~~~~~~~~~~~~~~~~~~~~~~~~~~~~~~~~~~~~
GAG TAT TGG CCG TCC GCT CTA CCG AAA GTT ACG GGC ACC ATT CAA CCC GGT CCA GCA CGG
                            ocs
~~~~~~~~~~~~~~~~~~~~~~~~~~~~~~~~~~~~~~~~~~~~~~~~~~~~~~~~~~~~~~~~~~~~~~~~~~~~~~~
CGG CCG GGT AAC CCA CTT GCT GCC CCG AGA ATT ATG CAG CAT TTT TTT GGT GTA TGT GGG
                            ocs
~~~~~~~~~~~~~~~~~~~~~~~~~~~~~~~~~~~~~~~~~~~~~~~~~~~~~~~~~~~~~~~~~~~~~~~~~~~~~~~
CCC CAA ATG AAG TGC AGG TCA AAC CTT GAC AGT GAC GAC AAA TCG TTG GGC GGG TCC AGG
                            ocs
~~~~~~~~~~~~~~~~~~~~~~~~~~~~~~~~~~~~~~~~~~~~~~~~~~~~~~~~~~~~~~~~~~~~~~~~~~~~~~~
GCG AAT TTT GCG ACA ACA TGT CGA GGC TCA GCA GGA CCT GCA GGC ATG CAA GCT AGC TTA
```

Figure 3 cont.

```
                    ocs
~~~~~~~~~~~~~~~~~~~~~~~~~~~~~~~~~~~~~~~~~~~~~~~~~~~~~~~~~~~~
CTA GTG ATG CAT ATT CTA TAG TGT CAC CTA AAT CT (SEQ ID NO:120)
```

Figure 3 cont.

CaMV 35S
~~~~~~~~~~~~~~~~~~~~~~~~~~~~~~~~~~~~~~~~
TCG ACG AAT TAA TTC CAA TCC CAC AAA AAT

CaMV 35S
~~~~~~~~~~~~~~~~~~~~~~~~~~~~~~~~~~~~~~~~~~~~~~~~~~~~~~~~~~~~~~~~~~~~~~~~~~~~~~~
CTG AGC TTA ACA GCA CAG TTG CTC CTC TCA GAG CAG AAT CGG GTA TTC AAC ACC CTC ATA

CaMV 35S
~~~~~~~~~~~~~~~~~~~~~~~~~~~~~~~~~~~~~~~~~~~~~~~~~~~~~~~~~~~~~~~~~~~~~~~~~~~~~~~
TCA ACT ACT ACG TTG TGT ATA ACG GTC CAC ATG CCG GTA TAT ACG ATG ACT GGG GTT GTA

CaMV 35S
~~~~~~~~~~~~~~~~~~~~~~~~~~~~~~~~~~~~~~~~~~~~~~~~~~~~~~~~~~~~~~~~~~~~~~~~~~~~~~~
CAA AGG CGG CAA CAA ACG GCG TTC CCG GAG TTG CAC ACA AGA AAT TTG CCA CTA TTA CAG

CaMV 35S
~~~~~~~~~~~~~~~~~~~~~~~~~~~~~~~~~~~~~~~~~~~~~~~~~~~~~~~~~~~~~~~~~~~~~~~~~~~~~~~
AGG CAA GAG CAG CAG CTG ACG CGT ACA CAA CAA GTC AGC AAA CAG ACA GGT TGA ACT TCA

CaMV 35S
~~~~~~~~~~~~~~~~~~~~~~~~~~~~~~~~~~~~~~~~~~~~~~~~~~~~~~~~~~~~~~~~~~~~~~~~~~~~~~~
TCC CCA AAG GAG AAG CTC AAC TCA AGC CCA AGA GCT TTG CTA AGG CCC TAA CAA GCC CAC

CaMV 35S
~~~~~~~~~~~~~~~~~~~~~~~~~~~~~~~~~~~~~~~~~~~~~~~~~~~~~~~~~~~~~~~~~~~~~~~~~~~~~~~
CAA AGC AAA AAG CCC ACT GGC TCA CGC TAG GAA CCA AAA GGC CCA GCA GTG ATC CAG CCC

CaMV 35S
~~~~~~~~~~~~~~~~~~~~~~~~~~~~~~~~~~~~~~~~~~~~~~~~~~~~~~~~~~~~~~~~~~~~~~~~~~~~~~~
CAA AAG AGA TCT CCT TTG CCC CGG AGA TTA CAA TGG ACG ATT TCC TCT ATC TTT ACG ATC

CaMV 35S
~~~~~~~~~~~~~~~~~~~~~~~~~~~~~~~~~~~~~~~~~~~~~~~~~~~~~~~~~~~~~~~~~~~~~~~~~~~~~~~
TAG GAA GGA AGT TCG AAG GTG AAG GTG ACG ACA CTA TGT TCA CCA CTG ATA ATG AGA AGG

CaMV 35S
~~~~~~~~~~~~~~~~~~~~~~~~~~~~~~~~~~~~~~~~~~~~~~~~~~~~~~~~~~~~~~~~~~~~~~~~~~~~~~~
TTA GCC TCT TCA ATT TCA GAA AGA ATG CTG ACC CAC AGA TGG TTA GAG AGG CCT ACG CAG

CaMV 35S
~~~~~~~~~~~~~~~~~~~~~~~~~~~~~~~~~~~~~~~~~~~~~~~~~~~~~~~~~~~~~~~~~~~~~~~~~~~~~~~
CAG GTC TCA TCA AGA CGA TCT ACC CGA GTA ACA ATC TCC AGG AGA TCA AAT ACC TTC CCA

CaMV 35S
~~~~~~~~~~~~~~~~~~~~~~~~~~~~~~~~~~~~~~~~~~~~~~~~~~~~~~~~~~~~~~~~~~~~~~~~~~~~~~~
AGA AGG TTA AAG ATG CAG TCA AAA GAT TCA GGA CTA ATT GCA TCA AGA ACA CAG AGA AAG

CaMV 35S
~~~~~~~~~~~~~~~~~~~~~~~~~~~~~~~~~~~~~~~~~~~~~~~~~~~~~~~~~~~~~~~~~~~~~~~~~~~~~~~
ACA TAT TTC TCA AGA TCA GAA GTA CTA TTC CAG TAT GGA CGA TTC AAG GCT TGC TTC ATA

CaMV 35S
~~~~~~~~~~~~~~~~~~~~~~~~~~~~~~~~~~~~~~~~~~~~~~~~~~~~~~~~~~~~~~~~~~~~~~~~~~~~~~~
AAC CAA GGC AAG TAA TAG AGA TTG GAG TCT CTA AAA AGG TAG TTC CTA CTG AAT CTA AGG

CaMV 35S
~~~~~~~~~~~~~~~~~~~~~~~~~~~~~~~~~~~~~~~~~~~~~~~~~~~~~~~~~~~~~~~~~~~~~~~~~~~~~~~
CCA TGC ATG GAG TCT AAG ATT CAA ATC GAG GAT CTA ACA GAA CTC GCC GTG AAG ACT GGC

Figure 4
~~~~~~~~~~~~~~~~~~~~~~~~~~~~~~~~~~~~~~~~~~~~~~~~~~~~~~~~~~~~~~~~~~~~~~~~~~~~~~~

```
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
GAA CAG TTC ATA CAG AGT CTT TTA CGA CTC AAT GAC AAG AAG AAA ATC TTC GTC AAC ATG
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
GTG GAG CAC GAC ACT CTG GTC TAC TCC AAA AAT GTC AAA GAT ACA GTC TCA GAA GAC CAA
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
AGG GCT ATT GAG ACT TTT CAA CAA AGG ATA ATT TCG GGA AAC CTC CTC GGA TTC CAT TGC
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
CCA GCT ATC TGT CAC TTC ATC GAA AGG ACA GTA GAA AAG GAA GGT GGC TCC TAC AAA TGC
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
CAT CAT TGC GAT AAA GGA AAG GCT ATC ATT CAA GAT CTC TCT GCC GAC AGT GGT CCC AAA
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
GAT GGA CCC CCA CCC ACG AGG AGC ATC GTG GAA AAA GAA GAC GTT CCA ACC ACG TCT TCA
                          CaMV 35S
~~~~~~~~~~~~~~~~~~~~~~~~~~~~~~~~~~~~~~~~~~~~~~~~~~~~~~~~~~~~~~~~~~~~~~~~~~~~~~~
AAG CAA GTG GAT TGA TGT GAC ATC TCC ACT GAC GTA AGG GAT GAC GCA CAA TCC CAC TAT
                         CaMV 35S
~~~~~~~~~~~~~~~~~~~~~~~~~~~~~~~~~~~~~~~~~~~~~~~~~~~~~~~~~~~~~~~~~~~~~~~~~
CCT TCG CAA GAC CCT TCC TCT ATA TAA GGA AGT TCA TTT CAT TTG GAG AGG ACA CGC TCG
                                  attB1
                          ~~~~~~~~~~~~~~~~~~~~~~~~~~~~
AGG AAT TCG GTA CCC CAT CAC AAG TTT GTA CAA AAA AGC AGG CTG CGG CCG CTT GCT CCC
                                  5' Oleo_3-1
                ~~~~~~~~~~~~~~~~~~~~~~~~~~~~~~~~~~~~~~~~~~~~~~~~~~~~~~~~~~~~~~~
            NcoI
           ~~~~~~~~
                M   A   C   H   Y   G   Q   Q   Q   Q   T   C   A   P   H   L
TTA AAA AAA ACC ATG GCA TGT CAT TAC GGA CAA CAG CAA CAG ACT TGT GCA CCT CAT CTT
                    5' Oleo_3-1
~~~~~~~~~~~~~~~~~~~~~~~~~~~~~~~~~~~~~~~~~~~~~~~~~~~~~~~~~~~~~~~~~~~~
                                                                         UBQ10
                                                                      ~~~~~~~~~~
 Q   L   Q   P   R   A   C   R   V   V   K   A   A   T   A   V   T  (SEQ ID NO:124)
CAG CTT CAA CCT AGA GCA TGT AGA GTT GTG AAG GCT GCT ACT GCT GTT ACT GTA AAT TTC
                           UBQ10
~~~~~~~~~~~~~~~~~~~~~~~~~~~~~~~~~~~~~~~~~~~~~~~~~~~~~~~~~~~~~~~~~~~~~~~~~~~~~~~
TGT GTT CCT TAT TCT CTC AAA ATC TTC GAT TTT GTT TTC GTT CGA TCC CAA TTT CGT ATA
                           UBQ10
~~~~~~~~~~~~~~~~~~~~~~~~~~~~~~~~~~~~~~~~~~~~~~~~~~~~~~~~~~~~~~~~~~~~~~~~~~~~~~~
TGT TCT TTG GTT TAG ATT CTG TTA ATC TTA GAT CGA AGA CGA TTT TCT GGG TTT GAT CGT
```

Figure 4 cont.

```
                       UBQ10
~~~~~~~~~~~~~~~~~~~~~~~~~~~~~~~~~~~~~~~~~~~~~~~~~~~~~~~~~~~~~~~~~~~~~~~~~~~~~~~
TAG ATA TCA TCT TAA TTC TCG ATT AGG GTT TCA TAG ATA TCA TCC GAT TTG TTC AAA TAA
                       UBQ10
~~~~~~~~~~~~~~~~~~~~~~~~~~~~~~~~~~~~~~~~~~~~~~~~~~~~~~~~~~~~~~~~~~~~~~~~~~~~~~~
TTT GAG TTT TGT CGA ATA ATT ACT CTT CGA TTT GTG ATT TCT ATC TAG ATC TGG TGT TAG
                                                                     3'Oleo_3-1
                                                                         ~~~~~~
                     UBQ10
~~~~~~~~~~~~~~~~~~~~~~~~~~~~~~~~~~~~~~~~~~~~~~~~~~~~~~~~~~~~~~~~~~~~~~~~~
                                                                         A   G
TTT CTA GTT TGT GCG ATC GAA TTT GTC GAT TAA TCT GAG TTT TTC TGA TTA ACA GGC TGG
                      3' Oleo_3-1
~~~~~~~~~~~~~~~~~~~~~~~~~~~~~~~~~~~~~~~~~~~~~~~~~~~~~~~~~~~~~~~~~~~~~~~~~~~~~~~
·G   S   L   L   V   L   S   G   L   T   L   A   G   T   V   I   A   L   T   I
AGG ATC TCT TCT TGT TCT CTC TGG ACT TAC TCT CGC TGG AAC TGT TAT CGC TCT CAC TAT
                      3' Oleo_3-1
~~~~~~~~~~~~~~~~~~~~~~~~~~~~~~~~~~~~~~~~~~~~~~~~~~~~~~~~~~~~~~~~~~~~~~~~~~~~~~~
·A   T   P   L   L   V   I   F   S   P   V   L   V   P   A   V   I   T   I   F
CGC TAC ACC TCT TCT CGT TAT CTT CTC TCC TGT TCT CGT TCC TGC TGT GAT CAC TAT CTT
                      3' Oleo_3-1
~~~~~~~~~~~~~~~~~~~~~~~~~~~~~~~~~~~~~~~~~~~~~~~~~~~~~~~~~~~~~~~~~~~~~~~~~~~~~~~
·L   L   G   A   G   F   L   A   S   G   G   F   G   V   A   A   L   S   V   L
CCT TCT CGG AGC TGG ATT TCT TGC TTC TGG TGG ATT TGG AGT TGC TGC TCT CTC TGT TCT
                      3' Oleo_3-1
~~~~~~~~~~~~~~~~~~~~~~~~~~~~~~~~~~~~~~~~~~~~~~~~~~~~~~~~~~~~~~~~~~~~~~~~~~~~~~~
·S   W   I   Y   R   Y   L   T   G   K   H   P   P   G   A   D   Q   L   E   S
CTC TTG GAT CTA CAG ATA CCT CAC TGG AAA ACA TCC TCC AGG TGC TGA TCA ACT TGA GTC
                      3' Oleo_3-1
~~~~~~~~~~~~~~~~~~~~~~~~~~~~~~~~~~~~~~~~~~~~~~~~~~~~~~~~~~~~~~~~~~~~~~~~~~~~~~~
·A   K   T   K   L   A   S   K   A   R   E   M   K   D   R   A   E   Q   F   S
TGC TAA GAC TAA GCT CGC TTC TAA GGC TAG AGA GAT GAA GGA TAG AGC AGA GCA ATT CTC
           3' Oleo_3-1                                       OCS terminator
~~~~~~~~~~~~~~~~~~~~~~~~~~~~~~~~~~~~~~~~~~~~~~~~~~~        ~~~~~~~~~~~~~~~~~~~~~
·C   Q   P   V   A   C   S   Q   T   S   (SEQ ID NO:125)
TTG TCA GCC TGT TGC TGG ATC TCA GAC TTC TTA ATG AAC ATA TGG TCC TGC TTT AAT GAG
                       OCS terminator
~~~~~~~~~~~~~~~~~~~~~~~~~~~~~~~~~~~~~~~~~~~~~~~~~~~~~~~~~~~~~~~~~~~~~~~~~~~~~~~
ATA TGC GAG ACG CCT ATG ATC GCA TGA TAT TTG CTT TCA ATT CTG TTG TGC ACG TTG TAA
                       OCS terminator
~~~~~~~~~~~~~~~~~~~~~~~~~~~~~~~~~~~~~~~~~~~~~~~~~~~~~~~~~~~~~~~~~~~~~~~~~~~~~~~
AAA ACC TGA GCA TGT GTA GCT CAG ATC CTT ACC GCC GGT TTC GGT TCA TTC TAA TGA ATA
                       OCS terminator
~~~~~~~~~~~~~~~~~~~~~~~~~~~~~~~~~~~~~~~~~~~~~~~~~~~~~~~~~~~~~~~~~~~~~~~~~~~~~~~
TAT CAC CCG TTA CTA TCG TAT TTT TAT GAA TAA TAT TCT CCG TTC AAT TTA CTG ATT GTA
```

Figure 4 cont.

```
                      OCS terminator
~~~~~~~~~~~~~~~~~~~~~~~~~~~~~~~~~~~~~~~~~~~~~~~~~~~~~~~~~~~~~~~~~~~~~~~~~~~~~~
CCC TAC TAC TTA TAT GTA CAA TAT TAA AAT GAA AAC AAT ATA TTG TGC TGA ATA GGT TTA
                      OCS terminator
~~~~~~~~~~~~~~~~~~~~~~~~~~~~~~~~~~~~~~~~~~~~~~~~~~~~~~~~~~~~~~~~~~~~~~~~~~~~~~
TAG CGA CAT CTA TGA TAG AGC GCC ACA ATA ACA AAC AAT TGC GTT TTA TTA TTA CAA ATC
                      OCS terminator
~~~~~~~~~~~~~~~~~~~~~~~~~~~~~~~~~~~~~~~~~~~~~~~~~~~~~~~~~~~~~~~~~~~~~~~~~~~~~~
CAA TTT TAA AAA AAG CGG CAG AAC CGG TCA AAC CTA AAA GAC TGA TTA CAT AAA TCT TAT
                      OCS terminator
~~~~~~~~~~~~~~~~~~~~~~~~~~~~~~~~~~~~~~~~~~~~~~~~~~~~~~~~~~~~~~~~~~~~~~~~~~~~~~
TCA AAT TTC AAA AGG CCC CAG GGG CTA GTA TCT ACG ACA CAC CGA GCG GCG AAC TAA TAA
                      OCS terminator
~~~~~~~~~~~~~~~~~~~~~~~~~~~~~~~~~~~~~~~~~~~~~~~~~~~~~~~~~~~~~~~~~~~~~~~~~~~~~~
CGT TCA CTG AAG GGA ACT CCG GTT CCC CGC CGG CGC GCA TGG GTG AGA TTC CTT GAA GTT
                      OCS terminator
~~~~~~~~~~~~~~~~~~~~~~~~~~~~~~~~~~~~~~~~~~~~~~~~~~~~~~~~~~~~~~~~~~~~~~~~~~~~~~
GAG TAT TGG CCG TCC GCT CTA CCG AAA GTT ACG GGC ACC ATT CAA CCC GGT CCA GCA CGG
                      OCS terminator
~~~~~~~~~~~~~~~~~~~~~~~~~~~~~~~~~~~~~~~~~~~~~~~~~~~~~~~~~~~~~~~~~~~~~~~~~~~~~~
CGG CCG GGT AAC CGA CTT GCT GCC CCG AGA ATT ATG CAG CAT TTT TTT GGT GTA TGT GGG
                      OCS terminator
~~~~~~~~~~~~~~~~~~~~~~~~~~~~~~~~~~~~~~~~~~~~~~~~~~~~~~~~~~~~~~~~~~~~~~~~~~~~~~
CCC CAA ATG AAG TGC AGG TCA AAC CTT GAC AGT GAC GAC AAA TCG TTG GGC GGG TCC AGG
                      OCS terminator
~~~~~~~~~~~~~~~~~~~~~~~~~~~~~~~~~~~~~~~~~~~~~~~~~~~~~~~~~~~~~~~~~~~~~~~~~~~~~~
GCG AAT TTT GCG ACA ACA TGT CGA GGC TCA GCA GGA CCT GCA GGC ATG CAA GCT AGC TTA
             OCS terminator
~~~~~~~~~~~~~~~~~~~~~~~~~~~~~~~~~~~~~~~~~~~~~
                                                       CaMV35S
                                             ~~~~~~~~~~~~~~~~~~~~~~~~~~~~~~~~~
CTA GTG ATG CAT ATT CTA TAG TGT CAC CTA AAT CTT CGA CGA ATT AAT TCC AAT CCC ACA
                         CaMV35S
~~~~~~~~~~~~~~~~~~~~~~~~~~~~~~~~~~~~~~~~~~~~~~~~~~~~~~~~~~~~~~~~~~~~~~~~~~~~~~
AAA ATC TGA GCT TAA CAG CAC AGT TGC TCC TCT CAG AGC AGA ATC GGG TAT TCA ACA CCC
                         CaMV35S
~~~~~~~~~~~~~~~~~~~~~~~~~~~~~~~~~~~~~~~~~~~~~~~~~~~~~~~~~~~~~~~~~~~~~~~~~~~~~~
TCA TAT CAA CTA CTA CGT TGT GTA TAA CGG TCC ACA TGC CGG TAT ATA CGA TGA CTG GGG
                         CaMV35S
~~~~~~~~~~~~~~~~~~~~~~~~~~~~~~~~~~~~~~~~~~~~~~~~~~~~~~~~~~~~~~~~~~~~~~~~~~~~~~
TTG TAC AAA GGC GGC AAC AAA CGG CGT TCC CGG AGT TGC ACA CAA GAA ATT TGC CAC TAT
                         CaMV35S
~~~~~~~~~~~~~~~~~~~~~~~~~~~~~~~~~~~~~~~~~~~~~~~~~~~~~~~~~~~~~~~~~~~~~~~~~~~~~~
TAC AGA GGC AAG AGC AGC AGC TGA CGC GTA CAC AAC AAG TCA GCA AAC AGA CAG GTT GAA
                         CaMV35S
```

Figure 4 cont.

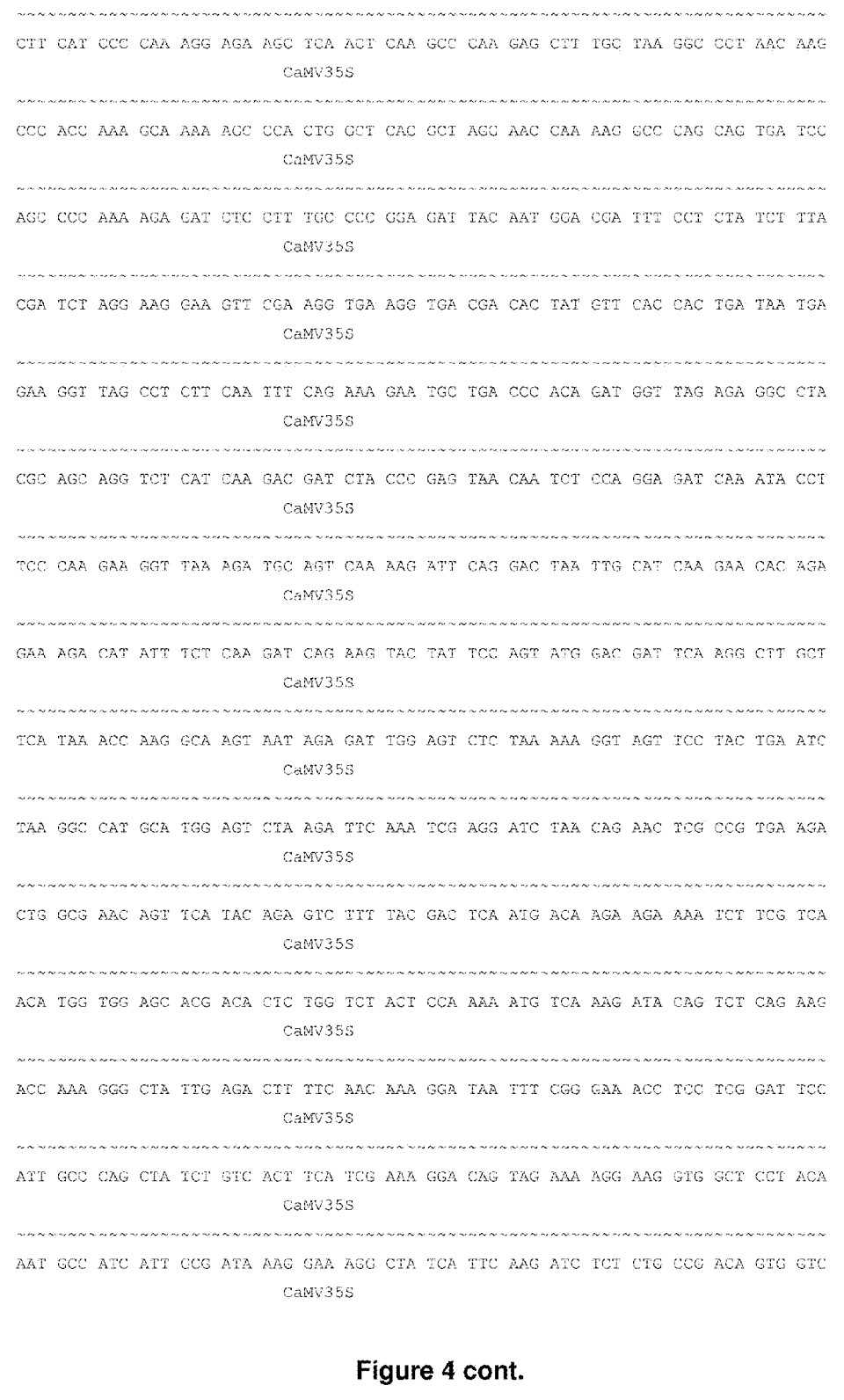

CTT CAT CCC CAA AGG AGA AGC TCA ACT CAA GCC CAA GAG CTT TGC TAA GGC CCT AAC AAG
CaMV35S

CCC ACC AAA GCA AAA AGC CCA CTG GCT CAC GCT AGC AAC CAA AAG GCC CAG CAG TGA TCC
CaMV35S

AGC CCC AAA AGA GAT CTC CTT TGC CCC GGA GAT TAC AAT GGA CGA TTT CCT CTA TCT TTA
CaMV35S

CGA TCT AGG AAG GAA GTT CGA AGG TGA AGG TGA CGA CAC TAT GTT CAC CAC TGA TAA TGA
CaMV35S

GAA GGT TAG CCT CTT CAA TTT CAG AAA GAA TGC TGA CCC ACA GAT GGT TAG AGA GGC CTA
CaMV35S

CGC AGC AGG TCT CAT CAA GAC GAT CTA CCC GAG TAA CAA TCT CCA GGA GAT CAA ATA CCT
CaMV35S

TCC CAA GAA GGT TAA AGA TGC AGT CAA AAG ATT CAG GAC TAA TTG CAT CAA GAA CAC AGA
CaMV35S

GAA AGA CAT ATT TCT CAA GAT CAG AAG TAC TAT TCC AGT ATG GAC GAT TCA AGG CTT GCT
CaMV35S

TCA TAA ACC AAG GCA AGT AAT AGA GAT TGG AGT CTC TAA AAA GGT AGT TCC TAC TGA ATC
CaMV35S

TAA GGC CAT GCA TGG AGT CTA AGA TTC AAA TCG AGG ATC TAA CAG AAC TCG CCG TGA AGA
CaMV35S

CTG GCG AAC AGT TCA TAC AGA GTC TTT TAC GAC TCA ATG ACA AGA AGA AAA TCT TCG TCA
CaMV35S

ACA TGG TGG AGC ACG ACA CTC TGG TCT ACT CCA AAA ATG TCA AAG ATA CAG TCT CAG AAG
CaMV35S

ACC AAA GGG CTA TTG AGA CTT TTC AAC AAA GGA TAA TTT CGG GAA ACC TCC TCG GAT TCC
CaMV35S

ATT GCC CAG CTA TCT GTC ACT TCA TCG AAA GGA CAG TAG AAA AGG AAG GTG GCT CCT ACA
CaMV35S

AAT GCC ATC ATT GCG ATA AAG GAA AGG CTA TCA TTC AAG ATC TCT CTG CCG ACA GTG GTC
CaMV35S

Figure 4 cont.

```
~~~~~~~~~~~~~~~~~~~~~~~~~~~~~~~~~~~~~~~~~~~~~~~~~~~~~~~~~~~~~~~~~~~~~~~~~~~~~~~~
CCA AAG ATG GAC CCC CAC CCA CGA GGA GCA TCG TGG AAA AAG AAG ACG TTC CAA CCA CGT
                          CaMV35S
~~~~~~~~~~~~~~~~~~~~~~~~~~~~~~~~~~~~~~~~~~~~~~~~~~~~~~~~~~~~~~~~~~~~~~~~~~~~~~~~
CTT CAA AGC AAG TGG ATT GAT GTG ACA TCT CCA CTG ACG TAA GGG ATG ACG CAC AAT CCC
                          CaMV35S
~~~~~~~~~~~~~~~~~~~~~~~~~~~~~~~~~~~~~~~~~~~~~~~~~~~~~~~~~~~~~~~~~~~~~~~~~~~~~~~~
ACT ATC CTT CGC AAG ACC CTT CCT CTA TAT AAG GAA GTT CAT TTC ATT TGG AGA GGA CAC
CaMV35S                                     5' DGAT1 (S205A)
~                                    ~~~~~~~~~~~~~~~~~~~~~~~~~~~~~~~~~~~~~~~~~~~
                                 NcoI
                                ~~~~~~~~
                                    M   A   I   L   D   S   A   G   V   T   T
GGG ATC CTT GCT CCG TTA AAA AAA ACC ATG GCT ATC CTC GAT TCT GCT GGT GTT ACT ACT
                    5' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
 V   T   E   N   G   G   G   E   F   V   D   L   D   R   L   R   R   R   K   S
GTG ACT GAG AAT GGT GGT GGA GAG TTC GTT GAT CTC GAT AGA CTC AGA AGA AGA AAG TCT
5' DGAT1 (S205A)
~~~~~~~~
                              UBQ10
        ~~~~~~~~~~~~~~~~~~~~~~~~~~~~~~~~~~~~~~~~~~~~~~~~~~~~~~~~~~~~~~~~~~~~~~~~
 R   S  (SEQ ID NO:115)
AGA TCT GTA AAT TTC TGT GTT CCT TAT TCT CTC AAA ATC TTC GAT TTT GTT TTC GTT CGA
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
TCC CAA TTT CGT ATA TGT TCT TTG GTT TAG ATT CTG TTA ATC TTA GAT CGA AGA CGA TTT
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
TCT GGG TTT GAT CGT TAG ATA TCA TCT TAA TTC TCG ATT AGG GTT TCA TAG ATA TCA TCC
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
GAT TTG TTC AAA TAA TTT GAG TTT TGT CGA ATA ATT ACT CTT CGA TTT GTG ATT TCT ATC
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
TAG ATC TGG TGT TAG TTT CTA GTT TGT GCG ATC GAA TTT GTC GAT TAA TCT GAG TTT TTC
  UBQ10
~~~~~~~~~~~~~
                             3' DGAT1 (S205A)
             ~~~~~~~~~~~~~~~~~~~~~~~~~~~~~~~~~~~~~~~~~~~~~~~~~~~~~~~~~~~~~~~~~~
             D   S   S   N   G   L   L   L   S   G   S   D   N   N   S   P   S
TGA TTA ACA GGA TTC TTC TAA CGG ACT TCT CCT CTC TGG ATC TGA TAA CAA CTC TCC TTC
                    3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
·D   D   V   G   A   P   A   D   V   R   D   R   I   D   S   V   V   N   D   D
```

Figure 4 cont.

TGA TGA TGT TGG TGC TCC TGC TGA TGT GAG AGA TAG AAT CGA TTC TGT GGT GAA CGA TGA
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
· A Q G T A N L A G D N N G G G D N N G G
TGC TCA AGG TAC TGC TAA CCT CGC TGG TGA TAA TAA CGG TGG AGG TGA TAA CAA TGG TGG
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
· G R G G G E G R G N A D A T F T Y R P S
AGG AAG AGG TGG AGG TGA AGG TAG AGG AAA CGC TGA TGC TAC TTT CAC TTA CAG ACC ATC
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
· V P A H R R A R E S P L S S D A I F K Q
TGT GCC TGC TCA TAG AAG AGC TAG AGA GTC TCC TCT CTC TTC TGA TGC TAT CTT CAA GCA
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
· S H A G L F N L C V V V L I A V N S R L
GTC TCA CGC TGG ACT TTT CAA CCT CTG TGT GGT GGT TCT TAT CGC TGT GAA CTC TAG ACT
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
· I I E N L M K Y G W L I R T D F W F S S
CAT CAT CGA GAA CCT CAT GAA GTA CGG ATG GCT CAT CAG AAC TGA TTT CTG GTT CTC TTC
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
· R S L R D W P L F M C C I S L S I F P L
TAG ATC TCT CAG ACA TTG GCC TCT TTT CAT GTG CTG CAT CTC ACT CTC AAT CTT CCC TCT
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
· A A F T V E K L V L Q K Y I A E P V V I
CGC TGC TTT TAC TGT TGA GAA GCT CGT GCT CCA GAA GTA TAT CGC TGA ACC TGT GGT GAT
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
· F L H I I I T M T E V L Y P V Y V T L R
CTT CCT CCA CAT CAT CAT CAC TAT GAC TGA GGT TCT CTA CCC TGT TTA CGT GAC TCT CAG
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
· C D S A F L S G V T L M L L T C I V W L
ATG CGA TTC TGC TTT CCT CTC TGG TGT TAC TCT TAT GCT CCT CAC TTG CAT TGT GTG GCT
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
· K L V S Y A H T S Y D I R S L A N A A D
TAA GCT CGT GTC TTA CGC TCA CAC TTC TTA CGA TAT CAG ATC TCT CGC TAA CGC TGC TGA
3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
· K A N P E V S Y Y V S L K S L A Y F M V
TAA GGC TAA CCC TGA AGT GTC TTA CTA CGT GTC TCT CAA GTC TCT CGC TTA CTT CAT GGT

Figure 4 cont.
~~~~~~~~~~~~~~~~~~~~~~~~~~~~~~~~~~~~~~~~~~~~~~~~~~~~~~~~~~~~~~~~~~~~~~~~~~~~~~~~

```
                    3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
·A   P   T   L   C   Y   Q   P   S   Y   P   R   S   A   C   I   R   K   G   W
TGC TCC TAC ACT TTG TTA CCA GCC ATC TTA CCC TAG ATC TGC TTG CAT TAG AAA GGG ATG
                    3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
·V   A   R   Q   F   A   K   L   V   I   F   T   G   F   M   G   F   I   I   E
GGT GGC AAG ACA ATT CGC TAA GTT GGT GAT CTT CAC TGG ATT CAT GGG ATT CAT CAT CGA
                    3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
·Q   Y   I   N   P   I   V   R   N   S   K   H   P   L   K   G   D   L   L   Y
GCA GTA CAT CAA CCC TAT TGT GAG AAA CTC TAA GCA CCC TCT CAA GGG TGA TCT TCT CTA
                    3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
·A   I   E   R   V   L   K   L   S   V   P   N   L   Y   V   W   L   C   M   F
CGC TAT CGA GAG AGT TCT TAA GCT CTC TGT GCC TAA CCT TTA TGT GTG GCT CTG CAT GTT
                    3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
·Y   C   F   F   H   L   W   L   N   I   L   A   E   L   L   C   F   G   D   R
CTA CTG TTT CTT CCA CCT CTG GCT TAA CAT CCT TGC TGA GTT GCT TTG CTT CGG AGA TAG
                    3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
·E   F   Y   K   D   W   W   N   A   K   S   V   G   D   Y   W   R   M   W   N
AGA GTT CTA CAA GGA TTG GTG GAA CGC TAA GTC TGT TGG AGA TTA TTG GAG AAT GTG GAA
                    3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
·M   P   V   H   K   W   M   V   R   H   I   Y   F   P   C   L   R   S   K   I
CAT GCC TGT GCA TAA GTG GAT GGT GCG TCA CAT CTA CTT CCC TTG CCT CAG ATC TAA GAT
                    3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
·P   K   T   L   A   I   I   I   A   F   L   V   S   A   V   F   H   E   L   C
CCC TAA GAC TCT CGC TAT CAT TAT CGC TTT CCT CGT GTC TGC TGT TTT CCA TGA GTT GTG
                    3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
·I   A   V   P   C   R   L   F   K   L   W   A   F   L   G   I   M   F   Q   V
TAT CGC TGT TCC TTG CAG ACT TTT CAA GCT TTG GGC TTT CCT CGG AAT CAT GTT CCA GGT
                    3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
·P   L   V   F   I   T   N   Y   L   Q   E   R   F   G   S   T   V   G   N   M
TCC ACT CGT GTT CAT CAC TAA CTA CCT CCA AGA GAG ATT CGG ATC TAC TGT TGG AAA CAT
                    3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~
·I   F   W   F   I   F   C   I   F   G   Q   P   M   C   V   L   L   Y   Y   H
CAT TTT CTG GTT CAT TTT CTG CAT CTT CGG ACA GCC TAT GTG CGT TCT CCT CTA CTA CCA
            3' DGAT1 (S205A)
```

Figure 4 cont.

```
~~~~~~~~~~~~~~~~~~~~~~~~~~~~~~~~~~~~~~~~~~~~~~~~~~~~~~~~~~~~
· D   L   M   N   R   K   G   S   M   S   (SEQ ID NO:116)
CGA TCT CAT GAA CAG AAA GGG ATC TAT GTC TTA ATG AAG GAT CCA CCC AGC TTT CTT GTA
                                                                attB2
                                                                ocs
                                                             ~~~~~~~~~~~~~~~~~~~
CAA AGT GGT GAT GGG TTC GAA ATC GAT AAG CTT GGA TCC TCT AGA GTC CTG CTT TAA TGA
~~~~~~~~~~
 attB2
                                   ocs
~~~~~~~~~~~~~~~~~~~~~~~~~~~~~~~~~~~~~~~~~~~~~~~~~~~~~~~~~~~~~~~~~~~~~~~~~~~~~~~
GAT ATG CGA GAC GCC TAT GAT CGC ATG ATA TTT GCT TTC AAT TCT GTT GTG CAC GTT GTA
                                   ocs
~~~~~~~~~~~~~~~~~~~~~~~~~~~~~~~~~~~~~~~~~~~~~~~~~~~~~~~~~~~~~~~~~~~~~~~~~~~~~~~
AAA AAC CTG AGC ATG TGT AGC TCA GAT CCT TAC CGC CGG TTT CGG TTC ATT CTA ATG AAT
                                   ocs
~~~~~~~~~~~~~~~~~~~~~~~~~~~~~~~~~~~~~~~~~~~~~~~~~~~~~~~~~~~~~~~~~~~~~~~~~~~~~~~
ATA TCA CCC GTT ACT ATC GTA TTT TTA TGA ATA ATA TTC TCC GTT CAA TTT ACT GAT TGT
                                   ocs
~~~~~~~~~~~~~~~~~~~~~~~~~~~~~~~~~~~~~~~~~~~~~~~~~~~~~~~~~~~~~~~~~~~~~~~~~~~~~~~
ACC CTA CTA CTT ATA TGT ACA ATA TTA AAA TGA AAA CAA TAT ATT GTG CTG AAT AGG TTT
                                   ocs
~~~~~~~~~~~~~~~~~~~~~~~~~~~~~~~~~~~~~~~~~~~~~~~~~~~~~~~~~~~~~~~~~~~~~~~~~~~~~~~
ATA GCG ACA TCT ATG ATA GAG CGC CAC AAT AAC AAA CAA TTG CGT TTT ATT ATT ACA AAT
                                   ocs
~~~~~~~~~~~~~~~~~~~~~~~~~~~~~~~~~~~~~~~~~~~~~~~~~~~~~~~~~~~~~~~~~~~~~~~~~~~~~~~
CCA ATT TTA AAA AAA GCG GCA GAA CCG GTC AAA CCT AAA AGA CTG ATT ACA TAA ATC TTA
                                   ocs
~~~~~~~~~~~~~~~~~~~~~~~~~~~~~~~~~~~~~~~~~~~~~~~~~~~~~~~~~~~~~~~~~~~~~~~~~~~~~~~
TTC AAA TTT CAA AAG GCC CCA GGG GCT AGT ATC TAC GAC ACA CCG AGC GGC GAA CTA ATA
                                   ocs
~~~~~~~~~~~~~~~~~~~~~~~~~~~~~~~~~~~~~~~~~~~~~~~~~~~~~~~~~~~~~~~~~~~~~~~~~~~~~~~
ACG TTC ACT GAA GGG AAC TCC GGT TCC CCG CCG GCG CGC ATG GGT GAG ATT CCT TGA AGT
                                   ocs
~~~~~~~~~~~~~~~~~~~~~~~~~~~~~~~~~~~~~~~~~~~~~~~~~~~~~~~~~~~~~~~~~~~~~~~~~~~~~~~
TGA GTA TTG GCC GTC CGC TCT ACC GAA AGT TAC GGG CAC CAT TCA ACC CGG TCC AGC ACG
                                   ocs
~~~~~~~~~~~~~~~~~~~~~~~~~~~~~~~~~~~~~~~~~~~~~~~~~~~~~~~~~~~~~~~~~~~~~~~~~~~~~~~
GCG GCC GGG TAA CCG ACT TGC TGC CCC GAG AAT TAT GCA GCA TTT TTT TGG TGT ATG TGG
                                   ocs
~~~~~~~~~~~~~~~~~~~~~~~~~~~~~~~~~~~~~~~~~~~~~~~~~~~~~~~~~~~~~~~~~~~~~~~~~~~~~~~
GCC CCA AAT GAA GTG CAG GTC AAA CCT TGA CAG TGA CGA CAA ATC GTT GGG CGG GTC CAG
                                   ocs
~~~~~~~~~~~~~~~~~~~~~~~~~~~~~~~~~~~~~~~~~~~~~~~~~~~~~~~~~~~~~~~~~~~~~~~~~~~~~~~
GGC GAA TTT TGC GAC AAC ATG TCG AGG CTC AGC AGG ACC TGC AGG CAT GCA AGC TAG CTT
```

Figure 4 cont.

ocs
~~~~~~~~~~~~~~~~~~~~~~~~~~~~~~~~~~~~~~~~~~~~~~~~

ACT AGT GAT GCA TAT TCT ATA GTG TCA CCT AAA TCT (SEQ ID NO:123)

Figure 4 cont.
~~~~~~~~~~~~~~~~~~~~~~~~~~~~~~~~~~~~~~~~~~~~~~~~

```
                                         CaMV 35S
                                   ~~~~~~~~~~~~~~~~~~~~~~~~~~~~~~~~~~~~~~~~~
                                   T CGA CGA ATT AAT TCC AAT CCC ACA AAA ATC
                    CaMV 35S
~~~~~~~~~~~~~~~~~~~~~~~~~~~~~~~~~~~~~~~~~~~~~~~~~~~~~~~~~~~~~~~~~~~~~~~~~~~~~~~
TGA GCT TAA CAG CAC AGT TGC TCC TCT CAG AGC AGA ATC GGG TAT TCA ACA CCC TCA TAT
                    CaMV 35S
~~~~~~~~~~~~~~~~~~~~~~~~~~~~~~~~~~~~~~~~~~~~~~~~~~~~~~~~~~~~~~~~~~~~~~~~~~~~~~~
CAA CTA CTA CGT TGT GTA TAA CGG TCC ACA TGC CGG TAT ATA CGA TGA CTG GGG TTG TAC
                    CaMV 35S
~~~~~~~~~~~~~~~~~~~~~~~~~~~~~~~~~~~~~~~~~~~~~~~~~~~~~~~~~~~~~~~~~~~~~~~~~~~~~~~
AAA GGC GGC AAC AAA CGG CGT TCC CGG AGT TGC ACA CAA GAA ATT TGC CAC TAT TAC AGA
                    CaMV 35S
~~~~~~~~~~~~~~~~~~~~~~~~~~~~~~~~~~~~~~~~~~~~~~~~~~~~~~~~~~~~~~~~~~~~~~~~~~~~~~~
GGC AAG AGC AGC AGC TGA CGC GTA CAC AAC AAG TCA GCA AAC AGA CAG GTT GAA CTT CAT
                    CaMV 35S
~~~~~~~~~~~~~~~~~~~~~~~~~~~~~~~~~~~~~~~~~~~~~~~~~~~~~~~~~~~~~~~~~~~~~~~~~~~~~~~
CCC CAA AGG AGA AGC TCA ACT CAA GCC CAA GAG CTT TGC TAA GGC CCT AAC AAG CCC ACC
                    CaMV 35S
~~~~~~~~~~~~~~~~~~~~~~~~~~~~~~~~~~~~~~~~~~~~~~~~~~~~~~~~~~~~~~~~~~~~~~~~~~~~~~~
AAA GCA AAA AGC CCA CTG GCT CAC GCT AGG AAC CAA AAG GCC CAG CAG TGA TCC AGC CCC
                    CaMV 35S
~~~~~~~~~~~~~~~~~~~~~~~~~~~~~~~~~~~~~~~~~~~~~~~~~~~~~~~~~~~~~~~~~~~~~~~~~~~~~~~
AAA AGA GAT CTC CTT TGC CCC GGA GAT TAC AAT GGA CGA TTT CCT CTA TCT TTA CGA TCT
                    CaMV 35S
~~~~~~~~~~~~~~~~~~~~~~~~~~~~~~~~~~~~~~~~~~~~~~~~~~~~~~~~~~~~~~~~~~~~~~~~~~~~~~~
AGG AAG GAA GTT CGA AGG TGA AGG TGA CGA CAC TAT GTT CAC CAC TGA TAA TGA GAA GGT
                    CaMV 35S
~~~~~~~~~~~~~~~~~~~~~~~~~~~~~~~~~~~~~~~~~~~~~~~~~~~~~~~~~~~~~~~~~~~~~~~~~~~~~~~
TAG CCT CTT CAA TTT CAG AAA GAA TGC TGA CCC ACA GAT GGT TAG AGA GGC CTA CGC AGC
                    CaMV 35S
~~~~~~~~~~~~~~~~~~~~~~~~~~~~~~~~~~~~~~~~~~~~~~~~~~~~~~~~~~~~~~~~~~~~~~~~~~~~~~~
AGG TCT CAT CAA GAC GAT CTA CCC GAG TAA CAA TCT CCA GGA GAT CAA ATA CCT TCC CAA
                    CaMV 35S
~~~~~~~~~~~~~~~~~~~~~~~~~~~~~~~~~~~~~~~~~~~~~~~~~~~~~~~~~~~~~~~~~~~~~~~~~~~~~~~
GAA GGT TAA AGA TGC AGT CAA AAG ATT CAG GAC TAA TTG CAT CAA GAA CAC AGA GAA AGA
                    CaMV 35S
~~~~~~~~~~~~~~~~~~~~~~~~~~~~~~~~~~~~~~~~~~~~~~~~~~~~~~~~~~~~~~~~~~~~~~~~~~~~~~~
CAT ATT TCT CAA GAT CAG AAG TAC TAT TCC AGT ATG GAC GAT TCA AGG CTT GCT TCA TAA
                    CaMV 35S
~~~~~~~~~~~~~~~~~~~~~~~~~~~~~~~~~~~~~~~~~~~~~~~~~~~~~~~~~~~~~~~~~~~~~~~~~~~~~~~
ACC AAG GCA AGT AAT AGA GAT TGG AGT CTC TAA AAA GGT AGT TCC TAC TGA ATC TAA GGC
                    CaMV 35S
~~~~~~~~~~~~~~~~~~~~~~~~~~~~~~~~~~~~~~~~~~~~~~~~~~~~~~~~~~~~~~~~~~~~~~~~~~~~~~~
CAT GCA TGG AGT CTA AGA TTC AAA TCG AGG ATC TAA CAG AAC TCG CCG TGA AGA CTG GCG
```

Figure 5

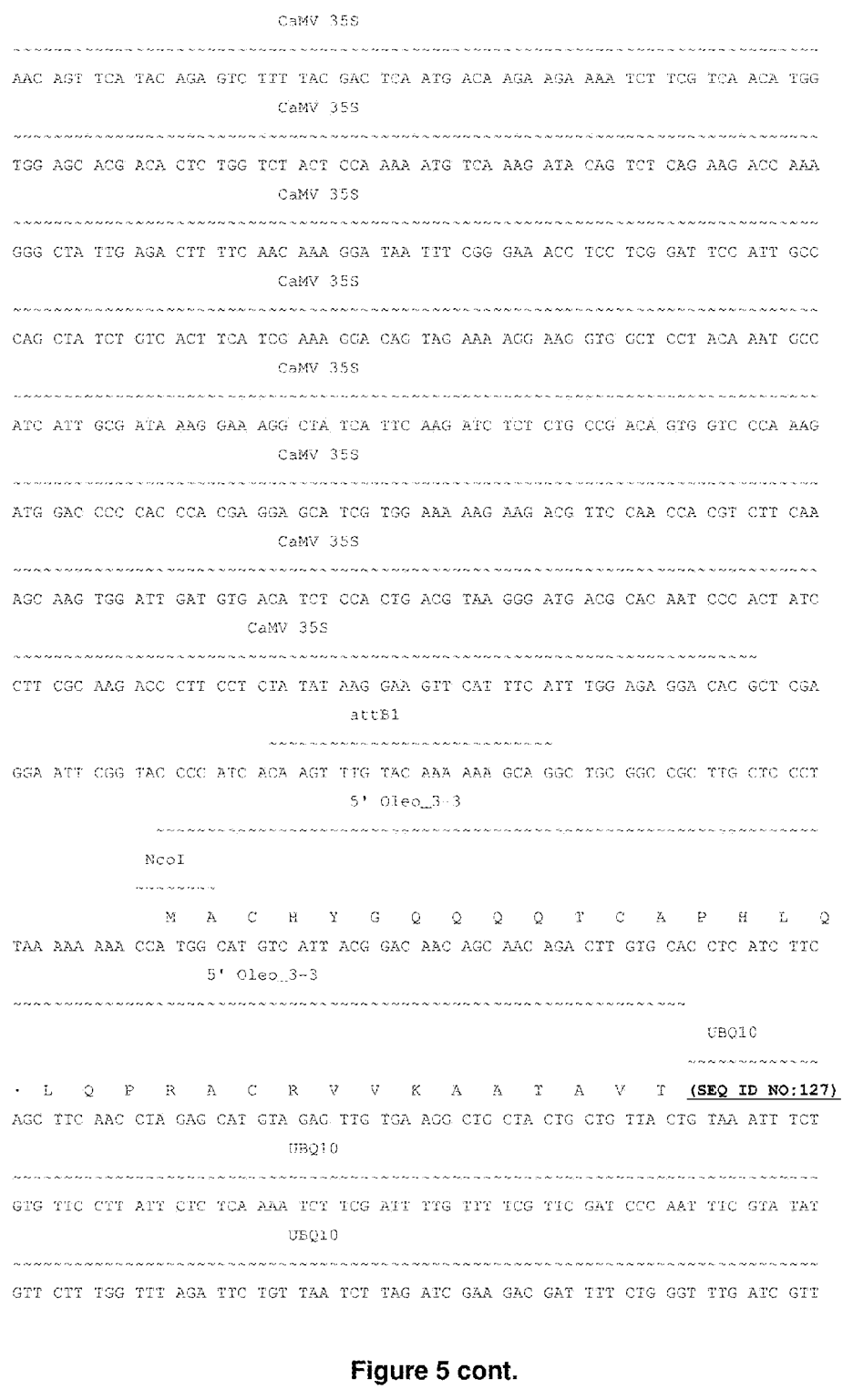

CaMV 35S

AAC AGT TCA TAC AGA GTC TTT TAC GAC TCA ATG ACA AGA AGA AAA TCT TCG TCA ACA TGG

CaMV 35S

TGG AGC ACG ACA CTC TGG TCT ACT CCA AAA ATG TCA AAG ATA CAG TCT CAG AAG ACC AAA

CaMV 35S

GGG CTA TTG AGA CTT TTC AAC AAA GGA TAA TTT CGG GAA ACC TCC TCG GAT TCC ATT GCC

CaMV 35S

CAG CTA TCT GTC ACT TCA TCG AAA GGA CAG TAG AAA AGG AAG GTG GCT CCT ACA AAT GCC

CaMV 35S

ATC ATT GCG ATA AAG GAA AGG CTA TCA TTC AAG ATC TCT CTG CCG ACA GTG GTC CCA AAG

CaMV 35S

ATG GAC CCC CAC CCA CGA GGA GCA TCG TGG AAA AAG AAG ACG TTC CAA CCA CGT CTT CAA

CaMV 35S

AGC AAG TGG ATT GAT GTG ACA TCT CCA CTG ACG TAA GGG ATG ACG CAC AAT CCC ACT ATC

CaMV 35S

CTT CGC AAG ACC CTT CCT CTA TAT AAG GAA GTT CAT TTC ATT TGG AGA GGA CAC GCT CGA attB1

GGA ATT CGG TAC CCC ATC ACA AGT TTG TAC AAA AAA GCA GGC TGC GGC CGC TTG CTC CCT

5' Oleo_3-3

NcoI

M A C H Y G Q Q Q Q T C A P H L Q

TAA AAA AAA CCA TGG CAT GTC ATT ACG GAC AAC AGC AAC AGA CTT GTG CAC CTC ATC TTC

5' Oleo_3-3

UBQ10

· L Q P R A C R V V K A A T A V T (SEQ ID NO:127)

AGC TTC AAC CTA GAG CAT GTA GAC TTG TGA AGG CTC CTA CTG CTG TTA CTG TAA ATT TCT

UBQ10

GTG TTC CTT ATT CTC TCA AAA TCT TCG ATT TTG TTT TCG TTC GAT CCC AAT TTC GTA TAT

UBQ10

GTT CTT TGG TTT AGA TTC TGT TAA TCT TAG ATC GAA GAC GAT TTT CTG GGT TTG ATC GTT

Figure 5 cont.

```
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
AGA TAT CAT CTT AAT TCT CGA TTA GGG TTT CAT AGA TAT CAT CCG ATT TGT TCA AAT AAT
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
TTG AGT TTT GTC GAA TAA TTA CTC TTC GAT TTG TGA TTT CTA TCT AGA TCT GGT GTT AGT
                                                                     3'Oleo_3-3
                                                                         ~~~~~~~
                        UBQ10
~~~~~~~~~~~~~~~~~~~~~~~~~~~~~~~~~~~~~~~~~~~~~~~~~~~~~~~~~~~~~~~~~~~~~~~~~
                                                                         A   G
TTC TAG TTT GTG CGA TCG AAT TTG TCG ATT AAT CTG AGT TTT TCT GAT TAA CAG GCT GGA
                        3' Oleo_3-3
~~~~~~~~~~~~~~~~~~~~~~~~~~~~~~~~~~~~~~~~~~~~~~~~~~~~~~~~~~~~~~~~~~~~~~~~~~~~~~~~
 G   S   L   L   V   L   S   G   L   T   L   A   G   T   V   I   A   L   T   I
GGA TCT CTT CTT GTT CTC TCT GGA CTT ACT CTC GCT GGA ACT GTT ATC GCT CTC ACT ATC
                        3' Oleo_3-3
~~~~~~~~~~~~~~~~~~~~~~~~~~~~~~~~~~~~~~~~~~~~~~~~~~~~~~~~~~~~~~~~~~~~~~~~~~~~~~~~
 A   T   P   L   L   V   I   F   S   P   V   L   V   P   A   V   I   T   I   F
GCT ACA CCT CTT CTC GTT ATC TTC TCT CCT GTT CTC GTT CCT GCT GTG ATC ACT ATC TTC
                        3' Oleo_3-3
~~~~~~~~~~~~~~~~~~~~~~~~~~~~~~~~~~~~~~~~~~~~~~~~~~~~~~~~~~~~~~~~~~~~~~~~~~~~~~~~
 L   L   G   A   G   F   L   A   S   G   G   F   G   V   A   A   L   S   V   L
CTT CTC GGA GCT GGA TTT CTT GCT TCT GGT GGA TTT GGA GTT GCT GCT CTC TCT GTT CTC
                        3' Oleo_3-3
~~~~~~~~~~~~~~~~~~~~~~~~~~~~~~~~~~~~~~~~~~~~~~~~~~~~~~~~~~~~~~~~~~~~~~~~~~~~~~~~
 S   W   I   Y   R   Y   L   T   G   K   H   P   P   G   A   D   C   L   E   S
TCT TGG ATC TAC AGA TAC CTC ACT GGA AAA CAT CCT CCA GGT GCT GAT TGT CTT GAG TCT
                        3' Oleo_3-3
~~~~~~~~~~~~~~~~~~~~~~~~~~~~~~~~~~~~~~~~~~~~~~~~~~~~~~~~~~~~~~~~~~~~~~~~~~~~~~~~
 A   K   T   K   L   A   S   C   A   R   E   M   K   D   R   A   E   Q   F   S
GCT AAG ACT AAG CTC GCT TCT TGT GCT AGA GAG ATG AAG GAT AGA GCA GAG CAA TTC TCT
           3' Oleo_3-3                                   OCS terminator
~~~~~~~~~~~~~~~~~~~~~~~~~~~~~~~~~~~~~~~~~~~~~~~~~~        ~~~~~~~~~~~~~~~~~~~~~~
 C   Q   P   V   A   G   S   Q   T   S   (SEQ ID NO:128)
TGT CAG CCT GTT GCT GGA TCT CAG ACT TCT TAA TGA ACA TAT GGT CCT GCT TTA ATG AGA
                       OCS terminator
~~~~~~~~~~~~~~~~~~~~~~~~~~~~~~~~~~~~~~~~~~~~~~~~~~~~~~~~~~~~~~~~~~~~~~~~~~~~~~~~
TAT GCG AGA CGC CTA TGA TCG CAT GAT ATT TGC TTT CAA TTC TGT TGT GCA CGT TGT AAA
                       OCS terminator
~~~~~~~~~~~~~~~~~~~~~~~~~~~~~~~~~~~~~~~~~~~~~~~~~~~~~~~~~~~~~~~~~~~~~~~~~~~~~~~~
AAA CCT GAG CAT GTG TAG CTC AGA TCC TTA CCG CCG GTT TCG GTT CAT TCT AAT GAA TAT
                       OCS terminator
~~~~~~~~~~~~~~~~~~~~~~~~~~~~~~~~~~~~~~~~~~~~~~~~~~~~~~~~~~~~~~~~~~~~~~~~~~~~~~~~
ATC ACC CGT TAC TAT CGT ATT TTT ATG AAT AAT ATT CTC CGT TCA ATT TAC TGA TTG TAC
```

Figure 5 cont.

```
                   OCS terminator
~~~~~~~~~~~~~~~~~~~~~~~~~~~~~~~~~~~~~~~~~~~~~~~~~~~~~~~~~~~~~~~~~~~~~~~~~~~~~~~~~
CCT ACT ACT TAT ATG TAC AAT ATT AAA ATG AAA ACA ATA TAT TGT GCT GAA TAG GTT TAT
                   OCS terminator
~~~~~~~~~~~~~~~~~~~~~~~~~~~~~~~~~~~~~~~~~~~~~~~~~~~~~~~~~~~~~~~~~~~~~~~~~~~~~~~~~
AGC GAC ATC TAT GAT AGA GCG CCA CAA TAA CAA ACA ATT GCG TTT TAT TAT TAC AAA TCC
                   OCS terminator
~~~~~~~~~~~~~~~~~~~~~~~~~~~~~~~~~~~~~~~~~~~~~~~~~~~~~~~~~~~~~~~~~~~~~~~~~~~~~~~~~
AAT TTT AAA AAA AGC GGC AGA ACC GGT CAA ACC TAA AAG ACT GAT TAC ATA AAT CTT ATT
                   OCS terminator
~~~~~~~~~~~~~~~~~~~~~~~~~~~~~~~~~~~~~~~~~~~~~~~~~~~~~~~~~~~~~~~~~~~~~~~~~~~~~~~~~
CAA ATT TCA AAA GGC CCC AGG GGC TAG TAT CTA CGA CAC ACC GAG CGG CGA ACT AAT AAC
                   OCS terminator
~~~~~~~~~~~~~~~~~~~~~~~~~~~~~~~~~~~~~~~~~~~~~~~~~~~~~~~~~~~~~~~~~~~~~~~~~~~~~~~~~
GTT CAC TGA AGG GAA CTC CGG TTC CCC GCC GGC GCG CAT GGG TGA GAT TCC TTG AAG TTG
                   OCS terminator
~~~~~~~~~~~~~~~~~~~~~~~~~~~~~~~~~~~~~~~~~~~~~~~~~~~~~~~~~~~~~~~~~~~~~~~~~~~~~~~~~
AGT ATT GGC CGT CCG CTC TAC CGA AAG TTA CGG GCA CCA TTC AAC CCG GTC CAG CAC GGC
                   OCS terminator
~~~~~~~~~~~~~~~~~~~~~~~~~~~~~~~~~~~~~~~~~~~~~~~~~~~~~~~~~~~~~~~~~~~~~~~~~~~~~~~~~
GGC CGG GTA ACC GAC TTG CTG CCC CGA GAA TTA TGC AGC ATT TTT TTG GTG TAT GTG GGC
                   OCS terminator
~~~~~~~~~~~~~~~~~~~~~~~~~~~~~~~~~~~~~~~~~~~~~~~~~~~~~~~~~~~~~~~~~~~~~~~~~~~~~~~~~
CCC AAA TGA AGT GCA GGT CAA ACC TTG ACA GTG ACG ACA AAT CGT TGG GCG GGT CCA GGG
                   OCS terminator
~~~~~~~~~~~~~~~~~~~~~~~~~~~~~~~~~~~~~~~~~~~~~~~~~~~~~~~~~~~~~~~~~~~~~~~~~~~~~~~~~
CGA ATT TTG CGA CAA CAT GTC GAG GCT CAG CAG GAC CTG CAG GCA TGC AAG CTA GCT TAC
          OCS terminator
~~~~~~~~~~~~~~~~~~~~~~~~~~~~~~~~~~~~~~~~~~~~~
                                                       CaMV35S
                                             ~~~~~~~~~~~~~~~~~~~~~~~~~~~~~~~~~~~~
TAG TGA TGC ATA TTC TAT AGT GTC ACC TAA ATC TTC GAC GAA TTA ATT CCA ATC CCA CAA
                          CaMV35S
~~~~~~~~~~~~~~~~~~~~~~~~~~~~~~~~~~~~~~~~~~~~~~~~~~~~~~~~~~~~~~~~~~~~~~~~~~~~~~~~~
AAA TCT GAG CTT AAC AGC ACA GTT GCT CCT CTC AGA GCA GAA TCG GGT ATT CAA CAC CCT
                          CaMV35S
~~~~~~~~~~~~~~~~~~~~~~~~~~~~~~~~~~~~~~~~~~~~~~~~~~~~~~~~~~~~~~~~~~~~~~~~~~~~~~~~~
CAT ATC AAC TAC TAC GTT GTG TAT AAC GGT CCA CAT GCC GGT ATA TAC GAT GAC TGG GGT
                          CaMV35S
~~~~~~~~~~~~~~~~~~~~~~~~~~~~~~~~~~~~~~~~~~~~~~~~~~~~~~~~~~~~~~~~~~~~~~~~~~~~~~~~~
TGT ACA AAG GCG GCA ACA AAC GGC GTT CCC GGA GTT GCA CAC AAG AAA TTT GCC ACT ATT
                          CaMV35S
~~~~~~~~~~~~~~~~~~~~~~~~~~~~~~~~~~~~~~~~~~~~~~~~~~~~~~~~~~~~~~~~~~~~~~~~~~~~~~~~~
ACA GAG GCA AGA GCA GCA GCT GAC GCG TAC ACA ACA AGT CAG CAA ACA GAC AGG TTG AAC
                          CaMV35S
```

Figure 5 cont.

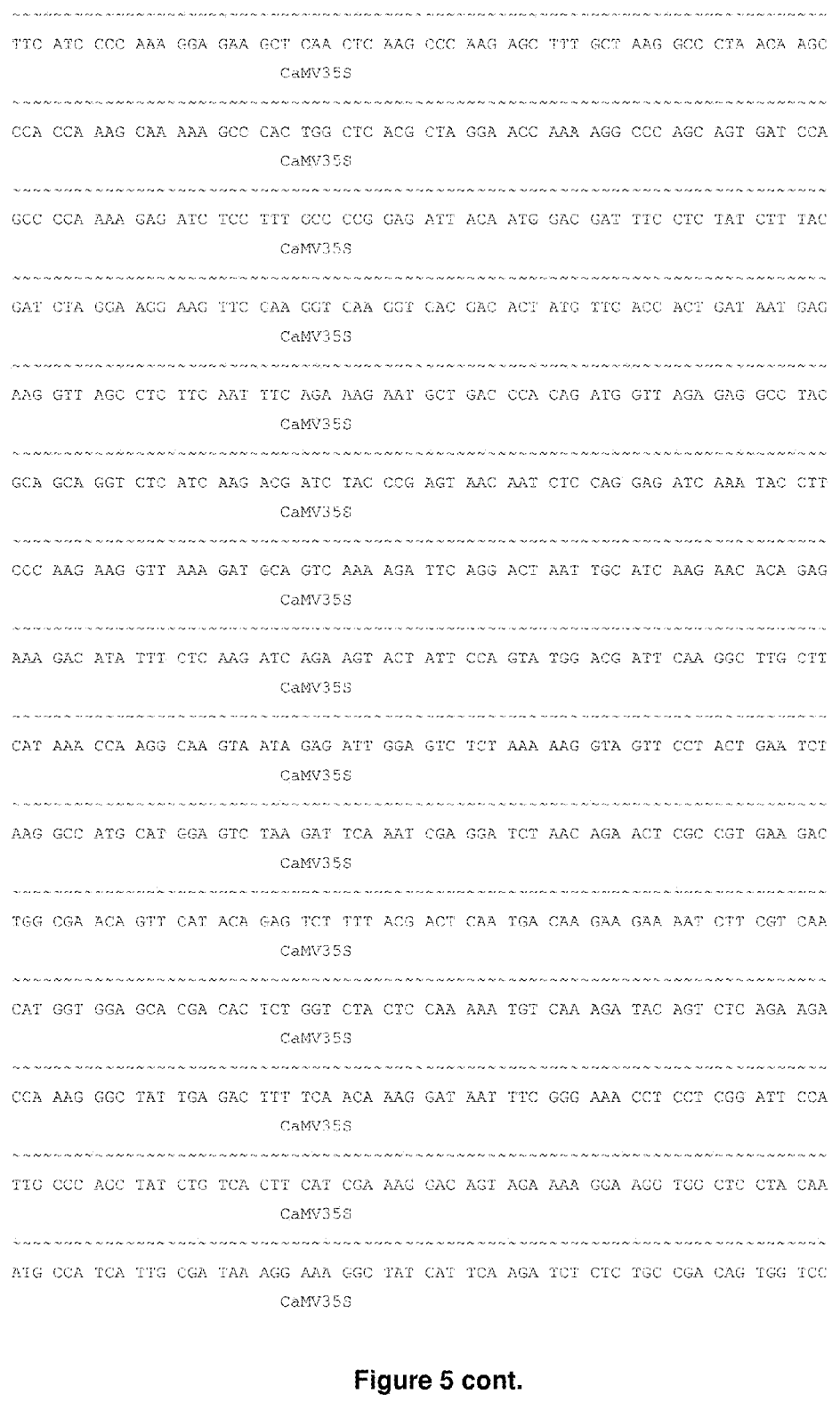

TTC ATC CCC AAA GGA GAA GCT CAA CTC AAG CCC AAG AGC TTT GCT AAG GCC CTA ACA AGC
CaMV35S

CCA CCA AAG CAA AAA GCC CAC TGG CTC ACG CTA GGA ACC AAA AGG CCC AGC AGT GAT CCA
CaMV35S

GCC CCA AAA GAG ATC TCC TTT GCC CCG GAG ATT ACA ATG GAC GAT TTC CTC TAT CTT TAC
CaMV35S

GAT CTA GGA ACG AAG TTC CAA GGT CAA GGT CAC GAC ACT ATG TTC ACC ACT GAT AAT GAG
CaMV35S

AAG GTT AGC CTC TTC AAT TTC AGA AAG AAT GCT GAC CCA CAG ATG GTT AGA GAG GCC TAC
CaMV35S

GCA GCA GGT CTC ATC AAG ACG ATC TAC CCG AGT AAC AAT CTC CAG GAG ATC AAA TAC CTT
CaMV35S

CCC AAG AAG GTT AAA GAT GCA GTC AAA AGA TTC AGG ACT AAT TGC ATC AAG AAC ACA GAG
CaMV35S

AAA GAC ATA TTT CTC AAG ATC AGA AGT ACT ATT CCA GTA TGG ACG ATT CAA GGC TTG CTT
CaMV35S

CAT AAA CCA AGG CAA GTA ATA GAG ATT GGA GTC TCT AAA AAG GTA GTT CCT ACT GAA TCT
CaMV35S

AAG GCC ATG CAT GGA GTC TAA GAT TCA AAT CGA GGA TCT AAC AGA ACT CGC CGT GAA GAC
CaMV35S

TGG CGA ACA GTT CAT ACA GAG TCT TTT ACG ACT CAA TGA CAA GAA GAA AAT CTT CGT CAA
CaMV35S

CAT GGT GGA GCA CGA CAC TCT GGT CTA CTC CAA AAA TGT CAA AGA TAC AGT CTC AGA AGA
CaMV35S

CCA AAG GGC TAT TGA GAC TTT TCA ACA AAG GAT AAT TTC GGG AAA CCT CCT CGG ATT CCA
CaMV35S

TTG CCC ACC TAT CTG TCA CTT CAT CGA AAG GAC AGT AGA AAA GGA AGG TGG CTC CTA CAA
CaMV35S

ATG CCA TCA TTG CGA TAA AGG AAA GGC TAT CAT TCA AGA TCT CTC TGC CGA CAG TGG TCC
CaMV35S

Figure 5 cont.

```
~~~~~~~~~~~~~~~~~~~~~~~~~~~~~~~~~~~~~~~~~~~~~~~~~~~~~~~~~~~~~~~~~~~~~~~~~~~~~~~~
CAA AGA TGG ACC CCC ACC CAC GAG GAG CAT CGT GGA AAA AGA AGA CGT TCC AAC CAC GTC
                          CaMV35S
~~~~~~~~~~~~~~~~~~~~~~~~~~~~~~~~~~~~~~~~~~~~~~~~~~~~~~~~~~~~~~~~~~~~~~~~~~~~~~~~
TTC AAA GCA AGT GGA TTG ATG TGA CAT CTC CAC TGA CGT AAG GGA TGA CGC ACA ATC CCA
                          CaMV35S
~~~~~~~~~~~~~~~~~~~~~~~~~~~~~~~~~~~~~~~~~~~~~~~~~~~~~~~~~~~~~~~~~~~~~~~~~~~~~~~~
CTA TCC TTC GCA AGA CCC TTC CTC TAT ATA AGG AAG TTC ATT TCA TTT GGA GAG GAC ACG
                                          5' DGAT1 (S205A)
                                  ~~~~~~~~~~~~~~~~~~~~~~~~~~~~~~~~~~~~~~~~~~~~~~
                              NcoI
                              ~~~~~~~~
                                M   A   I   L   D   S   A   G   V   T   T   V
GGA TCC TTG CTC CGT TAA AAA AAA CCA TGG CTA TCC TCG ATT CTG CTG GTG TTA CTA CTG
                      5' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
·  T   E   N   G   G   G   E   F   V   D   L   D   R   L   R   R   R   K   S   R
TGA CTG AGA ATG GTG GTG GAG AGT TCG TTG ATC TCG ATA GAC TCA GAA GAA GAA AGT CTA
5' DGAT1 (S205A)
~~~~~~
                             UBQ10
      ~~~~~~~~~~~~~~~~~~~~~~~~~~~~~~~~~~~~~~~~~~~~~~~~~~~~~~~~~~~~~~~~~~~~~~~~~~
·  S   (SEQ ID NO:115)
GAT CTG TAA ATT TCT GTG TTC CTT ATT CTC TCA AAA TCT TCG ATT TTG TTT TCG TTC GAT
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
CCC AAT TTC GTA TAT GTT CTT TGG TTT AGA TTC TGT TAA TCT TAG ATC GAA GAC GAT TTT
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
CTG GGT TTG ATC GTT AGA TAT CAT CTT AAT TCT CGA TTA GGG TTT CAT AGA TAT CAT CCG
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
ATT TGT TCA AAT AAT TTG AGT TTT GTC GAA TAA TTA CTC TTC GAT TTG TGA TTT CTA TCT
                           UBQ10
~~~~~~~~~~~~~~~~~~~~~~~~~~~~~~~~~~~~~~~~~~~~~~~~~~~~~~~~~~~~~~~~~~~~~~~~~~~~~~~~
AGA TCT GGT GTT AGT TTC TAG TTT GTG CGA TCG AAT TTG TCG ATT AAT CTG AGT TTT TCT
  UBQ10
~~~~~~~~~~~~
                             3' DGAT1 (S205A)
            ~~~~~~~~~~~~~~~~~~~~~~~~~~~~~~~~~~~~~~~~~~~~~~~~~~~~~~~~~~~~~~~~~~~~
             D   S   S   N   G   L   L   L   S   G   S   D   N   N   S   P   S
GAT TAA CAG GAT TCT TCT AAC GGA CTT CTC CTC TCT GGA TCT GAT AAC AAC TCT CCT TCT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~~
 D   D   V   G   A   P   A   D   V   R   D   R   I   D   S   V   V   N   D   D
```

Figure 5 cont.

```
GAT GAT GTT GGT GCT CCT GCT GAT GTG AGA GAT AGA ATC GAT TCT GTG GTG AAC GAT GAT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 A   Q   G   T   A   N   L   A   G   D   N   N   G   G   G   D   N   N   G   G
GCT CAA GGT ACT GCT AAC CTC GCT GGT GAT AAT AAC GGT GGA GGT GAT AAC AAT GGT GGA
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 G   R   G   G   G   E   G   R   G   N   A   D   A   T   F   T   Y   R   P   S
GGA AGA GGT GGA GGT GAA GGT AGA GGA AAC GCT GAT GCT ACT TTC ACT TAC AGA CCA TCT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 V   P   A   H   R   R   A   R   E   S   P   L   S   S   D   A   I   F   K   Q
GTG CCT GCT CAT AGA AGA GCT AGA GAG TCT CCT CTC TCT TCT GAT GCT ATC TTC AAG CAG
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 S   H   A   G   L   F   N   L   C   V   V   V   L   I   A   V   N   S   R   L
TCT CAC GCT GGA CTT TTC AAC CTC TGT GTG GTG GTT CTT ATC GCT GTG AAC TCT AGA CTC
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 I   I   E   N   L   M   K   Y   G   W   L   I   R   T   D   F   W   F   S   S
ATC ATC GAG AAC CTC ATG AAG TAC GGA TGG CTC ATC AGA ACT GAT TTC TGG TTC TCT TCT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 R   S   L   R   D   W   P   L   F   M   C   C   I   S   L   S   I   F   P   L
AGA TCT CTC AGA GAT TGG CCT CTT TTC ATG TGC TGC ATC TCA CTC TCA ATC TTC CCT CTC
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 A   A   F   T   V   E   K   L   V   L   Q   K   Y   I   A   E   P   V   V   I
GCT GCT TTT ACT GTT GAG AAG CTC GTG CTC CAG AAG TAT ATC GCT GAA CCT GTG GTG ATC
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 F   L   H   I   I   I   T   M   T   E   V   L   Y   P   V   Y   V   T   L   R
TTC CTC CAC ATC ATC ATC ACT ATG ACT GAG GTT CTC TAC CCT GTT TAC GTG ACT CTC AGA
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 C   D   S   A   F   L   S   G   V   T   L   M   L   L   T   C   I   V   W   L
TGC GAT TCT GCT TTC CTC TCT GGT GTT ACT CTT ATG CTC CTC ACT TGC ATT GTG TGG CTT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 K   L   V   S   Y   A   H   T   S   Y   D   I   R   S   L   A   N   A   A   D
AAG CTC GTG TCT TAC GCT CAC ACT TCT TAC GAT ATC AGA TCT CTC GCT AAC GCT GCT GAT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 K   A   N   P   E   V   S   Y   Y   V   S   L   K   S   L   A   Y   F   M   V
AAG GCT AAC CCT GAA GTG TCT TAC TAC GTG TCT CTC AAG TCT CTC GCT TAC TTC ATG GTT
```

Figure 5 cont.

```
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 A   P   T   L   C   Y   Q   P   S   Y   P   R   S   A   C   I   R   K   G   W
GCT CCT ACA CTT TGT TAC CAG CCA TCT TAC CCT AGA TCT GCT TGC ATT AGA AAG GGA TGG
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 V   A   R   Q   F   A   K   L   V   I   F   T   G   F   M   G   F   I   I   E
GTG GCA AGA CAA TTC GCT AAG TTG GTG ATC TTC ACT GGA TTC ATG GGA TTC ATC ATC GAG
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 Q   Y   I   N   P   I   V   R   N   S   K   H   P   L   K   G   D   L   L   Y
CAG TAC ATC AAC CCT ATT GTG AGA AAC TCT AAG CAC CCT CTC AAG GGT GAT CTT CTC TAC
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 A   I   E   R   V   L   K   L   S   V   P   N   L   Y   V   W   L   C   M   F
GCT ATC GAG AGA GTT CTT AAG CTC TCT GTG CCT AAC CTT TAT GTG TGG CTC TGC ATG TTC
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 Y   C   F   F   H   L   W   L   N   I   L   A   E   L   L   C   F   G   D   R
TAC TGT TTC TTC CAC CTC TGG CTT AAC ATC CTT GCT GAG TTG CTT TGC TTC GGA GAT AGA
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 E   F   Y   K   D   W   W   N   A   K   S   V   G   D   Y   W   R   M   W   N
GAG TTC TAC AAG GAT TGG TGG AAC GCT AAG TCT GTT GGA GAT TAT TGG AGA ATG TGG AAC
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 M   P   V   H   K   W   M   V   R   H   I   Y   F   P   C   L   R   S   K   I
ATG CCT GTG CAT AAG TGG ATG GTG CGT CAC ATC TAC TTC CCT TGC CTC AGA TCT AAG ATC
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 P   K   T   L   A   I   I   I   A   F   L   V   S   A   V   F   H   E   L   C
CCT AAG ACT CTC GCT ATC ATT ATC GCT TTC CTC GTG TCT GCT GTT TTC CAT GAG TTG TGT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 I   A   V   P   C   R   L   F   K   L   W   A   F   L   G   I   M   F   Q   V
ATC GCT GTT CCT TGC AGA CTT TTC AAG CTT TGG GCT TTC CTC GGA ATC ATG TTC CAG GTT
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 P   L   V   F   I   T   N   Y   L   Q   E   R   F   G   S   T   V   G   N   M
CCA CTC GTG TTC ATC ACT AAC TAC CTC CAA GAG AGA TTC GGA TCT ACT GTT GGA AAC ATG
                      3' DGAT1 (S205A)
~~~~~~~~~~~~~~~~~~~~~~~~~~~~~~~~~~~~~~~~~~~~~~~~~~~~~~~~~~~~~~~~~~~~~~~~~~~~~~~
 I   F   W   F   I   F   C   I   F   G   Q   P   M   C   V   L   L   Y   Y   H
ATT TTC TGG TTC ATT TTC TGC ATC TTC GGA CAG CCT ATG TGC GTT CTC CTC TAC TAC CAC
          3' DGAT1 (S205A)
```

Figure 5 cont.

```
~~~~~~~~~~~~~~~~~~~~~~~~~~~~~~~~~~~~~~~~~~~~~~~~~~~~~~~~~~~~
 D   L   M   N   R   K   G   S   M   S    (SEQ ID NO:116)
GAT CTC ATG AAC AGA AAG GGA TCT ATG TCT TAA TGA AGG ATC CAC CCA GCT TTC TTG TAC
                                                                attB2
                                                               ocs
                                                           ~~~~~~~~~~~~~~~~~~~~~~~~
AAA GTG GTG ATG GGT TCG AAA TCG ATA AGC TTG GAT CCT CTA GAG TCC TGC TTT AAT GAG
~~~~~~~~~~
 attB2
                            ocs
~~~~~~~~~~~~~~~~~~~~~~~~~~~~~~~~~~~~~~~~~~~~~~~~~~~~~~~~~~~~~~~~~~~~~~~~~~~~~~~~
ATA TGC GAG ACG CCT ATG ATC GCA TGA TAT TTG CTT TCA ATT CTG TTG TGC ACG TTG TAA
                            ocs
~~~~~~~~~~~~~~~~~~~~~~~~~~~~~~~~~~~~~~~~~~~~~~~~~~~~~~~~~~~~~~~~~~~~~~~~~~~~~~~~
AAA ACC TGA GCA TGT GTA GCT CAG ATC CTT ACC GCC GGT TTC GGT TCA TTC TAA TGA ATA
                            ocs
~~~~~~~~~~~~~~~~~~~~~~~~~~~~~~~~~~~~~~~~~~~~~~~~~~~~~~~~~~~~~~~~~~~~~~~~~~~~~~~~
TAT CAC CCG TTA CTA TCG TAT TTT TAT GAA TAA TAT TCT CCG TTC AAT TTA CTG ATT GTA
                            ocs
~~~~~~~~~~~~~~~~~~~~~~~~~~~~~~~~~~~~~~~~~~~~~~~~~~~~~~~~~~~~~~~~~~~~~~~~~~~~~~~~
CCC TAC TAC TTA TAT GTA CAA TAT TAA AAT GAA AAC AAT ATA TTG TGC TGA ATA GGT TTA
                            ocs
~~~~~~~~~~~~~~~~~~~~~~~~~~~~~~~~~~~~~~~~~~~~~~~~~~~~~~~~~~~~~~~~~~~~~~~~~~~~~~~~
TAG CGA CAT CTA TGA TAG AGC GCC ACA ATA ACA AAC AAT TGC GTT TTA TTA TTA CAA ATC
                            ocs
~~~~~~~~~~~~~~~~~~~~~~~~~~~~~~~~~~~~~~~~~~~~~~~~~~~~~~~~~~~~~~~~~~~~~~~~~~~~~~~~
CAA TTT TAA AAA AAG CGG CAG AAC CGG TCA AAC CTA AAA GAC TGA TTA CAT AAA TCT TAT
                            ocs
~~~~~~~~~~~~~~~~~~~~~~~~~~~~~~~~~~~~~~~~~~~~~~~~~~~~~~~~~~~~~~~~~~~~~~~~~~~~~~~~
TCA AAT TTC AAA AGG CCC CAG GGG CTA GTA TCT ACG ACA CAC CGA GCG GCG AAC TAA TAA
                            ocs
~~~~~~~~~~~~~~~~~~~~~~~~~~~~~~~~~~~~~~~~~~~~~~~~~~~~~~~~~~~~~~~~~~~~~~~~~~~~~~~~
CGT TCA CTG AAG GGA ACT CCG GTT CCC CGC CGG CGC GCA TGG GTG AGA TTC CTT GAA GTT
                            ocs
~~~~~~~~~~~~~~~~~~~~~~~~~~~~~~~~~~~~~~~~~~~~~~~~~~~~~~~~~~~~~~~~~~~~~~~~~~~~~~~~
GAG TAT TGG CCG TCC GCT CTA CCG AAA GTT ACG GGC ACC ATT CAA CCC GGT CCA GCA CGG
                            ocs
~~~~~~~~~~~~~~~~~~~~~~~~~~~~~~~~~~~~~~~~~~~~~~~~~~~~~~~~~~~~~~~~~~~~~~~~~~~~~~~~
CGG CCG GGT AAC CGA CTT GCT GCC CCG AGA ATT ATG CAG CAT TTT TTT GGT GTA TGT GGG
                            ocs
~~~~~~~~~~~~~~~~~~~~~~~~~~~~~~~~~~~~~~~~~~~~~~~~~~~~~~~~~~~~~~~~~~~~~~~~~~~~~~~~
CCC CAA ATG AAG TGC AGG TCA AAC CTT GAC AGT GAC GAC AAA TCG TTG GGC GGG TCC AGG
                            ocs
~~~~~~~~~~~~~~~~~~~~~~~~~~~~~~~~~~~~~~~~~~~~~~~~~~~~~~~~~~~~~~~~~~~~~~~~~~~~~~~~
GCG AAT TTT GCG ACA ACA TGT CGA GGC TCA GCA GGA CCT GCA GGC ATG CAA GCT AGC TTA
                  ocs
```

CTA GTG ATG CAT ATT CTA TAG TGT CAC CTA AAT CT (SEQ ID NO:126)

Figure 5 cont.
~~~~~~~~~~~~~~~~~~~~~~~~~~~~~~~~~~~~~~~~~~~~~~

Figure 34
Stage 3—Rosette growth
Control
OLE1_3,3
DAG
16
23
30

SEQUENCE LISTING

```
<160> NUMBER OF SEQ ID NOS: 128

<210> SEQ ID NO 1
<211> LENGTH: 579
<212> TYPE: DNA
<213> ORGANISM: Artificial Sequence
<220> FEATURE:
<223> OTHER INFORMATION: Synthetic vector

<400> SEQUENCE: 1
atgaaagaaa ccgctgctgc taaattcgaa cgccagcaca tggacagccc agatctgggt      60
accctggtgc cacgcggttc catggctgag cattatggtc aacaacagca gaccagggcg     120
cctcacctgc agctgcagcc gcgcgcccag cgggtagtga aggcggccac cgccgtgaca     180
gccggcggct cgcttctcgt cctctctggc ctcactttag ccggaactgt tattgcgctc     240
accatcgcca ctccgctgct tgtgatcttt agccccgttc tggtgccggc ggtcataacc     300
attttcttgc tgggtgcggg ttttctggca tccggaggct tcggcgtggc ggcgctgagt     360
gtgctgtcgt ggatttacag atatctgaca gggaaacacc cgccgggggc ggatcagctg     420
gaatcggcaa agacgaagct ggcgagcaag gcgcgagaga tgaaggatag ggcagagcag     480
ttctcgcagc agcctgttcc atggctgata tcggatccga attcgagctc cgtcgacaag     540
```
cttgcggccg cactcgagca ccaccaccac caccactga 579

<210> SEQ ID NO 2
<211> LENGTH: 531
<212> TYPE: DNA
<213> ORGANISM: Artificial Sequence
<220> FEATURE:
<223> OTHER INFORMATION: Synthetic vector

<400> SEQUENCE: 2
atgaaagaaa ccgctgctgc taaattcgaa cgccagcaca tggacagccc agatctgggt 60
accctggtgc cacgcggttc catggcttgt cattatggtc aacaacagca gaccagggcg 120
cctcacctgc agctgcagcc gcgcgcccag cgggtagtga aggcggccac cgccgtgaca 180
gccggcggat cccttctcgt cctctctggc ctcactttag ccggaactgt tattgcgctc 240
accatcgcca ctccgctgct tgtgatcttt agccccgttc tggtgccggc ggtcataacc 300 atttcttgc tgggtgcggg ttttctggca tccggaggct tcggcgtggc ggcgctgagt 360
gtgctgtcgt ggatttacag atatctgaca gggaaacacc cgccgggggc ggatcagctg 420
gaatcggcaa agacgaagct ggcgagcaag gcgcgagaga tgaaggatag ggcagagcag 480
ttctcgtgcc agcctgttcc gtggctcgag caccaccacc accaccactg a 531

<210> SEQ ID NO 3
<211> LENGTH: 531
<212> TYPE: DNA
<213> ORGANISM: Artificial Sequence
<220> FEATURE:
<223> OTHER INFORMATION: Synthetic vector

<400> SEQUENCE: 3
atgaaagaaa ccgctgctgc taaattcgaa cgccagcaca tggacagccc agatctgggt 60
accctggtgc cacgcggttc catggcttgt cattatggtc aacaacagca gaccagggcg 120
cctcacctgc agctgcagcc gcgcgcccag cgggtagtga aggcggccac cgccgtgaca 180
gccggcggat cccttctcgt cctctctggc ctcactttag ccggaactgt tattgcgctc 240
accatcgcca ctccgctgct tgtgatcttt agccccgttc tggtgccggc ggtcataacc 300 atttcttgc tgggtgcggg ttttctggca tccggaggct tcggcgtggc ggcgctgagt 360
gtgctgtcgt ggatttacag atatctgaca gggaaacacc cgccgggggc ggattgcctg 420
gaatcggcaa agacgaagct ggcgagctgt gcgcgagaga tgaaggatag ggcagagcag 480
ttctcgtgcc agcctgttcc gtggctcgag caccaccacc accaccactg a 531

<210> SEQ ID NO 4
<211> LENGTH: 531
<212> TYPE: DNA
<213> ORGANISM: Artificial Sequence
<220> FEATURE:
<223> OTHER INFORMATION: Synthetic vector

<400> SEQUENCE: 4
atgaaagaaa ccgctgctgc taaattcgaa cgccagcaca tggacagccc agatctgggt 60
accctggtgc cacgcggttc catggcttgt cattatggtc aacaacagca gacctgcgcg 120
cctcacctgc agctgcagcc gcgcgcctgt cgggtagtga aggcggccac cgccgtgaca 180
gcgggcggat cccttctcgt cctctctggc ctcactttag ccggtaccgt tattgcgctc 240
accatcgcca ctccgctgct tgtgatcttt agccccgttc tggttccggc ggtcataacc 300 atttcttgc tgggtgcggg ttttctggca tccggaggct tcggcgtggc ggcgctgagt 360
gtgctgtcgt ggatttacag atatctgaca gggaaacacc cgccgggggc ggatcagctg 420
gaatcggcaa agacgaagct ggcgagcaag gcgcgagaga tgaaggatag ggcagagcag 480
ttctcgtgcc agcctgttcc gtggctcgag caccaccacc accaccactg a 531

<210> SEQ ID NO 5
<211> LENGTH: 531
<212> TYPE: DNA
<213> ORGANISM: Artificial Sequence
<220> FEATURE:
<223> OTHER INFORMATION: Synthetic vector

<400> SEQUENCE: 5
atgaaagaaa ccgctgctgc taaattcgaa cgccagcaca tggacagccc agatctgggt 60
accctggtgc cacgcggttc catggcttgt cattatggtc aacaacagca gacctgcgcg 120
cctcacctgc agctgcagcc gcgcgcctgt cgggtagtga aggcggccac cgccgtgaca 180
gcgggcggat cccttctcgt cctctctggc ctcactttag ccggtaccgt tattgcgctc 240
accatcgcca ctccgctgct tgtgatcttt agccccgttc tggttccggc ggtcataacc 300
attttcttgc tgggtgcggg ttttctggca tccggaggct tcggcgtggc ggcgctgagt 360
gtgctgtcgt ggatttacag atatctgaca gggaaacacc cgccgggggc ggattgcctg 420
gaatcggcaa agacgaagct ggcgagctgt gcgcgagaga tgaaggatag ggcagagcag 480
ttctcgtgcc agcctgttcc gtggctcgag caccaccacc accaccactg a 531

<210> SEQ ID NO 6
<211> LENGTH: 193
<212> TYPE: PRT
<213> ORGANISM: Artificial Sequence
<220> FEATURE:
<223> OTHER INFORMATION: Synthetic peptide

<400> SEQUENCE: 6

Met Lys Glu Thr Ala Ala Ala Lys Phe Glu Arg Gln His Met Asp Ser
1 5 10 15

Pro Asp Leu Gly Thr Leu Val Pro Arg Gly Ser Met Ala Glu His Tyr
20 25 30

Gly Gln Gln Gln Gln Thr Arg Ala Pro His Leu Gln Leu Gln Pro Arg
35 40 45

Ala Gln Arg Val Val Lys Ala Ala Thr Ala Val Thr Ala Gly Gly Ser
50 55 60

Leu Leu Val Leu Ser Gly Leu Thr Leu Ala Gly Thr Val Ile Ala Leu
65 70 75 80

Thr Ile Ala Thr Pro Leu Leu Val Ile Phe Ser Pro Val Leu Val Pro
85 90 95

Ala Val Ile Thr Ile Phe Leu Leu Gly Ala Gly Phe Leu Ala Ser Gly
100 105 110

Gly Phe Gly Val Ala Ala Leu Ser Val Leu Ser Trp Ile Tyr Arg Tyr
115 120 125

Leu Thr Gly Lys His Pro Pro Gly Ala Asp Gln Leu Glu Ser Ala Lys
130 135 140

Thr Lys Leu Ala Ser Lys Ala Arg Glu Met Lys Asp Arg Ala Glu Gln
145 150 155 160

Phe Ser Gln Gln Pro Val Pro Trp Leu Ile Ser Asp Pro Asn Ser Ser
165 170 175

Ser Val Asp Lys Leu Ala Ala Ala Leu Glu His His His His His His 180 185 190

His

<210> SEQ ID NO 7
<211> LENGTH: 176
<212> TYPE: PRT
<213> ORGANISM: Artificial Sequence
<220> FEATURE:
<223> OTHER INFORMATION: Synthetic peptide

<400> SEQUENCE: 7

Met Lys Glu Thr Ala Ala Ala Lys Phe Glu Arg Gln His Met Asp Ser
1 5 10 15

Pro Asp Leu Gly Thr Leu Val Pro Arg Gly Ser Met Ala Cys His Tyr
20 25 30

Gly Gln Gln Gln Gln Thr Arg Ala Pro His Leu Gln Leu Gln Pro Arg
35 40 45

Ala Gln Arg Val Val Lys Ala Ala Thr Ala Val Thr Ala Gly Gly Ser
50 55 60

Leu Leu Val Leu Ser Gly Leu Thr Leu Ala Gly Thr Val Ile Ala Leu
65 70 75 80

Thr Ile Ala Thr Pro Leu Leu Val Ile Phe Ser Pro Val Leu Val Pro
85 90 95

Ala Val Ile Thr Ile Phe Leu Leu Gly Ala Gly Phe Leu Ala Ser Gly
100 105 110

Gly Phe Gly Val Ala Ala Leu Ser Val Leu Ser Trp Ile Tyr Arg Tyr
115 120 125

Leu Thr Gly Lys His Pro Pro Gly Ala Asp Gln Leu Glu Ser Ala Lys
130 135 140

Thr Lys Leu Ala Ser Lys Ala Arg Glu Met Lys Asp Arg Ala Glu Gln
145 150 155 160

Phe Ser Cys Gln Pro Val Pro Trp Leu Glu His His His His His His
165 170 175

<210> SEQ ID NO 8
<211> LENGTH: 176
<212> TYPE: PRT
<213> ORGANISM: Artificial Sequence
<220> FEATURE:
<223> OTHER INFORMATION: Synthetic peptide

<400> SEQUENCE: 8

Met Lys Glu Thr Ala Ala Ala Lys Phe Glu Arg Gln His Met Asp Ser
1 5 10 15

Pro Asp Leu Gly Thr Leu Val Pro Arg Gly Ser Met Ala Cys His Tyr
20 25 30

Gly Gln Gln Gln Gln Thr Arg Ala Pro His Leu Gln Leu Gln Pro Arg
35 40 45

Ala Gln Arg Val Val Lys Ala Ala Thr Ala Val Thr Ala Gly Gly Ser
50 55 60

Leu Leu Val Leu Ser Gly Leu Thr Leu Ala Gly Thr Val Ile Ala Leu
65 70 75 80

Thr Ile Ala Thr Pro Leu Leu Val Ile Phe Ser Pro Val Leu Val Pro
85 90 95

Ala Val Ile Thr Ile Phe Leu Leu Gly Ala Gly Phe Leu Ala Ser Gly
100 105 110

Gly Phe Gly Val Ala Ala Leu Ser Val Leu Ser Trp Ile Tyr Arg Tyr

-continued

```
        115                 120                 125

Leu Thr Gly Lys His Pro Pro Gly Ala Asp Cys Leu Glu Ser Ala Lys
    130                 135                 140

Thr Lys Leu Ala Ser Cys Ala Arg Glu Met Lys Asp Arg Ala Glu Gln
145                 150                 155                 160

Phe Ser Cys Gln Pro Val Pro Trp Leu Glu His His His His His His
                165                 170                 175

<210> SEQ ID NO 9
<211> LENGTH: 176
<212> TYPE: PRT
<213> ORGANISM: Artificial Sequence
<220> FEATURE:
<223> OTHER INFORMATION: Synthetic peptide

<400> SEQUENCE: 9

Met Lys Glu Thr Ala Ala Ala Lys Phe Glu Arg Gln His Met Asp Ser
1               5                   10                  15

Pro Asp Leu Gly Thr Leu Val Pro Arg Gly Ser Met Ala Cys His Tyr
            20                  25                  30

Gly Gln Gln Gln Gln Thr Cys Ala Pro His Leu Gln Leu Gln Pro Arg
        35                  40                  45

Ala Cys Arg Val Val Lys Ala Ala Thr Ala Val Thr Ala Gly Gly Ser
    50                  55                  60

Leu Leu Val Leu Ser Gly Leu Thr Leu Ala Gly Thr Val Ile Ala Leu
65                  70                  75                  80

Thr Ile Ala Thr Pro Leu Leu Val Ile Phe Ser Pro Val Leu Val Pro
                85                  90                  95

Ala Val Ile Thr Ile Phe Leu Leu Gly Ala Gly Phe Leu Ala Ser Gly
            100                 105                 110

Gly Phe Gly Val Ala Ala Leu Ser Val Leu Ser Trp Ile Tyr Arg Tyr
        115                 120                 125

Leu Thr Gly Lys His Pro Pro Gly Ala Asp Gln Leu Glu Ser Ala Lys
    130                 135                 140

Thr Lys Leu Ala Ser Lys Ala Arg Glu Met Lys Asp Arg Ala Glu Gln
145                 150                 155                 160

Phe Ser Cys Gln Pro Val Pro Trp Leu Glu His His His His His His
                165                 170                 175

<210> SEQ ID NO 10
<211> LENGTH: 176
<212> TYPE: PRT
<213> ORGANISM: Artificial Sequence
<220> FEATURE:
<223> OTHER INFORMATION: Synthetic peptide

<400> SEQUENCE: 10

Met Lys Glu Thr Ala Ala Ala Lys Phe Glu Arg Gln His Met Asp Ser
1               5                   10                  15

Pro Asp Leu Gly Thr Leu Val Pro Arg Gly Ser Met Ala Cys His Tyr
            20                  25                  30

Gly Gln Gln Gln Gln Thr Cys Ala Pro His Leu Gln Leu Gln Pro Arg
        35                  40                  45

Ala Cys Arg Val Val Lys Ala Ala Thr Ala Val Thr Ala Gly Gly Ser
    50                  55                  60

Leu Leu Val Leu Ser Gly Leu Thr Leu Ala Gly Thr Val Ile Ala Leu
65                  70                  75                  80
```

```
Thr Ile Ala Thr Pro Leu Leu Val Ile Phe Ser Pro Val Leu Val Pro
                85                  90                  95

Ala Val Ile Thr Ile Phe Leu Leu Gly Ala Gly Phe Leu Ala Ser Gly
            100                 105                 110

Gly Phe Gly Val Ala Ala Leu Ser Val Leu Ser Trp Ile Tyr Arg Tyr
        115                 120                 125

Leu Thr Gly Lys His Pro Pro Gly Ala Asp Cys Leu Glu Ser Ala Lys
    130                 135                 140

Thr Lys Leu Ala Ser Cys Ala Arg Glu Met Lys Asp Arg Ala Glu Gln
145                 150                 155                 160

Phe Ser Cys Gln Pro Val Pro Trp Leu Glu His His His His His His
                165                 170                 175
```

<210> SEQ ID NO 11
<211> LENGTH: 766
<212> TYPE: DNA
<213> ORGANISM: Artificial Sequence
<220> FEATURE:
<223> OTHER INFORMATION: Synthetic vector

<400> SEQUENCE: 11

```
ttgctccctt aaaaaaaacc atggctgagc attatggtca acaacagcag accagggcgc     60

ctcacctgca gctgcagccg cgcgcccagc gggtagtgaa ggcggccacc gccgtgacag    120

taaatttctg tgttccttat tctctcaaaa tcttcgattt tgttttcgtt cgatcccaat    180

ttcgtatatg ttctttggtt tagattctgt taatcttaga tcgaagacga ttttctgggt    240

ttgatcgtta gatatcatct taattctcga ttagggtttc atagatatca tccgatttgt    300

tcaaataatt tgagttttgt cgaataatta ctcttcgatt tgtgatttct atctagatct    360

ggtgttagtt tctagtttgt gcgatcgaat ttgtcgatta atctgagttt ttctgattaa    420

caggccggcg gctcgcttct cgtcctctct ggcctcactt tagccggaac tgttattgcg    480

ctcaccatcg ccactccgct gcttgtgatc tttagccccg ttctggtgcc ggcggtcata    540

accattttct tgctgggtgc gggttttctg gcatccggag gcttcggcgt ggcggcgctg    600

agtgtgctgt cgtggattta cagatatctg acagggaaac acccgccggg ggcggatcag    660

ctggaatcgg caaagacgaa gctggcgagc aaggcgcgag agatgaagga tagggcagag    720

cagttctcgc agcagcctgt tgcggggtct caaacttctt aatgaa                   766
```

<210> SEQ ID NO 12
<211> LENGTH: 766
<212> TYPE: DNA
<213> ORGANISM: Artificial Sequence
<220> FEATURE:
<223> OTHER INFORMATION: Synthetic vector

<400> SEQUENCE: 12

```
ttgctccctt aaaaaaaacc atggcttgtc attatggtca acaacagcag accagggcgc     60
ctcacctgca gctgcagccg cgcgcccagc gggtagtgaa ggcggccacc gccgtgacag    120
taaatttctg tgttccttat tctctcaaaa tcttcgattt tgttttcgtt cgatcccaat    180
ttcgtatatg ttctttggtt tagattctgt taatcttaga tcgaagacga ttttctgggt    240
ttgatcgtta gatatcatct taattctcga ttagggtttc atagatatca tccgatttgt    300
tcaaataatt tgagttttgt cgaataatta ctcttcgatt tgtgatttct atctagatct    360
ggtgttagtt tctagtttgt gcgatcgaat ttgtcgatta atctgagttt ttctgattaa    420
caggccggcg gctcgcttct cgtcctctct ggcctcactt tagccggaac tgttattgcg    480
```
ctcaccatcg ccactccgct gcttgtgatc tttagccccg ttctggtgcc ggcggtcata 540
accattttct tgctgggtgc gggttttctg gcatccggag gcttcggcgt ggcggcgctg 600
agtgtgctgt cgtggattta cagatatctg acagggaaac acccgccggg ggcggatcag 660
ctggaatcgg caaagacgaa gctggcgagc aaggcgcgag agatgaagga tagggcagag 720
cagttctcgt gtcagcctgt tgcggggtct caaacttctt aatgaa 766

<210> SEQ ID NO 13
<211> LENGTH: 766
<212> TYPE: DNA
<213> ORGANISM: Artificial Sequence
<220> FEATURE:
<223> OTHER INFORMATION: Synthetic vector

<400> SEQUENCE: 13
ttgctccctt aaaaaaaacc atggcttgtc attatggtca acaacagcag accagggcgc 60
ctcacctgca gctgcagccg cgcgcccagc gggtagtgaa ggcggccacc gccgtgacag 120
taaatttctg tgttccttat tctctcaaaa tcttcgattt tgttttcgtt cgatcccaat 180
ttcgtatatg ttctttggtt tagattctgt taatcttaga tcgaagacga ttttctgggt 240
ttgatcgtta gatatcatct taattctcga ttagggtttc atagatatca tccgatttgt 300
tcaaataatt tgagttttgt cgaataatta ctcttcgatt tgtgatttct atctagatct 360
ggtgttagtt tctagtttgt gcgatcgaat ttgtcgatta atctgagttt ttctgattaa 420
caggccggcg gctcgcttct cgtcctctct ggcctcactt tagccggaac tgttattgcg 480
ctcaccatcg ccactccgct gcttgtgatc tttagccccg ttctggtgcc ggcggtcata 540
accattttct tgctgggtgc gggttttctg gcatccggag gcttcggcgt ggcggcgctg 600
agtgtgctgt cgtggattta cagatatctg acagggaaac acccgccggg ggcggattgt 660
ctggaatcgg caaagacgaa gctggcgagc tgtgcgcgag agatgaagga tagggcagag 720
cagttctcgt gtcagcctgt tgcggggtct caaacttctt aatgaa 766

<210> SEQ ID NO 14
<211> LENGTH: 766
<212> TYPE: DNA
<213> ORGANISM: Artificial Sequence
<220> FEATURE:
<223> OTHER INFORMATION: Synthetic vector

<400> SEQUENCE: 14
ttgctccctt aaaaaaaacc atggcttgtc attatggtca acaacagcag acctgtgcgc 60
ctcacctgca gctgcagccg cgcgcctgtc gggtagtgaa ggcggccacc gccgtgacag 120
taaatttctg tgttccttat tctctcaaaa tcttcgattt tgttttcgtt cgatcccaat 180
ttcgtatatg ttctttggtt tagattctgt taatcttaga tcgaagacga ttttctgggt 240
ttgatcgtta gatatcatct taattctcga ttagggtttc atagatatca tccgatttgt 300
tcaaataatt tgagttttgt cgaataatta ctcttcgatt tgtgatttct atctagatct 360
ggtgttagtt tctagtttgt gcgatcgaat ttgtcgatta atctgagttt ttctgattaa 420
caggccggcg gctcgcttct cgtcctctct ggcctcactt tagccggaac tgttattgcg 480
ctcaccatcg ccactccgct gcttgtgatc tttagccccg ttctggtgcc ggcggtcata 540
accattttct tgctgggtgc gggttttctg gcatccggag gcttcggcgt ggcggcgctg 600
agtgtgctgt cgtggattta cagatatctg acagggaaac acccgccggg ggcggatcag 660
ctggaatcgg caaagacgaa gctggcgagc aaggcgcgag agatgaagga tagggcagag 720
cagttctcgt gtcagcctgt tgcggggtct caaacttctt aatgaa 766

<210> SEQ ID NO 15
<211> LENGTH: 766
<212> TYPE: DNA
<213> ORGANISM: Artificial Sequence
<220> FEATURE:
<223> OTHER INFORMATION: Synthetic vector

<400> SEQUENCE: 15
ttgctccctt aaaaaaaacc atggcttgtc attatggtca acaacagcag acctgtgcgc 60
ctcacctgca gctgcagccg cgcgcctgtc gggtagtgaa ggcggccacc gccgtgacag 120
taaatttctg tgttccttat tctctcaaaa tcttcgattt tgttttcgtt cgatcccaat 180
ttcgtatatg ttctttggtt tagattctgt taatcttaga tcgaagacga ttttctgggt 240
ttgatcgtta gatatcatct taattctcga ttagggtttc atagatatca tccgatttgt 300
tcaaataatt tgagttttgt cgaataatta ctcttcgatt tgtgatttct atctagatct 360
ggtgttagtt tctagtttgt gcgatcgaat ttgtcgatta atctgagttt ttctgattaa 420
caggccggcg gctcgcttct cgtcctctct ggcctcactt tagccggaac tgttattgcg 480
ctcaccatcg ccactccgct gcttgtgatc tttagccccg ttctggtgcc ggcggtcata 540
accattttct tgctgggtgc gggttttctg gcatccggag gcttcggcgt ggcggcgctg 600
agtgtgctgt cgtggattta cagatatctg acagggaaac acccgccggg ggcggattgt 660
ctggaatcgg caaagacgaa gctggcgagc tgtgcgcgag agatgaagga tagggcagag 720
cagttctcgt gtcagcctgt tgcggggtct caaacttctt aatgaa 766

<210> SEQ ID NO 16
<211> LENGTH: 145
<212> TYPE: PRT
<213> ORGANISM: Artificial Sequence
<220> FEATURE:
<223> OTHER INFORMATION: Synthetic peptide

<400> SEQUENCE: 16

Met Ala Glu His Tyr Gly Gln Gln Gln Gln Thr Arg Ala Pro His Leu
1 5 10 15

Gln Leu Gln Pro Arg Ala Gln Arg Val Val Lys Ala Ala Thr Ala Val
20 25 30

Thr Ala Gly Gly Ser Leu Leu Val Leu Ser Gly Leu Thr Leu Ala Gly
35 40 45

Thr Val Ile Ala Leu Thr Ile Ala Thr Pro Leu Leu Val Ile Phe Ser
50 55 60

Pro Val Leu Val Pro Ala Val Ile Thr Ile Phe Leu Leu Gly Ala Gly
65 70 75 80

Phe Leu Ala Ser Gly Gly Phe Gly Val Ala Ala Leu Ser Val Leu Ser
85 90 95

Trp Ile Tyr Arg Tyr Leu Thr Gly Lys His Pro Pro Gly Ala Asp Gln
100 105 110

Leu Glu Ser Ala Lys Thr Lys Leu Ala Ser Lys Ala Arg Glu Met Lys
115 120 125

Asp Arg Ala Glu Gln Phe Ser Gln Gln Pro Val Ala Gly Ser Gln Thr
130 135 140

Ser
145

<210> SEQ ID NO 17
<211> LENGTH: 145
<212> TYPE: PRT
<213> ORGANISM: Artificial Sequence
<220> FEATURE:
<223> OTHER INFORMATION: Synthetic peptide

<400> SEQUENCE: 17

```
Met Ala Cys His Tyr Gly Gln Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Cys Gln Pro Val Ala Gly Ser Gln Thr
    130                 135                 140

Ser
145
```

<210> SEQ ID NO 18
<211> LENGTH: 145
<212> TYPE: PRT
<213> ORGANISM: Artificial Sequence
<220> FEATURE:
<223> OTHER INFORMATION: Synthetic peptide

<400> SEQUENCE: 18

```
Met Ala Cys His Tyr Gly Gln Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Cys
            100                 105                 110

Leu Glu Ser Ala Lys Thr Lys Leu Ala Ser Cys Ala Arg Glu Met Lys
        115                 120                 125

Asp Arg Ala Glu Gln Phe Ser Cys Gln Pro Val Ala Gly Ser Gln Thr
    130                 135                 140

Ser
```

145

<210> SEQ ID NO 19
<211> LENGTH: 145
<212> TYPE: PRT
<213> ORGANISM: Artificial Sequence
<220> FEATURE:
<223> OTHER INFORMATION: Synthetic peptide

<400> SEQUENCE: 19

```
Met Ala Cys His Tyr Gly Gln Gln Gln Gln Thr Cys Ala Pro His Leu
1               5                   10                  15

Gln Leu Gln Pro Arg Ala Cys Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Cys Gln Pro Val Ala Gly Ser Gln Thr
    130                 135                 140

Ser
145
```

<210> SEQ ID NO 20
<211> LENGTH: 145
<212> TYPE: PRT
<213> ORGANISM: Artificial Sequence
<220> FEATURE:
<223> OTHER INFORMATION: Synthetic peptide

<400> SEQUENCE: 20

```
Met Ala Cys His Tyr Gly Gln Gln Gln Gln Thr Cys Ala Pro His Leu
1               5                   10                  15

Gln Leu Gln Pro Arg Ala Cys Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Cys
            100                 105                 110

Leu Glu Ser Ala Lys Thr Lys Leu Ala Ser Cys Ala Arg Glu Met Lys
        115                 120                 125

Asp Arg Ala Glu Gln Phe Ser Cys Gln Pro Val Ala Gly Ser Gln Thr
    130                 135                 140
```

Ser
145

<210> SEQ ID NO 21
<211> LENGTH: 810
<212> TYPE: DNA
<213> ORGANISM: Artificial Sequence
<220> FEATURE:
<223> OTHER INFORMATION: Synthetic vector

<400> SEQUENCE: 21
ggtaccgcgg ccgcttgctc ccttaaaaaa aaccatggca tgtcattacg gatgtggaca 60
acagcaacag acttgtgcac ctcatctttg tcagcttcaa cctagagcat gtagagttgt 120
gaaggctgct actgctgtta ctgtaaattt ctgtgttcct tattctctca aaatcttcga 180
ttttgttttc gttcgatccc aatttcgtat atgttctttg gtttagattc tgttaatctt 240
agatcgaaga cgattttctg ggtttgatcg ttagatatca tcttaattct cgattagggt 300
ttcatagata tcatccgatt tgttcaaata atttgagttt tgtcgaataa ttactcttcg 360
atttgtgatt tctatctaga tctggtgtta gtttctagtt tgtgcgatcg aatttgtcga 420
ttaatctgag tttttctgat taacaggctg gaggatctct tcttgttctc tctggactta 480
ctctcgctgg aactgttatc gctctcacta tcgctacacc tcttctcgtt atcttctctc 540
ctgttctcgt tcctgctgtg atcactatct tccttctcgg agctggattt cttgcttctg 600
gtggatttgg agttgctgct ctctctgttc tctcttggat ctacagatac ctcactggat 660
gtaaacatcc tccaggtgct gattgtcttg agtctgcttg taagactaag ctcgcttctt 720
gtgctagaga gatgaaggat tgtagagcag agcaattctc ttgtcagcct gttgctggat 780
ctcagacttc ttaatgaaca tatggagctc 810

<210> SEQ ID NO 22
<211> LENGTH: 831
<212> TYPE: DNA
<213> ORGANISM: Artificial Sequence
<220> FEATURE:
<223> OTHER INFORMATION: Synthetic vector

<400> SEQUENCE: 22
ggtaccgcgg ccgcttgctc ccttaaaaaa aaccatggca tgtcattacg gaatggcatg 60
tcattacgga tgtggacaac agcaacagac ttgtgcacct catctttgtc agcttcaacc 120
tagagcatgt agagttgtga aggctgctac tgctgttact gtaaatttct gtgttcctta 180
ttctctcaaa atcttcgatt ttgttttcgt tcgatcccaa tttcgtatat gttctttggt 240
ttagattctg ttaatcttag atcgaagacg attttctggg tttgatcgtt agatatcatc 300
ttaattctcg attagggttt catagatatc atccgatttg ttcaaataat ttgagttttg 360
tcgaataatt actcttcgat ttgtgatttc tatctagatc tggtgttagt ttctagtttg 420
tgcgatcgaa tttgtcgatt aatctgagtt tttctgatta acaggctgga ggatctcttc 480
ttgttctctc tggacttact ctcgctggaa ctgttatcgc tctcactatc gctacacctc 540
ttctcgttat cttctctcct gttctcgttc ctgctgtgat cactatcttc cttctcggag 600
ctggatttct tgcttctggt ggatttggag ttgctgctct ctctgttctc tcttggatct 660
acagatacct cactggatgt aaacatcctc caggtgctga ttgtcttgag tctgcttgta 720
agactaagct cgcttcttgt gctagagaga tgaaggattg tagagcagag caattctctt 780
gtcagcctgt tgctggatgt tctcagactt cttaatgaac atatggagct c 831

<210> SEQ ID NO 23
<211> LENGTH: 151
<212> TYPE: PRT
<213> ORGANISM: Artificial Sequence
<220> FEATURE:
<223> OTHER INFORMATION: Synthetic peptide

<400> SEQUENCE: 23

```
Met Ala Cys His Tyr Gly Cys Gly Gln Gln Gln Gln Thr Cys Ala Pro
1               5                   10                  15

His Leu Cys Gln Leu Gln Pro Arg Ala Cys Arg Val Val Lys Ala Ala
            20                  25                  30

Thr Ala Val Thr Ala Gly Gly Ser Leu Leu Val Leu Ser Gly Leu Thr
        35                  40                  45

Leu Ala Gly Thr Val Ile Ala Leu Thr Ile Ala Thr Pro Leu Leu Val
    50                  55                  60

Ile Phe Ser Pro Val Leu Val Pro Ala Val Ile Thr Ile Phe Leu Leu
65                  70                  75                  80

Gly Ala Gly Phe Leu Ala Ser Gly Gly Phe Gly Val Ala Ala Leu Ser
                85                  90                  95

Val Leu Ser Trp Ile Tyr Arg Tyr Leu Thr Gly Cys Lys His Pro Pro
            100                 105                 110

Gly Ala Asp Cys Leu Glu Ser Ala Cys Lys Thr Lys Leu Ala Ser Cys
        115                 120                 125

Ala Arg Glu Met Lys Asp Cys Arg Ala Glu Gln Phe Ser Cys Gln Pro
    130                 135                 140

Val Ala Gly Ser Gln Thr Ser
145                 150
```

<210> SEQ ID NO 24
<211> LENGTH: 158
<212> TYPE: PRT
<213> ORGANISM: Artificial Sequence
<220> FEATURE:
<223> OTHER INFORMATION: Synthetic peptide

<400> SEQUENCE: 24

```
Met Ala Cys His Tyr Gly Met Ala Cys His Tyr Gly Cys Gly Gln Gln
1               5                   10                  15

Gln Gln Thr Cys Ala Pro His Leu Cys Gln Leu Gln Pro Arg Ala Cys
            20                  25                  30

Arg Val Val Lys Ala Ala Thr Ala Val Thr Ala Gly Gly Ser Leu Leu
        35                  40                  45

Val Leu Ser Gly Leu Thr Leu Ala Gly Thr Val Ile Ala Leu Thr Ile
    50                  55                  60

Ala Thr Pro Leu Leu Val Ile Phe Ser Pro Val Leu Val Pro Ala Val
65                  70                  75                  80

Ile Thr Ile Phe Leu Leu Gly Ala Gly Phe Leu Ala Ser Gly Gly Phe
                85                  90                  95

Gly Val Ala Ala Leu Ser Val Leu Ser Trp Ile Tyr Arg Tyr Leu Thr
            100                 105                 110

Gly Cys Lys His Pro Pro Gly Ala Asp Cys Leu Glu Ser Ala Cys Lys
        115                 120                 125

Thr Lys Leu Ala Ser Cys Ala Arg Glu Met Lys Asp Cys Arg Ala Glu
    130                 135                 140

Gln Phe Ser Cys Gln Pro Val Ala Gly Cys Ser Gln Thr Ser
145                 150                 155
```

<210> SEQ ID NO 25
<211> LENGTH: 4104
<212> TYPE: DNA
<213> ORGANISM: Artificial Sequence
<220> FEATURE:
<223> OTHER INFORMATION: Synthetic vector

<400> SEQUENCE: 25
ggtaccacaa gtttgtacaa aaaagcaggc tgcggccgca aaattttcat atggtcctgc 60
tttaatgaga tatgcgagac gcctatgatc gcatgatatt tgctttcaat tctgttgtgc 120
acgttgtaaa aaacctgagc atgtgtagct cagatcctta ccgccggttt cggttcattc 180
taatgaatat atcacccgtt actatcgtat ttttatgaat aatattctcc gttcaattta 240
ctgattgtac cctactactt atatgtacaa tattaaaatg aaaacaatat attgtgctga 300
ataggtttat agcgacatct atgatagagc gccacaataa caaacaattg cgttttatta 360
ttacaaatcc aattttaaaa aaagcggcag aaccggtcaa acctaaaaga ctgattacat 420
aaatcttatt caaatttcaa aaggccccag gggctagtat ctacgacaca ccgagcggcg 480
aactaataac gttcactgaa gggaactccg gttccccgcc ggcgcgcatg ggtgagattc 540
cttgaagttg agtattggcc gtccgctcta ccgaaagtta cgggcaccat tcaacccggt 600
ccagcacggc ggccgggtaa ccgacttgct gccccgagaa ttatgcagca tttttttggt 660
gtatgtgggc cccaaatgaa gtgcaggtca aaccttgaca gtgacgacaa atcgttgggc 720
gggtccaggg cgaattttgc gacaacatgt cgaggctcag caggacctgc aggcatgcaa 780
gctagcttac tagtgatgca tattctatag tgtcacctaa atcttcgacg aattaattcc 840
aatcccacaa aaatctgagc ttaacagcac agttgctcct ctcagagcag aatcgggtat 900
tcaacaccct catatcaact actacgttgt gtataacggt ccacatgccg gtatatacga 960
tgactggggt tgtacaaagg cggcaacaaa cggcgttccc ggagttgcac acaagaaatt 1020
tgccactatt acagaggcaa gagcagcagc tgacgcgtac acaacaagtc agcaaacaga 1080
caggttgaac ttcatcccca aaggagaagc tcaactcaag cccaagagct ttgctaaggc 1140
cctaacaagc ccaccaaagc aaaaagccca ctggctcacg ctaggaacca aaaggcccag 1200
cagtgatcca gccccaaaag agatctcctt tgccccggag attacaatgg acgatttcct 1260
ctatctttac gatctaggaa ggaagttcga aggtgaaggt gacgacacta tgttcaccac 1320
tgataatgag aaggttagcc tcttcaattt cagaaagaat gctgacccac agatggttag 1380
agaggcctac gcagcaggtc tcatcaagac gatctacccg agtaacaatc tccaggagat 1440
caaatacctt cccaagaagg ttaaagatgc agtcaaaaga ttcaggacta attgcatcaa 1500
gaacacagag aaagacatat ttctcaagat cagaagtact attccagtat ggacgattca 1560
aggcttgctt cataaaccaa ggcaagtaat agagattgga gtctctaaaa aggtagttcc 1620
tactgaatct aaggccatgc atggagtcta agattcaaat cgaggatcta acagaactcg 1680
ccgtgaagac tggcgaacag ttcatacaga gtcttttacg actcaatgac aagaagaaaa 1740
tcttcgtcaa catggtggag cacgacactc tggtctactc caaaaatgtc aaagatacag 1800
tctcagaaga ccaaagggct attgagactt ttcaacaaag gataatttcg ggaaacctcc 1860
tcggattcca ttgcccagct atctgtcact tcatcgaaag gacagtagaa aaggaaggtg 1920
gctcctacaa atgccatcat tgcgataaag gaaaggctat cattcaagat ctctctgccg 1980
acagtggtcc caaagatgga cccccaccca cgaggagcat cgtggaaaaa gaagacgttc 2040
caaccacgtc ttcaaagcaa gtggattgat gtgacatctc cactgacgta agggatgacg 2100
cacaatccca ctatccttcg caagaccctt cctctatata aggaagttca tttcatttgg 2160
agaggacacg ggatccttgc tccgttaaaa aaaaccatgg ctatcctcga ttctgctggt 2220
gttactactg tgactgagaa tggtggtgga gagttcgttg atctcgatag actcagaaga 2280
agaaagtcta gatctgtaaa tttctgtgtt ccttattctc tcaaaatctt cgattttgtt 2340
ttcgttcgat cccaatttcg tatatgttct ttggtttaga ttctgttaat cttagatcga 2400
agacgatttt ctgggtttga tcgttagata tcatcttaat tctcgattag ggtttcatag 2460
atatcatccg atttgttcaa ataatttgag ttttgtcgaa taattactct tcgatttgtg 2520
atttctatct agatctggtg ttagtttcta gtttgtgcga tcgaatttgt cgattaatct 2580
gagtttttct gattaacagg attcttctaa cggacttctc ctctctggat ctgataacaa 2640
ctctccttct gatgatgttg gtgctcctgc tgatgtgaga gatagaatcg attctgtggt 2700
gaacgatgat gctcaaggta ctgctaacct cgctggtgat aataacggtg gaggtgataa 2760
caatggtgga ggaagaggtg gaggtgaagg tagaggaaac gctgatgcta ctttcactta 2820
cagaccatct gtgcctgctc atagaagagc tagagagtct cctctctctt ctgatgctat 2880
cttcaagcag tctcacgctg gacttttcaa cctctgtgtg gtggttctta tcgctgtgaa 2940
ctctagactc atcatcgaga acctcatgaa gtacggatgg ctcatcagaa ctgatttctg 3000
gttctcttct agatctctca gagattggcc tcttttcatg tgctgcatct cactctcaat 3060
cttccctctc gctgctttta ctgttgagaa gctcgtgctc cagaagtata tcgctgaacc 3120
tgtggtgatc ttcctccaca tcatcatcac tatgactgag gttctctacc ctgtttacgt 3180
gactctcaga tgcgattctg ctttcctctc tggtgttact cttatgctcc tcacttgcat 3240
tgtgtggctt aagctcgtgt cttacgctca cacttcttac gatatcagat ctctcgctaa 3300
cgctgctgat aaggctaacc ctgaagtgtc ttactacgtg tctctcaagt ctctcgctta 3360
cttcatggtt gctcctacac tttgttacca gccatcttac cctagatctg cttgcattag 3420
aaagggatgg gtggcaagac aattcgctaa gttggtgatc ttcactggat tcatgggatt 3480
catcatcgag cagtacatca accctattgt gagaaactct aagcaccctc tcaagggtga 3540
tcttctctac gctatcgaga gagttcttaa gctctctgtg cctaaccttt atgtgtggct 3600
ctgcatgttc tactgtttct tccacctctg gcttaacatc cttgctgagt tgctttgctt 3660
cggagataga gagttctaca aggattggtg gaacgctaag tctgttggag attattggag 3720
aatgtggaac atgcctgtgc ataagtggat ggtgcgtcac atctacttcc cttgcctcag 3780
atctaagatc cctaagactc tcgctatcat tatcgctttc ctcgtgtctg ctgttttcca 3840
tgagttgtgt atcgctgttc cttgcagact tttcaagctt tgggctttcc tcggaatcat 3900
gttccaggtt ccactcgtgt tcatcactaa ctacctccaa gagagattcg gatctactgt 3960
tggaaacatg attttctggt tcattttctg catcttcgga cagcctatgt gcgttctcct 4020
ctactaccac gatctcatga acagaaaggg atctatgtct taatgaagga tccacccagc 4080
tttcttgtac aaagtggtga gctc 4104

<210> SEQ ID NO 26
<211> LENGTH: 18784
<212> TYPE: DNA
<213> ORGANISM: Artificial Sequence
<220> FEATURE:
<223> OTHER INFORMATION: Synthetic vector

<400> SEQUENCE: 26

-continued

```
tcgacatcgt caacgttcac ttctaaagaa atagcgccac tcagcttcct cagcggcttt     60
atccagcgat ttcctattat gtcggcatag ttctcaagat cgacagcctg tcacggttaa    120
gcgagaaatg aataagaagg ctgataattc ggatctctgc gaggagatga tatttgatca    180
caggcagcaa cgctctgtca tcgttacaat caacatgcta ccctccgcga gatcatccgt    240
gtttcaaacc cggcagctta gttgccgttc ttccgaatag catcgggtaa catgagcaaa    300
gtctgccgcc ttacaacggc tctcccgctg acgccgtccc ggactgatgg gctgcctgta    360
tcgagtggtg attttgtgcc gagctgccgg tcggggagct gttggctggc tggtggcagg    420
atatattgtg gtgtaaacaa attgacgctt agacaactta ataacacatt gcggacgttt    480
ttaatgtact gaattcgccg ctcggtgtgt cgtagatact agcccctggg gcacttttga    540
aatttgaata agatttatgt aatcagtctt ttaggtttga ccggttctgc cgcttttttt    600
aaaattggat ttgtaataat aaaacgcaat tgtttgttat tgtggcgctc tatcatagat    660
gtcgctataa acctattcag cacaatatat tgttttcatt ttaatattgt acatataagt    720
agtagggtac aatcagtaaa ttgaacggag aatattattc ataaaaatac gatagtaacg    780
ggtgatatat tcattagaat gaaccgaaac cggcggtaag gatctgagct acacatgctc    840
aggtttttta caacgtgcac aacagaattg aaagcaaata tcatgcgatc ataggcgtct    900
cgcatatctc attaaacaag tgaagatttg attcaaactc cattgagagc cctgactatg    960
cattcggttt gacccttcca ggttgagaga cgatagcccc ctaccttaat taagggggcc   1020
cccctcgagg tcgacggtat cgataagctt gatatcgaat tcctgcagcc agggggatcc   1080
cccgggtcat cagatctcgg tgacgggcag gaccggacgg ggcggtaccg gcaggctgaa   1140
gtccagctgc cagaaaccca cgtcatgcca gttcccgtgc ttgaagccgg ccgcccgcag   1200
catgccgcgg ggggcatatc cgagcgcctc gtgcatgcgc acgctcgggt cgttgggcag   1260
cccgatgaca gcgaccacgc tcttgaagcc ctgtgcctcc agggacttca gcaggtgggt   1320
gtagagcgtg gagcccagtc ccgtccgctg gtggcggggg gagacgtaca cggtcgactc   1380
ggccgtccag tcgtaggcgt tgcgtgcctt ccaggggccc gcgtaggcga tgccggcgac   1440
ctcgccgtcc acctcggcga cgagccaggg atagcgctcc cgcagacgga cgaggtcgtc   1500
cgtccactcc tgcggttcct gcggctcggt acggaagttg accgtgcttg tctcgatgta   1560
gtggttgacg atggtgcaga ccgccggcat gtccgcctcg gtggcacggc ggatgtcggc   1620
cgggcgtcgt tctgggctca tggtagatcc cctcgagaga gatagatttg tagagagaga   1680
ctggtgattt cagcgtgtcc tctccaaatg aaatgaactt ccttatatag aggaaggtct   1740
tgcgaaggat agtgggattg tgcgtcatcc cttacgtcag tggagatatc acatcaatcc   1800
acttgctttg aagacgtggt tggaacgtct tctttttcca cgatgctcct cgtgggtggg   1860
ggtccatctt tgggaccact gtcggcagag gcatcttgaa cgatagcctt tcctttatcg   1920
caatgatggc atttgtaggt gccaccttcc ttttctactg tccttttgat gaagtgacag   1980
atagctgggc aatggaatcc gaggaggttt cccgatatta ccctttgttg aaaagtctca   2040
atagcccttt ggtcttctga gactgtatct ttgatattct tggagtagac gagagtgtcg   2100
tgctccacca tgttatcaca tcaatccact tgctttgaag acgtggttgg aacgtcttct   2160
ttttccacga tgctcctcgt gggtgggggt ccatctttgg gaccactgtc ggcagaggca   2220
tcttgaacga tagcctttcc tttatcgcaa tgatggcatt tgtaggtgcc accttccttt   2280
tctactgtcc ttttgatgaa gtgacagata gctgggcaat ggaatccgag gaggtttccc   2340
```

```
gatattaccc tttgttgaaa agtctcaata gccctttggt cttctgagac tgtatctttg   2400
atattcttgg agtagacgag agtgtcgtgc tccaccatgt tgctgatagt gaccttaggc   2460
gacttttgaa cgcgcaataa tggtttctga cgtatgtgct tagctcatta aactccagaa   2520
acccattaac gcttacaatt tccattcgcc attcaggctg cgcaactgtt gggaagggcg   2580
atcggtgcgg gcctcttcgc tattacgcca gctggcgaaa gggggatgtg ctgcaaggcg   2640
attaagttgg gtaacgccag ggttttccca gtcacgacgt tgtaaaacga cggccagtga   2700
attgtaatac gactcactat agggcgaatt gggcccgacg tcgcatgctc ccggccgcca   2760
tggccgcggg atatcactag tgcggccgct cgacgaatta attccaatcc cacaaaaatc   2820
tgagcttaac agcacagttg ctcctctcag agcagaatcg ggtattcaac accctcatat   2880
caactactac gttgtgtata acggtccaca tgccggtata tacgatgact ggggttgtac   2940
aaaggcggca acaaacggcg ttcccggagt tgcacacaag aaatttgcca ctattacaga   3000
ggcaagagca gcagctgacg cgtacacaac aagtcagcaa acagacaggt tgaacttcat   3060
ccccaaagga gaagctcaac tcaagcccaa gagctttgct aaggccctaa caagcccacc   3120
aaagcaaaaa gcccactggc tcacgctagg aaccaaaagg cccagcagtg atccagcccc   3180
aaaagagatc tcctttgccc cggagattac aatggacgat ttcctctatc tttacgatct   3240
aggaaggaag ttcgaaggtg aaggtgacga cactatgttc accactgata atgagaaggt   3300
tagcctcttc aatttcagaa agaatgctga cccacagatg gttagagagg cctacgcagc   3360
aggtctcatc aagacgatct acccgagtaa caatctccag gagatcaaat accttcccaa   3420
gaaggttaaa gatgcagtca aaagattcag gactaattgc atcaagaaca cagagaaaga   3480
catatttctc aagatcagaa gtactattcc agtatggacg attcaaggct tgcttcataa   3540
accaaggcaa gtaatagaga ttggagtctc taaaaaggta gttcctactg aatctaaggc   3600
catgcatgga gtctaagatt caaatcgagg atctaacaga actcgccgtg aagactggcg   3660
aacagttcat acagagtctt ttacgactca atgacaagaa gaaaatcttc gtcaacatgg   3720
tggagcacga cactctggtc tactccaaaa atgtcaaaga tacagtctca gaagaccaaa   3780
gggctattga gacttttcaa caaaggataa tttcgggaaa cctcctcgga ttccattgcc   3840
cagctatctg tcacttcatc gaaaggacag tagaaaagga aggtggctcc tacaaatgcc   3900
atcattgcga taaaggaaag gctatcattc aagatctctc tgccgacagt ggtcccaaag   3960
atggaccccc acccacgagg agcatcgtgg aaaaagaaga cgttccaacc acgtcttcaa   4020
agcaagtgga ttgatgtgac atctccactg acgtaaggga tgacgcacaa tcccactatc   4080
cttcgcaaga cccttcctct atataaggaa gttcatttca tttggagagg acacgctcga   4140
ggaattcggt accccatcac aagtttgtac aaaaaagcag gctgcggccg cttgctccct   4200
taaaaaaaac catggcagag cattacggac aacagcaaca gactagagca cctcatcttc   4260
agcttcaacc tagagcacag agagttgtga aggctgctac tgctgttact gtaaatttct   4320
gtgttcctta ttctctcaaa atcttcgatt ttgttttcgt tcgatcccaa tttcgtatat   4380
gttctttggt ttagattctg ttaatcttag atcgaagacg attttctggg tttgatcgtt   4440
agatatcatc ttaattctcg attagggttt catagatatc atccgatttg ttcaaataat   4500
ttgagttttg tcgaataatt actcttcgat ttgtgatttc tatctagatc tggtgttagt   4560
ttctagtttg tgcgatcgaa tttgtcgatt aatctgagtt tttctgatta acaggctgga   4620
ggatctcttc ttgttctctc tggacttact ctcgctggaa ctgttatcgc tctcactatc   4680
gctacacctc ttctcgttat cttctctcct gttctcgttc ctgctgtgat cactatcttc   4740
```

```
cttctcggag ctggatttct tgcttctggt ggatttggag ttgctgctct ctctgttctc   4800
tcttggatct acagatacct cactggaaaa catcctccag gtgctgatca acttgagtct   4860
gctaagacta agctcgcttc taaggctaga gagatgaagg atagagcaga gcaattctct   4920
caacagcctg ttgctggatc tcagacttct taatgaacat atggtcctgc tttaatgaga   4980
tatgcgagac gcctatgatc gcatgatatt tgctttcaat tctgttgtgc acgttgtaaa   5040
aaacctgagc atgtgtagct cagatcctta ccgccggttt cggttcattc taatgaatat   5100
atcacccgtt actatcgtat ttttatgaat aatattctcc gttcaattta ctgattgtac   5160
cctactactt atatgtacaa tattaaaatg aaaacaatat attgtgctga ataggtttat   5220
agcgacatct atgatagagc gccacaataa caaacaattg cgttttatta ttacaaatcc   5280
aattttaaaa aaagcggcag aaccggtcaa acctaaaaga ctgattacat aaatcttatt   5340
caaatttcaa aaggccccag gggctagtat ctacgacaca ccgagcggcg aactaataac   5400
gttcactgaa gggaactccg gttccccgcc ggcgcgcatg ggtgagattc cttgaagttg   5460
agtattggcc gtccgctcta ccgaaagtta cgggcaccat tcaacccggt ccagcacggc   5520
ggccgggtaa ccgacttgct gccccgagaa ttatgcagca tttttttggt gtatgtgggc   5580
cccaaatgaa gtgcaggtca aaccttgaca gtgacgacaa atcgttgggc gggtccaggg   5640
cgaattttgc gacaacatgt cgaggctcag caggacctgc aggcatgcaa gctagcttac   5700
tagtgatgca tattctatag tgtcacctaa atcttcgacg aattaattcc aatcccacaa   5760
aaatctgagc ttaacagcac agttgctcct ctcagagcag aatcgggtat tcaacaccct   5820
catatcaact actacgttgt gtataacggt ccacatgccg gtatatacga tgactggggt   5880
tgtacaaagg cggcaacaaa cggcgttccc ggagttgcac acaagaaatt tgccactatt   5940
acagaggcaa gagcagcagc tgacgcgtac acaacaagtc agcaaacaga caggttgaac   6000
ttcatcccca aaggagaagc tcaactcaag cccaagagct ttgctaaggc cctaacaagc   6060
ccaccaaagc aaaaagccca ctggctcacg ctaggaacca aaaggcccag cagtgatcca   6120
gccccaaaag agatctcctt tgccccggag attacaatgg acgatttcct ctatctttac   6180
gatctaggaa ggaagttcga aggtgaaggt gacgacacta tgttcaccac tgataatgag   6240
aaggttagcc tcttcaattt cagaaagaat gctgacccac agatggttag agaggcctac   6300
gcagcaggtc tcatcaagac gatctacccg agtaacaatc tccaggagat caaatacctt   6360
cccaagaagg ttaaagatgc agtcaaaaga ttcaggacta attgcatcaa gaacacagag   6420
aaagacatat ttctcaagat cagaagtact attccagtat ggacgattca aggcttgctt   6480
cataaaccaa ggcaagtaat agagattgga gtctctaaaa aggtagttcc tactgaatct   6540
aaggccatgc atggagtcta agattcaaat cgaggatcta acagaactcg ccgtgaagac   6600
tggcgaacag ttcatacaga gtcttttacg actcaatgac aagaagaaaa tcttcgtcaa   6660
catggtggag cacgacactc tggtctactc caaaaatgtc aaagatacag tctcagaaga   6720
ccaaagggct attgagactt ttcaacaaag gataatttcg ggaaacctcc tcggattcca   6780
ttgcccagct atctgtcact tcatcgaaag gacagtagaa aaggaaggtg gctcctacaa   6840
atgccatcat tgcgataaag gaaaggctat cattcaagat ctctctgccg acagtggtcc   6900
caaagatgga cccccaccca cgaggagcat cgtggaaaaa gaagacgttc caaccacgtc   6960
ttcaaagcaa gtggattgat gtgacatctc cactgacgta agggatgacg cacaatccca   7020
ctatccttcg caagaccctt cctctatata aggaagttca tttcatttgg agaggacacg   7080
```

```
ggatccttgc tccgttaaaa aaaaccatgg ctatcctcga ttctgctggt gttactactg   7140
tgactgagaa tggtggtgga gagttcgttg atctcgatag actcagaaga agaaagtcta   7200
gatctgtaaa tttctgtgtt ccttattctc tcaaaatctt cgattttgtt ttcgttcgat   7260
cccaatttcg tatatgttct ttggtttaga ttctgttaat cttagatcga agacgatttt   7320
ctgggtttga tcgttagata tcatcttaat tctcgattag ggtttcatag atatcatccg   7380
atttgttcaa ataatttgag ttttgtcgaa taattactct tcgatttgtg atttctatct   7440
agatctggtg ttagtttcta gtttgtgcga tcgaatttgt cgattaatct gagtttttct   7500
gattaacagg attcttctaa cggacttctc ctctctggat ctgataacaa ctctccttct   7560
gatgatgttg gtgctcctgc tgatgtgaga gatagaatcg attctgtggt gaacgatgat   7620
gctcaaggta ctgctaacct cgctggtgat aataacggtg gaggtgataa caatggtgga   7680
ggaagaggtg gaggtgaagg tagaggaaac gctgatgcta ctttcactta cagaccatct   7740
gtgcctgctc atagaagagc tagagagtct cctctctctt ctgatgctat cttcaagcag   7800
tctcacgctg gacttttcaa cctctgtgtg gtggttctta tcgctgtgaa ctctagactc   7860
atcatcgaga acctcatgaa gtacggatgg ctcatcagaa ctgatttctg gttctcttct   7920
agatctctca gagattggcc tcttttcatg tgctgcatct cactctcaat cttccctctc   7980
gctgctttta ctgttgagaa gctcgtgctc cagaagtata tcgctgaacc tgtggtgatc   8040
ttcctccaca tcatcatcac tatgactgag gttctctacc ctgtttacgt gactctcaga   8100
tgcgattctg ctttcctctc tggtgttact cttatgctcc tcacttgcat tgtgtggctt   8160
aagctcgtgt cttacgctca cacttcttac gatatcagat ctctcgctaa cgctgctgat   8220
aaggctaacc ctgaagtgtc ttactacgtg tctctcaagt ctctcgctta cttcatggtt   8280
gctcctacac tttgttacca gccatcttac cctagatctg cttgcattag aaagggatgg   8340
gtggcaagac aattcgctaa gttggtgatc ttcactggat tcatgggatt catcatcgag   8400
cagtacatca accctattgt gagaaactct aagcaccctc tcaagggtga tcttctctac   8460
gctatcgaga gagttcttaa gctctctgtg cctaaccttt atgtgtggct ctgcatgttc   8520
tactgtttct tccacctctg gcttaacatc cttgctgagt tgctttgctt cggagataga   8580
gagttctaca aggattggtg gaacgctaag tctgttggag attattggag aatgtggaac   8640
atgcctgtgc ataagtggat ggtgcgtcac atctacttcc cttgcctcag atctaagatc   8700
cctaagactc tcgctatcat tatcgctttc ctcgtgtctg ctgttttcca tgagttgtgt   8760
atcgctgttc cttgcagact tttcaagctt tgggctttcc tcggaatcat gttccaggtt   8820
ccactcgtgt tcatcactaa ctacctccaa gagagattcg gatctactgt tggaaacatg   8880
atttctggt tcattttctg catcttcgga cagcctatgt gcgttctcct ctactaccac   8940
gatctcatga acagaaaggg atctatgtct taatgaagga tccacccagc tttcttgtac   9000
aaagtggtga tgggttcgaa atcgataagc ttggatcctc tagagtcctg ctttaatgag   9060
atatgcgaga cgcctatgat cgcatgatat ttgctttcaa ttctgttgtg cacgttgtaa   9120
aaaacctgag catgtgtagc tcagatcctt accgccggtt tcggttcatt ctaatgaata   9180
tatcacccgt tactatcgta tttttatgaa taatattctc cgttcaattt actgattgta   9240
ccctactact tatatgtaca atattaaaat gaaaacaata tattgtgctg aataggttta   9300
tagcgacatc tatgatagag cgccacaata acaaacaatt gcgttttatt attacaaatc   9360
caattttaaa aaaagcggca gaaccggtca aacctaaaag actgattaca taaatcttat   9420
tcaaatttca aaaggcccca ggggctagta tctacgacac accgagcggc gaactaataa   9480
```
cgttcactga agggaactcc ggttccccgc cggcgcgcat gggtgagatt ccttgaagtt 9540
gagtattggc cgtccgctct accgaaagtt acgggcacca ttcaacccgg tccagcacgg 9600
cggccgggta accgacttgc tgccccgaga attatgcagc atttttttgg tgtatgtggg 9660
ccccaaatga agtgcaggtc aaaccttgac agtgacgaca aatcgttggg cgggtccagg 9720
gcgaattttg cgacaacatg tcgaggctca gcaggacctg caggcatgca agctagctta 9780
ctagtgatgc atattctata gtgtcaccta aatctgcggc cgcctgcagg tcgatatggg 9840
agagctccca acgcgttgga tgcatagctt gagtattcta tagtgtcacc taaatagctt 9900
ggcgtaatca tggtcatagc tgtttcctgt gtgaaattgt tatccgctca caattccaca 9960
caacatacga gccggaagca taaagtgtaa agcctggggt gcctaatgag tgagctaact 10020
cacattaatt gcgttgcgct cactgcccgc tttccagtcg ggaaacctgt cgtgccagct 10080
gcattaatga atcggccaac gcgcggggag aggcggtttg cgtattgggg ctgagtggct 10140
ccttcaacgt tgcggttctg tcagttccaa acgtaaaacg gcttgtcccg cgtcatcggc 10200
gggggtcata acgtgactcc cttaattctc cgctcatgat cagattgtcg tttcccgcct 10260
tcagtttaaa ctatcagtgt ttgacaggat atattggcgg gtaaacctaa gagaaaagag 10320
cgtttattag aataatcgga tatttaaaag ggcgtgaaaa ggtttatccg ttcgtccatt 10380
tgtatgtgca tgccaaccac agggttcccc tcgggagtgc ttggcattcc gtgcgataat 10440
gacttctgtt caaccaccca aacgtcggaa agcctgacga cggagcagca ttccaaaaag 10500
atcccttggc tcgtctgggt cggctagaag gtcgagtggg ctgctgtggc ttgatccctc 10560
aacgcggtcg cggacgtagc gcagcgccga aaaatcctcg atcgcaaatc cgacgctgtc 10620
gaaaatcgtg atctgcttgt cgctctttcg gccgacgtcc tggccagtca tcacgcgcca 10680
aagttccgtc acaggatgat ctggcgcgag ttgctggatc tcgccttcaa tccgggtctg 10740
tggcgggaac tccacgaaaa tatccgaacg cagcaagatg tcgacggatc ttttccgctg 10800
cataaccctg cttcggggtc attatagcga ttttttcggt atatccatcc tttttcgcac 10860
gatatacagg attttgccaa agggttcgtg tagactttcc ttggtgtatc caacggcgtc 10920
agccgggcag gataggtgaa gtaggcccac ccgcgagcgg gtgttccttc ttcactgtcc 10980
cttattcgca cctggcggtg ctcaacggga atcctgctct gcgaggctgg ccggctaccg 11040
ccggcgtaac agatgagggc aagcggatgg ctgatgaaac caagccaacc aggggtgatg 11100
ctgccaactt actgatttag tgtatgatgg tgtttttgag gtgctccagt ggcttctgtt 11160
tctatcagct gtccctcctg ttcagctact gacggggtgg tgcgtaacgg caaaagcacc 11220
gccggacatc agcgctatct ctgctctcac tgccgtaaaa catggcaact gcagttcact 11280
tacaccgctt ctcaacccgg tacgcaccag aaaatcattg atatggccat gaatggcgtt 11340
ggatgccggg caacagcccg cattatgggc gttggcctca acacgatttt acgtcactta 11400
aaaaactcag gccgcagtcg gtaacctcgc gcatacagcc gggcagtgac gtcatcgtct 11460
gcgcggaaat ggacgaacag tggggctatg tcggggctaa atcgcgccag cgctggctgt 11520
tttacgcgta tgacagtctc cggaagacgg ttgttgcgca cgtattcggt gaacgcacta 11580
tggcgacgct ggggcgtctt atgagcctgc tgtcaccctt tgacgtggtg atatggatga 11640
cggatggctg gccgctgtat gaatcccgcc tgaagggaaa gctgcacgta atcagcaagc 11700
gatatacgca gcgaattgag cggcataacc tgaatctgag gcagcacctg gcacggctgg 11760
gacggaagtc gctgtcgttc tcaaaatcgg tggagctgca tgacaaagtc atcgggcatt 11820
atctgaacat aaaacactat caataagttg gagtcattac ccaaccagga agggcagccc 11880
acctatcaag gtgtactgcc ttccagacga acgaagagcg attgaggaaa aggcggcggc 11940
ggccggcatg agcctgtcgg cctacctgct ggccgtcggc cagggctaca aaatcacggg 12000
cgtcgtggac tatgagcacg tccgcgagct ggcccgcatc aatggcgacc tgggccgcct 12060
gggcggcctg ctgaaactct ggctcaccga cgacccgcgc acggcgcggt tcggtgatgc 12120
cacgatcctc gccctgctgg cgaagatcga agagaagcag gacgagcttg gcaaggtcat 12180
gatgggcgtg gtccgcccga gggcagagcc atgacttttt tagccgctaa aacggccggg 12240
gggtgcgcgt gattgccaag cacgtcccca tgcgctccat caagaagagc gacttcgcgg 12300
agctggtatt cgtgcagggc aagattcgga ataccaagta cgagaaggac ggccagacgg 12360
tctacgggac cgacttcatt gccgataagg tggattatct ggacaccaag gcaccaggcg 12420
ggtcaaatca ggaataaggg cacattgccc cggcgtgagt cggggcaatc ccgcaaggag 12480
ggtgaatgaa tcggacgttt gaccggaagg catacaggca agaactgatc gacgcggggt 12540
tttccgccga ggatgccgaa accatcgcaa gccgcaccgt catgcgtgcg ccccgcgaaa 12600
ccttccagtc cgtcggctcg atggtccagc aagctacggc caagatcgag cgcgacagcg 12660
tgcaactggc tccccctgcc ctgcccgcgc catcggccgc cgtggagcgt tcgcgtcgtc 12720
tcgaacagga ggcggcaggt ttggcgaagt cgatgaccat cgacacgcga ggaactatga 12780
cgaccaagaa gcgaaaaacc gccggcgagg acctggcaaa acaggtcagc gaggccaagc 12840
aggccgcgtt gctgaaacac acgaagcagc agatcaagga aatgcagctt tccttgttcg 12900
atattgcgcc gtggccggac acgatgcgag cgatgccaaa cgacacggcc cgctctgccc 12960
tgttcaccac gcgcaacaag aaaatcccgc gcgaggcgct gcaaaacaag gtcattttcc 13020
acgtcaacaa ggacgtgaag atcacctaca ccggcgtcga gctgcgggcc gacgatgacg 13080
aactggtgtg gcagcaggtg ttggagtacg cgaagcgcac ccctatcggc gagccgatca 13140
ccttcacgtt ctacgagctt tgccaggacc tgggctggtc gatcaatggc cggtattaca 13200
cgaaggccga ggaatgcctg tcgcgcctac aggcgacggc gatgggcttc acgtccgacc 13260
gcgttgggca cctggaatcg gtgtcgctgc tgcaccgctt ccgcgtcctg gaccgtggca 13320
agaaaacgtc ccgttgccag gtcctgatcg acgaggaaat cgtcgtgctg tttgctggcg 13380
accactacac gaaattcata tgggagaagt accgcaagct gtcgccgacg gcccgacgga 13440
tgttcgacta tttcagctcg caccgggagc cgtacccgct caagctggaa accttccgcc 13500
tcatgtgcgg atcggattcc acccgcgtga agaagtggcg cgagcaggtc ggcgaagcct 13560
gcgaagagtt gcgaggcagc ggcctggtgg aacacgcctg ggtcaatgat gacctggtgc 13620
attgcaaacg ctagggcctt gtggggtcag ttccggctgg gggttcagca gccagcgctt 13680
tactggcatt tcaggaacaa gcgggcactg ctcgacgcac ttgcttcgct cagtatcgct 13740
cgggacgcac ggcgcgctct acgaactgcc gataaacaga ggattaaaat tgacaattgt 13800
gattaaggct cagattcgac ggcttggagc ggccgacgtg caggatttcc gcgagatccg 13860
attgtcggcc ctgaagaaag ctccagagat gttcgggtcc gtttacgagc acgaggagaa 13920
aaagcccatg gaggcgttcg ctgaacggtt gcgagatgcc gtggcattcg gcgcctacat 13980
cgacggcgag atcattgggc tgtcggtctt caaacaggag gacggcccca aggacgctca 14040
caaggcgcat ctgtccggcg ttttcgtgga gcccgaacag cgaggccgag gggtcgccgg 14100
tatgctgctg cgggcgttgc cggcgggttt attgctcgtg atgatcgtcc gacagattcc 14160
aacgggaatc tggtggatgc gcatcttcat cctcggcgca cttaatattt cgctattctg 14220
gagcttgttg tttatttcgg tctaccgcct gccgggcggg gtcgcggcga cggtaggcgc 14280
tgtgcagccg ctgatggtcg tgttcatctc tgccgctctg ctaggtagcc cgatacgatt 14340
gatggcggtc ctgggggcta tttgcggaac tgcgggcgtg gcgctgttgg tgttgacacc 14400
aaacgcagcg ctagatcctg tcggcgtcgc agcgggcctg gcgggggcgg tttccatggc 14460
gttcggaacc gtgctgaccc gcaagtggca acctcccgtg cctctgctca cctttaccgc 14520
ctggcaactg gcggccggag gacttctgct cgttccagta gctttagtgt ttgatccgcc 14580
aatcccgatg cctacaggaa ccaatgttct cggcctggcg tggctcggcc tgatcggagc 14640
gggtttaacc tacttccttt ggttccgggg gatctcgcga ctcgaaccta cagttgtttc 14700
cttactgggc tttctcagcc gggatggcgc taagaagcta ttgccgccga tcttcatatg 14760
cggtgtgaaa taccgcacag atgcgtaagg agaaaatacc gcatcaggcg ctcttccgct 14820
tcctcgctca ctgactcgct gcgctcggtc gttcggctgc ggcgagcggt atcagctcac 14880
tcaaaggcgg taatacggtt atccacagaa tcaggggata acgcaggaaa gaacatgtga 14940
gcaaaaggcc agcaaaaggc caggaaccgt aaaaaggccg cgttgctggc gtttttccat 15000
aggctccgcc cccctgacga gcatcacaaa aatcgacgct caagtcagag gtggcgaaac 15060
ccgacaggac tataaagata ccaggcgttt ccccctggaa gctccctcgt gcgctctcct 15120
gttccgaccc tgccgcttac cggatacctg tccgcctttc tcccttcggg aagcgtggcg 15180
ctttctcaat gctcacgctg taggtatctc agttcggtgt aggtcgttcg ctccaagctg 15240
ggctgtgtgc acgaaccccc cgttcagccc gaccgctgcg ccttatccgg taactatcgt 15300
cttgagtcca acccggtaag acacgactta tcgccactgg cagcagccac tggtaacagg 15360
attagcagag cgaggtatgt aggcggtgct acagagttct tgaagtggtg gcctaactac 15420
ggctacacta gaaggacagt atttggtatc tgcgctctgc tgaagccagt taccttcgga 15480
aaaagagttg gtagctcttg atccggcaaa caaaccaccg ctggtagcgg tggttttttt 15540
gtttgcaagc agcagattac gcgcagaaaa aaaggatatc aagaagatcc tttgatcttt 15600
tctacggggt ctgacgctca gtggaacgaa aactcacgtt aagggatttt ggtcatgaga 15660
ttatcaaaaa ggatcttcac ctagatcctt ttaaattaaa aatgaagttt taaatcaatc 15720
taaagtatat atgagtaaac ttggtctgac agttaccaat gcttaatcag tgaggcacct 15780
atctcagcga tctgtctatt tcgttcatcc atagttgcct gactccccgt cgtgtagata 15840
actacgatac gggagggctt accatctggc cccagtgctg caatgatacc gcgagaccca 15900
cgctcaccgg ctccagattt atcagcaata aaccagccag ccggaagggc cgagcgcaga 15960
agtggtcctg caactttatc cgcctccatc cagtctatta aacaagtggc agcaacggat 16020
tcgcaaacct gtcacgcctt ttgtgccaaa agccgcgcca ggtttgcgat ccgctgtgcc 16080
aggcgttagg cgtcatatga agatttcggt gatccctgag caggtggcgg aaacattgga 16140
tgctgagaac catttcattg ttcgtgaagt gttcgatgtg cacctatccg accaaggctt 16200
tgaactatct accagaagtg tgagccccta ccggaaggat tacatctcgg atgatgactc 16260
tgatgaagac tctgcttgct atggcgcatt catcgaccaa gagcttgtcg ggaagattga 16320
actcaactca acatggaacg atctagcctc tatcgaacac attgttgtgt cgcacacgca 16380
ccgaggcaaa ggagtcgcgc acagtctcat cgaatttgcg aaaaagtggg cactaagcag 16440
acagctcctt ggcatacgat tagagacaca aacgaacaat gtacctgcct gcaatttgta 16500
cgcaaaatgt ggctttactc tcggcggcat tgacctgttc acgtataaaa ctagacctca 16560

-continued

```
agtctcgaac gaaacagcga tgtactggta ctggttctcg ggagcacagg atgacgccta  16620
acaattcatt caagccgaca ccgcttcgcg gcgcggctta attcaggagt taaacatcat  16680
gagggaagcg gtgatcgccg aagtatcgac tcaactatca gaggtagttg gcgtcatcga  16740
gcgccatctc gaaccgacgt tgctggccgt acatttgtac ggctccgcag tggatggcgg  16800
cctgaagcca cacagtgata ttgatttgct ggttacggtg accgtaaggc ttgatgaaac  16860
aacgcggcga gctttgatca acgacctttt ggaaacttcg gcttcccctg gagagagcga  16920
gattctccgc gctgtagaag tcaccattgt tgtgcacgac gacatcattc cgtggcgtta  16980
tccagctaag cgcgaactgc aatttggaga atggcagcgc aatgacattc ttgcaggtat  17040
cttcgagcca gccacgatcg acattgatct ggctatcttg ctgacaaaag caagagaaca  17100
tagcgttgcc ttggtaggtc cagcggcgga ggaactcttt gatccggttc ctgaacagga  17160
tctatttgag gcgctaaatg aaaccttaac gctatggaac tcgccgcccg actgggctgg  17220
cgatgagcga aatgtagtgc ttacgttgtc ccgcatttgg tacagcgcag taaccggcaa  17280
aatcgcgccg aaggatgtcg ctgccgactg ggcaatggag cgcctgccgg cccagtatca  17340
gcccgtcata cttgaagcta ggcaggctta tcttggacaa gaagatcgct tggcctcgcg  17400
cgcagatcag ttggaagaat ttgttcacta cgtgaaaggc gagatcacca aggtagtcgg  17460
caaataatgt ctaacaattc gttcaagccg acgccgcttc gcggcgcggc ttaactcaag  17520
cgttagagag ctggggaaga ctatgcgcga tctgttgaag gtggttctaa gcctcgtact  17580
tgcgatggca tcggggcagg cacttgctga cctgccaatt gttttagtgg atgaagctcg  17640
tcttccctat gactactccc catccaacta cgacatttct ccaagcaact acgacaactc  17700
cataagcaat tacgacaata gtccatcaaa ttacgacaac tctgagagca actacgataa  17760
tagttcatcc aattacgaca atagtcgcaa cggaaatcgt aggcttatat atagcgcaaa  17820
tgggtctcgc actttcgccg gctactacgt cattgccaac aatgggacaa cgaacttctt  17880
ttccacatct ggcaaaagga tgttctacac cccaaaaggg gggcgcggcg tctatggcgg  17940
caaagatggg agcttctgcg gggcattggt cgtcataaat ggccaatttt cgcttgccct  18000
gacagataac ggcctgaaga tcatgtatct aagcaactag cctgctctct aataaaatgt  18060
taggagcttg gctgccattt ttggggtgag gccgttcgcg gccgaggggc gcagcccctg  18120
gggggatggg aggcccgcgt tagcgggccg ggagggttcg agaagggggg gcacccccct  18180
tcggcgtgcg cggtcacgcg ccagggcgca gccctggtta aaaacaaggt ttataaatat  18240
tggtttaaaa gcaggttaaa agacaggtta gcggtggccg aaaaacgggc ggaaaccctt  18300
gcaaatgctg gattttctgc ctgtggacag cccctcaaat gtcaataggt gcgcccctca  18360
tctgtcagca ctctgcccct caagtgtcaa ggatcgcgcc cctcatctgt cagtagtcgc  18420
gcccctcaag tgtcaatacc gcagggcact tatccccagg cttgtccaca tcatctgtgg  18480
gaaactcgcg taaaatcagg cgttttcgcc gatttgcgag gctggccagc tccacgtcgc  18540
cggccgaaat cgagcctgcc cctcatctgt caacgccgcg ccgggtgagt cggcccctca  18600
agtgtcaacg tccgcccctc atctgtcagt gagggccaag ttttccgcga ggtatccaca  18660
acgccggcgg ccggccgcgg tgtctcgcac acggcttcga cggcgtttct ggcgcgtttg  18720
cagggccata gacggccgcc agcccagcgg cgagggcaac cagcccggtg agcgtcggaa  18780
aggg                                                                18784
```

<210> SEQ ID NO 27
<211> LENGTH: 18784

```
<212> TYPE: DNA
<213> ORGANISM: Artificial Sequence
<220> FEATURE:
<223> OTHER INFORMATION: Synthetic vector

<400> SEQUENCE: 27
tcgacatcgt caacgttcac ttctaaagaa atagcgccac tcagcttcct cagcggcttt     60
atccagcgat ttcctattat gtcggcatag ttctcaagat cgacagcctg tcacggttaa    120
gcgagaaatg aataagaagg ctgataattc ggatctctgc gaggagatga tatttgatca    180
caggcagcaa cgctctgtca tcgttacaat caacatgcta ccctccgcga gatcatccgt    240
gtttcaaacc cggcagctta gttgccgttc ttccgaatag catcgggtaa catgagcaaa    300
gtctgccgcc ttacaacggc tctcccgctg acgccgtccc ggactgatgg gctgcctgta    360
tcgagtggtg attttgtgcc gagctgccgg tcggggagct gttggctggc tggtggcagg    420
atatattgtg gtgtaaacaa attgacgctt agacaactta ataacacatt gcggacgttt    480
ttaatgtact gaattcgccg ctcggtgtgt cgtagatact agcccctggg gcacttttga    540
aatttgaata agatttatgt aatcagtctt ttaggtttga ccggttctgc cgcttttttt    600
aaaattggat ttgtaataat aaaacgcaat tgtttgttat tgtggcgctc tatcatagat    660
gtcgctataa acctattcag cacaatatat tgttttcatt ttaatattgt acatataagt    720
agtagggtac aatcagtaaa ttgaacggag aatattattc ataaaaatac gatagtaacg    780
ggtgatatat tcattagaat gaaccgaaac cggcggtaag gatctgagct acacatgctc    840
aggtttttta caacgtgcac aacagaattg aaagcaaata tcatgcgatc ataggcgtct    900
cgcatatctc attaaacaag tgaagatttg attcaaactc cattgagagc cctgactatg    960
cattcggttt gacccttcca ggttgagaga cgatagcccc ctaccttaat taaggggccc   1020
cccctcgagg tcgacggtat cgataagctt gatatcgaat tcctgcagcc agggggatcc   1080
cccgggtcat cagatctcgg tgacgggcag gaccggacgg ggcggtaccg gcaggctgaa   1140
gtccagctgc cagaaaccca cgtcatgcca gttcccgtgc ttgaagccgg ccgcccgcag   1200
catgccgcgg ggggcatatc cgagcgcctc gtgcatgcgc acgctcgggt cgttgggcag   1260
cccgatgaca gcgaccacgc tcttgaagcc ctgtgcctcc agggacttca gcaggtgggt   1320
gtagagcgtg gagcccagtc ccgtccgctg gtggcggggg gagacgtaca cggtcgactc   1380
ggccgtccag tcgtaggcgt tgcgtgcctt ccaggggccc gcgtaggcga tgccggcgac   1440
ctcgccgtcc acctcggcga cgagccaggg atagcgctcc cgcagacgga cgaggtcgtc   1500
cgtccactcc tgcggttcct gcggctcggt acggaagttg accgtgcttg tctcgatgta   1560
gtggttgacg atggtgcaga ccgccggcat gtccgcctcg gtggcacggc ggatgtcggc   1620
cgggcgtcgt tctgggctca tggtagatcc cctcgagaga gatagatttg tagagagaga   1680
ctggtgattt cagcgtgtcc tctccaaatg aaatgaactt ccttatatag aggaaggtct   1740
tgcgaaggat agtgggattg tgcgtcatcc cttacgtcag tggagatatc acatcaatcc   1800
acttgctttg aagacgtggt tggaacgtct tctttttcca cgatgctcct cgtgggtggg   1860
ggtccatctt tgggaccact gtcggcagag gcatcttgaa cgatagcctt tcctttatcg   1920
caatgatggc atttgtaggt gccaccttcc ttttctactg tccttttgat gaagtgacag   1980
atagctgggc aatggaatcc gaggaggttt cccgatatta ccctttgttg aaaagtctca   2040
atagcccttt ggtcttctga gactgtatct ttgatattct tggagtagac gagagtgtcg   2100
tgctccacca tgttatcaca tcaatccact tgctttgaag acgtggttgg aacgtcttct   2160
```

-continued

```
ttttccacga tgctcctcgt gggtgggggt ccatctttgg gaccactgtc ggcagaggca   2220
tcttgaacga tagcctttcc tttatcgcaa tgatggcatt tgtaggtgcc accttccttt   2280
tctactgtcc ttttgatgaa gtgacagata gctgggcaat ggaatccgag gaggtttccc   2340
gatattaccc tttgttgaaa agtctcaata gccctttggt cttctgagac tgtatctttg   2400
atattcttgg agtagacgag agtgtcgtgc tccaccatgt tgctgatagt gaccttaggc   2460
gacttttgaa cgcgcaataa tggtttctga cgtatgtgct tagctcatta aactccagaa   2520
acccattaac gcttacaatt tccattcgcc attcaggctg cgcaactgtt gggaagggcg   2580
atcggtgcgg gcctcttcgc tattacgcca gctggcgaaa gggggatgtg ctgcaaggcg   2640
attaagttgg gtaacgccag ggttttccca gtcacgacgt tgtaaaacga cggccagtga   2700
attgtaatac gactcactat agggcgaatt gggcccgacg tcgcatgctc ccggccgcca   2760
tggccgcggg atatcactag tgcggccgct cgacgaatta attccaatcc cacaaaaatc   2820
tgagcttaac agcacagttg ctcctctcag agcagaatcg ggtattcaac accctcatat   2880
caactactac gttgtgtata acggtccaca tgccggtata tacgatgact ggggttgtac   2940
aaaggcggca acaaacggcg ttcccggagt tgcacacaag aaatttgcca ctattacaga   3000
ggcaagagca gcagctgacg cgtacacaac aagtcagcaa acagacaggt tgaacttcat   3060
ccccaaagga gaagctcaac tcaagcccaa gagctttgct aaggccctaa caagcccacc   3120
aaagcaaaaa gcccactggc tcacgctagg aaccaaaagg cccagcagtg atccagcccc   3180
aaaagagatc tcctttgccc cggagattac aatggacgat ttcctctatc tttacgatct   3240
aggaaggaag ttcgaaggtg aaggtgacga cactatgttc accactgata atgagaaggt   3300
tagcctcttc aatttcagaa agaatgctga cccacagatg gttagagagg cctacgcagc   3360
aggtctcatc aagacgatct acccgagtaa caatctccag gagatcaaat accttcccaa   3420
gaaggttaaa gatgcagtca aaagattcag gactaattgc atcaagaaca cagagaaaga   3480
catatttctc aagatcagaa gtactattcc agtatggacg attcaaggct tgcttcataa   3540
accaaggcaa gtaatagaga ttggagtctc taaaaaggta gttcctactg aatctaaggc   3600
catgcatgga gtctaagatt caaatcgagg atctaacaga actcgccgtg aagactggcg   3660
aacagttcat acagagtctt ttacgactca atgacaagaa gaaaatcttc gtcaacatgg   3720
tggagcacga cactctggtc tactccaaaa atgtcaaaga tacagtctca gaagaccaaa   3780
gggctattga gacttttcaa caaaggataa tttcgggaaa cctcctcgga ttccattgcc   3840
cagctatctg tcacttcatc gaaaggacag tagaaaagga aggtggctcc tacaaatgcc   3900
atcattgcga taaaggaaag gctatcattc aagatctctc tgccgacagt ggtcccaaag   3960
atggaccccc acccacgagg agcatcgtgg aaaaagaaga cgttccaacc acgtcttcaa   4020
agcaagtgga ttgatgtgac atctccactg acgtaaggga tgacgcacaa tcccactatc   4080
cttcgcaaga cccttcctct atataaggaa gttcatttca tttggagagg acacgctcga   4140
ggaattcggt accccatcac aagtttgtac aaaaaagcag gctgcggccg cttgctccct   4200
taaaaaaaac catggcatgt cattacggac aacagcaaca gactagagca cctcatcttc   4260
agcttcaacc tagagcacag agagttgtga aggctgctac tgctgttact gtaaatttct   4320
gtgttcctta ttctctcaaa atcttcgatt ttgttttcgt tcgatcccaa tttcgtatat   4380
gttctttggt ttagattctg ttaatcttag atcgaagacg attttctggg tttgatcgtt   4440
agatatcatc ttaattctcg attagggttt catagatatc atccgatttg ttcaaataat   4500
ttgagttttg tcgaataatt actcttcgat ttgtgatttc tatctagatc tggtgttagt   4560
```

-continued

```
ttctagtttg tgcgatcgaa tttgtcgatt aatctgagtt tttctgatta acaggctgga   4620
ggatctcttc ttgttctctc tggacttact ctcgctggaa ctgttatcgc tctcactatc   4680
gctacacctc ttctcgttat cttctctcct gttctcgttc ctgctgtgat cactatcttc   4740
cttctcggag ctggatttct tgcttctggt ggatttggag ttgctgctct ctctgttctc   4800
tcttggatct acagatacct cactggaaaa catcctccag gtgctgatca acttgagtct   4860
gctaagacta agctcgcttc taaggctaga gagatgaagg atagagcaga gcaattctct   4920
tgtcagcctg ttgctggatc tcagacttct taatgaacat atggtcctgc tttaatgaga   4980
tatgcgagac gcctatgatc gcatgatatt tgctttcaat tctgttgtgc acgttgtaaa   5040
aaacctgagc atgtgtagct cagatcctta ccgccggttt cggttcattc taatgaatat   5100
atcacccgtt actatcgtat ttttatgaat aatattctcc gttcaattta ctgattgtac   5160
cctactactt atatgtacaa tattaaaatg aaaacaatat attgtgctga ataggtttat   5220
agcgacatct atgatagagc gccacaataa caaacaattg cgttttatta ttacaaatcc   5280
aattttaaaa aaagcggcag aaccggtcaa acctaaaaga ctgattacat aaatcttatt   5340
caaatttcaa aaggccccag gggctagtat ctacgacaca ccgagcggcg aactaataac   5400
gttcactgaa gggaactccg gttccccgcc ggcgcgcatg ggtgagattc cttgaagttg   5460
agtattggcc gtccgctcta ccgaaagtta cgggcaccat tcaacccggt ccagcacggc   5520
ggccgggtaa ccgacttgct gccccgagaa ttatgcagca ttttttggt gtatgtgggc   5580
cccaaatgaa gtgcaggtca aaccttgaca gtgacgacaa atcgttgggc gggtccaggg   5640
cgaattttgc gacaacatgt cgaggctcag caggacctgc aggcatgcaa gctagcttac   5700
tagtgatgca tattctatag tgtcacctaa atcttcgacg aattaattcc aatcccacaa   5760
aaatctgagc ttaacagcac agttgctcct ctcagagcag aatcgggtat tcaacaccct   5820
catatcaact actacgttgt gtataacggt ccacatgccg gtatatacga tgactggggt   5880
tgtacaaagg cggcaacaaa cggcgttccc ggagttgcac acaagaaatt tgccactatt   5940
acagaggcaa gagcagcagc tgacgcgtac acaacaagtc agcaaacaga caggttgaac   6000
ttcatcccca aaggagaagc tcaactcaag cccaagagct ttgctaaggc cctaacaagc   6060
ccaccaaagc aaaaagccca ctggctcacg ctaggaacca aaaggcccag cagtgatcca   6120
gccccaaaag agatctcctt tgccccggag attacaatgg acgatttcct ctatctttac   6180
gatctaggaa ggaagttcga aggtgaaggt gacgacacta tgttcaccac tgataatgag   6240
aaggttagcc tcttcaattt cagaaagaat gctgacccac agatggttag agaggcctac   6300
gcagcaggtc tcatcaagac gatctacccg agtaacaatc tccaggagat caaatacctt   6360
cccaagaagg ttaaagatgc agtcaaaaga ttcaggacta attgcatcaa gaacacagag   6420
aaagacatat ttctcaagat cagaagtact attccagtat ggacgattca aggcttgctt   6480
cataaaccaa ggcaagtaat agagattgga gtctctaaaa aggtagttcc tactgaatct   6540
aaggccatgc atggagtcta agattcaaat cgaggatcta acagaactcg ccgtgaagac   6600
tggcgaacag ttcatacaga gtcttttacg actcaatgac aagaagaaaa tcttcgtcaa   6660
catggtggag cacgacactc tggtctactc caaaaatgtc aaagatacag tctcagaaga   6720
ccaaagggct attgagactt ttcaacaaag gataatttcg ggaaacctcc tcggattcca   6780
ttgcccagct atctgtcact tcatcgaaag gacagtagaa aaggaaggtg gctcctacaa   6840
atgccatcat tgcgataaag gaaaggctat cattcaagat ctctctgccg acagtggtcc   6900
```

-continued

```
caaagatgga cccccaccca cgaggagcat cgtggaaaaa gaagacgttc caaccacgtc   6960
ttcaaagcaa gtggattgat gtgacatctc cactgacgta agggatgacg cacaatccca   7020
ctatccttcg caagaccctt cctctatata aggaagttca tttcatttgg agaggacacg   7080
ggatccttgc tccgttaaaa aaaaccatgg ctatcctcga ttctgctggt gttactactg   7140
tgactgagaa tggtggtgga gagttcgttg atctcgatag actcagaaga agaaagtcta   7200
gatctgtaaa tttctgtgtt ccttattctc tcaaaatctt cgattttgtt ttcgttcgat   7260
cccaatttcg tatatgttct ttggtttaga ttctgttaat cttagatcga agacgatttt   7320
ctgggtttga tcgttagata tcatcttaat tctcgattag ggtttcatag atatcatccg   7380
atttgttcaa ataatttgag ttttgtcgaa taattactct tcgatttgtg atttctatct   7440
agatctggtg ttagtttcta gtttgtgcga tcgaatttgt cgattaatct gagtttttct   7500
gattaacagg attcttctaa cggacttctc ctctctggat ctgataacaa ctctccttct   7560
gatgatgttg gtgctcctgc tgatgtgaga gatagaatcg attctgtggt gaacgatgat   7620
gctcaaggta ctgctaacct cgctggtgat aataacggtg gaggtgataa caatggtgga   7680
ggaagaggtg gaggtgaagg tagaggaaac gctgatgcta ctttcactta cagaccatct   7740
gtgcctgctc atagaagagc tagagagtct cctctctctt ctgatgctat cttcaagcag   7800
tctcacgctg gacttttcaa cctctgtgtg gtggttctta tcgctgtgaa ctctagactc   7860
atcatcgaga acctcatgaa gtacggatgg ctcatcagaa ctgatttctg gttctcttct   7920
agatctctca gagattggcc tcttttcatg tgctgcatct cactctcaat cttccctctc   7980
gctgctttta ctgttgagaa gctcgtgctc cagaagtata tcgctgaacc tgtggtgatc   8040
ttcctccaca tcatcatcac tatgactgag gttctctacc ctgtttacgt gactctcaga   8100
tgcgattctg ctttcctctc tggtgttact cttatgctcc tcacttgcat tgtgtggctt   8160
aagctcgtgt cttacgctca cacttcttac gatatcagat ctctcgctaa cgctgctgat   8220
aaggctaacc ctgaagtgtc ttactacgtg tctctcaagt ctctcgctta cttcatggtt   8280
gctcctacac tttgttacca gccatcttac cctagatctg cttgcattag aaagggatgg   8340
gtggcaagac aattcgctaa gttggtgatc ttcactggat tcatgggatt catcatcgag   8400
cagtacatca accctattgt gagaaactct aagcaccctc tcaagggtga tcttctctac   8460
gctatcgaga gagttcttaa gctctctgtg cctaaccttt atgtgtggct ctgcatgttc   8520
tactgtttct tccacctctg gcttaacatc cttgctgagt tgctttgctt cggagataga   8580
gagttctaca aggattggtg gaacgctaag tctgttggag attattggag aatgtggaac   8640
atgcctgtgc ataagtggat ggtgcgtcac atctacttcc cttgcctcag atctaagatc   8700
cctaagactc tcgctatcat tatcgctttc ctcgtgtctg ctgttttcca tgagttgtgt   8760
atcgctgttc cttgcagact tttcaagctt tgggctttcc tcggaatcat gttccaggtt   8820
ccactcgtgt tcatcactaa ctacctccaa gagagattcg gatctactgt tggaaacatg   8880
attttctggt tcattttctg catcttcgga cagcctatgt gcgttctcct ctactaccac   8940
gatctcatga acagaaaggg atctatgtct taatgaagga tccacccagc tttcttgtac   9000
aaagtggtga tgggttcgaa atcgataagc ttggatcctc tagagtcctg ctttaatgag   9060
atatgcgaga cgcctatgat cgcatgatat ttgctttcaa ttctgttgtg cacgttgtaa   9120
aaaacctgag catgtgtagc tcagatcctt accgccggtt tcggttcatt ctaatgaata   9180
tatcacccgt tactatcgta tttttatgaa taatattctc cgttcaattt actgattgta   9240
ccctactact tatatgtaca atattaaaat gaaaacaata tattgtgctg aataggttta   9300
```
tagcgacatc tatgatagag cgccacaata acaaacaatt gcgttttatt attacaaatc 9360
caattttaaa aaaagcggca gaaccggtca aacctaaaag actgattaca taaatcttat 9420
tcaaatttca aaaggcccca ggggctagta tctacgacac accgagcggc gaactaataa 9480
cgttcactga agggaactcc ggttccccgc cggcgcgcat gggtgagatt ccttgaagtt 9540
gagtattggc cgtccgctct accgaaagtt acgggcacca ttcaacccgg tccagcacgg 9600
cggccgggta accgacttgc tgccccgaga attatgcagc atttttttgg tgtatgtggg 9660
ccccaaatga agtgcaggtc aaaccttgac agtgacgaca aatcgttggg cgggtccagg 9720
gcgaattttg cgacaacatg tcgaggctca gcaggacctg caggcatgca agctagctta 9780
ctagtgatgc atattctata gtgtcaccta aatctgcggc cgcctgcagg tcgatatggg 9840
agagctccca acgcgttgga tgcatagctt gagtattcta tagtgtcacc taaatagctt 9900
ggcgtaatca tggtcatagc tgtttcctgt gtgaaattgt tatccgctca caattccaca 9960
caacatacga gccggaagca taaagtgtaa agcctggggt gcctaatgag tgagctaact 10020
cacattaatt gcgttgcgct cactgcccgc tttccagtcg ggaaacctgt cgtgccagct 10080
gcattaatga atcggccaac gcgcggggag aggcggtttg cgtattgggg ctgagtggct 10140
ccttcaacgt tgcggttctg tcagttccaa acgtaaaacg gcttgtcccg cgtcatcggc 10200
gggggtcata acgtgactcc cttaattctc cgctcatgat cagattgtcg tttcccgcct 10260
tcagtttaaa ctatcagtgt ttgacaggat atattggcgg gtaaacctaa gagaaaagag 10320
cgtttattag aataatcgga tatttaaaag ggcgtgaaaa ggtttatccg ttcgtccatt 10380
tgtatgtgca tgccaaccac agggttcccc tcgggagtgc ttggcattcc gtgcgataat 10440
gacttctgtt caaccaccca aacgtcggaa agcctgacga cggagcagca ttccaaaaag 10500
atcccttggc tcgtctgggt cggctagaag gtcgagtggg ctgctgtggc ttgatccctc 10560
aacgcggtcg cggacgtagc gcagcgccga aaaatcctcg atcgcaaatc cgacgctgtc 10620
gaaaatcgtg atctgcttgt cgctctttcg gccgacgtcc tggccagtca tcacgcgcca 10680
aagttccgtc acaggatgat ctggcgcgag ttgctggatc tcgccttcaa tccgggtctg 10740
tggcgggaac tccacgaaaa tatccgaacg cagcaagatg tcgacggatc ttttccgctg 10800
cataaccctg cttcggggtc attatagcga ttttttcggt atatccatcc tttttcgcac 10860
gatatacagg attttgccaa agggttcgtg tagactttcc ttggtgtatc caacggcgtc 10920
agccgggcag gataggtgaa gtaggcccac ccgcgagcgg gtgttccttc ttcactgtcc 10980
cttattcgca cctggcggtg ctcaacggga atcctgctct gcgaggctgg ccggctaccg 11040
ccggcgtaac agatgagggc aagcggatgg ctgatgaaac caagccaacc aggggtgatg 11100
ctgccaactt actgatttag tgtatgatgg tgtttttgag gtgctccagt ggcttctgtt 11160
tctatcagct gtccctcctg ttcagctact gacggggtgg tgcgtaacgg caaaagcacc 11220
gccggacatc agcgctatct ctgctctcac tgccgtaaaa catggcaact gcagttcact 11280
tacaccgctt ctcaacccgg tacgcaccag aaaatcattg atatggccat gaatggcgtt 11340
ggatgccggg caacagcccg cattatgggc gttggcctca acacgatttt acgtcactta 11400
aaaaactcag gccgcagtcg gtaacctcgc gcatacagcc gggcagtgac gtcatcgtct 11460
gcgcggaaat ggacgaacag tggggctatg tcggggctaa atcgcgccag cgctggctgt 11520
tttacgcgta tgacagtctc cggaagacgg ttgttgcgca cgtattcggt gaacgcacta 11580
tggcgacgct ggggcgtctt atgagcctgc tgtcaccctt tgacgtggtg atatggatga 11640

-continued

```
cggatggctg gccgctgtat gaatcccgcc tgaagggaaa gctgcacgta atcagcaagc  11700
gatatacgca gcgaattgag cggcataacc tgaatctgag gcagcacctg gcacggctgg  11760
gacggaagtc gctgtcgttc tcaaaatcgg tggagctgca tgacaaagtc atcgggcatt  11820
atctgaacat aaaacactat caataagttg gagtcattac ccaaccagga agggcagccc  11880
acctatcaag gtgtactgcc ttccagacga acgaagagcg attgaggaaa aggcggcggc  11940
ggccggcatg agcctgtcgg cctacctgct ggccgtcggc cagggctaca aaatcacggg  12000
cgtcgtggac tatgagcacg tccgcgagct ggcccgcatc aatggcgacc tgggccgcct  12060
gggcggcctg ctgaaactct ggctcaccga cgacccgcgc acggcgcggt tcggtgatgc  12120
cacgatcctc gccctgctgg cgaagatcga agagaagcag gacgagcttg gcaaggtcat  12180
gatgggcgtg gtccgcccga gggcagagcc atgacttttt tagccgctaa aacggccggg  12240
gggtgcgcgt gattgccaag cacgtcccca tgcgctccat caagaagagc gacttcgcgg  12300
agctggtatt cgtgcagggc aagattcgga ataccaagta cgagaaggac ggccagacgg  12360
tctacgggac cgacttcatt gccgataagg tggattatct ggacaccaag gcaccaggcg  12420
ggtcaaatca ggaataaggg cacattgccc cggcgtgagt cggggcaatc ccgcaaggag  12480
ggtgaatgaa tcggacgttt gaccggaagg catacaggca agaactgatc gacgcggggt  12540
tttccgccga ggatgccgaa accatcgcaa gccgcaccgt catgcgtgcg ccccgcgaaa  12600
ccttccagtc cgtcggctcg atggtccagc aagctacggc caagatcgag cgcgacagcg  12660
tgcaactggc tccccctgcc ctgcccgcgc catcggccgc cgtggagcgt tcgcgtcgtc  12720
tcgaacagga ggcggcaggt ttggcgaagt cgatgaccat cgacacgcga ggaactatga  12780
cgaccaagaa gcgaaaaacc gccggcgagg acctggcaaa acaggtcagc gaggccaagc  12840
aggccgcgtt gctgaaacac acgaagcagc agatcaagga aatgcagctt tccttgttcg  12900
atattgcgcc gtggccggac acgatgcgag cgatgccaaa cgacacggcc cgctctgccc  12960
tgttcaccac gcgcaacaag aaaatcccgc gcgaggcgct gcaaaacaag gtcattttcc  13020
acgtcaacaa ggacgtgaag atcacctaca ccggcgtcga gctgcgggcc gacgatgacg  13080
aactggtgtg gcagcaggtg ttggagtacg cgaagcgcac ccctatcggc gagccgatca  13140
ccttcacgtt ctacgagctt tgccaggacc tgggctggtc gatcaatggc cggtattaca  13200
cgaaggccga ggaatgcctg tcgcgcctac aggcgacggc gatgggcttc acgtccgacc  13260
gcgttgggca cctggaatcg gtgtcgctgc tgcaccgctt ccgcgtcctg gaccgtggca  13320
agaaaacgtc ccgttgccag gtcctgatcg acgaggaaat cgtcgtgctg tttgctggcg  13380
accactacac gaaattcata tgggagaagt accgcaagct gtcgccgacg gcccgacgga  13440
tgttcgacta tttcagctcg caccgggagc cgtacccgct caagctggaa accttccgcc  13500
tcatgtgcgg atcggattcc acccgcgtga agaagtggcg cgagcaggtc ggcgaagcct  13560
gcgaagagtt gcgaggcagc ggcctggtgg aacacgcctg ggtcaatgat gacctggtgc  13620
attgcaaacg ctagggcctt gtggggtcag ttccggctgg gggttcagca gccagcgctt  13680
tactggcatt tcaggaacaa gcgggcactg ctcgacgcac ttgcttcgct cagtatcgct  13740
cgggacgcac ggcgcgctct acgaactgcc gataaacaga ggattaaaat tgacaattgt  13800
gattaaggct cagattcgac ggcttggagc ggccgacgtg caggatttcc gcgagatccg  13860
attgtcggcc ctgaagaaag ctccagagat gttcgggtcc gtttacgagc acgaggagaa  13920
aaagcccatg gaggcgttcg ctgaacggtt gcgagatgcc gtggcattcg gcgcctacat  13980
cgacggcgag atcattgggc tgtcggtctt caaacaggag gacggcccca aggacgctca  14040
```
caaggcgcat ctgtccggcg ttttcgtgga gcccgaacag cgaggccgag ggtcgccgg 14100 tatgctgctg cgggcgttgc cggcgggttt attgctcgtg atgatcgtcc gacagattcc 14160
aacgggaatc tggtggatgc gcatcttcat cctcggcgca cttaatattt cgctattctg 14220
gagcttgttg tttatttcgg tctaccgcct gccgggcggg gtcgcggcga cggtaggcgc 14280
tgtgcagccg ctgatggtcg tgttcatctc tgccgctctg ctaggtagcc cgatacgatt 14340
gatggcggtc ctgggggcta tttgcggaac tgcgggcgtg gcgctgttgg tgttgacacc 14400
aaacgcagcg ctagatcctg tcggcgtcgc agcgggcctg gcgggggcgg tttccatggc 14460
gttcggaacc gtgctgaccc gcaagtggca acctcccgtg cctctgctca cctttaccgc 14520
ctggcaactg gcggccggag gacttctgct cgttccagta gctttagtgt ttgatccgcc 14580
aatcccgatg cctacaggaa ccaatgttct cggcctggcg tggctcggcc tgatcggagc 14640
gggtttaacc tacttccttt ggttccgggg gatctcgcga ctcgaaccta cagttgtttc 14700
cttactgggc tttctcagcc gggatggcgc taagaagcta ttgccgccga tcttcatatg 14760
cggtgtgaaa taccgcacag atgcgtaagg agaaaatacc gcatcaggcg ctcttccgct 14820
tcctcgctca ctgactcgct gcgctcggtc gttcggctgc ggcgagcggt atcagctcac 14880
tcaaaggcgg taatacggtt atccacagaa tcaggggata acgcaggaaa gaacatgtga 14940
gcaaaaggcc agcaaaaggc caggaaccgt aaaaaggccg cgttgctggc gtttttccat 15000
aggctccgcc cccctgacga gcatcacaaa aatcgacgct caagtcagag gtggcgaaac 15060
ccgacaggac tataaagata ccaggcgttt ccccctggaa gctccctcgt gcgctctcct 15120
gttccgaccc tgccgcttac cggatacctg tccgcctttc tcccttcggg aagcgtggcg 15180
ctttctcaat gctcacgctg taggtatctc agttcggtgt aggtcgttcg ctccaagctg 15240
ggctgtgtgc acgaaccccc cgttcagccc gaccgctgcg ccttatccgg taactatcgt 15300
cttgagtcca acccggtaag acacgactta tcgccactgg cagcagccac tggtaacagg 15360
attagcagag cgaggtatgt aggcggtgct acagagttct tgaagtggtg gcctaactac 15420
ggctacacta gaaggacagt atttggtatc tgcgctctgc tgaagccagt taccttcgga 15480
aaaagagttg gtagctcttg atccggcaaa caaaccaccg ctggtagcgg tggttttttt 15540
gtttgcaagc agcagattac gcgcagaaaa aaaggatatc aagaagatcc tttgatcttt 15600
tctacggggt ctgacgctca gtggaacgaa aactcacgtt aagggatttt ggtcatgaga 15660
ttatcaaaaa ggatcttcac ctagatcctt ttaaattaaa aatgaagttt taaatcaatc 15720
taaagtatat atgagtaaac ttggtctgac agttaccaat gcttaatcag tgaggcacct 15780
atctcagcga tctgtctatt tcgttcatcc atagttgcct gactccccgt cgtgtagata 15840
actacgatac gggagggctt accatctggc cccagtgctg caatgatacc gcgagaccca 15900
cgctcaccgg ctccagattt atcagcaata aaccagccag ccggaagggc cgagcgcaga 15960
agtggtcctg caactttatc cgcctccatc cagtctatta aacaagtggc agcaacggat 16020
tcgcaaacct gtcacgcctt ttgtgccaaa agccgcgcca ggtttgcgat ccgctgtgcc 16080
aggcgttagg cgtcatatga agatttcggt gatccctgag caggtggcgg aaacattgga 16140
tgctgagaac catttcattg ttcgtgaagt gttcgatgtg cacctatccg accaaggctt 16200
tgaactatct accagaagtg tgagccccta ccggaaggat tacatctcgg atgatgactc 16260
tgatgaagac tctgcttgct atggcgcatt catcgaccaa gagcttgtcg ggaagattga 16320
actcaactca acatggaacg atctagcctc tatcgaacac attgttgtgt cgcacacgca 16380

```
ccgaggcaaa ggagtcgcgc acagtctcat cgaatttgcg aaaaagtggg cactaagcag  16440
acagctcctt ggcatacgat tagagacaca aacgaacaat gtacctgcct gcaatttgta  16500
cgcaaaatgt ggctttactc tcggcggcat tgacctgttc acgtataaaa ctagacctca  16560
agtctcgaac gaaacagcga tgtactggta ctggttctcg ggagcacagg atgacgccta  16620
acaattcatt caagccgaca ccgcttcgcg gcgcggctta attcaggagt taaacatcat  16680
gagggaagcg gtgatcgccg aagtatcgac tcaactatca gaggtagttg gcgtcatcga  16740
gcgccatctc gaaccgacgt tgctggccgt acatttgtac ggctccgcag tggatggcgg  16800
cctgaagcca cacagtgata ttgatttgct ggttacggtg accgtaaggc ttgatgaaac  16860
aacgcggcga gctttgatca acgacctttt ggaaacttcg gcttcccctg gagagagcga  16920
gattctccgc gctgtagaag tcaccattgt tgtgcacgac gacatcattc cgtggcgtta  16980
tccagctaag cgcgaactgc aatttggaga atggcagcgc aatgacattc ttgcaggtat  17040
cttcgagcca gccacgatcg acattgatct ggctatcttg ctgacaaaag caagagaaca  17100
tagcgttgcc ttggtaggtc cagcggcgga ggaactcttt gatccggttc ctgaacagga  17160
tctatttgag gcgctaaatg aaaccttaac gctatggaac tcgccgcccg actgggctgg  17220
cgatgagcga aatgtagtgc ttacgttgtc ccgcatttgg tacagcgcag taaccggcaa  17280
aatcgcgccg aaggatgtcg ctgccgactg ggcaatggag cgcctgccgg cccagtatca  17340
gcccgtcata cttgaagcta ggcaggctta tcttggacaa gaagatcgct tggcctcgcg  17400
cgcagatcag ttggaagaat ttgttcacta cgtgaaaggc gagatcacca aggtagtcgg  17460
caaataatgt ctaacaattc gttcaagccg acgccgcttc gcggcgcggc ttaactcaag  17520
cgttagagag ctggggaaga ctatgcgcga tctgttgaag gtggttctaa gcctcgtact  17580
tgcgatggca tcggggcagg cacttgctga cctgccaatt gttttagtgg atgaagctcg  17640
tcttccctat gactactccc catccaacta cgacatttct ccaagcaact acgacaactc  17700
cataagcaat tacgacaata gtccatcaaa ttacgacaac tctgagagca actacgataa  17760
tagttcatcc aattacgaca atagtcgcaa cggaaatcgt aggcttatat atagcgcaaa  17820
tgggtctcgc actttcgccg gctactacgt cattgccaac aatgggacaa cgaacttctt  17880
ttccacatct ggcaaaagga tgttctacac ccccaaaggg gggcgcggcg tctatggcgg  17940
caaagatggg agcttctgcg gggcattggt cgtcataaat ggccaatttt cgcttgccct  18000
gacagataac ggcctgaaga tcatgtatct aagcaactag cctgctctct aataaaatgt  18060
taggagcttg gctgccattt ttggggtgag gccgttcgcg gccgaggggc gcagcccctg  18120
gggggatggg aggcccgcgt tagcgggccg ggagggttcg agaagggggg gcaccccccct 18180
tcggcgtgcg cggtcacgcg ccagggcgca gccctggtta aaaacaaggt ttataaatat  18240
tggtttaaaa gcaggttaaa agacaggtta gcggtggccg aaaaacgggc ggaaaccctt  18300
gcaaatgctg gattttctgc ctgtggacag cccctcaaat gtcaataggt gcgcccctca  18360
tctgtcagca ctctgcccct caagtgtcaa ggatcgcgcc cctcatctgt cagtagtcgc  18420
gcccctcaag tgtcaatacc gcagggcact tatccccagg cttgtccaca tcatctgtgg  18480
gaaactcgcg taaaatcagg cgttttcgcc gatttgcgag gctggccagc tccacgtcgc  18540
cggccgaaat cgagcctgcc cctcatctgt caacgccgcg ccgggtgagt cggcccctca  18600
agtgtcaacg tccgcccctc atctgtcagt gagggccaag ttttccgcga ggtatccaca  18660
acgccggcgg ccggccgcgg tgtctcgcac acggcttcga cggcgtttct ggcgcgtttg  18720
cagggccata gacggccgcc agcccagcgg cgagggcaac cagcccggtg agcgtcggaa  18780
``` aggg 18784

<210> SEQ ID NO 28
<211> LENGTH: 18784
<212> TYPE: DNA
<213> ORGANISM: Artificial Sequence
<220> FEATURE:
<223> OTHER INFORMATION: Synthetic vector

<400> SEQUENCE: 28
tcgacatcgt caacgttcac ttctaaagaa atagcgccac tcagcttcct cagcggcttt 60
atccagcgat ttcctattat gtcggcatag ttctcaagat cgacagcctg tcacggttaa 120
gcgagaaatg aataagaagg ctgataattc ggatctctgc gaggagatga tatttgatca 180
caggcagcaa cgctctgtca tcgttacaat caacatgcta ccctccgcga gatcatccgt 240
gtttcaaacc cggcagctta gttgccgttc ttccgaatag catcgggtaa catgagcaaa 300
gtctgccgcc ttacaacggc tctcccgctg acgccgtccc ggactgatgg gctgcctgta 360
tcgagtggtg attttgtgcc gagctgccgg tcggggagct gttggctggc tggtggcagg 420
atatattgtg gtgtaaacaa attgacgctt agacaactta ataacacatt gcggacgttt 480
ttaatgtact gaattcgccg ctcggtgtgt cgtagatact agcccctggg gcacttttga 540
aatttgaata agatttatgt aatcagtctt ttaggtttga ccggttctgc cgcttttttt 600
aaaattggat ttgtaataat aaaacgcaat tgtttgttat tgtggcgctc tatcatagat 660
gtcgctataa acctattcag cacaatatat tgttttcatt ttaatattgt acatataagt 720
agtagggtac aatcagtaaa ttgaacggag aatattattc ataaaaatac gatagtaacg 780
ggtgatatat tcattagaat gaaccgaaac cggcggtaag gatctgagct acacatgctc 840
aggtttttta caacgtgcac aacagaattg aaagcaaata tcatgcgatc ataggcgtct 900
cgcatatctc attaaacaag tgaagatttg attcaaactc cattgagagc cctgactatg 960
cattcggttt gacccttcca ggttgagaga cgatagcccc ctaccttaat taaggggccc 1020
cccctcgagg tcgacggtat cgataagctt gatatcgaat tcctgcagcc agggggatcc 1080
cccgggtcat cagatctcgg tgacgggcag gaccggacgg ggcggtaccg gcaggctgaa 1140
gtccagctgc cagaaaccca cgtcatgcca gttcccgtgc ttgaagccgg ccgcccgcag 1200
catgccgcgg ggggcatatc cgagcgcctc gtgcatgcgc acgctcgggt cgttgggcag 1260
cccgatgaca gcgaccacgc tcttgaagcc ctgtgcctcc agggacttca gcaggtgggt 1320
gtagagcgtg gagcccagtc ccgtccgctg gtggcggggg gagacgtaca cggtcgactc 1380
ggccgtccag tcgtaggcgt tgcgtgcctt ccaggggccc gcgtaggcga tgccggcgac 1440
ctcgccgtcc acctcggcga cgagccaggg atagcgctcc cgcagacgga cgaggtcgtc 1500
cgtccactcc tgcggttcct gcggctcggt acggaagttg accgtgcttg tctcgatgta 1560
gtggttgacg atggtgcaga ccgccggcat gtccgcctcg gtggcacggc ggatgtcggc 1620
cgggcgtcgt tctgggctca tggtagatcc cctcgagaga gatagatttg tagagagaga 1680
ctggtgattt cagcgtgtcc tctccaaatg aaatgaactt ccttatatag aggaaggtct 1740
tgcgaaggat agtgggattg tgcgtcatcc cttacgtcag tggagatatc acatcaatcc 1800
acttgctttg aagacgtggt tggaacgtct tctttttcca cgatgctcct cgtgggtggg 1860
ggtccatctt tgggaccact gtcggcagag gcatcttgaa cgatagcctt tcctttatcg 1920
caatgatggc atttgtaggt gccaccttcc ttttctactg tccttttgat gaagtgacag 1980

-continued

```
atagctgggc aatggaatcc gaggaggttt cccgatatta ccctttgttg aaaagtctca   2040
atagcccttt ggtcttctga gactgtatct ttgatattct tggagtagac gagagtgtcg   2100
tgctccacca tgttatcaca tcaatccact tgctttgaag acgtggttgg aacgtcttct   2160
ttttccacga tgctcctcgt gggtgggggt ccatctttgg gaccactgtc ggcagaggca   2220
tcttgaacga tagcctttcc tttatcgcaa tgatggcatt tgtaggtgcc accttccttt   2280
tctactgtcc ttttgatgaa gtgacagata gctgggcaat ggaatccgag gaggtttccc   2340
gatattaccc tttgttgaaa agtctcaata gccctttggt cttctgagac tgtatctttg   2400
atattcttgg agtagacgag agtgtcgtgc tccaccatgt tgctgatagt gaccttaggc   2460
gacttttgaa cgcgcaataa tggtttctga cgtatgtgct tagctcatta aactccagaa   2520
acccattaac gcttacaatt tccattcgcc attcaggctg cgcaactgtt gggaagggcg   2580
atcggtgcgg gcctcttcgc tattacgcca gctggcgaaa gggggatgtg ctgcaaggcg   2640
attaagttgg gtaacgccag ggttttccca gtcacgacgt tgtaaaacga cggccagtga   2700
attgtaatac gactcactat agggcgaatt gggcccgacg tcgcatgctc ccggccgcca   2760
tggccgcggg atatcactag tgcggccgct cgacgaatta attccaatcc cacaaaaatc   2820
tgagcttaac agcacagttg ctcctctcag agcagaatcg ggtattcaac accctcatat   2880
caactactac gttgtgtata acggtccaca tgccggtata tacgatgact ggggttgtac   2940
aaaggcggca acaaacggcg ttcccggagt tgcacacaag aaatttgcca ctattacaga   3000
ggcaagagca gcagctgacg cgtacacaac aagtcagcaa acagacaggt tgaacttcat   3060
ccccaaagga gaagctcaac tcaagcccaa gagctttgct aaggccctaa caagcccacc   3120
aaagcaaaaa gcccactggc tcacgctagg aaccaaaagg cccagcagtg atccagcccc   3180
aaaagagatc tcctttgccc cggagattac aatggacgat ttcctctatc tttacgatct   3240
aggaaggaag ttcgaaggtg aaggtgacga cactatgttc accactgata atgagaaggt   3300
tagcctcttc aatttcagaa agaatgctga cccacagatg gttagagagg cctacgcagc   3360
aggtctcatc aagacgatct acccgagtaa caatctccag gagatcaaat accttcccaa   3420
gaaggttaaa gatgcagtca aaagattcag gactaattgc atcaagaaca cagagaaaga   3480
catatttctc aagatcagaa gtactattcc agtatggacg attcaaggct tgcttcataa   3540
accaaggcaa gtaatagaga ttggagtctc taaaaaggta gttcctactg aatctaaggc   3600
catgcatgga gtctaagatt caaatcgagg atctaacaga actcgccgtg aagactggcg   3660
aacagttcat acagagtctt ttacgactca atgacaagaa gaaaatcttc gtcaacatgg   3720
tggagcacga cactctggtc tactccaaaa atgtcaaaga tacagtctca gaagaccaaa   3780
gggctattga gacttttcaa caaaggataa tttcgggaaa cctcctcgga ttccattgcc   3840
cagctatctg tcacttcatc gaaaggacag tagaaaagga aggtggctcc tacaaatgcc   3900
atcattgcga taaaggaaag gctatcattc aagatctctc tgccgacagt ggtcccaaag   3960
atggaccccc acccacgagg agcatcgtgg aaaaagaaga cgttccaacc acgtcttcaa   4020
agcaagtgga ttgatgtgac atctccactg acgtaaggga tgacgcacaa tcccactatc   4080
cttcgcaaga cccttcctct atataaggaa gttcatttca tttggagagg acacgctcga   4140
ggaattcggt accccatcac aagtttgtac aaaaaagcag gctgcggccg cttgctccct   4200
taaaaaaaac catggcatgt cattacggac aacagcaaca gactagagca cctcatcttc   4260
agcttcaacc tagagcacag agagttgtga aggctgctac tgctgttact gtaaatttct   4320
gtgttcctta ttctctcaaa atcttcgatt ttgttttcgt tcgatcccaa tttcgtatat   4380
```

-continued

```
gttctttggt ttagattctg ttaatcttag atcgaagacg attttctggg tttgatcgtt   4440
agatatcatc ttaattctcg attagggttt catagatatc atccgatttg ttcaaataat   4500
ttgagttttg tcgaataatt actcttcgat ttgtgatttc tatctagatc tggtgttagt   4560
ttctagtttg tgcgatcgaa tttgtcgatt aatctgagtt tttctgatta acaggctgga   4620
ggatctcttc ttgttctctc tggacttact ctcgctggaa ctgttatcgc tctcactatc   4680
gctacacctc ttctcgttat cttctctcct gttctcgttc ctgctgtgat cactatcttc   4740
cttctcggag ctggatttct tgcttctggt ggatttggag ttgctgctct ctctgttctc   4800
tcttggatct acagatacct cactggaaaa catcctccag gtgctgattg tcttgagtct   4860
gctaagacta agctcgcttc ttgtgctaga gagatgaagg atagagcaga gcaattctct   4920
tgtcagcctg ttgctggatc tcagacttct taatgaacat atggtcctgc tttaatgaga   4980
tatgcgagac gcctatgatc gcatgatatt tgctttcaat tctgttgtgc acgttgtaaa   5040
aaacctgagc atgtgtagct cagatcctta ccgccggttt cggttcattc taatgaatat   5100
atcacccgtt actatcgtat ttttatgaat aatattctcc gttcaattta ctgattgtac   5160
cctactactt atatgtacaa tattaaaatg aaaacaatat attgtgctga ataggtttat   5220
agcgacatct atgatagagc gccacaataa caaacaattg cgttttatta ttacaaatcc   5280
aattttaaaa aaagcggcag aaccggtcaa acctaaaaga ctgattacat aaatcttatt   5340
caaatttcaa aaggccccag gggctagtat ctacgacaca ccgagcggcg aactaataac   5400
gttcactgaa gggaactccg gttccccgcc ggcgcgcatg ggtgagattc cttgaagttg   5460
agtattggcc gtccgctcta ccgaaagtta cgggcaccat tcaacccggt ccagcacggc   5520
ggccgggtaa ccgacttgct gccccgagaa ttatgcagca tttttttggt gtatgtgggc   5580
cccaaatgaa gtgcaggtca aaccttgaca gtgacgacaa atcgttgggc gggtccaggg   5640
cgaattttgc gacaacatgt cgaggctcag caggacctgc aggcatgcaa gctagcttac   5700
tagtgatgca tattctatag tgtcacctaa atcttcgacg aattaattcc aatcccacaa   5760
aaatctgagc ttaacagcac agttgctcct ctcagagcag aatcgggtat tcaacaccct   5820
catatcaact actacgttgt gtataacggt ccacatgccg gtatatacga tgactggggt   5880
tgtacaaagg cggcaacaaa cggcgttccc ggagttgcac acaagaaatt tgccactatt   5940
acagaggcaa gagcagcagc tgacgcgtac acaacaagtc agcaaacaga caggttgaac   6000
ttcatcccca aaggagaagc tcaactcaag cccaagagct ttgctaaggc cctaacaagc   6060
ccaccaaagc aaaaagccca ctggctcacg ctaggaacca aaaggcccag cagtgatcca   6120
gccccaaaag agatctcctt tgccccggag attacaatgg acgatttcct ctatctttac   6180
gatctaggaa ggaagttcga aggtgaaggt gacgacacta tgttcaccac tgataatgag   6240
aaggttagcc tcttcaattt cagaaagaat gctgacccac agatggttag agaggcctac   6300
gcagcaggtc tcatcaagac gatctacccg agtaacaatc tccaggagat caaatacctt   6360
cccaagaagg ttaaagatgc agtcaaaaga ttcaggacta attgcatcaa gaacacagag   6420
aaagacatat ttctcaagat cagaagtact attccagtat ggacgattca aggcttgctt   6480
cataaaccaa ggcaagtaat agagattgga gtctctaaaa aggtagttcc tactgaatct   6540
aaggccatgc atggagtcta agattcaaat cgaggatcta acagaactcg ccgtgaagac   6600
tggcgaacag ttcatacaga gtcttttacg actcaatgac aagaagaaaa tcttcgtcaa   6660
catggtggag cacgacactc tggtctactc caaaaatgtc aaagatacag tctcagaaga   6720
```

-continued

```
ccaaagggct attgagactt ttcaacaaag gataatttcg ggaaacctcc tcggattcca   6780
ttgcccagct atctgtcact tcatcgaaag gacagtagaa aaggaaggtg gctcctacaa   6840
atgccatcat tgcgataaag gaaaggctat cattcaagat ctctctgccg acagtggtcc   6900
caaagatgga cccccaccca cgaggagcat cgtggaaaaa gaagacgttc caaccacgtc   6960
ttcaaagcaa gtggattgat gtgacatctc cactgacgta agggatgacg cacaatccca   7020
ctatccttcg caagaccctt cctctatata aggaagttca tttcatttgg agaggacacg   7080
ggatccttgc tccgttaaaa aaaaccatgg ctatcctcga ttctgctggt gttactactg   7140
tgactgagaa tggtggtgga gagttcgttg atctcgatag actcagaaga agaaagtcta   7200
gatctgtaaa tttctgtgtt ccttattctc tcaaaatctt cgattttgtt ttcgttcgat   7260
cccaatttcg tatatgttct ttggtttaga ttctgttaat cttagatcga agacgatttt   7320
ctgggtttga tcgttagata tcatcttaat tctcgattag ggtttcatag atatcatccg   7380
atttgttcaa ataatttgag ttttgtcgaa taattactct tcgatttgtg atttctatct   7440
agatctggtg ttagtttcta gtttgtgcga tcgaatttgt cgattaatct gagtttttct   7500
gattaacagg attcttctaa cggacttctc ctctctggat ctgataacaa ctctccttct   7560
gatgatgttg gtgctcctgc tgatgtgaga gatagaatcg attctgtggt gaacgatgat   7620
gctcaaggta ctgctaacct cgctggtgat aataacggtg gaggtgataa caatggtgga   7680
ggaagaggtg gaggtgaagg tagaggaaac gctgatgcta ctttcactta cagaccatct   7740
gtgcctgctc atagaagagc tagagagtct cctctctctt ctgatgctat cttcaagcag   7800
tctcacgctg gacttttcaa cctctgtgtg gtggttctta tcgctgtgaa ctctagactc   7860
atcatcgaga acctcatgaa gtacggatgg ctcatcagaa ctgatttctg gttctcttct   7920
agatctctca gagattggcc tcttttcatg tgctgcatct cactctcaat cttccctctc   7980
gctgctttta ctgttgagaa gctcgtgctc cagaagtata tcgctgaacc tgtggtgatc   8040
ttcctccaca tcatcatcac tatgactgag gttctctacc ctgtttacgt gactctcaga   8100
tgcgattctg ctttcctctc tggtgttact cttatgctcc tcacttgcat tgtgtggctt   8160
aagctcgtgt cttacgctca cacttcttac gatatcagat ctctcgctaa cgctgctgat   8220
aaggctaacc ctgaagtgtc ttactacgtg tctctcaagt ctctcgctta cttcatggtt   8280
gctcctacac tttgttacca gccatcttac cctagatctg cttgcattag aaagggatgg   8340
gtggcaagac aattcgctaa gttggtgatc ttcactggat tcatgggatt catcatcgag   8400
cagtacatca accctattgt gagaaactct aagcaccctc tcaagggtga tcttctctac   8460
gctatcgaga gagttcttaa gctctctgtg cctaaccttt atgtgtggct ctgcatgttc   8520
tactgtttct tccacctctg gcttaacatc cttgctgagt tgctttgctt cggagataga   8580
gagttctaca aggattggtg gaacgctaag tctgttggag attattggag aatgtggaac   8640
atgcctgtgc ataagtggat ggtgcgtcac atctacttcc cttgcctcag atctaagatc   8700
cctaagactc tcgctatcat tatcgctttc ctcgtgtctg ctgttttcca tgagttgtgt   8760
atcgctgttc cttgcagact tttcaagctt tgggctttcc tcggaatcat gttccaggtt   8820
ccactcgtgt tcatcactaa ctacctccaa gagagattcg gatctactgt tggaaacatg   8880
attttctggt tcattttctg catcttcgga cagcctatgt gcgttctcct ctactaccac   8940
gatctcatga acagaaaggg atctatgtct taatgaagga tccacccagc tttcttgtac   9000
aaagtggtga tgggttcgaa atcgataagc ttggatcctc tagagtcctg ctttaatgag   9060
atatgcgaga cgcctatgat cgcatgatat ttgctttcaa ttctgttgtg cacgttgtaa   9120
```

```
aaaacctgag catgtgtagc tcagatcctt accgccggtt tcggttcatt ctaatgaata   9180
tatcacccgt tactatcgta tttttatgaa taatattctc cgttcaattt actgattgta   9240
ccctactact tatatgtaca atattaaaat gaaaacaata tattgtgctg aataggttta   9300
tagcgacatc tatgatagag cgccacaata acaaacaatt gcgttttatt attacaaatc   9360
caattttaaa aaaagcggca gaaccggtca aacctaaaag actgattaca taaatcttat   9420
tcaaatttca aaaggcccca ggggctagta tctacgacac accgagcggc gaactaataa   9480
cgttcactga agggaactcc ggttccccgc cggcgcgcat gggtgagatt ccttgaagtt   9540
gagtattggc cgtccgctct accgaaagtt acgggcacca ttcaacccgg tccagcacgg   9600
cggccgggta accgacttgc tgccccgaga attatgcagc attttttgg tgtatgtggg   9660
ccccaaatga agtgcaggtc aaaccttgac agtgacgaca aatcgttggg cgggtccagg   9720
gcgaattttg cgacaacatg tcgaggctca gcaggacctg caggcatgca agctagctta   9780
ctagtgatgc atattctata gtgtcaccta aatctgcggc cgcctgcagg tcgatatggg   9840
agagctccca acgcgttgga tgcatagctt gagtattcta tagtgtcacc taaatagctt   9900
ggcgtaatca tggtcatagc tgtttcctgt gtgaaattgt tatccgctca caattccaca   9960
caacatacga gccggaagca taaagtgtaa agcctggggt gcctaatgag tgagctaact  10020
cacattaatt gcgttgcgct cactgcccgc tttccagtcg ggaaacctgt cgtgccagct  10080
gcattaatga atcggccaac gcgcggggag aggcggtttg cgtattgggg ctgagtggct  10140
ccttcaacgt tgcggttctg tcagttccaa acgtaaaacg gcttgtcccg cgtcatcggc  10200
gggggtcata acgtgactcc cttaattctc cgctcatgat cagattgtcg tttcccgcct  10260
tcagtttaaa ctatcagtgt ttgacaggat atattggcgg gtaaacctaa gagaaaagag  10320
cgtttattag aataatcgga tatttaaaag ggcgtgaaaa ggtttatccg ttcgtccatt  10380
tgtatgtgca tgccaaccac agggttcccc tcgggagtgc ttggcattcc gtgcgataat  10440
gacttctgtt caaccaccca aacgtcggaa agcctgacga cggagcagca ttccaaaaag  10500
atcccttggc tcgtctgggt cggctagaag gtcgagtggg ctgctgtggc ttgatccctc  10560
aacgcggtcg cggacgtagc gcagcgccga aaaatcctcg atcgcaaatc cgacgctgtc  10620
gaaaatcgtg atctgcttgt cgctctttcg gccgacgtcc tggccagtca tcacgcgcca  10680
aagttccgtc acaggatgat ctggcgcgag ttgctggatc tcgccttcaa tccgggtctg  10740
tggcgggaac tccacgaaaa tatccgaacg cagcaagatg tcgacggatc ttttccgctg  10800
cataaccctg cttcggggtc attatagcga tttttttcggt atatccatcc tttttcgcac  10860
gatatacagg attttgccaa agggttcgtg tagactttcc ttggtgtatc caacggcgtc  10920
agccgggcag gataggtgaa gtaggcccac ccgcgagcgg gtgttccttc ttcactgtcc  10980
cttattcgca cctggcggtg ctcaacggga atcctgctct gcgaggctgg ccggctaccg  11040
ccggcgtaac agatgagggc aagcggatgg ctgatgaaac caagccaacc aggggtgatg  11100
ctgccaactt actgatttag tgtatgatgg tgtttttgag gtgctccagt ggcttctgtt  11160
tctatcagct gtccctcctg ttcagctact gacggggtgg tgcgtaacgg caaaagcacc  11220
gccggacatc agcgctatct ctgctctcac tgccgtaaaa catggcaact gcagttcact  11280
tacaccgctt ctcaacccgg tacgcaccag aaaatcattg atatggccat gaatggcgtt  11340
ggatgccggg caacagcccg cattatgggc gttggcctca acacgatttt acgtcactta  11400
aaaaactcag gccgcagtcg gtaacctcgc gcatacagcc gggcagtgac gtcatcgtct  11460
```

-continued

```
gcgcggaaat ggacgaacag tggggctatg tcggggctaa atcgcgccag cgctggctgt  11520
tttacgcgta tgacagtctc cggaagacgg ttgttgcgca cgtattcggt gaacgcacta  11580
tggcgacgct ggggcgtctt atgagcctgc tgtcaccctt tgacgtggtg atatggatga  11640
cggatggctg gccgctgtat gaatcccgcc tgaagggaaa gctgcacgta atcagcaagc  11700
gatatacgca gcgaattgag cggcataacc tgaatctgag gcagcacctg gcacggctgg  11760
gacggaagtc gctgtcgttc tcaaaatcgg tggagctgca tgacaaagtc atcgggcatt  11820
atctgaacat aaaacactat caataagttg gagtcattac ccaaccagga agggcagccc  11880
acctatcaag gtgtactgcc ttccagacga acgaagagcg attgaggaaa aggcggcggc  11940
ggccggcatg agcctgtcgg cctacctgct ggccgtcggc cagggctaca aaatcacggg  12000
cgtcgtggac tatgagcacg tccgcgagct ggcccgcatc aatggcgacc tgggccgcct  12060
gggcggcctg ctgaaactct ggctcaccga cgacccgcgc acggcgcggt tcggtgatgc  12120
cacgatcctc gccctgctgg cgaagatcga agagaagcag gacgagcttg gcaaggtcat  12180
gatgggcgtg gtccgcccga gggcagagcc atgacttttt tagccgctaa aacggccggg  12240
gggtgcgcgt gattgccaag cacgtcccca tgcgctccat caagaagagc gacttcgcgg  12300
agctggtatt cgtgcagggc aagattcgga ataccaagta cgagaaggac ggccagacgg  12360
tctacgggac cgacttcatt gccgataagg tggattatct ggacaccaag gcaccaggcg  12420
ggtcaaatca ggaataaggg cacattgccc cggcgtgagt cggggcaatc ccgcaaggag  12480
ggtgaatgaa tcggacgttt gaccggaagg catacaggca agaactgatc gacgcggggt  12540
tttccgccga ggatgccgaa accatcgcaa gccgcaccgt catgcgtgcg ccccgcgaaa  12600
ccttccagtc cgtcggctcg atggtccagc aagctacggc caagatcgag cgcgacagcg  12660
tgcaactggc tccccctgcc ctgcccgcgc catcggccgc cgtggagcgt tcgcgtcgtc  12720
tcgaacagga ggcggcaggt ttggcgaagt cgatgaccat cgacacgcga ggaactatga  12780
cgaccaagaa gcgaaaaacc gccggcgagg acctggcaaa acaggtcagc gaggccaagc  12840
aggccgcgtt gctgaaacac acgaagcagc agatcaagga aatgcagctt tccttgttcg  12900
atattgcgcc gtggccggac acgatgcgag cgatgccaaa cgacacggcc cgctctgccc  12960
tgttcaccac gcgcaacaag aaaatcccgc gcgaggcgct gcaaaacaag gtcattttcc  13020
acgtcaacaa ggacgtgaag atcacctaca ccggcgtcga gctgcgggcc gacgatgacg  13080
aactggtgtg gcagcaggtg ttggagtacg cgaagcgcac ccctatcggc gagccgatca  13140
ccttcacgtt ctacgagctt tgccaggacc tgggctggtc gatcaatggc cggtattaca  13200
cgaaggccga ggaatgcctg tcgcgcctac aggcgacggc gatgggcttc acgtccgacc  13260
gcgttgggca cctggaatcg gtgtcgctgc tgcaccgctt ccgcgtcctg gaccgtggca  13320
agaaaacgtc ccgttgccag gtcctgatcg acgaggaaat cgtcgtgctg tttgctggcg  13380
accactacac gaaattcata tgggagaagt accgcaagct gtcgccgacg gcccgacgga  13440
tgttcgacta tttcagctcg caccgggagc cgtacccgct caagctggaa accttccgcc  13500
tcatgtgcgg atcggattcc acccgcgtga agaagtggcg cgagcaggtc ggcgaagcct  13560
gcgaagagtt gcgaggcagc ggcctggtgg aacacgcctg ggtcaatgat gacctggtgc  13620
attgcaaacg ctagggcctt gtggggtcag ttccggctgg gggttcagca gccagcgctt  13680
tactggcatt tcaggaacaa gcgggcactg ctcgacgcac ttgcttcgct cagtatcgct  13740
cgggacgcac ggcgcgctct acgaactgcc gataaacaga ggattaaaat tgacaattgt  13800
gattaaggct cagattcgac ggcttggagc ggccgacgtg caggatttcc gcgagatccg  13860
```
attgtcggcc ctgaagaaag ctccagagat gttcgggtcc gtttacgagc acgaggagaa 13920
aaagcccatg gaggcgttcg ctgaacggtt gcgagatgcc gtggcattcg gcgcctacat 13980
cgacggcgag atcattgggc tgtcggtctt caaacaggag gacggcccca aggacgctca 14040
caaggcgcat ctgtccggcg ttttcgtgga gcccgaacag cgaggccgag gggtcgccgg 14100
tatgctgctg cgggcgttgc cggcgggttt attgctcgtg atgatcgtcc gacagattcc 14160
aacgggaatc tggtggatgc gcatcttcat cctcggcgca cttaatattt cgctattctg 14220
gagcttgttg tttatttcgg tctaccgcct gccgggcggg gtcgcggcga cggtaggcgc 14280
tgtgcagccg ctgatggtcg tgttcatctc tgccgctctg ctaggtagcc cgatacgatt 14340
gatggcggtc ctgggggcta tttgcggaac tgcgggcgtg gcgctgttgg tgttgacacc 14400
aaacgcagcg ctagatcctg tcggcgtcgc agcgggcctg gcgggggcgg tttccatggc 14460
gttcggaacc gtgctgaccc gcaagtggca acctcccgtg cctctgctca cctttaccgc 14520
ctggcaactg gcggccggag gacttctgct cgttccagta gctttagtgt ttgatccgcc 14580
aatcccgatg cctacaggaa ccaatgttct cggcctggcg tggctcggcc tgatcggagc 14640
gggtttaacc tacttccttt ggttccgggg gatctcgcga ctcgaaccta cagttgtttc 14700
cttactgggc tttctcagcc gggatggcgc taagaagcta ttgccgccga tcttcatatg 14760
cggtgtgaaa taccgcacag atgcgtaagg agaaaatacc gcatcaggcg ctcttccgct 14820
tcctcgctca ctgactcgct gcgctcggtc gttcggctgc ggcgagcggt atcagctcac 14880
tcaaaggcgg taatacggtt atccacagaa tcaggggata acgcaggaaa gaacatgtga 14940
gcaaaaggcc agcaaaaggc caggaaccgt aaaaaggccg cgttgctggc gtttttccat 15000
aggctccgcc cccctgacga gcatcacaaa aatcgacgct caagtcagag gtggcgaaac 15060
ccgacaggac tataaagata ccaggcgttt ccccctggaa gctccctcgt gcgctctcct 15120
gttccgaccc tgccgcttac cggatacctg tccgcctttc tcccttcggg aagcgtggcg 15180
ctttctcaat gctcacgctg taggtatctc agttcggtgt aggtcgttcg ctccaagctg 15240
ggctgtgtgc acgaaccccc cgttcagccc gaccgctgcg ccttatccgg taactatcgt 15300
cttgagtcca acccggtaag acacgactta tcgccactgg cagcagccac tggtaacagg 15360
attagcagag cgaggtatgt aggcggtgct acagagttct tgaagtggtg gcctaactac 15420
ggctacacta gaaggacagt atttggtatc tgcgctctgc tgaagccagt taccttcgga 15480
aaaagagttg gtagctcttg atccggcaaa caaaccaccg ctggtagcgg tggttttttt 15540
gtttgcaagc agcagattac gcgcagaaaa aaaggatatc aagaagatcc tttgatcttt 15600
tctacggggt ctgacgctca gtggaacgaa aactcacgtt aagggatttt ggtcatgaga 15660
ttatcaaaaa ggatcttcac ctagatcctt ttaaattaaa aatgaagttt taaatcaatc 15720
taaagtatat atgagtaaac ttggtctgac agttaccaat gcttaatcag tgaggcacct 15780
atctcagcga tctgtctatt tcgttcatcc atagttgcct gactccccgt cgtgtagata 15840
actacgatac gggagggctt accatctggc cccagtgctg caatgatacc gcgagaccca 15900
cgctcaccgg ctccagattt atcagcaata aaccagccag ccggaagggc cgagcgcaga 15960
agtggtcctg caactttatc cgcctccatc cagtctatta aacaagtggc agcaacggat 16020
tcgcaaacct gtcacgcctt ttgtgccaaa agccgcgcca ggtttgcgat ccgctgtgcc 16080
aggcgttagg cgtcatatga agatttcggt gatccctgag caggtggcgg aaacattgga 16140
tgctgagaac catttcattg ttcgtgaagt gttcgatgtg cacctatccg accaaggctt 16200

```
tgaactatct accagaagtg tgagccccta ccggaaggat tacatctcgg atgatgactc  16260
tgatgaagac tctgcttgct atggcgcatt catcgaccaa gagcttgtcg ggaagattga  16320
actcaactca acatggaacg atctagcctc tatcgaacac attgttgtgt cgcacacgca  16380
ccgaggcaaa ggagtcgcgc acagtctcat cgaatttgcg aaaaagtggg cactaagcag  16440
acagctcctt ggcatacgat tagagacaca aacgaacaat gtacctgcct gcaatttgta  16500
cgcaaaatgt ggctttactc tcggcggcat tgacctgttc acgtataaaa ctagacctca  16560
agtctcgaac gaaacagcga tgtactggta ctggttctcg ggagcacagg atgacgccta  16620
acaattcatt caagccgaca ccgcttcgcg gcgcggctta attcaggagt taaacatcat  16680
gagggaagcg gtgatcgccg aagtatcgac tcaactatca gaggtagttg gcgtcatcga  16740
gcgccatctc gaaccgacgt tgctggccgt acatttgtac ggctccgcag tggatggcgg  16800
cctgaagcca cacagtgata ttgatttgct ggttacggtg accgtaaggc ttgatgaaac  16860
aacgcggcga gctttgatca acgacctttt ggaaacttcg gcttcccctg gagagagcga  16920
gattctccgc gctgtagaag tcaccattgt tgtgcacgac gacatcattc cgtggcgtta  16980
tccagctaag cgcgaactgc aatttggaga atggcagcgc aatgacattc ttgcaggtat  17040
cttcgagcca gccacgatcg acattgatct ggctatcttg ctgacaaaag caagagaaca  17100
tagcgttgcc ttggtaggtc cagcggcgga ggaactcttt gatccggttc ctgaacagga  17160
tctatttgag gcgctaaatg aaaccttaac gctatggaac tcgccgcccg actgggctgg  17220
cgatgagcga aatgtagtgc ttacgttgtc ccgcatttgg tacagcgcag taaccggcaa  17280
aatcgcgccg aaggatgtcg ctgccgactg ggcaatggag cgcctgccgg cccagtatca  17340
gcccgtcata cttgaagcta ggcaggctta tcttggacaa gaagatcgct tggcctcgcg  17400
cgcagatcag ttggaagaat ttgttcacta cgtgaaaggc gagatcacca aggtagtcgg  17460
caaataatgt ctaacaattc gttcaagccg acgccgcttc gcggcgcggc ttaactcaag  17520
cgttagagag ctggggaaga ctatgcgcga tctgttgaag gtggttctaa gcctcgtact  17580
tgcgatggca tcggggcagg cacttgctga cctgccaatt gttttagtgg atgaagctcg  17640
tcttccctat gactactccc catccaacta cgacatttct ccaagcaact acgacaactc  17700
cataagcaat tacgacaata gtccatcaaa ttacgacaac tctgagagca actacgataa  17760
tagttcatcc aattacgaca atagtcgcaa cggaaatcgt aggcttatat atagcgcaaa  17820
tgggtctcgc actttcgccg gctactacgt cattgccaac aatgggacaa cgaacttctt  17880
ttccacatct ggcaaaagga tgttctacac cccaaaaggg gggcgcggcg tctatggcgg  17940
caaagatggg agcttctgcg gggcattggt cgtcataaat ggccaatttt cgcttgccct  18000
gacagataac ggcctgaaga tcatgtatct aagcaactag cctgctctct aataaaatgt  18060
taggagcttg gctgccattt ttggggtgag gccgttcgcg gccgaggggc gcagcccctg  18120
gggggatggg aggcccgcgt tagcgggccg ggagggttcg agaagggggg gcacccccct  18180
tcggcgtgcg cggtcacgcg ccagggcgca gccctggtta aaaacaaggt ttataaatat  18240
tggtttaaaa gcaggttaaa agacaggtta gcggtggccg aaaaacgggc ggaaaccctt  18300
gcaaatgctg gattttctgc ctgtggacag cccctcaaat gtcaataggt gcgcccctca  18360
tctgtcagca ctctgcccct caagtgtcaa ggatcgcgcc cctcatctgt cagtagtcgc  18420
gcccctcaag tgtcaatacc gcagggcact tatccccagg cttgtccaca tcatctgtgg  18480
gaaactcgcg taaaatcagg cgttttcgcc gatttgcgag gctggccagc tccacgtcgc  18540
cggccgaaat cgagcctgcc cctcatctgt caacgccgcg ccgggtgagt cggcccctca  18600
```
agtgtcaacg tccgcccctc atctgtcagt gagggccaag ttttccgcga ggtatccaca 18660
acgccggcgg ccggccgcgg tgtctcgcac acggcttcga cggcgtttct ggcgcgtttg 18720
cagggccata gacggccgcc agcccagcgg cgagggcaac cagcccggtg agcgtcggaa 18780
aggg 18784

<210> SEQ ID NO 29
<211> LENGTH: 18784
<212> TYPE: DNA
<213> ORGANISM: Artificial Sequence
<220> FEATURE:
<223> OTHER INFORMATION: Synthetic vector

<400> SEQUENCE: 29
gtcgacatcg tcaacgttca cttctaaaga aatagcgcca ctcagcttcc tcagcggctt 60
tatccagcga tttcctatta tgtcggcata gttctcaaga tcgacagcct gtcacggtta 120
agcgagaaat gaataagaag gctgataatt cggatctctg cgaggagatg atatttgatc 180
acaggcagca acgctctgtc atcgttacaa tcaacatgct accctccgcg agatcatccg 240
tgtttcaaac ccggcagctt agttgccgtt cttccgaata gcatcgggta acatgagcaa 300
agtctgccgc cttacaacgg ctctcccgct gacgccgtcc cggactgatg ggctgcctgt 360
atcgagtggt gattttgtgc cgagctgccg gtcggggagc tgttggctgg ctggtggcag 420
gatatattgt ggtgtaaaca aattgacgct tagacaactt aataacacat tgcggacgtt 480
tttaatgtac tgaattcgcc gctcggtgtg tcgtagatac tagcccctgg ggcacttttg 540
aaatttgaat aagatttatg taatcagtct tttaggtttg accggttctg ccgctttttt 600
taaaattgga tttgtaataa taaaacgcaa ttgtttgtta ttgtggcgct ctatcataga 660
tgtcgctata aacctattca gcacaatata ttgttttcat tttaatattg tacatataag 720
tagtagggta caatcagtaa attgaacgga gaatattatt cataaaaata cgatagtaac 780
gggtgatata ttcattagaa tgaaccgaaa ccggcggtaa ggatctgagc tacacatgct 840
caggtttttt acaacgtgca caacagaatt gaaagcaaat atcatgcgat cataggcgtc 900
tcgcatatct cattaaacaa gtgaagattt gattcaaact ccattgagag ccctgactat 960
gcattcggtt tgacccttcc aggttgagag acgatagccc cctaccttaa ttaaggggcc 1020
ccccctcgag gtcgacggta tcgataagct tgatatcgaa ttcctgcagc cagggggatc 1080
ccccgggtca tcagatctcg gtgacgggca ggaccggacg gggcggtacc ggcaggctga 1140
agtccagctg ccagaaaccc acgtcatgcc agttcccgtg cttgaagccg gccgcccgca 1200
gcatgccgcg gggggcatat ccgagcgcct cgtgcatgcg cacgctcggg tcgttgggca 1260
gcccgatgac agcgaccacg ctcttgaagc cctgtgcctc cagggacttc agcaggtggg 1320
tgtagagcgt ggagcccagt cccgtccgct ggtggcgggg ggagacgtac acggtcgact 1380
cggccgtcca gtcgtaggcg ttgcgtgcct tccaggggcc cgcgtaggcg atgccggcga 1440
cctcgccgtc cacctcggcg acgagccagg gatagcgctc ccgcagacgg acgaggtcgt 1500
ccgtccactc ctgcggttcc tgcggctcgg tacggaagtt gaccgtgctt gtctcgatgt 1560
agtggttgac gatggtgcag accgccggca tgtccgcctc ggtggcacgg cggatgtcgg 1620
ccgggcgtcg ttctgggctc atggtagatc ccctcgagag agatagattt gtagagagag 1680
actggtgatt tcagcgtgtc ctctccaaat gaaatgaact tccttatata gaggaaggtc 1740
ttgcgaagga tagtgggatt gtgcgtcatc ccttacgtca gtggagatat cacatcaatc 1800

-continued

```
cacttgcttt gaagacgtgg ttggaacgtc ttctttttcc acgatgctcc tcgtgggtgg   1860
gggtccatct ttgggaccac tgtcggcaga ggcatcttga acgatagcct ttcctttatc   1920
gcaatgatgg catttgtagg tgccaccttc cttttctact gtccttttga tgaagtgaca   1980
gatagctggg caatggaatc cgaggaggtt tcccgatatt accctttgtt gaaaagtctc   2040
aatagccctt tggtcttctg agactgtatc tttgatattc ttggagtaga cgagagtgtc   2100
gtgctccacc atgttatcac atcaatccac ttgctttgaa gacgtggttg gaacgtcttc   2160
tttttccacg atgctcctcg tgggtggggg tccatctttg ggaccactgt cggcagaggc   2220
atcttgaacg atagcctttc ctttatcgca atgatggcat ttgtaggtgc caccttcctt   2280
ttctactgtc cttttgatga agtgacagat agctgggcaa tggaatccga ggaggtttcc   2340
cgatattacc ctttgttgaa aagtctcaat agccctttgg tcttctgaga ctgtatcttt   2400
gatattcttg gagtagacga gagtgtcgtg ctccaccatg ttgctgatag tgaccttagg   2460
cgacttttga acgcgcaata atggtttctg acgtatgtgc ttagctcatt aaactccaga   2520
aacccattaa cgcttacaat ttccattcgc cattcaggct gcgcaactgt tgggaagggc   2580
gatcggtgcg ggcctcttcg ctattacgcc agctggcgaa aggggggatgt gctgcaaggc   2640
gattaagttg ggtaacgcca gggttttccc agtcacgacg ttgtaaaacg acggccagtg   2700
aattgtaata cgactcacta tagggcgaat tgggcccgac gtcgcatgct cccggccgcc   2760
atggccgcgg gatatcacta gtgcggccgc tcgacgaatt aattccaatc ccacaaaaat   2820
ctgagcttaa cagcacagtt gctcctctca gagcagaatc gggtattcaa caccctcata   2880
tcaactacta cgttgtgtat aacggtccac atgccggtat atacgatgac tggggttgta   2940
caaaggcggc aacaaacggc gttcccggag ttgcacacaa gaaatttgcc actattacag   3000
aggcaagagc agcagctgac gcgtacacaa caagtcagca aacagacagg ttgaacttca   3060
tccccaaagg agaagctcaa ctcaagccca agagctttgc taaggcccta acaagcccac   3120
caaagcaaaa agcccactgg ctcacgctag gaaccaaaag gcccagcagt gatccagccc   3180
caaaagagat ctcctttgcc ccggagatta caatggacga tttcctctat ctttacgatc   3240
taggaaggaa gttcgaaggt gaaggtgacg acactatgtt caccactgat aatgagaagg   3300
ttagcctctt caatttcaga aagaatgctg acccacagat ggttagagag gcctacgcag   3360
caggtctcat caagacgatc tacccgagta acaatctcca ggagatcaaa taccttccca   3420
agaaggttaa agatgcagtc aaaagattca ggactaattg catcaagaac acagagaaag   3480
acatatttct caagatcaga agtactattc cagtatggac gattcaaggc ttgcttcata   3540
aaccaaggca agtaatagag attggagtct ctaaaaaggt agttcctact gaatctaagg   3600
ccatgcatgg agtctaagat tcaaatcgag gatctaacag aactcgccgt gaagactggc   3660
gaacagttca tacagagtct tttacgactc aatgacaaga agaaaatctt cgtcaacatg   3720
gtggagcacg acactctggt ctactccaaa aatgtcaaag atacagtctc agaagaccaa   3780
agggctattg agacttttca acaaaggata atttcgggaa acctcctcgg attccattgc   3840
ccagctatct gtcacttcat cgaaaggaca gtagaaaagg aaggtggctc ctacaaatgc   3900
catcattgcg ataaaggaaa ggctatcatt caagatctct ctgccgacag tggtcccaaa   3960
gatggacccc cacccacgag gagcatcgtg gaaaaagaag acgttccaac cacgtcttca   4020
aagcaagtgg attgatgtga catctccact gacgtaaggg atgacgcaca atcccactat   4080
ccttcgcaag acccttcctc tatataagga agttcatttc atttggagag gacacgctcg   4140
aggaattcgg taccccatca caagtttgta caaaaaagca ggctgcggcc gcttgctccc   4200
```

-continued

```
ttaaaaaaaa ccatggcatg tcattacgga caacagcaac agacttgtgc acctcatctt   4260
cagcttcaac ctagagcatg tagagttgtg aaggctgcta ctgctgttac tgtaaatttc   4320
tgtgttcctt attctctcaa aatcttcgat tttgttttcg ttcgatccca atttcgtata   4380
tgttctttgg tttagattct gttaatctta gatcgaagac gattttctgg gtttgatcgt   4440
tagatatcat cttaattctc gattagggtt tcatagatat catccgattt gttcaaataa   4500
tttgagtttt gtcgaataat tactcttcga tttgtgattt ctatctagat ctggtgttag   4560
tttctagttt gtgcgatcga atttgtcgat taatctgagt tttctgatt aacaggctgg   4620
aggatctctt cttgttctct ctggacttac tctcgctgga actgttatcg ctctcactat   4680
cgctacacct cttctcgtta tcttctctcc tgttctcgtt cctgctgtga tcactatctt   4740
ccttctcgga gctggatttc ttgcttctgg tggatttgga gttgctgctc tctctgttct   4800
ctcttggatc tacagatacc tcactggaaa acatcctcca ggtgctgatc aacttgagtc   4860
tgctaagact aagctcgctt ctaaggctag agagatgaag gatagagcag agcaattctc   4920
ttgtcagcct gttgctggat ctcagacttc ttaatgaaca tatggtcctg ctttaatgag   4980
atatgcgaga cgcctatgat cgcatgatat ttgctttcaa ttctgttgtg cacgttgtaa   5040
aaaacctgag catgtgtagc tcagatcctt accgccggtt tcggttcatt ctaatgaata   5100
tatcacccgt tactatcgta tttttatgaa taatattctc cgttcaattt actgattgta   5160
ccctactact tatatgtaca atattaaaat gaaaacaata tattgtgctg aataggttta   5220
tagcgacatc tatgatagag cgccacaata acaaacaatt gcgttttatt attacaaatc   5280
caattttaaa aaaagcggca gaaccggtca aacctaaaag actgattaca taaatcttat   5340
tcaaatttca aaaggcccca ggggctagta tctacgacac accgagcggc gaactaataa   5400
cgttcactga agggaactcc ggttccccgc cggcgcgcat gggtgagatt ccttgaagtt   5460
gagtattggc cgtccgctct accgaaagtt acgggcacca ttcaacccgg tccagcacgg   5520
cggccgggta accgacttgc tgccccgaga attatgcagc attttttgg tgtatgtggg   5580
ccccaaatga agtgcaggtc aaaccttgac agtgacgaca aatcgttggg cgggtccagg   5640
gcgaattttg cgacaacatg tcgaggctca gcaggacctg caggcatgca agctagctta   5700
ctagtgatgc atattctata gtgtcaccta aatcttcgac gaattaattc caatcccaca   5760
aaaatctgag cttaacagca cagttgctcc tctcagagca gaatcgggta ttcaacaccc   5820
tcatatcaac tactacgttg tgtataacgg tccacatgcc ggtatatacg atgactgggg   5880
ttgtacaaag gcggcaacaa acggcgttcc cggagttgca cacaagaaat ttgccactat   5940
tacagaggca agagcagcag ctgacgcgta cacaacaagt cagcaaacag acaggttgaa   6000
cttcatcccc aaaggagaag ctcaactcaa gcccaagagc tttgctaagg ccctaacaag   6060
cccaccaaag caaaaagccc actggctcac gctaggaacc aaaaggccca gcagtgatcc   6120
agccccaaaa gagatctcct ttgccccgga gattacaatg gacgatttcc tctatcttta   6180
cgatctagga aggaagttcg aaggtgaagg tgacgacact atgttcacca ctgataatga   6240
gaaggttagc ctcttcaatt tcagaaagaa tgctgaccca cagatggtta gagaggccta   6300
cgcagcaggt ctcatcaaga cgatctaccc gagtaacaat ctccaggaga tcaaatacct   6360
tcccaagaag gttaaagatg cagtcaaaag attcaggact aattgcatca agaacacaga   6420
gaaagacata tttctcaaga tcagaagtac tattccagta tggacgattc aaggcttgct   6480
tcataaacca aggcaagtaa tagagattgg agtctctaaa aaggtagttc ctactgaatc   6540
```

-continued

```
taaggccatg catggagtct aagattcaaa tcgaggatct aacagaactc gccgtgaaga   6600
ctggcgaaca gttcatacag agtcttttac gactcaatga caagaagaaa atcttcgtca   6660
acatggtgga gcacgacact ctggtctact ccaaaaatgt caaagataca gtctcagaag   6720
accaaagggc tattgagact tttcaacaaa ggataatttc gggaaacctc ctcggattcc   6780
attgcccagc tatctgtcac ttcatcgaaa ggacagtaga aaaggaaggt ggctcctaca   6840
aatgccatca ttgcgataaa ggaaaggcta tcattcaaga tctctctgcc gacagtggtc   6900
ccaaagatgg acccccaccc acgaggagca tcgtggaaaa agaagacgtt ccaaccacgt   6960
cttcaaagca agtggattga tgtgacatct ccactgacgt aagggatgac gcacaatccc   7020
actatccttc gcaagaccct tcctctatat aaggaagttc atttcatttg gagaggacac   7080
gggatccttg ctccgttaaa aaaaaccatg gctatcctcg attctgctgg tgttactact   7140
gtgactgaga atggtggtgg agagttcgtt gatctcgata gactcagaag aagaaagtct   7200
agatctgtaa atttctgtgt tccttattct ctcaaaatct tcgattttgt tttcgttcga   7260
tcccaatttc gtatatgttc tttggtttag attctgttaa tcttagatcg aagacgattt   7320
tctgggtttg atcgttagat atcatcttaa ttctcgatta gggtttcata gatatcatcc   7380
gatttgttca aataatttga gttttgtcga ataattactc ttcgatttgt gatttctatc   7440
tagatctggt gttagtttct agtttgtgcg atcgaatttg tcgattaatc tgagtttttc   7500
tgattaacag gattcttcta acggacttct cctctctgga tctgataaca actctccttc   7560
tgatgatgtt ggtgctcctg ctgatgtgag agatagaatc gattctgtgg tgaacgatga   7620
tgctcaaggt actgctaacc tcgctggtga taataacggt ggaggtgata acaatggtgg   7680
aggaagaggt ggaggtgaag gtagaggaaa cgctgatgct actttcactt acagaccatc   7740
tgtgcctgct catagaagag ctagagagtc tcctctctct tctgatgcta tcttcaagca   7800
gtctcacgct ggacttttca acctctgtgt ggtggttctt atcgctgtga actctagact   7860
catcatcgag aacctcatga agtacggatg gctcatcaga actgatttct ggttctcttc   7920
tagatctctc agagattggc ctcttttcat gtgctgcatc tcactctcaa tcttccctct   7980
cgctgctttt actgttgaga agctcgtgct ccagaagtat atcgctgaac ctgtggtgat   8040
cttcctccac atcatcatca ctatgactga ggttctctac cctgtttacg tgactctcag   8100
atgcgattct gctttcctct ctggtgttac tcttatgctc ctcacttgca ttgtgtggct   8160
taagctcgtg tcttacgctc acacttctta cgatatcaga tctctcgcta acgctgctga   8220
taaggctaac cctgaagtgt cttactacgt gtctctcaag tctctcgctt acttcatggt   8280
tgctcctaca ctttgttacc agccatctta ccctagatct gcttgcatta gaaagggatg   8340
ggtggcaaga caattcgcta agttggtgat cttcactgga ttcatgggat tcatcatcga   8400
gcagtacatc aaccctattg tgagaaactc taagcaccct ctcaagggtg atcttctcta   8460
cgctatcgag agagttctta agctctctgt gcctaacctt tatgtgtggc tctgcatgtt   8520
ctactgtttc ttccacctct ggcttaacat ccttgctgag ttgctttgct tcggagatag   8580
agagttctac aaggattggt ggaacgctaa gtctgttgga gattattgga gaatgtggaa   8640
catgcctgtg cataagtgga tggtgcgtca catctacttc ccttgcctca gatctaagat   8700
ccctaagact ctcgctatca ttatcgcttt cctcgtgtct gctgttttcc atgagttgtg   8760
tatcgctgtt ccttgcagac ttttcaagct ttgggctttc ctcggaatca tgttccaggt   8820
tccactcgtg ttcatcacta actacctcca agagagattc ggatctactg ttggaaacat   8880
gattttctgg ttcattttct gcatcttcgg acagcctatg tgcgttctcc tctactacca   8940
```

```
cgatctcatg aacagaaagg gatctatgtc ttaatgaagg atccacccag ctttcttgta   9000
caaagtggtg atgggttcga aatcgataag cttggatcct ctagagtcct gctttaatga   9060
gatatgcgag acgcctatga tcgcatgata tttgctttca attctgttgt gcacgttgta   9120
aaaaacctga gcatgtgtag ctcagatcct taccgccggt ttcggttcat tctaatgaat   9180
atatcacccg ttactatcgt atttttatga ataatattct ccgttcaatt tactgattgt   9240
accctactac ttatatgtac aatattaaaa tgaaaacaat atattgtgct gaataggttt   9300
atagcgacat ctatgataga gcgccacaat aacaaacaat tgcgttttat tattacaaat   9360
ccaattttaa aaaaagcggc agaaccggtc aaacctaaaa gactgattac ataaatctta   9420
ttcaaatttc aaaaggcccc aggggctagt atctacgaca caccgagcgg cgaactaata   9480
acgttcactg aagggaactc cggttccccg ccggcgcgca tgggtgagat tccttgaagt   9540
tgagtattgg ccgtccgctc taccgaaagt tacgggcacc attcaacccg gtccagcacg   9600
gcggccgggt aaccgacttg ctgccccgag aattatgcag catttttttg gtgtatgtgg   9660
gccccaaatg aagtgcaggt caaaccttga cagtgacgac aaatcgttgg gcgggtccag   9720
ggcgaatttt gcgacaacat gtcgaggctc agcaggacct gcaggcatgc aagctagctt   9780
actagtgatg catattctat agtgtcacct aaatctgcgg ccgcctgcag gtcgatatgg   9840
gagagctccc aacgcgttgg atgcatagct tgagtattct atagtgtcac ctaaatagct   9900
tggcgtaatc atggtcatag ctgtttcctg tgtgaaattg ttatccgctc acaattccac   9960
acaacatacg agccggaagc ataaagtgta aagcctgggg tgcctaatga gtgagctaac  10020
tcacattaat tgcgttgcgc tcactgcccg ctttccagtc gggaaacctg tcgtgccagc  10080
tgcattaatg aatcggccaa cgcgcgggga gaggcggttt gcgtattggg gctgagtggc  10140
tccttcaacg ttgcggttct gtcagttcca aacgtaaaac ggcttgtccc gcgtcatcgg  10200
cgggggtcat aacgtgactc ccttaattct ccgctcatga tcagattgtc gtttcccgcc  10260
ttcagtttaa actatcagtg tttgacagga tatattggcg ggtaaaccta agagaaaaga  10320
gcgtttatta gaataatcgg atatttaaaa gggcgtgaaa aggtttatcc gttcgtccat  10380
ttgtatgtgc atgccaacca cagggttccc ctcgggagtg cttggcattc cgtgcgataa  10440
tgacttctgt tcaaccaccc aaacgtcgga aagcctgacg acggagcagc attccaaaaa  10500
gatcccttgg ctcgtctggg tcggctagaa ggtcgagtgg gctgctgtgg cttgatccct  10560
caacgcggtc gcggacgtag cgcagcgccg aaaaatcctc gatcgcaaat ccgacgctgt  10620
cgaaaatcgt gatctgcttg tcgctctttc ggccgacgtc ctggccagtc atcacgcgcc  10680
aaagttccgt cacaggatga tctggcgcga gttgctggat ctcgccttca atccgggtct  10740
gtggcgggaa ctccacgaaa atatccgaac gcagcaagat gtcgacggat cttttccgct  10800
gcataaccct gcttcggggt cattatagcg atttttttcgg tatatccatc ctttttcgca  10860
cgatatacag gattttgcca aagggttcgt gtagactttc cttggtgtat ccaacggcgt  10920
cagccgggca ggataggtga agtaggccca cccgcgagcg ggtgttcctt cttcactgtc  10980
ccttattcgc acctggcggt gctcaacggg aatcctgctc tgcgaggctg gccggctacc  11040
gccggcgtaa cagatgaggg caagcggatg gctgatgaaa ccaagccaac caggggtgat  11100
gctgccaact tactgattta gtgtatgatg gtgtttttga ggtgctccag tggcttctgt  11160
ttctatcagc tgtccctcct gttcagctac tgacggggtg gtgcgtaacg gcaaaagcac  11220
cgccggacat cagcgctatc tctgctctca ctgccgtaaa acatggcaac tgcagttcac  11280
```
ttacaccgct tctcaacccg gtacgcacca gaaaatcatt gatatggcca tgaatggcgt 11340
tggatgccgg gcaacagccc gcattatggg cgttggcctc aacacgattt tacgtcactt 11400
aaaaaactca ggccgcagtc ggtaacctcg cgcatacagc cgggcagtga cgtcatcgtc 11460
tgcgcggaaa tggacgaaca gtggggctat gtcggggcta aatcgcgcca gcgctggctg 11520
ttttacgcgt atgacagtct ccggaagacg gttgttgcgc acgtattcgg tgaacgcact 11580
atggcgacgc tggggcgtct tatgagcctg ctgtcaccct ttgacgtggt gatatggatg 11640
acggatggct ggccgctgta tgaatcccgc ctgaagggaa agctgcacgt aatcagcaag 11700
cgatatacgc agcgaattga gcggcataac ctgaatctga ggcagcacct ggcacggctg 11760
ggacggaagt cgctgtcgtt ctcaaaatcg gtggagctgc atgacaaagt catcgggcat 11820
tatctgaaca taaaacacta tcaataagtt ggagtcatta cccaaccagg aagggcagcc 11880
cacctatcaa ggtgtactgc cttccagacg aacgaagagc gattgaggaa aaggcggcgg 11940
cggccggcat gagcctgtcg gcctacctgc tggccgtcgg ccagggctac aaaatcacgg 12000
gcgtcgtgga ctatgagcac gtccgcgagc tggcccgcat caatggcgac ctgggccgcc 12060
tgggcggcct gctgaaactc tggctcaccg acgacccgcg cacggcgcgg ttcggtgatg 12120
ccacgatcct cgccctgctg gcgaagatcg aagagaagca ggacgagctt ggcaaggtca 12180
tgatgggcgt ggtccgcccg agggcagagc catgactttt ttagccgcta aaacggccgg 12240
ggggtgcgcg tgattgccaa gcacgtcccc atgcgctcca tcaagaagag cgacttcgcg 12300
gagctggtat tcgtgcaggg caagattcgg aataccaagt acgagaagga cggccagacg 12360
gtctacggga ccgacttcat tgccgataag gtggattatc tggacaccaa ggcaccaggc 12420
gggtcaaatc aggaataagg gcacattgcc ccggcgtgag tcggggcaat cccgcaagga 12480
gggtgaatga atcggacgtt tgaccggaag gcatacaggc aagaactgat cgacgcgggg 12540
ttttccgccg aggatgccga aaccatcgca agccgcaccg tcatgcgtgc gccccgcgaa 12600
accttccagt ccgtcggctc gatggtccag caagctacgg ccaagatcga gcgcgacagc 12660
gtgcaactgg ctcccccctgc cctgcccgcg ccatcggccg ccgtggagcg ttcgcgtcgt 12720
ctcgaacagg aggcggcagg tttggcgaag tcgatgacca tcgacacgcg aggaactatg 12780
acgaccaaga agcgaaaaac cgccggcgag gacctggcaa aacaggtcag cgaggccaag 12840
caggccgcgt tgctgaaaca cacgaagcag cagatcaagg aaatgcagct ttccttgttc 12900
gatattgcgc cgtggccgga cacgatgcga gcgatgccaa acgacacggc ccgctctgcc 12960
ctgttcacca cgcgcaacaa gaaaatcccg cgcgaggcgc tgcaaaacaa ggtcattttc 13020
cacgtcaaca aggacgtgaa gatcacctac accggcgtcg agctgcgggc cgacgatgac 13080
gaactggtgt ggcagcaggt gttggagtac gcgaagcgca cccctatcgg cgagccgatc 13140
accttcacgt tctacgagct ttgccaggac ctgggctggt cgatcaatgg ccggtattac 13200
acgaaggccg aggaatgcct gtcgcgccta caggcgacgg cgatgggctt cacgtccgac 13260
cgcgttgggc acctggaatc ggtgtcgctg ctgcaccgct tccgcgtcct ggaccgtggc 13320
aagaaaacgt cccgttgcca ggtcctgatc gacgaggaaa tcgtcgtgct gtttgctggc 13380
gaccactaca cgaaattcat atgggagaag taccgcaagc tgtcgccgac ggcccgacgg 13440
atgttcgact atttcagctc gcaccgggag ccgtacccgc tcaagctgga aaccttccgc 13500
ctcatgtgcg gatcggattc cacccgcgtg aagaagtggc gcgagcaggt cggcgaagcc 13560
tgcgaagagt tgcgaggcag cggcctggtg gaacacgcct gggtcaatga tgacctggtg 13620
cattgcaaac gctagggcct tgtggggtca gttccggctg ggggttcagc agccagcgct 13680
ttactggcat ttcaggaaca agcgggcact gctcgacgca cttgcttcgc tcagtatcgc 13740
tcgggacgca cggcgcgctc tacgaactgc cgataaacag aggattaaaa ttgacaattg 13800
tgattaaggc tcagattcga cggcttggag cggccgacgt gcaggatttc cgcgagatcc 13860
gattgtcggc cctgaagaaa gctccagaga tgttcgggtc cgtttacgag cacgaggaga 13920
aaaagcccat ggaggcgttc gctgaacggt tgcgagatgc cgtggcattc ggcgcctaca 13980
tcgacggcga gatcattggg ctgtcggtct tcaaacagga ggacggcccc aaggacgctc 14040
acaaggcgca tctgtccggc gttttcgtgg agcccgaaca gcgaggccga ggggtcgccg 14100
gtatgctgct gcgggcgttg ccggcgggtt tattgctcgt gatgatcgtc cgacagattc 14160
caacgggaat ctggtggatg cgcatcttca tcctcggcgc acttaatatt tcgctattct 14220
ggagcttgtt gtttatttcg gtctaccgcc tgccgggcgg ggtcgcggcg acggtaggcg 14280
ctgtgcagcc gctgatggtc gtgttcatct ctgccgctct gctaggtagc ccgatacgat 14340
tgatggcggt cctgggggct atttgcggaa ctgcgggcgt ggcgctgttg gtgttgacac 14400
caaacgcagc gctagatcct gtcggcgtcg cagcgggcct ggcgggggcg gtttccatgg 14460
cgttcggaac cgtgctgacc cgcaagtggc aacctcccgt gcctctgctc acctttaccg 14520
cctggcaact ggcggccgga ggacttctgc tcgttccagt agctttagtg tttgatccgc 14580
caatcccgat gcctacagga accaatgttc tcggcctggc gtggctcggc ctgatcggag 14640
cgggtttaac ctacttcctt tggttccggg ggatctcgcg actcgaacct acagttgttt 14700
ccttactggg ctttctcagc cgggatggcg ctaagaagct attgccgccg atcttcatat 14760
gcggtgtgaa ataccgcaca gatgcgtaag gagaaaatac cgcatcaggc gctcttccgc 14820
ttcctcgctc actgactcgc tgcgctcggt cgttcggctg cggcgagcgg tatcagctca 14880
ctcaaaggcg gtaatacggt tatccacaga atcaggggat aacgcaggaa agaacatgtg 14940
agcaaaaggc cagcaaaagg ccaggaaccg taaaaaggcc gcgttgctgg cgtttttcca 15000
taggctccgc ccccctgacg agcatcacaa aaatcgacgc tcaagtcaga ggtggcgaaa 15060
cccgacagga ctataaagat accaggcgtt tccccctgga agctccctcg tgcgctctcc 15120
tgttccgacc ctgccgctta ccggatacct gtccgccttt ctcccttcgg gaagcgtggc 15180
gctttctcaa tgctcacgct gtaggtatct cagttcggtg taggtcgttc gctccaagct 15240
gggctgtgtg cacgaacccc ccgttcagcc cgaccgctgc gccttatccg gtaactatcg 15300
tcttgagtcc aacccggtaa gacacgactt atcgccactg gcagcagcca ctggtaacag 15360
gattagcaga gcgaggtatg taggcggtgc tacagagttc ttgaagtggt ggcctaacta 15420
cggctacact agaaggacag tatttggtat ctgcgctctg ctgaagccag ttaccttcgg 15480
aaaaagagtt ggtagctctt gatccggcaa acaaaccacc gctggtagcg gtggtttttt 15540
tgtttgcaag cagcagatta cgcgcagaaa aaaaggatat caagaagatc ctttgatctt 15600
ttctacgggg tctgacgctc agtggaacga aaactcacgt taagggattt tggtcatgag 15660
attatcaaaa aggatcttca cctagatcct tttaaattaa aaatgaagtt ttaaatcaat 15720
ctaaagtata tatgagtaaa cttggtctga cagttaccaa tgcttaatca gtgaggcacc 15780
tatctcagcg atctgtctat ttcgttcatc catagttgcc tgactccccg tcgtgtagat 15840
aactacgata cgggagggct taccatctgg ccccagtgct gcaatgatac cgcgagaccc 15900
acgctcaccg gctccagatt tatcagcaat aaaccagcca gccggaaggg ccgagcgcag 15960
aagtggtcct gcaactttat ccgcctccat ccagtctatt aaacaagtgg cagcaacgga 16020

-continued

```
ttcgcaaacc tgtcacgcct tttgtgccaa aagccgcgcc aggtttgcga tccgctgtgc  16080
caggcgttag gcgtcatatg aagatttcgg tgatccctga gcaggtggcg gaaacattgg  16140
atgctgagaa ccatttcatt gttcgtgaag tgttcgatgt gcacctatcc gaccaaggct  16200
ttgaactatc taccagaagt gtgagcccct accggaagga ttacatctcg gatgatgact  16260
ctgatgaaga ctctgcttgc tatggcgcat tcatcgacca agagcttgtc gggaagattg  16320
aactcaactc aacatggaac gatctagcct ctatcgaaca cattgttgtg tcgcacacgc  16380
accgaggcaa aggagtcgcg cacagtctca tcgaatttgc gaaaaagtgg gcactaagca  16440
gacagctcct tggcatacga ttagagacac aaacgaacaa tgtacctgcc tgcaatttgt  16500
acgcaaaatg tggctttact ctcggcggca ttgacctgtt cacgtataaa actagacctc  16560
aagtctcgaa cgaaacagcg atgtactggt actggttctc gggagcacag gatgacgcct  16620
aacaattcat tcaagccgac accgcttcgc ggcgcggctt aattcaggag ttaaacatca  16680
tgagggaagc ggtgatcgcc gaagtatcga ctcaactatc agaggtagtt ggcgtcatcg  16740
agcgccatct cgaaccgacg ttgctggccg tacatttgta cggctccgca gtggatggcg  16800
gcctgaagcc acacagtgat attgatttgc tggttacggt gaccgtaagg cttgatgaaa  16860
caacgcggcg agctttgatc aacgaccttt tggaaacttc ggcttcccct ggagagagcg  16920
agattctccg cgctgtagaa gtcaccattg ttgtgcacga cgacatcatt ccgtggcgtt  16980
atccagctaa gcgcgaactg caatttggag aatggcagcg caatgacatt cttgcaggta  17040
tcttcgagcc agccacgatc gacattgatc tggctatctt gctgacaaaa gcaagagaac  17100
atagcgttgc cttggtaggt ccagcggcgg aggaactctt tgatccggtt cctgaacagg  17160
atctatttga ggcgctaaat gaaaccttaa cgctatggaa ctcgccgccc gactgggctg  17220
gcgatgagcg aaatgtagtg cttacgttgt cccgcatttg gtacagcgca gtaaccggca  17280
aaatcgcgcc gaaggatgtc gctgccgact gggcaatgga gcgcctgccg gcccagtatc  17340
agcccgtcat acttgaagct aggcaggctt atcttggaca agaagatcgc ttggcctcgc  17400
gcgcagatca gttggaagaa tttgttcact acgtgaaagg cgagatcacc aaggtagtcg  17460
gcaaataatg tctaacaatt cgttcaagcc gacgccgctt cgcggcgcgg cttaactcaa  17520
gcgttagaga gctggggaag actatgcgcg atctgttgaa ggtggttcta agcctcgtac  17580
ttgcgatggc atcggggcag gcacttgctg acctgccaat tgttttagtg gatgaagctc  17640
gtcttcccta tgactactcc ccatccaact acgacatttc tccaagcaac tacgacaact  17700
ccataagcaa ttacgacaat agtccatcaa attacgacaa ctctgagagc aactacgata  17760
atagttcatc caattacgac aatagtcgca acggaaatcg taggcttata tatagcgcaa  17820
atgggtctcg cactttcgcc ggctactacg tcattgccaa caatgggaca acgaacttct  17880
tttccacatc tggcaaaagg atgttctaca ccccaaaagg ggggcgcggc gtctatggcg  17940
gcaaagatgg gagcttctgc ggggcattgg tcgtcataaa tggccaattt tcgcttgccc  18000
tgacagataa cggcctgaag atcatgtatc taagcaacta gcctgctctc taataaaatg  18060
ttaggagctt ggctgccatt tttggggtga ggccgttcgc ggccgagggg cgcagcccct  18120
ggggggatgg gaggcccgcg ttagcgggcc gggagggttc gagaaggggg ggcacccccc  18180
ttcggcgtgc gcggtcacgc gccagggcgc agccctggtt aaaaacaagg tttataaata  18240
ttggtttaaa agcaggttaa aagacaggtt agcggtggcc gaaaaacggg cggaaaccct  18300
tgcaaatgct ggattttctg cctgtggaca gcccctcaaa tgtcaatagg tgcgcccctc  18360
atctgtcagc actctgcccc tcaagtgtca aggatcgcgc cctcatctg tcagtagtcg   18420
```
cgcccctcaa gtgtcaatac cgcagggcac ttatccccag gcttgtccac atcatctgtg 18480
ggaaactcgc gtaaaatcag gcgttttcgc cgatttgcga ggctggccag ctccacgtcg 18540
ccggccgaaa tcgagcctgc ccctcatctg tcaacgccgc gccgggtgag tcggcccctc 18600
aagtgtcaac gtccgcccct catctgtcag tgagggccaa gttttccgcg aggtatccac 18660
aacgccggcg gccggccgcg gtgtctcgca cacggcttcg acggcgtttc tggcgcgttt 18720
gcagggccat agacggccgc cagcccagcg gcgagggcaa ccagcccggt gagcgtcgga 18780
aagg 18784

<210> SEQ ID NO 30
<211> LENGTH: 18784
<212> TYPE: DNA
<213> ORGANISM: Artificial Sequence
<220> FEATURE:
<223> OTHER INFORMATION: Synthetic vector

<400> SEQUENCE: 30
tcgacatcgt caacgttcac ttctaaagaa atagcgccac tcagcttcct cagcggcttt 60
atccagcgat ttcctattat gtcggcatag ttctcaagat cgacagcctg tcacggttaa 120
gcgagaaatg aataagaagg ctgataattc ggatctctgc gaggagatga tatttgatca 180
caggcagcaa cgctctgtca tcgttacaat caacatgcta ccctccgcga gatcatccgt 240
gtttcaaacc cggcagctta gttgccgttc ttccgaatag catcgggtaa catgagcaaa 300
gtctgccgcc ttacaacggc tctcccgctg acgccgtccc ggactgatgg gctgcctgta 360
tcgagtggtg attttgtgcc gagctgccgg tcggggagct gttggctggc tggtggcagg 420
atatattgtg gtgtaaacaa attgacgctt agacaactta ataacacatt gcggacgttt 480
ttaatgtact gaattcgccg ctcggtgtgt cgtagatact agcccctggg gcacttttga 540
aatttgaata agatttatgt aatcagtctt ttaggtttga ccggttctgc cgcttttttt 600
aaaattggat ttgtaataat aaaacgcaat tgtttgttat tgtggcgctc tatcatagat 660
gtcgctataa acctattcag cacaatatat tgttttcatt ttaatattgt acatataagt 720
agtagggtac aatcagtaaa ttgaacggag aatattattc ataaaaaatac gatagtaacg 780 ggtgatatat tcattagaat gaaccgaaac cggcggtaag gatctgagct acacatgctc 840
aggtttttta caacgtgcac aacagaattg aaagcaaata tcatgcgatc ataggcgtct 900
cgcatatctc attaaacaag tgaagatttg attcaaactc cattgagagc cctgactatg 960
cattcggttt gacccttcca ggttgagaga cgatagcccc ctaccttaat taaggggccc 1020
cccctcgagg tcgacggtat cgataagctt gatatcgaat tcctgcagcc agggggatcc 1080
cccgggtcat cagatctcgg tgacgggcag gaccggacgg ggcggtaccg gcaggctgaa 1140
gtccagctgc cagaaaccca cgtcatgcca gttcccgtgc ttgaagccgg ccgcccgcag 1200
catgccgcgg ggggcatatc cgagcgcctc gtgcatgcgc acgctcgggt cgttgggcag 1260
cccgatgaca gcgaccacgc tcttgaagcc ctgtgcctcc agggacttca gcaggtgggt 1320
gtagagcgtg gagcccagtc ccgtccgctg gtggcggggg gagacgtaca cggtcgactc 1380
ggccgtccag tcgtaggcgt tgcgtgcctt ccaggggccc gcgtaggcga tgccggcgac 1440
ctcgccgtcc acctcggcga cgagccaggg atagcgctcc cgcagacgga cgaggtcgtc 1500
cgtccactcc tgcggttcct gcggctcggt acggaagttg accgtgcttg tctcgatgta 1560
gtggttgacg atggtgcaga ccgccggcat gtccgcctcg gtggcacggc ggatgtcggc 1620

-continued

```
cgggcgtcgt tctgggctca tggtagatcc cctcgagaga gatagatttg tagagagaga   1680
ctggtgattt cagcgtgtcc tctccaaatg aaatgaactt ccttatatag aggaaggtct   1740
tgcgaaggat agtgggattg tgcgtcatcc cttacgtcag tggagatatc acatcaatcc   1800
acttgctttg aagacgtggt tggaacgtct tctttttcca cgatgctcct cgtgggtggg   1860
ggtccatctt tgggaccact gtcggcagag gcatcttgaa cgatagcctt tcctttatcg   1920
caatgatggc atttgtaggt gccaccttcc ttttctactg tccttttgat gaagtgacag   1980
atagctgggc aatggaatcc gaggaggttt cccgatatta ccctttgttg aaaagtctca   2040
atagcccttt ggtcttctga gactgtatct ttgatattct tggagtagac gagagtgtcg   2100
tgctccacca tgttatcaca tcaatccact tgctttgaag acgtggttgg aacgtcttct   2160
ttttccacga tgctcctcgt gggtgggggt ccatctttgg gaccactgtc ggcagaggca   2220
tcttgaacga tagcctttcc tttatcgcaa tgatggcatt tgtaggtgcc accttccttt   2280
tctactgtcc ttttgatgaa gtgacagata gctgggcaat ggaatccgag gaggtttccc   2340
gatattaccc tttgttgaaa agtctcaata gccctttggt cttctgagac tgtatctttg   2400
atattcttgg agtagacgag agtgtcgtgc tccaccatgt tgctgatagt gaccttaggc   2460
gacttttgaa cgcgcaataa tggtttctga cgtatgtgct tagctcatta aactccagaa   2520
acccattaac gcttacaatt tccattcgcc attcaggctg cgcaactgtt gggaagggcg   2580
atcggtgcgg gcctcttcgc tattacgcca gctggcgaaa gggggatgtg ctgcaaggcg   2640
attaagttgg gtaacgccag ggttttccca gtcacgacgt tgtaaaacga cggccagtga   2700
attgtaatac gactcactat agggcgaatt gggcccgacg tcgcatgctc ccggccgcca   2760
tggccgcggg atatcactag tgcggccgct cgacgaatta attccaatcc cacaaaaatc   2820
tgagcttaac agcacagttg ctcctctcag agcagaatcg ggtattcaac accctcatat   2880
caactactac gttgtgtata acggtccaca tgccggtata tacgatgact ggggttgtac   2940
aaaggcggca acaaacggcg ttcccggagt tgcacacaag aaatttgcca ctattacaga   3000
ggcaagagca gcagctgacg cgtacacaac aagtcagcaa acagacaggt tgaacttcat   3060
ccccaaagga gaagctcaac tcaagcccaa gagctttgct aaggccctaa caagcccacc   3120
aaagcaaaaa gcccactggc tcacgctagg aaccaaaagg cccagcagtg atccagcccc   3180
aaaagagatc tcctttgccc cggagattac aatggacgat ttcctctatc tttacgatct   3240
aggaaggaag ttcgaaggtg aaggtgacga cactatgttc accactgata atgagaaggt   3300
tagcctcttc aatttcagaa agaatgctga cccacagatg gttagagagg cctacgcagc   3360
aggtctcatc aagacgatct acccgagtaa caatctccag gagatcaaat accttcccaa   3420
gaaggttaaa gatgcagtca aaagattcag gactaattgc atcaagaaca cagagaaaga   3480
catatttctc aagatcagaa gtactattcc agtatggacg attcaaggct tgcttcataa   3540
accaaggcaa gtaatagaga ttggagtctc taaaaaggta gttcctactg aatctaaggc   3600
catgcatgga gtctaagatt caaatcgagg atctaacaga actcgccgtg aagactggcg   3660
aacagttcat acagagtctt ttacgactca atgacaagaa gaaaatcttc gtcaacatgg   3720
tggagcacga cactctggtc tactccaaaa atgtcaaaga tacagtctca gaagaccaaa   3780
gggctattga gacttttcaa caaaggataa tttcgggaaa cctcctcgga ttccattgcc   3840
cagctatctg tcacttcatc gaaaggacag tagaaaagga aggtggctcc tacaaatgcc   3900
atcattgcga taaaggaaag gctatcattc aagatctctc tgccgacagt ggtcccaaag   3960
atggaccccc acccacgagg agcatcgtgg aaaaagaaga cgttccaacc acgtcttcaa   4020
```
agcaagtgga ttgatgtgac atctccactg acgtaaggga tgacgcacaa tcccactatc 4080
cttcgcaaga cccttcctct atataaggaa gttcatttca tttggagagg acacgctcga 4140
ggaattcggt accccatcac aagtttgtac aaaaaagcag gctgcggccg cttgctccct 4200
taaaaaaaac catggcatgt cattacggac aacagcaaca gacttgtgca cctcatcttc 4260
agcttcaacc tagagcatgt agagttgtga aggctgctac tgctgttact gtaaatttct 4320
gtgttcctta ttctctcaaa atcttcgatt ttgttttcgt tcgatcccaa tttcgtatat 4380
gttctttggt ttagattctg ttaatcttag atcgaagacg attttctggg tttgatcgtt 4440
agatatcatc ttaattctcg attagggttt catagatatc atccgatttg ttcaaataat 4500
ttgagttttg tcgaataatt actcttcgat ttgtgatttc tatctagatc tggtgttagt 4560
ttctagtttg tgcgatcgaa tttgtcgatt aatctgagtt tttctgatta acaggctgga 4620
ggatctcttc ttgttctctc tggacttact ctcgctggaa ctgttatcgc tctcactatc 4680
gctacacctc ttctcgttat cttctctcct gttctcgttc ctgctgtgat cactatcttc 4740
cttctcggag ctggatttct tgcttctggt ggatttggag ttgctgctct ctctgttctc 4800
tcttggatct acagatacct cactggaaaa catcctccag gtgctgattg tcttgagtct 4860
gctaagacta agctcgcttc ttgtgctaga gagatgaagg atagagcaga gcaattctct 4920
tgtcagcctg ttgctggatc tcagacttct taatgaacat atggtcctgc tttaatgaga 4980
tatgcgagac gcctatgatc gcatgatatt tgctttcaat tctgttgtgc acgttgtaaa 5040
aaacctgagc atgtgtagct cagatcctta ccgccggttt cggttcattc taatgaatat 5100
atcacccgtt actatcgtat ttttatgaat aatattctcc gttcaattta ctgattgtac 5160
cctactactt atatgtacaa tattaaaatg aaaacaatat attgtgctga ataggtttat 5220
agcgacatct atgatagagc gccacaataa caaacaattg cgttttatta ttacaaatcc 5280
aattttaaaa aaagcggcag aaccggtcaa acctaaaaga ctgattacat aaatcttatt 5340
caaatttcaa aaggccccag gggctagtat ctacgacaca ccgagcggcg aactaataac 5400
gttcactgaa gggaactccg gttccccgcc ggcgcgcatg ggtgagattc cttgaagttg 5460
agtattggcc gtccgctcta ccgaaagtta cgggcaccat tcaacccggt ccagcacggc 5520
ggccgggtaa ccgacttgct gccccgagaa ttatgcagca tttttttggt gtatgtgggc 5580
cccaaatgaa gtgcaggtca aaccttgaca gtgacgacaa atcgttgggc gggtccaggg 5640
cgaattttgc gacaacatgt cgaggctcag caggacctgc aggcatgcaa gctagcttac 5700
tagtgatgca tattctatag tgtcacctaa atcttcgacg aattaattcc aatcccacaa 5760
aaatctgagc ttaacagcac agttgctcct ctcagagcag aatcgggtat tcaacaccct 5820
catatcaact actacgttgt gtataacggt ccacatgccg gtatatacga tgactggggt 5880
tgtacaaagg cggcaacaaa cggcgttccc ggagttgcac acaagaaatt tgccactatt 5940
acagaggcaa gagcagcagc tgacgcgtac acaacaagtc agcaaacaga caggttgaac 6000
ttcatcccca aaggagaagc tcaactcaag cccaagagct ttgctaaggc cctaacaagc 6060
ccaccaaagc aaaaagccca ctggctcacg ctaggaacca aaaggcccag cagtgatcca 6120
gccccaaaag agatctcctt tgccccggag attacaatgg acgatttcct ctatctttac 6180
gatctaggaa ggaagttcga aggtgaaggt gacgacacta tgttcaccac tgataatgag 6240
aaggttagcc tcttcaattt cagaaagaat gctgacccac agatggttag agaggcctac 6300
gcagcaggtc tcatcaagac gatctacccg agtaacaatc tccaggagat caaatacctt 6360
cccaagaagg ttaaagatgc agtcaaaaga ttcaggacta attgcatcaa gaacacagag 6420
aaagacatat ttctcaagat cagaagtact attccagtat ggacgattca aggcttgctt 6480
cataaaccaa ggcaagtaat agagattgga gtctctaaaa aggtagttcc tactgaatct 6540
aaggccatgc atggagtcta agattcaaat cgaggatcta acagaactcg ccgtgaagac 6600
tggcgaacag ttcatacaga gtcttttacg actcaatgac aagaagaaaa tcttcgtcaa 6660
catggtggag cacgacactc tggtctactc caaaaatgtc aaagatacag tctcagaaga 6720
ccaaagggct attgagactt ttcaacaaag gataatttcg ggaaacctcc tcggattcca 6780
ttgcccagct atctgtcact tcatcgaaag gacagtagaa aaggaaggtg gctcctacaa 6840
atgccatcat tgcgataaag gaaaggctat cattcaagat ctctctgccg acagtggtcc 6900
caaagatgga cccccaccca cgaggagcat cgtggaaaaa gaagacgttc caaccacgtc 6960
ttcaaagcaa gtggattgat gtgacatctc cactgacgta agggatgacg cacaatccca 7020
ctatccttcg caagaccctt cctctatata aggaagttca tttcatttgg agaggacacg 7080
ggatccttgc tccgttaaaa aaaaccatgg ctatcctcga ttctgctggt gttactactg 7140
tgactgagaa tggtggtgga gagttcgttg atctcgatag actcagaaga agaaagtcta 7200
gatctgtaaa tttctgtgtt ccttattctc tcaaaatctt cgattttgtt ttcgttcgat 7260
cccaatttcg tatatgttct ttggtttaga ttctgttaat cttagatcga agacgatttt 7320
ctgggtttga tcgttagata tcatcttaat tctcgattag ggtttcatag atatcatccg 7380
atttgttcaa ataatttgag ttttgtcgaa taattactct tcgatttgtg atttctatct 7440
agatctggtg ttagtttcta gtttgtgcga tcgaatttgt cgattaatct gagtttttct 7500
gattaacagg attcttctaa cggacttctc ctctctggat ctgataacaa ctctccttct 7560
gatgatgttg gtgctcctgc tgatgtgaga gatagaatcg attctgtggt gaacgatgat 7620
gctcaaggta ctgctaacct cgctggtgat aataacggtg gaggtgataa caatggtgga 7680
ggaagaggtg gaggtgaagg tagaggaaac gctgatgcta ctttcactta cagaccatct 7740
gtgcctgctc atagaagagc tagagagtct cctctctctt ctgatgctat cttcaagcag 7800
tctcacgctg gacttttcaa cctctgtgtg gtggttctta tcgctgtgaa ctctagactc 7860
atcatcgaga acctcatgaa gtacggatgg ctcatcagaa ctgatttctg gttctcttct 7920
agatctctca gagattggcc tcttttcatg tgctgcatct cactctcaat cttccctctc 7980
gctgctttta ctgttgagaa gctcgtgctc cagaagtata tcgctgaacc tgtggtgatc 8040
ttcctccaca tcatcatcac tatgactgag gttctctacc ctgtttacgt gactctcaga 8100
tgcgattctg ctttcctctc tggtgttact cttatgctcc tcacttgcat tgtgtggctt 8160
aagctcgtgt cttacgctca cacttcttac gatatcagat ctctcgctaa cgctgctgat 8220
aaggctaacc ctgaagtgtc ttactacgtg tctctcaagt ctctcgctta cttcatggtt 8280
gctcctacac tttgttacca gccatcttac cctagatctg cttgcattag aaagggatgg 8340
gtggcaagac aattcgctaa gttggtgatc ttcactggat tcatgggatt catcatcgag 8400
cagtacatca accctattgt gagaaactct aagcaccctc tcaagggtga tcttctctac 8460
gctatcgaga gagttcttaa gctctctgtg cctaaccttt atgtgtggct ctgcatgttc 8520
tactgtttct tccacctctg gcttaacatc cttgctgagt tgctttgctt cggagataga 8580
gagttctaca aggattggtg gaacgctaag tctgttggag attattggag aatgtggaac 8640
atgcctgtgc ataagtggat ggtgcgtcac atctacttcc cttgcctcag atctaagatc 8700
cctaagactc tcgctatcat tatcgctttc ctcgtgtctg ctgttttcca tgagttgtgt 8760
atcgctgttc cttgcagact tttcaagctt tgggctttcc tcggaatcat gttccaggtt 8820
ccactcgtgt tcatcactaa ctacctccaa gagagattcg gatctactgt tggaaacatg 8880
attttctggt tcattttctg catcttcgga cagcctatgt gcgttctcct ctactaccac 8940
gatctcatga acagaaaggg atctatgtct taatgaagga tccacccagc tttcttgtac 9000
aaagtggtga tgggttcgaa atcgataagc ttggatcctc tagagtcctg ctttaatgag 9060
atatgcgaga cgcctatgat cgcatgatat ttgctttcaa ttctgttgtg cacgttgtaa 9120
aaaacctgag catgtgtagc tcagatcctt accgccggtt tcggttcatt ctaatgaata 9180
tatcacccgt tactatcgta tttttatgaa taatattctc cgttcaattt actgattgta 9240
ccctactact tatatgtaca atattaaaat gaaaacaata tattgtgctg aataggttta 9300
tagcgacatc tatgatagag cgccacaata acaaacaatt gcgttttatt attacaaatc 9360
caattttaaa aaaagcggca gaaccggtca aacctaaaag actgattaca taaatcttat 9420
tcaaatttca aaaggcccca ggggctagta tctacgacac accgagcggc gaactaataa 9480
cgttcactga agggaactcc ggttccccgc cggcgcgcat gggtgagatt ccttgaagtt 9540
gagtattggc cgtccgctct accgaaagtt acgggcacca ttcaacccgg tccagcacgg 9600
cggccgggta accgacttgc tgccccgaga attatgcagc atttttttgg tgtatgtggg 9660
ccccaaatga agtgcaggtc aaaccttgac agtgacgaca aatcgttggg cgggtccagg 9720
gcgaattttg cgacaacatg tcgaggctca gcaggacctg caggcatgca agctagctta 9780
ctagtgatgc atattctata gtgtcaccta aatctgcggc cgcctgcagg tcgatatggg 9840
agagctccca acgcgttgga tgcatagctt gagtattcta tagtgtcacc taaatagctt 9900
ggcgtaatca tggtcatagc tgtttcctgt gtgaaattgt tatccgctca caattccaca 9960
caacatacga gccggaagca taaagtgtaa agcctggggt gcctaatgag tgagctaact 10020
cacattaatt gcgttgcgct cactgcccgc tttccagtcg ggaaacctgt cgtgccagct 10080
gcattaatga atcggccaac gcgcggggag aggcggtttg cgtattgggg ctgagtggct 10140
ccttcaacgt tgcggttctg tcagttccaa acgtaaaacg gcttgtcccg cgtcatcggc 10200
gggggtcata acgtgactcc cttaattctc cgctcatgat cagattgtcg tttcccgcct 10260
tcagtttaaa ctatcagtgt ttgacaggat atattggcgg gtaaacctaa gagaaaagag 10320
cgtttattag aataatcgga tatttaaaag ggcgtgaaaa ggtttatccg ttcgtccatt 10380
tgtatgtgca tgccaaccac agggttcccc tcgggagtgc ttggcattcc gtgcgataat 10440
gacttctgtt caaccaccca aacgtcggaa agcctgacga cggagcagca ttccaaaaag 10500
atcccttggc tcgtctgggt cggctagaag gtcgagtggg ctgctgtggc ttgatccctc 10560
aacgcggtcg cggacgtagc gcagcgccga aaaatcctcg atcgcaaatc cgacgctgtc 10620
gaaaatcgtg atctgcttgt cgctctttcg gccgacgtcc tggccagtca tcacgcgcca 10680
aagttccgtc acaggatgat ctggcgcgag ttgctggatc tcgccttcaa tccgggtctg 10740
tggcgggaac tccacgaaaa tatccgaacg cagcaagatg tcgacggatc ttttccgctg 10800
cataaccctg cttcggggtc attatagcga ttttttcggt atatccatcc tttttcgcac 10860
gatatacagg attttgccaa agggttcgtg tagactttcc ttggtgtatc caacggcgtc 10920
agccgggcag gataggtgaa gtaggcccac ccgcgagcgg gtgttccttc ttcactgtcc 10980
cttattcgca cctggcggtg ctcaacggga atcctgctct gcgaggctgg ccggctaccg 11040
ccggcgtaac agatgagggc aagcggatgg ctgatgaaac caagccaacc aggggtgatg 11100

-continued ctgccaactt actgatttag tgtatgatgg tgtttttgag gtgctccagt ggcttctgtt 11160
tctatcagct gtccctcctg ttcagctact gacggggtgg tgcgtaacgg caaaagcacc 11220
gccggacatc agcgctatct ctgctctcac tgccgtaaaa catggcaact gcagttcact 11280
tacaccgctt ctcaacccgg tacgcaccag aaaatcattg atatggccat gaatggcgtt 11340
ggatgccggg caacagcccg cattatgggc gttggcctca acacgatttt acgtcactta 11400
aaaaactcag gccgcagtcg gtaacctcgc gcatacagcc gggcagtgac gtcatcgtct 11460
gcgcggaaat ggacgaacag tggggctatg tcggggctaa atcgcgccag cgctggctgt 11520
tttacgcgta tgacagtctc cggaagacgg ttgttgcgca cgtattcggt gaacgcacta 11580
tggcgacgct ggggcgtctt atgagcctgc tgtcaccctt tgacgtggtg atatggatga 11640
cggatggctg gccgctgtat gaatcccgcc tgaagggaaa gctgcacgta atcagcaagc 11700
gatatacgca gcgaattgag cggcataacc tgaatctgag gcagcacctg gcacggctgg 11760
gacggaagtc gctgtcgttc tcaaaatcgg tggagctgca tgacaaagtc atcgggcatt 11820
atctgaacat aaaacactat caataagttg gagtcattac ccaaccagga agggcagccc 11880
acctatcaag gtgtactgcc ttccagacga acgaagagcg attgaggaaa aggcggcggc 11940
ggccggcatg agcctgtcgg cctacctgct ggccgtcggc cagggctaca aaatcacggg 12000
cgtcgtggac tatgagcacg tccgcgagct ggcccgcatc aatggcgacc tgggccgcct 12060
gggcggcctg ctgaaactct ggctcaccga cgacccgcgc acggcgcggt tcggtgatgc 12120
cacgatcctc gccctgctgg cgaagatcga agagaagcag gacgagcttg gcaaggtcat 12180
gatgggcgtg gtccgcccga gggcagagcc atgacttttt tagccgctaa aacggccggg 12240
gggtgcgcgt gattgccaag cacgtcccca tgcgctccat caagaagagc gacttcgcgg 12300
agctggtatt cgtgcagggc aagattcgga ataccaagta cgagaaggac ggccagacgg 12360
tctacgggac cgacttcatt gccgataagg tggattatct ggacaccaag gcaccaggcg 12420
ggtcaaatca ggaataaggg cacattgccc cggcgtgagt cggggcaatc ccgcaaggag 12480
ggtgaatgaa tcggacgttt gaccggaagg catacaggca agaactgatc gacgcggggt 12540
tttccgccga ggatgccgaa accatcgcaa gccgcaccgt catgcgtgcg ccccgcgaaa 12600
ccttccagtc cgtcggctcg atggtccagc aagctacggc caagatcgag cgcgacagcg 12660
tgcaactggc tccccctgcc ctgcccgcgc catcggccgc cgtggagcgt tcgcgtcgtc 12720
tcgaacagga ggcggcaggt ttggcgaagt cgatgaccat cgacacgcga ggaactatga 12780
cgaccaagaa gcgaaaaacc gccggcgagg acctggcaaa acaggtcagc gaggccaagc 12840
aggccgcgtt gctgaaacac acgaagcagc agatcaagga aatgcagctt tccttgttcg 12900
atattgcgcc gtggccggac acgatgcgag cgatgccaaa cgacacggcc cgctctgccc 12960
tgttcaccac gcgcaacaag aaaatcccgc gcgaggcgct gcaaaacaag gtcattttcc 13020
acgtcaacaa ggacgtgaag atcacctaca ccggcgtcga gctgcgggcc gacgatgacg 13080
aactggtgtg gcagcaggtg ttggagtacg cgaagcgcac ccctatcggc gagccgatca 13140
ccttcacgtt ctacgagctt tgccaggacc tgggctggtc gatcaatggc cggtattaca 13200
cgaaggccga ggaatgcctg tcgcgcctac aggcgacggc gatgggcttc acgtccgacc 13260
gcgttgggca cctggaatcg gtgtcgctgc tgcaccgctt ccgcgtcctg gaccgtggca 13320
agaaaacgtc ccgttgccag gtcctgatcg acgaggaaat cgtcgtgctg tttgctggcg 13380
accactacac gaaattcata tgggagaagt accgcaagct gtcgccgacg gcccgacgga 13440
tgttcgacta tttcagctcg caccgggagc cgtacccgct caagctggaa accttccgcc 13500

-continued

```
tcatgtgcgg atcggattcc acccgcgtga agaagtggcg cgagcaggtc ggcgaagcct  13560
gcgaagagtt gcgaggcagc ggcctggtgg aacacgcctg ggtcaatgat gacctggtgc  13620
attgcaaacg ctagggcctt gtggggtcag ttccggctgg gggttcagca gccagcgctt  13680
tactggcatt tcaggaacaa gcgggcactg ctcgacgcac ttgcttcgct cagtatcgct  13740
cgggacgcac ggcgcgctct acgaactgcc gataaacaga ggattaaaat tgacaattgt  13800
gattaaggct cagattcgac ggcttggagc ggccgacgtg caggatttcc gcgagatccg  13860
attgtcggcc ctgaagaaag ctccagagat gttcgggtcc gtttacgagc acgaggagaa  13920
aaagcccatg gaggcgttcg ctgaacggtt gcgagatgcc gtggcattcg gcgcctacat  13980
cgacggcgag atcattgggc tgtcggtctt caaacaggag gacggcccca aggacgctca  14040
caaggcgcat ctgtccggcg ttttcgtgga gcccgaacag cgaggccgag ggtcgccgg  14100
tatgctgctg cgggcgttgc cggcgggttt attgctcgtg atgatcgtcc gacagattcc  14160
aacgggaatc tggtggatgc gcatcttcat cctcggcgca cttaatattt cgctattctg  14220
gagcttgttg tttatttcgg tctaccgcct gccgggcggg gtcgcggcga cggtaggcgc  14280
tgtgcagccg ctgatggtcg tgttcatctc tgccgctctg ctaggtagcc cgatacgatt  14340
gatggcggtc ctgggggcta tttgcggaac tgcgggcgtg gcgctgttgg tgttgacacc  14400
aaacgcagcg ctagatcctg tcggcgtcgc agcgggcctg gcgggggcgg tttccatggc  14460
gttcggaacc gtgctgaccc gcaagtggca acctcccgtg cctctgctca cctttaccgc  14520
ctggcaactg gcggccggag gacttctgct cgttccagta gctttagtgt ttgatccgcc  14580
aatcccgatg cctacaggaa ccaatgttct cggcctggcg tggctcggcc tgatcggagc  14640
gggtttaacc tacttccttt ggttccgggg gatctcgcga ctcgaaccta cagttgtttc  14700
cttactgggc tttctcagcc gggatggcgc taagaagcta ttgccgccga tcttcatatg  14760
cggtgtgaaa taccgcacag atgcgtaagg agaaaatacc gcatcaggcg ctcttccgct  14820
tcctcgctca ctgactcgct gcgctcggtc gttcggctgc ggcgagcggt atcagctcac  14880
tcaaaggcgg taatacggtt atccacagaa tcaggggata acgcaggaaa gaacatgtga  14940
gcaaaaggcc agcaaaaggc caggaaccgt aaaaaggccg cgttgctggc gtttttccat  15000
aggctccgcc cccctgacga gcatcacaaa aatcgacgct caagtcagag gtggcgaaac  15060
ccgacaggac tataaagata ccaggcgttt ccccctggaa gctccctcgt gcgctctcct  15120
gttccgaccc tgccgcttac cggatacctg tccgcctttc tcccttcggg aagcgtggcg  15180
ctttctcaat gctcacgctg taggtatctc agttcggtgt aggtcgttcg ctccaagctg  15240
ggctgtgtgc acgaaccccc cgttcagccc gaccgctgcg ccttatccgg taactatcgt  15300
cttgagtcca acccggtaag acacgactta tcgccactgg cagcagccac tggtaacagg  15360
attagcagag cgaggtatgt aggcggtgct acagagttct tgaagtggtg gcctaactac  15420
ggctacacta gaaggacagt atttggtatc tgcgctctgc tgaagccagt taccttcgga  15480
aaaagagttg gtagctcttg atccggcaaa caaaccaccg ctggtagcgg tggttttttt  15540
gtttgcaagc agcagattac gcgcagaaaa aaaggatatc aagaagatcc tttgatcttt  15600
tctacggggt ctgacgctca gtggaacgaa aactcacgtt aagggatttt ggtcatgaga  15660
ttatcaaaaa ggatcttcac ctagatcctt ttaaattaaa aatgaagttt taaatcaatc  15720
taaagtatat atgagtaaac ttggtctgac agttaccaat gcttaatcag tgaggcacct  15780
atctcagcga tctgtctatt tcgttcatcc atagttgcct gactccccgt cgtgtagata  15840
```
actacgatac gggagggctt accatctggc cccagtgctg caatgatacc gcgagaccca 15900
cgctcaccgg ctccagattt atcagcaata aaccagccag ccggaagggc cgagcgcaga 15960
agtggtcctg caactttatc cgcctccatc cagtctatta aacaagtggc agcaacggat 16020
tcgcaaacct gtcacgcctt ttgtgccaaa agccgcgcca ggtttgcgat ccgctgtgcc 16080
aggcgttagg cgtcatatga agatttcggt gatccctgag caggtggcgg aaacattgga 16140
tgctgagaac catttcattg ttcgtgaagt gttcgatgtg cacctatccg accaaggctt 16200
tgaactatct accagaagtg tgagccccta ccggaaggat tacatctcgg atgatgactc 16260
tgatgaagac tctgcttgct atggcgcatt catcgaccaa gagcttgtcg ggaagattga 16320
actcaactca acatggaacg atctagcctc tatcgaacac attgttgtgt cgcacacgca 16380
ccgaggcaaa ggagtcgcgc acagtctcat cgaatttgcg aaaaagtggg cactaagcag 16440
acagctcctt ggcatacgat tagagacaca aacgaacaat gtacctgcct gcaatttgta 16500
cgcaaaatgt ggctttactc tcggcggcat tgacctgttc acgtataaaa ctagacctca 16560
agtctcgaac gaaacagcga tgtactggta ctggttctcg ggagcacagg atgacgccta 16620
acaattcatt caagccgaca ccgcttcgcg gcgcggctta attcaggagt taaacatcat 16680
gagggaagcg gtgatcgccg aagtatcgac tcaactatca gaggtagttg gcgtcatcga 16740
gcgccatctc gaaccgacgt tgctggccgt acatttgtac ggctccgcag tggatggcgg 16800
cctgaagcca cacagtgata ttgatttgct ggttacggtg accgtaaggc ttgatgaaac 16860
aacgcggcga gctttgatca acgacctttt ggaaacttcg gcttcccctg gagagagcga 16920
gattctccgc gctgtagaag tcaccattgt tgtgcacgac gacatcattc cgtggcgtta 16980
tccagctaag cgcgaactgc aatttggaga atggcagcgc aatgacattc ttgcaggtat 17040
cttcgagcca gccacgatcg acattgatct ggctatcttg ctgacaaaag caagagaaca 17100
tagcgttgcc ttggtaggtc cagcggcgga ggaactcttt gatccggttc ctgaacagga 17160
tctatttgag gcgctaaatg aaaccttaac gctatggaac tcgccgcccg actgggctgg 17220
cgatgagcga aatgtagtgc ttacgttgtc ccgcatttgg tacagcgcag taaccggcaa 17280
aatcgcgccg aaggatgtcg ctgccgactg ggcaatggag cgcctgccgg cccagtatca 17340
gcccgtcata cttgaagcta ggcaggctta tcttggacaa gaagatcgct tggcctcgcg 17400
cgcagatcag ttggaagaat ttgttcacta cgtgaaaggc gagatcacca aggtagtcgg 17460
caaataatgt ctaacaattc gttcaagccg acgccgcttc gcggcgcggc ttaactcaag 17520
cgttagagag ctggggaaga ctatgcgcga tctgttgaag gtggttctaa gcctcgtact 17580
tgcgatggca tcggggcagg cacttgctga cctgccaatt gttttagtgg atgaagctcg 17640
tcttccctat gactactccc catccaacta cgacatttct ccaagcaact acgacaactc 17700
cataagcaat tacgacaata gtccatcaaa ttacgacaac tctgagagca actacgataa 17760
tagttcatcc aattacgaca atagtcgcaa cggaaatcgt aggcttatat atagcgcaaa 17820
tgggtctcgc actttcgccg gctactacgt cattgccaac aatgggacaa cgaacttctt 17880
ttccacatct ggcaaaagga tgttctacac ccccaaaggg gggcgcggcg tctatggcgg 17940
caaagatggg agcttctgcg gggcattggt cgtcataaat ggccaatttt cgcttgccct 18000
gacagataac ggcctgaaga tcatgtatct aagcaactag cctgctctct aataaaatgt 18060
taggagcttg gctgccattt ttggggtgag gccgttcgcg gccgaggggc gcagcccctg 18120
gggggatggg aggcccgcgt tagcgggccg ggagggttcg agaagggggg gcaccccccct 18180 tcggcgtgcg cggtcacgcg ccagggcgca gccctggtta aaaacaaggt ttataaatat 18240
tggtttaaaa gcaggttaaa agacaggtta gcggtggccg aaaaacgggc ggaaaccctt 18300
gcaaatgctg gattttctgc ctgtggacag cccctcaaat gtcaataggt gcgcccctca 18360
tctgtcagca ctctgcccct caagtgtcaa ggatcgcgcc cctcatctgt cagtagtcgc 18420
gcccctcaag tgtcaatacc gcagggcact tatccccagg cttgtccaca tcatctgtgg 18480
gaaactcgcg taaaatcagg cgttttcgcc gatttgcgag gctggccagc tccacgtcgc 18540
cggccgaaat cgagcctgcc cctcatctgt caacgccgcg ccgggtgagt cggcccctca 18600
agtgtcaacg tccgcccctc atctgtcagt gagggccaag ttttccgcga ggtatccaca 18660
acgccggcgg ccggccgcgg tgtctcgcac acggcttcga cggcgtttct ggcgcgtttg 18720
cagggccata gacggccgcc agcccagcgg cgagggcaac cagcccggtg agcgtcggaa 18780
aggg 18784

<210> SEQ ID NO 31
<211> LENGTH: 18802
<212> TYPE: DNA
<213> ORGANISM: Artificial Sequence
<220> FEATURE:
<223> OTHER INFORMATION: Synthetic vector

<400> SEQUENCE: 31
tcgacatcgt caacgttcac ttctaaagaa atagcgccac tcagcttcct cagcggcttt 60
atccagcgat ttcctattat gtcggcatag ttctcaagat cgacagcctg tcacggttaa 120
gcgagaaatg aataagaagg ctgataattc ggatctctgc gaggagatga tatttgatca 180
caggcagcaa cgctctgtca tcgttacaat caacatgcta ccctccgcga gatcatccgt 240
gtttcaaacc cggcagctta gttgccgttc ttccgaatag catcgggtaa catgagcaaa 300
gtctgccgcc ttacaacggc tctcccgctg acgccgtccc ggactgatgg gctgcctgta 360
tcgagtggtg attttgtgcc gagctgccgg tcggggagct gttggctggc tggtggcagg 420
atatattgtg gtgtaaacaa attgacgctt agacaactta ataacacatt gcggacgttt 480
ttaatgtact gaattcgccg ctcggtgtgt cgtagatact agcccctggg gcacttttga 540
aatttgaata agatttatgt aatcagtctt ttaggtttga ccggttctgc cgcttttttt 600
aaaattggat ttgtaataat aaaacgcaat tgtttgttat tgtggcgctc tatcatagat 660
gtcgctataa acctattcag cacaatatat tgttttcatt ttaatattgt acatataagt 720
agtagggtac aatcagtaaa ttgaacggag aatattattc ataaaaatac gatagtaacg 780
ggtgatatat tcattagaat gaaccgaaac cggcggtaag gatctgagct acacatgctc 840
aggtttttta caacgtgcac aacagaattg aaagcaaata tcatgcgatc ataggcgtct 900
cgcatatctc attaaacaag tgaagatttg attcaaactc cattgagagc cctgactatg 960
cattcggttt gacccttcca ggttgagaga cgatagcccc ctaccttaat taaggggccc 1020
cccctcgagg tcgacggtat cgataagctt gatatcgaat tcctgcagcc agggggatcc 1080
cccgggtcat cagatctcgg tgacgggcag gaccggacgg ggcggtaccg gcaggctgaa 1140
gtccagctgc cagaaaccca cgtcatgcca gttcccgtgc ttgaagccgg ccgcccgcag 1200
catgccgcgg ggggcatatc cgagcgcctc gtgcatgcgc acgctcgggt cgttgggcag 1260
cccgatgaca gcgaccacgc tcttgaagcc ctgtgcctcc agggacttca gcaggtgggt 1320
gtagagcgtg gagcccagtc ccgtccgctg gtggcggggg gagacgtaca cggtcgactc 1380
ggccgtccag tcgtaggcgt tgcgtgcctt ccaggggccc gcgtaggcga tgccggcgac 1440

-continued

```
ctcgccgtcc acctcggcga cgagccaggg atagcgctcc cgcagacgga cgaggtcgtc   1500
cgtccactcc tgcggttcct gcggctcggt acggaagttg accgtgcttg tctcgatgta   1560
gtggttgacg atggtgcaga ccgccggcat gtccgcctcg gtggcacggc ggatgtcggc   1620
cgggcgtcgt tctgggctca tggtagatcc cctcgagaga gatagatttg tagagagaga   1680
ctggtgattt cagcgtgtcc tctccaaatg aaatgaactt ccttatatag aggaaggtct   1740
tgcgaaggat agtgggattg tgcgtcatcc cttacgtcag tggagatatc acatcaatcc   1800
acttgctttg aagacgtggt tggaacgtct tctttttcca cgatgctcct cgtgggtggg   1860
ggtccatctt tgggaccact gtcggcagag gcatcttgaa cgatagcctt tcctttatcg   1920
caatgatggc atttgtaggt gccaccttcc ttttctactg tccttttgat gaagtgacag   1980
atagctgggc aatggaatcc gaggaggttt cccgatatta ccctttgttg aaaagtctca   2040
atagcccttt ggtcttctga gactgtatct ttgatattct tggagtagac gagagtgtcg   2100
tgctccacca tgttatcaca tcaatccact tgctttgaag acgtggttgg aacgtcttct   2160
ttttccacga tgctcctcgt gggtgggggt ccatctttgg gaccactgtc ggcagaggca   2220
tcttgaacga tagcctttcc tttatcgcaa tgatggcatt tgtaggtgcc accttccttt   2280
tctactgtcc ttttgatgaa gtgacagata gctgggcaat ggaatccgag gaggtttccc   2340
gatattaccc tttgttgaaa agtctcaata gccctttggt cttctgagac tgtatctttg   2400
atattcttgg agtagacgag agtgtcgtgc tccaccatgt tgctgatagt gaccttaggc   2460
gacttttgaa cgcgcaataa tggtttctga cgtatgtgct tagctcatta aactccagaa   2520
acccattaac gcttacaatt tccattcgcc attcaggctg cgcaactgtt gggaagggcg   2580
atcggtgcgg gcctcttcgc tattacgcca gctggcgaaa gggggatgtg ctgcaaggcg   2640
attaagttgg gtaacgccag ggttttccca gtcacgacgt tgtaaaacga cggccagtga   2700
attgtaatac gactcactat agggcgaatt gggcccgacg tcgcatgctc ccggccgcca   2760
tggccgcggg atatcactag tgcggccgct cgacgaatta attccaatcc cacaaaaatc   2820
tgagcttaac agcacagttg ctcctctcag agcagaatcg ggtattcaac accctcatat   2880
caactactac gttgtgtata acggtccaca tgccggtata tacgatgact ggggttgtac   2940
aaaggcggca acaaacggcg ttcccggagt tgcacacaag aaatttgcca ctattacaga   3000
ggcaagagca gcagctgacg cgtacacaac aagtcagcaa acagacaggt tgaacttcat   3060
ccccaaagga gaagctcaac tcaagcccaa gagctttgct aaggccctaa caagcccacc   3120
aaagcaaaaa gcccactggc tcacgctagg aaccaaaagg cccagcagtg atccagcccc   3180
aaaagagatc tcctttgccc cggagattac aatggacgat ttcctctatc tttacgatct   3240
aggaaggaag ttcgaaggtg aaggtgacga cactatgttc accactgata atgagaaggt   3300
tagcctcttc aatttcagaa agaatgctga cccacagatg gttagagagg cctacgcagc   3360
aggtctcatc aagacgatct acccgagtaa caatctccag gagatcaaat accttcccaa   3420
gaaggttaaa gatgcagtca aaagattcag gactaattgc atcaagaaca cagagaaaga   3480
catatttctc aagatcagaa gtactattcc agtatggacg attcaaggct tgcttcataa   3540
accaaggcaa gtaatagaga ttggagtctc taaaaaggta gttcctactg aatctaaggc   3600
catgcatgga gtctaagatt caaatcgagg atctaacaga actcgccgtg aagactggcg   3660
aacagttcat acagagtctt ttacgactca atgacaagaa gaaaatcttc gtcaacatgg   3720
tggagcacga cactctggtc tactccaaaa atgtcaaaga tacagtctca gaagaccaaa   3780
gggctattga gacttttcaa caaaggataa tttcgggaaa cctcctcgga ttccattgcc   3840
```
cagctatctg tcacttcatc gaaaggacag tagaaaagga aggtggctcc tacaaatgcc 3900
atcattgcga taaaggaaag gctatcattc aagatctctc tgccgacagt ggtcccaaag 3960
atggaccccc acccacgagg agcatcgtgg aaaaagaaga cgttccaacc acgtcttcaa 4020
agcaagtgga ttgatgtgac atctccactg acgtaaggga tgacgcacaa tcccactatc 4080
cttcgcaaga cccttcctct atataaggaa gttcatttca tttggagagg acacgctcga 4140
ggaattcggt accccatcac aagtttgtac aaaaaagcag gctgcggccg cttgctccct 4200
taaaaaaaac catggcatgt cattacggat gtggacaaca gcaacagact tgtgcacctc 4260
atctttgtca gcttcaacct agagcatgta gagttgtgaa ggctgctact gctgttactg 4320
taaatttctg tgttccttat tctctcaaaa tcttcgattt tgttttcgtt cgatcccaat 4380
ttcgtatatg ttctttggtt tagattctgt taatcttaga tcgaagacga ttttctgggt 4440
ttgatcgtta gatatcatct taattctcga ttagggtttc atagatatca tccgatttgt 4500
tcaaataatt tgagttttgt cgaataatta ctcttcgatt tgtgatttct atctagatct 4560
ggtgttagtt tctagtttgt gcgatcgaat ttgtcgatta atctgagttt ttctgattaa 4620
caggctggag gatctcttct tgttctctct ggacttactc tcgctggaac tgttatcgct 4680
ctcactatcg ctacacctct tctcgttatc ttctctcctg ttctcgttcc tgctgtgatc 4740
actatcttcc ttctcggagc tggatttctt gcttctggtg gatttggagt tgctgctctc 4800
tctgttctct cttggatcta cagatacctc actggatgta aacatcctcc aggtgctgat 4860
tgtcttgagt ctgcttgtaa gactaagctc gcttcttgtg ctagagagat gaaggattgt 4920
agagcagagc aattctcttg tcagcctgtt gctggatctc agacttctta atgaacatat 4980
ggtcctgctt taatgagata tgcgagacgc ctatgatcgc atgatatttg ctttcaattc 5040
tgttgtgcac gttgtaaaaa acctgagcat gtgtagctca gatccttacc gccggtttcg 5100
gttcattcta atgaatatat cacccgttac tatcgtattt ttatgaataa tattctccgt 5160
tcaatttact gattgtaccc tactacttat atgtacaata ttaaaatgaa aacaatatat 5220
tgtgctgaat aggtttatag cgacatctat gatagagcgc cacaataaca aacaattgcg 5280
ttttattatt acaaatccaa ttttaaaaaa agcggcagaa ccggtcaaac ctaaaagact 5340
gattacataa atcttattca aatttcaaaa ggccccaggg gctagtatct acgacacacc 5400
gagcggcgaa ctaataacgt tcactgaagg gaactccggt tccccgccgg cgcgcatggg 5460
tgagattcct tgaagttgag tattggccgt ccgctctacc gaaagttacg ggcaccattc 5520
aacccggtcc agcacggcgg ccgggtaacc gacttgctgc cccgagaatt atgcagcatt 5580
tttttggtgt atgtgggccc caaatgaagt gcaggtcaaa ccttgacagt gacgacaaat 5640
cgttgggcgg gtccagggcg aattttgcga caacatgtcg aggctcagca ggacctgcag 5700
gcatgcaagc tagcttacta gtgatgcata ttctatagtg tcacctaaat cttcgacgaa 5760
ttaattccaa tcccacaaaa atctgagctt aacagcacag ttgctcctct cagagcagaa 5820
tcgggtattc aacaccctca tatcaactac tacgttgtgt ataacggtcc acatgccggt 5880
atatacgatg actggggttg tacaaaggcg gcaacaaacg gcgttcccgg agttgcacac 5940
aagaaatttg ccactattac agaggcaaga gcagcagctg acgcgtacac aacaagtcag 6000
caaacagaca ggttgaactt catccccaaa ggagaagctc aactcaagcc caagagcttt 6060
gctaaggccc taacaagccc accaaagcaa aaagcccact ggctcacgct aggaaccaaa 6120
aggcccagca gtgatccagc cccaaaagag atctcctttg ccccggagat tacaatggac 6180

-continued gatttcctct atctttacga tctaggaagg aagttcgaag gtgaaggtga cgacactatg 6240
ttcaccactg ataatgagaa ggttagcctc ttcaatttca gaaagaatgc tgacccacag 6300
atggttagag aggcctacgc agcaggtctc atcaagacga tctacccgag taacaatctc 6360
caggagatca aataccttcc caagaaggtt aaagatgcag tcaaaagatt caggactaat 6420
tgcatcaaga acacagagaa agacatattt ctcaagatca gaagtactat tccagtatgg 6480
acgattcaag gcttgcttca taaaccaagg caagtaatag agattggagt ctctaaaaag 6540
gtagttccta ctgaatctaa ggccatgcat ggagtctaag attcaaatcg aggatctaac 6600
agaactcgcc gtgaagactg gcgaacagtt catacagagt cttttacgac tcaatgacaa 6660
gaagaaaatc ttcgtcaaca tggtggagca cgacactctg gtctactcca aaaatgtcaa 6720
agatacagtc tcagaagacc aaagggctat tgagactttt caacaaagga taatttcggg 6780
aaacctcctc ggattccatt gcccagctat ctgtcacttc atcgaaagga cagtagaaaa 6840
ggaaggtggc tcctacaaat gccatcattg cgataaagga aaggctatca ttcaagatct 6900
ctctgccgac agtggtccca aagatggacc cccacccacg aggagcatcg tggaaaaaga 6960
agacgttcca accacgtctt caaagcaagt ggattgatgt gacatctcca ctgacgtaag 7020
ggatgacgca caatcccact atccttcgca agacccttcc tctatataag gaagttcatt 7080
tcatttggag aggacacggg atccttgctc cgttaaaaaa aaccatggct atcctcgatt 7140
ctgctggtgt tactactgtg actgagaatg gtggtggaga gttcgttgat ctcgatagac 7200
tcagaagaag aaagtctaga tctgtaaatt tctgtgttcc ttattctctc aaaatcttcg 7260
atttgtttt cgttcgatcc caatttcgta tatgttcttt ggtttagatt ctgttaatct 7320
tagatcgaag acgatttct gggtttgatc gttagatatc atcttaattc tcgattaggg 7380
tttcatagat atcatccgat ttgttcaaat aatttgagtt ttgtcgaata attactcttc 7440
gatttgtgat ttctatctag atctggtgtt agtttctagt ttgtgcgatc gaatttgtcg 7500
attaatctga gtttttctga ttaacaggat tcttctaacg gacttctcct ctctggatct 7560
gataacaact ctccttctga tgatgttggt gctcctgctg atgtgagaga tagaatcgat 7620
tctgtggtga acgatgatgc tcaaggtact gctaacctcg ctggtgataa taacggtgga 7680
ggtgataaca atggtggagg aagaggtgga ggtgaaggta gaggaaacgc tgatgctact 7740
ttcacttaca gaccatctgt gcctgctcat agaagagcta gagagtctcc tctctcttct 7800
gatgctatct tcaagcagtc tcacgctgga cttttcaacc tctgtgtggt ggttcttatc 7860
gctgtgaact ctagactcat catcgagaac ctcatgaagt acggatggct catcagaact 7920
gatttctggt tctcttctag atctctcaga gattggcctc ttttcatgtg ctgcatctca 7980
ctctcaatct tccctctcgc tgcttttact gttgagaagc tcgtgctcca gaagtatatc 8040
gctgaacctg tggtgatctt cctccacatc atcatcacta tgactgaggt tctctaccct 8100
gtttacgtga ctctcagatg cgattctgct ttcctctctg gtgttactct tatgctcctc 8160
acttgcattg tgtggcttaa gctcgtgtct tacgctcaca cttcttacga tatcagatct 8220
ctcgctaacg ctgctgataa ggctaaccct gaagtgtctt actacgtgtc tctcaagtct 8280
ctcgcttact tcatggttgc tcctacactt tgttaccagc catcttaccc tagatctgct 8340
tgcattagaa agggatgggt ggcaagacaa ttcgctaagt tggtgatctt cactggattc 8400
atgggattca tcatcgagca gtacatcaac cctattgtga gaaactctaa gcaccctctc 8460
aagggtgatc ttctctacgc tatcgagaga gttcttaagc tctctgtgcc taacctttat 8520
gtgtggctct gcatgttcta ctgtttcttc cacctctggc ttaacatcct tgctgagttg 8580
ctttgcttcg gagatagaga gttctacaag gattggtgga acgctaagtc tgttggagat 8640
tattggagaa tgtggaacat gcctgtgcat aagtggatgg tgcgtcacat ctacttccct 8700
tgcctcagat ctaagatccc taagactctc gctatcatta tcgctttcct cgtgtctgct 8760
gttttccatg agttgtgtat cgctgttcct tgcagacttt tcaagctttg ggctttcctc 8820
ggaatcatgt tccaggttcc actcgtgttc atcactaact acctccaaga gagattcgga 8880
tctactgttg gaaacatgat tttctggttc attttctgca tcttcggaca gcctatgtgc 8940
gttctcctct actaccacga tctcatgaac agaaagggat ctatgtctta atgaaggatc 9000
cacccagctt tcttgtacaa agtggtgatg ggttcgaaat cgataagctt ggatcctcta 9060
gagtcctgct ttaatgagat atgcgagacg cctatgatcg catgatattt gctttcaatt 9120
ctgttgtgca cgttgtaaaa aacctgagca tgtgtagctc agatccttac cgccggtttc 9180
ggttcattct aatgaatata tcacccgtta ctatcgtatt tttatgaata atattctccg 9240
ttcaatttac tgattgtacc ctactactta tatgtacaat attaaaatga aaacaatata 9300
ttgtgctgaa taggtttata gcgacatcta tgatagagcg ccacaataac aaacaattgc 9360
gttttattat tacaaatcca attttaaaaa aagcggcaga accggtcaaa cctaaaagac 9420
tgattacata aatcttattc aaatttcaaa aggccccagg ggctagtatc tacgacacac 9480
cgagcggcga actaataacg ttcactgaag ggaactccgg ttccccgccg gcgcgcatgg 9540
gtgagattcc ttgaagttga gtattggccg tccgctctac cgaaagttac gggcaccatt 9600
caacccggtc cagcacggcg gccgggtaac cgacttgctg ccccgagaat tatgcagcat 9660
ttttttggtg tatgtgggcc ccaaatgaag tgcaggtcaa accttgacag tgacgacaaa 9720
tcgttgggcg ggtccagggc gaattttgcg acaacatgtc gaggctcagc aggacctgca 9780
ggcatgcaag ctagcttact agtgatgcat attctatagt gtcacctaaa tctgcggccg 9840
cctgcaggtc gatatgggag agctcccaac gcgttggatg catagcttga gtattctata 9900
gtgtcaccta aatagcttgg cgtaatcatg gtcatagctg tttcctgtgt gaaattgtta 9960
tccgctcaca attccacaca acatacgagc cggaagcata aagtgtaaag cctggggtgc 10020
ctaatgagtg agctaactca cattaattgc gttgcgctca ctgcccgctt tccagtcggg 10080
aaacctgtcg tgccagctgc attaatgaat cggccaacgc gcggggagag gcggtttgcg 10140
tattgggcgct gagtggctcc ttcaacgttg cggttctgtc agttccaaac gtaaaacggc 10200
ttgtcccgcg tcatcggcgg gggtcataac gtgactccct taattctccg ctcatgatca 10260
gattgtcgtt tcccgccttc agtttaaact atcagtgttt gacaggatat attggcgggt 10320
aaacctaaga gaaaagagcg tttattagaa taatcggata tttaaaaggg cgtgaaaagg 10380
tttatccgtt cgtccatttg tatgtgcatg ccaaccacag ggttcccctc gggagtgctt 10440
ggcattccgt gcgataatga cttctgttca accacccaaa cgtcggaaag cctgacgacg 10500
gagcagcatt ccaaaaagat cccttggctc gtctgggtcg gctagaaggt cgagtgggct 10560
gctgtggctt gatccctcaa cgcggtcgcg gacgtagcgc agcgccgaaa aatcctcgat 10620
cgcaaatccg acgctgtcga aaatcgtgat ctgcttgtcg ctctttcggc cgacgtcctg 10680
gccagtcatc acgcgccaaa gttccgtcac aggatgatct ggcgcgagtt gctggatctc 10740
gccttcaatc cgggtctgtg gcgggaactc cacgaaaata tccgaacgca gcaagatgtc 10800
gacggatctt ttccgctgca taaccctgct tcggggtcat tatagcgatt ttttcggtat 10860
atccatcctt tttcgcacga tatacaggat tttgccaaag ggttcgtgta gactttcctt 10920

-continued

```
ggtgtatcca acggcgtcag ccgggcagga taggtgaagt aggcccaccc gcgagcgggt  10980
gttccttctt cactgtccct tattcgcacc tggcggtgct caacgggaat cctgctctgc  11040
gaggctggcc ggctaccgcc ggcgtaacag atgagggcaa gcggatggct gatgaaacca  11100
agccaaccag gggtgatgct gccaacttac tgatttagtg tatgatggtg tttttgaggt  11160
gctccagtgg cttctgtttc tatcagctgt ccctcctgtt cagctactga cggggtggtg  11220
cgtaacggca aaagcaccgc cggacatcag cgctatctct gctctcactg ccgtaaaaca  11280
tggcaactgc agttcactta caccgcttct caacccggta cgcaccagaa aatcattgat  11340
atggccatga atggcgttgg atgccgggca acagcccgca ttatgggcgt tggcctcaac  11400
acgattttac gtcacttaaa aaactcaggc cgcagtcggt aacctcgcgc atacagccgg  11460
gcagtgacgt catcgtctgc gcggaaatgg acgaacagtg gggctatgtc ggggctaaat  11520
cgcgccagcg ctggctgttt tacgcgtatg acagtctccg gaagacggtt gttgcgcacg  11580
tattcggtga acgcactatg gcgacgctgg ggcgtcttat gagcctgctg tcaccctttg  11640
acgtggtgat atggatgacg gatggctggc cgctgtatga atcccgcctg aagggaaagc  11700
tgcacgtaat cagcaagcga tatacgcagc gaattgagcg gcataacctg aatctgaggc  11760
agcacctggc acggctggga cggaagtcgc tgtcgttctc aaaatcggtg gagctgcatg  11820
acaaagtcat cgggcattat ctgaacataa aacactatca ataagttgga gtcattaccc  11880
aaccaggaag ggcagcccac ctatcaaggt gtactgcctt ccagacgaac gaagagcgat  11940
tgaggaaaag gcggcggcgg ccggcatgag cctgtcggcc tacctgctgg ccgtcggcca  12000
gggctacaaa atcacgggcg tcgtggacta tgagcacgtc cgcgagctgg cccgcatcaa  12060
tggcgacctg ggccgcctgg gcggcctgct gaaactctgg ctcaccgacg acccgcgcac  12120
ggcgcggttc ggtgatgcca cgatcctcgc cctgctggcg aagatcgaag agaagcagga  12180
cgagcttggc aaggtcatga tgggcgtggt ccgcccgagg gcagagccat gactttttta  12240
gccgctaaaa cggccggggg gtgcgcgtga ttgccaagca cgtccccatg cgctccatca  12300
agaagagcga cttcgcggag ctggtattcg tgcagggcaa gattcggaat accaagtacg  12360
agaaggacgg ccagacggtc tacgggaccg acttcattgc cgataaggtg gattatctgg  12420
acaccaaggc accaggcggg tcaaatcagg aataagggca cattgccccg gcgtgagtcg  12480
gggcaatccc gcaaggaggg tgaatgaatc ggacgtttga ccggaaggca tacaggcaag  12540
aactgatcga cgcggggttt tccgccgagg atgccgaaac catcgcaagc cgcaccgtca  12600
tgcgtgcgcc ccgcgaaacc ttccagtccg tcggctcgat ggtccagcaa gctacggcca  12660
agatcgagcg cgacagcgtg caactggctc cccctgccct gcccgcgcca tcggccgccg  12720
tggagcgttc gcgtcgtctc gaacaggagg cggcaggttt ggcgaagtcg atgaccatcg  12780
acacgcgagg aactatgacg accaagaagc gaaaaaccgc cggcgaggac ctggcaaaac  12840
aggtcagcga ggccaagcag gccgcgttgc tgaaacacac gaagcagcag atcaaggaaa  12900
tgcagctttc cttgttcgat attgcgccgt ggccggacac gatgcgagcg atgccaaacg  12960
acacggcccg ctctgccctg ttcaccacgc gcaacaagaa aatcccgcgc gaggcgctgc  13020
aaaacaaggt cattttccac gtcaacaagg acgtgaagat cacctacacc ggcgtcgagc  13080
tgcgggccga cgatgacgaa ctggtgtggc agcaggtgtt ggagtacgcg aagcgcaccc  13140
ctatcggcga gccgatcacc ttcacgttct acgagctttg ccaggacctg ggctggtcga  13200
tcaatggccg gtattacacg aaggccgagg aatgcctgtc gcgcctacag gcgacggcga  13260
tgggcttcac gtccgaccgc gttgggcacc tggaatcggt gtcgctgctg caccgcttcc  13320
```

```
gcgtcctgga ccgtggcaag aaaacgtccc gttgccaggt cctgatcgac gaggaaatcg  13380
tcgtgctgtt tgctggcgac cactacacga aattcatatg ggagaagtac cgcaagctgt  13440
cgccgacggc ccgacggatg ttcgactatt tcagctcgca ccgggagccg tacccgctca  13500
agctggaaac cttccgcctc atgtgcggat cggattccac ccgcgtgaag aagtggcgcg  13560
agcaggtcgg cgaagcctgc gaagagttgc gaggcagcgg cctggtggaa cacgcctggg  13620
tcaatgatga cctggtgcat tgcaaacgct agggccttgt ggggtcagtt ccggctgggg  13680
gttcagcagc cagcgcttta ctggcatttc aggaacaagc gggcactgct cgacgcactt  13740
gcttcgctca gtatcgctcg ggacgcacgg cgcgctctac gaactgccga taaacagagg  13800
attaaaattg acaattgtga ttaaggctca gattcgacgg cttggagcgg ccgacgtgca  13860
ggatttccgc gagatccgat tgtcggccct gaagaaagct ccagagatgt tcgggtccgt  13920
ttacgagcac gaggagaaaa agcccatgga ggcgttcgct gaacggttgc gagatgccgt  13980
ggcattcggc gcctacatcg acggcgagat cattgggctg tcggtcttca aacaggagga  14040
cggccccaag gacgctcaca aggcgcatct gtccggcgtt ttcgtggagc ccgaacagcg  14100
aggccgaggg gtcgccggta tgctgctgcg ggcgttgccg gcgggtttat tgctcgtgat  14160
gatcgtccga cagattccaa cgggaatctg gtggatgcgc atcttcatcc tcggcgcact  14220
taatatttcg ctattctgga gcttgttgtt tatttcggtc taccgcctgc cgggcggggt  14280
cgcggcgacg gtaggcgctg tgcagccgct gatggtcgtg ttcatctctg ccgctctgct  14340
aggtagcccg atacgattga tggcggtcct gggggctatt tgcggaactg cgggcgtggc  14400
gctgttggtg ttgacaccaa acgcagcgct agatcctgtc ggcgtcgcag cgggcctggc  14460
gggggcggtt tccatggcgt tcggaaccgt gctgacccgc aagtggcaac ctcccgtgcc  14520
tctgctcacc tttaccgcct ggcaactggc ggccggagga cttctgctcg ttccagtagc  14580
tttagtgttt gatccgccaa tcccgatgcc tacaggaacc aatgttctcg gcctggcgtg  14640
gctcggcctg atcggagcgg gtttaaccta cttcctttgg ttccggggga tctcgcgact  14700
cgaacctaca gttgtttcct tactgggctt tctcagccgg gatggcgcta agaagctatt  14760
gccgccgatc ttcatatgcg gtgtgaaata ccgcacagat gcgtaaggag aaaataccgc  14820
atcaggcgct cttccgcttc ctcgctcact gactcgctgc gctcggtcgt tcggctgcgg  14880
cgagcggtat cagctcactc aaaggcggta atacggttat ccacagaatc aggggataac  14940
gcaggaaaga acatgtgagc aaaaggccag caaaaggcca ggaaccgtaa aaaggccgcg  15000
ttgctggcgt ttttccatag gctccgcccc cctgacgagc atcacaaaaa tcgacgctca  15060
agtcagaggt ggcgaaaccc gacaggacta taaagatacc aggcgtttcc ccctggaagc  15120
tccctcgtgc gctctcctgt tccgaccctg ccgcttaccg gatacctgtc cgcctttctc  15180
ccttcgggaa gcgtggcgct ttctcaatgc tcacgctgta ggtatctcag ttcggtgtag  15240
gtcgttcgct ccaagctggg ctgtgtgcac gaaccccccg ttcagcccga ccgctgcgcc  15300
ttatccggta actatcgtct tgagtccaac ccggtaagac acgacttatc gccactggca  15360
gcagccactg gtaacaggat tagcagagcg aggtatgtag gcggtgctac agagttcttg  15420
aagtggtggc ctaactacgg ctacactaga aggacagtat ttggtatctg cgctctgctg  15480
aagccagtta ccttcggaaa aagagttggt agctcttgat ccggcaaaca aaccaccgct  15540
ggtagcggtg gtttttttgt ttgcaagcag cagattacgc gcagaaaaaa aggatatcaa  15600
gaagatcctt tgatcttttc tacggggtct gacgctcagt ggaacgaaaa ctcacgttaa  15660
```
gggattttgg tcatgagatt atcaaaaagg atcttcacct agatcctttt aaattaaaaa 15720
tgaagtttta aatcaatcta aagtatatat gagtaaactt ggtctgacag ttaccaatgc 15780
ttaatcagtg aggcacctat ctcagcgatc tgtctatttc gttcatccat agttgcctga 15840
ctccccgtcg tgtagataac tacgatacgg gagggcttac catctggccc cagtgctgca 15900
atgataccgc gagacccacg ctcaccggct ccagatttat cagcaataaa ccagccagcc 15960
ggaagggccg agcgcagaag tggtcctgca actttatccg cctccatcca gtctattaaa 16020
caagtggcag caacggattc gcaaacctgt cacgcctttt gtgccaaaag ccgcgccagg 16080
tttgcgatcc gctgtgccag gcgttaggcg tcatatgaag atttcggtga tccctgagca 16140
ggtggcggaa acattggatg ctgagaacca tttcattgtt cgtgaagtgt tcgatgtgca 16200
cctatccgac caaggctttg aactatctac cagaagtgtg agcccctacc ggaaggatta 16260
catctcggat gatgactctg atgaagactc tgcttgctat ggcgcattca tcgaccaaga 16320
gcttgtcggg aagattgaac tcaactcaac atggaacgat ctagcctcta tcgaacacat 16380
tgttgtgtcg cacacgcacc gaggcaaagg agtcgcgcac agtctcatcg aatttgcgaa 16440
aaagtgggca ctaagcagac agctccttgg catacgatta gagacacaaa cgaacaatgt 16500
acctgcctgc aatttgtacg caaaatgtgg ctttactctc ggcggcattg acctgttcac 16560
gtataaaact agacctcaag tctcgaacga aacagcgatg tactggtact ggttctcggg 16620
agcacaggat gacgcctaac aattcattca agccgacacc gcttcgcggc gcggcttaat 16680
tcaggagtta aacatcatga gggaagcggt gatcgccgaa gtatcgactc aactatcaga 16740
ggtagttggc gtcatcgagc gccatctcga accgacgttg ctggccgtac atttgtacgg 16800
ctccgcagtg gatggcggcc tgaagccaca cagtgatatt gatttgctgg ttacggtgac 16860
cgtaaggctt gatgaaacaa cgcggcgagc tttgatcaac gaccttttgg aaacttcggc 16920
ttcccctgga gagagcgaga ttctccgcgc tgtagaagtc accattgttg tgcacgacga 16980
catcattccg tggcgttatc cagctaagcg cgaactgcaa tttggagaat ggcagcgcaa 17040
tgacattctt gcaggtatct tcgagccagc cacgatcgac attgatctgg ctatcttgct 17100
gacaaaagca agagaacata gcgttgcctt ggtaggtcca gcggcggagg aactctttga 17160
tccggttcct gaacaggatc tatttgaggc gctaaatgaa accttaacgc tatggaactc 17220
gccgcccgac tgggctggcg atgagcgaaa tgtagtgctt acgttgtccc gcatttggta 17280
cagcgcagta accggcaaaa tcgcgccgaa ggatgtcgct gccgactggg caatggagcg 17340
cctgccggcc cagtatcagc ccgtcatact tgaagctagg caggcttatc ttggacaaga 17400
agatcgcttg gcctcgcgcg cagatcagtt ggaagaattt gttcactacg tgaaaggcga 17460
gatcaccaag gtagtcggca aataatgtct aacaattcgt tcaagccgac gccgcttcgc 17520
ggcgcggctt aactcaagcg ttagagagct ggggaagact atgcgcgatc tgttgaaggt 17580
ggttctaagc ctcgtacttg cgatggcatc ggggcaggca cttgctgacc tgccaattgt 17640
tttagtggat gaagctcgtc ttccctatga ctactcccca tccaactacg acatttctcc 17700
aagcaactac gacaactcca taagcaatta cgacaatagt ccatcaaatt acgacaactc 17760
tgagagcaac tacgataata gttcatccaa ttacgacaat agtcgcaacg gaaatcgtag 17820
gcttatatat agcgcaaatg ggtctcgcac tttcgccggc tactacgtca ttgccaacaa 17880
tgggacaacg aacttctttt ccacatctgg caaaaggatg ttctacaccc caaaaggggg 17940
gcgcggcgtc tatggcggca aagatgggag cttctgcggg gcattggtcg tcataaatgg 18000
ccaattttcg cttgccctga cagataacgg cctgaagatc atgtatctaa gcaactagcc 18060
tgctctctaa taaaatgtta ggagcttggc tgccattttt ggggtgaggc cgttcgcggc 18120
cgaggggcgc agcccctggg gggatgggag gcccgcgtta gcgggccggg agggttcgag 18180 aaggggggc accccccttc ggcgtgcgcg gtcacgcgcc agggcgcagc cctggttaaa 18240
aacaaggttt ataaatattg gtttaaaagc aggttaaaag acaggttagc ggtggccgaa 18300
aaacgggcgg aaacccttgc aaatgctgga ttttctgcct gtggacagcc cctcaaatgt 18360
caataggtgc gcccctcatc tgtcagcact ctgcccctca agtgtcaagg atcgcgcccc 18420
tcatctgtca gtagtcgcgc ccctcaagtg tcaataccgc agggcactta tccccaggct 18480
tgtccacatc atctgtggga aactcgcgta aaatcaggcg ttttcgccga tttgcgaggc 18540
tggccagctc cacgtcgccg gccgaaatcg agcctgcccc tcatctgtca acgccgcgcc 18600
gggtgagtcg gcccctcaag tgtcaacgtc cgcccctcat ctgtcagtga gggccaagtt 18660
ttccgcgagg tatccacaac gccggcggcc ggccgcggtg tctcgcacac ggcttcgacg 18720
gcgtttctgg cgcgtttgca gggccataga cggccgccag cccagcggcg agggcaacca 18780
gcccggtgag cgtcggaaag gg 18802

<210> SEQ ID NO 32
<211> LENGTH: 18823
<212> TYPE: DNA
<213> ORGANISM: Artificial Sequence
<220> FEATURE:
<223> OTHER INFORMATION: Synthetic vector

<400> SEQUENCE: 32
tcgacatcgt caacgttcac ttctaaagaa atagcgccac tcagcttcct cagcggcttt 60
atccagcgat ttcctattat gtcggcatag ttctcaagat cgacagcctg tcacggttaa 120
gcgagaaatg aataagaagg ctgataattc ggatctctgc gaggagatga tatttgatca 180
caggcagcaa cgctctgtca tcgttacaat caacatgcta ccctccgcga gatcatccgt 240
gtttcaaacc cggcagctta gttgccgttc ttccgaatag catcgggtaa catgagcaaa 300
gtctgccgcc ttacaacggc tctcccgctg acgccgtccc ggactgatgg gctgcctgta 360
tcgagtggtg attttgtgcc gagctgccgg tcggggagct gttggctggc tggtggcagg 420
atatattgtg gtgtaaacaa attgacgctt agacaactta ataacacatt gcggacgttt 480
ttaatgtact gaattcgccg ctcggtgtgt cgtagatact agcccctggg gcacttttga 540
aatttgaata agatttatgt aatcagtctt ttaggtttga ccggttctgc cgcttttttt 600
aaaattggat ttgtaataat aaaacgcaat tgtttgttat tgtggcgctc tatcatagat 660
gtcgctataa acctattcag cacaatatat tgttttcatt ttaatattgt acatataagt 720
agtagggtac aatcagtaaa ttgaacggag aatattattc ataaaaatac gatagtaacg 780
ggtgatatat tcattagaat gaaccgaaac cggcggtaag gatctgagct acacatgctc 840
aggtttttta caacgtgcac aacagaattg aaagcaaata tcatgcgatc ataggcgtct 900
cgcatatctc attaaacaag tgaagatttg attcaaactc cattgagagc cctgactatg 960
cattcggttt gacccttcca ggttgagaga cgatagcccc ctaccttaat taaggggccc 1020
cccctcgagg tcgacggtat cgataagctt gatatcgaat tcctgcagcc agggggatcc 1080
cccgggtcat cagatctcgg tgacgggcag gaccggacgg ggcggtaccg gcaggctgaa 1140
gtccagctgc cagaaaccca cgtcatgcca gttcccgtgc ttgaagccgg ccgcccgcag 1200
catgccgcgg ggggcatatc cgagcgcctc gtgcatgcgc acgctcgggt cgttgggcag 1260

-continued

```
cccgatgaca gcgaccacgc tcttgaagcc ctgtgcctcc agggacttca gcaggtgggt   1320
gtagagcgtg gagcccagtc ccgtccgctg gtggcggggg gagacgtaca cggtcgactc   1380
ggccgtccag tcgtaggcgt tgcgtgcctt ccaggggccc gcgtaggcga tgccggcgac   1440
ctcgccgtcc acctcggcga cgagccaggg atagcgctcc cgcagacgga cgaggtcgtc   1500
cgtccactcc tgcggttcct gcggctcggt acggaagttg accgtgcttg tctcgatgta   1560
gtggttgacg atggtgcaga ccgccggcat gtccgcctcg gtggcacggc ggatgtcggc   1620
cgggcgtcgt tctgggctca tggtagatcc cctcgagaga gatagatttg tagagagaga   1680
ctggtgattt cagcgtgtcc tctccaaatg aaatgaactt ccttatatag aggaaggtct   1740
tgcgaaggat agtgggattg tgcgtcatcc cttacgtcag tggagatatc acatcaatcc   1800
acttgctttg aagacgtggt tggaacgtct tctttttcca cgatgctcct cgtgggtggg   1860
ggtccatctt tgggaccact gtcggcagag gcatcttgaa cgatagcctt tcctttatcg   1920
caatgatggc atttgtaggt gccaccttcc ttttctactg tccttttgat gaagtgacag   1980
atagctgggc aatggaatcc gaggaggttt cccgatatta ccctttgttg aaaagtctca   2040
atagcccttt ggtcttctga gactgtatct ttgatattct tggagtagac gagagtgtcg   2100
tgctccacca tgttatcaca tcaatccact tgctttgaag acgtggttgg aacgtcttct   2160
ttttccacga tgctcctcgt gggtgggggt ccatctttgg gaccactgtc ggcagaggca   2220
tcttgaacga tagcctttcc tttatcgcaa tgatggcatt tgtaggtgcc accttccttt   2280
tctactgtcc ttttgatgaa gtgacagata gctgggcaat ggaatccgag gaggtttccc   2340
gatattaccc tttgttgaaa agtctcaata gccctttggt cttctgagac tgtatctttg   2400
atattcttgg agtagacgag agtgtcgtgc tccaccatgt tgctgatagt gaccttaggc   2460
gacttttgaa cgcgcaataa tggtttctga cgtatgtgct tagctcatta aactccagaa   2520
acccattaac gcttacaatt tccattcgcc attcaggctg cgcaactgtt gggaagggcg   2580
atcggtgcgg gcctcttcgc tattacgcca gctggcgaaa gggggatgtg ctgcaaggcg   2640
attaagttgg gtaacgccag ggttttccca gtcacgacgt tgtaaaacga cggccagtga   2700
attgtaatac gactcactat agggcgaatt gggcccgacg tcgcatgctc ccggccgcca   2760
tggccgcggg atatcactag tgcggccgct cgacgaatta attccaatcc cacaaaaatc   2820
tgagcttaac agcacagttg ctcctctcag agcagaatcg ggtattcaac accctcatat   2880
caactactac gttgtgtata acggtccaca tgccggtata tacgatgact ggggttgtac   2940
aaaggcggca acaaacggcg ttcccggagt tgcacacaag aaatttgcca ctattacaga   3000
ggcaagagca gcagctgacg cgtacacaac aagtcagcaa acagacaggt tgaacttcat   3060
ccccaaagga gaagctcaac tcaagcccaa gagctttgct aaggccctaa caagcccacc   3120
aaagcaaaaa gcccactggc tcacgctagg aaccaaaagg cccagcagtg atccagcccc   3180
aaaagagatc tcctttgccc cggagattac aatggacgat ttcctctatc tttacgatct   3240
aggaaggaag ttcgaaggtg aaggtgacga cactatgttc accactgata atgagaaggt   3300
tagcctcttc aatttcagaa agaatgctga cccacagatg gttagagagg cctacgcagc   3360
aggtctcatc aagacgatct acccgagtaa caatctccag gagatcaaat accttcccaa   3420
gaaggttaaa gatgcagtca aaagattcag gactaattgc atcaagaaca cagagaaaga   3480
catatttctc aagatcagaa gtactattcc agtatggacg attcaaggct tgcttcataa   3540
accaaggcaa gtaatagaga ttggagtctc taaaaaggta gttcctactg aatctaaggc   3600
catgcatgga gtctaagatt caaatcgagg atctaacaga actcgccgtg aagactggcg   3660
```

-continued

```
aacagttcat acagagtctt ttacgactca atgacaagaa gaaaatcttc gtcaacatgg   3720
tggagcacga cactctggtc tactccaaaa atgtcaaaga tacagtctca gaagaccaaa   3780
gggctattga gacttttcaa caaaggataa tttcgggaaa cctcctcgga ttccattgcc   3840
cagctatctg tcacttcatc gaaaggacag tagaaaagga aggtggctcc tacaaatgcc   3900
atcattgcga taaaggaaag gctatcattc aagatctctc tgccgacagt ggtcccaaag   3960
atggaccccc acccacgagg agcatcgtgg aaaaagaaga cgttccaacc acgtcttcaa   4020
agcaagtgga ttgatgtgac atctccactg acgtaaggga tgacgcacaa tcccactatc   4080
cttcgcaaga cccttcctct atataaggaa gttcatttca tttggagagg acacgctcga   4140
ggaattcggt accccatcac aagtttgtac aaaaaagcag gctgcggccg cttgctccct   4200
taaaaaaaac catggcatgt cattacggaa tggcatgtca ttacggatgt ggacaacagc   4260
aacagacttg tgcacctcat ctttgtcagc ttcaacctag agcatgtaga gttgtgaagg   4320
ctgctactgc tgttactgta aatttctgtg ttccttattc tctcaaaatc ttcgattttg   4380
ttttcgttcg atcccaattt cgtatatgtt ctttggttta gattctgtta atcttagatc   4440
gaagacgatt ttctgggttt gatcgttaga tatcatctta attctcgatt agggtttcat   4500
agatatcatc cgatttgttc aaataatttg agttttgtcg aataattact cttcgatttg   4560
tgatttctat ctagatctgg tgttagtttc tagtttgtgc gatcgaattt gtcgattaat   4620
ctgagttttt ctgattaaca ggctggagga tctcttcttg ttctctctgg acttactctc   4680
gctggaactg ttatcgctct cactatcgct acacctcttc tcgttatctt ctctcctgtt   4740
ctcgttcctg ctgtgatcac tatcttcctt ctcggagctg gatttcttgc ttctggtgga   4800
tttggagttg ctgctctctc tgttctctct tggatctaca gatacctcac tggatgtaaa   4860
catcctccag gtgctgattg tcttgagtct gcttgtaaga ctaagctcgc ttcttgtgct   4920
agagagatga aggattgtag agcagagcaa ttctcttgtc agcctgttgc tggatgttct   4980
cagacttctt aatgaacata tggtcctgct ttaatgagat atgcgagacg cctatgatcg   5040
catgatattt gctttcaatt ctgttgtgca cgttgtaaaa aacctgagca tgtgtagctc   5100
agatccttac cgccggtttc ggttcattct aatgaatata tcacccgtta ctatcgtatt   5160
tttatgaata atattctccg ttcaatttac tgattgtacc ctactactta tatgtacaat   5220
attaaaatga aaacaatata ttgtgctgaa taggtttata gcgacatcta tgatagagcg   5280
ccacaataac aaacaattgc gttttattat tacaaatcca attttaaaaa aagcggcaga   5340
accggtcaaa cctaaaagac tgattacata aatcttattc aaatttcaaa aggccccagg   5400
ggctagtatc tacgacacac cgagcggcga actaataacg ttcactgaag ggaactccgg   5460
ttccccgccg gcgcgcatgg gtgagattcc ttgaagttga gtattggccg tccgctctac   5520
cgaaagttac gggcaccatt caacccggtc cagcacggcg gccgggtaac cgacttgctg   5580
ccccgagaat tatgcagcat ttttttggtg tatgtgggcc ccaaatgaag tgcaggtcaa   5640
accttgacag tgacgacaaa tcgttgggcg ggtccagggc gaattttgcg acaacatgtc   5700
gaggctcagc aggacctgca ggcatgcaag ctagcttact agtgatgcat attctatagt   5760
gtcacctaaa tcttcgacga attaattcca atcccacaaa aatctgagct taacagcaca   5820
gttgctcctc tcagagcaga atcgggtatt caacaccctc atatcaacta ctacgttgtg   5880
tataacggtc cacatgccgg tatatacgat gactggggtt gtacaaaggc ggcaacaaac   5940
ggcgttcccg gagttgcaca caagaaattt gccactatta cagaggcaag agcagcagct   6000
```

-continued

```
gacgcgtaca caacaagtca gcaaacagac aggttgaact tcatccccaa aggagaagct   6060
caactcaagc ccaagagctt tgctaaggcc ctaacaagcc caccaaagca aaaagcccac   6120
tggctcacgc taggaaccaa aaggcccagc agtgatccag ccccaaaaga gatctccttt   6180
gccccggaga ttacaatgga cgatttcctc tatctttacg atctaggaag gaagttcgaa   6240
ggtgaaggtg acgacactat gttcaccact gataatgaga aggttagcct cttcaatttc   6300
agaaagaatg ctgacccaca gatggttaga gaggcctacg cagcaggtct catcaagacg   6360
atctacccga gtaacaatct ccaggagatc aaataccttc ccaagaaggt taaagatgca   6420
gtcaaaagat tcaggactaa ttgcatcaag aacacagaga aagacatatt tctcaagatc   6480
agaagtacta ttccagtatg gacgattcaa ggcttgcttc ataaaccaag gcaagtaata   6540
gagattggag tctctaaaaa ggtagttcct actgaatcta aggccatgca tggagtctaa   6600
gattcaaatc gaggatctaa cagaactcgc cgtgaagact ggcgaacagt tcatacagag   6660
tcttttacga ctcaatgaca agaagaaaat cttcgtcaac atggtggagc acgacactct   6720
ggtctactcc aaaaatgtca aagatacagt ctcagaagac caaagggcta ttgagacttt   6780
tcaacaaagg ataatttcgg gaaacctcct cggattccat tgcccagcta tctgtcactt   6840
catcgaaagg acagtagaaa aggaaggtgg ctcctacaaa tgccatcatt gcgataaagg   6900
aaaggctatc attcaagatc tctctgccga cagtggtccc aaagatggac ccccacccac   6960
gaggagcatc gtggaaaaag aagacgttcc aaccacgtct tcaaagcaag tggattgatg   7020
tgacatctcc actgacgtaa gggatgacgc acaatcccac tatccttcgc aagacccttc   7080
ctctatataa ggaagttcat ttcatttgga gaggacacgg gatccttgct ccgttaaaaa   7140
aaaccatggc tatcctcgat tctgctggtg ttactactgt gactgagaat ggtggtggag   7200
agttcgttga tctcgataga ctcagaagaa gaaagtctag atctgtaaat ttctgtgttc   7260
cttattctct caaaatcttc gattttgttt tcgttcgatc ccaatttcgt atatgttctt   7320
tggtttagat tctgttaatc ttagatcgaa gacgattttc tgggtttgat cgttagatat   7380
catcttaatt ctcgattagg gtttcataga tatcatccga tttgttcaaa taatttgagt   7440
tttgtcgaat aattactctt cgatttgtga tttctatcta gatctggtgt tagtttctag   7500
tttgtgcgat cgaatttgtc gattaatctg agtttttctg attaacagga ttcttctaac   7560
ggacttctcc tctctggatc tgataacaac tctccttctg atgatgttgg tgctcctgct   7620
gatgtgagag atagaatcga ttctgtggtg aacgatgatg ctcaaggtac tgctaacctc   7680
gctggtgata ataacggtgg aggtgataac aatggtggag gaagaggtgg aggtgaaggt   7740
agaggaaacg ctgatgctac tttcacttac agaccatctg tgcctgctca tagaagagct   7800
agagagtctc ctctctcttc tgatgctatc ttcaagcagt ctcacgctgg acttttcaac   7860
ctctgtgtgg tggttcttat cgctgtgaac tctagactca tcatcgagaa cctcatgaag   7920
tacggatggc tcatcagaac tgatttctgg ttctcttcta gatctctcag agattggcct   7980
cttttcatgt gctgcatctc actctcaatc ttccctctcg ctgcttttac tgttgagaag   8040
ctcgtgctcc agaagtatat cgctgaacct gtggtgatct tcctccacat catcatcact   8100
atgactgagg ttctctaccc tgtttacgtg actctcagat gcgattctgc tttcctctct   8160
ggtgttactc ttatgctcct cacttgcatt gtgtggctta agctcgtgtc ttacgctcac   8220
acttcttacg atatcagatc tctcgctaac gctgctgata aggctaaccc tgaagtgtct   8280
tactacgtgt ctctcaagtc tctcgcttac ttcatggttg ctcctacact ttgttaccag   8340
ccatcttacc ctagatctgc ttgcattaga aagggatggg tggcaagaca attcgctaag   8400
```
ttggtgatct tcactggatt catgggattc atcatcgagc agtacatcaa ccctattgtg 8460
agaaactcta agcaccctct caagggtgat cttctctacg ctatcgagag agttcttaag 8520
ctctctgtgc ctaaccttta tgtgtggctc tgcatgttct actgtttctt ccacctctgg 8580
cttaacatcc ttgctgagtt gctttgcttc ggagatagag agttctacaa ggattggtgg 8640
aacgctaagt ctgttggaga ttattggaga atgtggaaca tgcctgtgca taagtggatg 8700
gtgcgtcaca tctacttccc ttgcctcaga tctaagatcc ctaagactct cgctatcatt 8760
atcgctttcc tcgtgtctgc tgttttccat gagttgtgta tcgctgttcc ttgcagactt 8820
ttcaagcttt gggctttcct cggaatcatg ttccaggttc cactcgtgtt catcactaac 8880
tacctccaag agagattcgg atctactgtt ggaaacatga ttttctggtt cattttctgc 8940
atcttcggac agcctatgtg cgttctcctc tactaccacg atctcatgaa cagaaaggga 9000
tctatgtctt aatgaaggat ccacccagct ttcttgtaca aagtggtgat gggttcgaaa 9060
tcgataagct tggatcctct agagtcctgc tttaatgaga tatgcgagac gcctatgatc 9120
gcatgatatt tgctttcaat tctgttgtgc acgttgtaaa aaacctgagc atgtgtagct 9180
cagatcctta ccgccggttt cggttcattc taatgaatat atcacccgtt actatcgtat 9240
ttttatgaat aatattctcc gttcaattta ctgattgtac cctactactt atatgtacaa 9300
tattaaaatg aaaacaatat attgtgctga ataggtttat agcgacatct atgatagagc 9360
gccacaataa caaacaattg cgttttatta ttacaaatcc aattttaaaa aaagcggcag 9420
aaccggtcaa acctaaaaga ctgattacat aaatcttatt caaatttcaa aaggccccag 9480
gggctagtat ctacgacaca ccgagcggcg aactaataac gttcactgaa gggaactccg 9540
gttccccgcc ggcgcgcatg ggtgagattc cttgaagttg agtattggcc gtccgctcta 9600
ccgaaagtta cgggcaccat tcaacccggt ccagcacggc ggccgggtaa ccgacttgct 9660
gccccgagaa ttatgcagca tttttttggt gtatgtgggc cccaaatgaa gtgcaggtca 9720
aaccttgaca gtgacgacaa atcgttgggc gggtccaggg cgaattttgc gacaacatgt 9780
cgaggctcag caggacctgc aggcatgcaa gctagcttac tagtgatgca tattctatag 9840
tgtcacctaa atctgcggcc gcctgcaggt cgatatggga gagctcccaa cgcgttggat 9900
gcatagcttg agtattctat agtgtcacct aaatagcttg gcgtaatcat ggtcatagct 9960
gtttcctgtg tgaaattgtt atccgctcac aattccacac aacatacgag ccggaagcat 10020
aaagtgtaaa gcctggggtg cctaatgagt gagctaactc acattaattg cgttgcgctc 10080
actgcccgct ttccagtcgg gaaacctgtc gtgccagctg cattaatgaa tcggccaacg 10140
cgcggggaga ggcggtttgc gtattgggcg ctcttccgct tcctcgctca ctgactcgct 10200
cagttccaaa cgtaaaacgg cttgtcccgc gtcatcggcg gggtcataa cgtgactccc 10260
ttaattctcc gctcatgatc agattgtcgt ttcccgcctt cagtttaaac tatcagtgtt 10320
tgacaggata tattggcggg taaacctaag agaaaagagc gtttattaga ataatcggat 10380
atttaaaagg gcgtgaaaag gtttatccgt tcgtccattt gtatgtgcat gccaaccaca 10440
gggttcccct cgggagtgct tggcattccg tgcgataatg acttctgttc aaccacccaa 10500
acgtcggaaa gcctgacgac ggagcagcat tccaaaaaga tcccttggct cgtctgggtc 10560
ggctagaagg tcgagtgggc tgctgtggct tgatccctca acgcggtcgc ggacgtagcg 10620
cagcgccgaa aaatcctcga tcgcaaatcc gacgctgtcg aaaatcgtga tctgcttgtc 10680
gctctttcgg ccgacgtcct ggccagtcat cacgcgccaa agttccgtca caggatgatc 10740

-continued

```
tggcgcgagt tgctggatct cgccttcaat ccgggtctgt ggcgggaact ccacgaaaat  10800
atccgaacgc agcaagatgt cgacggatct tttccgctgc ataaccctgc ttcggggtca  10860
ttatagcgat tttttcggta tatccatcct tttcgcacg atatacagga ttttgccaaa  10920
gggttcgtgt agactttcct tggtgtatcc aacggcgtca gccgggcagg ataggtgaag  10980
taggcccacc cgcgagcggg tgttccttct tcactgtccc ttattcgcac ctggcggtgc  11040
tcaacgggaa tcctgctctg cgaggctggc cggctaccgc cggcgtaaca gatgagggca  11100
agcggatggc tgatgaaacc aagccaacca ggggtgatgc tgccaactta ctgatttagt  11160
gtatgatggt gtttttgagg tgctccagtg gcttctgttt ctatcagctg tccctcctgt  11220
tcagctactg acggggtggt gcgtaacggc aaaagcaccg ccggacatca gcgctatctc  11280
tgctctcact gccgtaaaac atggcaactg cagttcactt acaccgcttc tcaacccggt  11340
acgcaccaga aaatcattga tatggccatg aatggcgttg gatgccgggc aacagcccgc  11400
attatgggcg ttggcctcaa cacgatttta cgtcacttaa aaaactcagg ccgcagtcgg  11460
taacctcgcg catacagccg ggcagtgacg tcatcgtctg cgcggaaatg gacgaacagt  11520
ggggctatgt cggggctaaa tcgcgccagc gctggctgtt ttacgcgtat gacagtctcc  11580
ggaagacggt tgttgcgcac gtattcggtg aacgcactat ggcgacgctg gggcgtctta  11640
tgagcctgct gtcacccttt gacgtggtga tatggatgac ggatggctgg ccgctgtatg  11700
aatcccgcct gaagggaaag ctgcacgtaa tcagcaagcg atatacgcag cgaattgagc  11760
ggcataacct gaatctgagg cagcacctgg cacggctggg acggaagtcg ctgtcgttct  11820
caaaatcggt ggagctgcat gacaaagtca tcgggcatta tctgaacata aaacactatc  11880
aataagttgg agtcattacc caaccaggaa gggcagccca cctatcaagg tgtactgcct  11940
tccagacgaa cgaagagcga ttgaggaaaa ggcggcggcg gccggcatga gcctgtcggc  12000
ctacctgctg gccgtcggcc agggctacaa aatcacgggc gtcgtggact atgagcacgt  12060
ccgcgagctg gcccgcatca atggcgacct gggccgcctg ggcggcctgc tgaaactctg  12120
gctcaccgac gacccgcgca cggcgcggtt cggtgatgcc acgatcctcg ccctgctggc  12180
gaagatcgaa gagaagcagg acgagcttgg caaggtcatg atgggcgtgg tccgcccgag  12240
ggcagagcca tgactttttt agccgctaaa acggccgggg ggtgcgcgtg attgccaagc  12300
acgtccccat gcgctccatc aagaagagcg acttcgcgga gctggtattc gtgcagggca  12360
agattcggaa taccaagtac gagaaggacg gccagacggt ctacgggacc gacttcattg  12420
ccgataaggt ggattatctg gacaccaagg caccaggcgg gtcaaatcag gaataagggc  12480
acattgcccc ggcgtgagtc ggggcaatcc cgcaaggagg gtgaatgaat cggacgtttg  12540
accggaaggc atacaggcaa gaactgatcg acgcggggtt ttccgccgag gatgccgaaa  12600
ccatcgcaag ccgcaccgtc atgcgtgcgc cccgcgaaac cttccagtcc gtcggctcga  12660
tggtccagca agctacggcc aagatcgagc gcgacagcgt gcaactggct ccccctgccc  12720
tgcccgcgcc atcggccgcc gtggagcgtt cgcgtcgtct cgaacaggag gcggcaggtt  12780
tggcgaagtc gatgaccatc gacacgcgag gaactatgac gaccaagaag cgaaaaaccg  12840
ccggcgagga cctggcaaaa caggtcagcg aggccaagca ggccgcgttg ctgaaacaca  12900
cgaagcagca gatcaaggaa atgcagcttt ccttgttcga tattgcgccg tggccggaca  12960
cgatgcgagc gatgccaaac gacacggccc gctctgccct gttcaccacg cgcaacaaga  13020
aaatcccgcg cgaggcgctg caaaacaagg tcattttcca cgtcaacaag gacgtgaaga  13080
tcacctacac cggcgtcgag ctgcgggccg acgatgacga actggtgtgg cagcaggtgt  13140
```

```
tggagtacgc gaagcgcacc cctatcggcg agccgatcac cttcacgttc tacgagcttt  13200
gccaggacct gggctggtcg atcaatggcc ggtattacac gaaggccgag gaatgcctgt  13260
cgcgcctaca ggcgacggcg atgggcttca cgtccgaccg cgttgggcac ctggaatcgg  13320
tgtcgctgct gcaccgcttc cgcgtcctgg accgtggcaa gaaaacgtcc cgttgccagg  13380
tcctgatcga cgaggaaatc gtcgtgctgt ttgctggcga ccactacacg aaattcatat  13440
gggagaagta ccgcaagctg tcgccgacgg cccgacggat gttcgactat ttcagctcgc  13500
accgggagcc gtacccgctc aagctggaaa ccttccgcct catgtgcgga tcggattcca  13560
cccgcgtgaa gaagtggcgc gagcaggtcg gcgaagcctg cgaagagttg cgaggcagcg  13620
gcctggtgga acacgcctgg gtcaatgatg acctggtgca ttgcaaacgc tagggccttg  13680
tggggtcagt tccggctggg ggttcagcag ccagcgcttt actggcattt caggaacaag  13740
cgggcactgc tcgacgcact tgcttcgctc agtatcgctc gggacgcacg gcgcgctcta  13800
cgaactgccg ataaacagag gattaaaatt gacaattgtg attaaggctc agattcgacg  13860
gcttggagcg gccgacgtgc aggatttccg cgagatccga ttgtcggccc tgaagaaagc  13920
tccagagatg ttcgggtccg tttacgagca cgaggagaaa aagcccatgg aggcgttcgc  13980
tgaacggttg cgagatgccg tggcattcgg cgcctacatc gacggcgaga tcattgggct  14040
gtcggtcttc aaacaggagg acggccccaa ggacgctcac aaggcgcatc tgtccggcgt  14100
tttcgtggag cccgaacagc gaggccgagg ggtcgccggt atgctgctgc gggcgttgcc  14160
ggcgggttta ttgctcgtga tgatcgtccg acagattcca acgggaatct ggtggatgcg  14220
catcttcatc ctcggcgcac ttaatatttc gctattctgg agcttgttgt ttatttcggt  14280
ctaccgcctg ccgggcgggg tcgcggcgac ggtaggcgct gtgcagccgc tgatggtcgt  14340
gttcatctct gccgctctgc taggtagccc gatacgattg atggcggtcc tgggggctat  14400
ttgcggaact gcgggcgtgg cgctgttggt gttgacacca aacgcagcgc tagatcctgt  14460
cggcgtcgca gcgggcctgg cgggggcggt ttccatggcg ttcggaaccg tgctgacccg  14520
caagtggcaa cctcccgtgc ctctgctcac ctttaccgcc tggcaactgg cggccggagg  14580
acttctgctc gttccagtag ctttagtgtt tgatccgcca atcccgatgc ctacaggaac  14640
caatgttctc ggcctggcgt ggctcggcct gatcggagcg ggtttaacct acttcctttg  14700
gttccggggg atctcgcgac tcgaacctac agttgtttcc ttactgggct ttctcagccg  14760
ggatggcgct aagaagctat tgccgccgat cttcatatgc ggtgtgaaat accgcacaga  14820
tgcgtaagga gaaaataccg catcaggcgc tcttccgctt cctcgctcac tgactcgctg  14880
cgctcggtcg ttcggctgcg gcgagcggta tcagctcact caaaggcggt aatacggtta  14940
tccacagaat caggggataa cgcaggaaag aacatgtgag caaaaggcca gcaaaaggcc  15000
aggaaccgta aaaaggccgc gttgctggcg tttttccata ggctccgccc ccctgacgag  15060
catcacaaaa atcgacgctc aagtcagagg tggcgaaacc cgacaggact ataaagatac  15120
caggcgtttc cccctggaag ctccctcgtg cgctctcctg ttccgaccct gccgcttacc  15180
ggatacctgt ccgcctttct cccttcggga agcgtggcgc tttctcaatg ctcacgctgt  15240
aggtatctca gttcggtgta ggtcgttcgc tccaagctgg gctgtgtgca cgaacccccc  15300
gttcagcccg accgctgcgc cttatccggt aactatcgtc ttgagtccaa cccggtaaga  15360
cacgacttat cgccactggc agcagccact ggtaacagga ttagcagagc gaggtatgta  15420
ggcggtgcta cagagttctt gaagtggtgg cctaactacg gctacactag aaggacagta  15480
```
tttggtatct gcgctctgct gaagccagtt accttcggaa aaagagttgg tagctcttga 15540
tccggcaaac aaaccaccgc tggtagcggt ggtttttttg tttgcaagca gcagattacg 15600
cgcagaaaaa aaggatatca agaagatcct ttgatctttt ctacggggtc tgacgctcag 15660
tggaacgaaa actcacgtta agggattttg gtcatgagat tatcaaaaag gatcttcacc 15720
tagatccttt taaattaaaa atgaagtttt aaatcaatct aaagtatata tgagtaaact 15780
tggtctgaca gttaccaatg cttaatcagt gaggcaccta tctcagcgat ctgtctattt 15840
cgttcatcca tagttgcctg actccccgtc gtgtagataa ctacgatacg ggagggctta 15900
ccatctggcc ccagtgctgc aatgataccg cgagacccac gctcaccggc tccagattta 15960
tcagcaataa accagccagc cggaagggcc gagcgcagaa gtggtcctgc aactttatcc 16020
gcctccatcc agtctattaa acaagtggca gcaacggatt cgcaaacctg tcacgccttt 16080
tgtgccaaaa gccgcgccag gtttgcgatc cgctgtgcca ggcgttaggc gtcatatgaa 16140
gatttcggtg atccctgagc aggtggcgga aacattggat gctgagaacc atttcattgt 16200
tcgtgaagtg ttcgatgtgc acctatccga ccaaggcttt gaactatcta ccagaagtgt 16260
gagcccctac cggaaggatt acatctcgga tgatgactct gatgaagact ctgcttgcta 16320
tggcgcattc atcgaccaag agcttgtcgg gaagattgaa ctcaactcaa catggaacga 16380
tctagcctct atcgaacaca ttgttgtgtc gcacacgcac cgaggcaaag gagtcgcgca 16440
cagtctcatc gaatttgcga aaaagtgggc actaagcaga cagctccttg gcatacgatt 16500
agagacacaa acgaacaatg tacctgcctg caatttgtac gcaaaatgtg gctttactct 16560
cggcggcatt gacctgttca cgtataaaac tagacctcaa gtctcgaacg aaacagcgat 16620
gtactggtac tggttctcgg gagcacagga tgacgcctaa caattcattc aagccgacac 16680
cgcttcgcgg cgcggcttaa ttcaggagtt aaacatcatg agggaagcgg tgatcgccga 16740
agtatcgact caactatcag aggtagttgg cgtcatcgag cgccatctcg aaccgacgtt 16800
gctggccgta catttgtacg gctccgcagt ggatggcggc ctgaagccac acagtgatat 16860
tgatttgctg gttacggtga ccgtaaggct tgatgaaaca acgcggcgag ctttgatcaa 16920
cgaccttttg gaaacttcgg cttcccctgg agagagcgag attctccgcg ctgtagaagt 16980
caccattgtt gtgcacgacg acatcattcc gtggcgttat ccagctaagc gcgaactgca 17040
atttggagaa tggcagcgca atgacattct tgcaggtatc ttcgagccag ccacgatcga 17100
cattgatctg gctatcttgc tgacaaaagc aagagaacat agcgttgcct tggtaggtcc 17160
agcggcggag gaactctttg atccggttcc tgaacaggat ctatttgagg cgctaaatga 17220
aaccttaacg ctatggaact cgccgcccga ctgggctggc gatgagcgaa atgtagtgct 17280
tacgttgtcc cgcatttggt acagcgcagt aaccggcaaa atcgcgccga aggatgtcgc 17340
tgccgactgg gcaatggagc gcctgccggc ccagtatcag cccgtcatac ttgaagctag 17400
gcaggcttat cttggacaag aagatcgctt ggcctcgcgc gcagatcagt tggaagaatt 17460
tgttcactac gtgaaaggcg agatcaccaa ggtagtcggc aaataatgtc taacaattcg 17520
ttcaagccga cgccgcttcg cggcgcggct taactcaagc gttagagagc tggggaagac 17580
tatgcgcgat ctgttgaagg tggttctaag cctcgtactt gcgatggcat cggggcaggc 17640
acttgctgac ctgccaattg ttttagtgga tgaagctcgt cttccctatg actactcccc 17700
atccaactac gacatttctc caagcaacta cgacaactcc ataagcaatt acgacaatag 17760
tccatcaaat tacgacaact ctgagagcaa ctacgataat agttcatcca attacgacaa 17820
tagtcgcaac ggaaatcgta ggcttatata tagcgcaaat gggtctcgca ctttcgccgg 17880

```
ctactacgtc attgccaaca atgggacaac gaacttcttt tccacatctg gcaaaaggat  17940

gttctacacc ccaaaagggg ggcgcggcgt ctatggcggc aaagatggga gcttctgcgg  18000

ggcattggtc gtcataaatg gccaattttc gcttgccctg acagataacg gcctgaagat  18060

catgtatcta agcaactagc ctgctctcta ataaaatgtt aggagcttgg ctgccatttt  18120

tggggtgagg ccgttcgcgg ccgaggggcg cagcccctgg ggggatggga ggcccgcgtt  18180

agcgggccgg gagggttcga gaaggggggg cacccccctt cggcgtgcgc ggtcacgcgc  18240

cagggcgcag ccctggttaa aaacaaggtt tataaatatt ggtttaaaag caggttaaaa  18300

gacaggttag cggtggccga aaaacgggcg gaaacccttg caaatgctgg atttctgcc  18360

tgtggacagc ccctcaaatg tcaataggtg cgcccctcat ctgtcagcac tctgcccctc  18420

aagtgtcaag gatcgcgccc ctcatctgtc agtagtcgcg cccctcaagt gtcaataccg  18480

cagggcactt atccccaggc ttgtccacat catctgtggg aaactcgcgt aaaatcaggc  18540

gttttcgccg atttgcgagg ctggccagct ccacgtcgcc ggccgaaatc gagcctgccc  18600

ctcatctgtc aacgccgcgc cgggtgagtc ggcccctcaa gtgtcaacgt ccgcccctca  18660

tctgtcagtg agggccaagt tttccgcgag gtatccacaa cgccggcggc cggccgcggt  18720

gtctcgcaca cggcttcgac ggcgtttctg gcgcgtttgc agggccatag acggccgcca  18780

gcccagcggc gagggcaacc agcccggtga gcgtcggaaa ggg                    18823
```

<210> SEQ ID NO 33
<211> LENGTH: 520
<212> TYPE: PRT
<213> ORGANISM: Artificial Sequence
<220> FEATURE:
<223> OTHER INFORMATION: Synthetic peptide

<400> SEQUENCE: 33

```
Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Val Val Val Leu Ile
    130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
            180                 185                 190
```

```
Phe Thr Val Glu Lys Leu Val Leu Gln Lys Tyr Ile Ala Glu Pro Val
        195                 200                 205

Val Ile Phe Leu His Ile Ile Ile Thr Met Thr Glu Val Leu Tyr Pro
    210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
            260                 265                 270

Asn Pro Glu Val Ser Tyr Tyr Val Ser Leu Lys Ser Leu Ala Tyr Phe
        275                 280                 285

Met Val Ala Pro Thr Leu Cys Tyr Gln Pro Ser Tyr Pro Arg Ser Ala
    290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                325                 330                 335

Val Arg Asn Ser Lys His Pro Leu Lys Gly Asp Leu Leu Tyr Ala Ile
            340                 345                 350

Glu Arg Val Leu Lys Leu Ser Val Pro Asn Leu Tyr Val Trp Leu Cys
        355                 360                 365

Met Phe Tyr Cys Phe Phe His Leu Trp Leu Asn Ile Leu Ala Glu Leu
    370                 375                 380

Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
                405                 410                 415

Met Val Arg His Ile Tyr Phe Pro Cys Leu Arg Ser Lys Ile Pro Lys
            420                 425                 430

Thr Leu Ala Ile Ile Ile Ala Phe Leu Val Ser Ala Val Phe His Glu
        435                 440                 445

Leu Cys Ile Ala Val Pro Cys Arg Leu Phe Lys Leu Trp Ala Phe Leu
    450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
            500                 505                 510

Met Asn Arg Lys Gly Ser Met Ser
        515                 520
```

<210> SEQ ID NO 34
<211> LENGTH: 501
<212> TYPE: DNA
<213> ORGANISM: S. indicum

<400> SEQUENCE: 34

```
atggcggacc gcgaccgtcc acacccccac caaattcaag tccaccctca acatccgcac      60
cgctatgaag gtggcgtcaa gtctctcctc cctcaaaagg gcccctccac cacccagatt     120
ctcgccataa tcaccctcct tcccatcagc ggcacgcttc tttgcctagc tgggatcacg     180
ctcgtcggga ccctcatcgg acttgcagtc gccaccccag tcttcgtgat cttcagccct     240
```

```
gttctggttc ccgcagccat actgatagcc ggcgcggtca cggcgttttt gacgtccggg    300
gcttttgggc tgacggggct ttcgtcgctt tcttgggttc tgaattcatt cagacgggcg    360
acggggcagg ggccgttgga gtacgcgaag cgaggcgtgc aggaggggac tttgtatgtg    420
ggagagaaga cgaagcaagc gggcgaagcg attaagagca cagccaagga aggagggcga    480
gaagggactg cacggacttg a                                              501

<210> SEQ ID NO 35
<211> LENGTH: 166
<212> TYPE: PRT
<213> ORGANISM: S. indicum

<400> SEQUENCE: 35

Met Ala Asp Arg Asp Arg Pro His Pro His Gln Ile Gln Val His Pro
1               5                   10                  15

Gln His Pro His Arg Tyr Glu Gly Gly Val Lys Ser Leu Leu Pro Gln
            20                  25                  30

Lys Gly Pro Ser Thr Thr Gln Ile Leu Ala Ile Ile Thr Leu Leu Pro
        35                  40                  45

Ile Ser Gly Thr Leu Leu Cys Leu Ala Gly Ile Thr Leu Val Gly Thr
    50                  55                  60

Leu Ile Gly Leu Ala Val Ala Thr Pro Val Phe Val Ile Phe Ser Pro
65                  70                  75                  80

Val Leu Val Pro Ala Ala Ile Leu Ile Ala Gly Ala Val Thr Ala Phe
                85                  90                  95

Leu Thr Ser Gly Ala Phe Gly Leu Thr Gly Leu Ser Ser Leu Ser Trp
            100                 105                 110

Val Leu Asn Ser Phe Arg Arg Ala Thr Gly Gln Gly Pro Leu Glu Tyr
        115                 120                 125

Ala Lys Arg Gly Val Gln Glu Gly Thr Leu Tyr Val Gly Glu Lys Thr
    130                 135                 140

Lys Gln Ala Gly Glu Ala Ile Lys Ser Thr Ala Lys Glu Gly Gly Arg
145                 150                 155                 160

Glu Gly Thr Ala Arg Thr
                165

<210> SEQ ID NO 36
<211> LENGTH: 559
<212> TYPE: DNA
<213> ORGANISM: S. indicum

<400> SEQUENCE: 36
ggcacgagcg ccgtccccat ggcggacgaa ccccacgacc agcgccccac cgacgtcatc     60
aagagctacc tccccgaaaa gggtccctcc acctctcaag tcctcgccgt cgtgaccctc    120
ttccccctcg gcgccgtcct cctctgccta gccggtctca ttcttaccgg gaccatcatc    180
ggcctcgccg tcgccacccc gctcttcgtc atcttcagcc ccatcttggt ccccgccgcc    240
ctaaccatcg ccctagccgt caccggtttc ttgacctccg gagctttcgg catcaccgcc    300
ctgtcctcga tttcgtggtt gctgaactac gttaggcgaa tgcgggggag cttgccagag    360
cagctggatc atgcacggcg gcgcgtgcag gagacggtgg gccagaagac aagggaggcg    420
gggcagagaa gccaagatgt aataagaccg tgaggttttt ggatattaga tgttggttaa    480
tttgtgtgtt taatgtatat atgaggggtt gaataagtta ataaaattgc ggatttggta    540
caaaaaaaaa aaaaaaaaa                                                 559
```

<210> SEQ ID NO 37
<211> LENGTH: 144
<212> TYPE: PRT
<213> ORGANISM: S. indicum

<400> SEQUENCE: 37

```
Met Ala Asp Glu Pro His Asp Gln Arg Pro Thr Asp Val Ile Lys Ser
1               5                   10                  15

Tyr Leu Pro Glu Lys Gly Pro Ser Thr Ser Gln Val Leu Ala Val Val
            20                  25                  30

Thr Leu Phe Pro Leu Gly Ala Val Leu Leu Cys Leu Ala Gly Leu Ile
        35                  40                  45

Leu Thr Gly Thr Ile Ile Gly Leu Ala Val Ala Thr Pro Leu Phe Val
    50                  55                  60

Ile Phe Ser Pro Ile Leu Val Pro Ala Ala Leu Thr Ile Ala Leu Ala
65                  70                  75                  80

Val Thr Gly Phe Leu Thr Ser Gly Ala Phe Gly Ile Thr Ala Leu Ser
                85                  90                  95

Ser Ile Ser Trp Leu Leu Asn Tyr Val Arg Arg Met Arg Gly Ser Leu
            100                 105                 110

Pro Glu Gln Leu Asp His Ala Arg Arg Arg Val Gln Glu Thr Val Gly
        115                 120                 125

Gln Lys Thr Arg Glu Ala Gly Gln Arg Ser Gln Asp Val Ile Arg Pro
    130                 135                 140
```

<210> SEQ ID NO 38
<211> LENGTH: 1800
<212> TYPE: DNA
<213> ORGANISM: A. thaliana

<400> SEQUENCE: 38

```
ccatggctat acccaacctc ggtcttggtc acaccaggaa ctctctggta agctagctcc      60
actccccaga aacaaccggc gccaaattgc cggaattgct gacctgaaga cggaacatca     120
tcgtcgggtc cttgggcgat tgcggcggaa gatgggtcag cttgggcttg aggacgagac     180
ccgaatcgag tctgttgaaa ggttgttcat tgggatttgt atacggagat tggtcgtcga     240
gaggtttgag ggaaaggaca aatgggtttg gctctggaga aagagagtgc ggctttagag     300
agagaattga gaggtttaga gagagatgcg gcggcgatga cgggaggaga gacgacgagg     360
acctgcatta tcaaagcagt gacgtggtga aatttggaac ttttaagagg cagatagatt     420
tattatttgt atccattttc ttcattgttc tagaatgtcg cggaacaaat tttaaaacta     480
aatcctaaat ttttctaatt ttgttgccaa tagtggatat gtgggccgta tagaaggaat     540
ctattgaagg cccaaaccca tactgacgag cccaaaggtt cgttttgcgt tttatgtttc     600
ggttcgatgc caacgccaca ttctgagcta ggcaaaaaac aaacgtgtct ttgaatagac     660
tcctctcgtt aacacatgca gcggctgcat ggtgacgcca ttaacacgtg gcctacaatt     720
gcatgatgtc tccattgaca cgtgacttct cgtctccttt cttaatatat ctaacaaaca     780
ctcctacctc ttccaaaata tatacacatc tttttgatca atctctcatt caaaatctca     840
ttctctctag taaacaagaa caaaaaaatg gcggatacag ctagaggaac ccatcacgat     900
atcatcggca gagaccagta cccgatgatg ggccgagacc gagaccagta ccagatgtcc     960
ggacgaggat ctgactactc caagtctagg cagattgcta aagctgcaac tgctgtcaca    1020
gctggtggtt ccctccttgt tctctccagc cttacccttg ttggaactgt catagctttg    1080
```

```
actgttgcaa cacctctgct cgttatcttc agcccaatcc ttgtcccggc tctcatcaca   1140

gttgcactcc tcatcaccgg ttttctttcc tctggagggt ttggcattgc cgctataacc   1200

gttttctctt ggatttacaa gtaagcacac atttatcatc ttacttcata attttgtgca   1260

atatgtgcat gcatgtgttg agccagtagc tttggatcaa tttttttggt cgaataacaa   1320

atgtaacaat aagaaattgc aaattctagg gaacatttgg ttaactaaat acgaaatttg   1380

acctagctag cttgaatgtg tctgtgtata tcatctatat aggtaaaatg cttggtatga   1440

tacctattga ttgtgaatag gtacgcaacg ggagagcacc cacagggatc agacaagttg   1500

gacagtgcaa ggatgaagtt gggaagcaaa gctcaggatc tgaaagacag agctcagtac   1560

tacggacagc aacatactgg tggggaacat gaccgtgacc gtactcgtgg tggccagcac   1620

actacttaag ttaccccact gatgtcatcg tcatagtcca ataactccaa tgtcggggag   1680

ttagtttatg aggaataaag tgtttagaat ttgatcaggg ggagataata aaagccgagt   1740

ttgaatcttt ttgttataag taatgtttat gtgtgtttct atatgttgtc aaatggtacc   1800
```

<210> SEQ ID NO 39
<211> LENGTH: 173
<212> TYPE: PRT
<213> ORGANISM: A. thaliana

<400> SEQUENCE: 39

```
Met Ala Asp Thr Ala Arg Gly Thr His His Asp Ile Ile Gly Arg Asp
1               5                   10                  15

Gln Tyr Pro Met Met Gly Arg Asp Arg Asp Gln Tyr Gln Met Ser Gly
            20                  25                  30

Arg Gly Ser Asp Tyr Ser Lys Ser Arg Gln Ile Ala Lys Ala Ala Thr
        35                  40                  45

Ala Val Thr Ala Gly Gly Ser Leu Leu Val Leu Ser Ser Leu Thr Leu
    50                  55                  60

Val Gly Thr Val Ile Ala Leu Thr Val Ala Thr Pro Leu Leu Val Ile
65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
            100                 105                 110

Phe Ser Trp Ile Tyr Lys Tyr Ala Thr Gly Glu His Pro Gln Gly Ser
        115                 120                 125

Asp Lys Leu Asp Ser Ala Arg Met Lys Leu Gly Ser Lys Ala Gln Asp
    130                 135                 140

Leu Lys Asp Arg Ala Gln Tyr Tyr Gly Gln Gln His Thr Gly Gly Glu
145                 150                 155                 160

His Asp Arg Asp Arg Thr Arg Gly Gly Gln His Thr Thr
                165                 170
```

<210> SEQ ID NO 40
<211> LENGTH: 450
<212> TYPE: DNA
<213> ORGANISM: A. thaliana

<400> SEQUENCE: 40

```
atggcggatc atcaacaaca tcagcaacaa caacaaccaa taatgaggag tctccatgaa     60
tcatcaccat cgactcggca gatagtgaga ttcgtaacgg cagctacgat cggcctatca    120
ctcctcgtgc tctcaggact aacactaacc ggaacggtga tcggtttgat cgtagcgacg    180
```

-continued

```
ccgttgatgg ttctgttcag cccggtgttg gtaccggcag tgataacgat agggcttctg    240

acgatgggat tcctattctc cggtggttgt ggggtggcag cagctacggc gttaacgtgg    300

atttataagt acgttaccgg aaaacacccg atgggagcgg ataaggtgga ttacgcgagg    360

atgaggatag cggagaaagc caaagagttg ggacattata cgcactcgca gccacaacaa    420

acacaccaaa ccacaacaac tactcattag                                     450
```

```
<210> SEQ ID NO 41
<211> LENGTH: 149
<212> TYPE: PRT
<213> ORGANISM: A. thaliana

<400> SEQUENCE: 41

Met Ala Asp His Gln Gln His Gln Gln Gln Gln Gln Pro Ile Met Arg
1               5                   10                  15

Ser Leu His Glu Ser Ser Pro Ser Thr Arg Gln Ile Val Arg Phe Val
            20                  25                  30

Thr Ala Ala Thr Ile Gly Leu Ser Leu Leu Val Leu Ser Gly Leu Thr
        35                  40                  45

Leu Thr Gly Thr Val Ile Gly Leu Ile Val Ala Thr Pro Leu Met Val
    50                  55                  60

Leu Phe Ser Pro Val Leu Val Pro Ala Val Ile Thr Ile Gly Leu Leu
65                  70                  75                  80

Thr Met Gly Phe Leu Phe Ser Gly Gly Cys Gly Val Ala Ala Ala Thr
                85                  90                  95

Ala Leu Thr Trp Ile Tyr Lys Tyr Val Thr Gly Lys His Pro Met Gly
            100                 105                 110

Ala Asp Lys Val Asp Tyr Ala Arg Met Arg Ile Ala Glu Lys Ala Lys
        115                 120                 125

Glu Leu Gly His Tyr Thr His Ser Gln Pro Gln Gln Thr His Gln Thr
    130                 135                 140

Thr Thr Thr Thr His
145
```

```
<210> SEQ ID NO 42
<211> LENGTH: 625
<212> TYPE: DNA
<213> ORGANISM: H. annuus

<400> SEQUENCE: 42
actaccacca cttacgaccg tcatttcacc accacccaac cccactaccg ccaagacgac     60
aggtcccgct acgaccagca aacccattcc cagtccacca gcaggacact cgccatcatc    120
gccctacttc ctgtcggcgg aatcttactc ggcttagccg ctctcacatt catcgggacg    180
cttatcgggc tcgccctcgc caccccgctt ttcgtcatat tcagcccgat catcgtgccg    240
gccgttctaa caatcgggct tgctgttaca ggctttttgg cgtcggggac gttcgggttg    300
acgggtttga gctcattgtc gtatttgttc aatatggtta ggcagacggc tgggtcggtg    360
cccgagtcct tggattatgt taaggggacg ttgcaggatg ccggtgagta tgccgggcag    420
aagacgaagg atttcgggca gaagattcag agcacggctc atgagatggg tgatcagggg    480
caggttggtg ttcatgctca agttggtggc gggaaagaag ggcgaaaaag cggtgatcgg    540
acttgaggat tcaaggttga tattgtggaa taataatgtt gatgtaagtt tttagtgtta    600
tcaaagcttt gtttgtttgt ttgta                                          625
```

<210> SEQ ID NO 43
<211> LENGTH: 181
<212> TYPE: PRT
<213> ORGANISM: H. annuus

<400> SEQUENCE: 43

```
Thr Thr Thr Thr Tyr Asp Arg His Phe Thr Thr Thr Gln Pro His Tyr
1               5                   10                  15

Arg Gln Asp Asp Arg Ser Arg Tyr Asp Gln Gln Thr His Ser Gln Ser
            20                  25                  30

Thr Ser Arg Thr Leu Ala Ile Ile Ala Leu Leu Pro Val Gly Gly Ile
        35                  40                  45

Leu Leu Gly Leu Ala Ala Leu Thr Phe Ile Gly Thr Leu Ile Gly Leu
    50                  55                  60

Ala Leu Ala Thr Pro Leu Phe Val Ile Phe Ser Pro Ile Ile Val Pro
65                  70                  75                  80

Ala Val Leu Thr Ile Gly Leu Ala Val Thr Gly Phe Leu Ala Ser Gly
                85                  90                  95

Thr Phe Gly Leu Thr Gly Leu Ser Ser Leu Ser Tyr Leu Phe Asn Met
            100                 105                 110

Val Arg Gln Thr Ala Gly Ser Val Pro Glu Ser Leu Asp Tyr Val Lys
        115                 120                 125

Gly Thr Leu Gln Asp Ala Gly Glu Tyr Ala Gly Gln Lys Thr Lys Asp
    130                 135                 140

Phe Gly Gln Lys Ile Gln Ser Thr Ala His Glu Met Gly Asp Gln Gly
145                 150                 155                 160

Gln Val Gly Val His Ala Gln Val Gly Gly Gly Lys Glu Gly Arg Lys
                165                 170                 175

Ser Gly Asp Arg Thr
            180
```

<210> SEQ ID NO 44
<211> LENGTH: 737
<212> TYPE: DNA
<213> ORGANISM: B. napus

<400> SEQUENCE: 44

```
gaattccatt caaactagta aacaatgggg atactcagga agaaaaaaca cgagcgaaag      60

ccgtcgttta agagtgtttt aaccgcaata ttagctacac atgccgcaac attcctcttg     120

ttgatcgccg gtgtatccct cgccggcaca gccgccgcat ttatcgctac catgccacta     180

ttcgtagtat tcagtccgat tctcgtacca gctggtatta ccactggttt actgactacg     240

ggtttagcag ccgccggtgg cgccggcgcg actgctgtca ccatcatcct gtggctctac     300

aagcgagcaa cgggcaaggc gccgccaaaa gtcctagaaa aagtcttgaa aaagataata     360

ccaggtgctg cagctgcacc agcagccgct ccaggagccg ctccagcagc ggcgccagca     420

gccgcaccag ctgtggcgcc agcagccgca ccagctgctg cgccagcacc taagccagca     480

gccccaccag cacctaagcc agcagccgca ccgagtatat gaaaagaagt ggtgggcatg     540

agtaaaggtt gatatggaaa actggataca tagaaaaaag agtaatccaa cttttaaaaa     600

ataaataaca acttcacgtg gggatagaaa aattttcaaa tattatttta ctaatggatg     660

tcgcggtaca aaataataac aaatgtaagc ctttttattg tatagtattt taagaacgaa     720

gctatgtagc gttgaca                                                    737
```

<210> SEQ ID NO 45

<211> LENGTH: 165
<212> TYPE: PRT
<213> ORGANISM: B. napus

<400> SEQUENCE: 45

Met Gly Ile Leu Arg Lys Lys Lys His Glu Arg Lys Pro Ser Phe Lys
1 5 10 15

Ser Val Leu Thr Ala Ile Leu Ala Thr His Ala Ala Thr Phe Leu Leu
20 25 30

Leu Ile Ala Gly Val Ser Leu Ala Gly Thr Ala Ala Ala Phe Ile Ala
35 40 45

Thr Met Pro Leu Phe Val Val Phe Ser Pro Ile Leu Val Pro Ala Gly
50 55 60

Ile Thr Thr Gly Leu Leu Thr Thr Gly Leu Ala Ala Ala Gly Gly Ala
65 70 75 80

Gly Ala Thr Ala Val Thr Ile Ile Leu Trp Leu Tyr Lys Arg Ala Thr
85 90 95

Gly Lys Ala Pro Pro Lys Val Leu Glu Lys Val Leu Lys Lys Ile Ile
100 105 110

Pro Gly Ala Ala Ala Ala Pro Ala Ala Ala Pro Gly Ala Ala Pro Ala
115 120 125

Ala Ala Pro Ala Ala Ala Pro Ala Val Ala Pro Ala Ala Ala Pro Ala
130 135 140

Ala Ala Pro Ala Pro Lys Pro Ala Ala Pro Pro Ala Pro Lys Pro Ala
145 150 155 160

Ala Ala Pro Ser Ile
165

<210> SEQ ID NO 46
<211> LENGTH: 1153
<212> TYPE: DNA
<213> ORGANISM: Z. mays

<400> SEQUENCE: 46
aactactccg tcactttgtt tgcaaagctc ctcctcgatc catcgatcac tgcaccggcc 60
ggcggcaccg cgctcgcagg ggctagccaa cgagacggca gcaatggcgg accgtgaccg 120
cagcggcatc tacggcggcg cccacgccac ctacgggcag cagcagcagc agggaggagg 180
cgggcgcccg atgggtgagc aggtgaaggg catgctccac gacaaggggc cgacggcgtc 240
gcaggcgctg acggtggcga cgctgttccc gctgggcggg ctgctgctgg tgctgtcggg 300
gctggcgctg acggcctccg tggtggggct ggccgtggcc acgccggtgt tcctgatctt 360
cagccccgtg ctggtccccg ccgcgctgct catcgggacg gccgtcatgg ggttcctcac 420
gtcgggcgcg ctggggctcg ggggcctgtc ctcgctcacg tgcctcgcca acacggcgcg 480
gcaggcgttc cagcgcaccc cggactacgt ggaggaggcg caccgcagga tggcggaggc 540
cgcggcgcac gcgggccaca agaccgcgca ggcaggccag gccatccagg gcagggcgca 600
ggaggccggc gccgggggag gtgcaggtgc cggcgctggc ggcggcggca gggcttcctc 660
gtaagcaagt catccatgca tggattatgg atagatgcgc gcgtgcgtgt ctatcagtat 720
cagcagccag cagggtcgtc gcggaatgct gtgttcctgt acgtgtgggt gaccgtcctt 780
ccgtccttcg tctttctccc cccgagtgtg tgttacgtat gtcctggtgt tcgtcgtgtg 840
tgttcatcgc cgctccagtt gaattccggt gtctgttcat cgccgctcca ggtcgtagat 900
gtgaatatac tttgctaggg gaataagtga taagtctgtc tggaaggtaa tgtttgagct 960
ttgctagtgt ggctgggcac tctggtcact ggttgtgttg tgcatgcatc agctgtatga 1020
tcgtcgtctg ttgtggaaaa ttggtcaatg tattctcttg ctgaataatt tgtgacatct 1080
aattgttatg tatcgtctct ttgctgaata atcagtttct gatttatctt gcattaaaaa 1140
aaaaaaaaaa aaa 1153

<210> SEQ ID NO 47
<211> LENGTH: 186
<212> TYPE: PRT
<213> ORGANISM: Z. mays

<400> SEQUENCE: 47

Met Ala Asp Arg Asp Arg Ser Gly Ile Tyr Gly Gly Ala His Ala Thr
1 5 10 15

Tyr Gly Gln Gln Gln Gln Gln Gly Gly Gly Gly Arg Pro Met Gly Glu
20 25 30

Gln Val Lys Gly Met Leu His Asp Lys Gly Pro Thr Ala Ser Gln Ala
35 40 45

Leu Thr Val Ala Thr Leu Phe Pro Leu Gly Gly Leu Leu Leu Val Leu
50 55 60

Ser Gly Leu Ala Leu Thr Ala Ser Val Val Gly Leu Ala Val Ala Thr
65 70 75 80

Pro Val Phe Leu Ile Phe Ser Pro Val Leu Val Pro Ala Ala Leu Leu
85 90 95

Ile Gly Thr Ala Val Met Gly Phe Leu Thr Ser Gly Ala Leu Gly Leu
100 105 110

Gly Gly Leu Ser Ser Leu Thr Cys Leu Ala Asn Thr Ala Arg Gln Ala
115 120 125

Phe Gln Arg Thr Pro Asp Tyr Val Glu Glu Ala His Arg Arg Met Ala
130 135 140

Glu Ala Ala Ala His Ala Gly His Lys Thr Ala Gln Ala Gly Gln Ala
145 150 155 160

Ile Gln Gly Arg Ala Gln Glu Ala Gly Ala Gly Gly Gly Ala Gly Ala
165 170 175

Gly Ala Gly Gly Gly Gly Arg Ala Ser Ser
180 185

<210> SEQ ID NO 48
<211> LENGTH: 447
<212> TYPE: DNA
<213> ORGANISM: O. sativa

<400> SEQUENCE: 48
atgggtgatc agcacagagg agtgatcggc ggtggcggct acggtgaccg tggtggccag 60
gagcagcagg agaagcagcc cttcatgatg acggctctga agacggtgac cgcggcgacg 120
gccgggggct cgattctggt gctgtccggg ctgatcctgg ccgggaccgt catcgcgctc 180
acggtggcca ccccggtgtt ggtcatcttc agccccgtgc tggtaccggc ggccatcgcg 240
ctggcgctca tggcggccgg gttcgtcacc tcggttggtc tcggtgtagc cgcgctctcc 300
gttttctcgt ggatgtacaa gtacctcacc gggaagcacc cgccgggcgc cgaccatctg 360
gaccacacca aggcgagggt cgcgtccaag ctccgcgaca tcaaggaggc ggcgcatcac 420
ctcatcgacc aggcgcaggc gtcttag 447

<210> SEQ ID NO 49
<211> LENGTH: 148

<212> TYPE: PRT
<213> ORGANISM: O. sativa

<400> SEQUENCE: 49

Met Gly Asp Gln His Arg Gly Val Ile Gly Gly Gly Gly Tyr Gly Asp
1               5                   10                  15

Arg Gly Gly Gln Glu Gln Gln Glu Lys Gln Pro Phe Met Met Thr Ala
            20                  25                  30

Leu Lys Thr Val Thr Ala Ala Thr Ala Gly Gly Ser Ile Leu Val Leu
        35                  40                  45

Ser Gly Leu Ile Leu Ala Gly Thr Val Ile Ala Leu Thr Val Ala Thr
    50                  55                  60

Pro Val Leu Val Ile Phe Ser Pro Val Leu Val Pro Ala Ala Ile Ala
65                  70                  75                  80

Leu Ala Leu Met Ala Ala Gly Phe Val Thr Ser Val Gly Leu Gly Val
                85                  90                  95

Ala Ala Leu Ser Val Phe Ser Trp Met Tyr Lys Tyr Leu Thr Gly Lys
            100                 105                 110

His Pro Pro Gly Ala Asp His Leu Asp His Thr Lys Ala Arg Val Ala
        115                 120                 125

Ser Lys Leu Arg Asp Ile Lys Glu Ala Ala His His Leu Ile Asp Gln
    130                 135                 140

Ala Gln Ala Ser
145

<210> SEQ ID NO 50
<211> LENGTH: 709
<212> TYPE: DNA
<213> ORGANISM: B. oleracea

<400> SEQUENCE: 50
gccgtttttt cagaatgttc tcttttatct tcccattgct gaacgttata aagcttatta 60
tagcttccgt gacctcctta gtctgcttag cgttttcttg tgtgacactc ggtggttcag 120
ccgtggcatt aatcgtatcc acaccacttt tcatcatatt tagtccaatt ctcgtacctg 180
ccactattgc cactaccctc ctagccagtg ggctcatggc gggtaccacc ctcggactga 240
ccggcatagg tctcatcacg gggctcgtta ggacggcagg aggagttaca ttggccgaat 300
caccgataag aagaattata ataaatagaa ttaaagcaag acttgggggt ggcggcggtt 360
cacgtctggc aatgctcaaa aaaattctgg gactcattaa aaagttgcgt ggtatgtctt 420
caggtggagc agcacctgcg ctgaagcagc accagcagct gcgcccgcgg atggagctgc 480
acccgcggca cctgcaccga cctaacaaag aacgttggtt catgctgttc caatatgtag 540
cacataaaaa ttgtgtaata attaacttaa gaatttatga ttcggaaact aaaaagaaaa 600
tagccctttt actatctttt atacaatata gttttctatg taataatgtt taatttgctt 660
ataactataa aagactcatg catagttgat taggaaaaaa aaaaaaaaa 709

<210> SEQ ID NO 51
<211> LENGTH: 216
<212> TYPE: PRT
<213> ORGANISM: B. oleracea

<400> SEQUENCE: 51

Arg Phe Phe Arg Met Phe Ser Phe Ile Phe Pro Leu Leu Asn Val Ile
1               5                   10                  15

Lys Leu Ile Ile Ala Ser Val Thr Ser Leu Val Cys Leu Ala Phe Ser

```
            20                  25                  30

Cys Val Thr Leu Gly Gly Ser Ala Val Ala Leu Ile Val Ser Thr Pro
        35                  40                  45

Leu Phe Ile Ile Phe Ser Pro Ile Leu Val Pro Ala Thr Ile Ala Thr
    50                  55                  60

Thr Leu Leu Ala Ser Gly Leu Met Ala Gly Thr Thr Leu Gly Leu Thr
65                  70                  75                  80

Gly Ile Gly Leu Ile Thr Gly Leu Val Arg Thr Ala Gly Gly Val Thr
                85                  90                  95

Leu Ala Glu Ser Pro Ile Arg Arg Ile Ile Ile Asn Arg Ile Lys Ala
            100                 105                 110

Arg Leu Gly Gly Gly Gly Gly Ser Arg Leu Ala Met Leu Lys Lys Ile
        115                 120                 125

Leu Gly Leu Ile Lys Lys Leu Arg Gly Met Ser Ser Gly Gly Ala Ala
    130                 135                 140

Pro Ala Leu Lys Gln His Gln Gln Leu Arg Pro Arg Met Glu Leu His
145                 150                 155                 160

Pro Arg His Leu His Arg Pro Asn Lys Glu Arg Trp Phe Met Leu Phe
                165                 170                 175

Gln Tyr Val Ala His Lys Asn Cys Val Ile Ile Asn Leu Arg Ile Tyr
            180                 185                 190

Asp Ser Glu Thr Lys Lys Lys Ile Ala Leu Leu Leu Ser Phe Ile Gln
        195                 200                 205

Tyr Ser Phe Leu Cys Asn Asn Val
    210                 215
```

<210> SEQ ID NO 52
<211> LENGTH: 447
<212> TYPE: DNA
<213> ORGANISM: C. arabica

<400> SEQUENCE: 52

```
atggctgagc actaccagct gcagcaacgc cccacagagg ccgtcaaaag cttccttcct      60

cagaagggtc catcaacttc acatgtgtta gcagttgtca cgctcctccc agttgcggga     120

gtcctgctag gcctttccgg gctgattctc gtcggaacgg tcatcggtct ggcggtgaca     180

accccgcttt tcgttatctt tagccccatt ttggtcccag ctgtatttgc cctagggctg     240

gccctggccg ggttcttgac ctccggtgct ttcgggatca ctgcacttgc ttcattgtcg     300

tggatgctga actacatccg actcatgaag gcgtcttccc aggagcaaat ggacctcgca     360

aagtggcgcg tgcaggacac tgccggccaa gttggtcaga aagcgagaga cgtgggccag     420

agaactcaag atgtagccag agcatga                                         447
```

<210> SEQ ID NO 53
<211> LENGTH: 148
<212> TYPE: PRT
<213> ORGANISM: C. arabica

<400> SEQUENCE: 53

```
Met Ala Glu His Tyr Gln Leu Gln Gln Arg Pro Thr Glu Ala Val Lys
1               5                   10                  15

Ser Phe Leu Pro Gln Lys Gly Pro Ser Thr Ser His Val Leu Ala Val
            20                  25                  30

Val Thr Leu Leu Pro Val Ala Gly Val Leu Leu Gly Leu Ser Gly Leu
        35                  40                  45
```

```
Ile Leu Val Gly Thr Val Ile Gly Leu Ala Val Thr Thr Pro Leu Phe
    50                  55                  60

Val Ile Phe Ser Pro Ile Leu Val Pro Ala Val Phe Ala Leu Gly Leu
65                  70                  75                  80

Ala Leu Ala Gly Phe Leu Thr Ser Gly Ala Phe Gly Ile Thr Ala Leu
                85                  90                  95

Ala Ser Leu Ser Trp Met Leu Asn Tyr Ile Arg Leu Met Lys Ala Ser
            100                 105                 110

Ser Gln Glu Gln Met Asp Leu Ala Lys Trp Arg Val Gln Asp Thr Ala
        115                 120                 125

Gly Gln Val Gly Gln Lys Ala Arg Asp Val Gly Gln Arg Thr Gln Asp
    130                 135                 140

Val Ala Arg Ala
145

<210> SEQ ID NO 54
<211> LENGTH: 348
<212> TYPE: PRT
<213> ORGANISM: S. indicum

<400> SEQUENCE: 54

Met Asp Leu Ile His Thr Phe Leu Asn Leu Ile Ala Pro Pro Phe Thr
1               5                   10                  15

Phe Phe Phe Leu Leu Phe Phe Leu Pro Pro Phe Gln Ile Phe Lys Phe
            20                  25                  30

Phe Leu Ser Ile Leu Gly Thr Leu Phe Ser Glu Asp Val Ala Gly Lys
        35                  40                  45

Val Val Val Ile Thr Gly Ala Ser Ser Gly Ile Gly Glu Ser Leu Ala
    50                  55                  60

Tyr Glu Tyr Ala Lys Arg Gly Ala Cys Leu Val Leu Ala Ala Arg Arg
65                  70                  75                  80

Glu Arg Ser Leu Gln Glu Val Ala Glu Arg Ala Arg Asp Leu Gly Ser
                85                  90                  95

Pro Asp Val Val Val Val Arg Ala Asp Val Ser Lys Ala Glu Asp Cys
            100                 105                 110

Arg Lys Val Val Asp Gln Thr Met Asn Arg Phe Gly Arg Leu Asp His
        115                 120                 125

Leu Val Asn Asn Ala Gly Ile Met Ser Val Ser Met Leu Glu Glu Val
    130                 135                 140

Glu Asp Ile Thr Gly Tyr Arg Glu Thr Met Asp Ile Asn Phe Trp Gly
145                 150                 155                 160

Tyr Val Tyr Met Thr Arg Phe Ala Ala Pro Tyr Leu Arg Asn Ser Arg
                165                 170                 175

Gly Arg Ile Val Val Leu Ser Ser Ser Ser Ser Trp Met Pro Thr Pro
            180                 185                 190

Arg Met Ser Phe Tyr Asn Ala Ser Lys Ala Ala Ile Ser Gln Phe Phe
        195                 200                 205

Glu Thr Leu Arg Val Glu Phe Gly Pro Asp Ile Gly Ile Thr Leu Val
    210                 215                 220

Thr Pro Gly Phe Ile Glu Ser Glu Leu Thr Gln Gly Lys Phe Tyr Asn
225                 230                 235                 240

Ala Gly Glu Arg Val Ile Asp Gln Asp Met Arg Asp Val Gln Val Ser
                245                 250                 255

Thr Thr Pro Ile Leu Arg Val Glu Ser Ala Ala Arg Ser Ile Val Arg
            260                 265                 270
```

```
Ser Ala Ile Arg Gly Glu Arg Tyr Val Thr Glu Pro Ala Trp Phe Arg
        275                 280                 285

Val Thr Tyr Trp Trp Lys Leu Phe Cys Pro Glu Val Met Glu Trp Val
    290                 295                 300

Phe Arg Leu Met Tyr Leu Ala Ser Pro Gly Glu Pro Glu Lys Glu Thr
305                 310                 315                 320

Phe Gly Lys Lys Val Leu Asp Tyr Thr Gly Val Lys Ser Leu Leu Tyr
                325                 330                 335

Pro Glu Thr Val Gln Val Pro Glu Pro Lys Asn Asp
            340                 345

<210> SEQ ID NO 55
<211> LENGTH: 348
<212> TYPE: PRT
<213> ORGANISM: S. indicum

<400> SEQUENCE: 55

Met Asp Leu Ile His Thr Phe Leu Asn Leu Ile Ala Pro Pro Phe Thr
1               5                   10                  15

Phe Phe Phe Leu Leu Phe Phe Leu Pro Pro Phe Gln Ile Phe Lys Phe
            20                  25                  30

Phe Leu Ser Ile Leu Gly Thr Leu Phe Ser Glu Asp Val Ala Gly Lys
        35                  40                  45

Val Val Val Ile Thr Gly Ala Ser Ser Gly Ile Gly Glu Ser Leu Ala
    50                  55                  60

Tyr Glu Tyr Ala Lys Arg Gly Ala Cys Leu Val Leu Ala Ala Arg Arg
65                  70                  75                  80

Glu Arg Ser Leu Gln Glu Val Ala Glu Arg Ala Arg Asp Leu Gly Ser
                85                  90                  95

Pro Asp Val Val Val Val Arg Ala Asp Val Ser Lys Ala Glu Asp Cys
            100                 105                 110

Arg Lys Val Val Asp Gln Thr Met Asn Arg Phe Gly Arg Leu Asp His
        115                 120                 125

Leu Val Asn Asn Ala Gly Ile Met Ser Val Ser Met Leu Glu Glu Val
    130                 135                 140

Glu Asp Ile Thr Gly Tyr Arg Glu Thr Met Asp Ile Asn Phe Trp Gly
145                 150                 155                 160

Tyr Val Tyr Met Thr Arg Phe Ala Ala Pro Tyr Leu Arg Asn Ser Arg
                165                 170                 175

Gly Arg Ile Val Val Leu Ser Ser Ser Ser Ser Trp Met Pro Thr Pro
            180                 185                 190

Arg Met Ser Phe Tyr Asn Ala Ser Lys Ala Ala Ile Ser Gln Phe Phe
        195                 200                 205

Glu Thr Leu Arg Val Glu Phe Gly Pro Asp Ile Gly Ile Thr Leu Val
    210                 215                 220

Thr Pro Gly Phe Ile Glu Ser Glu Leu Thr Gln Gly Lys Phe Tyr Asn
225                 230                 235                 240

Ala Gly Glu Arg Val Ile Asp Gln Asp Met Arg Asp Val Gln Val Ser
                245                 250                 255

Thr Thr Pro Ile Leu Arg Val Glu Ser Ala Ala Arg Ser Ile Val Arg
            260                 265                 270

Ser Ala Ile Arg Gly Glu Arg Tyr Val Thr Glu Pro Ala Trp Phe Arg
        275                 280                 285

Val Thr Tyr Trp Trp Lys Leu Phe Cys Pro Glu Val Met Glu Trp Val
```

```
    290                 295                 300

Phe Arg Leu Met Tyr Leu Ala Ser Pro Gly Glu Pro Glu Lys Glu Thr
305                 310                 315                 320

Phe Gly Lys Lys Val Leu Asp Tyr Thr Gly Val Lys Ser Leu Leu Tyr
                325                 330                 335

Pro Glu Thr Val Gln Val Pro Glu Pro Lys Asn Asp
            340                 345

<210> SEQ ID NO 56
<211> LENGTH: 1266
<212> TYPE: DNA
<213> ORGANISM: B. napus

<400> SEQUENCE: 56
ggtcgacggc cattacggcc gggatcccgt taatgtgtat tgtgttttga tcgaagatgg      60
aattgataaa cgatttcctc aatctaactg cacctttctt tactttcttt ggtctttgct     120
tcttcttgcc ccctttttat ttcttcaagt tcgtgcagtc tatcttctcg acaattttct     180
ctgaaaacgt atatgggaaa gtggttctca tcactggtgc ttcctccggg atcggcgagc     240
aattggcata tgagtacgca agtaaaggtg catgtttggc tctgactgcc cgaaggaaga     300
accgtctaga ggaagtggca gagattgctc gtgaagttgg atcccctaat gttgtcacag     360
ttcacgctga tgtttccaaa cctgatgatt gtagacgaat cgtcgatgag accatctccc     420
attttggcag attggatcat cttgtaaaca atgctggaat aatgcaaatt tcaatgttcg     480
aaaacattga agaaataact aggacaagag cagttatgga tactaacttt tggggagcgg     540
tttatacaac tcgtgctgcg cttccgtacc ttcgacaaag caatggtaag attgtggcta     600
tgtcgtcctc tgcggcatgg ctaaccgccc caaggatgag cttttataat gctagcaaag     660
cagctttgtt gaacttcttc gagacgttga ggattgagct tggtagcgat gtacacatta     720
caatcgtcac acctggttat attgaatctg aactcacaca aggcaagtac gtctctggtg     780
aaggcgagct agtagtcaac caagacatta gagatgttca aattggagca tttccggtaa     840
cgtcagtatc aggtcgtgcc aaggggatag tgaaaggtgt gtgtaggaaa gagagatacg     900
tgaccgaacc atcgtggttt aaggtgacgt acctttggaa agtgttttgt ccggaactga     960
tcgagtgggg ttgcagattg atgttcttgt ccggacatgg tacgccggag gaaaatgcac    1020
tcaacaagaa gatcctggac atacctggtg tacgtagtgc tctataccct gaacctatca    1080
gaacgccaga aatcaagtcg gagtagagtg aggttgatac ttaataagtg tctcataaag    1140
tggagccatg ttttgtaaat ggactttcta ttatgcacat gttactatga tgtatctgtt    1200
tgtttatgtg tataagaata agtgaacttt ggagctcaaa aaaaaaaaaa aaaaaaaaaa    1260
aaaaaa                                                               1266

<210> SEQ ID NO 57
<211> LENGTH: 349
<212> TYPE: PRT
<213> ORGANISM: B. napus

<400> SEQUENCE: 57

Met Glu Leu Ile Asn Asp Phe Leu Asn Leu Thr Ala Pro Phe Phe Thr
1               5                   10                  15

Phe Phe Gly Leu Cys Phe Phe Leu Pro Pro Phe Tyr Phe Phe Lys Phe
            20                  25                  30

Val Gln Ser Ile Phe Ser Thr Ile Phe Ser Glu Asn Val Tyr Gly Lys
        35                  40                  45
```

```
Val Val Leu Ile Thr Gly Ala Ser Ser Gly Ile Gly Glu Gln Leu Ala
    50                  55                  60

Tyr Glu Tyr Ala Ser Lys Gly Ala Cys Leu Ala Leu Thr Ala Arg Arg
65                  70                  75                  80

Lys Asn Arg Leu Glu Glu Val Ala Glu Ile Ala Arg Glu Val Gly Ser
                85                  90                  95

Pro Asn Val Val Thr Val His Ala Asp Val Ser Lys Pro Asp Asp Cys
            100                 105                 110

Arg Arg Ile Val Asp Glu Thr Ile Ser His Phe Gly Arg Leu Asp His
        115                 120                 125

Leu Val Asn Asn Ala Gly Ile Met Gln Ile Ser Met Phe Glu Asn Ile
    130                 135                 140

Glu Glu Ile Thr Arg Thr Arg Ala Val Met Asp Thr Asn Phe Trp Gly
145                 150                 155                 160

Ala Val Tyr Thr Thr Arg Ala Ala Leu Pro Tyr Leu Arg Gln Ser Asn
                165                 170                 175

Gly Lys Ile Val Ala Met Ser Ser Ser Ala Ala Trp Leu Thr Ala Pro
            180                 185                 190

Arg Met Ser Phe Tyr Asn Ala Ser Lys Ala Ala Leu Leu Asn Phe Phe
        195                 200                 205

Glu Thr Leu Arg Ile Glu Leu Gly Ser Asp Val His Ile Thr Ile Val
    210                 215                 220

Thr Pro Gly Tyr Ile Glu Ser Glu Leu Thr Gln Gly Lys Tyr Val Ser
225                 230                 235                 240

Gly Glu Gly Glu Leu Val Val Asn Gln Asp Ile Arg Asp Val Gln Ile
                245                 250                 255

Gly Ala Phe Pro Val Thr Ser Val Ser Gly Arg Ala Lys Gly Ile Val
            260                 265                 270

Lys Gly Val Cys Arg Lys Glu Arg Tyr Val Thr Glu Pro Ser Trp Phe
        275                 280                 285

Lys Val Thr Tyr Leu Trp Lys Val Phe Cys Pro Glu Leu Ile Glu Trp
    290                 295                 300

Gly Cys Arg Leu Met Phe Leu Ser Gly His Gly Thr Pro Glu Glu Asn
305                 310                 315                 320

Ala Leu Asn Lys Lys Ile Leu Asp Ile Pro Gly Val Arg Ser Ala Leu
                325                 330                 335

Tyr Pro Glu Pro Ile Arg Thr Pro Glu Ile Lys Ser Glu
            340                 345
```

<210> SEQ ID NO 58
<211> LENGTH: 1188
<212> TYPE: DNA
<213> ORGANISM: Z. mays

<400> SEQUENCE: 58

```
attgcgcaca ccttgatgct gggcatgagc aggacggggt tggccggagc ggcgctgcgg      60
gtggcgctga cggcgctgct gccgctggtc ctgccggcgt actacgtgta caagctgacc     120
acgtacctcc tcggcgccgt cttccccgag gacgtcgccg gcaaggtggt actcatcacc     180
ggcgcctcct ccggcatcgg cgagcacctg gcctatgagt acgcgaagcg gggagcctac     240
ctggcgctgg tggcgaggag ggaggcgagc ctccgcgagg tcggcgacgt cgcgctgggg     300
ctgggctcgc cgggcgtcct cgtcctcccg gctgacgtct ccaagcctcg ggactgcgag     360
ggcttcatcg acgacacgat tagctacttc ggtagactgg atcacctggt gaacaacgcg     420
```

```
tccatctggc aagtgtgcaa gttcgaagag atccaggacg tcaggcactt gagagccctg    480
atggacatca acttctgggg ccacgtgtac ccaacccggc tcgccatccc tcacctcagg    540
agaagccgtg gccggatcgt gggcgtcacc tccaactcgt cctacatatt catcgggagg    600
aacaccttct acaatgccag caaggcggcg gcgctcagct tctacgacac cctgaggatg    660
gagctgggca gcgacatccg catcaccgag gtggtgccag gcgtggtgga gtctgagatc    720
accaagggga agatgctcac caagggaggc gagatgaagg tggaccagga cgaaagagac    780
gccatcctgg ggccgacgcc ggccgagccc gtgggcgact tcgccaggac cgtggtgcgc    840
gacgtgtgcc ggggcgcgag gtacgtgttc gagcccaggt ggtacatggg cgtctacttg    900
ctgcgggcct gcctcccgga agtcctggcc tggaactccc gcctgctcac tgtcgacacg    960
gtcggcgcgt ccaccacgga cacgctcgga aagtggctgg tcgagctgcc cggcgtgcgc   1020
cgcgtcgtgc agccgccgtc gctccgctcg ccggagatca aggactagtg acggtgatcg   1080
tgtacgttct gtggccatgg atagcactag ctgtatgaga ccgaagttcc tttagacatc   1140
gacacgatta ataaaggact caattatctt aaaaaaaaaa aaaaaaaa                1188

<210> SEQ ID NO 59
<211> LENGTH: 350
<212> TYPE: PRT
<213> ORGANISM: Z. mays

<400> SEQUENCE: 59

Met Leu Gly Met Ser Arg Thr Gly Leu Ala Gly Ala Ala Leu Arg Val
1               5                   10                  15

Ala Leu Thr Ala Leu Leu Pro Leu Val Leu Pro Ala Tyr Tyr Val Tyr
            20                  25                  30

Lys Leu Thr Thr Tyr Leu Leu Gly Ala Val Phe Pro Glu Asp Val Ala
        35                  40                  45

Gly Lys Val Val Leu Ile Thr Gly Ala Ser Ser Gly Ile Gly Glu His
    50                  55                  60

Leu Ala Tyr Glu Tyr Ala Lys Arg Gly Ala Tyr Leu Ala Leu Val Ala
65                  70                  75                  80

Arg Arg Glu Ala Ser Leu Arg Glu Val Gly Asp Val Ala Leu Gly Leu
                85                  90                  95

Gly Ser Pro Gly Val Leu Val Leu Pro Ala Asp Val Ser Lys Pro Arg
            100                 105                 110

Asp Cys Glu Gly Phe Ile Asp Asp Thr Ile Ser Tyr Phe Gly Arg Leu
        115                 120                 125

Asp His Leu Val Asn Asn Ala Ser Ile Trp Gln Val Cys Lys Phe Glu
    130                 135                 140

Glu Ile Gln Asp Val Arg His Leu Arg Ala Leu Met Asp Ile Asn Phe
145                 150                 155                 160

Trp Gly His Val Tyr Pro Thr Arg Leu Ala Ile Pro His Leu Arg Arg
                165                 170                 175

Ser Arg Gly Arg Ile Val Gly Val Thr Ser Asn Ser Ser Tyr Ile Phe
            180                 185                 190

Ile Gly Arg Asn Thr Phe Tyr Asn Ala Ser Lys Ala Ala Ala Leu Ser
        195                 200                 205

Phe Tyr Asp Thr Leu Arg Met Glu Leu Gly Ser Asp Ile Arg Ile Thr
    210                 215                 220

Glu Val Val Pro Gly Val Val Glu Ser Glu Ile Thr Lys Gly Lys Met
225                 230                 235                 240
```

```
Leu Thr Lys Gly Gly Glu Met Lys Val Asp Gln Asp Glu Arg Asp Ala
                245                 250                 255

Ile Leu Gly Pro Thr Pro Ala Glu Pro Val Gly Asp Phe Ala Arg Thr
            260                 265                 270

Val Val Arg Asp Val Cys Arg Gly Ala Arg Tyr Val Phe Glu Pro Arg
        275                 280                 285

Trp Tyr Met Gly Val Tyr Leu Leu Arg Ala Cys Leu Pro Glu Val Leu
    290                 295                 300

Ala Trp Asn Ser Arg Leu Leu Thr Val Asp Thr Val Gly Ala Ser Thr
305                 310                 315                 320

Thr Asp Thr Leu Gly Lys Trp Leu Val Glu Leu Pro Gly Val Arg Arg
                325                 330                 335

Val Val Gln Pro Pro Ser Leu Arg Ser Pro Glu Ile Lys Asp
            340                 345                 350

<210> SEQ ID NO 60
<211> LENGTH: 890
<212> TYPE: DNA
<213> ORGANISM: B. napus

<400> SEQUENCE: 60
gtttccaaac ctgatgattg tagacgaatc gtcgatgaga ccatctccca ttttggcaga      60
ttggatcatc ttgtaaacaa tgctggaata atgcagattt caatgttcga aaacattgaa     120
gaaataacta ggacaagagc agttatggat actaactttt ggggatcggt ttatacaact     180
cgtgctgcgc ttccgtacct tcgacaaagc aatggtaaga ttgtggccat gtcgtcctct     240
gcggcatggc taaccgcccc aaggatgagc ttttataatg ctagcaaagc cgcattgttg     300
aacttcttcg agacgttgag gattgagctt ggcagcgatg tacacattac aatcgtcaca     360
cctggttata ttgaatctga actcacacaa ggcaagtact tctctggtga aggcgagcta     420
gtagtcaacc aagacattag agatgttcaa attggagcat ttccggtaac gtcggtatca     480
ggttgtgcca aggggatagt gaaaggtgtg tgtaggaaac agagatacgt gaccgaacca     540
tcgtggttta aggtgacgta cctttggaaa gtgttttgtc cggaactgat cgagtggggt     600
tgcaggttgc tgttcttgtc cggacatggt acgtcggaga aaaatgcact caacaagaag     660
atcttggaca tacctggtgt acgtagtgct ctataccctg aatctatcag aacgccagaa     720
atcaagtcgg agtagagtga ggttgatact taataagtgt ctcatatagt ggagccatgt     780
tttgtaaatg gactttctat tatgcacatg ttactatgat gtatccgttt gtttatgtgt     840
ataagaataa gtgaactttg gagctccaaa aaaaaaaaaa aaaaaaaaaa                890

<210> SEQ ID NO 61
<211> LENGTH: 244
<212> TYPE: PRT
<213> ORGANISM: B. napus

<400> SEQUENCE: 61

Val Ser Lys Pro Asp Asp Cys Arg Arg Ile Val Asp Glu Thr Ile Ser
1               5                   10                  15

His Phe Gly Arg Leu Asp His Leu Val Asn Asn Ala Gly Ile Met Gln
            20                  25                  30

Ile Ser Met Phe Glu Asn Ile Glu Glu Ile Thr Arg Thr Arg Ala Val
        35                  40                  45

Met Asp Thr Asn Phe Trp Gly Ser Val Tyr Thr Thr Arg Ala Ala Leu
    50                  55                  60
```

```
Pro Tyr Leu Arg Gln Ser Asn Gly Lys Ile Val Ala Met Ser Ser Ser
65                  70                  75                  80

Ala Ala Trp Leu Thr Ala Pro Arg Met Ser Phe Tyr Asn Ala Ser Lys
                85                  90                  95

Ala Ala Leu Leu Asn Phe Phe Glu Thr Leu Arg Ile Glu Leu Gly Ser
            100                 105                 110

Asp Val His Ile Thr Ile Val Thr Pro Gly Tyr Ile Glu Ser Glu Leu
        115                 120                 125

Thr Gln Gly Lys Tyr Phe Ser Gly Glu Gly Glu Leu Val Val Asn Gln
    130                 135                 140

Asp Ile Arg Asp Val Gln Ile Gly Ala Phe Pro Val Thr Ser Val Ser
145                 150                 155                 160

Gly Cys Ala Lys Gly Ile Val Lys Gly Val Cys Arg Lys Gln Arg Tyr
                165                 170                 175

Val Thr Glu Pro Ser Trp Phe Lys Val Thr Tyr Leu Trp Lys Val Phe
            180                 185                 190

Cys Pro Glu Leu Ile Glu Trp Gly Cys Arg Leu Leu Phe Leu Ser Gly
        195                 200                 205

His Gly Thr Ser Glu Lys Asn Ala Leu Asn Lys Lys Ile Leu Asp Ile
    210                 215                 220

Pro Gly Val Arg Ser Ala Leu Tyr Pro Glu Ser Ile Arg Thr Pro Glu
225                 230                 235                 240

Ile Lys Ser Glu

<210> SEQ ID NO 62
<211> LENGTH: 1030
<212> TYPE: DNA
<213> ORGANISM: S. indicum

<400> SEQUENCE: 62
ggcacgagag agaaaaaagg tgattttgtc aagggaaata tggcaactca tgttttggct     60
gctgcggcgg agagaaatgc tgcgttggcg ccggacgccc cgcttgctcc ggtgactatg    120
gagcgcccag tgcgcactga cttggagact tcgatcccga agccctatat ggcaagagga    180
ttggttgcac ctgatatgga tcaccccaac ggaacaccag gccatgtgca tgataatttg    240
agtgtgctgc aacagcattg tgctttcttt gatcaggatg ataacggaat catctatcca    300
tgggagactt actctggact tcgccaaatt ggtttcaatg tgatagcttc ccttataatg    360
gctatcgtca ttaatgtggc gctgagttat cctactctcc cgggttggat tccttctcct    420
tttttcccca tatatttgta caacatacac aaggccaaac atggaagcga ctccggaacc    480
tatgatactg aaggaaggta cctacctatg aattttgaga acctgttcag caagcatgcc    540
cggacaatgc ccgataggct cactctaggg gagctatgga gcatgactga agctaacaga    600
gaagcatttg acattttcgg ctggatcgca agcaaaatgg agtggactct cctctacatt    660
cttgcaagag accaggacgg tttcctgtcg aaagaagcca tcaggcggtg ttacgatggc    720
agtttgttcg agtactgtgc aaagatgcaa aggggagccg aggacaagat gaaatgaagg    780
aaatcggcta tcgcggtagg tgtaagttat gatgtggtgt gtatgatgga ttgaaagtgc    840
cagtgcttaa gttgtgtggc agagtcttgt gtaataacct ttgtgtacag atttaaggtc    900
tcggaattgg tgtaactgtg gagaagatgt tgactcctgt ttttgttcaa taagtccaac    960
tcttgacatt tggttggttt gcagggaaag atggggaatt ttgttttccg aaaaaaaaaa   1020
aaaaaaaaaa                                                          1030
```

<210> SEQ ID NO 63
<211> LENGTH: 245
<212> TYPE: PRT
<213> ORGANISM: S. indicum

<400> SEQUENCE: 63

Met Ala Thr His Val Leu Ala Ala Ala Ala Glu Arg Asn Ala Ala Leu
1 5 10 15

Ala Pro Asp Ala Pro Leu Ala Pro Val Thr Met Glu Arg Pro Val Arg
20 25 30

Thr Asp Leu Glu Thr Ser Ile Pro Lys Pro Tyr Met Ala Arg Gly Leu
35 40 45

Val Ala Pro Asp Met Asp His Pro Asn Gly Thr Pro Gly His Val His
50 55 60

Asp Asn Leu Ser Val Leu Gln Gln His Cys Ala Phe Phe Asp Gln Asp
65 70 75 80

Asp Asn Gly Ile Ile Tyr Pro Trp Glu Thr Tyr Ser Gly Leu Arg Gln
85 90 95

Ile Gly Phe Asn Val Ile Ala Ser Leu Ile Met Ala Ile Val Ile Asn
100 105 110

Val Ala Leu Ser Tyr Pro Thr Leu Pro Gly Trp Ile Pro Ser Pro Phe
115 120 125

Phe Pro Ile Tyr Leu Tyr Asn Ile His Lys Ala Lys His Gly Ser Asp
130 135 140

Ser Gly Thr Tyr Asp Thr Glu Gly Arg Tyr Leu Pro Met Asn Phe Glu
145 150 155 160

Asn Leu Phe Ser Lys His Ala Arg Thr Met Pro Asp Arg Leu Thr Leu
165 170 175

Gly Glu Leu Trp Ser Met Thr Glu Ala Asn Arg Glu Ala Phe Asp Ile
180 185 190

Phe Gly Trp Ile Ala Ser Lys Met Glu Trp Thr Leu Leu Tyr Ile Leu
195 200 205

Ala Arg Asp Gln Asp Gly Phe Leu Ser Lys Glu Ala Ile Arg Arg Cys
210 215 220

Tyr Asp Gly Ser Leu Phe Glu Tyr Cys Ala Lys Met Gln Arg Gly Ala
225 230 235 240

Glu Asp Lys Met Lys
245

<210> SEQ ID NO 64
<211> LENGTH: 985
<212> TYPE: DNA
<213> ORGANISM: G. max

<400> SEQUENCE: 64
atacgagaga gtgagtaatc gagaaagaga agaagcatat atatcaaaat ggctgcagag 60
atggagaggg agtcattgat aactgaagct cctaatgcac cagttactgc acagagaagg 120
gtcagaaatg acttagaaaa ttctctacca aaaccatact tgccaagagc attgaaagct 180
cctgatacgg gtcacccaaa tggaacagca ggccacaggc accacaactt atctgttctt 240
cagcagcatt gtgctttttt tgatcaagat gacaatggaa tcatttaccc ttgggaaact 300
tacatggggc tgcgttctat tggatttaat gttgttgcat ctgttattat ggctattgtt 360
atcaatgttg gattgagtta ccccactcta cctaattggt tcccttctct cctttttcct 420

```
atctacatac acaacataca caaagcaaag catgggagtg actctggagt ttatgacaca    480

gaaggacgtt atgtgccagc aaatattgag aacatattca gtaagtatgc tcgtacagta    540

cctgacaagc tcacacttgg ggagctctgg gacttgacag agggaaaccg aaatgctttt    600

gacatatttg gctggcttgc agcaaaattt gaatgggggg ttctgtacat tctggcaagg    660

gatgaggaag gtttcctgtc taaagaagct gttagaagat gctttgatgg gagcttattt    720

gaatactgtg ctaaaatgca tactactagt gatgccaaga tgagttgaaa ttggattatg    780

cagtgtgcat agttacgtgt gatgtgtcgt ttctgttaga catgttagtg gtgtaatgtg    840

aaaaaatagt aaaaaaataa acttattagg aactcgtggt ctgggattga tcagcataat    900

aaagagttta ctgtctctag catatgttgt tctcgagatg taatcctttc ctcacgtgtg    960

gaaagaagtt actctggttc ctaca                                          985
```

```
<210> SEQ ID NO 65
<211> LENGTH: 239
<212> TYPE: PRT
<213> ORGANISM: G. max

<400> SEQUENCE: 65

Met Ala Ala Glu Met Glu Arg Glu Ser Leu Ile Thr Glu Ala Pro Asn
1               5                   10                  15

Ala Pro Val Thr Ala Gln Arg Arg Val Arg Asn Asp Leu Glu Asn Ser
            20                  25                  30

Leu Pro Lys Pro Tyr Leu Pro Arg Ala Leu Lys Ala Pro Asp Thr Gly
        35                  40                  45

His Pro Asn Gly Thr Ala Gly His Arg His His Asn Leu Ser Val Leu
    50                  55                  60

Gln Gln His Cys Ala Phe Phe Asp Gln Asp Asp Asn Gly Ile Ile Tyr
65                  70                  75                  80

Pro Trp Glu Thr Tyr Met Gly Leu Arg Ser Ile Gly Phe Asn Val Val
                85                  90                  95

Ala Ser Val Ile Met Ala Ile Val Ile Asn Val Gly Leu Ser Tyr Pro
            100                 105                 110

Thr Leu Pro Asn Trp Phe Pro Ser Leu Leu Phe Pro Ile Tyr Ile His
        115                 120                 125

Asn Ile His Lys Ala Lys His Gly Ser Asp Ser Gly Val Tyr Asp Thr
    130                 135                 140

Glu Gly Arg Tyr Val Pro Ala Asn Ile Glu Asn Ile Phe Ser Lys Tyr
145                 150                 155                 160

Ala Arg Thr Val Pro Asp Lys Leu Thr Leu Gly Glu Leu Trp Asp Leu
                165                 170                 175

Thr Glu Gly Asn Arg Asn Ala Phe Asp Ile Phe Gly Trp Leu Ala Ala
            180                 185                 190

Lys Phe Glu Trp Gly Val Leu Tyr Ile Leu Ala Arg Asp Glu Glu Gly
        195                 200                 205

Phe Leu Ser Lys Glu Ala Val Arg Arg Cys Phe Asp Gly Ser Leu Phe
    210                 215                 220

Glu Tyr Cys Ala Lys Met His Thr Thr Ser Asp Ala Lys Met Ser
225                 230                 235
```

```
<210> SEQ ID NO 66
<211> LENGTH: 1326
<212> TYPE: DNA
<213> ORGANISM: Z. mays
```

-continued

<400> SEQUENCE: 66
atcccagcag caggtagcag cagcgcatga ctttgtatct gcaactcgtt tcgactagcc 60
tgcacgccgg gagccctcgt ctcgcccttc tccacctccg aaggtagggt acctgatact 120
tccctgcccc gcgcatcgca tccgcggttt tagtttgctg gcctcggttc cgatcgattc 180
ctatcctccc tccgggcggg cgtccaccga cttcatcatc cactcgccgg ccgaaccgat 240
ttgtttcgtt tgccgttcga tccgcagatc ctgcgagttc aacccgcgag tgagcatgtc 300
gtcctactcc ccgccgccgc cgccgccgcg ggaccagtcc atggacaccg aggcacccaa 360
cgcgcccatc accagggagc ggaggctcaa ccccgatctg caggagcagc tccccaagcc 420
atatctcgcg agagctctcg aggcggtgga cccgagccac ccgcagggga ccaaggggcg 480
cgacccccgc ggcatgagcg tgcttcagca gcacgccgcc ttcttcgacc gcaatggcga 540
cggcgtcatc taccccctggg agacgtttca aggactgcga gcgataggat gtggactcac 600
tgtatcattc gcgttctcca tactgatcaa cctcttcctc agttatccca ctcagccggg 660
atggttacct tctcctttgc tgtccatccg tatagacaac atccacaagg gtaagcacgg 720
gagtgattct gaaacctacg acactgaagg gaggtttgat ccatcaaagt tcgatgctat 780
attcagtaag tacggtcgaa cccatcctaa tgctataaca agagacgagt taagctcaat 840
gcttcaagga aaccgcaata cgtacgattt ccttggctgg ttggccgctg ccggtgaatg 900
gctcttactc tacagcttgg cgaaagacaa ggatggcctc ttgcagcgcg aaactgtccg 960
tggtctattt gatgggagcc tatttgagcg actggaagac gacaacaaca agaagaaatc 1020
gtcatgaatg ctgagcagcc ttgtacagct cagggaagtg ctgtcagtac aaaactacca 1080
gatataccat tggtcgtgtt caaataacaa atgcttcggc tttgttcatc cgtcattaac 1140
tatgagtgct gggatttgtt tgtatgtgtg tcgtgctacc agtttcttct cctgtcgtct 1200
cacacaggta ctgaattacg catgtgtttt ctagtgttcg tgcggaagct gtattataag 1260
ctgaaaaatg tgcgtttgaa atttatgggc aaaactgtct tcttggtctt aaaaaaaaaa 1320
aaaaaa 1326

<210> SEQ ID NO 67
<211> LENGTH: 243
<212> TYPE: PRT
<213> ORGANISM: Z. mays

<400> SEQUENCE: 67

Met Ser Ser Tyr Ser Pro Pro Pro Pro Pro Pro Arg Asp Gln Ser Met
1 5 10 15

Asp Thr Glu Ala Pro Asn Ala Pro Ile Thr Arg Glu Arg Arg Leu Asn
20 25 30

Pro Asp Leu Gln Glu Gln Leu Pro Lys Pro Tyr Leu Ala Arg Ala Leu
35 40 45

Glu Ala Val Asp Pro Ser His Pro Gln Gly Thr Lys Gly Arg Asp Pro
50 55 60

Arg Gly Met Ser Val Leu Gln Gln His Ala Ala Phe Phe Asp Arg Asn
65 70 75 80

Gly Asp Gly Val Ile Tyr Pro Trp Glu Thr Phe Gln Gly Leu Arg Ala
85 90 95

Ile Gly Cys Gly Leu Thr Val Ser Phe Ala Phe Ser Ile Leu Ile Asn
100 105 110

Leu Phe Leu Ser Tyr Pro Thr Gln Pro Gly Trp Leu Pro Ser Pro Leu
115 120 125

```
Leu Ser Ile Arg Ile Asp Asn Ile His Lys Gly Lys His Gly Ser Asp
    130                 135                 140

Ser Glu Thr Tyr Asp Thr Glu Gly Arg Phe Asp Pro Ser Lys Phe Asp
145                 150                 155                 160

Ala Ile Phe Ser Lys Tyr Gly Arg Thr His Pro Asn Ala Ile Thr Arg
                165                 170                 175

Asp Glu Leu Ser Ser Met Leu Gln Gly Asn Arg Asn Thr Tyr Asp Phe
            180                 185                 190

Leu Gly Trp Leu Ala Ala Ala Gly Glu Trp Leu Leu Leu Tyr Ser Leu
        195                 200                 205

Ala Lys Asp Lys Asp Gly Leu Leu Gln Arg Glu Thr Val Arg Gly Leu
    210                 215                 220

Phe Asp Gly Ser Leu Phe Glu Arg Leu Glu Asp Asp Asn Asn Lys Lys
225                 230                 235                 240

Lys Ser Ser

<210> SEQ ID NO 68
<211> LENGTH: 1058
<212> TYPE: DNA
<213> ORGANISM: B. napus

<400> SEQUENCE: 68
cttcccattc tcctctagag caaaaaagag cgagagatga gtacggcgac tgagataatg      60
gagagagacg caatggctgc ggtggctccc tacgctccgg tcacctttca ccgccgtgct     120
cgtgttgaca tggatgatag acttcctaaa ccttatatgc caagagcact gcaagcaccc     180
gacagagagc atccgtatgg aaccccaggc cataagaatt atggacttag tgttcttcaa     240
cagcacgtcg ccttcttcga tttagatgat aatggaatta tctacccttg ggagacctac     300
tctggactgc gaatgcttgg tttcaatatc attgtatcgc ttatcgcagc cgctgtaatc     360
aatttggccc ttagctatgc tactcttccg ggatggtttc cttcgccgtt cttcccaata     420
tacatacaca atatacacaa gtcaaagcat gggagcgact caagaacata tgacaatgaa     480
gggaggttta tgcctgtgaa tcttgagttg atatttagca aatatgcgaa aacattgcca     540
gacaagttga gtcttggaga attatgggag atgacacaag gacaacgtga cgcatgggac     600
atcttcggat ggttcgcaag caaaatagag tgggggttgt tgtacttgct agcgagggat     660
gaagaagggt ttctgtcaaa agaagcgatt aggaggtgtt ttgacgggag cttgttcgag     720
tattgtgcca agatatacgc aggtatcaat gaagacaaga cagcctacta ctaaaagtaa     780
atggtagagg agctttaggc tgataatcgt cgatgtgaat gtaacttgtg tctaaagcag     840
agtccatgtg tttgttatgt tatgtcaaaa tctgtaaggt agaagtatga tcagttgcag     900
ctggtataga aaaacttcta tgttgaataa tagtatgttt tgttgttgtg tttgtgtttg     960
tatcaaccct tttttagtta tttccagttc aaatgtaatt tttcattgtt gttacttggt    1020
attgagaatc atttcttgta taaaaaaaaa aaaaaaaa                            1058

<210> SEQ ID NO 69
<211> LENGTH: 245
<212> TYPE: PRT
<213> ORGANISM: B. napus

<400> SEQUENCE: 69

Met Ser Thr Ala Thr Glu Ile Met Glu Arg Asp Ala Met Ala Ala Val
1               5                   10                  15
```

```
Ala Pro Tyr Ala Pro Val Thr Phe His Arg Arg Ala Arg Val Asp Met
            20                  25                  30

Asp Asp Arg Leu Pro Lys Pro Tyr Met Pro Arg Ala Leu Gln Ala Pro
        35                  40                  45

Asp Arg Glu His Pro Tyr Gly Thr Pro Gly His Lys Asn Tyr Gly Leu
    50                  55                  60

Ser Val Leu Gln Gln His Val Ala Phe Phe Asp Leu Asp Asp Asn Gly
65                  70                  75                  80

Ile Ile Tyr Pro Trp Glu Thr Tyr Ser Gly Leu Arg Met Leu Gly Phe
                85                  90                  95

Asn Ile Ile Val Ser Leu Ile Ala Ala Ala Val Ile Asn Leu Ala Leu
            100                 105                 110

Ser Tyr Ala Thr Leu Pro Gly Trp Phe Pro Ser Pro Phe Phe Pro Ile
        115                 120                 125

Tyr Ile His Asn Ile His Lys Ser Lys His Gly Ser Asp Ser Arg Thr
    130                 135                 140

Tyr Asp Asn Glu Gly Arg Phe Met Pro Val Asn Leu Glu Leu Ile Phe
145                 150                 155                 160

Ser Lys Tyr Ala Lys Thr Leu Pro Asp Lys Leu Ser Leu Gly Glu Leu
                165                 170                 175

Trp Glu Met Thr Gln Gly Gln Arg Asp Ala Trp Asp Ile Phe Gly Trp
            180                 185                 190

Phe Ala Ser Lys Ile Glu Trp Gly Leu Leu Tyr Leu Leu Ala Arg Asp
        195                 200                 205

Glu Glu Gly Phe Leu Ser Lys Glu Ala Ile Arg Arg Cys Phe Asp Gly
    210                 215                 220

Ser Leu Phe Glu Tyr Cys Ala Lys Ile Tyr Ala Gly Ile Asn Glu Asp
225                 230                 235                 240

Lys Thr Ala Tyr Tyr
                245
```

<210> SEQ ID NO 70
<211> LENGTH: 1013
<212> TYPE: DNA
<213> ORGANISM: C. revoluta

<400> SEQUENCE: 70

```
acgcgggggc agttgaggtg atcctcaata tcgtagcgaa gatcgcccca aatggcttcc      60
gtcgagtctc ttcaaactac ggctctaagg gcaccagtta cactggaacg tagagtgaat     120
cccaatttgg atgatgaaat tccaaagcca tttctaccaa gagcgcttgt agctgtagat     180
acagagcatt tagatggatc cccgggacac cagcataaca acatgagtgt tcttcagcag     240
catgttgcat ttttcgatcg aaatcatgac ggaattgtgt atccttggga aacatacgaa     300
ggcttccgtg ccataggatt taacatcgtc atttccttaa tgtctgcact gttcatcaac     360
atagccttga gctatcttac tcttcctgga tggataccgt cactgctctt tccaatacat     420
ataaacagga ttcatcgagc aaaacatgga agtgattcag aggtgtatga caccgagggg     480
aggtttgttc catcgaaatt cgaggaaatt ttcactaaat atgcacgtgt acgtccagat     540
aggctcacat tctctgaaat actgttggcc ttgacggagg ccaatagaaa cgccaatgac     600
cctttcggat ggttaaccag caaggccaag tggggcctcc tctaccttct tgccaaggat     660
gatcaaggtt ttctgccgaa agaggcagtc agaggagttt atgatggcag tttgtttgag     720
ttattggaaa agcaacgatc atcccgtaag cagaaataaa atggcctttt gaattagacc     780
```

```
ctgaaagagc atgagtgaga aataaactgc acataaatgg cccactagcc catctatgct    840
gtgaaaaata tgatgtcatt agtcattgtc agttagcata ttttaacaag catgactttg    900
tacatattgc atgccgtatc atgaattatg ttcttggttg tgtgatctag actccatttc    960
ttaatgaaat gtcttcctta tttcataaaa aaaaaaaaaa aaaaaaaaaa aaa          1013

<210> SEQ ID NO 71
<211> LENGTH: 235
<212> TYPE: PRT
<213> ORGANISM: C. revoluta

<400> SEQUENCE: 71

Met Ala Ser Val Glu Ser Leu Gln Thr Thr Ala Leu Arg Ala Pro Val
1               5                   10                  15

Thr Leu Glu Arg Arg Val Asn Pro Asn Leu Asp Asp Glu Ile Pro Lys
            20                  25                  30

Pro Phe Leu Pro Arg Ala Leu Val Ala Val Asp Thr Glu His Leu Asp
        35                  40                  45

Gly Ser Pro Gly His Gln His Asn Asn Met Ser Val Leu Gln Gln His
    50                  55                  60

Val Ala Phe Phe Asp Arg Asn His Asp Gly Ile Val Tyr Pro Trp Glu
65                  70                  75                  80

Thr Tyr Glu Gly Phe Arg Ala Ile Gly Phe Asn Ile Val Ile Ser Leu
                85                  90                  95

Met Ser Ala Leu Phe Ile Asn Ile Ala Leu Ser Tyr Leu Thr Leu Pro
            100                 105                 110

Gly Trp Ile Pro Ser Leu Leu Phe Pro Ile His Ile Asn Arg Ile His
        115                 120                 125

Arg Ala Lys His Gly Ser Asp Ser Glu Val Tyr Asp Thr Glu Gly Arg
    130                 135                 140

Phe Val Pro Ser Lys Phe Glu Glu Ile Phe Thr Lys Tyr Ala Arg Val
145                 150                 155                 160

Arg Pro Asp Arg Leu Thr Phe Ser Glu Ile Leu Leu Ala Leu Thr Glu
                165                 170                 175

Ala Asn Arg Asn Ala Asn Asp Pro Phe Gly Trp Leu Thr Ser Lys Ala
            180                 185                 190

Lys Trp Gly Leu Leu Tyr Leu Leu Ala Lys Asp Asp Gln Gly Phe Leu
        195                 200                 205

Pro Lys Glu Ala Val Arg Gly Val Tyr Asp Gly Ser Leu Phe Glu Leu
    210                 215                 220

Leu Glu Lys Gln Arg Ser Ser Arg Lys Gln Lys
225                 230                 235

<210> SEQ ID NO 72
<211> LENGTH: 720
<212> TYPE: DNA
<213> ORGANISM: C. sativus

<400> SEQUENCE: 72
atgtctttga cgatggaaaa cgaagccacc gccaccgagg cccgattcgc gcccgtcact     60
cgggagcgaa gggttcgcaa cgacctcgaa accacgctcc ccaagccata tttggcgagg    120
gctttggtgg cggcggactc caaccacccc acggggacgg tggggcataa acactatgga    180
atgacagtgc ttcaacagca tgttgctttc tttgaccaag atgataatgg tatcgtttac    240
ccttgggaga cttatgttgg gctaagagcg attggattca acatgataat gtccctagtt    300
```
atggccgtta ttataaattt cgccatgagc tatcgcactc aacaaggatg gattccatca 360
cctttctttc ccatctatat ttacaatatt cacagagaca aacatggcag cgacactgga 420
acctatgaca ctgaaggaag gtatatagcg gcgaatttcg agaacatgtt cagcaagtac 480
gctagaacac aaccggacaa gttgtcgctt ggcgagatat gggacatgac tgaagccaac 540
cgtctagcgt tcgaccccta cggatggata gcggcgaaac tggaatggtt catattatac 600
gtgctggcta gggacgagga cgggtatctg tcgaaagagg ccgtaagaag atgttatgat 660
ggaagtttgt tcgagtattg tgcaaagatg aatatgagtg ctcaatacaa gatgtattga 720

<210> SEQ ID NO 73
<211> LENGTH: 239
<212> TYPE: PRT
<213> ORGANISM: C. sativus

<400> SEQUENCE: 73

Met Ser Leu Thr Met Glu Asn Glu Ala Thr Ala Thr Glu Ala Arg Phe
1 5 10 15

Ala Pro Val Thr Arg Glu Arg Arg Val Arg Asn Asp Leu Glu Thr Thr
20 25 30

Leu Pro Lys Pro Tyr Leu Ala Arg Ala Leu Val Ala Ala Asp Ser Asn
35 40 45

His Pro Thr Gly Thr Val Gly His Lys His Tyr Gly Met Thr Val Leu
50 55 60

Gln Gln His Val Ala Phe Phe Asp Gln Asp Asp Asn Gly Ile Val Tyr
65 70 75 80

Pro Trp Glu Thr Tyr Val Gly Leu Arg Ala Ile Gly Phe Asn Met Ile
85 90 95

Met Ser Leu Val Met Ala Val Ile Ile Asn Phe Ala Met Ser Tyr Arg
100 105 110

Thr Gln Gln Gly Trp Ile Pro Ser Pro Phe Phe Pro Ile Tyr Ile Tyr
115 120 125

Asn Ile His Arg Asp Lys His Gly Ser Asp Thr Gly Thr Tyr Asp Thr
130 135 140

Glu Gly Arg Tyr Ile Ala Ala Asn Phe Glu Asn Met Phe Ser Lys Tyr
145 150 155 160

Ala Arg Thr Gln Pro Asp Lys Leu Ser Leu Gly Glu Ile Trp Asp Met
165 170 175

Thr Glu Ala Asn Arg Leu Ala Phe Asp Pro Tyr Gly Trp Ile Ala Ala
180 185 190

Lys Leu Glu Trp Phe Ile Leu Tyr Val Leu Ala Arg Asp Glu Asp Gly
195 200 205

Tyr Leu Ser Lys Glu Ala Val Arg Arg Cys Tyr Asp Gly Ser Leu Phe
210 215 220

Glu Tyr Cys Ala Lys Met Asn Met Ser Ala Gln Tyr Lys Met Tyr
225 230 235

<210> SEQ ID NO 74
<211> LENGTH: 2074
<212> TYPE: DNA
<213> ORGANISM: A. thaliana

<400> SEQUENCE: 74
tgaatccttt ttcctttctt cttcttcttc tcttcagaga aaactttgct tctctttcta 60
taaggaacca gacacgaatc ccattcccac cgatttctta gcttcttcct tcaatccgct 120

```
ctttccctct ccattagatt ctgtttcctc tttcaatttc ttctgcatgc ttctcgattc    180
tctctgacgc ctcttttctc ccgacgctgt ttcgtcaaac gcttttcgaa atggcgattt    240
tggattctgc tggcgttact acggtgacgg agaacggtgg cggagagttc gtcgatcttg    300
ataggcttcg tcgacggaaa tcgagatcgg attcttctaa cggacttctt ctctctggtt    360
ccgataataa ttctccttcg gatgatgttg gagctcccgc cgacgttagg gatcggattg    420
attccgttgt taacgatgac gctcagggaa cagccaattt ggccggagat aataacggtg    480
gtggcgataa taacggtggt ggaagaggcg gcggagaagg aagaggaaac gccgatgcta    540
cgtttacgta tcgaccgtcg gttccagctc atcggagggc gagagagagt ccacttagct    600
ccgacgcaat cttcaaacag agccatgccg gattattcaa cctctgtgta gtagttctta    660
ttgctgtaaa cagtagactc atcatcgaaa atcttatgaa gtatggttgg ttgatcagaa    720
cggatttctg gtttagttca agatcgctgc gagattggcc gcttttcatg tgttgtatat    780
ccctttcgat ctttcctttg gctgccttta cggttgagaa attggtactt cagaaataca    840
tatcagaacc tgttgtcatc tttcttcata ttattatcac catgacagag gttttgtatc    900
cagtttacgt caccctaagg tgtgattctg ctttttatc aggtgtcact ttgatgctcc    960
tcacttgcat tgtgtggcta aagttggttt cttatgctca tactagctat gacataagat   1020
ccctagccaa tgcagctgat aaggccaatc ctgaagtctc ctactacgtt agcttgaaga   1080
gcttggcata tttcatggtc gctcccacat tgtgttatca gccaagttat ccacgttctg   1140
catgtatacg gaagggttgg gtggctcgtc aatttgcaaa actggtcata ttcaccggat   1200
tcatgggatt tataatagaa caatatataa atcctattgt caggaactca aagcatcctt   1260
tgaaaggcga tcttctatat gctattgaaa gagtgttgaa gctttcagtt ccaaatttat   1320
atgtgtggct ctgcatgttc tactgcttct tccacctttg gttaaacata ttggcagagc   1380
ttctctgctt cggggatcgt gaattctaca aagattggtg gaatgcaaaa agtgtgggag   1440
attactggag aatgtggaat atgcctgttc ataaatggat ggttcgacat atatacttcc   1500
cgtgcttgcg cagcaagata ccaaagacac tcgccattat cattgcttc ctagtctctg   1560 cagtctttca tgagctatgc atcgcagttc cttgtcgtct cttcaagcta tgggcttttc   1620
ttgggattat gtttcaggtg cctttggtct tcatcacaaa ctatctacag gaaaggtttg   1680
gctcaacggt ggggaacatg atcttctggt tcatcttctg cattttcgga caaccgatgt   1740
gtgtgcttct ttattaccac gacctgatga accgaaaagg atcgatgtca tgaaacaact   1800
gttcaaaaaa tgactttctt caaacatcta tggcctcgtt ggatctccgt tgatgttgtg   1860
gtggttctga tgctaaaacg acaaatagtg ttataaccat tgaagaagaa aagaaaatta   1920
gagttgttgt atctgcaaaa attttggtag agacacgcga acccgtttgg attttgttat   1980
ggtgtaaaga aatttcaatc aaaaaactgt tgtaataatt gttaccaaaa agaaatgctt   2040
ttctggaaac gaggggaaaa atagtagttt tgtt                               2074

<210> SEQ ID NO 75
<211> LENGTH: 520
<212> TYPE: PRT
<213> ORGANISM: A. thaliana

<400> SEQUENCE: 75

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30
```

```
Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Val Val Val Leu Ile
    130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
            180                 185                 190

Phe Thr Val Glu Lys Leu Val Leu Gln Lys Tyr Ile Ser Glu Pro Val
        195                 200                 205

Val Ile Phe Leu His Ile Ile Ile Thr Met Thr Glu Val Leu Tyr Pro
    210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
            260                 265                 270

Asn Pro Glu Val Ser Tyr Tyr Val Ser Leu Lys Ser Leu Ala Tyr Phe
        275                 280                 285

Met Val Ala Pro Thr Leu Cys Tyr Gln Pro Ser Tyr Pro Arg Ser Ala
    290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                325                 330                 335

Val Arg Asn Ser Lys His Pro Leu Lys Gly Asp Leu Leu Tyr Ala Ile
            340                 345                 350

Glu Arg Val Leu Lys Leu Ser Val Pro Asn Leu Tyr Val Trp Leu Cys
        355                 360                 365

Met Phe Tyr Cys Phe Phe His Leu Trp Leu Asn Ile Leu Ala Glu Leu
    370                 375                 380

Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
                405                 410                 415

Met Val Arg His Ile Tyr Phe Pro Cys Leu Arg Ser Lys Ile Pro Lys
            420                 425                 430

Thr Leu Ala Ile Ile Ile Ala Phe Leu Val Ser Ala Val Phe His Glu
        435                 440                 445
```

-continued

```
Leu Cys Ile Ala Val Pro Cys Arg Leu Phe Lys Leu Trp Ala Phe Leu
    450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
            500                 505                 510

Met Asn Arg Lys Gly Ser Met Ser
        515                 520
```

<210> SEQ ID NO 76
<211> LENGTH: 2090
<212> TYPE: DNA
<213> ORGANISM: T. majus

<400> SEQUENCE: 76

```
acgcggggag ttttcaaaat catattatgc tttttcttca ctactgcatg aactttcttt      60
ctacttcttg caactgattt gtaatcctta cacatgtttc tagttttctc catataaaaa     120
aaatattctc tgagcttctc gattctctag agagagaagg ccaaaaaaaa atggcggtgg     180
cagagtcgtc acagaacacg acaaccatga gtggtcacgg cgactcggat ctcaacaatt     240
tccgtagaag gaaaccgagt tcctccgtga ttgaaccttc gtcgtccggt tttacatcca     300
ccaatggcgt accggcgact ggccacgtgg ctgagaatcg tgaccaggat cgggtagggg     360
ctatggagaa cgcaacagga tcggtcaact taattggaaa tggtggaggc gtggttatcg     420
ggaatgaaga gaaacaggta ggggagactg atatacgatt cacttaccgg ccttcgtttc     480
cggctcatcg gagggtgagg gagagtcctc ttagctctga tgcaatcttc aaacagagcc     540
atgcgggttt attcaacttg tgtatagtag tgctcattgc agtaaacagt aggcttatca     600
tcgaaaatct tatgaagtat ggttggttga tcgatactgg tttctggttt agctcaagat     660
cactgggtga ttggtccatc tttatgtgct gtcttacact cccaattttc ccacttgctg     720
cttttattgt tgaaaagctg gtgcagcgaa atcatatatc tgaacttgtt gctgttctcc     780
ttcatgtaat cgtttctacc gctgcagttt tatatccagt tattgtgatc ttaacgtgtg     840
attcggtgta tatgtctggt gtggtattga tgctctttgg ttgcattatg tggttgaagc     900
tggtgtcata tgcacatact agttctgata ttagaacact ggccaaatct ggctataagg     960
gggatgcgca ccccaattca accattgtga gttgctcata tgatgttagc ttgaagagtt    1020
tggcatactt catggttgct ccgacattat gttaccagcc tagctatcct cgttcgtcgt    1080
gtatccgcaa gggttgggtt gttcgtcaat ttgtcaaact aatagttttc ataggactca    1140
tggggttcat tatagaacaa tatattaatc ctatcgttcg aaattccaaa cacccattga    1200
aaggagattt tttatatgca atagaaagag ttttgaagct ttcagttcca aatctatatg    1260
tttggctttg catgttctac tctttttcc acctctggtt gaacatactg gctgagcttc    1320
ttcgctttgg tgatcgtgaa ttctacaaag attggtggaa tgcaaaaact gttgcggagt    1380
attggaaaat gtggaatatg cctgttcata gatggatggt tcgtcatcta tattttccct    1440
gtttgaggaa tgggataccc aaggaaggtg ccattattat cgcgttctta gtttctggtg    1500
ctttccatga gctctgcatt gcagttcctt gccacgtatt caagttatgg gcctttatag    1560
gcattatgtt tcaggttccc ttggtattga ttacgaatta tctacaagaa aagttcagta    1620
attctatggt gggcaatatg atcttctggt tcatcttctg catacttggc caacctatgt    1680
```

-continued

```
gtgtccttct atattaccat gacctgataa atctaaagga aaagtgaaaa aatggaagtt   1740
gcctatgctc agagtattcc tatcccaatg cacacattat atggttctgt acaatctgtg   1800 ccccttcat cctttacacg tacccatgct ggttcctgca cgatgatttg ccttttgttt   1860
gtaagcaata tttggagaga gtccaattta ggaagtgact agtgtggctt atatcttgta   1920
tactaccttt agtcatgggg gggtttttat attactagta ccaaaagtca agttgtatat   1980
gatttacggt ttagtttctt tcatgttttt tgtttttgtg taaatatacg tttcatatat   2040
cactgttttt tcaaagtaaa atcaataata ccccatagat gttgaaactg              2090

<210> SEQ ID NO 77
<211> LENGTH: 518
<212> TYPE: PRT
<213> ORGANISM: T. majus

<400> SEQUENCE: 77

Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
            20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Ile Ala Val Asn Ser Arg Leu Ile Ile
    130                 135                 140

Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
                165                 170                 175

Leu Pro Ile Phe Pro Leu Ala Ala Phe Ile Val Glu Lys Leu Val Gln
            180                 185                 190

Arg Asn His Ile Ser Glu Leu Val Ala Val Leu Leu His Val Ile Val
        195                 200                 205

Ser Thr Ala Ala Val Leu Tyr Pro Val Ile Val Ile Leu Thr Cys Asp
    210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
                245                 250                 255

Leu Ala Lys Ser Gly Tyr Lys Gly Asp Ala His Pro Asn Ser Thr Ile
            260                 265                 270

Val Ser Cys Ser Tyr Asp Val Ser Leu Lys Ser Leu Ala Tyr Phe Met
        275                 280                 285

Val Ala Pro Thr Leu Cys Tyr Gln Pro Ser Tyr Pro Arg Ser Ser Cys
    290                 295                 300
```

-continued

```
Ile Arg Lys Gly Trp Val Val Arg Gln Phe Val Lys Leu Ile Val Phe
305                 310                 315                 320

Ile Gly Leu Met Gly Phe Ile Ile Glu Gln Tyr Ile Asn Pro Ile Val
                325                 330                 335

Arg Asn Ser Lys His Pro Leu Lys Gly Asp Phe Leu Tyr Ala Ile Glu
            340                 345                 350

Arg Val Leu Lys Leu Ser Val Pro Asn Leu Tyr Val Trp Leu Cys Met
        355                 360                 365

Phe Tyr Ser Phe Phe His Leu Trp Leu Asn Ile Leu Ala Glu Leu Leu
    370                 375                 380

Arg Phe Gly Asp Arg Glu Phe Tyr Lys Asp Trp Trp Asn Ala Lys Thr
385                 390                 395                 400

Val Ala Glu Tyr Trp Lys Met Trp Asn Met Pro Val His Arg Trp Met
                405                 410                 415

Val Arg His Leu Tyr Phe Pro Cys Leu Arg Asn Gly Ile Pro Lys Glu
            420                 425                 430

Gly Ala Ile Ile Ile Ala Phe Leu Val Ser Gly Ala Phe His Glu Leu
        435                 440                 445

Cys Ile Ala Val Pro Cys His Val Phe Lys Leu Trp Ala Phe Ile Gly
    450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
                485                 490                 495

Cys Ile Leu Gly Gln Pro Met Cys Val Leu Leu Tyr Tyr His Asp Leu
            500                 505                 510

Ile Asn Leu Lys Glu Lys
        515
```

<210> SEQ ID NO 78
<211> LENGTH: 1485
<212> TYPE: DNA
<213> ORGANISM: Z. mays

<400> SEQUENCE: 78

```
atggccccgc ccccctccat gcctgccgcc tccgatcgcg ccggccctgg ccgcgacgcg      60
ggcgactcgt cctcccttcg cctccgccgc gccccctcag ccgacgccgg cgaccttgcc     120
ggcgattcct cgggaggctt gcgggagaac ggcgagccgc aatcgccgac gaatccgccg     180
ccgcaggagc agcagcagca cgagatgcta tactaccgcg cgtcggcgcc cgcccaccgc     240
cgcgtcaagg agagccccct cagctctgac gccatcttcc ggcagagcca tgctggtctt     300
ctgaatctat gcattgttgt tctgatcgca gtgaacagca gactcattat tgagaattta     360
atgaagtatg gcctgttgat aagagctgga ttttggttta gtgcaagatc gctgggtgac     420 tggcccctttc taatgtgctg cctcactcta ccagttttcc cactagttgc actcatggct     480
gagaagctga tcacaagaaa gctcattggt gaacatgtgg ttattctact ccatatcatt     540
attacaacat ctgccattgt ctatccagtt gttgtgactc ttaagtgtga ctcagcagta     600
ctatctggat ttgtgctaat gtttcttgcg agcatcatgt ggatgaagct tgtctcttat     660
gcacatacaa attatgatat aagggtattg tccaaaagta ctgaaaaggg tgctgcatat     720
ggaaattatg tcgatcctga gaatatgaaa gatccaacct ttaaaagtct agtgtacttt     780
atgttggccc caacactttg ttaccagcca acttatcctc aaactacatg tattagaaag     840
ggttgggtga cccagcaact cataaagtgc gtggttttta caggcttgat gggcttcata     900
```

```
attgagcaat atataaaccc aattgtgaag aattccaaac atccactgaa agggaatttt    960
ttgaatgcta tagaaagagt cttaaaactc tcagtgccaa cattatatgt atggctttgc   1020
atgttctatt gctttttca tttatggctg aacattgtag ctgaactcct ctgtttcggt   1080
gaccgtgaat tctataagga ctggtggaat gccaaaactg ttgaagagta ctggaggatg   1140
tggaacatgc ctgttcataa gtggatcatc agacacatat attttccatg tataaggaaa   1200
ggcttttcca ggggtgtagc tattctaatc tcgtttctgg tttcagctgt atttcatgag   1260
atatgtattg cggtgccttg ccacattttc aaattctggg cattttctgg gatcatgttt   1320
cagataccct tggtattctt gacaagatat ctccatgcta cgttcaagca tgtaatggtg   1380
ggcaacatga tattttggtt cttcttcagt atagtcggac agccgatgtg tgtccttcta   1440
tactaccatg acgtcatgaa caggcaggcc caggcaagta gatag                   1485

<210> SEQ ID NO 79
<211> LENGTH: 494
<212> TYPE: PRT
<213> ORGANISM: Z. mays

<400> SEQUENCE: 79

Met Ala Pro Pro Pro Ser Met Pro Ala Ala Ser Asp Arg Ala Gly Pro
1               5                   10                  15

Gly Arg Asp Ala Gly Asp Ser Ser Ser Leu Arg Leu Arg Arg Ala Pro
            20                  25                  30

Ser Ala Asp Ala Gly Asp Leu Ala Gly Asp Ser Ser Gly Gly Leu Arg
        35                  40                  45

Glu Asn Gly Glu Pro Gln Ser Pro Thr Asn Pro Pro Pro Gln Glu Gln
    50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Arg Gln Ser
                85                  90                  95

His Ala Gly Leu Leu Asn Leu Cys Ile Val Val Leu Ile Ala Val Asn
            100                 105                 110

Ser Arg Leu Ile Ile Glu Asn Leu Met Lys Tyr Gly Leu Leu Ile Arg
        115                 120                 125

Ala Gly Phe Trp Phe Ser Ala Arg Ser Leu Gly Asp Trp Pro Leu Leu
    130                 135                 140

Met Cys Cys Leu Thr Leu Pro Val Phe Pro Leu Val Ala Leu Met Ala
145                 150                 155                 160

Glu Lys Leu Ile Thr Arg Lys Leu Ile Gly Glu His Val Val Ile Leu
                165                 170                 175

Leu His Ile Ile Ile Thr Thr Ser Ala Ile Val Tyr Pro Val Val Val
            180                 185                 190

Thr Leu Lys Cys Asp Ser Ala Val Leu Ser Gly Phe Val Leu Met Phe
        195                 200                 205

Leu Ala Ser Ile Met Trp Met Lys Leu Val Ser Tyr Ala His Thr Asn
    210                 215                 220

Tyr Asp Ile Arg Val Leu Ser Lys Ser Thr Glu Lys Gly Ala Ala Tyr
225                 230                 235                 240

Gly Asn Tyr Val Asp Pro Glu Asn Met Lys Asp Pro Thr Phe Lys Ser
                245                 250                 255

Leu Val Tyr Phe Met Leu Ala Pro Thr Leu Cys Tyr Gln Pro Thr Tyr
            260                 265                 270
```

```
Pro Gln Thr Thr Cys Ile Arg Lys Gly Trp Val Thr Gln Gln Leu Ile
        275                 280                 285

Lys Cys Val Val Phe Thr Gly Leu Met Gly Phe Ile Ile Glu Gln Tyr
    290                 295                 300

Ile Asn Pro Ile Val Lys Asn Ser Lys His Pro Leu Lys Gly Asn Phe
305                 310                 315                 320

Leu Asn Ala Ile Glu Arg Val Leu Lys Leu Ser Val Pro Thr Leu Tyr
                325                 330                 335

Val Trp Leu Cys Met Phe Tyr Cys Phe Phe His Leu Trp Leu Asn Ile
            340                 345                 350

Val Ala Glu Leu Leu Cys Phe Gly Asp Arg Glu Phe Tyr Lys Asp Trp
        355                 360                 365

Trp Asn Ala Lys Thr Val Glu Glu Tyr Trp Arg Met Trp Asn Met Pro
    370                 375                 380

Val His Lys Trp Ile Ile Arg His Ile Tyr Phe Pro Cys Ile Arg Lys
385                 390                 395                 400

Gly Phe Ser Arg Gly Val Ala Ile Leu Ile Ser Phe Leu Val Ser Ala
                405                 410                 415

Val Phe His Glu Ile Cys Ile Ala Val Pro Cys His Ile Phe Lys Phe
            420                 425                 430

Trp Ala Phe Ser Gly Ile Met Phe Gln Ile Pro Leu Val Phe Leu Thr
        435                 440                 445

Arg Tyr Leu His Ala Thr Phe Lys His Val Met Val Gly Asn Met Ile
    450                 455                 460

Phe Trp Phe Phe Phe Ser Ile Val Gly Gln Pro Met Cys Val Leu Leu
465                 470                 475                 480

Tyr Tyr His Asp Val Met Asn Arg Gln Ala Gln Ala Ser Arg
                485                 490

<210> SEQ ID NO 80
<211> LENGTH: 1330
<212> TYPE: DNA
<213> ORGANISM: A. thaliana

<400> SEQUENCE: 80
agttaaaaga ttggttattt gggctctgca ctcaagtgag agagaagata gatagatctg      60
agtagaatct tcgattcatt attcgttgtc gtcgttcatc tgtgagaagc ggacaaacca     120
aagaatccac cggagctagt gatatgggtg gttccagaga gttccgagct gaggaacatt     180
caaatcaatt ccactctatc atcgccatgg ccatctggct tggcgccatt cacttcaacg     240
tcgctcttgt tctctgttct ctcattttcc ttcctccttc tctatctctc atggtcttgg     300
gcttgctctc tctgtttatc tttatcccaa tcgatcatcg tagcaaatat ggtcgtaagc     360
tcgctaggta catatgcaag cacgcgtgta attatttccc cgtctctctg tacgtcgagg     420
attacgaagc tttccagcct aatcgtgcct atgtctttgg ttatgaacca cattcggtgc     480
taccgattgg agttgttgct ctttgtgatc tcacagggtt tatgcctatt cctaacatta     540
aagttcttgc aagtagtgct atattctaca ctccctttct aaggcatata tggacatggt     600
tagggctcac cgctgcttct aggaagaatt tcacttccct tttggattct ggctacagtt     660
gtgttcttgt acctggtggt gtgcaggaga cttttcatat gcaacatgat gctgagaatg     720
tcttcctttc aaggagaaga ggatttgtgc gcatagccat ggaacagggg agccctctgg     780
ttccagtatt ctgctttggt caggcacgcg tgtacaaatg gtggaagccg gattgtgatc     840
```

-continued

```
tctatcttaa actatctaga gcaatcagat tcaccccgat ctgcttctgg ggagtttttg     900
gatcaccatt accgtgtcga cagcctatgc atgtggtcgt tggtaaacca atagaagtca     960
caaaaactct gaagccaact gacgaagaga ttgctaagtt tcatggccag tatgtggaag    1020
cgcttaggga tctgtttgag aggcacaagt cccgagtcgg ctatgatctt gagctgaaaa    1080
ttctttgaac aaaatctcca atggaaataa ttacttgtgt gtatccttca ttaattgtta    1140
ccttggagct ggatttggac ttaatataaa tgactacatc atgtagtcta catgtattgc    1200
atgtctttag catcgactgt tgaagtaatg gaatacgttt ataaagcctg taaattacat    1260
gtcgtcttgc acaagagtat gtggtaataa taacatttga cccaaaaata atactagtta    1320
aatttttcct                                                           1330

<210> SEQ ID NO 81
<211> LENGTH: 314
<212> TYPE: PRT
<213> ORGANISM: A. thaliana

<400> SEQUENCE: 81

Met Gly Gly Ser Arg Glu Phe Arg Ala Glu Glu His Ser Asn Gln Phe
1               5                   10                  15

His Ser Ile Ile Ala Met Ala Ile Trp Leu Gly Ala Ile His Phe Asn
            20                  25                  30

Val Ala Leu Val Leu Cys Ser Leu Ile Phe Leu Pro Pro Ser Leu Ser
        35                  40                  45

Leu Met Val Leu Gly Leu Leu Ser Leu Phe Ile Phe Ile Pro Ile Asp
    50                  55                  60

His Arg Ser Lys Tyr Gly Arg Lys Leu Ala Arg Tyr Ile Cys Lys His
65                  70                  75                  80

Ala Cys Asn Tyr Phe Pro Val Ser Leu Tyr Val Glu Asp Tyr Glu Ala
                85                  90                  95

Phe Gln Pro Asn Arg Ala Tyr Val Phe Gly Tyr Glu Pro His Ser Val
            100                 105                 110

Leu Pro Ile Gly Val Val Ala Leu Cys Asp Leu Thr Gly Phe Met Pro
        115                 120                 125

Ile Pro Asn Ile Lys Val Leu Ala Ser Ser Ala Ile Phe Tyr Thr Pro
    130                 135                 140

Phe Leu Arg His Ile Trp Thr Trp Leu Gly Leu Thr Ala Ala Ser Arg
145                 150                 155                 160

Lys Asn Phe Thr Ser Leu Leu Asp Ser Gly Tyr Ser Cys Val Leu Val
                165                 170                 175

Pro Gly Gly Val Gln Glu Thr Phe His Met Gln His Asp Ala Glu Asn
            180                 185                 190

Val Phe Leu Ser Arg Arg Arg Gly Phe Val Arg Ile Ala Met Glu Gln
        195                 200                 205

Gly Ser Pro Leu Val Pro Val Phe Cys Phe Gly Gln Ala Arg Val Tyr
    210                 215                 220

Lys Trp Trp Lys Pro Asp Cys Asp Leu Tyr Leu Lys Leu Ser Arg Ala
225                 230                 235                 240

Ile Arg Phe Thr Pro Ile Cys Phe Trp Gly Val Phe Gly Ser Pro Leu
                245                 250                 255

Pro Cys Arg Gln Pro Met His Val Val Val Gly Lys Pro Ile Glu Val
            260                 265                 270

Thr Lys Thr Leu Lys Pro Thr Asp Glu Glu Ile Ala Lys Phe His Gly
        275                 280                 285
```

```
Gln Tyr Val Glu Ala Leu Arg Asp Leu Phe Glu Arg His Lys Ser Arg
    290                 295                 300

Val Gly Tyr Asp Leu Glu Leu Lys Ile Leu
305                 310

<210> SEQ ID NO 82
<211> LENGTH: 954
<212> TYPE: DNA
<213> ORGANISM: B. napus

<400> SEQUENCE: 82
atgggcaaag tcagagactt tggagctgag gatcatatcc catcaaacat attccatgca      60
gtgaccgcca tatccatctg cctcagcgcc atttacttga acctcgctct tgttctcatc     120
tccctcttct tcctcccaac ttctctctcc ctcctggtct tgggcctgct ctctctgttt     180
atcatcatcc ctatagatga tcgtagcaag tacggtctta agctggctag gtacatatgc     240
aagcacgcgg ctagttactt ccccgttact ctgcatgtcg aagactacga agctttcaag     300
cctgatcgct cctatgtatt tggttatgaa ccacactcgg tgtggcccat tggagctgtt     360
gcacttgttg atctggcagg gtttatgcct cttcctaaca tcaaacttct tgcaagcaat     420
gctatattct acacgccgtt tctaaggcac atgtgggcat ggttagggct cgcctctgct     480
tctaggaaga gtttctcttc tcttctggag tctggctata gttgtatcct tgtacctggt     540
ggtgtgcagg aaacatttca cttgcaacat gatgttgaga acgtcttcct ttcatcgaga     600
agaggatttg tgcgcatcgc catggaacaa ggggcacctc ttgttccagt tttctgcttt     660
ggtcagtccc gtgcgtacaa gtggtggaag ccggattgtg acctttattt taaactagca     720
agagcgatca ggtttactcc tatctgtttc tggggagttt tcggatcccc aataccatat     780
agacacccta ttcatgtggt ggttggtaaa ccaatacaag ttgcaaagtc tctgcagcca     840
actgatgaag agattgatga gttgcatggc cagtttgtgg aagcgcttaa ggatctgttt     900
gagaggcaca aggccggagc aggctactct gatctgcagt tgaacattct ttga           954

<210> SEQ ID NO 83
<211> LENGTH: 317
<212> TYPE: PRT
<213> ORGANISM: B. napus

<400> SEQUENCE: 83

Met Gly Lys Val Arg Asp Phe Gly Ala Glu Asp His Ile Pro Ser Asn
1               5                   10                  15

Ile Phe His Ala Val Thr Ala Ile Ser Ile Cys Leu Ser Ala Ile Tyr
            20                  25                  30

Leu Asn Leu Ala Leu Val Leu Ile Ser Leu Phe Phe Leu Pro Thr Ser
        35                  40                  45

Leu Ser Leu Leu Val Leu Gly Leu Leu Ser Leu Phe Ile Ile Ile Pro
    50                  55                  60

Ile Asp Asp Arg Ser Lys Tyr Gly Leu Lys Leu Ala Arg Tyr Ile Cys
65                  70                  75                  80

Lys His Ala Ala Ser Tyr Phe Pro Val Thr Leu His Val Glu Asp Tyr
                85                  90                  95

Glu Ala Phe Lys Pro Asp Arg Ser Tyr Val Phe Gly Tyr Glu Pro His
            100                 105                 110

Ser Val Trp Pro Ile Gly Ala Val Ala Leu Val Asp Leu Ala Gly Phe
        115                 120                 125
```

```
Met Pro Leu Pro Asn Ile Lys Leu Leu Ala Ser Asn Ala Ile Phe Tyr
    130                 135                 140

Thr Pro Phe Leu Arg His Met Trp Ala Trp Leu Gly Leu Ala Ser Ala
145                 150                 155                 160

Ser Arg Lys Ser Phe Ser Ser Leu Leu Glu Ser Gly Tyr Ser Cys Ile
                165                 170                 175

Leu Val Pro Gly Gly Val Gln Glu Thr Phe His Leu Gln His Asp Val
            180                 185                 190

Glu Asn Val Phe Leu Ser Ser Arg Arg Gly Phe Val Arg Ile Ala Met
        195                 200                 205

Glu Gln Gly Ala Pro Leu Val Pro Val Phe Cys Phe Gly Gln Ser Arg
    210                 215                 220

Ala Tyr Lys Trp Trp Lys Pro Asp Cys Asp Leu Tyr Phe Lys Leu Ala
225                 230                 235                 240

Arg Ala Ile Arg Phe Thr Pro Ile Cys Phe Trp Gly Val Phe Gly Ser
                245                 250                 255

Pro Ile Pro Tyr Arg His Pro Ile His Val Val Val Gly Lys Pro Ile
            260                 265                 270

Gln Val Ala Lys Ser Leu Gln Pro Thr Asp Glu Glu Ile Asp Glu Leu
        275                 280                 285

His Gly Gln Phe Val Glu Ala Leu Lys Asp Leu Phe Glu Arg His Lys
    290                 295                 300

Ala Gly Ala Gly Tyr Ser Asp Leu Gln Leu Asn Ile Leu
305                 310                 315
```

<210> SEQ ID NO 84
<211> LENGTH: 1637
<212> TYPE: DNA
<213> ORGANISM: A. hypogaea

<400> SEQUENCE: 84

```
aatgaacttg acataaagtg gttgtttgta acaccccatt tagtgttttg cttagatgtt      60
gagagttcta taaacttttg tactatttgg taccccgtaa ttaatagaaa tagaaatgtg     120
ataatggttc tatgtttcat tccagaaaaa aattgtcatt ttaaaaagtt ttcttaaatt     180
ctgaatggga atgatgatca ttcagatcaa taaggttaac actttttat atgatatttt      240 atgtaatctg attaattttt ttttggtgac aaaaaaactcg tgccgaattc ggcacgaggt    300
caaaacctca gaagagagaa aaggagaatt tggttcctaa ttaattctca ccatcaacga     360
tggaggtttc aggcgccgtt ctaaggaatg tcacgtgccc ttccttttct gtgcacgtga     420
gttcccgtcg tcgtggtggt gatagttgtg ttacagtgcc ggtgaggatg agaaaaaagg     480
cggtggtgcg ttgttgctgc gggttcagtg attcggggca tgtgcagtat tacggggacg     540
agaagaagaa ggagaatgga accgctatgt tgagcaccaa gaagaagctc aagatgctga     600
agaaacgtgt ccttttcgat gatcttcaag gaaacctgac ttgggatgct gctatggttt     660
tgatgaagca gctagagcaa gtaagggcag aggagaagga attgaagaaa aaaaggaagc     720
aagagaagaa ggaggcaaaa ctcaaagcct ctaagatgaa caccaatcct gattgcgaat     780
cgtcatcgtc atcgtcatca tctgaatctg aatctgaatc aagtgagagt gaatgtgaca     840
atgaggtggt tgacatgaag aagaacatta aggttggtgt tgccgttgct gttgccgatt     900
ccccacgaaa ggcggaaacc atgattctat acacctccct tgttgcccga gatgttagtg     960
ctaatcatca tcatcataat gccgtggaat tattctctag aaacaatgac atatcagttg    1020
gaagcattaa tggtggcctt aagaatgaga atactgcggt tattaccact gaagctattc    1080
```

```
ctcagaagag gattgaggta tgcatgggaa acaagtgcaa gaaatccgga tctattgcat   1140

tgttgcaaga atttgagaga gtggttggtg ctgaaggagg tgctgctgct gcagttgttg   1200

gatgcaagtg catggggaag tgcaagagtg cacctaatgt gaggattcag aactctactg   1260

cagataaaat agctgagggg ttcaatgatt cagttaaggt tccagctaac cctctttgca   1320

ttggggttgc atggaggatg ttgaaaccat tgtggcttag attcttgggc gagaatcagg   1380

aaagtactaa tgaataattt gctggtatgc tgtttggaaa attgtatata cgtagtgcca   1440

gaacctatca gattgttgtt ttattttata taaacataga ctgcatattg ttgtgagatt   1500

cgatttcctc atttattgga acttccagag cctgatttgt gtccattcga gctcgactca   1560

aagatttaca tggcctgctc aatctatgaa ttcaaatttg agggccctgt ttggcattaa   1620

tattaatata ttaatat                                                  1637
```

<210> SEQ ID NO 85
<211> LENGTH: 345
<212> TYPE: PRT
<213> ORGANISM: A. hypogaea

<400> SEQUENCE: 85

```
Met Glu Val Ser Gly Ala Val Leu Arg Asn Val Thr Cys Pro Ser Phe
1               5                   10                  15

Ser Val His Val Ser Ser Arg Arg Arg Gly Gly Asp Ser Cys Val Thr
            20                  25                  30

Val Pro Val Arg Met Arg Lys Lys Ala Val Val Arg Cys Cys Cys Gly
        35                  40                  45

Phe Ser Asp Ser Gly His Val Gln Tyr Tyr Gly Asp Glu Lys Lys Lys
    50                  55                  60

Glu Asn Gly Thr Ala Met Leu Ser Thr Lys Lys Lys Leu Lys Met Leu
65                  70                  75                  80

Lys Lys Arg Val Leu Phe Asp Asp Leu Gln Gly Asn Leu Thr Trp Asp
                85                  90                  95

Ala Ala Met Val Leu Met Lys Gln Leu Glu Gln Val Arg Ala Glu Glu
            100                 105                 110

Lys Glu Leu Lys Lys Lys Arg Lys Gln Glu Lys Lys Glu Ala Lys Leu
        115                 120                 125

Lys Ala Ser Lys Met Asn Thr Asn Pro Asp Cys Glu Ser Ser Ser Ser
    130                 135                 140

Ser Ser Ser Ser Glu Ser Glu Ser Glu Ser Ser Glu Ser Glu Cys Asp
145                 150                 155                 160

Asn Glu Val Val Asp Met Lys Lys Asn Ile Lys Val Gly Val Ala Val
                165                 170                 175

Ala Val Ala Asp Ser Pro Arg Lys Ala Glu Thr Met Ile Leu Tyr Thr
            180                 185                 190

Ser Leu Val Ala Arg Asp Val Ser Ala Asn His His His His Asn Ala
        195                 200                 205

Val Glu Leu Phe Ser Arg Asn Asn Asp Ile Ser Val Gly Ser Ile Asn
    210                 215                 220

Gly Gly Leu Lys Asn Glu Asn Thr Ala Val Ile Thr Thr Glu Ala Ile
225                 230                 235                 240

Pro Gln Lys Arg Ile Glu Val Cys Met Gly Asn Lys Cys Lys Lys Ser
                245                 250                 255

Gly Ser Ile Ala Leu Leu Gln Glu Phe Glu Arg Val Val Gly Ala Glu
            260                 265                 270
```

```
Gly Gly Ala Ala Ala Ala Val Val Gly Cys Lys Cys Met Gly Lys Cys
        275                 280                 285

Lys Ser Ala Pro Asn Val Arg Ile Gln Asn Ser Thr Ala Asp Lys Ile
    290                 295                 300

Ala Glu Gly Phe Asn Asp Ser Val Lys Val Pro Ala Asn Pro Leu Cys
305                 310                 315                 320

Ile Gly Val Ala Trp Arg Met Leu Lys Pro Leu Trp Leu Arg Phe Leu
                325                 330                 335

Gly Glu Asn Gln Glu Ser Thr Asn Glu
            340                 345

<210> SEQ ID NO 86
<211> LENGTH: 2811
<212> TYPE: DNA
<213> ORGANISM: A. thaliana

<400> SEQUENCE: 86
cccaagtgta atattgttat taatacatgg gctatactaa aagccccacg aaaagtttac     60
tgaactattt gaggcccaac aagagcctat cggattaacg cctactgcag aagaaaatct    120
gtctgcactc cacccaagaa aacgcagact aattaatgaa atcaacgaaa cggataggtc    180
gggtctaagg ttgaccatga accgcaacct gaaccaggag caaagtggtc aagttttgcc    240
atccggtccg agtcccttgg aggaataata ccagaacaga aaaaaacaga aaagtcgaca    300
ataaacaaaa gagacaaatt tgatttgatt ggttccagaa attcgcagag aaacagctct    360
ttgtctctct cgactgatct aacaatccct aatctgtgtt ctaaattcct ggacgagatt    420
tgacaaagtc cgtatagctt aacctggttt aatttcaagt gacagatatg ccccttattc    480
atcggaaaaa gccgacggag aaaccatcga cgccgccatc tgaagaggtg gtgcacgatg    540
aggattcgca aaagaaacca cacgaatctt ccaaatccca ccataagaaa tcgaacggag    600
gagggaagtg gtcgtgcatc gattcttgtt gttggttcat tgggtgtgtg tgtgtaacct    660
ggtggtttct tctcttcctt tacaacgcaa tgcctgcgag cttccctcag tatgtaacgg    720
agcgaatcac gggtcctttg cctgacccgc ccggtgttaa gctcaaaaaa gaaggtctta    780
aggcgaaaca tcctgttgtc ttcattcctg ggattgtcac cggtgggctc gagctttggg    840
aaggcaaaca atgcgctgat ggtttattta gaaaacgttt gtggggtgga acttttggtg    900
aagtctacaa aaggcctcta tgttgggtgg aacacatgtc acttgacaat gaaactgggt    960
tggatccagc tggtattaga gttcgagctg tatcaggact cgtggctgct gactactttg   1020
ctcctggcta ctttgtctgg gcagtgctga ttgctaacct tgcacatatt ggatatgaag   1080
agaaaaatat gtacatggct gcatatgact ggcggctttc gtttcagaac acagaggtac   1140
gtgatcagac tcttagccgt atgaaaagta atatagagtt gatggtttct accaacggtg   1200
gaaaaaaagc agttatagtt ccgcattcca tgggggtctt gtattttcta cattttatga   1260
agtgggttga ggcaccagct cctctgggtg gcgggggtgg gccagattgg tgtgcaaagt   1320
atattaaggc ggtgatgaac attggtggac catttcttgg tgttccaaaa gctgttgcag   1380
ggcttttctc tgctgaagca aaggatgttg cagttgccag agcgattgcc ccaggattct   1440
tagacaccga tatatttaga cttcagacct tgcagcatgt aatgagaatg acacgcacat   1500
gggactcaac aatgtctatg ttaccgaagg gaggtgacac gatatggggc gggcttgatt   1560
ggtcaccgga gaaaggccac acctgttgtg ggaaaaagca aaagaacaac gaaacttgtg   1620
gtgaagcagg tgaaaacgga gtttccaaga aaagtcctgt taactatgga aggatgatat   1680
```

-continued

```
cttttgggaa agaagtagca gaggctgcgc catctgagat taataatatt gattttcgag   1740

gtgctgtcaa aggtcagagt atcccaaatc acacctgtcg tgacgtgtgg acagagtacc   1800

atgacatggg aattgctggg atcaaagcta tcgctgagta taaggtctac actgctggtg   1860

aagctataga tctactacat tatgttgctc ctaagatgat ggcgcgtggt gccgctcatt   1920

tctcttatgg aattgctgat gatttggatg acaccaagta tcaagatccc aaatactggt   1980

caaatccgtt agagacaaaa ttaccgaatg ctcctgagat ggaaatctac tcattatacg   2040

gagtggggat accaacggaa cgagcatacg tatacaagct taaccagtct cccgacagtt   2100

gcatcccctt tcagatattc acttctgctc acgaggagga cgaagatagc tgtctgaaag   2160

caggagttta caatgtggat ggggatgaaa cagtacccgt cctaagtgcc gggtacatgt   2220

gtgcaaaagc gtggcgtggc aagacaagat tcaacccttc cggaatcaag acttatataa   2280

gagaatacaa tcactctccg ccggctaacc tgttggaagg gcgcgggacg cagagtggtg   2340

cccatgttga tatcatggga aactttgctt tgatcgaaga tatcatgagg gttgccgccg   2400

gaggtaacgg gtctgatata ggacatgacc aggtccactc tggcatattt gaatggtcgg   2460

agcgtattga cctgaagctg tgaatatcat gatctcttta agctgtcctg tcagcttatg   2520

tgaatccaat actttgaaag agagatcatc atcaattcat catcatcgtc atcatcatga   2580

tgctcaactc acaaagaagc ctgagaatga tactttggtg cgaaattctc aatacctctt   2640

taatattctt attgaatgta aattatacaa tcctatctaa tgtttgaacg ataacacaaa   2700

acttgctgcg ccatgtttgt ttgtcttgtc aaaagcatca atttgtgggt tatacgtagt   2760

gtagaggatg attcaaattt gtgataaatt tggtaatcaa agttaattct g            2811
```

```
<210> SEQ ID NO 87
<211> LENGTH: 671
<212> TYPE: PRT
<213> ORGANISM: A. thaliana

<400> SEQUENCE: 87

Met Pro Leu Ile His Arg Lys Lys Pro Thr Glu Lys Pro Ser Thr Pro
1               5                   10                  15

Pro Ser Glu Glu Val Val His Asp Glu Asp Ser Gln Lys Lys Pro His
            20                  25                  30

Glu Ser Ser Lys Ser His His Lys Lys Ser Asn Gly Gly Gly Lys Trp
        35                  40                  45

Ser Cys Ile Asp Ser Cys Cys Trp Phe Ile Gly Cys Val Cys Val Thr
    50                  55                  60

Trp Trp Phe Leu Leu Phe Leu Tyr Asn Ala Met Pro Ala Ser Phe Pro
65                  70                  75                  80

Gln Tyr Val Thr Glu Arg Ile Thr Gly Pro Leu Pro Asp Pro Pro Gly
                85                  90                  95

Val Lys Leu Lys Lys Glu Gly Leu Lys Ala Lys His Pro Val Val Phe
            100                 105                 110

Ile Pro Gly Ile Val Thr Gly Gly Leu Glu Leu Trp Glu Gly Lys Gln
        115                 120                 125

Cys Ala Asp Gly Leu Phe Arg Lys Arg Leu Trp Gly Gly Thr Phe Gly
    130                 135                 140

Glu Val Tyr Lys Arg Pro Leu Cys Trp Val Glu His Met Ser Leu Asp
145                 150                 155                 160

Asn Glu Thr Gly Leu Asp Pro Ala Gly Ile Arg Val Arg Ala Val Ser
                165                 170                 175
```

```
Gly Leu Val Ala Ala Asp Tyr Phe Ala Pro Gly Tyr Phe Val Trp Ala
            180                 185                 190

Val Leu Ile Ala Asn Leu Ala His Ile Gly Tyr Glu Glu Lys Asn Met
        195                 200                 205

Tyr Met Ala Ala Tyr Asp Trp Arg Leu Ser Phe Gln Asn Thr Glu Val
    210                 215                 220

Arg Asp Gln Thr Leu Ser Arg Met Lys Ser Asn Ile Glu Leu Met Val
225                 230                 235                 240

Ser Thr Asn Gly Gly Lys Lys Ala Val Ile Val Pro His Ser Met Gly
                245                 250                 255

Val Leu Tyr Phe Leu His Phe Met Lys Trp Val Glu Ala Pro Ala Pro
            260                 265                 270

Leu Gly Gly Gly Gly Gly Pro Asp Trp Cys Ala Lys Tyr Ile Lys Ala
        275                 280                 285

Val Met Asn Ile Gly Gly Pro Phe Leu Gly Val Pro Lys Ala Val Ala
    290                 295                 300

Gly Leu Phe Ser Ala Glu Ala Lys Asp Val Ala Val Ala Arg Ala Ile
305                 310                 315                 320

Ala Pro Gly Phe Leu Asp Thr Asp Ile Phe Arg Leu Gln Thr Leu Gln
                325                 330                 335

His Val Met Arg Met Thr Arg Thr Trp Asp Ser Thr Met Ser Met Leu
            340                 345                 350

Pro Lys Gly Gly Asp Thr Ile Trp Gly Gly Leu Asp Trp Ser Pro Glu
        355                 360                 365

Lys Gly His Thr Cys Cys Gly Lys Lys Gln Lys Asn Asn Glu Thr Cys
    370                 375                 380

Gly Glu Ala Gly Glu Asn Gly Val Ser Lys Lys Ser Pro Val Asn Tyr
385                 390                 395                 400

Gly Arg Met Ile Ser Phe Gly Lys Glu Val Ala Glu Ala Ala Pro Ser
                405                 410                 415

Glu Ile Asn Asn Ile Asp Phe Arg Gly Ala Val Lys Gly Gln Ser Ile
            420                 425                 430

Pro Asn His Thr Cys Arg Asp Val Trp Thr Glu Tyr His Asp Met Gly
        435                 440                 445

Ile Ala Gly Ile Lys Ala Ile Ala Glu Tyr Lys Val Tyr Thr Ala Gly
    450                 455                 460

Glu Ala Ile Asp Leu Leu His Tyr Val Ala Pro Lys Met Met Ala Arg
465                 470                 475                 480

Gly Ala Ala His Phe Ser Tyr Gly Ile Ala Asp Asp Leu Asp Asp Thr
                485                 490                 495

Lys Tyr Gln Asp Pro Lys Tyr Trp Ser Asn Pro Leu Glu Thr Lys Leu
            500                 505                 510

Pro Asn Ala Pro Glu Met Glu Ile Tyr Ser Leu Tyr Gly Val Gly Ile
        515                 520                 525

Pro Thr Glu Arg Ala Tyr Val Tyr Lys Leu Asn Gln Ser Pro Asp Ser
    530                 535                 540

Cys Ile Pro Phe Gln Ile Phe Thr Ser Ala His Glu Glu Asp Glu Asp
545                 550                 555                 560

Ser Cys Leu Lys Ala Gly Val Tyr Asn Val Asp Gly Asp Glu Thr Val
                565                 570                 575

Pro Val Leu Ser Ala Gly Tyr Met Cys Ala Lys Ala Trp Arg Gly Lys
            580                 585                 590
```

```
Thr Arg Phe Asn Pro Ser Gly Ile Lys Thr Tyr Ile Arg Glu Tyr Asn
        595                 600                 605

His Ser Pro Pro Ala Asn Leu Leu Glu Gly Arg Gly Thr Gln Ser Gly
    610                 615                 620

Ala His Val Asp Ile Met Gly Asn Phe Ala Leu Ile Glu Asp Ile Met
625                 630                 635                 640

Arg Val Ala Ala Gly Gly Asn Gly Ser Asp Ile Gly His Asp Gln Val
                645                 650                 655

His Ser Gly Ile Phe Glu Trp Ser Glu Arg Ile Asp Leu Lys Leu
            660                 665                 670

<210> SEQ ID NO 88
<211> LENGTH: 2473
<212> TYPE: DNA
<213> ORGANISM: R. communis

<400> SEQUENCE: 88
cttgaatttt gtttcgatta ctttaaaaaa aattgccttt ttctgaaagc gcttctagtt      60
tgatcttaat ggattattta cttttcagaa attagtagct caaacaaaat taagagagaa     120
aaagagatcg tgggtttttt caaagaaaaa gtttcaaaca gaaagcacaa actttccgat     180
gtggcttgcg aggaagttgg ggatgacata aattcttctg ccagtccgaa gttttggata     240
taaagcagtg gtttttgtat tttccttttt ccttttctgt atcgtttagt aaagtcacat     300
ttggcttatt gggtttgttt tatttcctct gtatttgctt tctgtacaaa gactatcaat     360
aattagttaa taagcttaac aaatttaaaa atcttatttt tctttaaacc cagaaatgcc     420
tgtaattcgg aggaaaaaac ccacttctga acccaacaaa aattcagcat cagactcaaa     480
aacgccaagc gaggaagagg aacatgaaca agaacaggaa caagaagaag ataaaaaataa     540 caaaaagaaa tacccaaaga agaagagcag tgaaatcaat gcaaaaaaat ggtcatgcat     600
agacagctgt tgttggtttg ttggttgcat ctgcgtgacg tggtgggttt tactatttct     660
ttacaatgca gtgcctgcgt ctttgcctca atacgtaact gaggcaatca cgggtccttt     720
acccgatcca cctggtgtta agctgaaaaa agagggatta acagcaaagc atccagtggt     780
ttttgtacct gggattgtta ccgcggggct tgaattgtgg gaaggccatc agtgtgctga     840
tgggctgttt aggaaacggc tctggggtgg aacttttgga gaagtttata agaggcctct     900
ctgctgggta gagcatatgt ctctagacaa tgaaactgga ttggatcctc ctggtataag     960
ggtcaggcca gtctctggac ttgtggctgc tgattacttt gctccaggct attttgtgtg    1020
ggctgttctg attgctaatt tggcacgcat tggatatgag gagaaaacaa tgttcatggc    1080
ctcatacgat tggagacttt catttcagaa cactgaggtc cgtgaccaaa cattaagccg    1140
gatgaagagt aatatagaac ttatggtttc tatcaatggt ggaaataagg cagttattgt    1200
tccacattcc atgggtgttt tgtactttct gcattttatg aagtgggttg aggcaccagc    1260
tccaatggga ggaggtggtg gaccagattg gtgtgctaag catatcaagg cagtcatgaa    1320
cattggtggt ccatttttag gtgttcccaa agctgttgct gggcttttct cggctgaagc    1380
aagagatatt gcagttgcca gggccatagc accaggtttc ttagataatg atatgttccg    1440
cctacaaaca ttgcaacaca tgatgaggat gtctcgcaca tgggattcga ccatgtcaat    1500
gataccaaga ggtggggaca ctatctgggg cgatcttgat tggtcacctg aagaaggtta    1560
cattcctaga aagaaaaggc agagaaataa tgcaactgat aatgtaaacg aaggtggggc    1620
cgaaagtgag atttctcaaa gaaagattgt tagatatgga agaatgatat catttgggaa    1680
```

```
aaatatagca gaggcacctt catatgatat tgaaaggatt gactttaggg atgctgttaa   1740

aggtcgtagt gtggcaaata atacctgcct tgatgtgtgg actgaatacc atgaaatggg   1800

attcggaggt attaaagccg ttgcagagta taaggtctac actgctggat ctactataga   1860

gctgcttcag tttgtcgccc caaaaatgat ggagcgtggt agtgctcatt tttcttatgg   1920

aattgctgac aatttggagg acccaaaata tgagcactac aaatactggt caaatcccct   1980

ggagacaaag ttacctaatg ctccagaaat ggaaatattt tccatgtatg gagttggcat   2040

accaacagaa agagcttatg tttatgagtt ttctcctgct gctgagtgct acattccatt   2100

tcagattgat acatcagcta atgatggcga tgaagatggc tgtctgaaag atggagtcta   2160

tactgttgat ggggatgaga ctgttcctgt tttaagtgca ggcttcatgt gtgctaaagc   2220

ttggcgtggg aaaaccagat ttaatccttc aggaagtcga acatacatta gagagtacga   2280

tcattctcct ccagctaatt tgctagaggg ccgaggcacc caaagtggtg cccatgttga   2340

tataatgggt aattttgctt taatcgagga tattatgagg gtggcagccg ggggctacagg  2400

agaagatttg ggaggcgatc aagtgtattc agatatcttt aagtggtctc agaagatcaa   2460

attaccactg taa                                                      2473
```

<210> SEQ ID NO 89
<211> LENGTH: 685
<212> TYPE: PRT
<213> ORGANISM: R. communis

<400> SEQUENCE: 89

```
Met Pro Val Ile Arg Arg Lys Lys Pro Thr Ser Glu Pro Asn Lys Asn
1               5                   10                  15

Ser Ala Ser Asp Ser Lys Thr Pro Ser Glu Glu Glu Glu His Glu Gln
            20                  25                  30

Glu Gln Glu Gln Glu Glu Asp Lys Asn Asn Lys Lys Lys Tyr Pro Lys
        35                  40                  45

Lys Lys Ser Ser Glu Ile Asn Ala Lys Lys Trp Ser Cys Ile Asp Ser
    50                  55                  60

Cys Cys Trp Phe Val Gly Cys Ile Cys Val Thr Trp Trp Val Leu Leu
65                  70                  75                  80

Phe Leu Tyr Asn Ala Val Pro Ala Ser Leu Pro Gln Tyr Val Thr Glu
                85                  90                  95

Ala Ile Thr Gly Pro Leu Pro Asp Pro Pro Gly Val Lys Leu Lys Lys
            100                 105                 110

Glu Gly Leu Thr Ala Lys His Pro Val Val Phe Val Pro Gly Ile Val
        115                 120                 125

Thr Ala Gly Leu Glu Leu Trp Glu Gly His Gln Cys Ala Asp Gly Leu
    130                 135                 140

Phe Arg Lys Arg Leu Trp Gly Gly Thr Phe Gly Glu Val Tyr Lys Arg
145                 150                 155                 160

Pro Leu Cys Trp Val Glu His Met Ser Leu Asp Asn Glu Thr Gly Leu
                165                 170                 175

Asp Pro Pro Gly Ile Arg Val Arg Pro Val Ser Gly Leu Val Ala Ala
            180                 185                 190

Asp Tyr Phe Ala Pro Gly Tyr Phe Val Trp Ala Val Leu Ile Ala Asn
        195                 200                 205

Leu Ala Arg Ile Gly Tyr Glu Glu Lys Thr Met Phe Met Ala Ser Tyr
    210                 215                 220

Asp Trp Arg Leu Ser Phe Gln Asn Thr Glu Val Arg Asp Gln Thr Leu
```

-continued

```
225                 230                 235                 240

Ser Arg Met Lys Ser Asn Ile Glu Leu Met Val Ser Ile Asn Gly Gly
                245                 250                 255

Asn Lys Ala Val Ile Val Pro His Ser Met Gly Val Leu Tyr Phe Leu
            260                 265                 270

His Phe Met Lys Trp Val Glu Ala Pro Ala Pro Met Gly Gly Gly Gly
        275                 280                 285

Gly Pro Asp Trp Cys Ala Lys His Ile Lys Ala Val Met Asn Ile Gly
    290                 295                 300

Gly Pro Phe Leu Gly Val Pro Lys Ala Val Ala Gly Leu Phe Ser Ala
305                 310                 315                 320

Glu Ala Arg Asp Ile Ala Val Ala Arg Ala Ile Ala Pro Gly Phe Leu
                325                 330                 335

Asp Asn Asp Met Phe Arg Leu Gln Thr Leu Gln His Met Met Arg Met
            340                 345                 350

Ser Arg Thr Trp Asp Ser Thr Met Ser Met Ile Pro Arg Gly Gly Asp
        355                 360                 365

Thr Ile Trp Gly Asp Leu Asp Trp Ser Pro Glu Glu Gly Tyr Ile Pro
    370                 375                 380

Arg Lys Lys Arg Gln Arg Asn Asn Ala Thr Asp Asn Val Asn Glu Gly
385                 390                 395                 400

Gly Ala Glu Ser Glu Ile Ser Gln Arg Lys Ile Val Arg Tyr Gly Arg
                405                 410                 415

Met Ile Ser Phe Gly Lys Asn Ile Ala Glu Ala Pro Ser Tyr Asp Ile
            420                 425                 430

Glu Arg Ile Asp Phe Arg Asp Ala Val Lys Gly Arg Ser Val Ala Asn
        435                 440                 445

Asn Thr Cys Leu Asp Val Trp Thr Glu Tyr His Glu Met Gly Phe Gly
    450                 455                 460

Gly Ile Lys Ala Val Ala Glu Tyr Lys Val Tyr Thr Ala Gly Ser Thr
465                 470                 475                 480

Ile Glu Leu Leu Gln Phe Val Ala Pro Lys Met Met Glu Arg Gly Ser
                485                 490                 495

Ala His Phe Ser Tyr Gly Ile Ala Asp Asn Leu Glu Asp Pro Lys Tyr
            500                 505                 510

Glu His Tyr Lys Tyr Trp Ser Asn Pro Leu Glu Thr Lys Leu Pro Asn
        515                 520                 525

Ala Pro Glu Met Glu Ile Phe Ser Met Tyr Gly Val Gly Ile Pro Thr
    530                 535                 540

Glu Arg Ala Tyr Val Tyr Glu Phe Ser Pro Ala Ala Glu Cys Tyr Ile
545                 550                 555                 560

Pro Phe Gln Ile Asp Thr Ser Ala Asn Asp Gly Asp Glu Asp Gly Cys
                565                 570                 575

Leu Lys Asp Gly Val Tyr Thr Val Asp Gly Asp Glu Thr Val Pro Val
            580                 585                 590

Leu Ser Ala Gly Phe Met Cys Ala Lys Ala Trp Arg Gly Lys Thr Arg
        595                 600                 605

Phe Asn Pro Ser Gly Ser Arg Thr Tyr Ile Arg Glu Tyr Asp His Ser
    610                 615                 620

Pro Pro Ala Asn Leu Leu Glu Gly Arg Gly Thr Gln Ser Gly Ala His
625                 630                 635                 640

Val Asp Ile Met Gly Asn Phe Ala Leu Ile Glu Asp Ile Met Arg Val
                645                 650                 655
```

```
Ala Ala Gly Ala Thr Gly Glu Asp Leu Gly Gly Asp Gln Val Tyr Ser
            660                 665                 670

Asp Ile Phe Lys Trp Ser Gln Lys Ile Lys Leu Pro Leu
        675                 680                 685

<210> SEQ ID NO 90
<211> LENGTH: 380
<212> TYPE: PRT
<213> ORGANISM: B. oleraceae

<400> SEQUENCE: 90

Met Arg Asn Glu Ile Gln Asn Glu Thr Ala Gln Thr Asp Gln Thr Gln
1               5                   10                  15

Gly Ser Met Phe Ser Phe Phe Asp Leu Phe Pro Phe Leu Leu Pro Met
            20                  25                  30

Phe Glu Val Ile Lys Met Val Val Ala Ser Val Ala Ser Val Val Tyr
        35                  40                  45

Leu Gly Phe Ala Gly Val Thr Leu Ser Gly Ser Ala Val Ala Leu Ala
    50                  55                  60

Val Ser Thr Pro Leu Phe Ile Ile Phe Ser Pro Ile Leu Leu Pro Ala
65                  70                  75                  80

Ile Ala Ala Thr Thr Val Leu Ala Ala Gly Leu Gly Ser Lys Lys Val
                85                  90                  95

Ala Ala Ala Pro Ala Ala Ser Pro Ser Leu Ser Leu Leu Gly Ile Pro
            100                 105                 110

Glu Ser Ile Lys Pro Ser Asn Val Ile Pro Glu Ser Ile Lys Pro Ser
        115                 120                 125

Asn Ile Ile Pro Glu Ser Ile Lys Pro Ser Asn Ile Ile Pro Glu Ser
    130                 135                 140

Val Lys Pro Ser Asn Ile Lys Asp Lys Ile Lys Asp Thr Ile Gly Lys
145                 150                 155                 160

Val Lys Asn Lys Ile Asn Ala Lys Lys Glu Glu Lys Ser Lys Gly Lys
                165                 170                 175

Ser Glu Asp Ser Ser Lys Gly Lys Gly Lys Ser Lys Gly Glu Asp Thr
            180                 185                 190

Thr Thr Asp Glu Asp Lys Pro Gly Ser Gly Gly Lys His Gly Lys Gly
        195                 200                 205

Glu Ser Lys His Gly Lys Gly Glu Ser Thr His Gly Lys Gly Gly Lys
    210                 215                 220

His Gly Ser Glu Gly Ser Ser Met Asp Glu Gly Lys His Gly Gly Lys
225                 230                 235                 240

His Gly Ser Gly Gly Ser Pro Met Gly Val Gly Lys His Gly Ser Gly
                245                 250                 255

Gly Lys His Glu Ser Gly Gly Ser Pro Met Gly Gly Gly Lys His Gly
            260                 265                 270

Ser Gly Gly Lys His Glu Ser Gly Gly Ala Ser Met Gly Gly Gly Lys
        275                 280                 285

His Gly Ser Gly Gly Arg His Glu Gly Gly Gly Ser Ala Met Gly Gly
    290                 295                 300

Gly Lys His Gly Ser Gly Gly Lys His Gly Ser Glu Gly Lys His Gly
305                 310                 315                 320

Gly Glu Gly Ser Ser Met Gly Lys Asn Ser Leu Ser Lys Asn Lys Lys
                325                 330                 335

Glu Phe His Tyr Arg Asp Gln Ala Met Asp Ala Ser Ser Thr Ser Glu
```

```
            340                 345                 350

Ser Ser Asp Gly Ser Ser Asp Gly Ser Ser Ser Asp Gly Ser Ser Ser
        355                 360                 365

Asp Gly Ser Ser His Gly Ser Gly Gly Lys His Ile
    370                 375                 380

<210> SEQ ID NO 91
<211> LENGTH: 186
<212> TYPE: PRT
<213> ORGANISM: Z. mays

<400> SEQUENCE: 91

Met Ala Asp Arg Asp Arg Ser Gly Ile Tyr Gly Gly Ala His Ala Thr
1               5                   10                  15

Tyr Gly Gln Gln Gln Gln Gln Gly Gly Gly Gly Arg Pro Met Gly Glu
            20                  25                  30

Gln Val Lys Gly Met Leu His Asp Lys Gly Pro Thr Ala Ser Gln Ala
        35                  40                  45

Leu Thr Val Ala Thr Leu Phe Pro Leu Gly Gly Leu Leu Leu Val Leu
    50                  55                  60

Ser Gly Leu Ala Leu Thr Ala Ser Val Val Gly Leu Ala Val Ala Thr
65                  70                  75                  80

Pro Val Phe Leu Ile Phe Ser Pro Val Leu Val Pro Ala Ala Leu Leu
                85                  90                  95

Ile Gly Thr Ala Val Met Gly Phe Leu Thr Ser Gly Ala Leu Gly Leu
            100                 105                 110

Gly Gly Leu Ser Ser Leu Thr Cys Leu Ala Asn Thr Ala Arg Gln Ala
        115                 120                 125

Phe Gln Arg Thr Pro Asp Tyr Val Glu Glu Ala His Arg Arg Met Ala
    130                 135                 140

Glu Ala Ala Ala His Ala Gly His Lys Thr Ala Gln Ala Gly Gln Ala
145                 150                 155                 160

Ile Gln Gly Arg Ala Gln Glu Ala Gly Ala Gly Gly Gly Ala Gly Ala
                165                 170                 175

Gly Ala Gly Gly Gly Gly Arg Ala Ser Ser
            180                 185

<210> SEQ ID NO 92
<211> LENGTH: 148
<212> TYPE: PRT
<213> ORGANISM: O. sativa

<400> SEQUENCE: 92

Met Gly Asp Gln His Arg Gly Val Ile Gly Gly Gly Gly Tyr Gly Asp
1               5                   10                  15

Arg Gly Gly Gln Glu Gln Gln Glu Lys Gln Pro Phe Met Met Thr Ala
            20                  25                  30

Leu Lys Thr Val Thr Ala Ala Thr Ala Gly Gly Ser Ile Leu Val Leu
        35                  40                  45

Ser Gly Leu Ile Leu Ala Gly Thr Val Ile Ala Leu Thr Val Ala Thr
    50                  55                  60

Pro Val Leu Val Ile Phe Ser Pro Val Leu Val Pro Ala Ala Ile Ala
65                  70                  75                  80

Leu Ala Leu Met Ala Ala Gly Phe Val Thr Ser Val Gly Leu Gly Val
                85                  90                  95

Ala Ala Leu Ser Val Phe Ser Trp Met Tyr Lys Tyr Leu Thr Gly Lys
```

```
            100                 105                 110

His Pro Pro Gly Ala Asp His Leu Asp His Thr Lys Ala Arg Val Ala
        115                 120                 125

Ser Lys Leu Arg Asp Ile Lys Glu Ala Ala His His Leu Ile Asp Gln
    130                 135                 140

Ala Gln Ala Ser
145

<210> SEQ ID NO 93
<211> LENGTH: 245
<212> TYPE: PRT
<213> ORGANISM: S. indicum

<400> SEQUENCE: 93

Met Ala Thr His Val Leu Ala Ala Ala Ala Glu Arg Asn Ala Ala Leu
1               5                   10                  15

Ala Pro Asp Ala Pro Leu Ala Pro Val Thr Met Glu Arg Pro Val Arg
            20                  25                  30

Thr Asp Leu Glu Thr Ser Ile Pro Lys Pro Tyr Met Ala Arg Gly Leu
        35                  40                  45

Val Ala Pro Asp Met Asp His Pro Asn Gly Thr Pro Gly His Val His
    50                  55                  60

Asp Asn Leu Ser Val Leu Gln Gln His Cys Ala Phe Phe Asp Gln Asp
65                  70                  75                  80

Asp Asn Gly Ile Ile Tyr Pro Trp Glu Thr Tyr Ser Gly Leu Arg Gln
                85                  90                  95

Ile Gly Phe Asn Val Ile Ala Ser Leu Ile Met Ala Ile Val Ile Asn
            100                 105                 110

Val Ala Leu Ser Tyr Pro Thr Leu Pro Gly Trp Ile Pro Ser Pro Phe
        115                 120                 125

Phe Pro Ile Tyr Leu Tyr Asn Ile His Lys Ala Lys His Gly Ser Asp
    130                 135                 140

Ser Gly Thr Tyr Asp Thr Glu Gly Arg Tyr Leu Pro Met Asn Phe Glu
145                 150                 155                 160

Asn Leu Phe Ser Lys His Ala Arg Thr Met Pro Asp Arg Leu Thr Leu
                165                 170                 175

Gly Glu Leu Trp Ser Met Thr Glu Ala Asn Arg Glu Ala Phe Asp Ile
            180                 185                 190

Phe Gly Trp Ile Ala Ser Lys Met Glu Trp Thr Leu Leu Tyr Ile Leu
        195                 200                 205

Ala Arg Asp Gln Asp Gly Phe Leu Ser Lys Glu Ala Ile Arg Arg Cys
    210                 215                 220

Tyr Asp Gly Ser Leu Phe Glu Tyr Cys Ala Lys Met Gln Arg Gly Ala
225                 230                 235                 240

Glu Asp Lys Met Lys
                245

<210> SEQ ID NO 94
<211> LENGTH: 239
<212> TYPE: PRT
<213> ORGANISM: G. max

<400> SEQUENCE: 94

Met Ala Ala Glu Met Glu Arg Glu Ser Leu Ile Thr Glu Ala Pro Asn
1               5                   10                  15

Ala Pro Val Thr Ala Gln Arg Arg Val Arg Asn Asp Leu Glu Asn Ser
```

```
            20                  25                  30

Leu Pro Lys Pro Tyr Leu Pro Arg Ala Leu Lys Ala Pro Asp Thr Gly
        35                  40                  45

His Pro Asn Gly Thr Ala Gly His Arg His His Asn Leu Ser Val Leu
    50                  55                  60

Gln Gln His Cys Ala Phe Phe Asp Gln Asp Asp Asn Gly Ile Ile Tyr
65                  70                  75                  80

Pro Trp Glu Thr Tyr Met Gly Leu Arg Ser Ile Gly Phe Asn Val Val
                85                  90                  95

Ala Ser Val Ile Met Ala Ile Val Ile Asn Val Gly Leu Ser Tyr Pro
            100                 105                 110

Thr Leu Pro Asn Trp Phe Pro Ser Leu Leu Phe Pro Ile Tyr Ile His
        115                 120                 125

Asn Ile His Lys Ala Lys His Gly Ser Asp Ser Gly Val Tyr Asp Thr
    130                 135                 140

Glu Gly Arg Tyr Val Pro Ala Asn Ile Glu Asn Ile Phe Ser Lys Tyr
145                 150                 155                 160

Ala Arg Thr Val Pro Asp Lys Leu Thr Leu Gly Glu Leu Trp Asp Leu
                165                 170                 175

Thr Glu Gly Asn Arg Asn Ala Phe Asp Ile Phe Gly Trp Leu Ala Ala
            180                 185                 190

Lys Phe Glu Trp Gly Val Leu Tyr Ile Leu Ala Arg Asp Glu Glu Gly
        195                 200                 205

Phe Leu Ser Lys Glu Ala Val Arg Arg Cys Phe Asp Gly Ser Leu Phe
    210                 215                 220

Glu Tyr Cys Ala Lys Met His Thr Thr Ser Asp Ala Lys Met Ser
225                 230                 235

<210> SEQ ID NO 95
<211> LENGTH: 243
<212> TYPE: PRT
<213> ORGANISM: Z. mays

<400> SEQUENCE: 95

Met Ser Ser Tyr Ser Pro Pro Pro Pro Pro Pro Arg Asp Gln Ser Met
1               5                   10                  15

Asp Thr Glu Ala Pro Asn Ala Pro Ile Thr Arg Glu Arg Arg Leu Asn
            20                  25                  30

Pro Asp Leu Gln Glu Gln Leu Pro Lys Pro Tyr Leu Ala Arg Ala Leu
        35                  40                  45

Glu Ala Val Asp Pro Ser His Pro Gln Gly Thr Lys Gly Arg Asp Pro
    50                  55                  60

Arg Gly Met Ser Val Leu Gln Gln His Ala Ala Phe Phe Asp Arg Asn
65                  70                  75                  80

Gly Asp Gly Val Ile Tyr Pro Trp Glu Thr Phe Gln Gly Leu Arg Ala
                85                  90                  95

Ile Gly Cys Gly Leu Thr Val Ser Phe Ala Phe Ser Ile Leu Ile Asn
            100                 105                 110

Leu Phe Leu Ser Tyr Pro Thr Gln Pro Gly Trp Leu Pro Ser Pro Leu
        115                 120                 125

Leu Ser Ile Arg Ile Asp Asn Ile His Lys Gly Lys His Gly Ser Asp
    130                 135                 140

Ser Glu Thr Tyr Asp Thr Glu Gly Arg Phe Asp Pro Ser Lys Phe Asp
145                 150                 155                 160
```

```
Ala Ile Phe Ser Lys Tyr Gly Arg Thr His Pro Asn Ala Ile Thr Arg
                165                 170                 175

Asp Glu Leu Ser Ser Met Leu Gln Gly Asn Arg Asn Thr Tyr Asp Phe
            180                 185                 190

Leu Gly Trp Leu Ala Ala Ala Gly Glu Trp Leu Leu Leu Tyr Ser Leu
        195                 200                 205

Ala Lys Asp Lys Asp Gly Leu Leu Gln Arg Glu Thr Val Arg Gly Leu
    210                 215                 220

Phe Asp Gly Ser Leu Phe Glu Arg Leu Glu Asp Asp Asn Asn Lys Lys
225                 230                 235                 240

Lys Ser Ser

<210> SEQ ID NO 96
<211> LENGTH: 348
<212> TYPE: PRT
<213> ORGANISM: S. indicum

<400> SEQUENCE: 96

Met Asp Leu Ile His Thr Phe Leu Asn Leu Ile Ala Pro Pro Phe Thr
1               5                   10                  15

Phe Phe Phe Leu Leu Phe Phe Leu Pro Pro Phe Gln Ile Phe Lys Phe
            20                  25                  30

Phe Leu Ser Ile Leu Gly Thr Leu Phe Ser Glu Asp Val Ala Gly Lys
        35                  40                  45

Val Val Val Ile Thr Gly Ala Ser Ser Gly Ile Gly Glu Ser Leu Ala
    50                  55                  60

Tyr Glu Tyr Ala Lys Arg Gly Ala Cys Leu Val Leu Ala Ala Arg Arg
65                  70                  75                  80

Glu Arg Ser Leu Gln Glu Val Ala Glu Arg Ala Arg Asp Leu Gly Ser
                85                  90                  95

Pro Asp Val Val Val Val Arg Ala Asp Val Ser Lys Ala Glu Asp Cys
            100                 105                 110

Arg Lys Val Val Asp Gln Thr Met Asn Arg Phe Gly Arg Leu Asp His
        115                 120                 125

Leu Val Asn Asn Ala Gly Ile Met Ser Val Ser Met Leu Glu Glu Val
    130                 135                 140

Glu Asp Ile Thr Gly Tyr Arg Glu Thr Met Asp Ile Asn Phe Trp Gly
145                 150                 155                 160

Tyr Val Tyr Met Thr Arg Phe Ala Ala Pro Tyr Leu Arg Asn Ser Arg
                165                 170                 175

Gly Arg Ile Val Val Leu Ser Ser Ser Ser Ser Trp Met Pro Thr Pro
            180                 185                 190

Arg Met Ser Phe Tyr Asn Ala Ser Lys Ala Ala Ile Ser Gln Phe Phe
        195                 200                 205

Glu Thr Leu Arg Val Glu Phe Gly Pro Asp Ile Gly Ile Thr Leu Val
    210                 215                 220

Thr Pro Gly Phe Ile Glu Ser Glu Leu Thr Gln Gly Lys Phe Tyr Asn
225                 230                 235                 240

Ala Gly Glu Arg Val Ile Asp Gln Asp Met Arg Asp Val Gln Val Ser
                245                 250                 255

Thr Thr Pro Ile Leu Arg Val Glu Ser Ala Ala Arg Ser Ile Val Arg
            260                 265                 270

Ser Ala Ile Arg Gly Glu Arg Tyr Val Thr Glu Pro Ala Trp Phe Arg
        275                 280                 285
```

Val Thr Tyr Trp Trp Lys Leu Phe Cys Pro Glu Val Met Glu Trp Val
290 295 300

Phe Arg Leu Met Tyr Leu Ala Ser Pro Gly Glu Pro Glu Lys Glu Thr
305 310 315 320

Phe Gly Lys Lys Val Leu Asp Tyr Thr Gly Val Lys Ser Leu Leu Tyr
325 330 335

Pro Glu Thr Val Gln Val Pro Glu Pro Lys Asn Asp
340 345

<210> SEQ ID NO 97
<211> LENGTH: 349
<212> TYPE: PRT
<213> ORGANISM: Brassica napus

<400> SEQUENCE: 97

Met Glu Leu Ile Asn Asp Phe Leu Asn Leu Thr Ala Pro Phe Phe Thr
1 5 10 15

Phe Phe Gly Leu Cys Phe Phe Leu Pro Pro Phe Tyr Phe Phe Lys Phe
20 25 30

Val Gln Ser Ile Phe Ser Thr Ile Phe Ser Glu Asn Val Tyr Gly Lys
35 40 45

Val Val Leu Ile Thr Gly Ala Ser Ser Gly Ile Gly Glu Gln Leu Ala
50 55 60

Tyr Glu Tyr Ala Ser Lys Gly Ala Cys Leu Ala Leu Thr Ala Arg Arg
65 70 75 80

Lys Asn Arg Leu Glu Glu Val Ala Glu Ile Ala Arg Glu Val Gly Ser
85 90 95

Pro Asn Val Val Thr Val His Ala Asp Val Ser Lys Pro Asp Asp Cys
100 105 110

Arg Arg Ile Val Asp Glu Thr Ile Ser His Phe Gly Arg Leu Asp His
115 120 125

Leu Val Asn Asn Ala Gly Ile Met Gln Ile Ser Met Phe Glu Asn Ile
130 135 140

Glu Glu Ile Thr Arg Thr Arg Ala Val Met Asp Thr Asn Phe Trp Gly
145 150 155 160

Ala Val Tyr Thr Thr Arg Ala Ala Leu Pro Tyr Leu Arg Gln Ser Asn
165 170 175

Gly Lys Ile Val Ala Met Ser Ser Ser Ala Ala Trp Leu Thr Ala Pro
180 185 190

Arg Met Ser Phe Tyr Asn Ala Ser Lys Ala Ala Leu Leu Asn Phe Phe
195 200 205

Glu Thr Leu Arg Ile Glu Leu Gly Ser Asp Val His Ile Thr Ile Val
210 215 220

Thr Pro Gly Tyr Ile Glu Ser Glu Leu Thr Gln Gly Lys Tyr Val Ser
225 230 235 240

Gly Glu Gly Glu Leu Val Val Asn Gln Asp Ile Arg Asp Val Gln Ile
245 250 255

Gly Ala Phe Pro Val Thr Ser Val Ser Gly Arg Ala Lys Gly Ile Val
260 265 270

Lys Gly Val Cys Arg Lys Glu Arg Tyr Val Thr Glu Pro Ser Trp Phe
275 280 285

Lys Val Thr Tyr Leu Trp Lys Val Phe Cys Pro Glu Leu Ile Glu Trp
290 295 300

Gly Cys Arg Leu Met Phe Leu Ser Gly His Gly Thr Pro Glu Glu Asn
305 310 315 320

```
Ala Leu Asn Lys Lys Ile Leu Asp Ile Pro Gly Val Arg Ser Ala Leu
                325                 330                 335

Tyr Pro Glu Pro Ile Arg Thr Pro Glu Ile Lys Ser Glu
            340                 345

<210> SEQ ID NO 98
<211> LENGTH: 350
<212> TYPE: PRT
<213> ORGANISM: Zea mays

<400> SEQUENCE: 98

Met Leu Gly Met Ser Arg Thr Gly Leu Ala Gly Ala Ala Leu Arg Val
1               5                   10                  15

Ala Leu Thr Ala Leu Leu Pro Leu Val Leu Pro Ala Tyr Tyr Val Tyr
            20                  25                  30

Lys Leu Thr Thr Tyr Leu Leu Gly Ala Val Phe Pro Glu Asp Val Ala
        35                  40                  45

Gly Lys Val Val Leu Ile Thr Gly Ala Ser Ser Gly Ile Gly Glu His
    50                  55                  60

Leu Ala Tyr Glu Tyr Ala Lys Arg Gly Ala Tyr Leu Ala Leu Val Ala
65                  70                  75                  80

Arg Arg Glu Ala Ser Leu Arg Glu Val Gly Asp Val Ala Leu Gly Leu
                85                  90                  95

Gly Ser Pro Gly Val Leu Val Leu Pro Ala Asp Val Ser Lys Pro Arg
            100                 105                 110

Asp Cys Glu Gly Phe Ile Asp Asp Thr Ile Ser Tyr Phe Gly Arg Leu
        115                 120                 125

Asp His Leu Val Asn Asn Ala Ser Ile Trp Gln Val Cys Lys Phe Glu
    130                 135                 140

Glu Ile Gln Asp Val Arg His Leu Arg Ala Leu Met Asp Ile Asn Phe
145                 150                 155                 160

Trp Gly His Val Tyr Pro Thr Arg Leu Ala Ile Pro His Leu Arg Arg
                165                 170                 175

Ser Arg Gly Arg Ile Val Gly Val Thr Ser Asn Ser Ser Tyr Ile Phe
            180                 185                 190

Ile Gly Arg Asn Thr Phe Tyr Asn Ala Ser Lys Ala Ala Ala Leu Ser
        195                 200                 205

Phe Tyr Asp Thr Leu Arg Met Glu Leu Gly Ser Asp Ile Arg Ile Thr
    210                 215                 220

Glu Val Val Pro Gly Val Val Glu Ser Glu Ile Thr Lys Gly Lys Met
225                 230                 235                 240

Leu Thr Lys Gly Gly Glu Met Lys Val Asp Gln Asp Glu Arg Asp Ala
                245                 250                 255

Ile Leu Gly Pro Thr Pro Ala Glu Pro Val Gly Asp Phe Ala Arg Thr
            260                 265                 270

Val Val Arg Asp Val Cys Arg Gly Ala Arg Tyr Val Phe Glu Pro Arg
        275                 280                 285

Trp Tyr Met Gly Val Tyr Leu Leu Arg Ala Cys Leu Pro Glu Val Leu
    290                 295                 300

Ala Trp Asn Ser Arg Leu Leu Thr Val Asp Thr Val Gly Ala Ser Thr
305                 310                 315                 320

Thr Asp Thr Leu Gly Lys Trp Leu Val Glu Leu Pro Gly Val Arg Arg
                325                 330                 335

Val Val Gln Pro Pro Ser Leu Arg Ser Pro Glu Ile Lys Asp
```

340 345 350

<210> SEQ ID NO 99
<211> LENGTH: 380
<212> TYPE: PRT
<213> ORGANISM: Brassica oleracea

<400> SEQUENCE: 99

Met Arg Asn Cys Ile Gln Asn Glu Thr Ala Gln Thr Cys Gln Thr Gln
1 5 10 15

Gly Ser Met Phe Ser Phe Phe Cys Leu Phe Pro Phe Leu Leu Pro Met
20 25 30

Phe Glu Val Ile Lys Met Val Val Ala Ser Val Ala Ser Val Val Tyr
35 40 45

Leu Gly Phe Ala Gly Val Thr Leu Ser Gly Ser Ala Val Ala Leu Ala
50 55 60

Val Ser Thr Pro Leu Phe Ile Ile Phe Ser Pro Ile Leu Leu Pro Ala
65 70 75 80

Ile Ala Ala Thr Thr Val Leu Ala Ala Gly Leu Gly Ser Lys Lys Val
85 90 95

Ala Ala Ala Pro Ala Ala Ser Pro Ser Leu Ser Leu Leu Gly Ile Pro
100 105 110

Glu Ser Ile Lys Pro Ser Asn Val Ile Pro Glu Ser Ile Lys Pro Ser
115 120 125

Asn Ile Ile Pro Glu Ser Ile Lys Pro Ser Asn Ile Ile Pro Glu Ser
130 135 140

Val Lys Pro Ser Asn Ile Lys Asp Lys Ile Lys Asp Thr Ile Gly Lys
145 150 155 160

Val Lys Asn Lys Ile Asn Ala Lys Lys Glu Glu Lys Ser Lys Gly Lys
165 170 175

Ser Glu Asp Ser Ser Lys Gly Lys Gly Lys Ser Lys Gly Glu Asp Thr
180 185 190

Thr Thr Asp Glu Asp Lys Pro Gly Ser Gly Gly Lys His Gly Lys Gly
195 200 205

Glu Ser Lys His Gly Lys Gly Glu Ser Thr His Gly Lys Gly Gly Lys
210 215 220

His Gly Ser Glu Gly Ser Ser Met Asp Glu Gly Lys His Gly Gly Lys
225 230 235 240

His Gly Ser Gly Gly Ser Pro Met Gly Val Gly Lys His Gly Ser Gly
245 250 255

Gly Lys His Glu Ser Gly Gly Ser Pro Met Gly Gly Gly Lys His Gly
260 265 270

Ser Gly Gly Lys His Glu Ser Gly Gly Ala Ser Met Gly Gly Gly Lys
275 280 285

His Gly Ser Gly Gly Arg His Glu Gly Gly Gly Ser Ala Met Gly Gly
290 295 300

Gly Lys His Gly Ser Gly Gly Lys His Gly Ser Glu Gly Lys His Gly
305 310 315 320

Gly Glu Gly Ser Ser Met Gly Lys Asn Ser Leu Ser Lys Asn Lys Lys
325 330 335

Glu Phe His Tyr Arg Asp Gln Ala Met Cys Ala Ser Ser Thr Ser Glu
340 345 350

Ser Ser Asp Gly Ser Ser Cys Gly Ser Ser Ser Asp Gly Ser Ser Ser
355 360 365

```
Cys Gly Ser Ser His Gly Ser Gly Gly Lys His Ile
    370                 375                 380

<210> SEQ ID NO 100
<211> LENGTH: 186
<212> TYPE: PRT
<213> ORGANISM: Zea mays

<400> SEQUENCE: 100

Met Ala Asp Arg Cys Arg Ser Gly Ile Tyr Gly Gly Ala His Ala Thr
1               5                   10                  15

Tyr Gly Gln Gln Gln Gln Gln Gly Gly Gly Gly Arg Pro Met Gly Cys
            20                  25                  30

Gln Val Lys Gly Met Leu His Cys Lys Gly Pro Thr Ala Ser Gln Ala
        35                  40                  45

Leu Thr Val Ala Thr Leu Phe Pro Leu Gly Gly Leu Leu Leu Val Leu
    50                  55                  60

Ser Gly Leu Ala Leu Thr Ala Ser Val Val Gly Leu Ala Val Ala Thr
65                  70                  75                  80

Pro Val Phe Leu Ile Phe Ser Pro Val Leu Val Pro Ala Ala Leu Leu
                85                  90                  95

Ile Gly Thr Ala Val Met Gly Phe Leu Thr Ser Gly Ala Leu Gly Leu
            100                 105                 110

Gly Gly Leu Ser Ser Leu Thr Cys Leu Ala Asn Thr Ala Arg Gln Ala
        115                 120                 125

Phe Gln Arg Thr Pro Asp Tyr Val Cys Glu Ala His Arg Arg Met Ala
    130                 135                 140

Cys Ala Ala Ala His Ala Gly His Lys Thr Ala Gln Ala Gly Gln Ala
145                 150                 155                 160

Ile Gln Gly Arg Ala Gln Cys Ala Gly Ala Gly Gly Gly Ala Gly Ala
                165                 170                 175

Gly Ala Gly Gly Gly Gly Arg Ala Ser Ser
            180                 185

<210> SEQ ID NO 101
<211> LENGTH: 148
<212> TYPE: PRT
<213> ORGANISM: Oryza sativa

<400> SEQUENCE: 101

Met Gly Asp Gln His Cys Gly Val Ile Gly Gly Gly Gly Tyr Gly Cys
1               5                   10                  15

Arg Gly Gly Gln Glu Gln Gln Cys Lys Gln Pro Phe Met Met Thr Ala
            20                  25                  30

Leu Lys Thr Val Thr Ala Ala Thr Ala Gly Gly Ser Ile Leu Val Leu
        35                  40                  45

Ser Gly Leu Ile Leu Ala Gly Thr Val Ile Ala Leu Thr Val Ala Thr
    50                  55                  60

Pro Val Leu Val Ile Phe Ser Pro Val Leu Val Pro Ala Ala Ile Ala
65                  70                  75                  80

Leu Ala Leu Met Ala Ala Gly Phe Val Thr Ser Val Gly Leu Gly Val
                85                  90                  95

Ala Ala Leu Ser Val Phe Ser Trp Met Tyr Lys Tyr Leu Thr Gly Lys
            100                 105                 110

His Pro Pro Gly Ala Asp His Leu Cys His Thr Lys Ala Arg Val Ala
        115                 120                 125
```

Ser Lys Leu Arg Cys Ile Lys Glu Ala Ala His His Leu Ile Cys Gln
130 135 140

Ala Gln Ala Ser
145

<210> SEQ ID NO 102
<211> LENGTH: 245
<212> TYPE: PRT
<213> ORGANISM: S. indicum

<400> SEQUENCE: 102

Met Ala Thr His Val Leu Ala Ala Ala Ala Cys Arg Asn Ala Ala Leu
1 5 10 15

Ala Pro Cys Ala Pro Leu Ala Pro Val Thr Met Cys Arg Pro Val Arg
20 25 30

Thr Asp Leu Glu Thr Ser Ile Pro Lys Pro Tyr Met Ala Arg Gly Leu
35 40 45

Val Ala Pro Asp Met Asp His Pro Asn Gly Thr Pro Gly His Val His
50 55 60

Asp Asn Leu Ser Val Leu Gln Gln His Cys Ala Phe Phe Asp Gln Asp
65 70 75 80

Asp Asn Gly Ile Ile Tyr Pro Trp Glu Thr Tyr Ser Gly Leu Arg Gln
85 90 95

Ile Gly Phe Asn Val Ile Ala Ser Leu Ile Met Ala Ile Val Ile Asn
100 105 110

Val Ala Leu Ser Tyr Pro Thr Leu Pro Gly Trp Ile Pro Ser Pro Phe
115 120 125

Phe Pro Ile Tyr Leu Tyr Asn Ile His Lys Ala Lys His Gly Ser Asp
130 135 140

Ser Gly Thr Tyr Asp Thr Glu Gly Arg Tyr Leu Pro Met Asn Phe Glu
145 150 155 160

Asn Leu Phe Ser Lys His Ala Arg Thr Met Pro Asp Arg Leu Thr Leu
165 170 175

Gly Glu Leu Trp Ser Met Thr Glu Ala Asn Arg Glu Ala Phe Asp Ile
180 185 190

Phe Gly Trp Ile Ala Ser Lys Met Glu Trp Thr Leu Leu Tyr Ile Leu
195 200 205

Ala Arg Cys Gln Asp Gly Phe Leu Ser Cys Glu Ala Ile Arg Arg Cys
210 215 220

Tyr Asp Gly Ser Leu Phe Glu Tyr Cys Ala Lys Met Gln Arg Gly Ala
225 230 235 240

Glu Asp Lys Met Cys
245

<210> SEQ ID NO 103
<211> LENGTH: 239
<212> TYPE: PRT
<213> ORGANISM: G. soja

<400> SEQUENCE: 103

Met Ala Ala Cys Met Glu Arg Glu Ser Leu Ile Thr Cys Ala Pro Asn
1 5 10 15

Ala Pro Val Thr Ala Gln Arg Cys Val Arg Asn Asp Leu Glu Asn Ser
20 25 30

Leu Pro Lys Pro Tyr Leu Pro Arg Ala Leu Lys Ala Pro Asp Thr Gly
35 40 45

His Pro Asn Gly Thr Ala Gly His Arg His His Asn Leu Ser Val Leu
50 55 60

Gln Gln His Cys Ala Phe Phe Asp Gln Asp Asp Asn Gly Ile Ile Tyr
65 70 75 80

Pro Trp Glu Thr Tyr Met Gly Leu Arg Ser Ile Gly Phe Asn Val Val
85 90 95

Ala Ser Val Ile Met Ala Ile Val Ile Asn Val Gly Leu Ser Tyr Pro
100 105 110

Thr Leu Pro Asn Trp Phe Pro Ser Leu Leu Phe Pro Ile Tyr Ile His
115 120 125

Asn Ile His Lys Ala Lys His Gly Ser Asp Ser Gly Val Tyr Asp Thr
130 135 140

Glu Gly Arg Tyr Val Pro Ala Asn Ile Glu Asn Ile Phe Ser Lys Tyr
145 150 155 160

Ala Arg Thr Val Pro Asp Lys Leu Thr Leu Gly Glu Leu Trp Asp Leu
165 170 175

Thr Glu Gly Asn Arg Asn Ala Phe Asp Ile Phe Gly Trp Leu Ala Ala
180 185 190

Lys Phe Glu Trp Gly Val Leu Tyr Ile Leu Ala Arg Cys Glu Glu Gly
195 200 205

Phe Leu Ser Lys Cys Ala Val Arg Arg Cys Phe Asp Gly Ser Leu Phe
210 215 220

Glu Tyr Cys Ala Lys Met His Thr Thr Ser Asp Ala Cys Met Ser
225 230 235

<210> SEQ ID NO 104
<211> LENGTH: 243
<212> TYPE: PRT
<213> ORGANISM: Z. mays

<400> SEQUENCE: 104

Met Ser Ser Tyr Ser Pro Pro Pro Pro Pro Pro Arg Asp Gln Ser Met
1 5 10 15

Asp Thr Cys Ala Pro Asn Ala Pro Ile Thr Cys Glu Arg Arg Leu Asn
20 25 30

Pro Asp Leu Gln Cys Gln Leu Pro Lys Pro Tyr Leu Ala Arg Ala Leu
35 40 45

Glu Ala Val Asp Pro Ser His Pro Gln Gly Thr Lys Gly Arg Asp Pro
50 55 60

Arg Gly Met Ser Val Leu Gln Gln His Ala Ala Phe Phe Asp Arg Asn
65 70 75 80

Gly Asp Gly Val Ile Tyr Pro Trp Glu Thr Phe Gln Gly Leu Arg Ala
85 90 95

Ile Gly Cys Gly Leu Thr Val Ser Phe Ala Phe Ser Ile Leu Ile Asn
100 105 110

Leu Phe Leu Ser Tyr Pro Thr Gln Pro Gly Trp Leu Pro Ser Pro Leu
115 120 125

Leu Ser Ile Arg Ile Asp Asn Ile His Lys Gly Lys His Gly Ser Asp
130 135 140

Ser Glu Thr Tyr Asp Thr Glu Gly Arg Phe Asp Pro Ser Lys Phe Asp
145 150 155 160

Ala Ile Phe Ser Lys Tyr Gly Arg Thr His Pro Asn Ala Ile Thr Arg
165 170 175

Asp Glu Leu Ser Ser Met Leu Gln Gly Asn Arg Asn Thr Tyr Asp Phe
180 185 190

Leu Gly Trp Leu Ala Ala Ala Gly Glu Trp Leu Leu Leu Tyr Ser Leu
195 200 205

Ala Lys Asp Lys Asp Gly Leu Leu Gln Arg Cys Thr Val Arg Gly Leu
210 215 220

Phe Asp Gly Ser Leu Phe Cys Arg Leu Glu Asp Asp Asn Asn Lys Lys
225 230 235 240

Cys Ser Ser

<210> SEQ ID NO 105
<211> LENGTH: 348
<212> TYPE: PRT
<213> ORGANISM: S. indicum

<400> SEQUENCE: 105

Met Asp Leu Ile Cys Thr Phe Leu Asn Leu Ile Ala Pro Pro Phe Thr
1 5 10 15

Phe Phe Phe Leu Leu Phe Phe Leu Pro Pro Phe Cys Ile Phe Lys Phe
20 25 30

Phe Leu Cys Ile Leu Gly Thr Leu Phe Ser Glu Asp Val Ala Gly Lys
35 40 45

Val Val Val Ile Thr Gly Ala Ser Ser Gly Ile Gly Glu Ser Leu Ala
50 55 60

Tyr Glu Tyr Ala Lys Arg Gly Ala Cys Leu Val Leu Ala Ala Arg Arg
65 70 75 80

Glu Arg Ser Leu Gln Glu Val Ala Glu Arg Ala Arg Asp Leu Gly Ser
85 90 95

Pro Asp Val Val Val Val Arg Ala Asp Val Ser Lys Ala Glu Asp Cys
100 105 110

Arg Lys Val Val Asp Gln Thr Met Asn Arg Phe Gly Arg Leu Asp His
115 120 125

Leu Val Asn Asn Ala Gly Ile Met Ser Val Ser Met Leu Glu Glu Val
130 135 140

Glu Asp Ile Thr Gly Tyr Arg Glu Thr Met Asp Ile Asn Phe Trp Gly
145 150 155 160

Tyr Val Tyr Met Thr Arg Phe Ala Ala Pro Tyr Leu Arg Asn Ser Arg
165 170 175

Gly Arg Ile Val Val Leu Ser Ser Ser Ser Ser Trp Met Pro Thr Pro
180 185 190

Arg Met Ser Phe Tyr Asn Ala Ser Lys Ala Ala Ile Ser Gln Phe Phe
195 200 205

Glu Thr Leu Arg Val Glu Phe Gly Pro Asp Ile Gly Ile Thr Leu Val
210 215 220

Thr Pro Gly Phe Ile Glu Ser Glu Leu Thr Gln Gly Lys Phe Tyr Asn
225 230 235 240

Ala Gly Glu Arg Val Ile Asp Gln Asp Met Arg Asp Val Gln Val Ser
245 250 255

Thr Thr Pro Ile Leu Arg Val Glu Ser Ala Ala Arg Ser Ile Val Arg
260 265 270

Ser Ala Ile Arg Gly Glu Arg Tyr Val Thr Glu Pro Ala Trp Phe Arg
275 280 285

Val Thr Tyr Trp Trp Lys Leu Phe Cys Pro Glu Val Met Glu Trp Val
290 295 300

Phe Arg Leu Met Tyr Leu Ala Ser Pro Gly Cys Pro Glu Lys Cys Thr
305 310 315 320

```
Phe Gly Lys Lys Val Leu Cys Tyr Thr Gly Val Lys Ser Leu Leu Tyr
                325                 330                 335

Pro Glu Thr Val Gln Val Pro Glu Pro Lys Asn Asp
            340                 345

<210> SEQ ID NO 106
<211> LENGTH: 349
<212> TYPE: PRT
<213> ORGANISM: Brassica napus

<400> SEQUENCE: 106

Met Glu Leu Ile Asn Cys Phe Leu Asn Leu Thr Ala Pro Phe Phe Thr
1               5                   10                  15

Phe Phe Gly Leu Cys Phe Phe Leu Pro Pro Phe Tyr Phe Phe Cys Phe
            20                  25                  30

Val Gln Cys Ile Phe Ser Thr Ile Phe Ser Glu Asn Val Tyr Gly Lys
        35                  40                  45

Val Val Leu Ile Thr Gly Ala Ser Ser Gly Ile Gly Glu Gln Leu Ala
    50                  55                  60

Tyr Glu Tyr Ala Ser Lys Gly Ala Cys Leu Ala Leu Thr Ala Arg Arg
65                  70                  75                  80

Lys Asn Arg Leu Glu Glu Val Ala Glu Ile Ala Arg Glu Val Gly Ser
                85                  90                  95

Pro Asn Val Val Thr Val His Ala Asp Val Ser Lys Pro Asp Asp Cys
            100                 105                 110

Arg Arg Ile Val Asp Glu Thr Ile Ser His Phe Gly Arg Leu Asp His
        115                 120                 125

Leu Val Asn Asn Ala Gly Ile Met Gln Ile Ser Met Phe Glu Asn Ile
    130                 135                 140

Glu Glu Ile Thr Arg Thr Arg Ala Val Met Asp Thr Asn Phe Trp Gly
145                 150                 155                 160

Ala Val Tyr Thr Thr Arg Ala Ala Leu Pro Tyr Leu Arg Gln Ser Asn
                165                 170                 175

Gly Lys Ile Val Ala Met Ser Ser Ser Ala Ala Trp Leu Thr Ala Pro
            180                 185                 190

Arg Met Ser Phe Tyr Asn Ala Ser Lys Ala Ala Leu Leu Asn Phe Phe
        195                 200                 205

Glu Thr Leu Arg Ile Glu Leu Gly Ser Asp Val His Ile Thr Ile Val
    210                 215                 220

Thr Pro Gly Tyr Ile Glu Ser Glu Leu Thr Gln Gly Lys Tyr Val Ser
225                 230                 235                 240

Gly Glu Gly Glu Leu Val Val Asn Gln Asp Ile Arg Asp Val Gln Ile
                245                 250                 255

Gly Ala Phe Pro Val Thr Ser Val Ser Gly Arg Ala Lys Gly Ile Val
            260                 265                 270

Lys Gly Val Cys Arg Lys Glu Arg Tyr Val Thr Glu Pro Ser Trp Phe
        275                 280                 285

Lys Val Thr Tyr Leu Trp Lys Val Phe Cys Pro Glu Leu Ile Glu Trp
    290                 295                 300

Gly Cys Arg Leu Met Phe Leu Ser Gly His Gly Thr Pro Cys Glu Asn
305                 310                 315                 320

Ala Leu Asn Lys Lys Ile Leu Asp Ile Pro Gly Val Arg Ser Ala Leu
                325                 330                 335

Tyr Pro Cys Pro Ile Arg Thr Pro Cys Ile Lys Ser Glu
```

340 345

<210> SEQ ID NO 107
<211> LENGTH: 349
<212> TYPE: PRT
<213> ORGANISM: Z. mays

<400> SEQUENCE: 107

```
Met Glu Leu Ile Asn Cys Phe Leu Asn Leu Thr Ala Pro Phe Phe Thr
1               5                   10                  15

Phe Phe Gly Leu Cys Phe Phe Leu Pro Pro Phe Tyr Phe Phe Cys Phe
            20                  25                  30

Val Gln Cys Ile Phe Ser Thr Ile Phe Ser Glu Asn Val Tyr Gly Lys
        35                  40                  45

Val Val Leu Ile Thr Gly Ala Ser Ser Gly Ile Gly Glu Gln Leu Ala
    50                  55                  60

Tyr Glu Tyr Ala Ser Lys Gly Ala Cys Leu Ala Leu Thr Ala Arg Arg
65                  70                  75                  80

Lys Asn Arg Leu Glu Glu Val Ala Glu Ile Ala Arg Glu Val Gly Ser
                85                  90                  95

Pro Asn Val Val Thr Val His Ala Asp Val Ser Lys Pro Asp Asp Cys
            100                 105                 110

Arg Arg Ile Val Asp Glu Thr Ile Ser His Phe Gly Arg Leu Asp His
        115                 120                 125

Leu Val Asn Asn Ala Gly Ile Met Gln Ile Ser Met Phe Glu Asn Ile
    130                 135                 140

Glu Glu Ile Thr Arg Thr Arg Ala Val Met Asp Thr Asn Phe Trp Gly
145                 150                 155                 160

Ala Val Tyr Thr Thr Arg Ala Ala Leu Pro Tyr Leu Arg Gln Ser Asn
                165                 170                 175

Gly Lys Ile Val Ala Met Ser Ser Ser Ala Ala Trp Leu Thr Ala Pro
            180                 185                 190

Arg Met Ser Phe Tyr Asn Ala Ser Lys Ala Ala Leu Leu Asn Phe Phe
        195                 200                 205

Glu Thr Leu Arg Ile Glu Leu Gly Ser Asp Val His Ile Thr Ile Val
    210                 215                 220

Thr Pro Gly Tyr Ile Glu Ser Glu Leu Thr Gln Gly Lys Tyr Val Ser
225                 230                 235                 240

Gly Glu Gly Glu Leu Val Val Asn Gln Asp Ile Arg Asp Val Gln Ile
                245                 250                 255

Gly Ala Phe Pro Val Thr Ser Val Ser Gly Arg Ala Lys Gly Ile Val
            260                 265                 270

Lys Gly Val Cys Arg Lys Glu Arg Tyr Val Thr Glu Pro Ser Trp Phe
        275                 280                 285

Lys Val Thr Tyr Leu Trp Lys Val Phe Cys Pro Glu Leu Ile Glu Trp
    290                 295                 300

Gly Cys Arg Leu Met Phe Leu Ser Gly His Gly Thr Pro Cys Glu Asn
305                 310                 315                 320

Ala Leu Asn Lys Lys Ile Leu Asp Ile Pro Gly Val Arg Ser Ala Leu
                325                 330                 335

Tyr Pro Cys Pro Ile Arg Thr Pro Cys Ile Lys Ser Glu
            340                 345
```

<210> SEQ ID NO 108
<211> LENGTH: 11

<212> TYPE: PRT
<213> ORGANISM: Artificial sequence
<220> FEATURE:
<223> OTHER INFORMATION: Consensus sequence of Tropaeolum majus DGAT1 sequences
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid

<400> SEQUENCE: 108

```
Xaa Leu Xaa Lys Xaa Xaa Ser Xaa Xaa Xaa Val
1               5                   10
```

<210> SEQ ID NO 109
<211> LENGTH: 12
<212> TYPE: PRT
<213> ORGANISM: Artificial sequence
<220> FEATURE:
<223> OTHER INFORMATION: GlcF protein consensus sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid

<400> SEQUENCE: 109

```
Cys Xaa Xaa Cys Xaa Xaa Cys Xaa Xaa Xaa Cys Pro
1               5                   10
```

<210> SEQ ID NO 110
<211> LENGTH: 12
<212> TYPE: DNA
<213> ORGANISM: Artificial sequence
<220> FEATURE:
<223> OTHER INFORMATION: Example of inverted repeat sequence

<400> SEQUENCE: 110

```
gatctataga tc                                                          12
```

<210> SEQ ID NO 111
<211> LENGTH: 12
<212> TYPE: DNA
<213> ORGANISM: Artificial sequence
<220> FEATURE:
<223> OTHER INFORMATION: Example of inverted repeat sequence

<400> SEQUENCE: 111

```
ctagatatct ag                                                          12
```

<210> SEQ ID NO 112
<211> LENGTH: 7026

<212> TYPE: DNA
<213> ORGANISM: Artificial sequence
<220> FEATURE:
<223> OTHER INFORMATION: Synthetic construct

<400> SEQUENCE: 112
tcgacgaatt aattccaatc ccacaaaaat ctgagcttaa cagcacagtt gctcctctca 60
gagcagaatc gggtattcaa caccctcata tcaactacta cgttgtgtat aacggtccac 120
atgccggtat atacgatgac tggggttgta caaaggcggc aacaaacggc gttcccggag 180
ttgcacacaa gaaatttgcc actattacag aggcaagagc agcagctgac gcgtacacaa 240
caagtcagca aacagacagg ttgaacttca tccccaaagg agaagctcaa ctcaagccca 300
agagctttgc taaggcccta acaagcccac caaagcaaaa agcccactgg ctcacgctag 360
gaaccaaaag gcccagcagt gatccagccc caaaagagat ctcctttgcc ccggagatta 420
caatggacga tttcctctat ctttacgatc taggaaggaa gttcgaaggt gaaggtgacg 480
acactatgtt caccactgat aatgagaagg ttagcctctt caatttcaga aagaatgctg 540
acccacagat ggttagagag gcctacgcag caggtctcat caagacgatc tacccgagta 600
acaatctcca ggagatcaaa taccttccca agaaggttaa agatgcagtc aaaagattca 660
ggactaattg catcaagaac acagagaaag acatatttct caagatcaga agtactattc 720
cagtatggac gattcaaggc ttgcttcata aaccaaggca agtaatagag attggagtct 780
ctaaaaaggt agttcctact gaatctaagg ccatgcatgg agtctaagat tcaaatcgag 840
gatctaacag aactcgccgt gaagactggc gaacagttca tacagagtct tttacgactc 900
aatgacaaga agaaaatctt cgtcaacatg gtggagcacg acactctggt ctactccaaa 960
aatgtcaaag atacagtctc agaagaccaa agggctattg agacttttca acaaaggata 1020
atttcgggaa acctcctcgg attccattgc ccagctatct gtcacttcat cgaaaggaca 1080
gtagaaaagg aaggtggctc ctacaaatgc catcattgcg ataaaggaaa ggctatcatt 1140
caagatctct ctgccgacag tggtcccaaa gatggacccc cacccacgag gagcatcgtg 1200
gaaaaagaag acgttccaac cacgtcttca aagcaagtgg attgatgtga catctccact 1260
gacgtaaggg atgacgcaca atcccactat ccttcgcaag acccttcctc tatataagga 1320
agttcatttc atttggagag gacacgctcg aggaattcgg taccccatca caagtttgta 1380
caaaaaagca ggctgcggcc gcttgctccc ttaaaaaaaa ccatggcaga gcattacgga 1440
caacagcaac agactagagc acctcatctt cagcttcaac ctagagcaca gagagttgtg 1500
aaggctgcta ctgctgttac tgtaaatttc tgtgttcctt attctctcaa aatcttcgat 1560
tttgttttcg ttcgatccca atttcgtata tgttctttgg tttagattct gttaatctta 1620
gatcgaagac gattttctgg gtttgatcgt tagatatcat cttaattctc gattagggtt 1680
tcatagatat catccgattt gttcaaataa tttgagtttt gtcgaataat tactcttcga 1740
tttgtgattt ctatctagat ctggtgttag tttctagttt gtgcgatcga atttgtcgat 1800
taatctgagt ttttctgatt aacaggctgg aggatctctt cttgttctct ctggacttac 1860
tctcgctgga actgttatcg ctctcactat cgctacacct cttctcgtta tcttctctcc 1920
tgttctcgtt cctgctgtga tcactatctt ccttctcgga gctggatttc ttgcttctgg 1980
tggatttgga gttgctgctc tctctgttct ctcttggatc tacagatacc tcactggaaa 2040
acatcctcca ggtgctgatc aacttgagtc tgctaagact aagctcgctt ctaaggctag 2100
agagatgaag gatagagcag agcaattctc tcaacagcct gttgctggat ctcagacttc 2160

-continued

```
ttaatgaaca tatggtcctg ctttaatgag atatgcgaga cgcctatgat cgcatgatat   2220
ttgctttcaa ttctgttgtg cacgttgtaa aaaacctgag catgtgtagc tcagatcctt   2280
accgccggtt tcggttcatt ctaatgaata tatcacccgt tactatcgta tttttatgaa   2340
taatattctc cgttcaattt actgattgta ccctactact tatatgtaca atattaaaat   2400
gaaaacaata tattgtgctg aataggttta tagcgacatc tatgatagag cgccacaata   2460
acaaacaatt gcgttttatt attacaaatc caattttaaa aaaagcggca gaaccggtca   2520
aacctaaaag actgattaca taaatcttat tcaaatttca aaaggcccca ggggctagta   2580
tctacgacac accgagcggc gaactaataa cgttcactga agggaactcc ggttccccgc   2640
cggcgcgcat gggtgagatt ccttgaagtt gagtattggc cgtccgctct accgaaagtt   2700
acgggcacca ttcaacccgg tccagcacgg cggccgggta accgacttgc tgccccgaga   2760
attatgcagc atttttttgg tgtatgtggg ccccaaatga agtgcaggtc aaaccttgac   2820
agtgacgaca aatcgttggg cgggtccagg gcgaattttg cgacaacatg tcgaggctca   2880
gcaggacctg caggcatgca agctagctta ctagtgatgc atattctata gtgtcaccta   2940
aatcttcgac gaattaattc caatcccaca aaaatctgag cttaacagca cagttgctcc   3000
tctcagagca gaatcgggta ttcaacaccc tcatatcaac tactacgttg tgtataacgg   3060
tccacatgcc ggtatatacg atgactgggg ttgtacaaag gcggcaacaa acggcgttcc   3120
cggagttgca cacaagaaat ttgccactat tacagaggca agagcagcag ctgacgcgta   3180
cacaacaagt cagcaaacag acaggttgaa cttcatcccc aaaggagaag ctcaactcaa   3240
gcccaagagc tttgctaagg ccctaacaag cccaccaaag caaaaagccc actggctcac   3300
gctaggaacc aaaaggccca gcagtgatcc agccccaaaa gagatctcct ttgccccgga   3360
gattacaatg gacgatttcc tctatcttta cgatctagga aggaagttcg aaggtgaagg   3420
tgacgacact atgttcacca ctgataatga gaaggttagc ctcttcaatt tcagaaagaa   3480
tgctgaccca cagatggtta gagaggccta cgcagcaggt ctcatcaaga cgatctaccc   3540
gagtaacaat ctccaggaga tcaaatacct tcccaagaag gttaaagatg cagtcaaaag   3600
attcaggact aattgcatca agaacacaga gaaagacata tttctcaaga tcagaagtac   3660
tattccagta tggacgattc aaggcttgct tcataaacca aggcaagtaa tagagattgg   3720
agtctctaaa aaggtagttc ctactgaatc taaggccatg catggagtct aagattcaaa   3780
tcgaggatct aacagaactc gccgtgaaga ctggcgaaca gttcatacag agtcttttac   3840
gactcaatga caagaagaaa atcttcgtca acatggtgga gcacgacact ctggtctact   3900
ccaaaaatgt caaagataca gtctcagaag accaaagggc tattgagact tttcaacaaa   3960
ggataatttc gggaaacctc ctcggattcc attgcccagc tatctgtcac ttcatcgaaa   4020
ggacagtaga aaaggaaggt ggctcctaca aatgccatca ttgcgataaa ggaaaggcta   4080
tcattcaaga tctctctgcc gacagtggtc ccaaagatgg acccccaccc acgaggagca   4140
tcgtggaaaa agaagacgtt ccaaccacgt cttcaaagca agtggattga tgtgacatct   4200
ccactgacgt aagggatgac gcacaatccc actatccttc gcaagaccct tcctctatat   4260
aaggaagttc atttcatttg gagaggacac gggatccttg ctccgttaaa aaaaaccatg   4320
gctatcctcg attctgctgg tgttactact gtgactgaga atggtggtgg agagttcgtt   4380
gatctcgata gactcagaag aagaaagtct agatctgtaa atttctgtgt tccttattct   4440
ctcaaaatct tcgattttgt tttcgttcga tcccaatttc gtatatgttc tttggtttag   4500
attctgttaa tcttagatcg aagacgattt tctgggtttg atcgttagat atcatcttaa   4560
```
ttctcgatta gggtttcata gatatcatcc gatttgttca aataatttga gttttgtcga 4620
ataattactc ttcgatttgt gatttctatc tagatctggt gttagtttct agtttgtgcg 4680
atcgaatttg tcgattaatc tgagtttttc tgattaacag gattcttcta acggacttct 4740
cctctctgga tctgataaca actctccttc tgatgatgtt ggtgctcctg ctgatgtgag 4800
agatagaatc gattctgtgg tgaacgatga tgctcaaggt actgctaacc tcgctggtga 4860
taataacggt ggaggtgata acaatggtgg aggaagaggt ggaggtgaag gtagaggaaa 4920
cgctgatgct actttcactt acagaccatc tgtgcctgct catagaagag ctagagagtc 4980
tcctctctct tctgatgcta tcttcaagca gtctcacgct ggacttttca acctctgtgt 5040
ggtggttctt atcgctgtga actctagact catcatcgag aacctcatga agtacggatg 5100
gctcatcaga actgatttct ggttctcttc tagatctctc agagattggc ctcttttcat 5160
gtgctgcatc tcactctcaa tcttccctct cgctgctttt actgttgaga agctcgtgct 5220
ccagaagtat atcgctgaac ctgtggtgat cttcctccac atcatcatca ctatgactga 5280
ggttctctac cctgtttacg tgactctcag atgcgattct gctttcctct ctggtgttac 5340
tcttatgctc ctcacttgca ttgtgtggct taagctcgtg tcttacgctc acacttctta 5400
cgatatcaga tctctcgcta acgctgctga taaggctaac cctgaagtgt cttactacgt 5460
gtctctcaag tctctcgctt acttcatggt tgctcctaca ctttgttacc agccatctta 5520
ccctagatct gcttgcatta gaaagggatg ggtggcaaga caattcgcta agttggtgat 5580
cttcactgga ttcatgggat tcatcatcga gcagtacatc aaccctattg tgagaaactc 5640
taagcaccct ctcaagggtg atcttctcta cgctatcgag agagttctta agctctctgt 5700
gcctaacctt tatgtgtggc tctgcatgtt ctactgtttc ttccacctct ggcttaacat 5760
ccttgctgag ttgctttgct tcggagatag agagttctac aaggattggt ggaacgctaa 5820
gtctgttgga gattattgga gaatgtggaa catgcctgtg cataagtgga tggtgcgtca 5880
catctacttc ccttgcctca gatctaagat ccctaagact ctcgctatca ttatcgcttt 5940
cctcgtgtct gctgttttcc atgagttgtg tatcgctgtt ccttgcagac ttttcaagct 6000
ttgggctttc ctcggaatca tgttccaggt tccactcgtg ttcatcacta actacctcca 6060
agagagattc ggatctactg ttggaaacat gatttctgg ttcattttct gcatcttcgg 6120
acagcctatg tgcgttctcc tctactacca cgatctcatg aacagaaagg gatctatgtc 6180
ttaatgaagg atccacccag ctttcttgta caaagtggtg atgggttcga aatcgataag 6240
cttggatcct ctagagtcct gctttaatga gatatgcgag acgcctatga tcgcatgata 6300
tttgctttca attctgttgt gcacgttgta aaaaacctga gcatgtgtag ctcagatcct 6360
taccgccggt ttcggttcat tctaatgaat atatcacccg ttactatcgt atttttatga 6420
ataatattct ccgttcaatt tactgattgt accctactac ttatatgtac aatattaaaa 6480
tgaaaacaat atattgtgct gaataggttt atagcgacat ctatgataga gcgccacaat 6540
aacaaacaat tgcgttttat tattacaaat ccaattttaa aaaaagcggc agaaccggtc 6600
aaacctaaaa gactgattac ataaatctta ttcaaatttc aaaaggcccc aggggctagt 6660
atctacgaca caccgagcgg cgaactaata acgttcactg aagggaactc cggttccccg 6720
ccggcgcgca tgggtgagat tccttgaagt tgagtattgg ccgtccgctc taccgaaagt 6780
tacgggcacc attcaacccg gtccagcacg gcggccgggt aaccgacttg ctgccccgag 6840
aattatgcag catttttttg gtgtatgtgg gccccaaatg aagtgcaggt caaaccttga 6900

-continued

```
cagtgacgac aaatcgttgg gcgggtccag ggcgaatttt gcgacaacat gtcgaggctc   6960

agcaggacct gcaggcatgc aagctagctt actagtgatg catattctat agtgtcacct   7020

aaatct                                                              7026
```

<210> SEQ ID NO 113
<211> LENGTH: 33
<212> TYPE: PRT
<213> ORGANISM: Artificial sequence
<220> FEATURE:
<223> OTHER INFORMATION: Synthetic peptide

<400> SEQUENCE: 113

```
Met Ala Glu His Tyr Gly Gln Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr
```

<210> SEQ ID NO 114
<211> LENGTH: 112
<212> TYPE: PRT
<213> ORGANISM: Artificial sequence
<220> FEATURE:
<223> OTHER INFORMATION: Synthetic peptide

<400> SEQUENCE: 114

```
Ala Gly Gly Ser Leu Leu Val Leu Ser Gly Leu Thr Leu Ala Gly Thr
1               5                   10                  15

Val Ile Ala Leu Thr Ile Ala Thr Pro Leu Leu Val Ile Phe Ser Pro
            20                  25                  30

Val Leu Val Pro Ala Val Ile Thr Ile Phe Leu Leu Gly Ala Gly Phe
        35                  40                  45

Leu Ala Ser Gly Gly Phe Gly Val Ala Ala Leu Ser Val Leu Ser Trp
    50                  55                  60

Ile Tyr Arg Tyr Leu Thr Gly Lys His Pro Pro Gly Ala Asp Gln Leu
65                  70                  75                  80

Glu Ser Ala Lys Thr Lys Leu Ala Ser Lys Ala Arg Glu Met Lys Asp
                85                  90                  95

Arg Ala Glu Gln Phe Ser Gln Gln Pro Val Ala Gly Ser Gln Thr Ser
            100                 105                 110
```

<210> SEQ ID NO 115
<211> LENGTH: 33
<212> TYPE: PRT
<213> ORGANISM: Artificial sequence
<220> FEATURE:
<223> OTHER INFORMATION: Synthetic peptide

<400> SEQUENCE: 115

```
Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser
```

<210> SEQ ID NO 116
<211> LENGTH: 487
<212> TYPE: PRT
<213> ORGANISM: Artificial sequence
<220> FEATURE:

-continued

<223> OTHER INFORMATION: Synthetic peptide

<400> SEQUENCE: 116

```
Asp Ser Ser Asn Gly Leu Leu Leu Ser Gly Ser Asp Asn Asn Ser Pro
1               5                   10                  15

Ser Asp Asp Val Gly Ala Pro Ala Asp Val Arg Asp Arg Ile Asp Ser
            20                  25                  30

Val Val Asn Asp Asp Ala Gln Gly Thr Ala Asn Leu Ala Gly Asp Asn
        35                  40                  45

Asn Gly Gly Gly Asp Asn Asn Gly Gly Gly Arg Gly Gly Gly Glu Gly
    50                  55                  60

Arg Gly Asn Ala Asp Ala Thr Phe Thr Tyr Arg Pro Ser Val Pro Ala
65                  70                  75                  80

His Arg Arg Ala Arg Glu Ser Pro Leu Ser Ser Asp Ala Ile Phe Lys
                85                  90                  95

Gln Ser His Ala Gly Leu Phe Asn Leu Cys Val Val Val Leu Ile Ala
            100                 105                 110

Val Asn Ser Arg Leu Ile Ile Glu Asn Leu Met Lys Tyr Gly Trp Leu
        115                 120                 125

Ile Arg Thr Asp Phe Trp Phe Ser Ser Arg Ser Leu Arg Asp Trp Pro
    130                 135                 140

Leu Phe Met Cys Cys Ile Ser Leu Ser Ile Phe Pro Leu Ala Ala Phe
145                 150                 155                 160

Thr Val Glu Lys Leu Val Leu Gln Lys Tyr Ile Ala Glu Pro Val Val
                165                 170                 175

Ile Phe Leu His Ile Ile Ile Thr Met Thr Glu Val Leu Tyr Pro Val
            180                 185                 190

Tyr Val Thr Leu Arg Cys Asp Ser Ala Phe Leu Ser Gly Val Thr Leu
        195                 200                 205

Met Leu Leu Thr Cys Ile Val Trp Leu Lys Leu Val Ser Tyr Ala His
    210                 215                 220

Thr Ser Tyr Asp Ile Arg Ser Leu Ala Asn Ala Ala Asp Lys Ala Asn
225                 230                 235                 240

Pro Glu Val Ser Tyr Tyr Val Ser Leu Lys Ser Leu Ala Tyr Phe Met
                245                 250                 255

Val Ala Pro Thr Leu Cys Tyr Gln Pro Ser Tyr Pro Arg Ser Ala Cys
            260                 265                 270

Ile Arg Lys Gly Trp Val Ala Arg Gln Phe Ala Lys Leu Val Ile Phe
        275                 280                 285

Thr Gly Phe Met Gly Phe Ile Ile Glu Gln Tyr Ile Asn Pro Ile Val
    290                 295                 300

Arg Asn Ser Lys His Pro Leu Lys Gly Asp Leu Leu Tyr Ala Ile Glu
305                 310                 315                 320

Arg Val Leu Lys Leu Ser Val Pro Asn Leu Tyr Val Trp Leu Cys Met
                325                 330                 335

Phe Tyr Cys Phe Phe His Leu Trp Leu Asn Ile Leu Ala Glu Leu Leu
            340                 345                 350

Cys Phe Gly Asp Arg Glu Phe Tyr Lys Asp Trp Trp Asn Ala Lys Ser
        355                 360                 365

Val Gly Asp Tyr Trp Arg Met Trp Asn Met Pro Val His Lys Trp Met
    370                 375                 380

Val Arg His Ile Tyr Phe Pro Cys Leu Arg Ser Lys Ile Pro Lys Thr
385                 390                 395                 400
```

```
Leu Ala Ile Ile Ile Ala Phe Leu Val Ser Ala Val Phe His Glu Leu
                405                 410                 415

Cys Ile Ala Val Pro Cys Arg Leu Phe Lys Leu Trp Ala Phe Leu Gly
            420                 425                 430

Ile Met Phe Gln Val Pro Leu Val Phe Ile Thr Asn Tyr Leu Gln Glu
        435                 440                 445

Arg Phe Gly Ser Thr Val Gly Asn Met Ile Phe Trp Phe Ile Phe Cys
    450                 455                 460

Ile Phe Gly Gln Pro Met Cys Val Leu Leu Tyr Tyr His Asp Leu Met
465                 470                 475                 480

Asn Arg Lys Gly Ser Met Ser
                485

<210> SEQ ID NO 117
<211> LENGTH: 7026
<212> TYPE: DNA
<213> ORGANISM: Artificial sequence
<220> FEATURE:
<223> OTHER INFORMATION: Synthetic construct

<400> SEQUENCE: 117
tcgacgaatt aattccaatc ccacaaaaat ctgagcttaa cagcacagtt gctcctctca     60
gagcagaatc gggtattcaa caccctcata tcaactacta cgttgtgtat aacggtccac    120
atgccggtat atacgatgac tggggttgta caaaggcggc aacaaacggc gttcccggag    180
ttgcacacaa gaaatttgcc actattacag aggcaagagc agcagctgac gcgtacacaa    240
caagtcagca aacagacagg ttgaacttca tccccaaagg agaagctcaa ctcaagccca    300
agagctttgc taaggcccta acaagcccac caaagcaaaa agcccactgg ctcacgctag    360
gaaccaaaag gcccagcagt gatccagccc caaaagagat ctcctttgcc ccggagatta    420
caatggacga tttcctctat ctttacgatc taggaaggaa gttcgaaggt gaaggtgacg    480
acactatgtt caccactgat aatgagaagg ttagcctctt caatttcaga aagaatgctg    540
acccacagat ggttagagag gcctacgcag caggtctcat caagacgatc tacccgagta    600
acaatctcca ggagatcaaa taccttccca agaaggttaa agatgcagtc aaaagattca    660
ggactaattg catcaagaac acagagaaag acatatttct caagatcaga agtactattc    720
cagtatggac gattcaaggc ttgcttcata aaccaaggca agtaatagag attggagtct    780
ctaaaaaggt agttcctact gaatctaagg ccatgcatgg agtctaagat tcaaatcgag    840
gatctaacag aactcgccgt gaagactggc gaacagttca tacagagtct tttacgactc    900
aatgacaaga agaaaatctt cgtcaacatg gtggagcacg acactctggt ctactccaaa    960
aatgtcaaag atacagtctc agaagaccaa agggctattg agacttttca acaaaggata   1020
atttcgggaa acctcctcgg attccattgc ccagctatct gtcacttcat cgaaaggaca   1080
gtagaaaagg aaggtggctc ctacaaatgc catcattgcg ataaaggaaa ggctatcatt   1140
caagatctct ctgccgacag tggtcccaaa gatggacccc cacccacgag gagcatcgtg   1200
gaaaaagaag acgttccaac cacgtcttca aagcaagtgg attgatgtga catctccact   1260
gacgtaaggg atgacgcaca atcccactat ccttcgcaag acccttcctc tatataagga   1320
agttcatttc atttggagag gacacgctcg aggaattcgg taccccatca caagtttgta   1380
caaaaaagca ggctgcggcc gcttgctccc ttaaaaaaaa ccatggcatg tcattacgga   1440
caacagcaac agactagagc acctcatctt cagcttcaac ctagagcaca gagagttgtg   1500
aaggctgcta ctgctgttac tgtaaatttc tgtgttcctt attctctcaa aatcttcgat   1560
```

```
tttgttttcg ttcgatccca atttcgtata tgttctttgg tttagattct gttaatctta   1620
gatcgaagac gattttctgg gtttgatcgt tagatatcat cttaattctc gattagggtt   1680
tcatagatat catccgattt gttcaaataa tttgagtttt gtcgaataat tactcttcga   1740
tttgtgattt ctatctagat ctggtgttag tttctagttt gtgcgatcga atttgtcgat   1800
taatctgagt ttttctgatt aacaggctgg aggatctctt cttgttctct ctggacttac   1860
tctcgctgga actgttatcg ctctcactat cgctacacct cttctcgtta tcttctctcc   1920
tgttctcgtt cctgctgtga tcactatctt ccttctcgga gctggatttc ttgcttctgg   1980
tggatttgga gttgctgctc tctctgttct ctcttggatc tacagatacc tcactggaaa   2040
acatcctcca ggtgctgatc aacttgagtc tgctaagact aagctcgctt ctaaggctag   2100
agagatgaag gatagagcag agcaattctc ttgtcagcct gttgctggat ctcagacttc   2160
ttaatgaaca tatggtcctg ctttaatgag atatgcgaga cgcctatgat cgcatgatat   2220
ttgctttcaa ttctgttgtg cacgttgtaa aaaacctgag catgtgtagc tcagatcctt   2280
accgccggtt tcggttcatt ctaatgaata tatcacccgt tactatcgta tttttatgaa   2340
taatattctc cgttcaattt actgattgta ccctactact tatatgtaca atattaaaat   2400
gaaaacaata tattgtgctg aataggttta tagcgacatc tatgatagag cgccacaata   2460
acaaacaatt gcgttttatt attacaaatc caattttaaa aaaagcggca gaaccggtca   2520
aacctaaaag actgattaca taaatcttat tcaaatttca aaaggcccca ggggctagta   2580
tctacgacac accgagcggc gaactaataa cgttcactga agggaactcc ggttccccgc   2640
cggcgcgcat gggtgagatt ccttgaagtt gagtattggc cgtccgctct accgaaagtt   2700
acgggcacca ttcaacccgg tccagcacgg cggccgggta accgacttgc tgccccgaga   2760
attatgcagc atttttttgg tgtatgtggg ccccaaatga agtgcaggtc aaaccttgac   2820
agtgacgaca aatcgttggg cgggtccagg gcgaattttg cgacaacatg tcgaggctca   2880
gcaggacctg caggcatgca agctagctta ctagtgatgc atattctata gtgtcaccta   2940
aatcttcgac gaattaattc caatcccaca aaaatctgag cttaacagca cagttgctcc   3000
tctcagagca gaatcgggta ttcaacaccc tcatatcaac tactacgttg tgtataacgg   3060
tccacatgcc ggtatatacg atgactgggg ttgtacaaag gcggcaacaa acggcgttcc   3120
cggagttgca cacaagaaat ttgccactat tacagaggca agagcagcag ctgacgcgta   3180
cacaacaagt cagcaaacag acaggttgaa cttcatcccc aaaggagaag ctcaactcaa   3240
gcccaagagc tttgctaagg ccctaacaag cccaccaaag caaaaagccc actggctcac   3300
gctaggaacc aaaaggccca gcagtgatcc agccccaaaa gagatctcct ttgccccgga   3360
gattacaatg gacgatttcc tctatcttta cgatctagga aggaagttcg aaggtgaagg   3420
tgacgacact atgttcacca ctgataatga gaaggttagc ctcttcaatt tcagaaagaa   3480
tgctgaccca cagatggtta gagaggccta cgcagcaggt ctcatcaaga cgatctaccc   3540
gagtaacaat ctccaggaga tcaaatacct tcccaagaag gttaaagatg cagtcaaaag   3600
attcaggact aattgcatca agaacacaga gaaagacata tttctcaaga tcagaagtac   3660
tattccagta tggacgattc aaggcttgct tcataaacca aggcaagtaa tagagattgg   3720
agtctctaaa aaggtagttc ctactgaatc taaggccatg catggagtct aagattcaaa   3780
tcgaggatct aacagaactc gccgtgaaga ctggcgaaca gttcatacag agtcttttac   3840
gactcaatga caagaagaaa atcttcgtca acatggtgga gcacgacact ctggtctact   3900
```

-continued

```
ccaaaaatgt caaagataca gtctcagaag accaaagggc tattgagact tttcaacaaa   3960
ggataatttc gggaaacctc ctcggattcc attgcccagc tatctgtcac ttcatcgaaa   4020
ggacagtaga aaaggaaggt ggctcctaca aatgccatca ttgcgataaa ggaaaggcta   4080
tcattcaaga tctctctgcc gacagtggtc ccaaagatgg acccccaccc acgaggagca   4140
tcgtggaaaa agaagacgtt ccaaccacgt cttcaaagca agtggattga tgtgacatct   4200
ccactgacgt aagggatgac gcacaatccc actatccttc gcaagaccct tcctctatat   4260
aaggaagttc atttcatttg gagaggacac gggatccttg ctccgttaaa aaaaaccatg   4320
gctatcctcg attctgctgg tgttactact gtgactgaga atggtggtgg agagttcgtt   4380
gatctcgata gactcagaag aagaaagtct agatctgtaa atttctgtgt tccttattct   4440
ctcaaaatct tcgattttgt tttcgttcga tcccaatttc gtatatgttc tttggtttag   4500
attctgttaa tcttagatcg aagacgattt tctgggtttg atcgttagat atcatcttaa   4560
ttctcgatta gggtttcata gatatcatcc gatttgttca aataatttga gttttgtcga   4620
ataattactc ttcgatttgt gatttctatc tagatctggt gttagtttct agtttgtgcg   4680
atcgaatttg tcgattaatc tgagtttttc tgattaacag gattcttcta acggacttct   4740
cctctctgga tctgataaca actctccttc tgatgatgtt ggtgctcctg ctgatgtgag   4800
agatagaatc gattctgtgg tgaacgatga tgctcaaggt actgctaacc tcgctggtga   4860
taataacggt ggaggtgata acaatggtgg aggaagaggt ggaggtgaag gtagaggaaa   4920
cgctgatgct actttcactt acagaccatc tgtgcctgct catagaagag ctagagagtc   4980
tcctctctct tctgatgcta tcttcaagca gtctcacgct ggacttttca acctctgtgt   5040
ggtggttctt atcgctgtga actctagact catcatcgag aacctcatga agtacggatg   5100
gctcatcaga actgatttct ggttctcttc tagatctctc agagattggc ctcttttcat   5160
gtgctgcatc tcactctcaa tcttccctct cgctgctttt actgttgaga agctcgtgct   5220
ccagaagtat atcgctgaac ctgtggtgat cttcctccac atcatcatca ctatgactga   5280
ggttctctac cctgtttacg tgactctcag atgcgattct gctttcctct ctggtgttac   5340
tcttatgctc ctcacttgca ttgtgtggct taagctcgtg tcttacgctc acacttctta   5400
cgatatcaga tctctcgcta acgctgctga taaggctaac cctgaagtgt cttactacgt   5460
gtctctcaag tctctcgctt acttcatggt tgctcctaca ctttgttacc agccatctta   5520
ccctagatct gcttgcatta gaaagggatg ggtggcaaga caattcgcta agttggtgat   5580
cttcactgga ttcatgggat tcatcatcga gcagtacatc aaccctattg tgagaaactc   5640
taagcaccct ctcaagggtg atcttctcta cgctatcgag agagttctta agctctctgt   5700
gcctaacctt tatgtgtggc tctgcatgtt ctactgtttc ttccacctct ggcttaacat   5760
ccttgctgag ttgctttgct tcggagatag agagttctac aaggattggt ggaacgctaa   5820
gtctgttgga gattattgga gaatgtggaa catgcctgtg cataagtgga tggtgcgtca   5880
catctacttc ccttgcctca gatctaagat ccctaagact ctcgctatca ttatcgcttt   5940
cctcgtgtct gctgttttcc atgagttgtg tatcgctgtt ccttgcagac ttttcaagct   6000
ttgggctttc ctcggaatca tgttccaggt tccactcgtg ttcatcacta actacctcca   6060
agagagattc ggatctactg ttggaaacat gattttctgg ttcattttct gcatcttcgg   6120
acagcctatg tgcgttctcc tctactacca cgatctcatg aacagaaagg gatctatgtc   6180
ttaatgaagg atccacccag ctttcttgta caaagtggtg atgggttcga aatcgataag   6240
cttggatcct ctagagtcct gctttaatga gatatgcgag acgcctatga tcgcatgata   6300
```

```
tttgctttca attctgttgt gcacgttgta aaaaacctga gcatgtgtag ctcagatcct   6360
taccgccggt ttcggttcat tctaatgaat atatcacccg ttactatcgt atttttatga   6420
ataatattct ccgttcaatt tactgattgt accctactac ttatatgtac aatattaaaa   6480
tgaaaacaat atattgtgct gaataggttt atagcgacat ctatgataga gcgccacaat   6540
aacaaacaat tgcgttttat tattacaaat ccaattttaa aaaaagcggc agaaccggtc   6600
aaacctaaaa gactgattac ataaatctta ttcaaatttc aaaaggcccc aggggctagt   6660
atctacgaca caccgagcgg cgaactaata acgttcactg aagggaactc cggttccccg   6720
ccggcgcgca tgggtgagat tccttgaagt tgagtattgg ccgtccgctc taccgaaagt   6780
tacgggcacc attcaacccg gtccagcacg gcggccgggt aaccgacttg ctgccccgag   6840
aattatgcag catttttttg gtgtatgtgg gccccaaatg aagtgcaggt caaaccttga   6900
cagtgacgac aaatcgttgg gcgggtccag ggcgaatttt gcgacaacat gtcgaggctc   6960
agcaggacct gcaggcatgc aagctagctt actagtgatg catattctat agtgtcacct   7020
aaatct                                                              7026

<210> SEQ ID NO 118
<211> LENGTH: 33
<212> TYPE: PRT
<213> ORGANISM: Artificial sequence
<220> FEATURE:
<223> OTHER INFORMATION: Synthetic peptide

<400> SEQUENCE: 118

Met Ala Cys His Tyr Gly Gln Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr

<210> SEQ ID NO 119
<211> LENGTH: 112
<212> TYPE: PRT
<213> ORGANISM: Artificial sequence
<220> FEATURE:
<223> OTHER INFORMATION: Synthetic peptide

<400> SEQUENCE: 119

Ala Gly Gly Ser Leu Leu Val Leu Ser Gly Leu Thr Leu Ala Gly Thr
1               5                   10                  15

Val Ile Ala Leu Thr Ile Ala Thr Pro Leu Leu Val Ile Phe Ser Pro
            20                  25                  30

Val Leu Val Pro Ala Val Ile Thr Ile Phe Leu Leu Gly Ala Gly Phe
        35                  40                  45

Leu Ala Ser Gly Gly Phe Gly Val Ala Ala Leu Ser Val Leu Ser Trp
    50                  55                  60

Ile Tyr Arg Tyr Leu Thr Gly Lys His Pro Pro Gly Ala Asp Gln Leu
65                  70                  75                  80

Glu Ser Ala Lys Thr Lys Leu Ala Ser Lys Ala Arg Glu Met Lys Asp
                85                  90                  95

Arg Ala Glu Gln Phe Ser Cys Gln Pro Val Ala Gly Ser Gln Thr Ser
            100                 105                 110

<210> SEQ ID NO 120
<211> LENGTH: 7026
```

<212> TYPE: DNA
<213> ORGANISM: Artificial sequence
<220> FEATURE:
<223> OTHER INFORMATION: Synthetic construct

<400> SEQUENCE: 120
tcgacgaatt aattccaatc ccacaaaaat ctgagcttaa cagcacagtt gctcctctca 60
gagcagaatc gggtattcaa caccctcata tcaactacta cgttgtgtat aacggtccac 120
atgccggtat atacgatgac tggggttgta caaaggcggc aacaaacggc gttcccggag 180
ttgcacacaa gaaatttgcc actattacag aggcaagagc agcagctgac gcgtacacaa 240
caagtcagca aacagacagg ttgaacttca tccccaaagg agaagctcaa ctcaagccca 300
agagctttgc taaggcccta acaagcccac caaagcaaaa agcccactgg ctcacgctag 360
gaaccaaaag gcccagcagt gatccagccc caaaagagat ctcctttgcc ccggagatta 420
caatggacga tttcctctat ctttacgatc taggaaggaa gttcgaaggt gaaggtgacg 480
acactatgtt caccactgat aatgagaagg ttagcctctt caatttcaga aagaatgctg 540
acccacagat ggttagagag gcctacgcag caggtctcat caagacgatc tacccgagta 600
acaatctcca ggagatcaaa taccttccca agaaggttaa agatgcagtc aaaagattca 660
ggactaattg catcaagaac acagagaaag acatatttct caagatcaga agtactattc 720
cagtatggac gattcaaggc ttgcttcata aaccaaggca agtaatagag attggagtct 780
ctaaaaaggt agttcctact gaatctaagg ccatgcatgg agtctaagat tcaaatcgag 840
gatctaacag aactcgccgt gaagactggc gaacagttca tacagagtct tttacgactc 900
aatgacaaga agaaaatctt cgtcaacatg gtggagcacg acactctggt ctactccaaa 960
aatgtcaaag atacagtctc agaagaccaa agggctattg agacttttca acaaaggata 1020
atttcgggaa acctcctcgg attccattgc ccagctatct gtcacttcat cgaaaggaca 1080
gtagaaaagg aaggtggctc ctacaaatgc catcattgcg ataaaggaaa ggctatcatt 1140
caagatctct ctgccgacag tggtcccaaa gatggacccc cacccacgag gagcatcgtg 1200
gaaaaagaag acgttccaac cacgtcttca aagcaagtgg attgatgtga catctccact 1260
gacgtaaggg atgacgcaca atcccactat ccttcgcaag acccttcctc tatataagga 1320
agttcatttc atttggagag gacacgctcg aggaattcgg taccccatca caagtttgta 1380
caaaaaagca ggctgcggcc gcttgctccc ttaaaaaaaa ccatggcatg tcattacgga 1440
caacagcaac agactagagc acctcatctt cagcttcaac ctagagcaca gagagttgtg 1500
aaggctgcta ctgctgttac tgtaaatttc tgtgttcctt attctctcaa aatcttcgat 1560
tttgttttcg ttcgatccca atttcgtata tgttctttgg tttagattct gttaatctta 1620
gatcgaagac gattttctgg gtttgatcgt tagatatcat cttaattctc gattagggtt 1680
tcatagatat catccgattt gttcaaataa tttgagtttt gtcgaataat tactcttcga 1740
tttgtgattt ctatctagat ctggtgttag tttctagttt gtgcgatcga atttgtcgat 1800
taatctgagt ttttctgatt aacaggctgg aggatctctt cttgttctct ctggacttac 1860
tctcgctgga actgttatcg ctctcactat cgctacacct cttctcgtta tcttctctcc 1920
tgttctcgtt cctgctgtga tcactatctt ccttctcgga gctggatttc ttgcttctgg 1980
tggatttgga gttgctgctc tctctgttct ctcttggatc tacagatacc tcactggaaa 2040
acatcctcca ggtgctgatt gtcttgagtc tgctaagact aagctcgctt cttgtgctag 2100
agagatgaag gatagagcag agcaattctc ttgtcagcct gttgctggat ctcagacttc 2160
ttaatgaaca tatggtcctg ctttaatgag atatgcgaga cgcctatgat cgcatgatat 2220
ttgctttcaa ttctgttgtg cacgttgtaa aaaacctgag catgtgtagc tcagatcctt 2280
accgccggtt tcggttcatt ctaatgaata tatcacccgt tactatcgta tttttatgaa 2340
taatattctc cgttcaattt actgattgta ccctactact tatatgtaca atattaaaat 2400
gaaaacaata tattgtgctg aataggttta tagcgacatc tatgatagag cgccacaata 2460
acaaacaatt gcgttttatt attacaaatc caattttaaa aaaagcggca gaaccggtca 2520
aacctaaaag actgattaca taaatcttat tcaaatttca aaaggcccca ggggctagta 2580
tctacgacac accgagcggc gaactaataa cgttcactga agggaactcc ggttccccgc 2640
cggcgcgcat gggtgagatt ccttgaagtt gagtattggc cgtccgctct accgaaagtt 2700
acgggcacca ttcaacccgg tccagcacgg cggccgggta accgacttgc tgccccgaga 2760
attatgcagc attttttgg tgtatgtggg ccccaaatga agtgcaggtc aaaccttgac 2820
agtgacgaca aatcgttggg cgggtccagg gcgaattttg cgacaacatg tcgaggctca 2880
gcaggacctg caggcatgca agctagctta ctagtgatgc atattctata gtgtcaccta 2940
aatcttcgac gaattaattc caatcccaca aaaatctgag cttaacagca cagttgctcc 3000
tctcagagca gaatcgggta ttcaacaccc tcatatcaac tactacgttg tgtataacgg 3060
tccacatgcc ggtatatacg atgactgggg ttgtacaaag gcggcaacaa acggcgttcc 3120
cggagttgca cacaagaaat ttgccactat tacagaggca agagcagcag ctgacgcgta 3180
cacaacaagt cagcaaacag acaggttgaa cttcatcccc aaaggagaag ctcaactcaa 3240
gcccaagagc tttgctaagg ccctaacaag cccaccaaag caaaaagccc actggctcac 3300
gctaggaacc aaaaggccca gcagtgatcc agccccaaaa gagatctcct ttgccccgga 3360
gattacaatg gacgatttcc tctatcttta cgatctagga aggaagttcg aaggtgaagg 3420
tgacgacact atgttcacca ctgataatga gaaggttagc ctcttcaatt tcagaaagaa 3480
tgctgaccca cagatggtta gagaggccta cgcagcaggt ctcatcaaga cgatctaccc 3540
gagtaacaat ctccaggaga tcaaatacct tcccaagaag gttaaagatg cagtcaaaag 3600
attcaggact aattgcatca agaacacaga gaaagacata tttctcaaga tcagaagtac 3660
tattccagta tggacgattc aaggcttgct tcataaacca aggcaagtaa tagagattgg 3720
agtctctaaa aaggtagttc ctactgaatc taaggccatg catggagtct aagattcaaa 3780
tcgaggatct aacagaactc gccgtgaaga ctggcgaaca gttcatacag agtcttttac 3840
gactcaatga caagaagaaa atcttcgtca acatggtgga gcacgacact ctggtctact 3900
ccaaaaatgt caaagataca gtctcagaag accaaagggc tattgagact tttcaacaaa 3960
ggataatttc gggaaacctc ctcggattcc attgcccagc tatctgtcac ttcatcgaaa 4020
ggacagtaga aaaggaaggt ggctcctaca aatgccatca ttgcgataaa ggaaaggcta 4080
tcattcaaga tctctctgcc gacagtggtc ccaaagatgg acccccaccc acgaggagca 4140
tcgtggaaaa agaagacgtt ccaaccacgt cttcaaagca agtggattga tgtgacatct 4200
ccactgacgt aagggatgac gcacaatccc actatccttc gcaagaccct tcctctatat 4260
aaggaagttc atttcatttg gagaggacac gggatccttg ctccgttaaa aaaaaccatg 4320
gctatcctcg attctgctgg tgttactact gtgactgaga atggtggtgg agagttcgtt 4380
gatctcgata gactcagaag aagaaagtct agatctgtaa atttctgtgt tccttattct 4440
ctcaaaatct tcgattttgt tttcgttcga tcccaatttc gtatatgttc tttggtttag 4500
attctgttaa tcttagatcg aagacgattt tctgggtttg atcgttagat atcatcttaa 4560

-continued ttctcgatta gggtttcata gatatcatcc gatttgttca aataatttga gttttgtcga 4620
ataattactc ttcgatttgt gatttctatc tagatctggt gttagtttct agtttgtgcg 4680
atcgaatttg tcgattaatc tgagtttttc tgattaacag gattcttcta acggacttct 4740
cctctctgga tctgataaca actctccttc tgatgatgtt ggtgctcctg ctgatgtgag 4800
agatagaatc gattctgtgg tgaacgatga tgctcaaggt actgctaacc tcgctggtga 4860
taataacggt ggaggtgata acaatggtgg aggaagaggt ggaggtgaag gtagaggaaa 4920
cgctgatgct actttcactt acagaccatc tgtgcctgct catagaagag ctagagagtc 4980
tcctctctct tctgatgcta tcttcaagca gtctcacgct ggacttttca acctctgtgt 5040
ggtggttctt atcgctgtga actctagact catcatcgag aacctcatga agtacggatg 5100
gctcatcaga actgatttct ggttctcttc tagatctctc agagattggc ctcttttcat 5160
gtgctgcatc tcactctcaa tcttccctct cgctgctttt actgttgaga agctcgtgct 5220
ccagaagtat atcgctgaac ctgtggtgat cttcctccac atcatcatca ctatgactga 5280
ggttctctac cctgtttacg tgactctcag atgcgattct gctttcctct ctggtgttac 5340
tcttatgctc ctcacttgca ttgtgtggct taagctcgtg tcttacgctc acacttctta 5400
cgatatcaga tctctcgcta acgctgctga taaggctaac cctgaagtgt cttactacgt 5460
gtctctcaag tctctcgctt acttcatggt tgctcctaca ctttgttacc agccatctta 5520
ccctagatct gcttgcatta gaaagggatg ggtggcaaga caattcgcta agttggtgat 5580
cttcactgga ttcatgggat tcatcatcga gcagtacatc aaccctattg tgagaaactc 5640
taagcaccct ctcaagggtg atcttctcta cgctatcgag agagttctta agctctctgt 5700
gcctaacctt tatgtgtggc tctgcatgtt ctactgtttc ttccacctct ggcttaacat 5760
ccttgctgag ttgctttgct tcggagatag agagttctac aaggattggt ggaacgctaa 5820
gtctgttgga gattattgga gaatgtggaa catgcctgtg cataagtgga tggtgcgtca 5880
catctacttc ccttgcctca gatctaagat ccctaagact ctcgctatca ttatcgcttt 5940
cctcgtgtct gctgttttcc atgagttgtg tatcgctgtt ccttgcagac ttttcaagct 6000
ttgggctttc ctcggaatca tgttccaggt tccactcgtg ttcatcacta actacctcca 6060
agagagattc ggatctactg ttggaaacat gatttctggt ttcattttct gcatcttcgg 6120
acagcctatg tgcgttctcc tctactacca cgatctcatg aacagaaagg gatctatgtc 6180
ttaatgaagg atccacccag ctttcttgta caaagtggtg atgggttcga aatcgataag 6240
cttggatcct ctagagtcct gctttaatga gatatgcgag acgcctatga tcgcatgata 6300
tttgctttca attctgttgt gcacgttgta aaaaacctga gcatgtgtag ctcagatcct 6360
taccgccggt ttcggttcat tctaatgaat atatcacccg ttactatcgt atttttatga 6420
ataatattct ccgttcaatt tactgattgt accctactac ttatatgtac aatattaaaa 6480
tgaaaacaat atattgtgct gaataggttt atagcgacat ctatgataga gcgccacaat 6540
aacaaacaat tgcgttttat tattacaaat ccaattttaa aaaaagcggc agaaccggtc 6600
aaacctaaaa gactgattac ataaatctta ttcaaatttc aaaaggcccc aggggctagt 6660
atctacgaca caccgagcgg cgaactaata acgttcactg aagggaactc cggttccccg 6720
ccggcgcgca tgggtgagat tccttgaagt tgagtattgg ccgtccgctc taccgaaagt 6780
tacgggcacc attcaacccg gtccagcacg gcggccgggt aaccgacttg ctgccccgag 6840
aattatgcag catttttttg gtgtatgtgg gccccaaatg aagtgcaggt caaaccttga 6900
cagtgacgac aaatcgttgg gcgggtccag ggcgaatttt gcgacaacat gtcgaggctc 6960
agcaggacct gcaggcatgc aagctagctt actagtgatg catattctat agtgtcacct 7020
aaatct 7026

<210> SEQ ID NO 121
<211> LENGTH: 33
<212> TYPE: PRT
<213> ORGANISM: Artificial sequence
<220> FEATURE:
<223> OTHER INFORMATION: Synthetic peptide

<400> SEQUENCE: 121

Met Ala Cys His Tyr Gly Gln Gln Gln Gln Thr Arg Ala Pro His Leu
1 5 10 15

Gln Leu Gln Pro Arg Ala Gln Arg Val Val Lys Ala Ala Thr Ala Val
20 25 30

Thr

<210> SEQ ID NO 122
<211> LENGTH: 112
<212> TYPE: PRT
<213> ORGANISM: Artificial sequence
<220> FEATURE:
<223> OTHER INFORMATION: Synthetic peptide

<400> SEQUENCE: 122

Ala Gly Gly Ser Leu Leu Val Leu Ser Gly Leu Thr Leu Ala Gly Thr
1 5 10 15

Val Ile Ala Leu Thr Ile Ala Thr Pro Leu Leu Val Ile Phe Ser Pro
20 25 30

Val Leu Val Pro Ala Val Ile Thr Ile Phe Leu Leu Gly Ala Gly Phe
35 40 45

Leu Ala Ser Gly Gly Phe Gly Val Ala Ala Leu Ser Val Leu Ser Trp
50 55 60

Ile Tyr Arg Tyr Leu Thr Gly Lys His Pro Pro Gly Ala Asp Cys Leu
65 70 75 80

Glu Ser Ala Lys Thr Lys Leu Ala Ser Cys Ala Arg Glu Met Lys Asp
85 90 95

Arg Ala Glu Gln Phe Ser Cys Gln Pro Val Ala Gly Ser Gln Thr Ser
100 105 110

<210> SEQ ID NO 123
<211> LENGTH: 7026
<212> TYPE: DNA
<213> ORGANISM: Artificial sequence
<220> FEATURE:
<223> OTHER INFORMATION: Synthetic construct

<400> SEQUENCE: 123
tcgacgaatt aattccaatc ccacaaaaat ctgagcttaa cagcacagtt gctcctctca 60
gagcagaatc gggtattcaa caccctcata tcaactacta cgttgtgtat aacggtccac 120
atgccggtat atacgatgac tggggttgta caaaggcggc aacaaacggc gttcccggag 180
ttgcacacaa gaaatttgcc actattacag aggcaagagc agcagctgac gcgtacacaa 240
caagtcagca aacagacagg ttgaacttca tccccaaagg agaagctcaa ctcaagccca 300
agagctttgc taaggcccta acaagcccac caaagcaaaa agcccactgg ctcacgctag 360
gaaccaaaag gcccagcagt gatccagccc caaaagagat ctcctttgcc ccggagatta 420

-continued

```
caatggacga tttcctctat ctttacgatc taggaaggaa gttcgaaggt gaaggtgacg    480
acactatgtt caccactgat aatgagaagg ttagcctctt caatttcaga aagaatgctg    540
acccacagat ggttagagag gcctacgcag caggtctcat caagacgatc tacccgagta    600
acaatctcca ggagatcaaa taccttccca agaaggttaa agatgcagtc aaaagattca    660
ggactaattg catcaagaac acagagaaag acatatttct caagatcaga agtactattc    720
cagtatggac gattcaaggc ttgcttcata aaccaaggca agtaatagag attggagtct    780
ctaaaaaggt agttcctact gaatctaagg ccatgcatgg agtctaagat tcaaatcgag    840
gatctaacag aactcgccgt gaagactggc gaacagttca tacagagtct tttacgactc    900
aatgacaaga agaaaatctt cgtcaacatg gtggagcacg acactctggt ctactccaaa    960
aatgtcaaag atacagtctc agaagaccaa agggctattg agacttttca acaaaggata   1020
atttcgggaa acctcctcgg attccattgc ccagctatct gtcacttcat cgaaaggaca   1080
gtagaaaagg aaggtggctc ctacaaatgc catcattgcg ataaaggaaa ggctatcatt   1140
caagatctct ctgccgacag tggtcccaaa gatggacccc cacccacgag gagcatcgtg   1200
gaaaaagaag acgttccaac cacgtcttca aagcaagtgg attgatgtga catctccact   1260
gacgtaaggg atgacgcaca atcccactat ccttcgcaag acccttcctc tatataagga   1320
agttcatttc atttggagag gacacgctcg aggaattcgg taccccatca caagtttgta   1380
caaaaaagca ggctgcggcc gcttgctccc ttaaaaaaaa ccatggcatg tcattacgga   1440
caacagcaac agacttgtgc acctcatctt cagcttcaac ctagagcatg tagagttgtg   1500
aaggctgcta ctgctgttac tgtaaatttc tgtgttcctt attctctcaa aatcttcgat   1560
tttgttttcg ttcgatccca atttcgtata tgttctttgg tttagattct gttaatctta   1620
gatcgaagac gattttctgg gtttgatcgt tagatatcat cttaattctc gattagggtt   1680
tcatagatat catccgattt gttcaaataa tttgagtttt gtcgaataat tactcttcga   1740
tttgtgattt ctatctagat ctggtgttag tttctagttt gtgcgatcga atttgtcgat   1800
taatctgagt ttttctgatt aacaggctgg aggatctctt cttgttctct ctggacttac   1860
tctcgctgga actgttatcg ctctcactat cgctacacct cttctcgtta tcttctctcc   1920
tgttctcgtt cctgctgtga tcactatctt ccttctcgga gctggatttc ttgcttctgg   1980
tggatttgga gttgctgctc tctctgttct ctcttggatc tacagatacc tcactggaaa   2040
acatcctcca ggtgctgatc aacttgagtc tgctaagact aagctcgctt ctaaggctag   2100
agagatgaag gatagagcag agcaattctc ttgtcagcct gttgctggat ctcagacttc   2160
ttaatgaaca tatggtcctg ctttaatgag atatgcgaga cgcctatgat cgcatgatat   2220
ttgctttcaa ttctgttgtg cacgttgtaa aaaacctgag catgtgtagc tcagatcctt   2280
accgccggtt tcggttcatt ctaatgaata tatcacccgt tactatcgta tttttatgaa   2340
taatattctc cgttcaattt actgattgta ccctactact tatatgtaca atattaaaat   2400
gaaaacaata tattgtgctg aataggttta tagcgacatc tatgatagag cgccacaata   2460
acaaacaatt gcgttttatt attacaaatc caattttaaa aaaagcggca gaaccggtca   2520
aacctaaaag actgattaca taaatcttat tcaaatttca aaaggcccca ggggctagta   2580
tctacgacac accgagcggc gaactaataa cgttcactga agggaactcc ggttccccgc   2640
cggcgcgcat gggtgagatt ccttgaagtt gagtattggc cgtccgctct accgaaagtt   2700
acgggcacca ttcaacccgg tccagcacgg cggccgggta accgacttgc tgccccgaga   2760
attatgcagc atttttttgg tgtatgtggg ccccaaatga agtgcaggtc aaaccttgac   2820
```

```
agtgacgaca aatcgttggg cgggtccagg gcgaattttg cgacaacatg tcgaggctca   2880
gcaggacctg caggcatgca agctagctta ctagtgatgc atattctata gtgtcaccta   2940
aatcttcgac gaattaattc caatcccaca aaaatctgag cttaacagca cagttgctcc   3000
tctcagagca gaatcgggta ttcaacaccc tcatatcaac tactacgttg tgtataacgg   3060
tccacatgcc ggtatatacg atgactgggg ttgtacaaag gcggcaacaa acggcgttcc   3120
cggagttgca cacaagaaat ttgccactat tacagaggca agagcagcag ctgacgcgta   3180
cacaacaagt cagcaaacag acaggttgaa cttcatcccc aaaggagaag ctcaactcaa   3240
gcccaagagc tttgctaagg ccctaacaag cccaccaaag caaaaagccc actggctcac   3300
gctaggaacc aaaaggccca gcagtgatcc agccccaaaa gagatctcct ttgccccgga   3360
gattacaatg gacgatttcc tctatcttta cgatctagga aggaagttcg aaggtgaagg   3420
tgacgacact atgttcacca ctgataatga gaaggttagc ctcttcaatt tcagaaagaa   3480
tgctgaccca cagatggtta gagaggccta cgcagcaggt ctcatcaaga cgatctaccc   3540
gagtaacaat ctccaggaga tcaaatacct tcccaagaag gttaaagatg cagtcaaaag   3600
attcaggact aattgcatca agaacacaga gaaagacata tttctcaaga tcagaagtac   3660
tattccagta tggacgattc aaggcttgct tcataaacca aggcaagtaa tagagattgg   3720
agtctctaaa aaggtagttc ctactgaatc taaggccatg catggagtct aagattcaaa   3780
tcgaggatct aacagaactc gccgtgaaga ctggcgaaca gttcatacag agtcttttac   3840
gactcaatga caagaagaaa atcttcgtca acatggtgga gcacgacact ctggtctact   3900
ccaaaaatgt caaagataca gtctcagaag accaaagggc tattgagact tttcaacaaa   3960
ggataatttc gggaaacctc ctcggattcc attgcccagc tatctgtcac ttcatcgaaa   4020
ggacagtaga aaaggaaggt ggctcctaca aatgccatca ttgcgataaa ggaaaggcta   4080
tcattcaaga tctctctgcc gacagtggtc ccaaagatgg acccccaccc acgaggagca   4140
tcgtggaaaa agaagacgtt ccaaccacgt cttcaaagca agtggattga tgtgacatct   4200
ccactgacgt aagggatgac gcacaatccc actatccttc gcaagaccct tcctctatat   4260
aaggaagttc atttcatttg gagaggacac gggatccttg ctccgttaaa aaaaaccatg   4320
gctatcctcg attctgctgg tgttactact gtgactgaga atggtggtgg agagttcgtt   4380
gatctcgata gactcagaag aagaaagtct agatctgtaa atttctgtgt tccttattct   4440
ctcaaaatct tcgattttgt tttcgttcga tcccaatttc gtatatgttc tttggtttag   4500
attctgttaa tcttagatcg aagacgattt tctgggtttg atcgttagat atcatcttaa   4560
ttctcgatta gggtttcata gatatcatcc gatttgttca aataatttga gttttgtcga   4620
ataattactc ttcgatttgt gatttctatc tagatctggt gttagtttct agtttgtgcg   4680
atcgaatttg tcgattaatc tgagtttttc tgattaacag gattcttcta acggacttct   4740
cctctctgga tctgataaca actctccttc tgatgatgtt ggtgctcctg ctgatgtgag   4800
agatagaatc gattctgtgg tgaacgatga tgctcaaggt actgctaacc tcgctggtga   4860
taataacggt ggaggtgata acaatggtgg aggaagaggt ggaggtgaag gtagaggaaa   4920
cgctgatgct actttcactt acagaccatc tgtgcctgct catagaagag ctagagagtc   4980
tcctctctct tctgatgcta tcttcaagca gtctcacgct ggacttttca acctctgtgt   5040
ggtggttctt atcgctgtga actctagact catcatcgag aacctcatga agtacggatg   5100
gctcatcaga actgatttct ggttctcttc tagatctctc agagattggc ctcttttcat   5160
```

-continued gtgctgcatc tcactctcaa tcttccctct cgctgctttt actgttgaga agctcgtgct 5220
ccagaagtat atcgctgaac ctgtggtgat cttcctccac atcatcatca ctatgactga 5280
ggttctctac cctgtttacg tgactctcag atgcgattct gctttcctct ctggtgttac 5340
tcttatgctc ctcacttgca ttgtgtggct taagctcgtg tcttacgctc acacttctta 5400
cgatatcaga tctctcgcta acgctgctga taaggctaac cctgaagtgt cttactacgt 5460
gtctctcaag tctctcgctt acttcatggt tgctcctaca ctttgttacc agccatctta 5520
ccctagatct gcttgcatta gaaagggatg ggtggcaaga caattcgcta agttggtgat 5580
cttcactgga ttcatgggat tcatcatcga gcagtacatc aaccctattg tgagaaactc 5640
taagcaccct ctcaagggtg atcttctcta cgctatcgag agagttctta agctctctgt 5700
gcctaacctt tatgtgtggc tctgcatgtt ctactgtttc ttccacctct ggcttaacat 5760
ccttgctgag ttgctttgct tcggagatag agagttctac aaggattggt ggaacgctaa 5820
gtctgttgga gattattgga gaatgtggaa catgcctgtg cataagtgga tggtgcgtca 5880
catctacttc ccttgcctca gatctaagat ccctaagact ctcgctatca ttatcgcttt 5940
cctcgtgtct gctgttttcc atgagttgtg tatcgctgtt ccttgcagac ttttcaagct 6000
ttgggctttc ctcggaatca tgttccaggt tccactcgtg ttcatcacta actacctcca 6060
agagagattc ggatctactg ttggaaacat gattttctgg ttcattttct gcatcttcgg 6120
acagcctatg tgcgttctcc tctactacca cgatctcatg aacagaaagg gatctatgtc 6180
ttaatgaagg atccacccag ctttcttgta caaagtggtg atgggttcga aatcgataag 6240
cttggatcct ctagagtcct gctttaatga gatatgcgag acgcctatga tcgcatgata 6300
tttgctttca attctgttgt gcacgttgta aaaaacctga gcatgtgtag ctcagatcct 6360
taccgccggt ttcggttcat tctaatgaat atatcacccg ttactatcgt atttttatga 6420
ataatattct ccgttcaatt tactgattgt accctactac ttatatgtac aatattaaaa 6480
tgaaaacaat atattgtgct gaataggttt atagcgacat ctatgataga gcgccacaat 6540
aacaaacaat tgcgttttat tattacaaat ccaattttaa aaaaagcggc agaaccggtc 6600
aaacctaaaa gactgattac ataaatctta ttcaaatttc aaaaggcccc aggggctagt 6660
atctacgaca caccgagcgg cgaactaata acgttcactg aagggaactc cggttccccg 6720
ccggcgcgca tgggtgagat tccttgaagt tgagtattgg ccgtccgctc taccgaaagt 6780
tacgggcacc attcaacccg gtccagcacg gcggccgggt aaccgacttg ctgccccgag 6840
aattatgcag catttttttg gtgtatgtgg gccccaaatg aagtgcaggt caaaccttga 6900
cagtgacgac aaatcgttgg gcgggtccag ggcgaatttt gcgacaacat gtcgaggctc 6960
agcaggacct gcaggcatgc aagctagctt actagtgatg catattctat agtgtcacct 7020
aaatct 7026

<210> SEQ ID NO 124
<211> LENGTH: 33
<212> TYPE: PRT
<213> ORGANISM: Artificial sequence
<220> FEATURE:
<223> OTHER INFORMATION: Synthetic peptide

<400> SEQUENCE: 124

Met Ala Cys His Tyr Gly Gln Gln Gln Gln Thr Cys Ala Pro His Leu
1               5                   10                  15

Gln Leu Gln Pro Arg Ala Cys Arg Val Val Lys Ala Ala Thr Ala Val
            20                  25                  30

Thr

<210> SEQ ID NO 125
<211> LENGTH: 112
<212> TYPE: PRT
<213> ORGANISM: Artificial sequence
<220> FEATURE:
<223> OTHER INFORMATION: Synthetic peptide

<400> SEQUENCE: 125

```
Ala Gly Gly Ser Leu Leu Val Leu Ser Gly Leu Thr Leu Ala Gly Thr
1               5                   10                  15

Val Ile Ala Leu Thr Ile Ala Thr Pro Leu Leu Val Ile Phe Ser Pro
            20                  25                  30

Val Leu Val Pro Ala Val Ile Thr Ile Phe Leu Leu Gly Ala Gly Phe
        35                  40                  45

Leu Ala Ser Gly Gly Phe Gly Val Ala Ala Leu Ser Val Leu Ser Trp
    50                  55                  60

Ile Tyr Arg Tyr Leu Thr Gly Lys His Pro Pro Gly Ala Asp Gln Leu
65                  70                  75                  80

Glu Ser Ala Lys Thr Lys Leu Ala Ser Lys Ala Arg Glu Met Lys Asp
                85                  90                  95

Arg Ala Glu Gln Phe Ser Cys Gln Pro Val Ala Gly Ser Gln Thr Ser
            100                 105                 110
```

<210> SEQ ID NO 126
<211> LENGTH: 7026
<212> TYPE: DNA
<213> ORGANISM: Artificial sequence
<220> FEATURE:
<223> OTHER INFORMATION: Synthetic construct

<400> SEQUENCE: 126

```
tcgacgaatt aattccaatc ccacaaaaat ctgagcttaa cagcacagtt gctcctctca      60
gagcagaatc gggtattcaa caccctcata tcaactacta cgttgtgtat aacggtccac     120
atgccggtat atacgatgac tggggttgta caaaggcggc aacaaacggc gttcccggag     180
ttgcacacaa gaaatttgcc actattacag aggcaagagc agcagctgac gcgtacacaa     240
caagtcagca aacagacagg ttgaacttca tccccaaagg agaagctcaa ctcaagccca     300
agagctttgc taaggcccta acaagcccac caaagcaaaa agcccactgg ctcacgctag     360
gaaccaaaag gcccagcagt gatccagccc caaaagagat ctcctttgcc ccggagatta     420
caatggacga tttcctctat ctttacgatc taggaaggaa gttcgaaggt gaaggtgacg     480
acactatgtt caccactgat aatgagaagg ttagcctctt caatttcaga aagaatgctg     540
acccacagat ggttagagag gcctacgcag caggtctcat caagacgatc tacccgagta     600
acaatctcca ggagatcaaa taccttccca agaaggttaa agatgcagtc aaaagattca     660
ggactaattg catcaagaac acagagaaag acatatttct caagatcaga agtactattc     720
cagtatggac gattcaaggc ttgcttcata aaccaaggca agtaatagag attggagtct     780
ctaaaaaggt agttcctact gaatctaagg ccatgcatgg agtctaagat tcaaatcgag     840
gatctaacag aactcgccgt gaagactggc gaacagttca tacagagtct tttacgactc     900
aatgacaaga agaaaatctt cgtcaacatg gtggagcacg acactctggt ctactccaaa     960
aatgtcaaag atacagtctc agaagaccaa agggctattg agacttttca acaaaggata    1020
atttcgggaa acctcctcgg attccattgc ccagctatct gtcacttcat cgaaaggaca    1080
```

```
gtagaaaagg aaggtggctc ctacaaatgc catcattgcg ataaaggaaa ggctatcatt   1140
caagatctct ctgccgacag tggtcccaaa gatggacccc cacccacgag gagcatcgtg   1200
gaaaaagaag acgttccaac cacgtcttca aagcaagtgg attgatgtga catctccact   1260
gacgtaaggg atgacgcaca atcccactat ccttcgcaag acccttcctc tatataagga   1320
agttcatttc atttggagag gacacgctcg aggaattcgg taccccatca caagtttgta   1380
caaaaaagca ggctgcggcc gcttgctccc ttaaaaaaaa ccatggcatg tcattacgga   1440
caacagcaac agacttgtgc acctcatctt cagcttcaac ctagagcatg tagagttgtg   1500
aaggctgcta ctgctgttac tgtaaatttc tgtgttcctt attctctcaa aatcttcgat   1560
tttgttttcg ttcgatccca atttcgtata tgttctttgg tttagattct gttaatctta   1620
gatcgaagac gattttctgg gtttgatcgt tagatatcat cttaattctc gattagggtt   1680
tcatagatat catccgattt gttcaaataa tttgagtttt gtcgaataat tactcttcga   1740
tttgtgattt ctatctagat ctggtgttag tttctagttt gtgcgatcga atttgtcgat   1800
taatctgagt ttttctgatt aacaggctgg aggatctctt cttgttctct ctggacttac   1860
tctcgctgga actgttatcg ctctcactat cgctacacct cttctcgtta tcttctctcc   1920
tgttctcgtt cctgctgtga tcactatctt ccttctcgga gctggatttc ttgcttctgg   1980
tggatttgga gttgctgctc tctctgttct ctcttggatc tacagatacc tcactggaaa   2040
acatcctcca ggtgctgatt gtcttgagtc tgctaagact aagctcgctt cttgtgctag   2100
agagatgaag gatagagcag agcaattctc ttgtcagcct gttgctggat ctcagacttc   2160
ttaatgaaca tatggtcctg ctttaatgag atatgcgaga cgcctatgat cgcatgatat   2220
ttgctttcaa ttctgttgtg cacgttgtaa aaaacctgag catgtgtagc tcagatcctt   2280
accgccggtt tcggttcatt ctaatgaata tatcacccgt tactatcgta tttttatgaa   2340
taatattctc cgttcaattt actgattgta ccctactact tatatgtaca atattaaaat   2400
gaaaacaata tattgtgctg aataggttta tagcgacatc tatgatagag cgccacaata   2460
acaaacaatt gcgttttatt attacaaatc caattttaaa aaaagcggca gaaccggtca   2520
aacctaaaag actgattaca taaatcttat tcaaatttca aaaggcccca ggggctagta   2580
tctacgacac accgagcggc gaactaataa cgttcactga agggaactcc ggttccccgc   2640
cggcgcgcat gggtgagatt ccttgaagtt gagtattggc cgtccgctct accgaaagtt   2700
acgggcacca ttcaacccgg tccagcacgg cggccgggta accgacttgc tgccccgaga   2760
attatgcagc atttttttgg tgtatgtggg ccccaaatga agtgcaggtc aaaccttgac   2820
agtgacgaca aatcgttggg cgggtccagg gcgaattttg cgacaacatg tcgaggctca   2880
gcaggacctg caggcatgca agctagctta ctagtgatgc atattctata gtgtcaccta   2940
aatcttcgac gaattaattc caatcccaca aaaatctgag cttaacagca cagttgctcc   3000
tctcagagca gaatcgggta ttcaacaccc tcatatcaac tactacgttg tgtataacgg   3060
tccacatgcc ggtatatacg atgactgggg ttgtacaaag gcggcaacaa acggcgttcc   3120
cggagttgca cacaagaaat ttgccactat tacagaggca agagcagcag ctgacgcgta   3180
cacaacaagt cagcaaacag acaggttgaa cttcatcccc aaaggagaag ctcaactcaa   3240
gcccaagagc tttgctaagg ccctaacaag cccaccaaag caaaaagccc actggctcac   3300
gctaggaacc aaaaggccca gcagtgatcc agccccaaaa gagatctcct ttgccccgga   3360
gattacaatg gacgatttcc tctatcttta cgatctagga aggaagttcg aaggtgaagg   3420
```

-continued

```
tgacgacact atgttcacca ctgataatga gaaggttagc ctcttcaatt tcagaaagaa   3480
tgctgaccca cagatggtta gagaggccta cgcagcaggt ctcatcaaga cgatctaccc   3540
gagtaacaat ctccaggaga tcaaatacct tcccaagaag gttaaagatg cagtcaaaag   3600
attcaggact aattgcatca agaacacaga gaaagacata tttctcaaga tcagaagtac   3660
tattccagta tggacgattc aaggcttgct tcataaacca aggcaagtaa tagagattgg   3720
agtctctaaa aaggtagttc ctactgaatc taaggccatg catggagtct aagattcaaa   3780
tcgaggatct aacagaactc gccgtgaaga ctggcgaaca gttcatacag agtcttttac   3840
gactcaatga caagaagaaa atcttcgtca acatggtgga gcacgacact ctggtctact   3900
ccaaaaatgt caaagataca gtctcagaag accaaagggc tattgagact tttcaacaaa   3960
ggataatttc gggaaacctc ctcggattcc attgcccagc tatctgtcac ttcatcgaaa   4020
ggacagtaga aaaggaaggt ggctcctaca aatgccatca ttgcgataaa ggaaaggcta   4080
tcattcaaga tctctctgcc gacagtggtc ccaaagatgg acccccaccc acgaggagca   4140
tcgtggaaaa agaagacgtt ccaaccacgt cttcaaagca agtggattga tgtgacatct   4200
ccactgacgt aagggatgac gcacaatccc actatccttc gcaagaccct tcctctatat   4260
aaggaagttc atttcatttg gagaggacac gggatccttg ctccgttaaa aaaaaccatg   4320
gctatcctcg attctgctgg tgttactact gtgactgaga atggtggtgg agagttcgtt   4380
gatctcgata gactcagaag aagaaagtct agatctgtaa atttctgtgt tccttattct   4440
ctcaaaatct tcgattttgt tttcgttcga tcccaatttc gtatatgttc tttggtttag   4500
attctgttaa tcttagatcg aagacgattt tctgggtttg atcgttagat atcatcttaa   4560
ttctcgatta gggtttcata gatatcatcc gatttgttca aataatttga gttttgtcga   4620
ataattactc ttcgatttgt gatttctatc tagatctggt gttagtttct agtttgtgcg   4680
atcgaatttg tcgattaatc tgagtttttc tgattaacag gattcttcta acggacttct   4740
cctctctgga tctgataaca actctccttc tgatgatgtt ggtgctcctg ctgatgtgag   4800
agatagaatc gattctgtgg tgaacgatga tgctcaaggt actgctaacc tcgctggtga   4860
taataacggt ggaggtgata acaatggtgg aggaagaggt ggaggtgaag gtagaggaaa   4920
cgctgatgct actttcactt acagaccatc tgtgcctgct catagaagag ctagagagtc   4980
tcctctctct tctgatgcta tcttcaagca gtctcacgct ggacttttca acctctgtgt   5040
ggtggttctt atcgctgtga actctagact catcatcgag aacctcatga agtacggatg   5100
gctcatcaga actgatttct ggttctcttc tagatctctc agagattggc ctcttttcat   5160
gtgctgcatc tcactctcaa tcttccctct cgctgctttt actgttgaga agctcgtgct   5220
ccagaagtat atcgctgaac ctgtggtgat cttcctccac atcatcatca ctatgactga   5280
ggttctctac cctgtttacg tgactctcag atgcgattct gctttcctct ctggtgttac   5340
tcttatgctc ctcacttgca ttgtgtggct taagctcgtg tcttacgctc acacttctta   5400
cgatatcaga tctctcgcta acgctgctga taaggctaac cctgaagtgt cttactacgt   5460
gtctctcaag tctctcgctt acttcatggt tgctcctaca ctttgttacc agccatctta   5520
ccctagatct gcttgcatta gaaagggatg ggtggcaaga caattcgcta agttggtgat   5580
cttcactgga ttcatgggat tcatcatcga gcagtacatc aaccctattg tgagaaactc   5640
taagcaccct ctcaagggtg atcttctcta cgctatcgag agagttctta agctctctgt   5700
gcctaacctt tatgtgtggc tctgcatgtt ctactgtttc ttccacctct ggcttaacat   5760
ccttgctgag ttgctttgct tcggagatag agagttctac aaggattggt ggaacgctaa   5820
```
gtctgttgga gattattgga gaatgtggaa catgcctgtg cataagtgga tggtgcgtca 5880
catctacttc ccttgcctca gatctaagat ccctaagact ctcgctatca ttatcgcttt 5940
cctcgtgtct gctgttttcc atgagttgtg tatcgctgtt ccttgcagac ttttcaagct 6000
ttgggctttc ctcggaatca tgttccaggt tccactcgtg ttcatcacta actacctcca 6060
agagagattc ggatctactg ttggaaacat gattttctgg ttcattttct gcatcttcgg 6120
acagcctatg tgcgttctcc tctactacca cgatctcatg aacagaaagg gatctatgtc 6180
ttaatgaagg atccacccag ctttcttgta caaagtggtg atgggttcga aatcgataag 6240
cttggatcct ctagagtcct gctttaatga gatatgcgag acgcctatga tcgcatgata 6300
tttgctttca attctgttgt gcacgttgta aaaaacctga gcatgtgtag ctcagatcct 6360
taccgccggt ttcggttcat tctaatgaat atatcacccg ttactatcgt atttttatga 6420
ataatattct ccgttcaatt tactgattgt accctactac ttatatgtac aatattaaaa 6480
tgaaaacaat atattgtgct gaataggttt atagcgacat ctatgataga gcgccacaat 6540
aacaaacaat tgcgttttat tattacaaat ccaattttaa aaaaagcggc agaaccggtc 6600
aaacctaaaa gactgattac ataaatctta ttcaaatttc aaaaggcccc aggggctagt 6660
atctacgaca caccgagcgg cgaactaata acgttcactg aagggaactc cggttccccg 6720
ccggcgcgca tgggtgagat tccttgaagt tgagtattgg ccgtccgctc taccgaaagt 6780
tacgggcacc attcaacccg gtccagcacg gcggccgggt aaccgacttg ctgccccgag 6840
aattatgcag catttttttg gtgtatgtgg gccccaaatg aagtgcaggt caaaccttga 6900
cagtgacgac aaatcgttgg gcgggtccag ggcgaatttt gcgacaacat gtcgaggctc 6960
agcaggacct gcaggcatgc aagctagctt actagtgatg catattctat agtgtcacct 7020
aaatct 7026

<210> SEQ ID NO 127
<211> LENGTH: 33
<212> TYPE: PRT
<213> ORGANISM: Artificial sequence
<220> FEATURE:
<223> OTHER INFORMATION: Synthetic peptide

<400> SEQUENCE: 127

Met Ala Cys His Tyr Gly Gln Gln Gln Gln Thr Cys Ala Pro His Leu
1               5                   10                  15

Gln Leu Gln Pro Arg Ala Cys Arg Val Val Lys Ala Ala Thr Ala Val
            20                  25                  30

Thr

<210> SEQ ID NO 128
<211> LENGTH: 112
<212> TYPE: PRT
<213> ORGANISM: Artificial sequence
<220> FEATURE:
<223> OTHER INFORMATION: Synthetic peptide

<400> SEQUENCE: 128

Ala Gly Gly Ser Leu Leu Val Leu Ser Gly Leu Thr Leu Ala Gly Thr
1               5                   10                  15

Val Ile Ala Leu Thr Ile Ala Thr Pro Leu Leu Val Ile Phe Ser Pro
            20                  25                  30

Val Leu Val Pro Ala Val Ile Thr Ile Phe Leu Leu Gly Ala Gly Phe
        35                  40                  45

-continued

```
Leu Ala Ser Gly Gly Phe Gly Val Ala Ala Leu Ser Val Leu Ser Trp
    50                  55                  60

Ile Tyr Arg Tyr Leu Thr Gly Lys His Pro Pro Gly Ala Asp Cys Leu
65                  70                  75                  80

Glu Ser Ala Lys Thr Lys Leu Ala Ser Cys Ala Arg Glu Met Lys Asp
                85                  90                  95

Arg Ala Glu Gln Phe Ser Cys Gln Pro Val Ala Gly Ser Gln Thr Ser
            100                 105                 110
```

MODIFIED OIL ENCAPSULATING PROTEINS AND USES THEREOF

CROSS-REFERENCE TO RELATED APPLICATION

This application is a continuation-in-part of pending International Application PCT/NZ2010/000218, filed on Oct. 29, 2010, which claims priority to U.S. Provisional Application 61/256,689, filed on Oct. 30, 2009. This application also claims priority to U.S. Provisional Application 61/515,610, filed on Aug. 5, 2011, all of which are incorporated by reference in their entireties to the extent there is no inconsistency with the present disclosure.

BACKGROUND OF THE INVENTION

The invention relates to compositions and methods for the production and modification of oil bodies in various host cell types. The invention relates to methods for the production of photosynthetic cells and plants with increased $CO_2$ assimilation rates and methods for the production of oil from plants.

In nature, flowering plants efficiently store energy in their seeds through the accumulation of oil, namely triacylglycerol (TAG) and store it in discreet oil bodies by embedding a phospholipid protein monolayer around the oil body. These seed crops have been used in a variety of agricultural applications as feed and more recently also as a feedstock source for biofuels. On a per weight basis, lipids have approximately double the energy content of either proteins or carbohydrates and as such, substantial focus has been placed on raising the oil content of various species, most notably plants. Beyond the energy aspect, the oil bodies themselves also have unique properties and form the basis for a number of biotechnical applications including but not limited to the purification of recombinant proteins, formation of multimeric protein complexes, emulsification and the delivery of bio-actives.

Unfortunately plant seeds represent a very small percentage of total plant biomass and with the demand for improved agricultural productivity and alternative energies it is recognised that current oil production from a number of devoted seed crops is insufficient. Research efforts have focused on not only increasing the productivity of oil production within plant seeds but also oil production in other cell types and species.

Traditional breeding and mutagenesis have offered incremental successes in this area; however genetic engineering has made the furthest strides in modifying organisms to produce elevated oil levels. While certain groups have worked along various parts of the oil synthesis pathway to up-regulate oil production within the seed, others groups have focused on increasing oil in cell types that represent a larger portion of the biomass.

While genetic engineering has made some progress in increasing oil content in certain targets, significant challenges still remain. Further productivity increases can still be realized in oil body production in the seed and the means to produce oil bodies similar to those of a plant seed in other cell types and species has yet to be achieved.

The increasing global population presents demand for higher yielding crops with enhanced production (photosynthetic carbon assimilation).

Ribulose biphosphate carboxlase (Rubisco) is the key enzyme responsible for photosynthetic carbon assimilation. In the presence of $O_2$, Rubisco also performs an oxygenase reaction which initiates the photorespiratory cycle which results in an indirect loss of fixed nitrogen and $CO_2$ from the cell which need to be recovered. Genetic modification to increase the specificity of Rubisco for $CO_2$ relative to $O_2$ and to increase the catalytic rate of Rubisco in crop plants would be of great agronomic value. Parry et al, (2003) reviewed the progress to date, concluding that there are still many technical barriers to overcome and to date all engineering attempts have thus far failed to produce a better Rubisco (Peterhansel et al. 2008).

In nature, a number of higher plants (C4 plants) have evolved energy requiring mechanisms to increase the concentration of intracellular $CO_2$ in close proximity to Rubisco thereby increasing the proportion of carboxylase reactions. Maize for example has achieved this by a manipulation of the plant's architecture enabling a different initial process of fixing $CO_2$, known as C4 metabolism. The agronomic downside of this evolved modification is an increase in leaf fibre resulting in a comparatively poor digestibility of leaves from C4 plants. C4 photosynthesis is thought to be a product of convergent evolution having developed on separate occasions in very different taxa. However, this adaptation is only possible for multi-cellular organisms (and not for photosynthetic unicellular organisms such as algae). Algae have a variety of different mechanisms to concentrate CO2; however, there appears to be a continuum in the degree to which the CO2 concentration mechanism (CCM) is expressed in response to external dissolved inorganic carbon (DIC) concentration, with higher concentrations leading to a greater degree of suppression of CCM activity. Two reviews have covered the CCMs in algae as well as their modulation and mechanisms and are incorporated herein by reference (Giordano, Beardall et al. 2005; Moroney and Ynalvez 2007). The vascular plants that currently constituted the largest percentage of the human staple diet are C3 (rice and tubers) and not C4 plants. Similarly, many oil seed crops (canola, sunflower, safflower) and many meat and dairy animal feed crops (legumes, cereals, soy, forage grasses) are C3 plants.

Increasing the efficiency of $CO_2$ assimilation, should therefore concurrently increase abiotic stress tolerance and nitrogen use efficiency and would be of significant agronomical benefit for C3 plants and photosynthetic microorganisms.

Therefore, mechanisms for elevating $CO_2$ concentration in the chloroplast, reducing photorespiration and subsequently increasing abiotic stress tolerance and productivity would be of significant agronomical benefit for C3 plants and photosynthetic microorganisms.

It is an object of the invention to provide methods for increasing the rate of $CO_2$ assimilation in photosynthetic cells and plants, and methods for producing photosynthetic cells and plants with an increased rate of $CO_2$ assimilation.

In nature, flowering plants efficiently store energy in their seeds through the accumulation of oil, namely triacylglycerol (TAG) and store it in discreet oil bodies by embedding a phospholipid protein monolayer around the oil body. These seed crops have been used in a variety of agricultural applications as feed and more recently also as a feedstock source for biofuels. On a per weight basis, lipids have approximately double the energy content of either proteins or carbohydrates and as such, substantial focus has been placed on raising the oil content of various species, most notably plants.

Unfortunately plant seeds represent a very small percentage of total plant biomass and with the demand for improved agricultural productivity and alternative energies it is recognised that current oil production from a number of devoted seed crops is insufficient. Research efforts have focused on not only increasing the productivity of oil production within plant seeds but also oil production in other cell types and species.

Traditional breeding and mutagenesis have offered incremental successes in this area; however genetic engineering has made the furthest strides in modifying organisms to produce elevated oil levels. While certain groups have worked along various parts of the oil synthesis pathway to up-regulate oil production within the seed, others groups have focused on increasing oil in cell types that represent a larger portion of the biomass.

It is therefore a further object of the invention to provide methods for increasing the level of oil production in plant tissues/organs and/or methods for increasing the production of oil from plants.

SUMMARY OF THE INVENTION

The present invention provides compositions and methods for producing oil bodies with varying degrees of stability. The invention involves producing modified oleosins with artificially introduced cysteine residues. The artificially introduced cysteine residues are preferably introduced in the N- and C-terminal hydrophilic arms of the modified oleosins.

Expression of the modified oleosins allows for the creation of stable oil bodies beyond the reproductive tissue of vascular plants into new cell types and even other species. When combined with a TAG synthesising enzyme, the invention leads to the accumulation and storage of TAG in eukaryotic cells as stable oil bodies. Compared with an unmodified cell or even one expressing just a TAG synthesis enzyme, the invention allows for the accumulation of TAG in excess levels achieved by other means.

For example the invention has shown that one can accumulate higher levels of stable oil bodies beyond the seed, in the vegetative portion of vascular plants.

Plants with increased levels of TAG in their vegetative tissues provide a valuable energy source for both animal feedstock and biofuel feedstock applications.

In addition recombinant modified oleosins purified from a host cell (such as *E. coli, P. pastoris, S. ceriviseae, Dunaliella, C. reinhardtii*) can be used to generate artificial oil bodies. The modified oleosins in artificial oil bodies, or those purified form transformed cells, can optionally be made to cross-link via the cysteine residues in the modified oleosin. The degree of cross-linking may be controlled manipulating the redox environment. The degree of cross-linking can also be tailored by altering the number of cysteines in the modified oleosins.

Using combinations of these techniques the oil bodies formed with the modified oleosins can be tailored for their emulsification properties, to regulate thermal stability, chemical stability, and peptidase resistance.

The modified oleosins can also be fused to a protein of interest, to form a fusion protein. The fusion protein (modified oleosin plus protein of interest) can be recombinantly expressed in a cell or organism. In this way oil bodies containing the expressed fusion proteins can be used to purify and deliver the protein of interest, for a variety of applications.

In addition the oil bodies can protect, or at least delay, degradation and/or biohydrogenation, of TAG, within the stomach and/or rumen of an animal, allowing the intact individual lipids from the TAG to be absorbed by the animal in the intestine. Therefore, the invention is also useful in terms of dietary intake of an animal, particularly through expression of the modified oleosins in plants.

The invention also provides methods for increasing the rate of $CO_2$ assimilation in photosynthetic cells and plants. This aspect of the invention involves reducing lipid recycling and/or expressing modified oleosins with artificially introduced cysteine residues in the photosynthetic cells and plants.

The invention also provides methods for increasing oil production in plants, via expression of modified oleosins with artificially introduced cysteine residues in the non-photosynthetic tissues/organs of plants. The applicants have surprisingly shown that the non-photostnthetic tissues/organs of plants expressing such modified oleosins accumulate oil to a higher level than do other tissues of the plant. The method also optionally includes the step of extracting the oil from the non-photostnthetic tissues/organs of the plant, or processing the oil rich non-photosynthetic tissues/organs into animal or biofuel feedstocks Polynucleotides Encoding Modified Oleosins with Artificially Introduced Cysteines In the first aspect the invention provides a polynucleotide encoding a modified oleosin including at least one artificially introduced cysteine. The term oleosin also includes steroleosin and caloleosin. The modified oleosin may therefore be selected from a modified oleosin, a modified caloleosin or a modified steroleosin. In one embodiment the modified oleosin is a modified oleosin. In another embodiment the modified oleosin is a modified caloleosin. In another embodiment the modified oleosin is a modified steroleosin. Examples of each type of oleosin (oleosin, caloleosin and steroleosin) are described herein In one embodiment, the modified oleosin includes at least two cysteines, at least one of which is artificially introduced. In a further embodiment, the modified oleosin includes at least two to at least thirteen (i.e., 2, 3, 4, 5, 6, 7, 8, 9, 10, 1, 12, 13, 14 or more) artificially introduced cysteines. In one embodiment the cysteines are artificially introduced in the N-terminal hydrophilic region of the oleosin, or in the C-terminal hydrophilic region of the oleosin. In a further embodiment the modified oleosin includes at least one cysteine in the N-terminal hydrophilic region, and at least one cysteine in the C-terminal hydrophilic region. In a further embodiment the cysteines are distributed substantially evenly over the N-terminal and C-terminal hydrophilic regions of the oleosin.

In a further embodiment the polynucleotide encodes a fusion protein including the modified oleosin fused to a protein of interest.

Constructs

In a further aspect the invention provides a genetic construct comprising a polynucleotide of the invention. In a further aspect the invention provides an expression construct comprising a polynucleotide of the invention. In one embodiment the polynucleotide in the construct is operably linked to a promoter sequence. In one embodiment the promoter sequence is capable of driving expression of the polynucleotide in a vegetative tissue of a plant. In a further embodiment the promoter sequence is capable of driving expression of the polynucleotide in a seed of a plant. In a further embodiment the promoter sequence is capable of driving expression of the polynucleotide in the pollen of a plant. In a further embodiment the promoter sequence is capable of driving expression of the polynucleotide in an *E. coli* cell. In a further embodiment the promoter sequence is capable of driving expression of the polynucleotide in a yeast cell. In a further embodiment the promoter sequence is capable of driving expression of the polynucleotide in an algal cell.

In another aspect, the invention provides a construct containing a polynucleotide that encodes a modified neutral lipid protein. In one embodiment, the construct also contains a second polynucleotide that encodes a triacylglycerol (TAG) synthesizing enzyme. In various embodiments, the construct can be linked to a promoter sequence capable of driving its expression in various host cells. As such, the invention also provides use of the constructs to induce a host cell to express a modified oleosin and/or a TAG synthesizing enzyme. In various embodiments, the construct expressing a modified oleosin and the construct expressing a TAG synthesizing enzyme may be driven by the same or by different promoters. In yet another embodiment the construct is located in an appropriate position and orientation of a suitable functional endogenous promoter such that the expression of the construct occurs. In various embodiments, the construct can be expressed in a bacterial, plant, fungal or algal cell. In one embodiment where the construct is expressed in a plant cell, the cell may be of vegetative, seed, pollen or fruit tissue.

Host Cells

In a further aspect the invention provides a host cell comprising a construct of the invention. In a further aspect the invention provides a host cell genetically modified to comprise a polynucleotide of the invention. In a further aspect the invention provides a host cell genetically modified to express a polynucleotide of the invention.

Host Cell Also Expressing a Tag Synthesising Enzyme

In a further embodiment the host cell is also genetically modified to express a triacylglycerol (TAG) synthesising enzyme. In a further embodiment the host cell is genetically modified to comprise a nucleic acid sequence encoding a triacylglycerol (TAG) synthesising enzyme. In a further embodiment the host cell comprises an expression construct including a nucleic acid sequence encoding a triacylglycerol (TAG) synthesising enzyme.

In a further embodiment the nucleic acid is operably linked to a promoter sequence. In a further embodiment the promoter sequence is capable of driving expression of the nucleic acid sequence in a vegetative tissue of a plant. In one embodiment the promoter sequence is capable of driving expression of the nucleic acid sequence in a seed of a plant. In one embodiment the promoter sequence is capable of driving expression of the nucleic acid sequence in the pollen of a plant.

In a further embodiment the promoter sequence is capable of driving expression of the polynucleotide in an *E. coli* cell. In a further embodiment the promoter sequence is capable of driving expression of the polynucleotide in a yeast cell. In a further embodiment the promoter sequence is capable of driving expression of the polynucleotide in an algal cell.

Host Cell Types

The host cell may be any type of cell. In on embodiment the host cell is a prokaryotic cell. In a further embodiment the host cell is a eukaryotic cell. In one embodiment the host cell is selected from a bacterial cell, a yeast cell, a fungal cell, an insect cell, algal cell, and a plant cell. In one embodiment the host cell is a bacterial cell. In a further embodiment the host cell is a yeast cell. In further embodiment the host cell is a fungal cell. In further embodiment the host cell is an insect cell. In further embodiment the host cell is an algal cell. In a further embodiment the host cell is a plant cell.

Plants

In a further aspect the invention provides a plant comprising a plant cell of the invention. In a further aspect the invention provides a plant comprising a construct of the invention. In a further aspect the invention provides a plant genetically modified to comprise a polynucleotide of the invention. In a further aspect the invention provides a plant genetically modified to express a polynucleotide of the invention. In a further embodiment the plant expresses a modified oleosin encoded by the polynucleotide of the invention.

In a further embodiment the modified oleosin is expressed in a vegetative tissue of the plant. In a further embodiment the modified oleosin is expressed in a seed of the plant. In a further embodiment the modified oleosin is expressed in the pollen of the plant.

Plant Also Expresses a TAG Enzyme

In a further embodiment the plant is also genetically modified to express a triacylglycerol (TAG) synthesising enzyme. In a further embodiment the triacylglycerol (TAG) synthesising enzyme is expressed in the same tissue as the modified oleosin.

In a further embodiment the plant is genetically modified to comprise a nucleic acid sequence encoding a triacylglycerol (TAG) synthesising enzyme. In a further embodiment the plant comprises an expression construct including a nucleic acid sequence encoding a triacylglycerol (TAG) synthesising enzyme.

In a further embodiment the nucleic acid is operably linked to a promoter sequence.

In a further embodiment the promoter sequence is capable of driving expression of the nucleic acid sequence in a vegetative tissue of a plant. In one embodiment the promoter sequence is capable of driving expression of the nucleic acid sequence in a seed of a plant. In one embodiment the promoter sequence is capable of driving expression of the nucleic acid sequence in the pollen of a plant.

Modified Oleosin Polypeptides with Artificially Introduced Cysteines

In a further aspect the invention provides a modified oleosin including at least one artificially introduced cysteine. In a further aspect the invention provides a modified oleosin encode by a polynucleotide of the invention. In one embodiment, the modified oleosin includes at least two cysteines, at least one of which is artificially introduced. In a further embodiment, the modified oleosin includes at least two to at least thirteen (i.e., 2, 3, 4, 5, 6, 7, 8, 9, 10, 1, 12, 13, 14 or more) artificially introduced cysteines.

In a further embodiment the modified oleosin includes at least one cysteine in the N-terminal hydrophilic region, and at least one cysteine in the C-terminal hydrophilic region. In a preferred embodiment the cysteins are artificially introduced in the N-terminal hydrophilic region of the oleosin, or in the C-terminal hydrophilic region of the oleosin. Preferably the cysteins are distributed substantially evenly between the N-terminal and C-terminal hydrophilic region of the oleosin.

Fusion Proteins with Modified Oleosins Including Artificially Introduced Cysteines In a further aspect the invention provides a fusion protein comprising a modified oleosin of the invention and a protein of interest. The fusion protein thus comprises a modified oleosin portion, and a protein of interest portion.

Oil Bodies Comprising Modified Oleosins

In a further aspect the invention provides an oil body comprising a modified oleosin of the invention. In a further aspect the invention provides an oil body comprising at least two modified oleosins of the invention. In one embodiment at least two of the modified oleosins are cross-linked to each other via disulphide bridges between cysteine residues in the modified oleosins. In a further embodiment the modified oleosins are cross-linked via the artificially introduced cysteine residues in the modified oleosins.

In a further embodiment the oil body additionally comprises a fusion protein, wherein the fusion protein includes an oleosin fused to a protein of interest. In this embodiment, the oleosin in the fusion protein need not include an artificially introduced cysteine. Preferably the oleosin in the fusion protein does not include an artificially introduced cysteine.

The oil bodies of this embodiment are useful for purifying and delivering the protein of interest, as discussed in Roberts et al., (2008).

However in this embodiment it is possible to take advantage of the option to vary the stability/integrity of the oil body provided by presence of the modified oleosins in the oil body, hence allowing for more stringent purification and delivery procedures.

Oil Bodies Comprising Fusion Proteins with Modified Oleosisn

In a further aspect the invention provides an oil body comprising a fusion protein of the invention, the fusion protein comprising a modified oleosin of the invention and a protein of interest. The fusion protein thus comprises a modified oleosin portion, and a protein of interest portion.

In one embodiment the oil body comprises at least two fusion proteins of the invention.

In one embodiment at least two of the fusion proteins are cross-linked to each other via disulphide bridges between cysteine residues in the modified oleosin portion of the fusion proteins. In one embodiment the fusion proteins are cross-linked via the artificially introduced cysteine residues in the modified oleosin portion of the fusion proteins.

In a further embodiment the oil body comprises at least one modified oleosin of the invention. In a further embodiment at least one fusion protein is cross-linked to at least one modified oleosin, via a cysteine in the modified oleosin portion of the fusion protein and a cysteine in the modified oleosin.

Again, the oil bodies of this embodiment are useful for purifying and delivering the protein of interest, as discussed in Roberts et al., (2008).

However in this embodiment it is possible to take advantage of the option to vary the stability/integrity of the oil body provided by presence of the modified oleosins in the oil body, hence allowing for more stringent purification and delivery procedures.

Emulsion

In a further aspect the invention provides an emulsion comprising a modified oleosin of the invention. In one embodiment the emulsion comprises the modified oleosin and a suitable carrier. The carrier may be buffered, with the appropriate redox environment to retain the desired degree of cross-linking of the oleosins.

To resuspend the modified oleosin in the carrier may require sonication or high pressure homogenising, followed by exposure to the appropriate oxidising conditions.

Compositions

In a further aspect the invention provides a composition comprising a modified oleosin of the invention. In one embodiment the composition comprises the modified oleosin and a suitable carrier. The carrier may be buffered, with the appropriate redox environment to attain the desired degree of cross-linking of the modified oleosins.

To resuspend the modified oleosins in the carrier may require sonication or high pressure homogenising, followed by exposure to the appropriate oxidising conditions.

In a further aspect the invention provides a composition comprising an oil body of the invention. In one embodiment the composition comprises the oil body and a suitable carrier. The carrier may be buffered, with the appropriate redox environment to retain the desired degree of cross-linking of the modified oleosins. In a further embodiment the invention provides a composition formulated for dermal application comprising an oil body of the invention.

Plants, and Parts Thereof, Comprising Oil Bodies of the Invention

In a further aspect the invention provides a plant, or part thereof, comprising an oil body of the invention. In a further aspect the invention provides a vegetative tissue of a plant, comprising an oil body of the invention. In a further aspect the invention provides a seed of a plant, comprising an oil body of the invention.

Animal Feed Comprising Oil Bodies of the Invention

In a further aspect the invention provides an animal feed comprising an oil body of the invention. In a further aspect the invention provides an animal feed comprising a plant, or part thereof, of the invention.

Methods for Producing Oil Bodies

In a further aspect invention provides a method for producing an oil body, the method comprising the step of combining:

a) at least two modified oleosins, each including at least one artificially introduced cysteine,
b) triacylglycerol, and
c) phospholipid.

In one embodiment, the modified oleosins each include at least two cysteines, at least one of which is artificially introduced. In a further embodiment the modified oleosins each include at least one cysteine in the N-terminal hydrophilic region of the oleosin, and at least one cysteine in the C-terminal hydrophilic region of the oleosin.

In a further embodiment, the modified oleosin includes at least two to at least thirteen (i.e., 2, 3, 4, 5, 6, 7, 8, 9, 10, 1, 12, 13, 14 or more) artificially introduced cysteines.

In one embodiment the cysteines are artificially introduced in the N-terminal hydrophilic region of the oleosins, or in the C-terminal hydrophilic region of the oleosins. In a further embodiment the cysteines are distributed substantially evenly between the N-terminal and C-terminal hydrophilic region of the oleosins. In a further embodiment the modified oleosins are cross-linked via disulphide bridges between cysteine residues in the oleosins. In a further embodiment embodiment the modified oleosins are cross-linked between the artificially introduced cysteine residues in the oleosins.

In one embodiment the modified oleosins are part of fusion proteins wherein the fusion proteins comprise a modified oleosin, and a protein of interest.

In one embodiment the method comprises the additional step of regulating the degree of cross-linking of modified oleosins in the oil body by controlling the redox environment of the oil body produced.

All Components Combined In Vivo (In Vivo Oil Bodies)

In one embodiment the components of a), b) and c) are combined within a host cell. In this embodiment the modified oleosins are preferably expressed in the host cell.

The host cell is preferably genetically modified to express the modified oleosins.

The host cell is preferably comprises a construct of the invention. The host cell is preferably genetically modified to comprise a polynucleotide of the invention. The host cell is preferably genetically modified to express a polynucleotide of the invention.

Host Cell Also Expresses a TAG Synthesising Enzyme

In a further embodiment the host cell is also genetically modified to express a triacylglycerol (TAG) synthesising enzyme. In a further embodiment the host cell comprises an expression construct including a nucleic acid sequence encoding a triacylglycerol (TAG) synthesising enzyme.

In a further embodiment the nucleic acid sequence is operably linked to a promoter sequence. In one embodiment the promoter sequence is capable of driving expression of the nucleic acid sequence in a vegetative tissue of a plant. In one embodiment the promoter sequence is capable of driving expression of the nucleic acid sequence in a seed of a plant. In one embodiment the promoter sequence is capable of driving expression of the nucleic acid sequence in the pollen of a plant.

In a further embodiment the host cell is also genetically modified to comprise a nucleic acid sequence encoding a triacylglycerol (TAG) synthesising enzyme. In a further embodiment the host cell is also genetically modified to express a nucleic acid sequence encoding a triacylglycerol (TAG) synthesising enzyme.

It will be understood by those skilled in the art that the polynucleotide encoding the modified oleosin and the nucleic acid sequence encoding a triacylglycerol (TAG) synthesising enzyme can be placed on the same construct or on separate constructs to be transformed into the host cell. Expression of each can be driven by the same or different promoters, which may be included in the construct to be transformed. It will also be understood by those skilled in the art that alternatively the polynucleotide and nucleic acid can be transformed into the cell without a promoter, but expression of either the polynucleotide and nucleic acid could be driven by a promoter or promoters endogenous to the cell transformed.

In a further embodiment the host cell forms part of an organism. In a preferred embodiment the organism is a plant.

In a further embodiment the oil is produced in the vegetative tissues of the plant.

In one embodiment of the method the plant acumulates about 50% to about 400% more lipid than does a suitable control plant. In a further embodiment of the method the plant acumulates about 100% to about 300% more lipid than does a suitable control plant. In a further embodiment of the method the plant acumulates about 150% to about 250% more lipid than does a suitable control plant. Suitable control plants include non-transformed or wild-type versions of plant of the same variety and or species as the transformed plant used in the method of the invention.

In a further embodiment the plant is processed into an animal feed.

In a further embodiment the plant is processed into a biofuel feed stock.

Additional Method Step to Purify the In Vivo Produced Oil Bodies

In one embodiment the method includes the additional step of purifying the oil bodies from the cell or organisim.

Additional Method Step to Vary Degree of Cross-Linking of In Vivo Produced Purified Oil Bodies In a further embodiment the method comprises the additional step of regulating the degree of cross-linking of modified oleosins in the in vivo produced purified oil bodies by controlling the redox environment of the purified oil bodies. In one embodiment the degree of cross-linking is increased by use of an oxidising environment. In a further embodiment the degree of cross-linking is decreased by use of a reducing environment.

Components Combined In Vitro (In Vitro/Artificial Oil Bodies)

In certain embodiments the components of a), b) and c) may be combined in vitro.

In one embodiment, the modified oleosin of a) has been recombinantly expressed in, and purified from a host cell of the invention, before being combined with the components of b) and c).

Additional Method Step to Vary Degree of Cross-Linking of In Vitro/Artificial Oil Bodies In a further embodiment the method comprises the additional step of regulating the degree of cross-linking by controlling the redox environment in which the components of a), b) and c) are combined. In one embodiment the degree of cross-linking is increased by combining the components of a), b) and c) in on oxidising environment. In a further embodiment the degree of cross-linking is decreased by combining the components of a), b) and c) in a reducing environment. The degree of cross-linking may also be regulated after the oil body is formed, by controlling the redox environment in which the oil body is contained.

In a further aspect the invention provides a method of producing a plant that accumulates more oil than a suitable control plant the method comprising providing a plant transformed with a polynucleotide of the invention that expresses a modified oleosin encode by the polynucleotide.

In one embodiment the plant is also transformed with a polynucleotide encoding a TAG synthesising enzyme to express the TAG synthesising enzyme and thus synthesise TAG.

In one embodiment the plant the plant is produced by transforming a single plant, or plant cell, with both the polynucleotide of any one the invention and the polynucleotide encoding the TAG synthesising enzyme.

In a further embodiment the plant is produced by crossing a first plant transformed with a polynucleotide of any one of the invention, with second plant transformed the polynucleotide encoding the TAG synthesising enzyme, to produce the plant transformed with both a polynucleotide of the invention, and a polynucleotide encoding the TAG synthesising enzyme.

In a further embodiment the oil is TAG. In a further embodiment the oil is produced in the vegetative tissues of the plant.

In one embodiment of the method the plant acumulates about 50% to about 400% more lipid than does a suitable control plant. In a further embodiment of the method the plant acumulates about 100% to about 300% more lipid than does a suitable control plant. In a further embodiment of the method the plant acumulates about 150% to about 250% more lipid than does a suitable control plant In a further embodiment the plant is processed into an animal feed.

In a further embodiment the plant is processed into a biofuel feed stock.

In a further aspect invention provides a method for producing an oil body in a host cell, the method comprising:

a) introducing into a host cell at least one nucleic acid molecule encoding a modified oleosin of the invention; and
b) culturing the host cell in order to express the modified oleosin.

In a further aspect invention provides a method for producing an oil body in a host cell, the method comprising:

a) introducing into a host cell at least one nucleic acid molecule encoding a modified oleosin of the invention and a nucleic acid molecule encoding a TAG synthesizing enzyme; and
b) culturing the host cell in order to express the modified oleosin and the TAG synthesizing enzyme.

The host cell may be a host cell as herein described.

Oil Bodies

In a further aspect invention provides an oil body produced by a method of the invention.

Compositions

In a further aspect the invention provides a composition comprising an oil body of the invention. In one embodiment the composition comprises the oil body and a suitable carrier. The carrier may be buffered to provide the appropriate redox environment to retain the desired degree of cross-linking of the modified oleosin. In a further embodiment the invention provides a composition formulated for dermal application comprising an oil body of the invention.

Plants, and Parts Thereof, Comprising Oil Bodies of the Invention

In a further aspect the invention provides a plant, or part thereof, comprising an oil body of the invention. In a further aspect the invention provides a vegetative tissue of a plant, comprising an oil body of the invention. In a further aspect the invention provides a seed of a plant, comprising an oil body of the invention. In a further aspect the invention provides pollen of a plant, comprising an oil body of the invention. In a further aspect the invention provides a fruit, or fruiting body, of a plant, comprising an oil body of the invention.

Animal Feed Comprising Oil Bodies of the Invention

In a further aspect the invention provides an animal feed comprising an oil body of the invention. In a further aspect the invention provides an animal feed comprising a plant, or part thereof, of the invention.

In one embodiment the feed is suitable for a mammalian animal including humans. In a further embodiment the feed is suitable for non-human mammals. Preferred animals include farm animals such as but not limited to cows, sheep, horses, goats, pigs, chickens, and the like.

Plants

The modified oleosins may be modified naturally occurring oleosins. The plants from which the un-modified oleosin sequences are derived may be from any plant species that contains oleosins and polynucleotide sequences encoding oleosins.

The plant cells, in which the modified oleosins are expressed, may be from any plant species. The plants, in which the modified oleosins are expressed, may be from any plant species.

In one embodiment the plant cell or plant, is derived from a gymnosperm plant species.

In a further embodiment the plant cell or plant, is derived from an angiosperm plant species.

In a further embodiment the plant cell or plant, is derived from a from dicotyledonous plant species.

In a further embodiment the plant cell or plant, is derived from a monocotyledonous plant species.

Other preferred plants are forage plant species from a group comprising but not limited to the following genera: *Zea, Lolium, Hordium, Miscanthus, Saccharum, Festuca, Dactylis, Bromus, Thinopyrum, Trifolium, Medicago, Pheleum, Phalaris, Holcus, Glycine, Lotus, Plantago* and *Cichorium.*

Other preferred plants are leguminous plants. The leguminous plant or part thereof may encompass any plant in the plant family Leguminosae or Fabaceae. For example, the plants may be selected from forage legumes including, alfalfa, clover; leucaena; grain legumes including, beans, lentils, lupins, peas, peanuts, soy bean; bloom legumes including lupin, pharmaceutical or industrial legumes; and fallow or green manure legume species.

A particularly preferred genus is *Trifolium*. Preferred *Trifolium* species include *Trifolium repens; Trifolium arvense; Trifolium affine*; and *Trifolium occidentale*. A particularly preferred *Trifolium* species is *Trifolium repens.*

Another preferred genus is *Medicago*. Preferred *Medicago* species include *Medicago sativa* and *Medicago truncatula*. A particularly preferred *Medicago* species is *Medicago sativa*, commonly known as alfalfa.

Another preferred genus is *Glycine*. Preferred *Glycine* species include *Glycine max* and *Glycine wightii* (also known as *Neonotonia wightii*). A particularly preferred *Glycine* species is *Glycine max*, commonly known as soy bean. A particularly preferred *Glycine* species is *Glycine wightii*, commonly known as perennial soybean.

Another preferred genus is *Vigna*. A particularly preferred *Vigna* species is *Vigna unguiculata* commonly known as cowpea.

Another preferred genus is *Mucana*. Preferred *Mucana* species include *Mucana pruniens*. A particularly preferred *Mucana* species is *Mucana pruniens* commonly known as velvetbean.

Another preferred genus is *Arachis*. A particularly preferred *Arachis* species is *Arachis glabrata* commonly known as perennial peanut.

Another preferred genus is *Pisum*. A preferred *Pisum* species is *Pisum sativum* commonly known as pea.

Another preferred genus is *Lotus*. Preferred *Lotus* species include *Lotus corniculatus, Lotus pedunculatus, Lotus glabar, Lotus tenuis* and *Lotus uliginosus*. A preferred *Lotus* species is *Lotus corniculatus* commonly known as Birdsfoot Trefoil. Another preferred *Lotus* species is *Lotus glabar* commonly known as Narrow-leaf Birdsfoot Trefoil. Another preferred *Lotus* species is *Lotus pedunculatus* commonly known as Big trefoil. Another preferred *Lotus* species is *Lotus tenuis* commonly known as Slender trefoil.

Another preferred genus is *Brassica*. A preferred *Brassica* species is *Brassica oleracea*, commonly known as forage kale and cabbage.

Other preferred species are oil seed crops including but not limited to the following genera: *Brassica, Carthumus, Helianthus, Zea* and *Sesamum.*

A preferred oil seed genera is *Brassica*. A preferred oil seed species is *Brassica napus.*

A preferred oil seed genera is *Brassica*. A preferred oil seed species is *Brassica oleraceae.*

A preferred oil seed genera is *Zea*. A preferred oil seed species is *Zea mays.*

A preferred oil seed genera is *Carthamus*. A preferred oil seed species is *Carthamus tinctorius.*

A preferred oil seed genera is *Helianthus*. A preferred oil seed species is *Helianthus annuus.*

A preferred oil seed genera is *Zea*. A preferred oil seed species is *Zea mays.*

A preferred oil seed genera is *Sesamum*. A preferred oil seed species is *Sesamum indicum.*

A preferred silage genera is *Zea*. A preferred silage species is *Zea mays.*

A preferred grain producing genera is *Hordeum*. A preferred grain producing species is *Hordeum vulgare.*

A preferred grazing genera is *Lolium*. A preferred grazing species is *Lolium perenne.*

A preferred grazing genera is *Lolium*. A preferred grazing species is *Lolium arundinaceum.*

A preferred grazing genera is *Trifolium*. A preferred grazing species is *Trifolium repens.*

A preferred grazing genera is *Hordeum*. A preferred grazing species is *Hordeum vulgare.*

Preferred plants also include forage, or animal feedstock plants. Such plants include but are not limited to the following genera: *Miscanthus, Saccharum, Panicum.*

A preferred biofuel genera is *Miscanthus*. A preferred biofuel species is *Miscanthus giganteus.*

A preferred biofuel genera is *Saccharum*. A preferred biofuel species is *Saccharum officinarum.*

A preferred biofuel genera is *Panicum*. A preferred biofuel speices is *Panicum virgatum.*

In a further aspect the invention provides a method for producing a photosynthetic cell with an increased rate of $CO_2$ assimilation, the method comprising at least one of the steps:

a) genetically modifying the photosynthetic cell to reduce or prevent lipid recycling, and b) transforming the photosynthetic cell with a polynucleotide encoding a modified oleosin including at least one artificially introduced cysteine.

In one embodiment the method comprises the step of genetically modifying the photosynthetic cell to reduce or prevent lipid recycling.

In another embodiment, the method comprises the step of transforming the photosynthetic cell with a polynucleotide encoding a modified oleosin including at least one artificially introduced cysteine.

In one embodiment the cell is genetically modified to prevent lipid recycling, by transforming the photosynthetic cell with a polynucleotide encoding a modified oleosin including at least one artificially introduced cysteine.

In a preferred embodiment the modified oleosin is expressed in the photosynthetic cell. In one embodiment expression of the modified oleosin causes the increased rate of $CO_2$ assimilation. In one embodiment, expression of the modified oleosin reduces or prevents lipid recycling in the photosynthetic cell. In a preferred embodiment the reduced or prevented lipid recycling causes the increased $CO_2$ assimilation.

In a further embodiment the lipid recycling is initiated by the action of lipases releasing free fatty acids from a glycerol backbone. In a further embodiment the lipid recycling is driven by the reincorporation of fatty acids into glycerol backbones within the endoplasmic reticulum of the cell.

In one embodiment the rate of $CO_2$ assimilation is increased by at least 1%, more preferably at least 2%, more preferably at least 3%, more preferably at least 4%, more preferably at least 5%, more preferably at least 10%, more preferably at least 15%, more preferably at least 20%, more preferably at least 25%, more preferably at least 30%, more preferably at least 35%, more preferably at least 40%, more preferably at least 45%, more preferably at least 50%, relative to a control plant.

In one embodiment the rate of $CO_2$ assimilation increase is in the range of 1% to 50%, more preferably 2% to 40%, more preferably 3% to 30%, more preferably 4% to 25%, more preferably 5% to 20%, relative to a control plant.

In one embodiment the increase in $CO_2$ assimilation results from an elevated concentration of $CO_2$ in the chloroplast.

Modified Oleosin

The term oleosin also includes steroleosin and caloleosin. The modified oleosin may therefore be selected from a modified oleosin, a modified caloleosin or a modified steroleosin. In one embodiment the modified oleosin is a modified oleosin. In another embodiment the modified oleosin is a modified caloleosin. In another embodiment the modified oleosin is a modified steroleosin. Examples of each type of oleosin (oleosin, caloleosin and steroleosin) are described herein In one embodiment, the modified oleosin includes at least two cysteines, at least one of which is artificially introduced. In a further embodiment, the modified oleosin includes at least two to at least thirteen (i.e., 2, 3, 4, 5, 6, 7, 8, 9, 10, 11, 12, 13, 14 or more) artificially introduced cysteines. In one embodiment the cysteines are artificially introduced in the N-terminal hydrophilic region of the oleosin, or in the C-terminal hydrophilic region of the oleosin. In a further embodiment the modified oleosin includes at least one cysteine in the N-terminal hydrophilic region, and at least one cysteine in the C-terminal hydrophilic region. In a further embodiment the cysteines are distributed substantially evenly over the N-terminal and C-terminal hydrophilic regions of the oleosin. In a further embodiment the cysteines are distributed evenly over the N-terminal and C-terminal hydrophilic regions of the oleosin.

Other Associated Phenotypes of the Photosynthetic Cell

In a further embodiment, in addition to the increased rate of $CO_2$ assimilation the method produces a photosynthetic cell with at least one of:

a) an increased rate of photosynthesis, and b) increased water use efficiency, and c) an increased growth rate d) increased chloroplast $CO_2$ concentration, e) a decreased rate of photorespiration, f) increased high temperature tolerance, g) increased high oxygen concentration tolerance, h) increased nitrogen use efficiency, and i) decreased loss of fixed carbon.

Preferably the photosynthetic cell produced has all of a) to i).

Promoters

In one embodiment the polynucleotide is operably linked to a promoter polynucleotide.

In one embodiment the promoter is capable of driving expression of the polynucleotide in a photosynthetic cell. In one embodiment the promoter drives expression of the polynucleotide preferentially in photosynthetic cells. In one embodiment the promoter is a photosynthetic cell preferred promoter. In a further embodiment the promoter is a photosynthetic cell specific promoter. In a further embodiment the promoter is a light regulated promoter.

Polynucleotide is Part of a Genetic Construct

In one embodiment the polynucleotide is transformed as part of a genetic construct. Preferably the genetic construct is an expression construct. Preferably the expression construct includes the polynucleotide operably linked to the promoter. In a further embodiment the polynucleotide is operably linked to a terminator sequence Photosynthetic Cell is Also Transformed with a TAG Synthesising Enzyme In a further embodiment the photosynthetic cell is also genetically modified to express a triacylglycerol (TAG) synthesising enzyme. In a further embodiment the photosynthetic cell is genetically modified to comprise a nucleic acid sequence encoding a triacylglycerol (TAG) synthesising enzyme. In a further embodiment the photosynthetic cell comprises an expression construct including a nucleic acid sequence encoding a triacylglycerol (TAG) synthesising enzyme.

In a further embodiment the nucleic acid is operably linked to a promoter polynucleotide.

In one embodiment the promoter is capable of driving expression of the polynucleotide in the photosynthetic cell. In one embodiment the promoter is a photosynthetic cell preferred promoter. In a further embodiment the promoter is a photosynthetic cell specific promoter. In a further embodiment the promoter is a light regulated promoter.

It will be understood by those skilled in the art that the polynucleotide encoding the modified oleosin and the nucleic acid sequence encoding a triacylglycerol (TAG) synthesising enzyme can be placed on the same construct or on separate constructs to be transformed into the host cell. Expression of each can be driven by the same or different promoters, which may be included in the construct to be transformed. It will also be understood by those skilled in the art that alternatively the polynucleotide and nucleic acid can be transformed into the cell without a promoter, but expression of either or both of the polynucleotide and nucleic acid could be driven by a promoter or promoters endogenous to the cell transformed.

Photosynthetic Cell Types

The photosynthetic cell may be of any type. In one embodiment the photosynthetic cell is a prokaryotic cell. In a further embodiment the photosynthetic cell is a eukaryotic cell. In one embodiment the photosynthetic cell is selected from a photosynthetic bacterial cell, a photosynthetic yeast cell, a photosynthetic fungal cell, a photosynthetic algal cell, and a plant cell. In one embodiment the photosynthetic cell is a bacterial cell. In a further embodiment the photosynthetic cell is a yeast cell. In further embodiment the photosynthetic cell is a fungal cell. In further embodiment the photosynthetic cell is an algal cell.

Photosynthetic Cell is an Algal Cell

In a preferred embodiment the photosynthetic cell is an algal cell. In one embodiment the photosynthetic algal cell is an algal cell selected from one of the following divisions: Chlorophyta (green algae), Rhodophyta (red algae), Phaeophyceae (brown algae), Bacillariophycaeae (diatoms), and Dinoflagellata (dinoflagellates).

In one embodiment the algal cell shows an increased growth rate, relative to a control algal cell, at an elevated concentration of oxygen ($O_2$).

In a further embodiment, the concentration of $O_2$ is elevated to at least 1.1 times air saturation, more preferably at least 1.5 times air saturation, more preferably at least 2 times air saturation, more preferably at least 4 times air saturation, more preferably at least 8 times air saturation, more preferably at least 16 times air saturation.

In a further embodiment, the increased growth rate of the algal cell is at least 10%, more preferably at least 20%, more preferably at least 30%, more preferably at least 40%, more preferably at least 50%, more preferably at least 60%, more preferably at least 70%, more preferably at least 80%, more preferably at least 90%, more preferably at least 100% more than the growth rate of a control algal cell at the same $O_2$ concentration.

In a further embodiment, the increased growth rate of the algal cell is in the range 10% to about 130% more preferably 20% to 120%, more preferably 30% to 110%, more preferably 40% to 100%, more preferably 50% to 90%, more than the growth rate of a control algal cell at the same $O_2$ concentration.

Photosynthetic Cell is Part of a Plant.

In a further preferred embodiment the photosynthetic cell is a plant cell. In a preferred embodiment the plant cell is part of a plant.

Thus the invention provides a method for producing a photosynthetic cell, or plant, with an increased rate of $CO_2$ assimilation.

Promoters for Plants

In one embodiment the promoter operably linked to the polynucleotide is capable of driving expression of the polynucleotide in a photosynthetic tissue of a plant. In one embodiment the promoter is a photosynthetic cell preferred promoter. In a further embodiment the promoter is a photosynthetic cell specific promoter. In a further embodiment the promoter is capable of driving expression of the polynucleotide in a vegetative photosynthetic tissue of a plant. In a further embodiment the promoter is capable of driving expression of the polynucleotide in a leaf of a plant.

Further Associated Phenotypes for Plants

In a further embodiment, in addition to the increased rate of $CO_2$ assimilation the plant also has at least one of:

a) an increased rate of photosynthesis, and
b) increased water use efficiency, and
c) an increased growth rate.

Preferably the plant has all of a) to c).

In a further embodiment, in addition to the increased rate of $CO_2$ assimilation the plant also has at least one of:

d) increased biomass,
e) delayed flowering,
f) increased chloroplast $CO_2$ concentration,
g) a decreased rate of photorespiration,
h) increased seed, fruit or storage organ yield,
i) increased drought tolerance,
j) increased high temperature tolerance,
k) increased high oxygen concentration tolerance,
l) increased nitrogen use efficiency, and
m) decreased loss of fixed carbon.

Preferably the plant has all of a) to m).

In one embodiment biomass is increased by at least 5%, preferably by at least 10%, preferably by at least 20%, preferably by at least 30%, preferably by at least 40%, preferably by at least 50%, preferably by at least 60% relative to a control plant.

In one embodiment the increase in biomass is in the range 2% to 100%, preferably 4% to 90%, preferably 6% to 80%, preferably 8% to 70%, preferably 10% to 60% relative to a control plant.

Plant Types

In one embodiment the plant is a C3 plant.

In one embodiment the plant is selected from: rice, soybean, wheat, rye, oats, millet, barley, potato, canola, sunflower and safflower.

Preferred plants include those from the following genera: *Oryza, Glycine, Hordeum, Secale, Avena, Pennisetum, Setaria, Panicum, Eleusine, Solanum, Brassica, Helianthus* and *Carthamus.*

Preferred *Oryza* species include *Oryza sativa* and *Oryza minuta.*

Preferred *Glycine* species include *Glycine max* and *Glycine wightii* (also known as *Neonotonia wightii*). A particularly preferred *Glycine* species is *Glycine max*, commonly known as soy bean. A particularly preferred *Glycine* species is *Glycine wightii*, commonly known as perennial soybean.

A preferred *Hordeum* species is *Hordeum vulgare.*

Preferred *Triticum* species include *Triticum aestivum, Triticum durum* and *Triticum monococcum.*

A preferred *Secale* species is *Secale* cereal.

A preferred *Avena* species is *Avena sativa.*

Preferred millet species include *Pennisetum glaucum, Setaria italica, Panicum miliaceum* and *Eleusine coracana.*

Preferred *Sorghum* species include *Sorghum bicolor* and *Sorghum propinquum*

Preferred *Solanum* species include *Solanum habrochaites, Solanum lycopersicum, Solanum nigrum*, and *Solanum tuberosum.*

Preferred *Brassica* species include *Brassica napus, Brassica campestris* and *Brassica Rapa.*

Preferred *Helianthus* species include *Helianthus annuus* and *Helianthus argophyllus.*

A preferred *Carthamus* species is *Carthamus tinctorius*

In a further aspect the invention provides a method for producing oil, the method comprising the steps:

a) providing a plant comprising a polynucleotide encoding a modified oleosin including at least one artificially introduced cysteine,
b) cultivating the plant to express the modified oleosin and produce oil in its non-photosynthetic tissues/organs.

Level of Total Lipid Production in Non-Photosynthetic Tissues/Organs.

In one embodiment the plant accumulates more total lipid in its non-photosynthetic tissues/organs than does a control plant.

In a further embodiment the plant accumulates at least 10%, more preferably at least 20%, more preferably at least 50%, more preferably at least 100%, more preferably 150%, more preferably 200%, more preferably 250%, more preferably 300%, more preferably 350%, more preferably 400%, more preferably 450%, more preferably 500%, more total lipid in its non-photosynthetic tissues/organs than does a control plant.

In one embodiment the plant produces total lipid in its non-photosynthetic tissues/organs in the range 100% to 900%, more preferably 200% to 800%, more preferably 300% to 700%, more preferably 400% to 600%, more than a control plant.

Level Oil Production in Non-Photosynthetic Tissues/Organs.

In one embodiment the plant accumulates more oil in its non-photosynthetic tissues/organs than does a control plant.

In one embodiment the plant accumulates at least 1.2×, at least 1.5×, at least 2×, more preferably at least 3×, more preferably at least 4×, more preferably at least 5×, more preferably at least 6×, more preferably at least 7×, more preferably at least 8×, more preferably at least 9×, more preferably at least 10×, more preferably at least 11×, more preferably at least 12×, more preferably at least 13×, more preferably at least 14×, more preferably at least 15×, more oil in its non-photosynthetic tissues/organs than does a control plant.

In one embodiment the plant produce oil in its non-photosynthetic tissues/organs in the range 3× to 15×, more preferably 4× to 14×, more preferably 5× to 13×, more preferably 6× to 12×, more preferably 7× to 11×, more preferably 8× to 10× more than a control plant.

Suitable control plants include non-transformed or wild-type versions of plant of the same variety and/or species as the transformed plant used in the method of the invention. Suitable control plants also include plants of the same variety and or species as the transformed plant that are transformed with a control construct. Suitable control plants also include plants that have not been transformed with a polynucleotide encoding a modified oleosin including at least one artificially introduced cysteine. Suitable control plants also include plants that do not express a modified oleosin including at least one artificially introduced cysteine.

In a preferred embodiment oil is produced at a higher level in the non-photosynthetic tissues/organs than in other tissues/organs of the plant.

Preferably the increased level of oil production in the non-photosynthetic tissues/organs is caused by expression of the modified oleosin in the non-photosynthetic tissues/organs.

Non-Photosynthetic Tissues/Organs

In one embodiment the non-photosynthetic tissue/organ is selected from below ground tissue/organs of the plant. In a further embodiment the below ground tissue/organ is selected from root, tuber, bulb, corm and rhizome. In a further embodiment the non-photosynthetic tissue/organ is selected from root, tuber, bulb, corm, rhizome, and endosperm. In a further embodiment the non-photosynthetic tissue/organ is root.

Genetic Modification

In one embodiment the method includes the step of transforming the plant with the polynucleotide encoding a modified oleosin including at least one artificially introduced cysteine.

Promoters

In one embodiment the polynucleotide is operably linked to a promoter polynucleotide.

In one embodiment the promoter is capable of driving expression of the polynucleotide in the non-photosynthetic tissues of the plant. In one embodiment the promoter is a constitutive promoter. In one embodiment the promoter is a non-photosynthetic tissue preferred promoter. In a further embodiment the promoter is a root preferred promoter. In a further embodiment the promoter is a root specific promoter. In a further embodiment the promoter is a tuber preferred promoter. In a further embodiment the promoter is a tuber specific promoter. In a further embodiment the promoter is a bulb preferred promoter. In a further embodiment the promoter is a bulb specific promoter. In a further embodiment the promoter is a corm preferred promoter. In a further embodiment the promoter is a corm specific promoter. In a further embodiment the promoter is a rhizome preferred promoter. In a further embodiment the promoter is a rhizome specific promoter. In a further embodiment the promoter is an endosperm preferred promoter. In a further embodiment the promoter is an endosperm specific promoter.

Polynucleotide is Part of a Genetic Construct

In one embodiment the polynucleotide is transformed as part of a genetic construct. Preferably the genetic construct is an expression construct. Preferably the expression construct includes the polynucleotide operable linked to the promoter. In a further embodiment the polynucleotide is operably linked to a terminator sequence Plant is Also Transformed with a TAG Synthesising Enzyme In a further embodiment the plant is also genetically modified to express a triacylglycerol (TAG) synthesising enzyme. In a further embodiment the plant is genetically modified to comprise a nucleic acid sequence encoding a triacylglycerol (TAG) synthesising enzyme. In a further embodiment the plant comprises an expression construct including a nucleic acid sequence encoding a triacylglycerol (TAG) synthesising enzyme.

In a further embodiment the nucleic acid is operably linked to a promoter polynucleotide.

In one embodiment the promoter is capable of driving expression of the polynucleotide in the non-photosynthetic tissues of the plant. In one embodiment the promoter is a constitutive promoter. In one embodiment the promoter is a non-photosynthetic tissue preferred promoter. In a further embodiment the promoter is a root preferred promoter. In a further embodiment the promoter is a root specific promoter. In a further embodiment the promoter is a tuber preferred promoter. In a further embodiment the promoter is a tuber specific promoter. In a further embodiment the promoter is a corm preferred promoter. In a further embodiment the promoter is a corm specific promoter. In a further embodiment the promoter is a rhizome preferred promoter. In a further embodiment the promoter is a rhizome specific promoter. In a further embodiment the promoter is an endosperm preferred promoter. In a further embodiment the promoter is an endosperm specific promoter.

It will be understood by those skilled in the art that the polynucleotide encoding the modified oleosin and the nucleic acid sequence encoding a triacylglycerol (TAG) synthesising enzyme can be placed on the same construct or on separate constructs to be transformed into the host cell. Expression of each can be driven by the same or different promoters, which may be included in the construct to be transformed. It will also be understood by those skilled in the art that alternatively the polynucleotide and nucleic acid can be transformed into the cell without a promoter, but expression of either or both of the polynucleotide and nucleic acid could be driven by a promoter, or promoters, endogenous to the plant transformed.

Methods Including Further Processing Steps

In one embodiment the method comprises the additional step of processing the non-photosynthetic tissue/organ of the plant into an animal feedstock.

In a further embodiment the method comprises the additional step of processing the non-photosynthetic tissue/organ of the plant into a biofuel feedstock.

In a further embodiment the method comprises the additional step of extracting oil from the non-photosynthetic tissue/organ of the plant.

In a further embodiment the method comprises the additional step of processing the non-photosynthetic tissue/organ into an oil fraction.

In a further embodiment the oil from the non-photosynthetic tissue/organ is processed into a fuel, oleochemical or nutritional or cosmetic oil, a polyunsaturated fatty acid (PUFA) or a combination thereof.

Non-Photosynthetic Tissue/Organ of the Plant Produced by the Method of the Invention In a further embodiment the invention provides a non-photosynthetic tissue/organ of a plant produced by a method of the invention. In one embodiment the non-photosynthetic tissue/organ is selected from below ground tissue/organs of the plant. In a further embodiment the below ground tissue/organ is selected from root, tuber, bulb, corm and rhizome. In a further embodiment the non-photosynthetic tissue/organ is selected from root, tuber, bulb, corm, rhizome, and endosperm. In a further embodiment the non-photosynthetic tissue/organ is root.

In one embodiment the non-photosynthetic tissue/organ contains at least 100%, more preferably 150%, more preferably 200%, more preferably 250%, more preferably 300%, more preferably 350%, more preferably 400%, more preferably 450%, more preferably 500%, more total lipid than the corresponding non-photosynthetic tissue/organ of a control plant.

In one embodiment the non-photosynthetic tissue/organ contains 100% to 900%, more preferably 200% to 800%, more preferably 300% to 700%, more preferably 400% to 600%, more total lipid than the corresponding non-photosynthetic tissue/organ of a control plant.

Level Oil Production in Non-Photosynthetic Tissues/Organs.

In one embodiment the non-photosynthetic tissues/organ contains at least 2×, more preferably 3×, more preferably 4×, more preferably 5×, more preferably 6×, more preferably 7×, more preferably 8×, more preferably 9×, more preferably 10×, more preferably 11×, more preferably 12×, more preferably 13×, more preferably 14×, more preferably 15×, more oil than the corresponding non-photosynthetic tissue/organ of a control plant.

In one embodiment the non-photosynthetic tissue/organ contains 3× to 15×, more preferably 4× to 14×, more preferably 5× to 13×, more preferably 6× to 12×, more preferably 7× to 11×, more preferably 8× to 10× more oil than the corresponding non-photosynthetic tissue/organ of a control plant.

Suitable control plants include non-transformed or wild-type versions of plant of the same variety and or species as the transformed plant used in the method of the invention. Suitable control plants also include plants of the same variety and or species as the transformed plant that are transformed with a control construct. Suitable control plants also include plants that have not been transformed with a polynucleotide encoding a modified oleosin including at least one artificially introduced cysteine. Suitable control plants also include plants that do not express a modified oleosin including at least one artificially introduced cysteine.

Preferably the increased level of oil production is caused by expression of the modified oleosin including at least one artificially introduced cysteine.

Animal Feed Comprising Non-Photosynthetic Tissue/Organ of the Invention

In a further aspect the invention provides an animal feed comprising the non-photosynthetic tissue/organ of the invention.

Biofuel Feedstock Comprising Non-Photosynthetic Tissue/Organ of the Invention

In a further aspect the invention provides a biofuel feedstock comprising the non-photosynthetic tissue/organ of the invention.

Source of Oleosins and Plants

The modified oleosins may be modified naturally occurring oleosins. The plants from which the un-modified oleosin sequences are derived may be from any plant species that contains oleosins and polynucleotide sequences encoding oleosins.

The plant cells, in which the modified oleosins are expressed, may be from any plant species. The plants, in which the modified oleosins are expressed, may be from any plant species.

In one embodiment the plant cell or plant, is derived from a gymnosperm plant species. In a further embodiment the plant cell or plant, is derived from an angiosperm plant species. In a further embodiment the plant cell or plant, is derived from a from dicotyledonous plant species. In a further embodiment the plant cell or plant, is derived from a monocotyledonous plant species.

Preferred plant species are those that produce tubers (modified stems) such as but not limited to *Solanum* species. Other preferred plant species are those that produce bulbs (below ground storage leaves) such as but not limited to *Lilaceae, Amaryllis, Hippeastrum, Narcissus, Iridaceae*, and *Oxalis* species. Other preferred plant species are those that produce corms (swollen underground stems) such as but not limited to *Musa, Elocharis, Gladiolus* and *Colocasia* species. Other preferred plant species are those that produce rhizomes (underground storage stem) such as but not limited to *Asparagus, Zingiber* and *Bambuseae* species. Other preferred are those that produce substantial endosperm in their seeds, such as but not limited to maize and sorghum.

Preferred plants incude those from the following genera: *Brassica, Solanum, Raphanus, Allium, Foeniculum, Lilaceae, Amaryllis, Hippeastrum, Narcissus, Iridaceae, Oxalis, Musa, Eleocharis, Gladiolus, Colocasia, Asparagus, Zingiber*, and *Bambuseae.*

A preferred *Brassica* species is *Brassica rapa* var. *rapa* (turnip)

Preferred *Solanum* species are those which produce tubers. A preferred *Solanum* species is *Solanum tuberosum* (potato)

Preferred *Raphanus* species include *Raphanus raphanistrum, Raphanus caudatu*, and *Raphanus sativus*. A preferred *Raphanus* species is *Raphanus sativus* (radish)

Preferred *Allium* species include: *Allium cepa* (onion, shallot), *Allium fistulosum* (bunching onion), *Allium schoenoprasum* (chives), *Allium tuberosum* (Chinese chives), *Allium ampeloprasum* (leek, kurrat, great-headed garlic, pearl onion), *Allium sativum* (garlic) and *Allium chinense* (rakkyo). A preferred *Allium* species is *Allium cepa* (onion)

Preferred *Musa* species include: *Musa acuminata* and *Musa balbisiana*. A preferred *Musa* species is *Musa acuminata* (banana, plantains)

A preferred *Zingiber* species is *Zingiber officinale* (ginger)

A preferred *Oxalis* species is *Oxalis tuberosa* (yam)

A preferred *Colocasia* species is *Colocasia esculenta* (taro).

Another preferred genera is Zea. A preferred Zea species is *Zea mays.*

Another preferred genera is *Sorghum*. A preferred *Sorghum* species is *Sorghum bicolor.*

Other preferred plants are forage plant species from a group comprising but not limited to the following genera: *Zea, Lolium, Hordium, Miscanthus, Saccharum, Festuca, Dactylis, Bromus, Thinopyrum, Trifolium, Medicago, Pheleum, Phalaris, Holcus, Glycine, Lotus, Plantago* and *Cichorium.*

Other preferred plants are leguminous plants. The leguminous plant or part thereof may encompass any plant in the plant family Leguminosae or Fabaceae. For example, the plants may be selected from forage legumes including, alfalfa, clover; leucaena; grain legumes including, beans, lentils, lupins, peas, peanuts, soy bean; bloom legumes including lupin, pharmaceutical or industrial legumes; and fallow or green manure legume species.

A particularly preferred genus is *Trifolium*. Preferred *Trifolium* species include *Trifolium repens; Trifolium arvense; Trifolium affine*; and *Trifolium occidentale*. A particularly preferred *Trifolium* species is *Trifolium repens.*

Another preferred genus is *Medicago*. Preferred *Medicago* species include *Medicago sativa* and *Medicago truncatula*. A particularly preferred *Medicago* species is *Medicago sativa*, commonly known as alfalfa.

Another preferred genus is *Glycine*. Preferred *Glycine* species include *Glycine max* and *Glycine wightii* (also known as *Neonotonia wightii*). A particularly preferred Glycine species is *Glycine max*, commonly known as soy bean. A particularly preferred Glycine species is *Glycine wightii*, commonly known as perennial soybean.

Another preferred genus is *Vigna*. A particularly preferred *Vigna* species is *Vigna unguiculata* commonly known as cowpea.

Another preferred genus is *Mucana*. Preferred *Mucana* species include *Mucana pruniens*. A particularly preferred *Mucana* species is *Mucana pruniens* commonly known as velvetbean.

Another preferred genus is *Arachis*. A particularly preferred *Arachis* species is *Arachis glabrata* commonly known as perennial peanut.

Another preferred genus is *Pisum*. A preferred *Pisum* species is *Pisum sativum* commonly known as pea.

Another preferred genus is *Lotus*. Preferred *Lotus* species include *Lotus corniculatus, Lotus pedunculatus, Lotus glabar, Lotus tenuis* and *Lotus uliginosus*. A preferred *Lotus* species is *Lotus corniculatus* commonly known as Birdsfoot Trefoil. Another preferred *Lotus* species is *Lotus glabar* commonly known as Narrow-leaf Birdsfoot Trefoil. Another preferred *Lotus* species is *Lotus pedunculatus* commonly known as Big trefoil. Another preferred *Lotus* species is *Lotus tenuis* commonly known as Slender trefoil.

Another preferred genus is *Brassica*. A preferred *Brassica* species is *Brassica oleracea*, commonly known as forage kale and cabbage.

Other preferred species are oil seed crops including but not limited to the following genera: *Brassica, Carthumus, Helianthus, Zea* and *Sesamum.*

A preferred oil seed genera is *Brassica*. A preferred oil seed species is *Brassica napus.*

A preferred oil seed genera is *Brassica*. A preferred oil seed species is *Brassica oleraceae.*

A preferred oil seed genera is *Carthamus*. A preferred oil seed species is *Carthamus tinctorius.*

A preferred oil seed genera is *Helianthus*. A preferred oil seed species is *Helianthus annuus.*

A preferred oil seed genera is *Zea*. A preferred oil seed species is *Zea mays.*

A preferred oil seed genera is *Sesamum*. A preferred oil seed species is *Sesamum indicum.*

A preferred silage genera is Zea. A preferred silage species is *Zea mays.*

A preferred grain producing genera is *Hordeum*. A preferred grain producing species is *Hordeum vulgare.*

A preferred grazing genera is *Lolium*. A preferred grazing species is *Lolium perenne.*

A preferred grazing genera is *Lolium*. A preferred grazing species is *Lolium arundinaceum.*

A preferred grazing genera is *Trifolium*. A preferred grazing species is *Trifolium repens.*

A preferred grazing genera is *Hordeum*. A preferred grazing species is *Hordeum vulgare.*

Preferred plants also include forage, or animal feedstock plants. Such plants include but are not limited to the following genera: *Miscanthus, Saccharum, Panicum.*

A preferred biofuel genera is *Miscanthus*. A preferred biofuel species is *Miscanthus giganteus.*

A preferred biofuel genera is *Saccharum*. A preferred biofuel species is *Saccharum officinarum.*

A preferred biofuel genera is *Panicum*. A preferred biofuel species is *Panicum virgatum.*

BRIEF DESCRIPTION OF THE FIGURES

Figure 1:
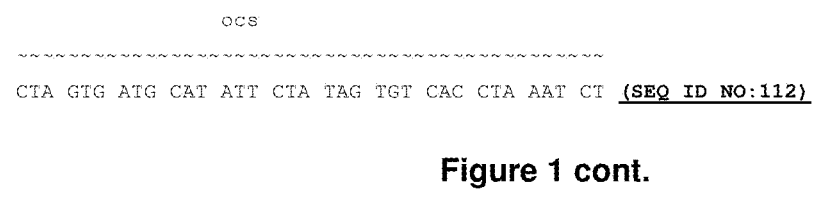

FIG. 1 shows the sequence of the Oleosin_0-0 and DGAT1 (S205A) construct. CaMV35 is the Cauliflower Mosais Virus 35S promoter. attB1 is the GATEWAY™ recombination site. UBQ10 is the intron from the *A. thaliana* UBQ10 gene. OCS terminator is the octopine synthase terminator.

FIG. 2 shows the Oleosin_1-1 and DGAT1 (S205A) construct arrangement, as transformed into *Arabidopsis thaliana.*

FIG. 3 shows the sequence of the Oleosin_1-3 and DGAT1 (S205A) construct. CaMV35 is the Cauliflower Mosais Virus 35S promoter. attB1 is the GATEWAY™ recombination site. UBQ10 is the intron from the *A. thaliana* UBQ10 gene. OCS terminator is the octopine synthase terminator.

FIG. 4 shows the Oleosin_3-1 and DGAT1 (S205A) construct. CaMV35 is the Cauliflower Mosais Virus 35S promoter. attB1 is the GATEWAY™ recombination site. UBQ10 is the intron from the *A. thaliana* UBQ10 gene. OCS terminator is the octopine synthase terminator.

FIG. 5 shows the Oleosin_3-3 and DGAT1 (S205A) construct. CaMV35 is the Cauliflower Mosais Virus 35S promoter. attB1 is the GATEWAY™ recombination site. UBQ10 is the intron from the *A. thaliana* UBQ10 gene. OCS terminator is the octopine synthase terminator.

Figure 6:
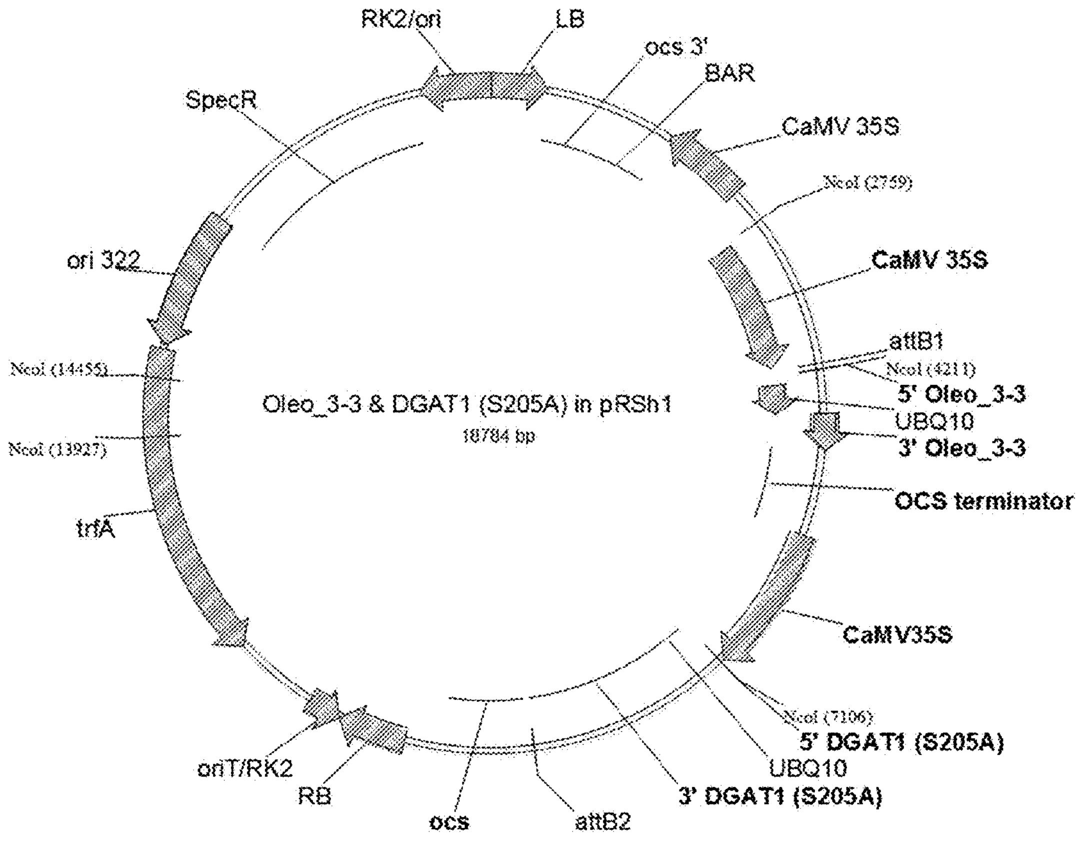
FIG. 6 shows a map of the construct pRSh1 used for transforming plants. The map shows the arrangement of the oleosins, with artificially introduced cysteines (in this case Oleo_3-3) under the control of the CaMV35s promoter as well as *Arabidopsis thaliana* DGAT1 (S205A) also under the control of the CaMV35s promoter. Other oleosin sequences and TAG synthesising enzyme sequences can of course be substituted for Oleo_3-3 and DGAT1 respectively.

Trace A shows TAG extracted from 100 mg of roots from plants transformed with DGAT1-Ole_3,3.

Trace B shows TAG extracted from 100 mg of leaves from plants transformed with DGAT1-Ole_3,3

Trace C shows TAG extracted from 100 mg of roots from wild type plants.

Trace D shows TAG extracted from 100 mg of leaves from wild type plants.

DETAILED DESCRIPTION OF THE INVENTION

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term “comprising” as used in this specification means “consisting at least in part of”. When interpreting each statement in this specification that includes the term “comprising”, features other than that or those prefaced by the term may also be present. Related terms such as “comprise” and “comprises” are to be interpreted in the same manner.

On a weight for weight basis lipids have approximately double the energy content of either proteins or carbohydrates. The bulk of the world’s lipids are produced by plants and the densest form of lipid is as a triacylglycerol (TAG). Dicotyledonous plants can accumulate up to approximately 60% of their seed weight as TAG which is subsequently used as an energy source for germination. As such there have been a number of efforts targeted at using seeds rich in oils to sustainably produce sufficient lipids for both animal and biofuel feed stock.

Given that there is only a limited quantity of TAG able to be produced by seeds alternative approaches are being made to produce additional lipid (preferentially TAGs) in vegetative tissues. The majority of these approaches have pursued the up regulation or over expression of one or several enzymes in the Kennedy pathway in the leaves of plants in order to synthesise TAG. Typically however, the majority of additional lipids produced by this approach are re-mobilised within the plant by a combination of lipases and β-oxidation resulting in a limited increase in lipid content (usually 2-4% of the DM).

The TAG produced in developing seeds is typically contained within discreet structures called oil bodies (OBs) which are highly stable and remain as discrete tightly packed organelles without coalescing even when the cells desiccate or undergo freezing conditions (Siloto et al., 2006; Shimada et al., 2008). OBs consist of a TAG core surrounded by a phospholipid monolayer embedded with proteinaceous emulsifiers. The latter make up 0.5-3.5% of the OB; of this, 80-90% is oleosin with the remainder predominantly consisting of the calcium binding (caloleosin) and sterol binding (steroleosin) proteins (Lin and Tzen, 2004). The emulsification properties of oleosins derives from their three functional domains which consist of an amphipathic N-terminal arm, a highly conserved central hydrophobic core (~72 residues) and a C-terminal amphipathic arm. Similarly, both caloleosin and steroleosin possess hydrophilic N and C-terminal arms and their own conserved hydrophobic core.

It was previously speculated that the constitutive expression of oleosin or polyoleosin (tandem head-to-tale fusions of oleosins) with TAG synthesising enzymes in the leaves would result in the formation of stable oil bodies leading to the accumulation of TAG. We have subsequently found however, that oleosin and polyoleosins are ineffective and promoting the accumulation of TAG when co-expressed with DGAT1 in plant leaves (Roberts et al., unpublished data).

The current invention provides modified oleosins which contain one or more artificially introduced cysteine residues. The encapsulation of the neutral lipids by oleosins containing engineered cysteines provides an alternative mechanism to accumulate appreciable quantities of TAG in leaves without the requirement to wait until senescence and without producing extreme phenotypes. In addition the modified oleosin has a number of other applications involving modifying OB stability, emulsion properties as well as the generation and purification of recombinant proteins.

It has been shown (WO 2011/053169) that expression of modified oleosins with artificially introduced cysteines can produce increased level of oil in the leaves of plants. However, the present applicants have now surprisingly shown that it is possible to accumulate significantly higher levels in the non-photosynthetic tissues of plants than in the other tissues of the plants.

Oil Bodies

OBs generally range from 0.5-2.5 μm in diameter and consist of a TAG core surrounded by a phospholipid monolayer embedded with proteinaceous emulsifiers—predominantly oleosins (Tzen et al, 1993; Tzen, et al 1997). OBs consist of only 0.5-3.5% protein; of this 80-90% is oleosin with the remainder predominantly consisting of the calcium binding (caleosin) and sterol binding (steroleosin) proteins (Lin and Tzen, 2004). The ratio of oleosin to TAG within the plant cell influences the size and number of oil bodies within the cell (Sarmiento et al., 1997; Siloto et al., 2006).

While OBs are naturally produced predominantly in the seeds and pollen of many plants they are also found in some other organs (e.g., specific tubers).

Oleosins are comparatively small (15 24 kDa) proteins that are embedded in the surface of OBs.

Oil Body Stability

The suitability of oil bodies, and artificial oil bodies, for the applications discussed above, among others, is limited at least in part, by their stability. One approach to address oil body stability was to generate oil bodies comprising so-called polyoleosin. Polyoleosin is the head to tail fusion of two or more oleosin units (Roberts et al., 2008). Altering the number of oleosin units enables the properties (thermal stability and degradation rate) of the oil bodies to be tailored. Expression of polyoleosin in planta leads to incorporation of the polyoleosin units to the oil bodies as per single oleosin units (Scott et al., 2007). Multiple oleosin units in tandem head-to-tail arrangements were used to create polyoleosin. Separate constructs (containing from one to six oleosin repeats) were specifically designed for expression in planta and in *E. coli*. The majority of recombinant polyoleosin accumulated in the oil bodies of transgenic plants and in the inclusion bodies of *E. coli*. Purified prokaryotically produced polyoleosin was used to generate artificial oil bodies. Oil body and artificial oil body thermal stability and structural integrity in proteinase-K were raised by polyoleosin.

However, there are several limiting factors determining the degree of protection/stability that polyoleosin can provide; these relate to the number of tandem repeats that can be joined before the process of translation and oil body targeting becomes limiting (Scott et al., 2007); while another limitation comes from the nature of the oleosin fusion which is achieved by generating a transcript with a head to tail fusion arrangement. This is essentially a linear protein of multimeric oleosin repeats that has a number of covalent-links and position of covalent-links per individual oleosin repeat (i.e., a maximum of one at each end). In addition this arrangement only affords protection against N-terminal degrading proteins but it does not provide any additional protection against other proteolytic enzymes that recognise specific internal peptide sequences. Furthermore, the linking between oleosin units in a polyoleosin molecule formed by tandem head to tail repeats is not readily altered in situ. While specific protease specific sites could be engineered into the joining regions in order to break apart fused polyoleosin molecules embedded into an oil body or artificial oil body they could not be re-fused easily.

Oleosins embedded in oil bodies have previously covalently cross-linked by the addition of cross-linking agents such as glutaraldehyde or genepin (Peng et al., 2004 & 2006), however, this random cross-linking requires the addition of cross-linking agents to oil body preparations, and is not easy to reverse.

Artificial Oil Bodies

Prokaryotically expressed recombinant oleosins can be used to generate artificial oil bodies (AOBs) who's properties are very similar to plant derived OBs (Peng et al. 2004; Roux et al. 2004; Chiang et al. 2005; Chiang et al. 2007).

Applications of Oil Bodies and Artificial Oil Bodies

The unique properties of oil bodies, and their constituent oleosins, form the basis of a number of biotechnical applications including: purifying recombinant proteins; formation of multimeric protein complexes; emulsification; delivery of bioactives; generation of multivalent bioactives and even as a potential flavour enhancer (for reviews see Capuano et al., 2007 and Roberts et al., 2008).

Emulsions

Emulsions are produced when one or more liquids that are immiscible in another liquid, usually due to different polarities and thus different hydrophobicities, are uniformly suspended within that liquid. Examples include oil droplets uniformly dispersed in water, or water droplets uniformly dispersed in oil. Generation of a relatively stable emulsion requires the use of an emulsifier, which lowers the interfacial tension between the liquids. The stability of an emulsion is generally measured in terms of the duration that the uniform dispersion persists under specified conditions. Emulsifiers are commonly used in the food and cosmetic industry; so need to have high emulsion stability and be safe for consumption and topical application.

Intact oil bodies containing oleosin naturally form a surfactant-free, oil-in water emulsion. It has been found that intact oil bodies or oil bodies in which the majority of TAG has been removed have a broad range of emulsification applications in food, topical personal care (skin creams) and pharmaceutical formulations (Harada et al., 2002; Deckers et al., 2003; Hou et al., 2003).

Biohydrogenation

It has been demonstrated that the lipid profile of ruminant animal feed in turn influences the lipid profile of meat and dairy products (Demeyer and Doreau, 1999). Different plants have different lipid profiles; by selectively feeding animals only plants with the desired lipid profile it is possible to positively influence the lipid profile of downstream meat and dairy products. In ruminants the final lipid make up of the meat and milk is not only influenced by the dietary lipids but is also heavily influenced by biohydrogenation (Jenkins and McGuire 2006; Firkins et al., 2006; Lock and Bauman, 2004). Biohydrogenation is the hydrogenation of non-reduced compounds (such as unsaturated fats) by the biota present in the rumen. Biohydrogenation can be prevented/delayed by encapsulating the lipids in a protein or proteins that provide resistance to microbial degradation (Jenkins and Bridges 2007). The prevention of biohydrogenation by encapsulating triacylglycerides in polyoleosin or oleosins in planta was reported by Scott et al., (2007), Cookson et al., (2009) and Roberts et al., (2008).

Oleosins

Oleosins are comparatively small (15 to 24 kDa) proteins which allow the OBs to become tightly packed discrete organelles without coalescing as the cells desiccate or undergo freezing conditions (Leprince et al., 1998; Siloto et al., 2006; Slack et al., 1980; Shimada et al. 2008).

Oleosins have three functional domains consisting of an amphipathic N-terminal arm, a highly conserved central hydrophobic core (~72 residues) and a C-terminal amphipathic arm. The accepted topological model is one in which the N- and C-terminal amphipathic arms are located on the outside of the OBs and the central hydrophobic core is located inside the OB (Huang, 1992; Loer and Herman, 1993; Murphy 1993). The negatively charged residues of the N- and C-terminal amphipathic arms are exposed to the aqueous exterior whereas the positively charged residues are exposed to the OB interior and face the negatively charged lipids. Thus, the amphipathic arms with their outward facing negative charge are responsible for maintaining the OBs as individual entities via steric hinderance and electrostatic repulsion both in vivo and in isolated preparation (Tzen et al, 1992). The N-terminal amphipathic arm is highly variable and as such no specific secondary structure can describe all examples. In comparison the C-terminal arm contains a $\alpha$-helical domain of 30-40 residues (Tzen et al, 2003). The central core is highly conserved and thought to be the longest hydrophobic region known to occur in nature; at the center is a conserved 12 residue proline knot motif which includes three spaced proline residues (for reviews see Frandsen et al, 2001; Tzen et al, 2003). The secondary, tertiary and quaternary structure of the central domain is still unclear. Modelling, Fourier Transformation-Infra Red (FT-IR) and Circular Dichromism (CD) evidence exists for a number of different arrangements (for review see Roberts et al., 2008).

The properties of the major oleosins is relatively conserved between plants and is characterised by the following:

15-25 kDa protein corresponding to approximately 140-230 amino acid residues.

The protein sequence can be divided almost equally along its length into 4 parts which correspond to a N-terminal hydrophilic region, two centre hydrophobic regions (joined by a proline knot or knob) and a C-terminal hydrophilic region.

The topology of oleosin is attributed to its physical properties which includes a folded hydrophobic core flanked by hydrophilic domains. This arrangement confers an amphipathic nature to oleosin resulting in the hydrophobic domain being embedded in the phospholipid monolayer (Tzen et al., 1992) while the flanking hydrophilic domains are exposed to the aqueous environment of the cytoplasm.

Typically oleosins do not contain cysteines

Preferred oleosins for use in the invention are those which contain a central domain of approximately 70 non-polar amino acid residues (including a proline knot) uninterrupted by any charged residues, flanked by two hydrophilic arms.

Caloleosins

Caloleosins (Frandsen et al., 2001) have a slightly different proline knot than do the basic oleosins, and contain a calcium-binding motif and several potential phosphorylation sites in the hydrophilic arms. Similar to oleosin, caloleosin is proposed to have three structural domains, where the N- and C-terminal arms are hydrophilic while the central domain is hydrophobic and acts as the oil body anchor. The N-terminal hydrophilic domain consists of a helix-turn-helix calcium binding EF-hand motif of 28 residues including an invariable glycine residue as a structural turning point and five conserved oxygen-containing residues as calcium-binding ligands (Chen et al., 1999; Frandsen et al., 2001). The C-terminal hydrophilic domain contains several phosphorylation sites and near the C-terminus is an invariable cysteine that is not involved in any intra- or inter-disulfide linkages (Peng, 2004). The hydrophilic N- and C-termini of caloleosin are approximately 3 times larger than those of oleosin (Lin and Tzen, 2004). The hydrophobic domain is thought to consist of an amphipathic α-helix and an anchoring region (which includes a proline knot).

Examples of oleosin (oleosins, steroleosin and caloleosin) sequences suitable to be modified for use in the invention, by the addition of at least one artificially introduced cysteine, are shown in Table 1 below. The sequences (both polynucleotide and polypeptide are provided in the Sequence Listing)

TABLE 1

| Oleosin | Species | cDNA accession no. | SEQ ID NO: | Protein accession no. | SEQ ID NO: |
|---|---|---|---|---|---|
| Oleosin | *S. indicum* | AF302907 | 34 | AAG23840 | 35 |
| Oleosin | *S. indicum* | U97700 | 36 | AAB58402 | 37 |
| Oleosin | *A. thaliana* | X62353 | 38 | CAA44225 | 39 |
| Oleosin | *A. thaliana* | BT023738 | 40 | AAZ23930 | 41 |
| Oleosin | *H. annuus* | X62352.1 | 42 | CAA44224.1 | 43 |
| Oleosin | *B. napus* | X82020.1 | 44 | CAA57545.1 | 45 |
| Oleosin | *Z. mays* | NM_001153560.1 | 46 | NP_001147032.1 | 47 |
| Oleosin | *O. sativa* | AAL40177.1 | 48 | AAL40177.1 | 49 |
| Oleosin | *B. oleracea* | AF117126.1 | 50 | AAD24547.1 | 51 |
| Oleosin | *C. arabica* | AY928084.1 | 52 | AAY14574.1 | 53 |
| Steroleosin | *S. indicum* | AAL13315 | 54 | AAL13315 | 55 |
| Steroleosin | *A. napus* | EU678274 | 56 | ACG69522 | 57 |
| Steroleosin | *Z. mays* | NM_001159142.1 | 58 | NP_001152614.1 | 59 |
| Steroleosin | *B. napus* | EF143915.1 | 60 | ABM30178.1 | 61 |
| Caloleosin | *S. indicum* | AF109921 | 62 | AAF13743 | 63 |
| Caloleosin | *G. max* | AF004809 | 64 | AAB71227 | 65 |
| Caloleosin | *Z. mays* | NM_001158434.1 | 66 | NP_001151906 | 67 |
| Caloleosin | *B. napus* | AY966447.1 | 68 | AAY40837 | 69 |
| Caloleosin | *C. revoluta* | FJ455154.1 | 70 | ACJ70083 | 71 |
| Caloleosin | *C. sativus* | EU232173.1 | 72 | ABY56103.1 | 73 |

The term "oleosin" as used herein also includes steroleosin and caloleosin

Steroleosins

Steroleosins comprises an N-terminal anchoring segment comprising two amphipathic α-helices 912 residues in each helix) connected by a hydrophobic anchoring region of 14 residues. The soluble dehydrogenase domain contains a NADP+-binding subdomain and a sterol-binding subdomain. The apparent distinction between steroleosins-A and -B occurs in their diverse sterol-binding subdomains (Lin and Tzen, 2004). Steroleosins have a proline knob in their hydrophobic domain and contains a sterol-binding dehydrogenase in one of their hydrophilic arms.

Oleosin, steroleosin and caloleosins are well known to those skilled in the art. Further sequences from many different species can be readily identified by methods well-known to those skilled in the art. For example, further sequences can be easily identified by an NCBI Entrez Cross-Database Search (available at ncbi<dot>nlm<dot>nih<dot>gov/sites/gquery) using any one of the terms oleosin, steroleosin and caloleosin.

Plant Lipids Biosynthesis

All plant cells produce fatty acids from actetyl-CoA by a common pathway localized in plastids. Although a portion of the newly synthesized acyl chains is then used for lipid biosynthesis within the plastid (the prokaryotic pathway), a major portion is exported into the cytosol for glycerolipid assembly at the endoplasmic reticulum (ER) or other sites (the eukaryotic pathway). In addition, some of the extraplastidial glycerolipids return to the plastid, which results in considerable intermixing between the plastid and ER lipid pools (Ohlrogge and Jaworski 1997).

The simplest description of the plastidial pathway of fatty acid biosynthesis consists of two enzyme systems: acetyl-CoA carboxylase (ACCase) and fatty acid synthase (FAS). ACCase catalyzes the formation of malonyl-CoA from acetyl-CoA, and FAS transfers the malonyl moiety to acyl carrier protein (ACP) and catalyzes the extension of the growing acyl chain with malonyl-ACP.

The initial fatty acid synthesis reaction is catalyzed by 3-ketoacyl-ACP III (KAS III) which results in the condensation of acetyl-CoA and malonyl-ACP. Subsequent condensations are catalyzed by KAS I and KAS II. Before a subsequent cycle of fatty acid synthesis begins, the 3-ketoacyl-ACP intermediate is reduced to the saturated acyl-ACP in the remaining FAS reactions, catalyzed sequentially by the 3-ketoacyl-ACP reductase, 3 hydroxyacyl-ACP dehydrase, and the enoyl-ACP reductase.

The final products of FAS are usually 16:0 and 18:0-ACP, and the final fatty acid composition of a plant cell is in large part determined by activities of several enzymes that use these acyl-ACPs at the termination phase of fatty acid synthesis. Stearoyl-ACP desatruase modifies the final product of FAS by insertion of a cis double bond at the 9 position of the C18:0-ACP. Reactions of fatty acid synthesis are terminated by hydrolysis or transfer of the acyl chain from the ACP. Hydrolysis is catalyzed by acyl-ACP thioesterases, of which there are two main types: one thioesterase relatively specific for 18:1-ACP and a second more specific for saturated acyl-ACPs. Fatty acids that have been released from ACPs by thioesterases leave the plastid and enter into the eukaryotic lipid pathway, where they are primarily esterified to glycerolipids on the ER. Acyl transferases in the plastid, in contrast to thioesterases, terminate fatty acid synthesis by transesterifying acyl moieties from ACP to glycerol, and they are an essential part of the prokaryotic lipid pathway leading to plastid glycerolipid assembly.

Triacylglycerol Biosynthesis

The only committed step in TAG biosynthesis is the last one, i.e. the addition of a third fatty acid to an existing diacylglycerol, thus generating TAG. In plants this step is predominantly (but not exclusively) performed by one of five (predominantly ER localised) TAG synthesising enzymes including: acyl CoA: diacylglycerol acyltransferase (DGAT1); an unrelated acyl CoA: diacylglycerol acyl transferase (DGAT2); a soluble DGAT (DGAT3) which has less than 10% identity with DGAT1 or DGAT2 (Saha et al., 2006); phosphatidylcholine-sterol O-acyltransferase (PDAT); and a wax synthase (WSD1, Li et al., 2008). The DGAT1 and DGAT2 proteins are eoncoded by two distinct gene families, with DGAT1 containing approximately 500 amino acids and 10 predicted transmembrane domains and DGAT2 has only 320 amino acids and two transmembrane domains (Shockey et al., 2006).

The term "triacylglycerol synthesising enzyme" or "TAG synthesising enzyme" as used herein means an enzyme capable of catalysing the addition of a third fatty acid to an existing diacylglycerol, thus generating TAG. Preferred TAG synthesising enzymes include but are not limited to: acyl CoA: diacylglycerol acyltransferase) (DGAT1); diacylglycerol acyl transferase2 (DGAT2); phosphatidylcholine-sterol O-acyltransferase (PDAT) and cytosolic soluble form of DGAT (soluble DGAT or DGAT3).

Given that endogenous DGAT1 and DGAT2 appear to play roles in mature and senescing leaves (Kaup et al. 2002; Shockey et al. 2006), it is likely that plants possess a number of feedback mechanisms to control their activity. Indeed, Zou et al. (2008) recently identified a consensus sequence (X-Leu-X-Lys-X-X-Ser-X-X-X-Val (SEQ ID NO:108) within Tropaeolum majus (garden nasturtium) DGAT1 (TmDGAT1) sequences as a targeting motif typical of members of the SNF1-related protein kinase-1 (SnRK1) with Ser being the residue for phosphorylation. The SnRK1 proteins are a class of Ser/Thr protein kinases that have been increasingly implicated in the global regulation of carbon metabolism in plants, e.g. the inactivation of sucrose phosphate synthase by phosphorylation (Halford & Hardie 1998). Zou et al. (2008) went on to demonstrate that the obliteration of a potential SnRK1 phosphorylation site in DGAT1 by single point mutation (Ser197Ala of TmDGAT1) led to the accumulation of significantly higher levels of TAG in the seed. This mutation increased activity by 38-80%, which led to a 20-50% increase in oil content on a per seed basis in Arabidopsis.

Phospholipid:DGA acyltransferase (PDAT) forms TAG from a molecule of phospholipid and a molecule of diacylglycerol. PDAT is quite active when expressed in yeast but does not appreciably increase TAG yields when expressed in plant seeds. PDAT and a proposed DAG:DAG transacylase are neutral lipid synthesizing enzymes that produce TAG, but are not considered part of the Kennedy Pathway.

A combination of wax ester synthase and DGAT enzyme (WS/DGAT) has been found in all neutral lipid producing prokaryotes studied so far. WS/DAGAT has extraordinary broad activity on a variety of unusual fatty acids, alcohols and even thiols. This enzyme has a putative membrane-spanning region but shows no sequence homology to the DGAT1 and DGAT2 families from eukaryotes or the WE synthase from jojoba (Jojoba is the only eukaryote that has been found to accumulate wax ester).

It should be noted that Lecithin-Cholesterol AcylTransferase (LCAT) and Acyl-coenzyme:Cholesterol AcylTransferase (ACAT) are enzymes that produce sterol esters (a form of neutral lipid) not TAGs.

In applications requiring the increase of neutral lipids evidence suggests that the higher activity and broader specificity of DGAT1 relative to DGAT2 is preferential. Where a specific fatty acid is preferred, such as a long-chain PUFA, DGAT1 is still applicable, provided it accepts the fatty acid of choice. Plants generally incorporate long chain PUFAs in the sn-2 position. It is not known whether this is due to high activity of LPAT or low activity of DGAT1 on this substrate. For the improved specificity for PUFAs, a DGAT2 that prefers these fatty acids may be preferable, or the properties of DGAT1 could be altered using directed evolution or an equivalent procedure.

Examples of these TAG synthesising enzymes, suitable for use in the methods and compositions of the invention, from members of several plant species are provided in Table 2 below. The sequences (both polynucleotide and polypeptide are provided in the Sequence Listing)

TABLE 2

| TAG synthesising enzyme | Species | cDNA accession no. | SEQ ID NO: | Protein accession no. | SEQ ID NO: |
|---|---|---|---|---|---|
| DGAT1 | *A. thaliana* | NM_127503 | 74 | NP_179535 | 75 |
| DGAT1 | *T. majus* | AY084052 | 76 | AAM03340 | 77 |
| DGAT1 | *Z. mays* | EU039830 | 78 | ABV91586 | 79 |
| DGAT2 | *A. thaliana* | NM_115011 | 80 | NP_566952 | 81 |
| DGAT2 | *B. napus* | FJ858270 | 82 | AC090187 | 83 |
| DGAT3 (soluble DGAT) | *A. hypogaea* | AY875644 | 84 | AAX62735 | 85 |
| PDAT | *A. thaliana* | NM_121367 | 86 | NP_196868 | 87 |
| PDAT | *R. communis* | XM_002521304 | 88 | XP_002521350 | 89 |

The inventions also contemplates use of modified TAG synthesizing enzymes, that are modified (for example in their sequence by substitutions, insertions or additions an the like) to alter their specificity and or activity.

TAG Accumulation in Leaves

A recent field survey of 302 angiosperm species in the north-central USA found that 24% have conspicuous cytosolic oil droplets in leaves, with usually one large oil droplet per mesophyll cell (Lersten et al., 2006 [from Slocombe et al 2009]). The role of cytosolic leaf TAG is thought to be involved in carbon storage and/or membrane lipid re-modelling (for review see Slocombe et al., 2009). Indeed, in senescing leaves, plastidial fatty acids are partitioned into TAG prior for further mobilization, and DGAT1 is thought to be instrumental in this process (Kaup et al., 2002).

There have been several attempts to engineer plants to accumulate elevated levels of TAG in their leaves. The success of these has been somewhat limited by the relatively low level of TAG that accumulated and in some cases the majority of TAG accumulated in senescing leaves only, thus limiting the flexibility of harvesting and proportion of crop accumulating TAG at any one time (Bouvier-Nave et al, 2001; Xu et al., 2005; Winichayakul et al., 2008; Andrianov et al., 2010; Slocombe et al., 2009 and references therein).

To date the attempts to accumulate TAG in leaves have predominantly focussed on three particular gene candidates including over expression of DGAT (TAG biosynthesis), mutation of TGD1 or CTS (resulting in the prevention of lipid remobilisation), and over expression of LEC1, LEC2 and WRI1 (transcriptional factors involved in storage oil and protein accumulation in developing seeds). Over expression of TAG and other neutral lipid synthesizing enzymes relies on the presence of sufficient substrate, in the expanding and or mature leaf this is assumed to be provided by the plastid (chloroplast in the case of the leaf) which synthesises lipids for membranes. In photosynthetic leaves of *Arabidopsis* it has been estimated that the turnover of membrane lipids is 4% of total fatty acids per day (Bao et al, 2000). In senescing leaves, the existing plastidal membranes provide the bulk of fatty acids for partitioning into TAG prior to further mobilization.

Over-expression of the *Arabidopsis* DGAT1 gene in tobacco leaves results in enhanced TAG accumulation (Bouvier-Nave et al., 2001), this was later repeated and quantified by Andrianov et al., (2010). They calculated the TAG level increased 20 fold and lead to a doubling of lipid content from ~3% to ~6% of dry matter in mature leaves. A further increase to 6.8% was achieved by the over expression of LEC2 (a master regulator of seed maturation and seed oil storage) in mature leaves using the inducible Alc promoter (Andrianov et al., 2010). No estimation of the extractable TAG was given, nor was there any calculation on the accumulation of TAG in expanding leaves.

Mutations in a permease-like protein TRIGALACTOSYLDIACYLGLYCEROL (TGD1), in *Arabidopsis thaliana* caused the accumulation of TAGs, oligogalactolipids and phosphatidate; this was accompanied by a high incidence of embryo abortion and comparatively poor overall plant growth (Xu et al., 2005).

Winichayakul et al., (2008) over expressed *Arabidopsis thaliana* DGAT1 in the leaves of ryegrass (*Lolium perenne*) and found this lead to a 50% elevation of total extractable leaf lipid (from ~4% to 6% of dry matter). Furthermore, the elevated lipid level was present in new leaves generated by repeated harvests spaced 2-3 weeks apart, indicating that the new emerging leaves were also capable of accumulating additional lipid. However, the elevated lipid level in these leaves typically began to decline to wild type levels when the leaves were more than 2 weeks old indicating that the lipids were being re-mobilised via catabolism (release from the glycerol backbone by lipase followed by β-oxidation).

Slocombe et al., (2009) demonstrated that mutations in the CTS peroxisomal ABC transporter (cts-2) led to accumulation of up to 1.4% TAG in leaves, particularly during the onset of senescence. They also ectopically expressed LEC2 during senescence in the cts-2 background; while this did not elevate the overall accumulation of TAG over the cts-2 mutant it did increase the accumulation of seed oil type species of TAG in senescing tissue. While cts-2 blocks fatty acid breakdown it also led to a severe phenotype. Slocombe et al., (2009) concluded that recycled membrane fatty acids may be able to be re-directed to TAG by expressing the seed-programme in senescing tissue or by a block in fatty acid breakdown.

Scott et al., (2007) claimed that the co-expression of a triacylglyceride synthesising enzyme and polyoleosin (two or more oleosin units fused in a tandem head-to-tail arrangement) would enable the storage of lipid in a plant cell. Similarly, Cookson et al., (2009) claimed that producing a single oleosin and a TAG synthesising enzyme within vegetative portions of a plant would lead to increased number of oil bodies and TAG in the vegetative tissue. Using either of these techniques leads to a maximum increase in lipid content (not necessarily in the form of TAG) of up to approximately 50%. Furthermore this level begins to decline as the leaves mature; typically in leaves greater than 2 weeks old (unpublished data).

Hence, the degree to which TAG can be accumulated in vegetative tissues appears to be limited to some extent by the fact that the endogenous fixed-carbon recovery machinery catabolises the TAG.

Leaf Senescence—Recycling of Lipids Via TAG Intermediates

Leaf senescence is a highly controlled sequence of events leading ultimately to the death of cells, tissues and finally the whole organ. This entails regulated recruitment of nutrients together with their translocation from the senescing tissue to other tissues that are still growing and developing. The chloroplast is the first organelle of mesophyll cells to show symptoms of senescence and although breakdown of thylakoid membranes is initiated early in the leaf senescence cascade, the chloroplast envelope remains relatively intact until the very late stages of senescence. DGAT1 is up-regulated during senescence of *Arabidopsis* leaves and this is temporally correlated with increased levels of TAG-containing fatty acids commonly found in chloroplast galactolipids. Recruitment of membrane carbon from senescing leaves, particularly senescing chloroplasts, to growing parts of the plant is a key feature of leaf senescence, and it involves de-esterification of thylakoid lipids and conversion of the resultant free fatty acids to phloem-mobile sucrose. De-esterification of thylakoid lipids appears to be mediated by one or more senescence induced galactolipases. The formation of TAG appears to be an intermediate step in the mobilisation of membrane lipid carbon to phloem mobile sucrose during senescence (Kaup et al., 2002).

Modified Oleosins Engineered to Include Artificially Introduced Cysteines

The modified oleosins of the invention, or for use in the methods of the invention, are modified to contain at least one artificially introduced cysteine residue. Preferably the engineered oleosins contain at least two cysteines.

The encapsulation of the neutral lipids by oleosins containing engineered cysteines provides an alternative mechanism to accumulate appreciable quantities of TAG in leaves without the requirement to wait until senescence and without producing extreme phenotypes.

Various methods well-known to those skilled in the art may be used in production of the modified oleosins with artificially introduced cysteines.

Such methods include site directed mutagenesis (U.S. Pat. No. 6,448,048) in which the polynucleotide encoding an oleosin is modified to introduce a cysteine into the encoded oleosin protein.

Alternatively the polynucleotide encoding the modified oleosins, may be synthesed in its entirety.

Further methodology for producing modified oleosins of the invention and for use in the methods of the invention, is provided in the Examples section.

The introduced cysteine may be an additional amino acid (i.e. an insertion) or may replace an existing amino acid (i.e. a replacement). Preferably the introduced cysteine replaces an existing amino acid. In a preferred embodiment the replaced amino acid is a charged residue. Preferably the charged residue is predicted to be in the hydrophilic domains and therefore likely to be located on the surface of the oil body.

The hydrophilic, and hydrophobic regions/arms of the oleosin can be easily identified by those skilled in the art using standard methodology (for example: Kyte and Doolitle (1982).

The modified oleosins of the invention are preferably range in molecular weight from 5 to 50 kDa, more preferably, 10 to 40 kDa, more preferably 15 to 25 kDa.

The modified oleosins of the invention are preferably in the size range 100 to 300 amino acids, more preferably 110 to 260 amino acids, more preferably 120 to 250 amino acids, more preferably 130 to 240 amino acids, more preferably 140 to 230 amino acids.

Preferably the modified oleosins comprise an N-terminal hydrophilic region, two centre hydrophobic regions (joined by a proline knot or knob) and a C-terminal hydrophilic region.

Preferably the modified oleosins can be divided almost equally their length into four parts which correspond to the N-terminal hydrophilic region (or arm), the two centre hydrophobic regions (joined by a proline knot or knob) and a C-terminal hydrophilic region (or arm).

Preferably the topology of modified oleosin is attributed to its physical properties which include a folded hydrophobic core flanked by hydrophilic domains.

Preferably the modified oleosins can be formed into oil bodies when combined with triacylglycerol (TAG) and phospholipid.

Preferably topology confers an amphipathic nature to modified oleosin resulting in the hydrophobic domain being embedded in the phospholipid monolayer of the oil body while the flanking hydrophilic domains are exposed to the aqueous environment outside the oil body, such as in the cytoplasm.

In one embodiment the modified oleosin of the invention or used in the method of the invention, comprises a sequence with at least 70% identity the hydrophobic domain of any of the oleosin protein sequences referred to in Table 1 above.

In one embodiment the modified oleosin of the invention or used in the method of the invention, comprises a sequence with at least 70% identity to any of the protein sequences referred to in Table 1 above.

In further embodiment the modified oleosin is essentially the same as any of the oleosins referred to in Table 1 above, apart from the additional artificially introduced cysteine or cysteines.

In a further embodiment the modified oleosin of the invention or used in the method of the invention, comprises a sequence with at least 70% identity to the oleosin sequence of SEQ ID NO: 16.

In further embodiment the modified oleosin has the same amino acid sequence as that of SEQ ID NO: 16, apart from the additional artificially introduced cysteine or cysteines.

In further embodiment the modified oleosin is has the amino acid sequence of any one of SEQ ID NO: 16 to 20.

Fusion Proteins with Modified Oleosins

The invention also provides a fusion proteins including a modified oleosin of the invention fused to a protein of interest.

Preferably the protein of interest is at the N- or C-terminal end of the fusion protein.

Methods for recombinantly expressing fusion proteins are well known to those skilled in the art (Papapostolou and Howorka, 2009). Production of the fusion protein of the invention may typically involve fusing the coding sequence of the protein of interest to the coding sequence of the modified oleosin.

Such fusion proteins may be included in, or expressed in, the oil bodies of the invention and used to purify and deliver the protein of interest for a variety of applications, as discussed in Roberts et al, (2008).

However in the invention makes it possible to take advantage of the option to vary the stability/integrity of the oil body provided by presence of the modified oleosins in the oil body, hence allowing for more stringent purification and delivery procedures.

Fusion Proteins with Un-Modified Oleosins

The invention also involves use of fusion protein including un-modified oleosin fused to a protein of interest. Production of the fusion protein of the invention may typically involve fusing the coding sequence of the protein of interest to the coding sequence of the un-modified oleosin.

Preferably the protein of interest is at the N- or C-terminal end of the fusion protein.

Such fusion proteins may be included or expressed in the oil bodies of the invention and used to purify and deliver the protein of interest for a variety of applications, as discussed in Roberts et al., (2008).

The present invention however, takes advantage of the option to vary the stability/integrity of the oil body provided by presence of the modified oleosins in the oil body of the invention, hence allowing for more stringent purification and delivery procedures.

Overview of Photosynthesis

Figure 19:
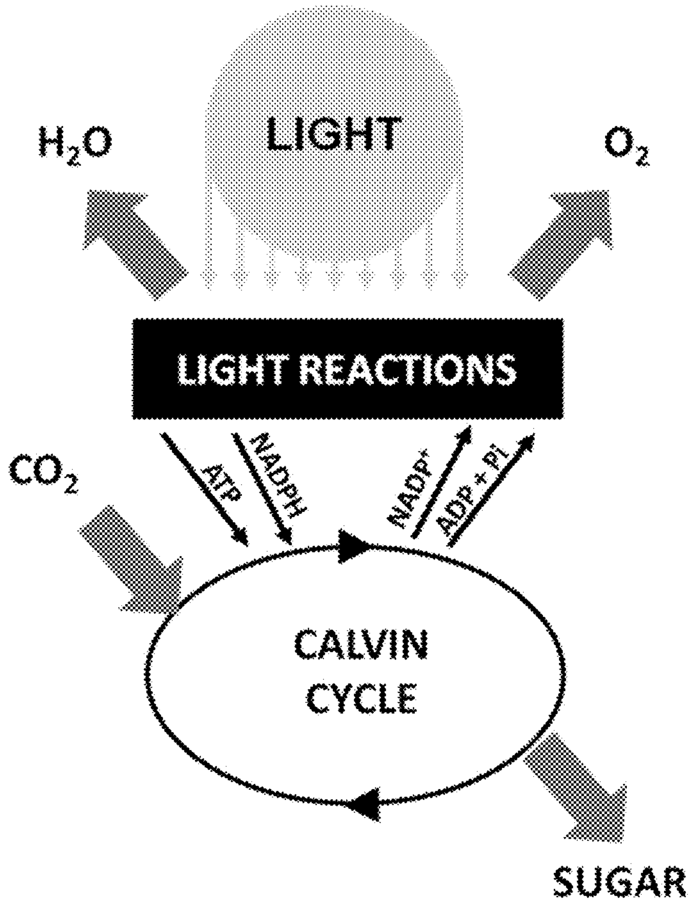
FIG. 19 shows schematic presentation of the order of events in photosynthesis, including the Hill Reaction (Light reactions) and carbon fixation (Calvin Cycle).

The overall process whereby algae and plants use light to synthesize organic compounds is called photosynthesis (FIG. 19). Photosynthesis encompasses a complex series of reactions that involve light absorption, production of stored energy and reducing power (the Light Reactions). It also includes a multistep enzymatic pathway that uses these to convert $CO_2$ and water into carbohydrates (the Calvin cycle, FIG. 20). In plants the biophysical and biochemical reactions of photosynthesis occur within a single chloroplast (C3 photosynthesis) but can also be separated into chloroplasts of differing cell types (C4 photosynthesis).

Carbon fixation is a redox reaction, photosynthesis provides both the energy to drive this process as well as the electrons required to convert $CO_2$ to carbohydrate (FIG. 19). These two processes take place through a different sequence of chemical reactions and in different cellular compartments. In the first stage, light is used to generate the energy storage molecules ATP and NADPH. The thylakoid membranes contain the multiprotein photosynthetic complexes Photosystems I and II (PSI and PSII) which include the reaction centres responsible for converting light energy into chemical bond energy (via an electron transfer chain). The photosynthetic electron transfer chain moves electrons from water into the thylakoid lumen to soluble redox-active compounds in the stroma. A byproduct of this process (Hill Reaction) is oxygen.

The second part of the photosynthetic cycle is the fixation of $CO_2$ into sugars (Calvin Cycle, FIG. 20); this occurs in the stroma and uses the ATP and NADPH generated from the light reaction.

Rubisco

Ribulose biphosphate carboxlase (Rubisco) is the key enzyme responsible for photosynthetic carbon assimilation in catalysing the reaction of $CO_2$ with ribulose 1,5biophosphate (RuBP) to form two molecules of D-phosphoglyceric acid (PGA) (Parry et al, 2003). Since Rubisco works very slowly, catalyzing only the reaction of a few molecules per second, large quantities of the enzyme are required; consequently Rubisco makes up 30-50% of the soluble protein in leaves (Bock and Khan, 2004). Genetic modification to increase the catalytic rate of Rubisco would have great importance. Parry et al, (2003) reviewed the progress to date, concluding that there are still many technical barriers to overcome and to date all engineering attempts have failed to produce a better Rubisco.

Figure 21:
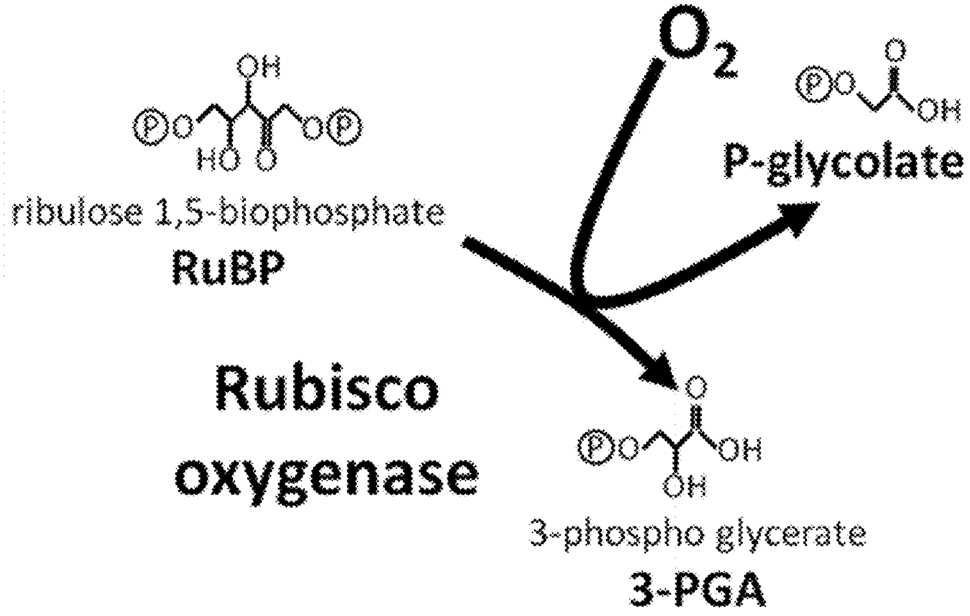
FIG. 21 shows schematic presentation of the oxygenase reaction of Rubisco.

In the presence of $O_2$, Rubisco also performs an oxygenase reaction which initiates photorespiratory or C2 cycle (FIG. 21) by the formation of phosphoglycolate and 3-phosphoglycerate (3-PGA). The recycling of phosphoglycolate results in an indirect loss of fixed nitrogen and $CO_2$ from the cell which need to be recovered. Genetic modification to increase the specificity of Rubisco for $CO_2$ relative to $O_2$ and to increase the catalytic rate of Rubisco in crop plants would have great agronomic importance. Parry et al, (2003) reviewed the progress to date, concluding that there are still many technical barriers to overcome and to date all engineering attempts have thus far failed to produce a better Rubisco (Peterhansel et al. 2008). Furthermore, it has been demonstrated that photorespiration is required in C3 plants to protect plants from photoxidation under high light intensity (Kozaki and Takeba 1996).

C3 and C2 Cycles

Figure 20:
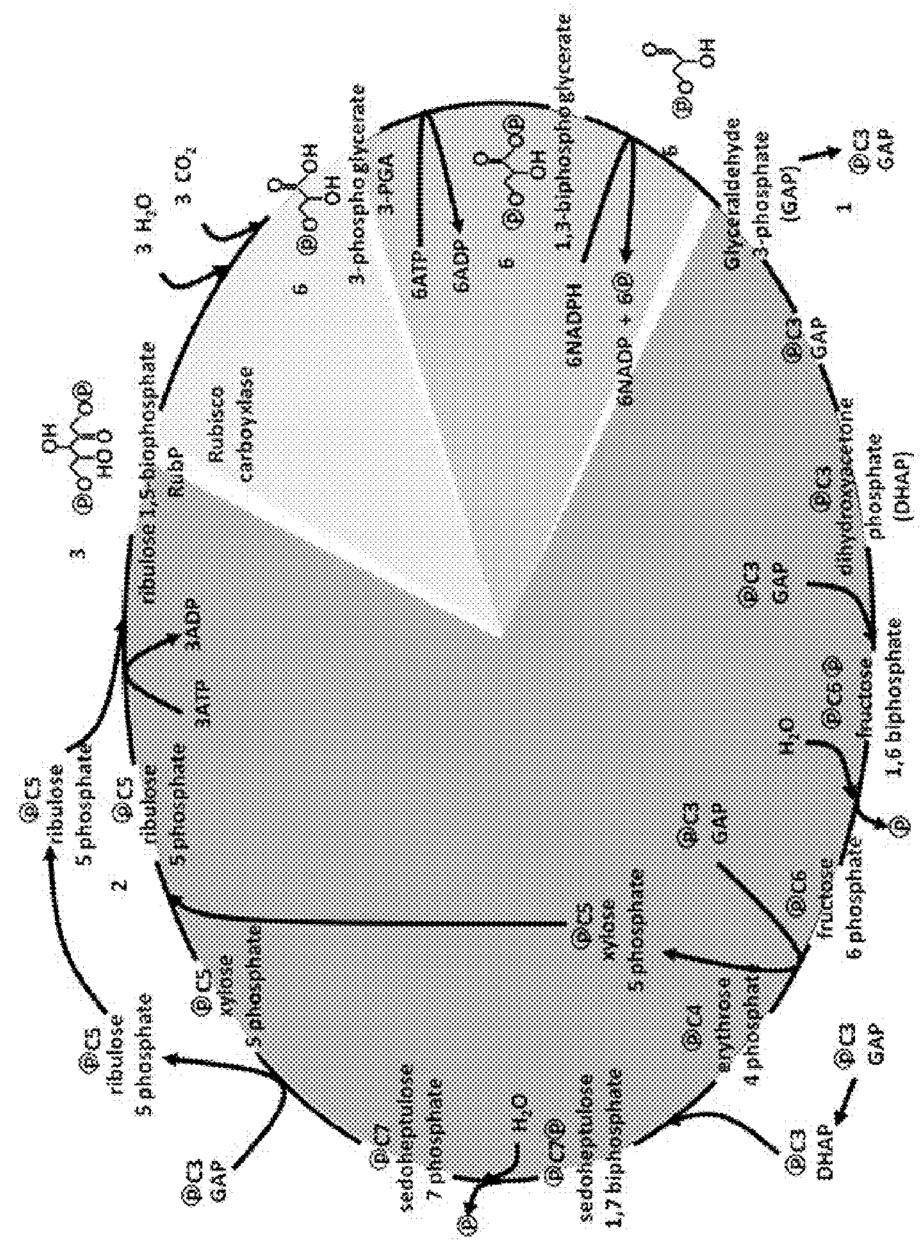
FIG. 20 shows schematic presentation of the Calvin ($C_3$) Cycle. Light grey, darker grey and darkest grey segments show carboxylation, reduction and regeneration reactions respectively. For 3 molecules of $CO_2$ fixed one molecule of glyceraldehydes 3-phosphate (GAP) is available for biosynthsis and energy The general equation for photosynthesis by algae and plants (where the electron donor is water) is: 2n $CO_2$+2n $H_2O$+photons→2($CH_2O$)n+2n $O_2$
Figure 22:
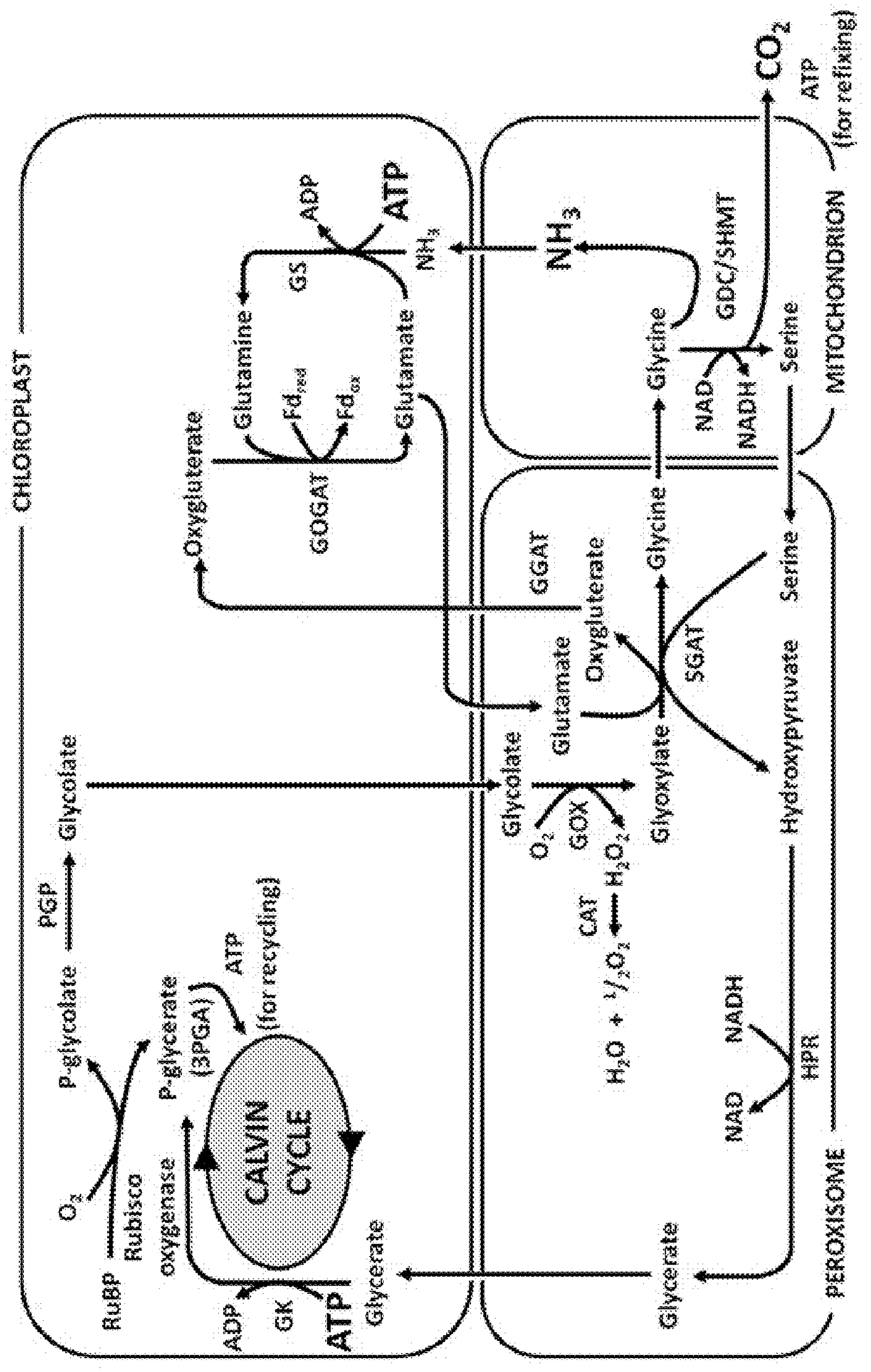
FIG. 22 shows photorespiratory pathway in the higher plant. The Calvin cycle is shown in shaded grey and demonstrates the return point for the recycled glycolate (now in the form of 3-phospho glycerate).

In C3 plants under atmospheric conditions, approximately three out of four Rubisco enzymic reactions in C3 plants fix $CO_2$ (carboxylase reaction, C3 cycle, FIG. 20). The fourth reaction; however, catalyses an oxygenase reaction (FIG. 3) which indirectly results in a net loss of fixed $CO_2$ and $NH_4^+$ and the production of a number of intermediate metabolites via the C2 (photorespiration) cycle (FIG. 22). Ultimately, this incurs a substantial metabolic cost through the refixing of $CO_2$ and $NH_4^+$ as well as the recycling of the intermediates. Furthermore, when C3 plants experience water stress and/or elevated temperatures the portion of oxygenase to carboxylase reactions rises courtesy of the elevated $O_2$ within the leaf. Nonetheless it has been demonstrated that photorespiration is required in C3 plants to protect plants from photoxidation under high light intensity (Kozaki and Takeba, 1996) and appears to provide much of the reducing power required for $NO_3^-$ assimilation in the leaf (Rachmilevitch et al., 2004).

Organisms capable of oxygenic photosynthesis began their evolution in a vastly different atmosphere (Giordano et al. 2005). One of the most dramatic changes has been the rise in the $O_2$:$CO_2$ ratio, where the competition between these two gasses for the active site of Rubisco has become progressively restrictive to the rate of carbon fixation. However, some have suggested that the gradual change appears to have provided a lack of evolutionary pressure for Rubisco with a high affinity for $CO_2$ or a Rubisco without oxygenase activity. Indeed, plant Rubiscos are considerd more evolutionarily recent than algal Rubiscos and as such they are much more selective for $CO_2$ over $O_2$. Genetic modifications to increase the specificity of Rubisco for $CO_2$ relative to $O_2$ have failed (Parry, Andralojc et al. 2003).

A significant role of the $C_2$ oxidative photosynthetic carbon cycle or photorespiratory pathway is the recycling of 2-phosphoglycolate (2PG) produced by the oxygenase activity of Rubisco (Tolbert 1997). 2PG is toxic to the cell; hence it is rapidly dephosphorylated (via phosphoglycolate phosphatase, PGP) to glycolate (Tolbert et al, 1983). Furthermore, it has been demonstrated that photorespiration is required in C3 plants to protect plants from photoxidation under high light intensity (Kozaki and Takeba 1996).

The enzymes that oxidise glycolate to glycoxylate in the photorespiratory pathway are characterised into two structurally different groups. In higher plants, the peroxisome-localized, FMN-containing glycolate oxygenase, GOX (EC 1.1.3.15 ) catalyzes glycolate oxidation using molecular oxygen as the terminal electron acceptor and has a stereopsecificity for L-lactate as an alternative substrate. In contrast, glycolate dehydrogenase, GDH (EC 1.1.99.14) has been characterized only by its non-oxygen-requiring enzymatic reaction and its stereospecificity for D-lactate as an alternative substrate. In most algae, glycolate is oxidised in the mitochondria using a monomeric GDH which is dependent on organic co-factors. The capacity of the reaction seems to be limited by the organic co-factors and consequently many algae excrete glycolate into the medium under photorespiratory growth conditions (Bari et a1,2009; Colman et al, 1974). GDH in *C. reinhardtii* is a mitochondrially located, low-$CO_2$-responsive gene (Nakamura et al, 2005). Other GDH homologs include the so-called glycolate oxidase (GOX) of *E. coli* and other bacteria. In *E. coli*, the GOX complex is composed of three functional subunits, GlcD, GIcE, and GIcF of which GlcD and GIcE share a highly conserved amino acid sequence that includes a putative flavin-binding region. In the GlcF protein, two highly conserved CxxCxxCxxxCP (SEQ ID NO:109) motifs have been recognized, which represent the typical 2x[4Fe-4S] iron-sulfur clusters, as found also in the GlpC subunit of anaerobic G3P dehydrogenase, and ubiquinone oxidoreductase homologs from prokaryotes and eukaryotes (Nakamura et al, 2005).

C4 Cycle

Not all plants use Rubisco to generate 3-PGA as the first stable photosynthetic intermediate. Maize, sugarcane, numerous tropical grasses and some dicotyledonous plants (e.g., *Amaranthus*) initially use phosphoenolpyruvate to fix carbon, forming 4-carbon organic acids ($C_4$ plants). C4 plants avoid the C2 cycle through modifications to their architecture involving two different types of chloroplast containing cells, mesophyll cells and bundle sheath cells which isolates Rubisco in a relatively rich $CO_2$ environment thereby increasing the proportion of carboxylase reactions. This enables these plants to initially use phosphoenolpyruvate to fix carbon, forming 4-carbon organic acids (hence $C_4$ plants). Thus the C4 metabolism involves fixing inorganic carbon in one cell type (mesophyll), transporting it to a cell type partially shielded from atmospheric oxygen (bundle sheath), and releasing the inorganic carbon near Rubsico in this oxygen deprived environment.

The leaves of $C_4$ plants demonstrate an unusual anatomy involving two different types of chloroplast containing cells, mesophyll cells and bundle sheath cells. Where the mesophyll cells surround the bundle sheath cells which in turn surround the vascular tissue; the chloroplasts of the mesophyll cells contain all the trasmembrane complexes required for the light reactions of photosynthesis but little or no Rubisco while the bundle sheath cell chloroplasts lack stacked thylakoids and contain little PSII. $C_4$ plants concentrate $CO_2$ in the bundle sheath cells effectively suppressing Rubiscos oxygenase activity and eliminating photorespiration.

Oxaloacetate is generated from $HCO_3^-$ and phosphoenolpyruvate (PEP) by phosphoenolpyruvate carboxylase (PEPC) in the cytosol of mesophyll cells. The $HCO_3^-$ ion is used since its aqueous equilibrium is favoured over gaseous $CO_2$. Moreover, PEP carboxylase cannot fix oxygen, which has a 3D structure similar to that of $CO_2$ but not $HCO_3^-$. Depending on the $C_4$ plant, oxaloacetate is oxidised to malate or condensed with glutamate to form aspartate and $\alpha$ Keto glutarate. The malate and aspartate are transported into the bundle sheath cells and decarboxylated releasing $CO_2$ which is then available for Rubisco and incorporation into the Calvin cycle.

The agronomic downside of this evolved modification is an increase in leaf fibre resulting in a comparatively poor digestibility of leaves from C4 plants (e.g., maize, sugarcane, numerous tropical grasses and some dicotyledonous plants such as *Amaranthus*). To date, the modification of a C3 plant to emulate the whole C4 process is beyond current biotechnology. Furthermore, attempts to engineer Rubisco to either obliterate oxygenase activity or to decrease the affinity for $O_2$ have failed (for review see Peterhansel et al. 2008).

Interaction with of Nitrate Assimilation

Reducing photorespiration through manipulation of atmospheric $CO_2$ over long periods has led to the unexpected reduction of nitrate assimilation in C3 plants (Rachmilevitch et al., 2004). There are a number of possible explanations including the lowering of available reducing power, reduced ferredoxin and NADH, the former is required for nitrate reductase and glytamate synthetase while latter is required for the reduction of $NO_3^-$ (where NADH is produced during the glycine decarboxylase photorespiratory step in the mitochondria). In addition, transport of $NO_2^-$ from the cytosol into the chloroplast involves the net diffusion of $HNO_2$ or co-transport of protons and $NO_2^-$ across the chloroplast membrane. This requires the stroma to be more alkaline than the cytosol but the pH gradient is somewhat dissipated by elevated $CO_2$ levels. Rachmilevitch et al (2004) concluded that nitrate reductase activity by itself was not limiting to nitrate assimilation under lowered photorespiration. They also concluded that it was the form of nitrogen available to the plant that determined the degree to which elevated $CO_2$ levels would result in an increase in net primary production, i.e., where $NH_4^+$ is the dominant nitrogen form. This would suggest that in the absence of changing agronomic fertilisation practices, the legumes stand to benefit most by the reduction of photorespiration since the rhizobial/legume symbiosis results in the fixation of atmospheric nitrogen in the form of $NH_4^+$ rather than $NO_3^-$.

Figure 23:
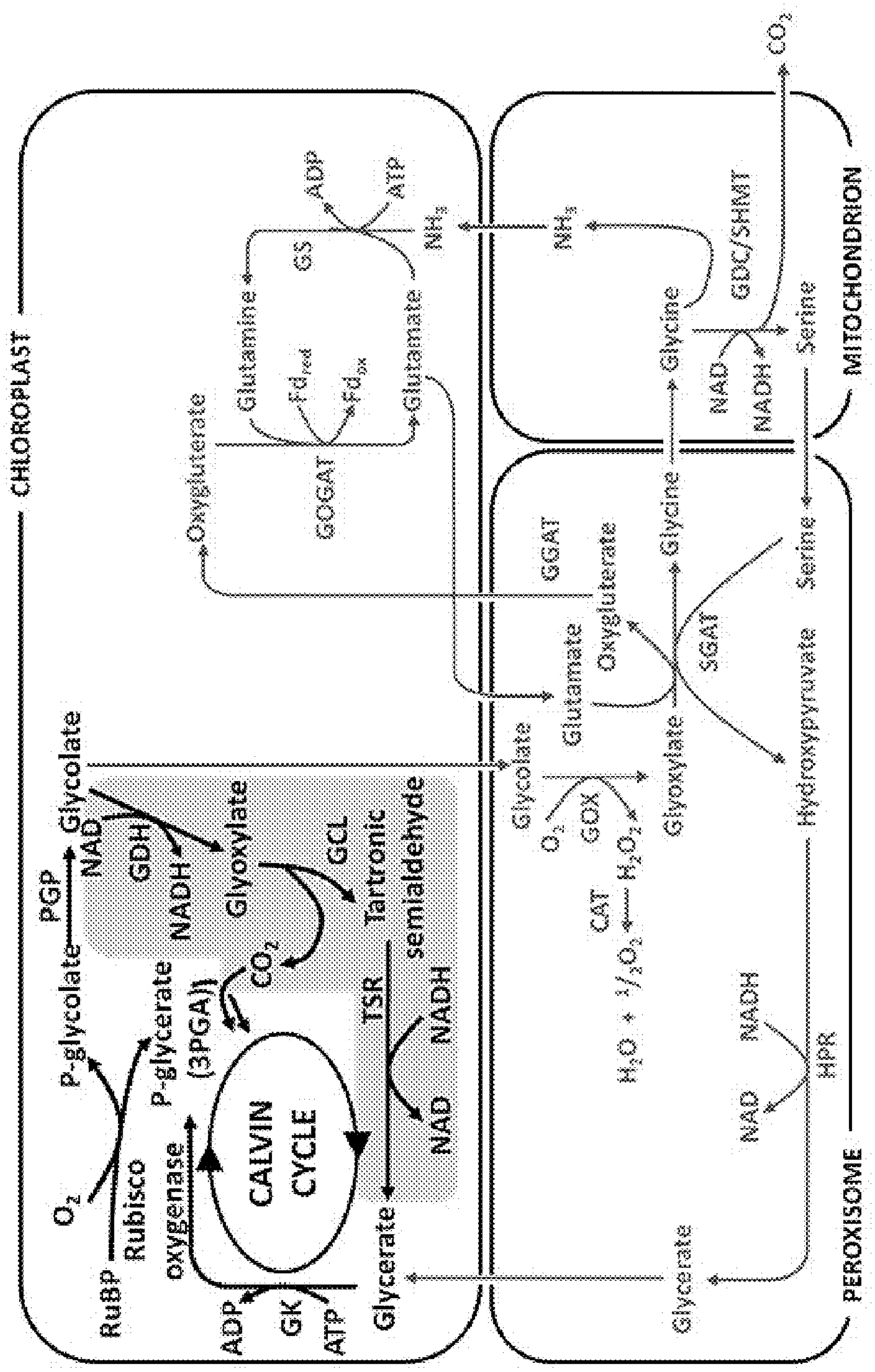
FIG. 23 shows photorespiratory bypass as per Kebeish et al, (2007). Shaded area shows the effect of circumventing the steps normally involving the peroxisome as well as the mitochondria, leading to an elevation of $CO_2$ concentration in the chloroplast as well as a more efficient recycling of glycolate.
Figure 24:
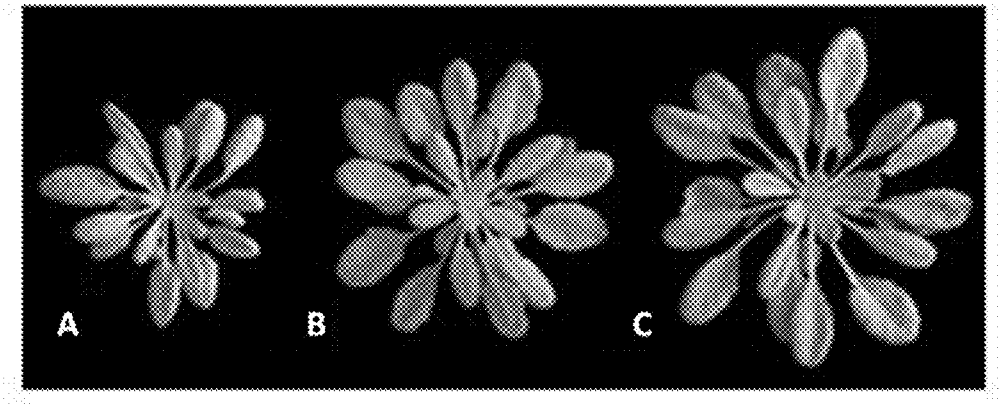
FIG. 24 shows comparison of transgenic *Arabidopsis* growth patterns. A) wild type; B) plant transformed with GDH only; C) plant transformed with GDH, GCL and TSR. (Kebeish et al. 2007).

Previous Efforts to Engineering Higher Chloroplast $CO_2$ Levels and Reduced Photorespiration in C3 Plants A number of investigations have been performed in higher plants to address the limitations of photorespiration. Essentially only one of these appears to have potential applications in the adaptation to higher plants. A recent photorespiratory bypass which increased the efficiency of glycolate recycling was successfuly engineered into *Arabidopsis* and resulted in a 30% increase in leaf biomass (Kebeish et al., 2007). Kebeish et al (2007) transformed *Arabidopsis* to express three genes from *E. coli: glycolate dehydrogenase* (GDH), glyoxylate carboxyligase (GCL), tartronic semialdehyde reductase (TSR) in their chloroplasts (FIG. 23). Combined, these genes recycled glycolate to glycerate in the chloroplast, in other words without the involvement of the peroxisome or mitochondrion. GDH from *E. coli* is a heterotrimer, consisting of glcD, glcE and glcF resulting in plants with a 30% increase in leaf biomass by the end of the growth period (FIG. 24). This pathway included a chloroplast $CO_2$ release step which further reduced RubisCO's oxygenase activity in vivo. Moreover, energy and reducing equivalents were thought to be saved by the bypass as it no longer results in the release of ammonium and the energy from glycolate oxidation is saved in reducing equivalents and not consumed during the formation of $H_2O_2$ (Maurino and Peterhansel 2010). Peterhansel (2011) concluded that to truly transform a C3 plant into a C4 plant will require the efficient transfer of multiple genes.

Plant Lipid Biosynthesis

Figure 25:
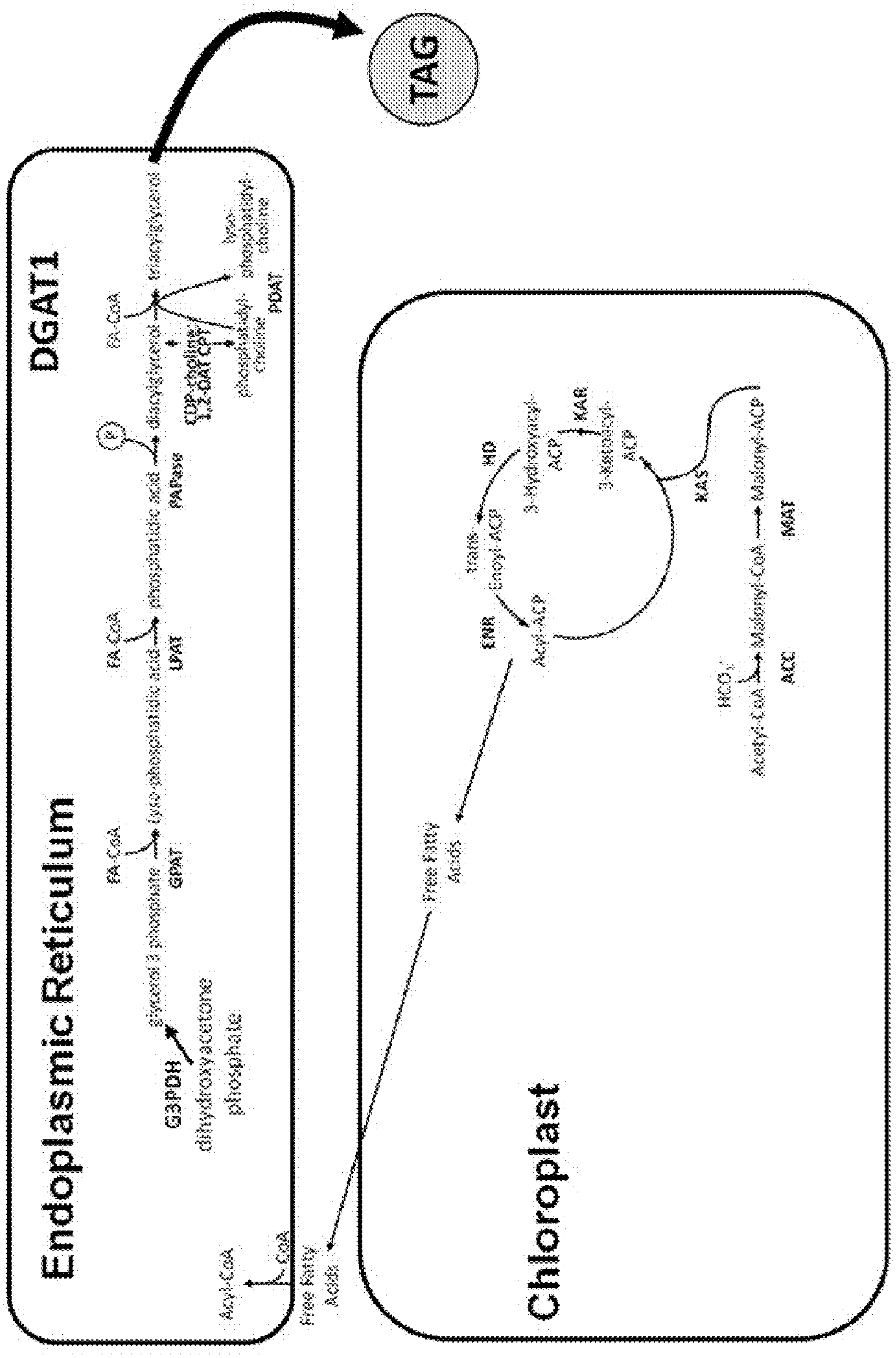
FIG. 25 shows schematic presentation of triacylglyceride biosynthesis in photosynthetic organisms. Fatty acids are synthesised in the plastid transported to the endoplasmic reticulum, sequentially acylated onto a glycerol backbone via the Kennedy pathway; this culminates in the production of triacylglyceride via over expression of the enzyme DGAT.

All plant cells produce fatty acids from actetyl-CoA by a common pathway localized in plastids (FIG. 25). A portion of the newly synthesized acyl chains is then used for lipid biosynthesis within the plastid (the prokaryotic pathway); however, a major portion is exported into the cytosol for glycerolipid assembly at the endoplasmic reticulum (ER) or other sites (the eukaryotic pathway). In addition, some of the extraplastidial glycerolipids return to the plastid, which results in considerable intermixing between the plastid and ER lipid pools (Ohlrogge and Jaworski 1997).

The simplest description of the plastidial pathway of fatty acid biosynthesis consists of two enzyme systems: acetyl-CoA carboxylase (ACCase) and fatty acid synthase (FAS). ACCase catalyzes the formation of malonyl-CoA from acetyl-CoA, and FAS transfers the malonyl moiety to acyl carrier protein (ACP) and catalyzes the extension of the growing acyl chain with malonyl-ACP.

The initial fatty acid synthesis reaction is catalyzed by 3-ketoacyl-ACP III (KAS III) which results in the condensation of acetyl-CoA and malonyl-ACP. Subsequent condensations are catalyzed by KAS I and KAS II. Before a subsequent cycle of fatty acid synthesis begins, the 3-ketoacyl-ACP intermediate is reduced to the saturated acyl-ACP in the remaining FAS reactions, catalyzed sequentially by the 3-ketoacyl-ACP reductase, 3 hydroxyacyl-ACP dehydrase, and the enoyl-ACP reductase.

The final products of FAS are usually 16:0 and 18:0-ACP, and the final fatty acid composition of a plant cell is in large part determined by activities of several enzymes that use these acyl-ACPs at the termination phase of fatty acid synthesis. Stearoyl-ACP desaturase modifies the final product of FAS by insertion of a cis double bond at the 9 position of the C18:0-ACP. Reactions of fatty acid synthesis are terminated by hydrolysis or transfer of the acyl chain from the ACP. Hydrolysis is catalyzed by acyl-ACP thioesterases, of which there are two main types: one thioesterase relatively specific for 18:1-ACP and a second more specific for saturated acyl-ACPs. Fatty acids that have been released from ACPs by thioesterases leave the plastid and enter into the eukaryotic lipid pathway, where they are primarily esterified to glycerolipids on the ER. Acyl transferases in the plastid, in contrast to thioesterases, terminate fatty acid synthesis by transesterifying acyl moieties from ACP to glycerol, and they are an essential part of the prokaryotic lipid pathway leading to plastid glycerolipid assembly.

Predicted Link Between Elevating Lipid Biosynthesis, Higher Chloroplast $CO_2$ Levels and Reducing Chloroplast Photorespiration In green seeds it was recently discovered that Rubisco with out the Calvin cycle bypasses the upper part of glycolysis in plastids and provides a higher carbon-use efficiency that allows re-fixation of $CO_2$ formed by the plastid pyruvate dehydrogenase complex (Schwender et al., 2004). Acetyl CoA produced in plastids from pyruvate is activated to malonyl CoA; the malonyl group is subsequently transferred to ACP giving rise to malonyl ACP, the primary substrate of the fatty acid synthase complex. The formation of malonyl CoA is the committed step in fatty acid synthesis and is catalyzed by the highly regulated plastidic acetyl CoA carboxylase complex (Nikolau et al., 2003).

Figure 26:
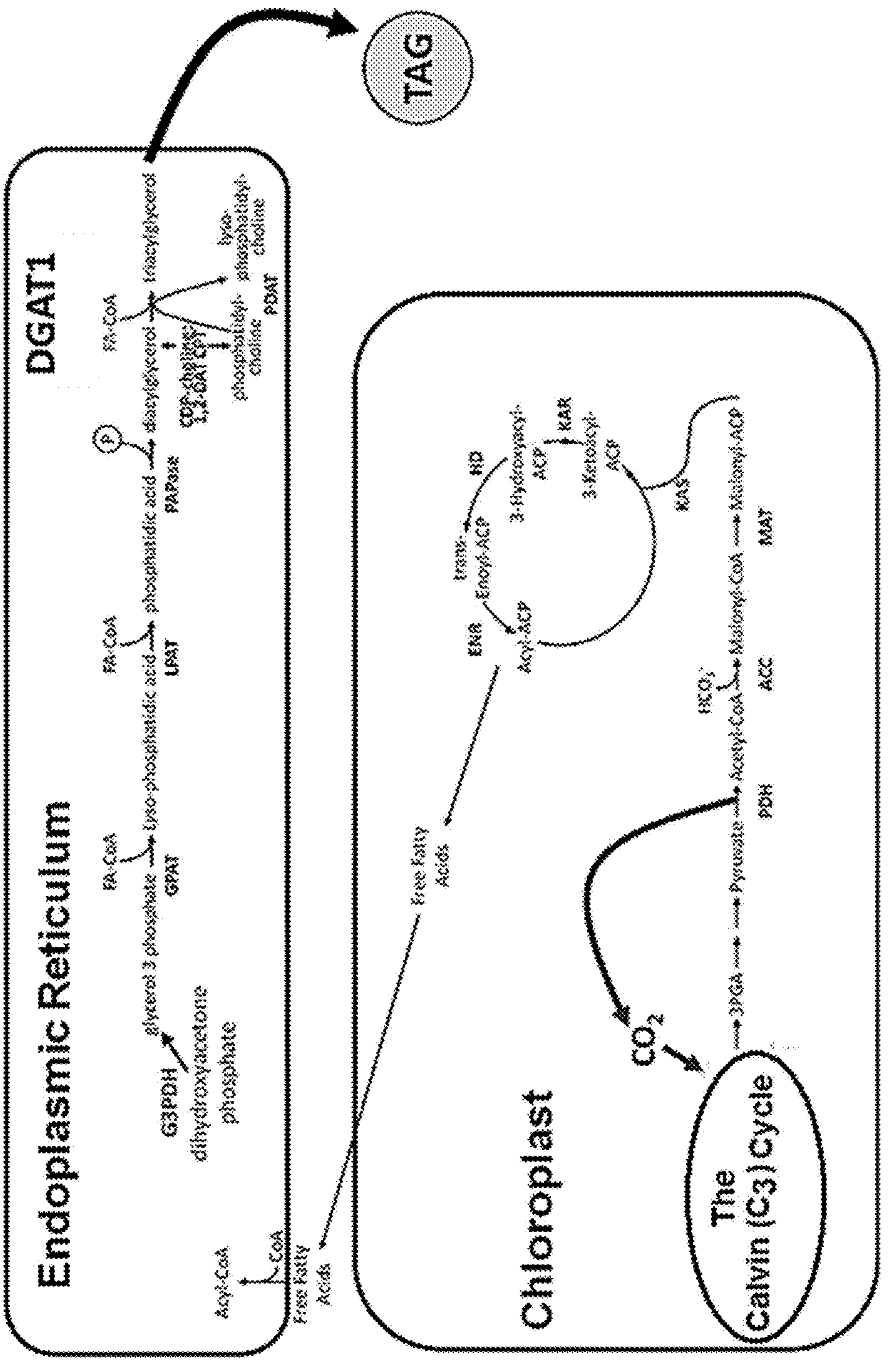
FIG. 26 shows schematic presentation of the influence of continual lipid biosynthesis in the transgenic leaf. Fatty acids are synthesised in the plastid transported to the endoplasmic reticulum, sequentially acylated onto a glycerol backbone via the Kennedy pathway; this culminates in the production of triacylglyceride via over expression of the enzyme DGAT. In this case the 3-phosphoglyceric acid is synthesised by Rubisco (without the Calvin cycle) rather than the transformation of sugars. The subsequent transformation of this to acetyl-CoA (via the pyruvate intermediate) results in the release of $CO_2$ in the chloroplast. This increases the partial pressure of $CO_2$ relative to $O_2$ in the chloroplast thus reducing the proportion of C2 to C3 cycles initiated by Rubisco and increasing the rate of $CO_2$ assimilation.
Figure 27:
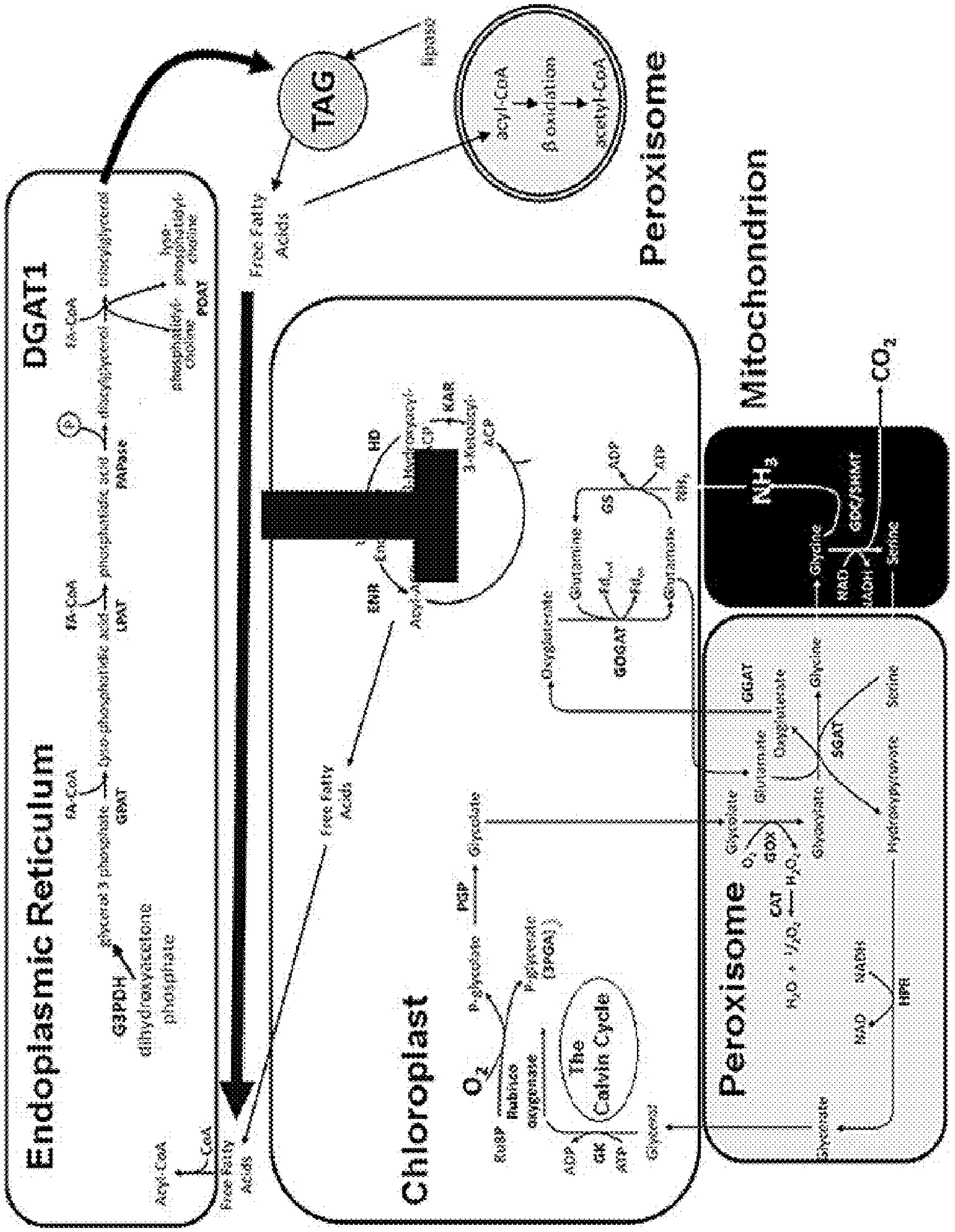
FIG. 27 shows schematic presentation of the catabolism of unprotected TAG produced in the transgenic leaf. The over expression of DGAT leads to the accumulation of TAG which is subsequently degraded by lipases resulting in the release of free fatty acids. Some of these free fatty acids are catabolised by β-oxidation in the peroxisome while others set up a futile cycle by re-entering the endoplasmic reticulum where they are re-incorporated into TAG. This futile cycle reduced the demand for the de-novo synthesis of new lipids; subsequently the level of $CO_2$ recycling within the chloroplast is reduced to or close to wild type levels which leads to the resumption of the wild type ratio of C2 to C3 cycles being performed by Rubisco within the C3 photosynthetic cell.

It has been speculated that when leaves synthesize triacylglyceride (TAG) the re-fixation of $CO_2$ released by the activation of pyruvate to malonyl CoA will be re-fixed by photosynthesis (Durret et al 2008). Fatty acids synthesised in the plastid are transported to the ER and sequentially acylated onto a glycerol backbone via the Kennedy pathway. This culminates in the production of TAG via over expression of the enzyme DGAT. In this case the 3-phosphoglyceric acid is synthesised by Rubisco (without the Calvin cycle) rather than the transformation of sugars. The subsequent transformation of this to acetyl-CoA (via the pyruvate intermediate) results in the release of $CO_2$ in the chloroplast (FIG. 26). This increases the partial pressure of $CO_2$ relative to $O_2$ in the chloroplast thus reducing the proportion of C2 to C3 cycles initiated by Rubisco. However, it has been found that the subsequent catabolism of this TAG negates this advantage (Winichayakul et al., 2008). The over expression of DGAT leads to the accumulation of TAG which is subsequently degraded by lipases resulting in the release of free fatty acids. Some of these free fatty acids are catabolised by β-oxidation in the peroxisome while others set up a futile cycle by re-entering the ER where they are re-incorporated into TAG (FIG. 27). This resulting futile cycle reduces the demand for the de-novo synthesis of new lipids; subsequently the level of $CO_2$ recycling within the chloroplast is reduced to (or close to) wild type levels which leads to the resumption of the wild type ratio of $C_2$ to $C_3$ cycles being performed by Rubisco within the C3 photosynthetic cell.

Figure 28:
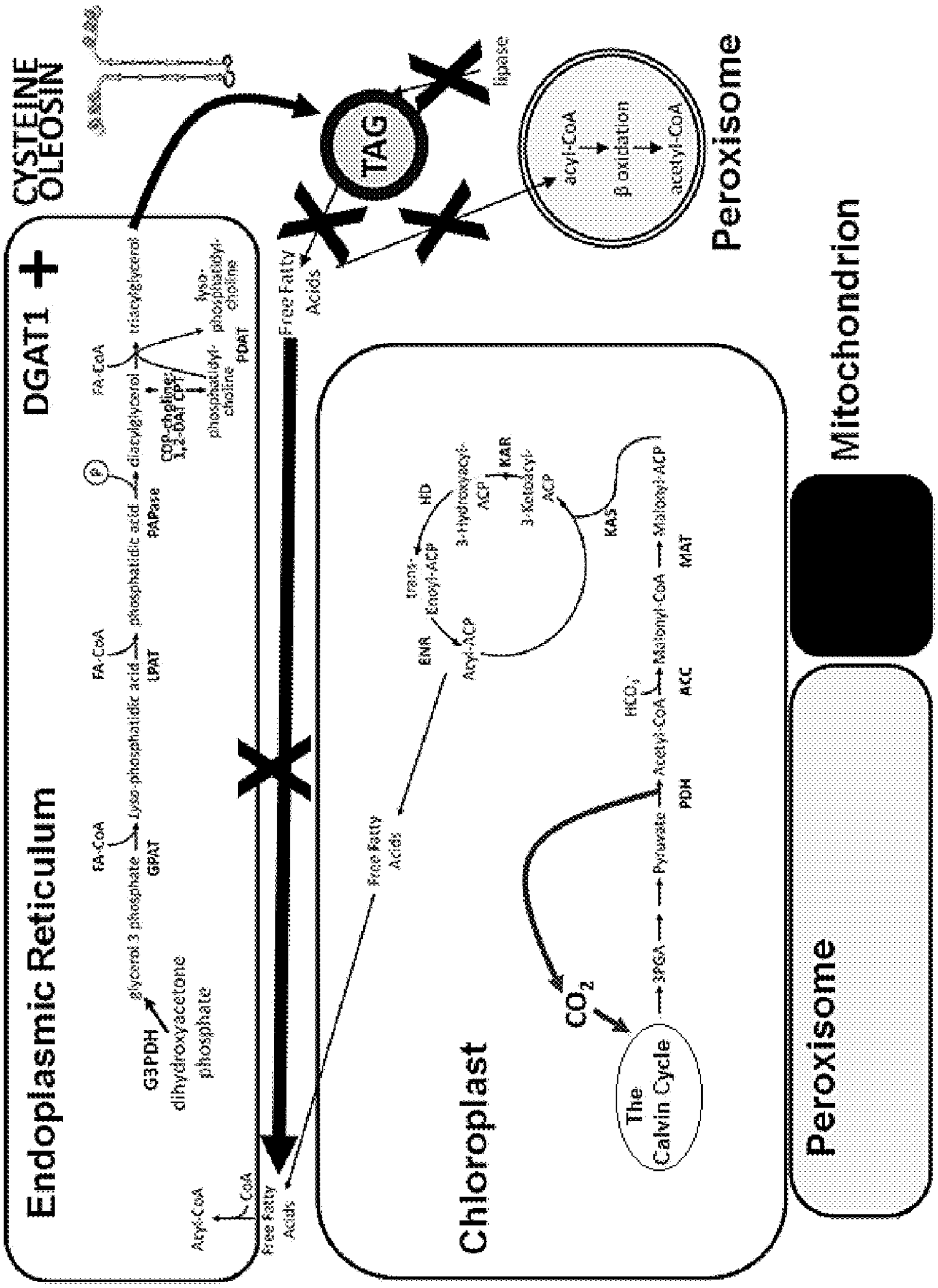
FIG. 28 shows schematic presentation of the influence of preventing TAG catabolism on photorespiration in the transgenic leaf. The over expression of DGAT leads to the accumulation of TAG which is subsequently encapsulated by co-expressed oleosin containing engineered cysteine residues. This prevents the degradation of TAG by lipases and thus also prevents futile lipid recycling (see crosses). Consequently there is a continual demand for the de-novo lipid synthesis and elevated $CO_2$ partial pressure in the photosynthetic cell which results in a continued suppression of C2 cycles relative to C3 cycles.
Figure 29:
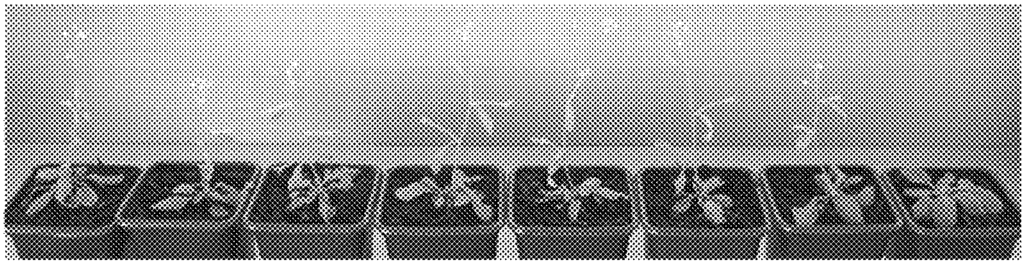
FIG. 29 shows comparison of 3 growth patterns of wild type and *Arabidopsis* transformed with DGAT1, DGAT1-Ole 0,0, DGAT1-Ole 1,1, DGAT1-Ole 1,3, DGAT1-Ole 3,1 and DGAT1-Ole 3, approximately 27 days after germination.

Without being limited by theory, the applicants propose the following model for the observed increase in $CO_2$ assimilation. The co-expression of DGAT and a modified oleosin containing engineered cysteine residues leads to the accumulation of TAG which is encapsulated by the modified oleosin containing engineered cysteine residues (FIG. 28). This prevents the degradation of TAG by lipases and thus also prevents futile lipid recycling. Consequently, this ensures a continual demand for the de-novo lipid synthesis and the subsequent elevation of $CO_2$ partial pressure in the photosynthetic cell which inturn results in a continued suppression of C2 cycles relative to C3 cycles and an elevation of the $CO_2$ assimilation rate.

Subsequently this should result in a number of benefits for all multicellular and unicellular organisms initially fixing carbon using the C3 photosynthetic pathway, including:

Increase chloroplast $CO_2$ concentration
Decreased photorespiration
Elevated biomass
Elevated seed/fruit/storage organ yield
Elevated water use efficiency
Elevated drought tolerance
Elevated tolerance to oxygen
Elevated nitrogen use efficiency
Decreased loss of fixed carbon
Delayed flowering Vegetative Tissues Vegetative tissue include, shoots, leaves, roots, stems. A preferred vegetative tissue is a leaf.

Non-Photosynthetic Tissues/Organs

The term non-photosynthetic tissues/organs means tissues or organs of the plant which do not undergo substantive photosynthesis during the normal life cycle of the plant.

It is understood by those skilled in the art that even non-photosynthetic tissues/organs can be made to photosynthesise by exposure to light but when they do so the level of photosynthesis is not "substantive" and is inconsequential relative to that performed by normal photosynthetic tissues.

In one embodiment the non-photosynthetic tissue/organ is selected from below ground tissue/organs of the plant. In a further embodiment the below ground tissue/organ is selected from root, tuber, bulb, corm and rhizome. In a further embodiment the non-photosynthetic tissue/organ is selected from root, tuber, bulb, corm, rhizome, and endosperm. In a further embodiment the non-photosynthetic tissue/organ is root.

Tissue/Organ Specific and Preferred Promoters

A tissue/organ preferred promoter is a promoter that drives expression of an operably linked polynucleotide in a particular tissue/organ at a higher level than in other tissues/organs. A tissue specific promoter is a promoter that drives expression of an operably linked polynucleotide speicifically in a particular tissue/organ. Even with tissue/organ specific promoters, there is usually a small amount of expression in at least one other tissue. A tissue specific promoter is by definition also a tissue preferred promoter.

Vegetative Tissue Specific Promoters

An example of a vegetative specific promoter is found in U.S. Pat. No. 6,229,067; and 7,629,454; and 7,153,953; and 6,228,643.

Pollen Specific Promoters

An example of a pollen specific promoter is found in U.S. Pat. Nos. 7,141,424; and 5,545,546; and 5,412,085; and 5,086,169; and 7,667,097.

Seed Specific Promoters

An example of a seed specific promoter is found in U.S. Pat. Nos. 6,342,657; and 7,081,565; and 7,405,345; and 7,642,346; and 7,371,928.

Fruit Specific Promoters

An example of a fruit specific promoter is found in U.S. Pat. Nos. 5,536,653; and 6,127,179; and 5,608,150; and 4,943,674.

Non-Photosynthetic Tissue Preferred Promoters

Non-photosynthetic tissue preferred promoters include those preferentially expressed in non-photosynthetic tissues/organs of the plant.

Non-photosynthetic tissue preferred promoters may also include light repressed promoters.

Light Repressed Promoters

An example of a light repressed promoter is found in U.S. Pat. Nos. 5,639,952 and in 5,656,496.

Root Specific Promoters

An example of a root specific promoter is found in U.S. Pat. No. 5,837,848; and US 2004/0067506 and US 2001/0047525.

Tuber Specific Promoters

An example of a tuber specific promoter is found in U.S. Pat. No. 6,184,443.

Bulb Specific Promoters

An example of a bulb specific promoter is found in Smeets et al., (1997) Plant Physiol. 113:765-771.

Rhizome Preferred Promoters

An example of a rhizome preferred promoter is found Seong Jang et al., (2006) Plant Physiol. 142:1148-1159.

Endosperm Specific Promoters

An example of an endosperm specific promoter is found in U.S. Pat. No. 7,745,697.

Corm Promoters

An example of a promoter capable of driving expression in a corm is found in Schenk et al., (2001) Plant Molecular Biology, 47:399-412.

Photosythetic Tissue Preferred Promoters

Photosythetic tissue preferred promoters include those that are preferrentially expressed in photosynthetic tissues of the plants. Photosynthetic tissues of the plant include leaves, stems, shoots and above ground parts of the plant. Photosythetic tissue preferred promoters include light regulated promoters.

Light Regulated Promoters

Numerous light regulated promoters are known to those skilled in the art and include for example chlorophyll a/b (Cab) binding protein promoters and Rubisco Small Subunit (SSU) promoters. An example of a light regulated promoter is found in U.S. Pat. No. 5,750,385. Light regulated in this context means light inducible or light induced.

Relative Terms

The relative terms, such as increased and reduced as used herein with respect to plants, are relative to a control plant. Suitable control plants include non-transformed or wild-type versions of plant of the same variety and/or species as the transformed plant used in the method of the invention. Suitable control plants also include plants of the same variety and/or species as the transformed plant that are transformed with a control construct. Suitable control constructs include empty vector constructs, known to those skilled in the art. Suitable control plants also include plants that have not been transformed with a polynucleotide encoding a modified oleosin including at least one artificially introduced cysteine. Suitable control plants also include plants that do not express a modified oleosin including at least one artificially introduced cysteine.

The term "total lipid" as used herein includes fats, oils, waxes, sterols, glycerol lipids, monoglycerides, diglycerides, phospholipids, monogalactolipids, digalactolipids, phosphatidylcholines, phosphatidylethanolamine, phosphatidylglycerol, phosphatidylinositol, sulfoguinovosyldiacylglycerol, and triglycerides.

The term "oil" as used herein preferably refers to triacylglycerol (TAG)

The term "biomass" refers to the size and/or mass and/or number of vegetative organs of the plant at a particular age or developmental stage. Thus a plant with increased biomass has increased size and/or mass and/or number of vegetative organs than a suitable control plant of the same age or at an equivalent developmental stage. Increased biomass may also involve an increase in rate of growth and/or rate offormation of vegetative organs during some or all periods of the life cycle of a plant relative to a suitable control. Thus increased biomass may result in an advance in the time taken for such a plant to reach a certain developmental stage.

The terms "seed yield", "fruit yield" and "organ yield" refer to the size and/or mass and/or number of seed, fruit or organs produced by a plant. Thus a plant with increased seed, fruit or organ yield has increased size and/or mass and/or number of seeds, fruit or organs respectively, relative to a control plant at the same age or an equivalent developmental stage.

The terms "increased drought tolerance" and "increased water use efficiency" or grammatical equivalents thereof, is intended to describe a plant which performs more favourably in any aspect of growth and development under, or after, sub-optimal hydration conditions than do control plants in the same conditions.

The term "increased high temperature tolerance" or grammatical equivalents thereof, is intended to describe plant which performs more favourably in any aspect of growth and development under, or after, sub-optimal elevated temperature conditions than do control plants in the same conditions.

The term "increased high oxygen concentration tolerance" or grammatical equivalents thereof is intended to describe plant which performs more favourably in any aspect of growth and development under, or after, sub-optimal elevated oxygen concentrations than do control plants in the same conditions.

The term "increased nitrogen use efficiency" or grammatical equivalents thereof is intended to describe plant which performs more favourably in any aspect of growth and development under, or after, sub-optimal reduced nitrogen conditions than do control plants in the same conditions.

The term "increased rate of $CO_2$ assimilation" or grammatical equivalents thereof is intended to describe plant which assimilates more $CO_2$ under any given conditions than does a control plant in the same conditions.

The term "increased rate of photosynthesis" or grammatical equivalents thereof is intended to describe plant which accumulates more photosynthate under any given conditions than does a control plant in the same conditions.

The term "increased growth rate" or grammatical equivalents thereof is intended to describe plant which grows more quickly under any given conditions than does a control plant in the same conditions.

The term "delayed flowering" or grammatical equivalents thereof is intended to describe plant which flowers later under any given conditions than does a control plant in the same conditions.

The term "increased chloroplast $CO_2$ concentation" or grammatical equivalents thereof is intended to describe a plant has a higher concentration of $CO_2$ in the chloroplast under any given conditions than does a control plant in the same conditions.

The term "decreased rate of photorespiration" or grammatical equivalents thereof, is intended to describe a plant which shows less photorespiration under any given conditions than does a control plant in the same conditions.

The term "decreased loss of fixed carbon" or grammatical equivalents thereof, is intended to describe plant which loses less fixed carbon under any given conditions than does a control plant in the same conditions.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides that is capable of specific hybridization to a target of interest, e.g., a sequence that is at least 15 nucleotides in length. The fragments of the invention comprise 15 nucleotides, preferably at least 16 nucleotides, more preferably at least 17 nucleotides, more preferably at least 18 nucleotides, more preferably at least 19 nucleotides, more preferably at least 20 nucleotides, more preferably at least 21 nucleotides, more preferably at least 22 nucleotides, more preferably at least 23 nucleotides, more preferably at least 24 nucleotides, more preferably at least 25 nucleotides, more preferably at least 26 nucleotides, more preferably at least 27 nucleotides, more preferably at least 28 nucleotides, more preferably at least 29 nucleotides, more preferably at least 30 nucleotides, more preferably at least 31 nucleotides, more preferably at least 32 nucleotides, more preferably at least 33 nucleotides, more preferably at least 34 nucleotides, more preferably at least 35 nucleotides, more preferably at least 36 nucleotides, more preferably at least 37 nucleotides, more preferably at least 38 nucleotides, more preferably at least 39 nucleotides, more preferably at least 40 nucleotides, more preferably at least 41 nucleotides, more preferably at least 42 nucleotides, more preferably at least 43 nucleotides, more preferably at least 44 nucleotides, more preferably at least 45 nucleotides, more preferably at least 46 nucleotides, more preferably at least 47 nucleotides, more preferably at least 48 nucleotides, more preferably at least 49 nucleotides, more preferably at least 50 nucleotides, more preferably at least 51 nucleotides, more preferably at least 52 nucleotides, more preferably at least 53 nucleotides, more preferably at least 54 nucleotides, more preferably at least 55 nucleotides, more preferably at least 56 nucleotides, more preferably at least 57 nucleotides, more preferably at least 58 nucleotides, more preferably at least 59 nucleotides, more preferably at least 60 nucleotides, more preferably at least 61 nucleotides, more preferably at least 62 nucleotides, more preferably at least 63 nucleotides, more preferably at least 64 nucleotides, more preferably at least 65 nucleotides, more preferably at least 66 nucleotides, more preferably at least 67 nucleotides, more preferably at least 68 nucleotides, more preferably at least 69 nucleotides, more preferably at least 70 nucleotides, more preferably at least 71 nucleotides, more preferably at least 72 nucleotides, more preferably at least 73 nucleotides, more preferably at least 74 nucleotides, more preferably at least 75 nucleotides, more preferably at least 76 nucleotides, more preferably at least 77 nucleotides, more preferably at least 78 nucleotides, more preferably at least 79 nucleotides, more preferably at least 80 nucleotides, more preferably at least 81 nucleotides, more preferably at least 82 nucleotides, more preferably at least 83 nucleotides, more preferably at least 84 nucleotides, more preferably at least 85 nucleotides, more preferably at least 86 nucleotides, more preferably at least 87 nucleotides, more preferably at least 88 nucleotides, more preferably at least 89 nucleotides, more preferably at least 90 nucleotides, more preferably at least 91 nucleotides, more preferably at least 92 nucleotides, more preferably at least 93 nucleotides, more preferably at least 94 nucleotides, more preferably at least 95 nucleotides, more preferably at least 96 nucleotides, more preferably at least 97 nucleotides, more preferably at least 98 nucleotides, more preferably at least 99 nucleotides, more preferably at least 100 nucleotides, more preferably at least 150 nucleotides, more preferably at least 200 nucleotides, more preferably at least 250 nucleotides, more preferably at least 300 nucleotides, more preferably at least 350 nucleotides, more preferably at least 400 nucleotides, more preferably at least 450 nucleotides and most preferably at least 500 nucleotides of contiguous nucleotides of a polynucleotide disclosed. A fragment of a polynucleotide sequence can be used in antisense, RNA interference (RNAi), gene silencing, triple helix or ribozyme technology, or as a primer, a probe, included in a microarray, or used in polynucleotide-based selection methods of the invention.

The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence that is complementary to the probe, in a hybridization-based assay. The probe may consist of a "fragment" of a polynucleotide as defined herein.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention, or used in the methods of the invention, may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genera or species, means that the polynucleotide or polypeptide has the same sequence as a polynucleotide or polypeptide found naturally in that genera or species. The polynucleotide or polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polypeptides possess biological activities that are the same or similar to those of the inventive polypeptides or polypeptides. The term "variant" with reference to polypeptides and polypeptides encompasses all forms of polypeptides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequence of the present invention. Identity is found over a comparison window of at least 20 nucleotide positions, preferably at least 50 nucleotide positions, more preferably at least 100 nucleotide positions, and most preferably over the entire length of a polynucleotide of the invention.

Polynucleotide sequence identity can be determined in the following manner. The subject polynucleotide sequence is compared to a candidate polynucleotide sequence using BLASTN (from the BLAST suite of programs, version 2.2.5 [Nov. 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI (ftp://ftp.ncbi.nih.gov/blast/). The default parameters of bl2seq are utilized except that filtering of low complexity parts should be turned off.

The identity of polynucleotide sequences may be examined using the following unix command line parameters:

bl2seq –i nucleotideseq1 –j nucleotideseq2 –F F –p blastn

The parameter –F F turns off filtering of low complexity sections. The parameter –p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice,P. Longden,l. and Bleasby,A. EMBOSS: The European Molecular Biology Open Software Suite, Trends in Genetics June 2000, vol 16, No 6. pp.276-277) which can be obtained from www<dot>hgmp<dot>mrc<dot>ac <dot>uk/Software/EMBOSS/. The European Bioinformatics Institute server also provides the facility to perform EMBOSS-needle global alignments between two sequences on line at www<dot>ebi<dot>ac<dot>uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

A preferred method for calculating polynucleotide % sequence identity is based on aligning sequences to be compared using Clustal X (Jeanmougin et al., 1998, Trends Biochem. Sci. 23, 403-5.)

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [Nov. 2002]) from NCBI (ftp://ftp.ncbi.nih.gov/blast/).

The similarity of polynucleotide sequences may be examined using the following unix command line parameters:

bl2seq –i nucleotideseq1 –j nucleotideseq2 –F F –p tblastx

The parameter –F F turns off filtering of low complexity sections. The parameter –p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-6}$ more preferably less than $1\times10^{-9}$, more preferably less than $1\times10^{-12}$, more preferably less than $1\times10^{-15}$, more preferably less than $1\times10^{-18}$, more preferably less than $1\times10^{-21}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$ and most preferably less than $1\times10^{-100}$ when compared with any one of the specifically identified sequences.

Alternatively, variant polynucleotides of the present invention, or used in the methods of the invention, hybridize to the specified polynucleotide sequences, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing,). Tm for polynucleotide molecules greater than about 100 bases can be calculated by the formula Tm=81. 5+0.41% (G+C-log(Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides of the present invention, or used in the methods of the invention, also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [Nov. 2002]) from NCBI (ftp://ftp.ncbi.nih.gov/blast/) via the tblastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [Nov. 2002]) in bl2seq, which is publicly available from NCBI (ftp://ftp.ncbi.nih.gov/blast/). The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at www<dot>ebi<dot>ac<dot>uk/emboss/align/)and GAP (Huang, X. (1994) On Global Sequence Alignment. Computer Applications in the Biosciences 10, 227-235.) as discussed above are also suitable global sequence alignment programs for calculating polypeptide sequence identity.

A preferred method for calculating polypeptide % sequence identity is based on aligning sequences to be compared using Clustal X (Jeanmougin et al., 1998, Trends Biochem. Sci. 23, 403-5.)

Polypeptide variants of the present invention, or used in the methods of the invention, also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [Nov. 2002]) from NCBI (ftp://ftp.ncbi.nih.gov/blast/). The similarity of polypeptide sequences may be examined using the following unix command line parameters:

bl2seq –i peptideseq1 –j peptideseq2 –F F –p blastp

Variant polypeptide sequences preferably exhibit an E value of less than 1×10–6 more preferably less than 1×10–9, more preferably less than 1×10–12, more preferably less than 1×10–15, more preferably less than 1×10–18, more preferably less than 1×10–21, more preferably less than 1×10–30, more preferably less than 1×10–40, more preferably less than 1×10–50, more preferably less than 1×10–60, more preferably less than 1×10–70, more preferably less than 1×10–80, more preferably less than 1×10–90 and most preferably 1×10–100 when compared with any one of the specifically identified sequences.

The parameter –F F turns off filtering of low complexity sections. The parameter –p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Constructs, Vectors and Components Thereof.

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as *E. coli.*

The term "expression construct" refers to a genetic construct that includes the necessary elements that permit transcribing the insert polynucleotide molecule, and, optionally, translating the transcript into a polypeptide. An expression construct typically comprises in a 5' to 3' direction:

a) a promoter functional in the host cell into which the construct will be transformed,
b) the polynucleotide to be expressed, and
c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence may, in some cases, identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination, mRNA stability, and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors. Introns within coding sequences can also regulate transcription and influence post-transcriptional processing (including splicing, capping and polyadenylation).

A promoter may be homologous with respect to the polynucleotide to be expressed. This means that the promoter and polynucleotide are found operably linked in nature.

Alternatively the promoter may be heterologous with respect to the polynucleotide to be expressed. This means that the promoter and the polynucleotide are not found operably linked in nature.

A "transgene" is a polynucleotide that is taken from one organism and introduced into a different organism by transformation. The transgene may be derived from the same species or from a different species as the species of the organism into which the transgene is introduced.

An "inverted repeat" is a sequence that is repeated, where the second half of the repeat is in the complementary strand, e.g.,

```
(5')GATCTA.......TAGATC(3')     (SEQ ID NO: 110)

(3')CTAGAT.......ATCTAG(5')     (SEQ ID NO: 111)
```

Read-through transcription will produce a transcript that undergoes complementary base-pairing to form a hairpin structure provided that there is a 3-5 bp spacer between the repeated regions.

Host Cells

Host cells may be derived from, for example, bacterial, fungal, yeast, insect, mammalian, algal or plant organisms. Host cells may also be synthetic cells. Preferred host cells are eukaryotic cells. A particularly preferred host cell is a plant cell, particularly a plant cell in a vegetative tissue of a plant.

A "transgenic plant" refers to a plant which contains new genetic material as a result of genetic manipulation or transformation. The new genetic material may be derived from a plant of the same species as the resulting transgenic plant or from a different species.

Methods for Isolating or Producing Polynucleotides

The polynucleotide molecules of the invention can be isolated by using a variety of techniques known to those of ordinary skill in the art. By way of example, such polypeptides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides of the invention include use of all, or portions of, the polypeptides having the sequence set forth herein as hybridization probes. The technique of hybridizing labelled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5. 0×SSC, 0.5% sodium dodecyl sulfate, 1×Denhardt's solution; washing (three washes of twenty minutes each at 55° C.) in 1. 0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence. Such methods include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, Nucleic Acids Res 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species.

Variants (including orthologues) may be identified by the methods described.

Methods for Identifying Variants

Physical Methods

Variant polypeptides may be identified using PCR-based methods (Mullis et al., Eds. 1994 The Polymerase Chain Reaction, Birkhauser). Typically, the polynucleotide sequence of a primer, useful to amplify variants of polynucleotide molecules of the invention by PCR, may be based on a sequence encoding a conserved region of the corresponding amino acid sequence.

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [Nov. 2002]) including BLASTN, BLASTP, BLASTX, tBLASTN and tBLASTX, which are publicly available from (ftp://ftp.ncbi.nih.gov/blast/) or from the National Center for Biotechnology Information (NCBI), National Library of Medicine, Building 38A, Room $8N_{805}$, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences.

The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J.D., Higgins, D.G. and Gibson, T.J. (1994) CLUSTALW: improving the sensitivity of progressive multiple sequence alignment through sequence weighting, positions-specific gap penalties and weight matrix choice. Nucleic Acids Research, 22:4673-4680, www-igbmc<dot>u-strasbg<dot>fr/BioInfo/ClustalW/Top<dot>html) or T-COFFEE (Cedric Notredame, Desmond G. Higgins, Jaap Heringa, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Isolating Polypeptides

The polypeptides of the invention, or used in the methods of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention, or used in the methods of the invention, may also be purified from natural sources using a variety of techniques that are well known in the art (e.g. Deutscher, 1990, Ed, Methods in Enzymology, Vol. 182, Guide to Protein Purification,).

Alternatively the polypeptides and variant polypeptides of the invention, or used in the methods of the invention, may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Polynucleotides, Constructs or Vectors The invention provides a host cell which comprises a genetic construct or vector of the invention.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide of the invention, or used in the methods of the invention. Plants comprising such cells also form an aspect of the invention.

Methods for transforming plant cells, plants and portions thereof with polypeptides are described in Draper et al., 1988, Plant Genetic Transformation and Gene Expression. A Laboratory Manual. Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of plant transformation strategies are available (e.g. Birch, 1997, Ann Rev Plant Phys Plant Mol Biol, 48, 297, Hellens R P, et al (2000) Plant Mol Biol 42: 819-32, Hellens R et al Plant Meth 1: 13). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detect presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

The following are representative publications disclosing genetic transformation protocols that can be used to genetically transform the following plant species: Rice (Alam et al., 1999, Plant Cell Rep. 18, 572); apple (Yao et al., 1995, Plant Cell Reports 14, 407-412); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9, :821); cassaya (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792, 935); soybean (U.S. Pat. Nos. 5,416,011; 5,569,834; 5,824, 877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); *brassica* (U.S. Pat. Nos. 5,188,958; 5,463,174 and 5,750,871); cereals (U.S. Pat. No. 6,074,877); pear (Matsuda et al., 2005, Plant Cell Rep. 24(1):45-51); *Prunus* (Ramesh et al., 2006 Plant Cell Rep. 25(8):821-8; Song and Sink 2005 Plant Cell Rep. 2006; 25(2):117-23; Gonzalez Padilla et al., 2003 Plant Cell Rep. 22(1):38-45); strawberry (Oosumi et al., 2006 Planta. 223(6):1219-30; Folta et al., 2006 Planta April 14; PMID: 16614818), rose (Li et al., 2003), *Rubus* (Graham et al., 1995 Methods Mol. Biol. 1995; 44:129-33), tomato (Dan et al., 2006, Plant Cell Reports V25:432-441), apple (Yao et al., 1995, *Plant Cell Rep.* 14, 407-412), Canola (*Brassica napus* L.). (Cardoza and Stewart, 2006 Methods Mol. Biol. 343: 257-66), safflower (Orlikowska et al, 1995, Plant Cell Tissue and Organ Culture 40:85-91), ryegrass (Altpeter et al, 2004 Developments in Plant Breeding 11(7):255-250), rice (Christou et al, 1991 Nature Biotech. 9:957-962), maize (Wang et al 2009 In: Handbook of Maize pp. 609-639) and *Actinidia eriantha* (Wang et al., 2006, Plant Cell Rep. 25, 5: 425-31). Transformation of other species is also contemplated by the invention. Suitable methods and protocols are available in the scientific literature.

Plants

The term "plant" is intended to include a whole plant, any part of a plant, a seed, a fruit, propagules and progeny of a plant.

The term 'propagule' means any part of a plant that may be used in reproduction or propagation, either sexual or asexual, including seeds and cuttings.

The plants of the invention may be grown and either self-ed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the present invention.

Abbreviations

Oleosin (or Ole)_0-0 means an oleosin without engineered cysteines.

Oleosin (or Ole)_1-1 means an oleosin with one engineered cysteine in each hydrophilic arm.

Oleosin (or Ole)_1-3 means an oleosin with one engineered cysteine in the N-terminal hydrophilic arm and three engineered cysteines in the C-terminal hydrophilic arm.

Oleosin (or Ole)_3-1 means an oleosin with three engineered cysteines in the N-terminal hydrophilic arm and one engineered cysteine in the C-terminal hydrophilic arm.

Oleosin (or Ole)_3-3 means an oleosin with three engineered cysteines in the N-terminal hydrophilic arm and three engineered cysteines in the C-terminal hydrophilic arm.

Oleosin (or Ole)_5-6 means an oleosin with five engineered cysteines in the N-terminal hydrophilic arm and six engineered cysteines in the C-terminal hydrophilic arm.

Oleosin (or Ole)_6-7 means an oleosin with six engineered cysteines in the N-terminal hydrophilic arm and seven engineered cysteines in the C-terminal hydrophilic arm.

EXAMPLES

This invention will now be illustrated with reference to the following non-limiting examples.

Example 1

Creating Rabbit Anti-Sesame Seed Oleosin Antibodies

Generating Rabbit Anti-Sesame Seed Oleosin Antibodies

Full length sesame seed oleosin containing a C-terminal His tag (nucleotide sequence is shown in SEQ ID NO: 1) was expressed in *E. coli* and inclusion bodies were prepared by standard techniques. The inclusion bodies were solubilised in Binding Buffer (100 mM phosphate buffer pH 8.0, 500 mM NaCl, 8M urea and 10 mM imidazole) and loaded onto a column containing equilibrated ion metal affinity chromatography (IMAC) Ni agarose (Invitrogen). Non-bound proteins were removed from the column by washing with 6 volumes of Wash Buffer (100 mM phosphate buffer pH 8.0, 500 mM NaCl, 6M urea and 50 mM imidazole). Protein was eluted in 1 vol. aliquots of Elution Buffer (100 mM phosphate buffer pH 8.0, 500 mM NaCl, 6M urea and 250 mM imidazole). Eluted fractions were analysed by SDS-PAGE/Coomassie stain and the protein concentration measured using the Bradford's Assay. 265 μg of the IMAC-purified recombinant oleosin protein was mixed with an equal amount of Freunds Complete Adjuvant to a final volume of 0.5 mL. Following collection of the pre-bleed, the first injection was administered into multiple sites across the back of the neck and shoulder area of a rabbit. Booster shots containing 77 μg of the purified oleosin were delivered at three and seven weeks after the primary, and a test bleed of ~3 mL was removed for preliminary analysis at nine weeks. Serum was preserved by the addition of 0.25% v/v phenol and 0.01% v/v merthiolate, and stored in 200 μL aliquots at −20° C.

Figure 7:
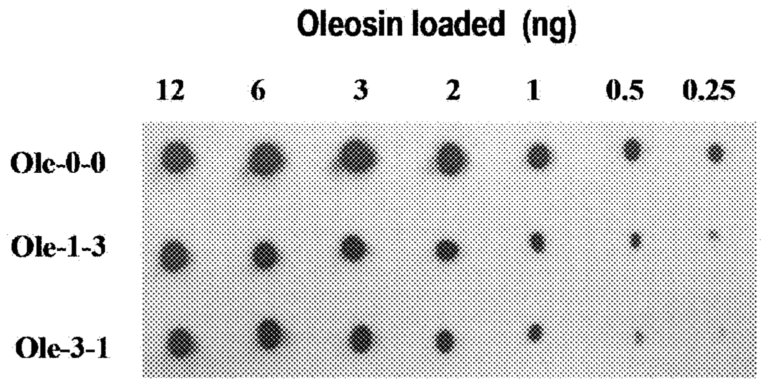
FIG. 7 shows dot blot comparison of anti-sesame seed oleosin antibodies binding to purified recombinant sesame seed oleosin with and without engineered cysteine residues.

The sensitivity of the rabbit anti-sesame seed oleosin antibodies was evaluated by immuno-dotting which indicated that 0.25 ng of sesame seed oleosin could be regularly detected with a 1/2,000 dilution of the antibody (FIG. 7).

Example 2

Design and *E. Coli* Expression of Modified Oleosins Containing One or More Artificially Introduced Cysteine Residue Construct Design for Expression in *E. coli*

A number of modified oleosin constructs for expression in *E. coli* were designed. These contained either one or three cysteine residues on the N-terminal and C-terminal hydrophilic arms. The constructs were based on the nucleotide sequence and translated polypeptide sequence from a sesame seed oleosin, GenBank clone AF091840 which contains no cysteine residues (SEQ ID NO: 16).

All clones were subcloned into pET29b using engineered NdeI/XhoI sites. In addition, a ProTrp coding sequence was added to the coding region of the 3' end of the C-terminal hydrophilic arm to mimic the amino acid residues encoded for by the NcoI site previously engineered by Peng et al (2006) Stability enhancement of native and artificial oil bodies by genipin crosslink. Taiwan Patent I 250466.

Oleosin-cysteine proteins mutated to include cysteine residues in both the N- and C-terminal hydrophilic regions described here are designated Ole-1-1, Ole-1-3, Ole-3-1, and Ole-3-3 (SEQ ID NO 2, 3, 4, and 5 respectively), where the first and the second numeral digits correspond to the number of disulfide bonds in the N- and C-terminus, respectively. The standard oleosin without the cysteine residues was used as a control and was designated as Ole-0-0 (SEQ ID NO 1).

The cysteines were substituted for charged residues predicted to be on the surface of the oil bodies and are listed below.

N-terminal single cysteine (Ole-1-x) Glu3Cys

N-terminal triple cysteine (Ole-3-x) Glu3Cys Arg12Cys Gln23Cys

C-terminal single cysteine (Ole-x-1) Gln137Cys

C-terminal triple cysteine (Ole-x-3) Gln112Cys Lys123Cys Gln137Cys

The constructs were designed so could be relatively simply sub cloned from the GENEART provided backbone (pCR4Blunt-TOPO) into pET29b (Novogen) via NcoI/XhoI digestion and ligation. This placed the oleosin coding sequence downstream of the pET29 N-terminal S•tag fusion and upstream of the C-terminal His tag (FIGS. 1-5 and SEQ ID Nos 1-10). The oleosin and modified oleosin sequences used are summarised in the Summary of Sequences table.

Expression in *E. coli* and Purification of Modified Oleosins Containing at Least One Artificially Introduced Cysteine Expression of the recombinant sesame seed oleosins (with and without engineered cysteines) in the *E. coli* expression system was evaluated by SDS-PAGE/Coomassie brilliant blue staining and SDS-PAGE/immunoblot analysis using antibodies raised against the sesame seed oleosin (described in Example 1).

Expression of recombinant modified oleosin was induced in a freshly inoculated 10 mL culture of *E. coli* (BL21 Rosetta-Gami) containing an oleosin (with or without engineered cysteine residues) coding sequence in the pET29 expression vector. The culture was grown at 37° C., 220 rpm, until mid log phase ($OD_{600}$0.5-0.7); expression was induced by the addition of IPTG to 1 mM final concentration. The induced culture was incubated at 37° C., 220 rpm, for a further 2-3 h. Given the properties of modified oleosin the applicants did not attempt to express it in a soluble form but rather chose to extract it from inclusion bodies. Aliquots (1 mL) of the culture were transferred to 1.5 mL microfuge tubes and the cells pelleted by centrifugation (2655×g for 5 min at 4° C.).

Pelleted cells were resuspended in BugBuster® Reagent (Merck) at 5 mL/g of wet cell pellet, with the addition of DNase to 40 μg/mL and mixed gently on a rotator for 30 min followed by centrifugation at 8000 g for 10 min at 4° C. The resultant cell pellet was retreated with BugBuster® and DNase as above. The remaining soluble protein and suspended cell debris was separated from the insoluble inclusion bodies by centrifugation at 8000 g for 10 min at 4° C.

Recombinant oleosins were further purified from the inclusion bodies using a procedure adapted from D'Andréa et al. (2007). Briefly: the inclusion body preparation was washed by re-suspension in 200 mM sodium carbonate buffer pH 11 (5 mL per gram of original cell pellet) and re-pelleted by centrifugation at 8000×g for 10 min at 4° C. The washed inclusion body pellet was again re-suspended in 5 mL 200 mM sodium carbonate buffer per gram of pellet and added to 9 volumes of freshly prepared chloroform:methanol mix (5:4 v/v) giving a final ratio of 5:4:1 (chloroform:methanol:buffer). The suspension was gently mixed for 5 min which formed a milky, single phase mixture; this was centrifuged at 10,000×g for 10 min at 4° C., and the supernatant containing the modified oleosin was carefully separated from the pellet and transferred into a new tube. Aliquots of the supernatant were dried down under a stream of nitrogen and the protein re-solubilised in 8M urea and quantified by Qubit™ (Invitrogen).

Example 3

Use of Anti-Sesame Seed Oleosin Antibodies to Bind Sesame Seed Oleosin with Artificially Introduced Cysteines A dot-blot was used to compare the ability of the anti-sesame seed oleosin antibodies (Abs) described in Example 1 to bind to oleosin without cysteines versus the oleosins containing cysteines (described in Example 2). Dilution series from 12 to 0.25 ng of purified Ole-0-0, Ole-1-3 and Ole-3-1 were spotted onto a pre-equilibrated Hybond-P PVDF Transfer membrane. This was incubated with the anti-sesame seed oleosin antibodies at 1:2000 as the primary Ab. The blot was then incubated with the appropriate secondary Ab and developed by chemiluminescence (FIG. 7). The results indicate that on an immunoblot, the anti-sesame seed oleosin antibodies are up to an order of magnitude more sensitive to the oleosin without cysteine residues than the oleosins with cysteine residues. As a consequence of the different sensitivities it was necessary to load different quantities of recombinant protein onto the gels for analysis by immunoblotting. Despite the non uniform lane loading it is still possible to compare different oleosins between lanes in terms of their relative distribution between monomeric and oligomeric forms.

Example 4

Creation of Artificial Oil Bodies with *E. coli* Expressed Modified Oleosins Containing at Least One Artificially Introduced Cysteine and Altering the Degree of Cross Linking Preparation of Artificial Oil Bodies Artificial oil bodies (AOBs) were then prepared by drying down aliquots of the supernatant described in Example 3, calculated to contain either 150 μg or 1 mg of recombinant oleosin.

The process of generating AOBs involved combining PL, TAG, and the recombinant oleosin/modified oleosin. In the absence of strong chaotropic agents the disruptive force required to dissociate individual recombinant oleosins from the purified fraction involved several alternating cycles of sonicating and cooling. This was achieved by solubilising the 150 μg and 1 mg oleosin/modified oleosin samples in 20 μL chloroform containing 150 μg PL (Sigma, Cat#P3644) and mixed with 60 μL of purified sesame seed oil (Tzen and Huang 1992) and 940 μL of AOB buffer (50 mM sodium phosphate buffer pH 8.0, 100 mM NaCl). The complete mixture was then sonicated three times for 30 sec (Sonics & Materials Vibra~Cell VC600, 600 W, 20 kHz; ⅛" tapered micro-tip probe, power setting #3).

The applicants also found that the purification procedure could be successfully scaled up and when a 50 g cell pellet was used as the starting material it was necessary to substitute the stream of nitrogen with a rotary vacuum evaporator to remove the chloroform and the majority of the methanol. At this point the majority of oleosin/modified oleosin precipitated out of the azeotropic solvent and was separated by centrifugation at 12,000 g for 10 min.

Inclusion bodies were suspended in 1 mL AOB Buffer II (50 mM sodium phosphate, pH 8.0, 100 mM NaCl, 20 mM β-mercaptoethanol, 10 mM DTT and 5% [v/v] sesame oil) and then sonicated 4×. AOBs were concentrated by centrifugation at 12,000 rpm for 10 min, this resulted in the formation of a suspension of AOBs overlaying the aqueous fraction. The underlying aqueous fraction was removed by pipette, and the remaining AOBs were washed (to remove soluble proteins and reducing agents) by gentle agitation in 1 mL AOB Buffer III (50 mM sodium phosphate, pH 8.0, 100 mM NaCl). After washing, the AOBs were re-concentrated by centrifugation, and the underlying aqueous fraction removed, then re-suspended by vortexing in AOB Buffer IV (50 mM sodium phosphate buffer, pH 8.0, 100 mM NaCl, 1 mM GSSG) and the AOBs stored at 4° C. for further analyses.

Figure 9:
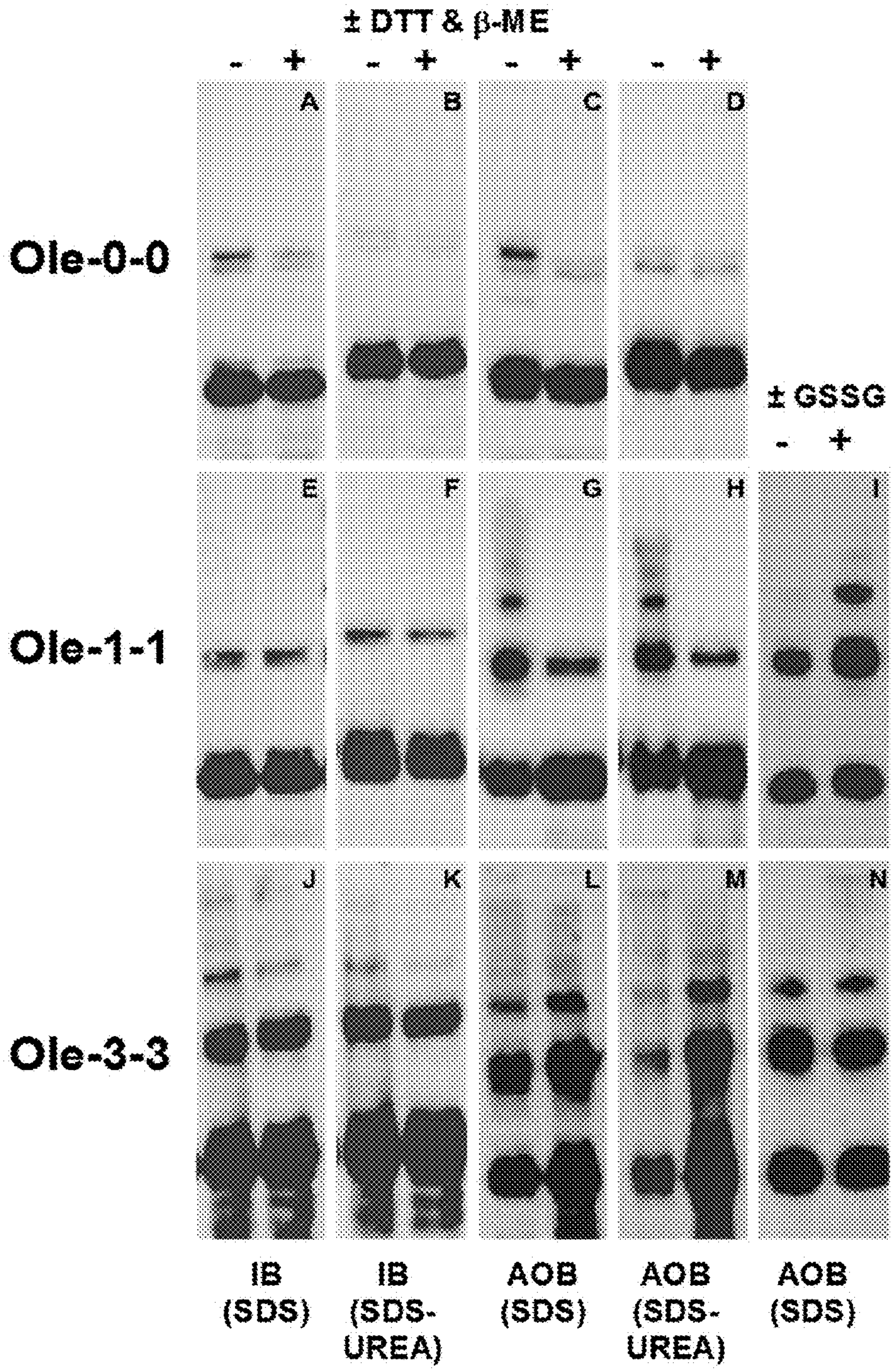
FIG. 9 shows SDS and SDS-UREA PAGE/immunoblot analysis of *E. coli* expressed Ole-0-0, Ole-1-1 and Ole-3-3. Samples were prepared from inclusion bodies (IB) and artificial oil bodies (AOBs) in the presence and absence of reducing agents (DTT and β-ME) or oxidising agent (GSSG), where equal amounts of protein were loaded in adjacent lanes.

Recombinant Ole-0-0, and all variations of the oleosin-cysteines were successfully expressed and located in *E. coli* inclusion bodies (FIG. 9). Ole-0-0 was predominantly present as a monomer (in both inclusion bodies as well as AOBs); this migrated fractionally faster than the 20 kDa molecular weight marker (in reducing and non reducing SDS and SDS-UREA PAGE). Also present were two slower migrating immunoreactive bands of approximately 35 and 36 kDa which likely correspond to two forms of dimeric oleosin. While Ole-0-0 is not predicted to contain any cysteine residues the overall intensity and ratio of the two apparent dimers was influenced by the presence of reducing agents (β-ME @ 5% of the sample loading buffer and 10 mM DTT).

In the inclusion bodies, the predominant form of Ole-1-1 is monomeric. Only one dimeric form appeared to be present and this was not influenced by reducing agents or urea. Ole-1-1 from AOBs (generated in the presence of reducing agent and then in the presence of oxidising agent) showed a large increase in the ratio of dimer to monomer as well as the formation of trimeric, tetrameric and likely pentameric oligomers (the electrophoretic focus of these oligomers was considerably improved in the SDS-UREA gel). Removal of the GSSG and re-introduction of reducing agents to the AOBs resulted in the presence of only monomer and dimer in similar proportions seen in the inclusion bodies. AOBs generated with Ole-1-1 (in the absence of both reducing agents and GSSG) showed the presence of almost equal portions of monomer and dimer and a small amount of trimer, indicating that the conditions under which the AOBs are formed have some reducing potential. The subsequent addition of GSSG resulted in an increase in the oligomeric portions as well as the appearance of a tetrameric form.

Figure 8:
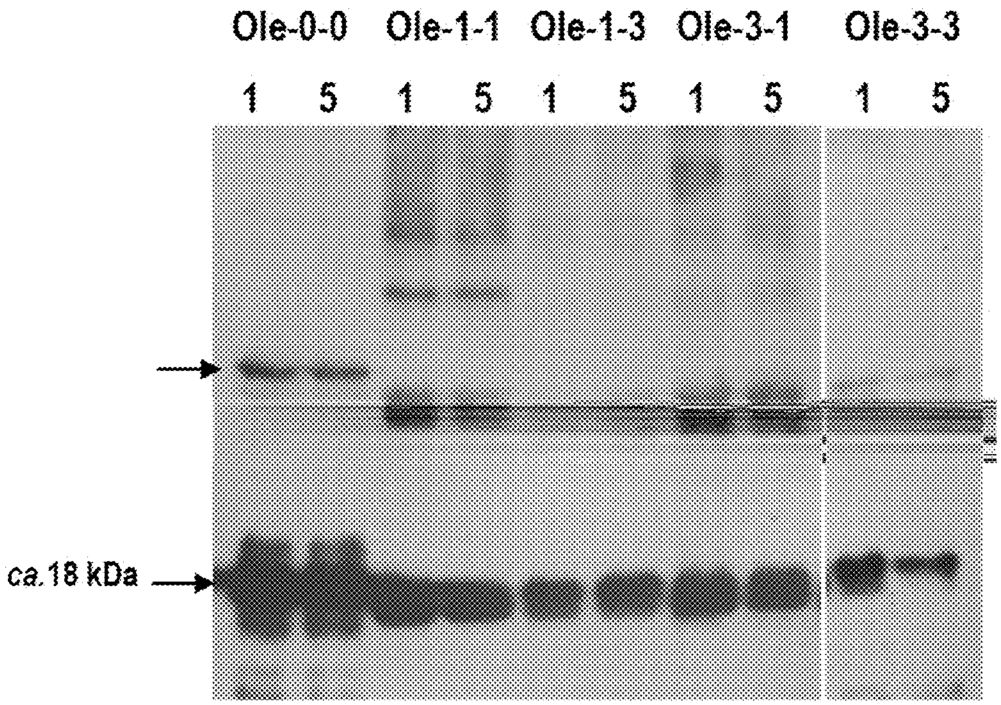
FIG. 8 shows immunoblot analysis to detect *E. coli* expressed oleosin cysteine proteins in AOBs. Equal volume of AOB (7.5 μL including 2×SDS loading dye without reducing agent) was loaded per lane. The mM concentration of GSSG is indicated above each lane.

While the monomer was the predominant form of Ole-3-3 in the inclusion bodies, a comparatively high percentage was also present in multiple oligomeric forms. The proportion of oligomers declined to a small extent with the addition of reducing agent and slightly more by the addition of both reducing and chaotropic agents. Oligomeric forms of Ole-3-3 that were larger than a trimer were poorly resolved when the recombinant protein was extracted from AOBs. The creation of large oligomeric forms was promoted by the addition of GSSG and in the absence of reducing and chaotropic agents a portion of these oligomeric forms failed to enter the stacking gel. Combined, these results indicate that on the AOBs, Ole-3-3 was highly cross-linked and the position of the cross-links was more variable compared to the Ole-3-3 recovered from the inclusion bodies. This suggests that, despite considerable pre-existing cross-linking (within the inclusion bodies), on the AOB Ole-3-3 has access to a high number of potential partners for cross-linking. Similarly for Ole-1-3 and Ole-3-1, the number of cross-linked species increased when there was more than one cysteine on one or both hydrophilic regions (FIGS. 8 and 9).

It could be anticipated that in non-reducing SDS-PAGE, oligomers containing the same number of oleosins but with the disulfide bonds in different positions would migrate differently to each other. Indeed this can be seen in FIG. 8 where the data indicates that the position of the oleosin arms, relative to one another are at different positions over the oil body. For example the Ole-1-1 can only form one disulfide bond per arm and this has to form at the same position, where as the presence of three cysteines enables more than one disulfide bond to form but it also allows the disulfide bonds to form with different degrees of hydrophilic arm overlap as well as having multiple oleosins bound to the same arm (FIGS. 8 and 9).

The addition of SDS and reducing agents (DTT and (3-ME) decreased the number of oligomeric complexes (FIG. 9). The addition of SDS and urea results in a similar pattern to SDS alone except that the previously resolved multiple dimeric forms migrated as one and the trimeric and tetrameric forms appear to be in higher abundance presumably because they are also migrating as single bands which increases intensity correspondingly (FIG. 9). In contrast, the presence of SDS, reducing agent and urea resulted in fewer oligomeric forms of Ole-1-1 and Ole-1-3 but not Ole-3-1 or Ole-3-3 (FIG. 9). In the case of Ole-3-1 and Ole-3-3 it appears that the urea does not completely denature the disulfides oleosins and may indeed prevent the complete reduction of the disulfide bonds. It could be that these bonds are formed during the generation of inclusion bodies (would need to see reduced and non reduced inclusion body preps). Furthermore, the presence of the dimeric oleosin formed in the absence of engineered cysteine residues (FIGS. 8 and 9) indicates that some oligomerisation is due to other types of attraction, e.g, strong hydrophobic bonding that is not fully disrupted by SDS but can be almost completely disrupted by the combination of both SDS and urea (FIGS. 8 and 9).

The effect of increasing the number of potential crosslinking sites in an oleosin peptide on AOB integrity and emulsion stability can be assessed as follows.

Quantitative Determination of AOB Integrity

Assessment of AOB stability and integrity using either absorbance ($OD_{600}$), direct counting of AOBs using a hemocytometer, or visual evaluation of coalescence by microscopy proved to be highly variable and amongst other things was influenced by the: degree of pre-sampling agitation; quantity of sample removed; time left under the microscope. To avoid this the applicants devised a simple method to quantify the amount of TAG released from the AOBs into the surrounding media during a variety of treatments as a means of comparing integrity. Essentially equal quantities (based on FAMES-GC/MS estimation of TAG and Bradfords determination of protein) of AOB preparations are made up to a total volume of 200 μL using AOB buffer (containing Proteinase K [PNK] when appropriate at a 1:1 ratio of PNK:total proteins in OB or AOB samples in a 250 μL GC glass insert tubes and covered with a plastic cap. Following the treatment (elevated temperature or exposure to PNK) 15 μL of fish oil (Vitamax®, Australia) is added to the sample and mixed by vortexing followed by centrifugation at 5,200 g for 1 min. The addition of fish oil followed by vortexing enables any TAG that had leaked from the AOBs to mix with the added fish oil and be floated by brief centrifugation. 4 μL of the oil phase is sampled and subjected to fatty acid methyl esterification (FAME) and then analysed by GC-MS (Shimadzu model numbers, fitted with a 50mQC2/BPX70-0.25 GC capillary column (SGE) as described by Browse et al. (1986). In the absence of added fish oil the quantity of TAG that had leaked from the AOBs was too small to form a samplable visible layer even after centrifugation, in such a case the maximum volume would have been 6 μL. The very different lipid profiles of fish oil and sesame oil enabled us to easily distinguish the leaked TAG from the added TAG.

Using the internal C15:0 and C17:0 standards the applicants can calculate the absolute amounts of C18:2 (the major lipid in sesame seed oil) recovered after treatment.

Determination of AOB Integrity and Emulsion Stability at Elevated Temperature

Oil in water emulsions are less stable at elevated temperatures; hence, it is of interest to investigate if modified oleosins with varying numbers in introduced cysteines influence AOB integrity at elevated temperature. To achieve this the applicants determine the integrity (using the method described above) of OBs and AOBs (containing different oleosins) in a phosphate buffer (50 mM Na-phosphate buffer pH8, 100 mM NaCl) at 95° C. AOBs are heated for 2 h. Integrity is determined as above.

The effect of higher ratios of crosslinked oleosin:TAG on the stability of AOBs in rumen fluid can be assessed as follows.

Determination of AOB Integrity in Rumen Fluid

One of the aims of disulfide was to provide some degree of protection from biohydrogenation by rumen microflora. Assessment of AOB stability with rumen fluid can be assessed as follows. AOBs are added to an equal volume (25 μL) of rumen fluid. Samples are incubated at 39° C. for 0, 15, 30, 60, 120 and 240 min, at the end of the incubation an equal volume of loading buffer (Invitrogen) is added, mixed and heated at 70° C. for 10 min. 15 μL of each sample/loading buffer mix is compared by SDS-PAGE/immunoblot. Integrity is determined as above.

Analysis of AOB Integrity in Proteinase K

To investigate the influence of modified oleosin in a controllable and repeatable highly degradative environment integrity is determined (using the method described above) of AOBs (containing different modified oleosins) after incubation in an phosphate buffer (50 mM Na-phosphate buffer pH8, 100 mM NaCl) containing 1:1 (g/g protein) Proteinase K (Invitrogen) at 37° C. for 4 h. While the maximum activity of Proteinase K is achieved below 65° C. the lower temperature is used in order to reduce the influence of temperature on AOB instability. Integrity is determined as above.

Example 5

Design and in Planta Expression of Modified Oleosin Containing One or More Artificially Introduced Cysteines Construct Design for Expression in Planta The applicants synthesised individual coding sequences for the sesame seed oleosin (based on GenBank clone AF091840) with different numbers of cysteines in the N- and C-terminal arms. The coding sequence was flanked by a 5' NotI site and a 3' NdeI site. A separate acceptor cassette was synthesised containing an attL1 site, a NotI site and NdeI site followed by a nos termination sequence, a forward facing CaMV35s promoter, the *Arabidopsis thaliana* DGAT1 (S205A) (SEQ ID NOs 11-20 and FIGS. 1-5) plus its own UBQ10 intron, an attL2 site. The sesame seed oleosins with different numbers of cysteines were individually transferred to the acceptor cassette via the NotI and NdeI sites. Each of these completed cassettes were then transferred to a plant binary vector pRSh1, FIG. 6 (Winichayakul et al., 2008) via the LR recombination reaction. This placed the oleosin downstream of a CaMV35S promoter (already contained within pRSh1) and placed a nos terminator (already contained within pRSh1) downstream of the *Arabidopsis* DGAT1

(S205A) (FIGS. 1-5). The nucleotide sequences encoding the sesame seed oleosins (with cysteines) and DGAT1 were optimised for expression in *Arabidopsis thaliana*, this included optimisation of codon frequency, GC content, removal of cryptic splice sites, removal of mRNA instability sequences, removal of potential polyadenylation recognition sites, and addition of tetranucleotide stop codon (Brown et al, 1990; Beelman and Parker, 1995; Rose, 2004; Rose and Beliakoff, 2000; Norris et al., 1993).

It should be noted that the oleosin sequence used is for example only. Any oleosin or steroleosin or caoleosin sequences could be engineered to contain cross-linking regions. The coding sequences of the complete ORFs (after splicing) were checked against repeat of the original oleosin translated sequence and found to be identical over the oleosin coding regions.

Transformation of *Arabidopsis thaliana* with Sesame Seed Oleosins Containing Cysteines Transformation of *Arabidopsis thaliana* var *Columbia* (with constructs described above), analyses of T2 seeds for modified oleosin, immunoblot analysis of *Arabidopsis thaliana* oil bodies containing sesame seed oleosin with different numbers of cysteines was performed as described previously (Scott et al., 2007).

Figure 10:
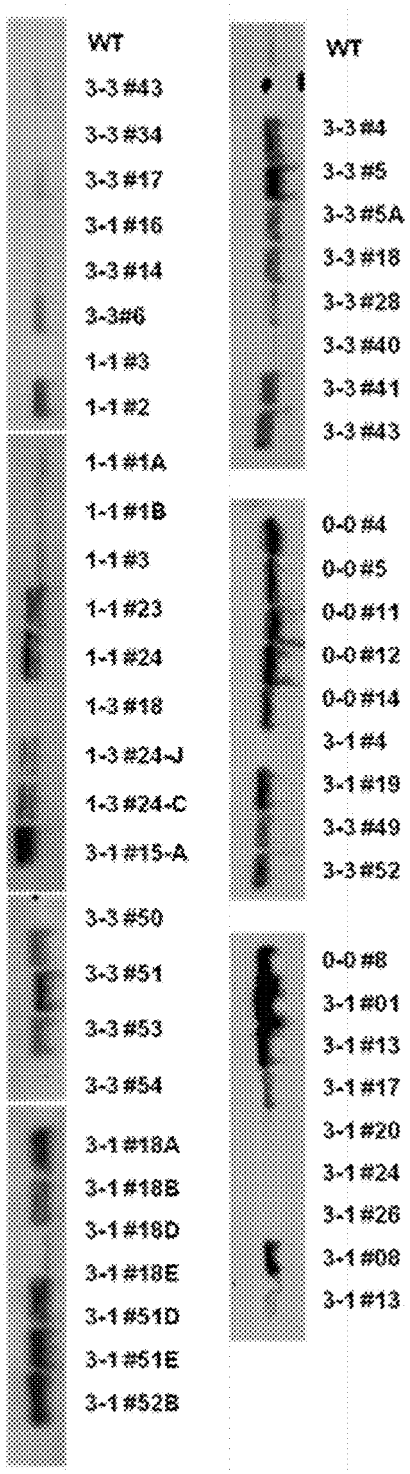
FIG. 10 shows immunoblot analysis of oleosin (Oleo__0-0, Oleo__1-3, Oleo__3-1, and Oleo__3-3, SEQ ID NOs 11-20) accumulation in the seeds of transgenic *Arabidopsis thaliana* expressing both DGAT1 (S205A) and a sesame oleosin under the control of CaMV35S promoters.

Both the floral-dip (Clough, 1998) and floral-drop methods (Martinez-Trujillo, 2004) were used in the transformation of *Arabidopsis* by *Agrobacterium tumefaciens* GV3101 containing the binary constructs. T1 seed was collected from the treated plants, germinated and selected by spraying at 14 d and 21 d post-germination with Basta®. Basta® resistant T1 plants (71, 62 and 23 transformants containing the single sesame seed oleosin, and modified oldeosin constructs respectively) were transplanted, allowed to self-fertilise, set seed and the T2 seed was collected. Equal quantities of seed extract from Basta® resistant *Arabidopsis* plants were analysed by SDS-PAGE/immunoblot with the anti-sesame seed oleosin antibodies; recombinant sesame seed oleosin and modified oldeosin of the appropriate size was observed in the majority of samples (FIG. 10). Southern blot analysis was performed on selected T2 lines to determine the number of insertion sites.

Example 6

Extraction and Purificiation Oil Bodies with Modified Oleosins Containing at Least One Artificially Introduced Cysteine from the Seeds of *Arabidopsis thaliana*

Crude Oil Body Preparations from *Arabidopsis thaliana* Seeds

Crude OB preparations were prepared, from seed of plants produced as described in Example 5, by either grinding 200 mg seed with a mortar and pestle containing a spatula tip of sand and 750 μL Extraction Buffer (10 mM phosphate buffer, pH 7.5 containing 600 mM sucrose) or by homogenising 25 mg of seed in 300 μL Extraction Buffer using a Wiggenhauser D-130 Homogenizer. A further 750 μL Extraction Buffer was added and the slurry in the mortar and transferred to a 2 mL microfuge tube whereas the homogenizer tip was rinsed in 1 mL Extraction Buffer and this volume was added to the homogenised seed. Samples were then centrifuged at 20,000×g for 5 min; this left a pellet and aqueous supernatant which was overlaid by an immiscible oily layer containing both intact and disrupted oil bodies as well as free TAG. The upper oil layer was gently pushed to the side of the tube, and the aqueous layer and pelleted material discarded. The oil layer was then re-suspended from the side of the tube by vortexing in Extraction Buffer and placed in a fresh 2 mL microfuge tube. The final volume was made up to 0.5 mL with Extraction Buffer.

Purified Oil Body Preparations from *Arabidopsis thaliana* Seeds and Cross Linking Cysteine Residues Between the Engineered Oleosins 25 mg of *Arabidopsis* seed (of plants transformed as described in Example 5) was ground in 300 μl extraction buffer (10 mM Phosphate buffer, pH 7.5 containing 600 mM sucrose) using a Wiggenhauser D-130 Homogenizer. Seed was ground until crushed and the sample appeared "creamy" and frothy as starch was released from the seeds. The homogenizer tip was rinsed in 1 ml buffer and this volume was added to the crushed seed. Samples were prepared up to this point in lots of 4, then centrifuged 14,000 rpm for 5 mins. A thin gel loading tip was used to gently push the oil layer to the side of the tube, and the aqueous layer removed to a fresh tube. The oil layer was resuspended from the side of the tube using extraction buffer and placed in a fresh 2 ml tube. The final volume was made up to 0.5 ml (as read on the side of the tube) with extraction buffer, samples were divided into two and oxidising agent (3 mM GSSG) was added to one tube and incubated at room temperature for 10 min. Oil body preparations were then added to an equal volume of 2× gel loading buffer and boiled for 5 min before loading on to a gel.

Samples were run either on pre-cast NuPAGE Novex 4-12% Bis-Tris Midi Gels(Invitrogen) on a Criterion gel rig system (Bio-Rad), or NuPAGE® Novex 12% Bis-Tris gradient Gel 1.0 mm, 15 well, cat# NP0343BOX, with NuPAGE® MES SDS Running Buffer (for Bis-Tris Gels only) (20×), cat# NP0002-02, or on hand-cast Tris-HCl gels. Gels were stained by SafeStain (Invitrogen) to show total protein loaded or blotted onto Nitrocellulose membrane using the iBlot system (Invitrogen). In each case, the negative control was a sample extracted from wild type Columbia seed and the positive control was the same extraction method (although grinding was by mortar and pestle) performed on wild type sesame seed. 10 μl of each sample and the negative control were loaded onto the gel, and 5 μl was used for the positive control.

Following blotting, the membrane was blocked in a solution of 12.5% skim milk powder in TBST (50 mM Tris pH 7.4, 100 mM NaCl, 0.2% Tween) for at least 1.5 hours. The membrane was then washed in TBST 3×5 mins before incubating with primary antibody (anti-sesame) at 1/1000 in TBST for 1 hour at room temperature. Following 3 further TBST washes, incubation with secondary antibody (anti-rabbit) at 1/5000 was carried out for 1 hour at room temperature. The membrane underwent 3 further washes then the signal was developed using standard chemiluminesence protocol.

Figure 11:
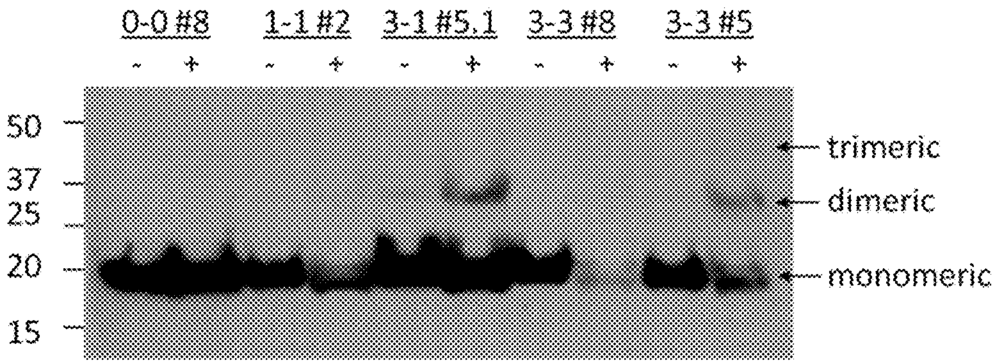
FIG. 11 shows immunoblot analysis of oleosin (Oleo__0-0, Oleo__1-3, Oleo__3-1, and Oleo__3-3, SEQ ID NOs 11-20) accumulation in the oil bodies of transgenic *Arabidopsis thaliana* expressing both DGAT1 (S205A) and a sesame oleosin under the control of CaMV35S promoters. The appearance of the oligomeric oleosin bands (dimeric and trimeric) in the presence of oxidising agent (+) indicates the disulfide bonds are able to form on the outside of native oil bodies.

FIG. 11 shows the accumulation of sesame seed oleosin units on the oil bodies under the control of the CaMV35S promoter. It can be seen that recombinant oleosin and polyoleosin was found to accumulate in the seeds of *Arabidopsis thaliana* and was correctly targeted to the oil bodies (FIG. 11). In addition, it can be seen that in the presence of oxidising agent for 10 minutes the recombinant oleosins containing cysteines formed cross-links as evidenced by the appearance of oligomers and corresponding disappearance of the monomeric forms in these samples and not in the wild type or non oxidised transgenic oil bodies.

The effect of increasing the number of potential cross-linking sites in an oleosin peptide on in planta OB integrity and emulsion stability can be assessed as follows.

Quantitative Determination of OB Integrity

Assessment of OB stability and integrity using either absorbance ($OD_{600}$), direct counting of AOBs using a hemocytometer, or visual evaluation of coalescence by microscopy proved to be highly variable and amongst other things was influenced by the: degree of pre-sampling agitation; quantity of sample removed; time left under the microscope. To avoid this the applicants devised a simple method to quantify the amount of TAG released from the OBs into the surrounding media during a variety of treatments as a means of comparing integrity. Essentially equal quantities (based on FAMES-GC/MS estimation of TAG and Bradfords determination of protein) of OB preparations are made up to a total volume of 200 μL using AOB buffer (containing Proteinase K [PNK] when appropriate at a 1:1 ratio of PNK:total proteins in OB samples in a 250 μL GC glass insert tubes and covered with a plastic cap. Following the treatment (elevated temperature or exposure to PNK) 15 μL of fish oil (Vitamax®, Australia) is added to the sample and mixed by vortexing followed by centrifugation at 5,200 g for 1 min. The addition of fish oil followed by vortexing enables any TAG that had leaked from the OBs to mix with the added fish oil and be floated by brief centrifugation. 4 μL of the oil phase is sampled and subjected to fatty acid methyl esterification (FAME) and then analysed by GC-MS (Shimadzu model numbers, fitted with a 50mQC2/BPX70-0.25 GC capillary column (SGE) as described by Browse et al. (1986). In the absence of added fish oil the quantity of TAG that had leaked from the OBs was too small to form a samplable visible layer even after centrifugation, in such a case the maximum volume would have been 6 μL. The very different lipid profiles of fish oil and sesame oil enabled us to easily distinguish the leaked TAG from the added TAG.

Using the internal C15:0 and C17:0 standards the applicants can calculate the absolute amounts of C18:2 (the major lipid in sesame seed oil) recovered after treatment.

Determination of OB Integrity and Emulsion Stability at Elevated Temperature

Oil in water emulsions are less stable at elevated temperatures; hence, it is of interest to investigate if modified oleosins with varying numbers in introduced cysteines influence OB and AOB integrity at elevated temperature. To achieve this the applicants determine the integrity (using the method described above) of OBs (containing different oleosins) in an phosphate buffer (50 mM Na-phosphate buffer pH8, 100 mM NaCl) at 95° C. AOBs are heated for 2 h. Integrity is determined as above.

The effect of higher ratios of crosslinked oleosin:TAG increase the stability of OBs in rumen fluid can be assessed as follows:

Determination of OB Integrity in Rumen Fluid

One of the aims of disulfide was to provide some degree of protection from biohydrogenation by rumen microflora. Assessment of OB stability with rumen fluid can be assessed as follows. OBs are added to an equal volume (25 μL) of rumen fluid. Samples are incubated at 39° C. for 0, 15, 30, 60, 120 and 240 min, at the end of the incubation an equal volume of loading buffer (Invitrogen) is added, mixed and heated at 70° C. for 10 min. 15 μL of each sample/loading buffer mix is compared by SDS-PAGE/immunoblot. Integrity is determined as above.

Analysis of OB Integrity in Proteinase K

To investigate the influence of modified oleosin in a controllable and repeatable highly degradative environment integrity is determined (using the method described above) of AOBs (containing different modified oleosins) after incubation in an phosphate buffer (50 mM Na-phosphate buffer pH8, 100 mM NaCl) containing 1:1 (g/g protein) Proteinase K (Invitrogen) at 37° C. for 4 h. While the maximum activity of Proteinase K is achieved below 65° C. the lower temperature is used in order to reduce the influence of temperature on OB instability. Integrity is determined as above.

Example 7

Production of Oil Bodies in the Leaves of *Arabidopsis thaliana*

In order to produce oil bodies in vegetative tissue, it is necessary to produce triacyclglycerol in such tissue (e.g. leaves).

Production of Triacylglycerol in the Vegetative Portions of the Plant

In most plants (including *Lolium perenne*) the majority of leaf lipids are attached to a glycerol backbone and exist as diacylglycerols. These are incorporated into lipid bi-layers where they function as membranes of multiple sub-cellular organelles or the as the membrane of the cell itself. The majority of lipid bilayer in the leaf is the chloroplast thylakoid membrane. A smaller amount of leaf lipid exists as epicuticular waxes and an even smaller percentage is present in the form of triacylglycerol (TAG).

Most plants synthesise and store TAG in developing embryos and pollen cells where it is subsequently utilised to provide catabolizable energy during germination and pollen tube growth. Dicotyledonous plants can accumulate up to approximately 60% of their seed weight as TAG. Ordinarily, this level is considerably lower in the monocotyledonous seeds where the main form of energy storage is carbohydrates (e.g., starch) The only committed step in TAG biosynthesis is the last one, i.e., the addition of a third fatty acid to an existing diacylglycerol, thus generating TAG. In plants this step is performed by one of three enzymes including: acyl CoA: diacylglycerol acyltransferase (DGAT1), an unrelated acyl CoA:diacylglycerol acyl transferase (DGAT2), and phospholipid:diacylglycerol acyltransferase (Zou et al., 1999; Bouvier-Navé et al., 2000; Dahlqvist et al., 2000; Lardizabal et al., 2001). Over expression of the transcribed region of any of these genes in the vegetative portions of plants leads to the formation of TAG droplets in the cytoplasm of leaf cells, as demonstrated by the over expression of: *Arabidopsis* DGAT1 in tobacco by Bouvier-Navé et al., (2000); Tung tree DGAT2 in yeast and tobacco by Shockey et al., (2006); *Arabidopsis* PDAT in *Arabidopsis* by Stahl et al., (2004). Over expression of *Arabidopsis* DGAT1 in some cases was demonstrated to increase the total lipid level but not necessarily by the accumulation of TAG, e.g. in *Lotus japonicus* hairy roots (Bryan et al., 2004) and in *Lolium perenne* leaves (Cookson et al., 2009).

To demonstrate the accumulation of TAG in the leaves of these plants you can compare the total quantity of lipid extract from leaves of these plants with those of untransformed plants or plants transformed with the empty binary vector. Ensuring the plants are grown under the same environmental conditions and that the leaves sampled are physiologically equivalent. With the appropriate internal standards the quantification of the total lipid extract can be achieved using FAMES GC-MS analysis (as described by Winichayakul et al, 2008 Delivery of grasses with high levels of unsaturated, protected fatty acids. Proceedings of the New Zealand Grassland Association, 70:211-216.). Alternatively, the total lipids can be extracted using the Folsch method (Folsch et al., 1957J. Folsch, M. Lees and G. A. Slone-Stanley, A simple method for the determination of total lipid extraction and purification, Journal of Biological Chemistry 226 (1957), pp. 497-507.)

and quantified using appropriate internal standards with a GC-MS fitted with a Restek (Restek Corp., Bellefonte, Pa.) RTX65TG column.

Figure 12:
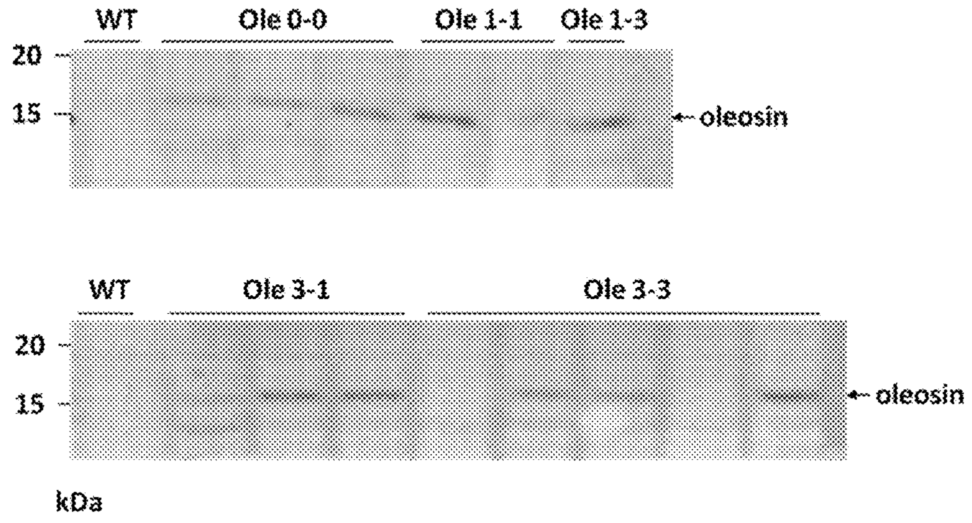
FIG. 12 shows immunoblot analysis of oleosin (Oleo__0-0, Oleo__1-3, Oleo__3-1, and Oleo__3-3, SEQ ID NOs 11-20) accumulation in the leaves of transgenic *Arabidopsis thaliana* expressing both DGAT1 (S205A) and a sesame oleosin under the control of CaMV35S promoters.
Figure 13:
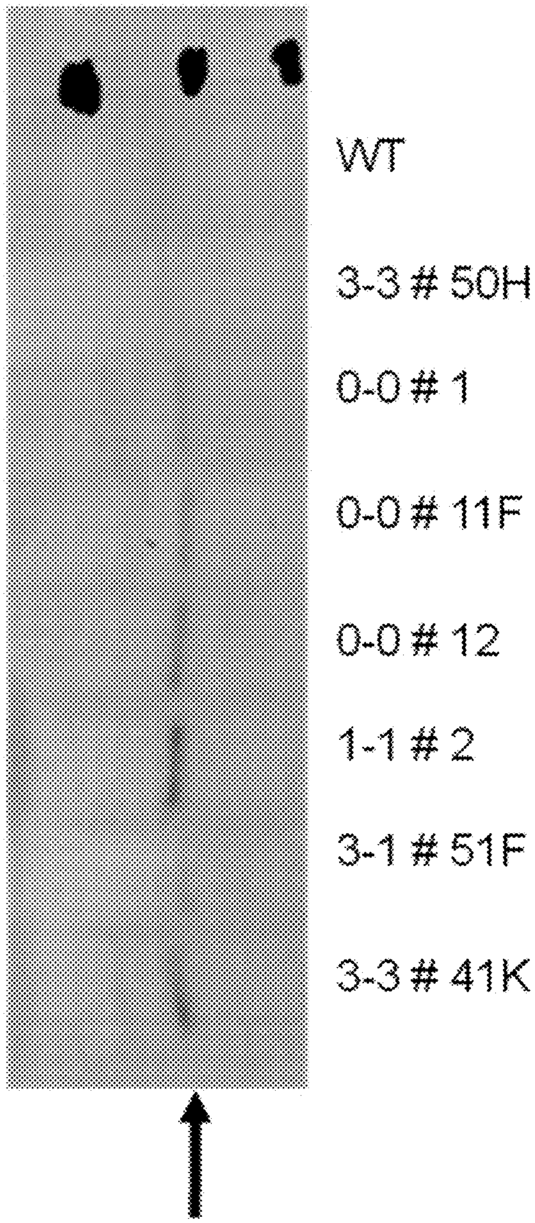
FIG. 13 shows immunoblot of recombinant oleosin accumulation (black arrow) in transgenic *Arabidopsis* leaves.
Figure 14:
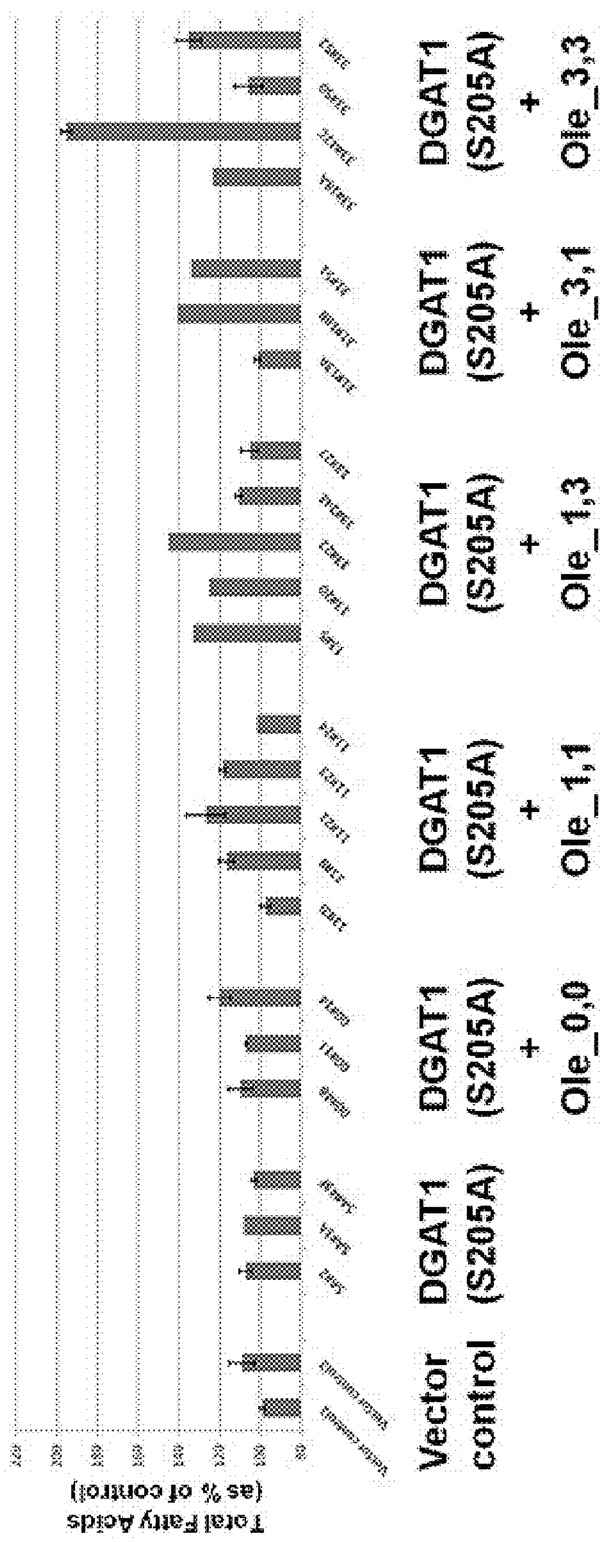
FIG. 14 shows FAMES GC/MS results demonstratinging accumulation of additional lipids (black arrows) in *Arabidopsis* leaves over expressing DGAT1 (S205A) and Ole__3,3.
Figure 15:
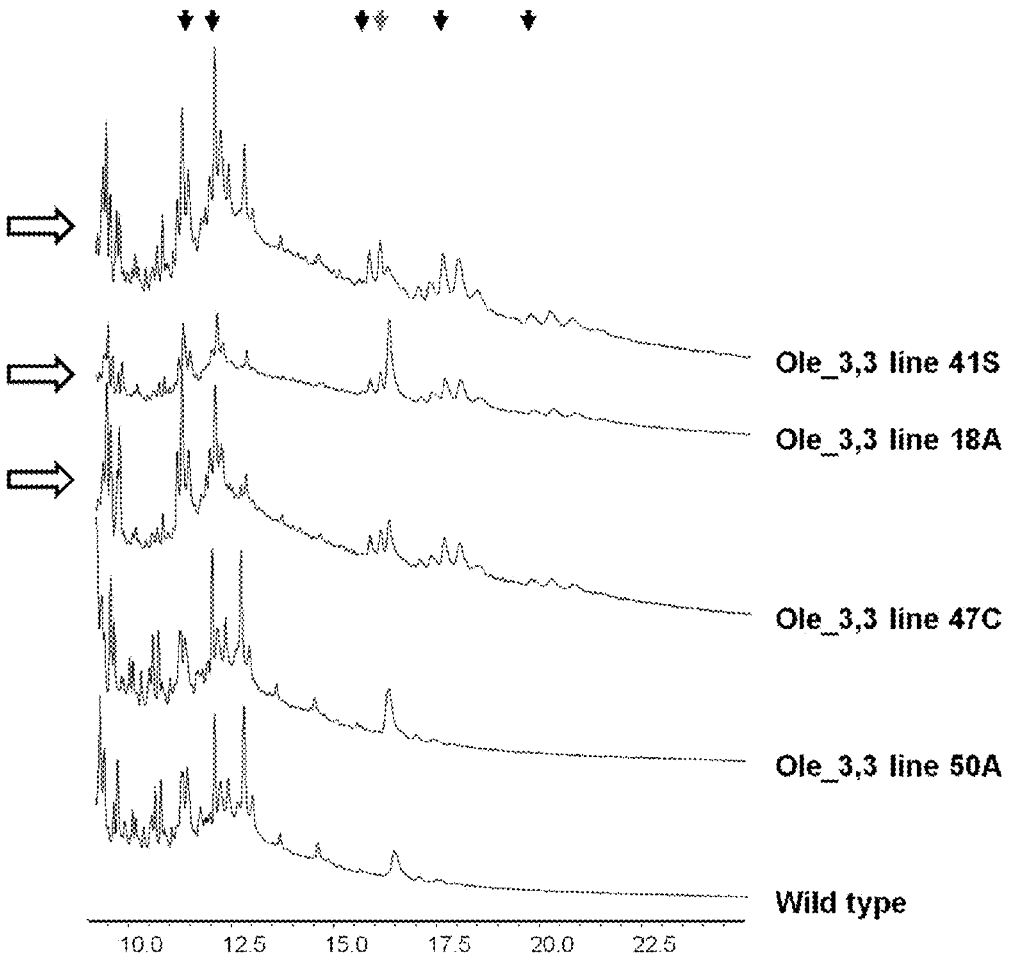
FIG. 15 shows GC/MS results for total leaf lipid profile of wild type and independent lines of transgenic *Arabidopsis* containing DGAT1 (S205A) and Ole__3,3. Grey arrow indicates internal standard. Black arrows indicate additional neutral lipids (wax esters, sterol esters and TAGs. Open arrows show three lines (41S, 18A and 47C) which accumulate substantial quantities of neutral lipids in their leaves compared to wild type (and line 50A)
Figure 16:
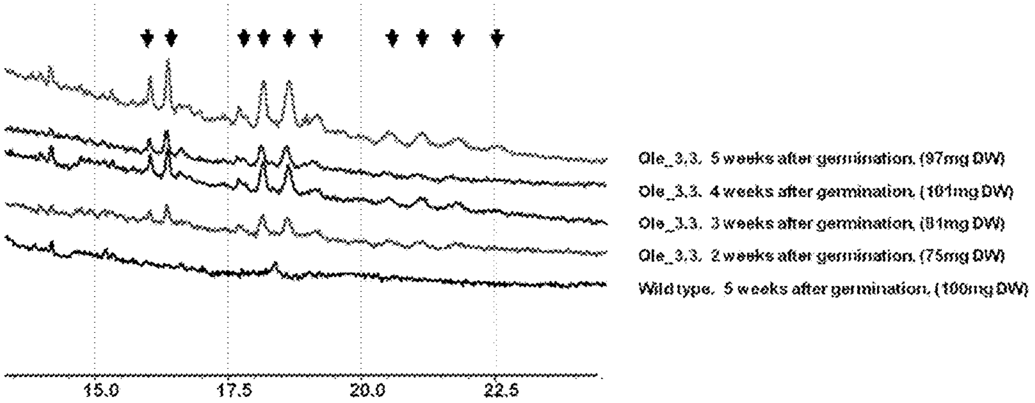
FIG. 16 shows GC/MS results showing total TAG profile of wild type and transgenic *Arabidopsis* (containing DGAT1 (S205A) and Ole__3,3) 2, 3, 4 and 5 weeks after germination. Black arrows indicate additional TAGs found in transgenic leaves but not wild type.

Leaves were sampled from plants over expressing the *A. thaliana* DGAT1 (S205A) and the sesame seed oleosin construct (either Oleo_0-0, or Oleo_1-1, or Oleo_1-3, or Oleo_3-1, or Oleo_3-3, SEQ ID NOs 11-20, FIGS. 1-5) and analysed by SDS-PAGE/immunoblot using the polyclonal anti-sesame seed oleosin antisera. It can be seen that recombinant oleosin was found to accumulate in the leaves of *Arabidopsis thaliana* leaves (FIG. 12).

The simultaneous expression and accumulation of oleosin/modified oleosin protein in the same cell (for example leaf cell) will result in the production of triglyceride oil bodies encapsulated by a phospholipid monolayer embedded with oleosin; this has been demonstrated with un-modified oleosin in yeast (Ting et al., 1997) and seeds (Abell et al., 2004).

Oil Body Preparations from the Leaves of Transgenic *Arabidopsis thaliana*

Oil bodies can be extracted from the leaves of transgenic *Arabidopsis thaliana* expressing DGAT1 (S205A) and the sesame seed oleosin construct (either Oleo_0-0, or Oleo_1-1, or Oleo_1-3, or Oleo_3-1, or Oleo_3-3, SEQ ID NOs 11-20, FIGS. 1-5).

The effect of increasing the number of potential cross-linking sites in an oleosin peptide on the OBs of such plants can be assessed by measuring OB integrity and emulsion stability can as described in Example 6.

Design and Construction of Oleosins Containing More than Three Cysteine Residues in Each Hydrophilic Arms The ole-3,3 lines had substantial levels of elevated lipid levels in the form of TAGs when co-expressed with DGAT1 (S205A) while the lines containing ole-0,0 did not have elevated lipid levels above the DGAT1 over expressing control. The ole-1,1, ole-1,3 and ole-3,1 showed there was a correlation between the level of lipid accumulation in the leaf and the increase in the number of cysteines engineered into each arm (Table 3).

since their ability to come into contact would be limited by their freedom to move on the OB.

Maintaining the proportion of +, − and amphipahthic residues—if the balance of these residues and distribution of these residues is altered dramatically it is likely that the hydrophilic arms would not actually interact with the surface of the OB and as such would not provide any protection against lipases or coalescence.

Sulfur availability—increasing the number of cysteines per oleosin molecule may place the plant under nutritional stress if sulphur is limiting.

The original cysteine-oleosin was engineered to carry 3 relatively evenly spaced unpaired cysteines in each arm by replacing amino acids and predominantly those that could be predicted to be neutral or charged but not hydrophobic.

The oleosin presumably needs to have a certain level of negative charge and in the C-terminus this appears to be achieved by K (Lys), hence continuing the strategy of swapping charged or neutral residues with additional cysteines may result in poor stability in terms of preventing coalescence. Furthermore, in the N-terminal hydrophilic region there appears to be too few residues left between the engineered cysteines to enable further substitution of residues whilst maintaining the spacing and oscillation between positive and negatively charged amino acids. Hence, for both N- and C-termini added additional residues (cysteines) rather than substitute existing residues with cysteines. Alternatively, an oleosin with longer hydrophilic arms could have been used.

Two additional constructs (Ole-5, 6 and Ole-6,7) were also designed. These are not purposely unbalanced in terms of cysteine residues per arm but organised to attempt to give typically 4-5 residues between each cysteine. In fact to increase the cysteines to 6 in the N-terminal arm it was necessary to generate additional residues (as opposed to substitution of existing residues); this as achieved by replicate the first 6 residues from the Ole-3,3.

TABLE 3

Fatty acid composition (as % Dry Weight) of *Arabidopsis* leaves expressing either vector control, DGAT1 (S205A) alone, or DGAT1 (S205A) and different forms of oleosin (containing either no additional cysteines or up to 3 additional cysteines in each hydrophilic arm).

| Fatty acid profile | Vector control | DGAT1 ALONE DGAT1SA #2 | DGAT1 + OLE 0-0 (#11) | DGAT1 + OLE 1-1 (#9) | DGAT1 + OLE 1-3 (#5) | DGAT1 + OLE 3-1 (#18) | DGAT1 + OLE 3-3 (#47) |
|---|---|---|---|---|---|---|---|
| C16:0 | 0.55 ± 0.035 | 0.55 ± 0.001 | 0.54 ± 0.014 | 0.57 ± 0.001 | 0.68 ± 0.042* | 0.62 ± 0.084 | 0.95 ± 0.049* |
| C16:1 | 0.085 ± 0.007 | 0.105 ± 0.007 | 0.11 ± 0.001 | 0.13 ± 0.014 | 0.1 ± 0.001 | 0.135 ± 0.021 | 0.11 ± 0.001 |
| C16:3 | 0.34 ± 0.021 | 0.41 ± 0.028 | 0.42 ± 0.007 | 0.48 ± 0.028 | 0.51 ± 0.035 | 0.55 ± 0.071* | 0.62 ± 0.049* |
| C18:1 | 0.095 ± 0.007 | 0.075 ± 0.007 | 0.1 ± 0.001 | 0.185 ± 0.007* | 0.345 ± 0.007* | 0.2 ± 0.014* | 0.61 ± 0.014* |
| C18:2 | 0.55 ± 0.014 | 0.46 ± 0.035 | 0.56 ± 0.014 | 0.77 ± 0.049* | 0.97 ± 0.007* | 0.79 ± 0.113* | 1.82 ± 0.113* |
| C18:3 | 1.67 ± 0.056 | 1.91 ± 0.028 | 1.78 ± 0.014 | 1.68 ± 0.028 | 1.74 ± 0.014 | 1.9 ± 0.28 | 2.29 ± 0.056* |
| C20:0 | Not detected | Not detected | Not detected | Not detected | Not detected | Not detected | 0.054 ± 0.003 |

The correlation between the increase in total lipid (shown to be TAG) and the number of cysteines engineered into the hydrophilic domains indicated that the number of cysteines may be a way to influence the level of TAG desired. Consequently new constructs containing more than 3 cysteines per hydrophilic arm were designed. While it is not possible to put an infinite number of cysteines/hydrophilic arm; the limitations include:

Length of the arms—if additional residues were added to make space for the cysteines then eventually the degree of hydrophobic domain interaction would be reduced Rather than have completely new nucleotide sequences designed the triplet TGT to code for cysteine was added (where appropriate) to generate Ole_5,6. For additional glutamine residues the codon triplet GGA was used. For the additional N-terminal 6 residues on Ole_6-7 the N-terminus of Ole_3,3 was replicated and fused in frame.

Sublconing strategy was designed to be identical to initial cysteine oleosins, i.e., subcloned into oleoacceptor by NotI/NdeI. This is then recombined by LR reaction into pRSH1 (Winichayakul et al., 2008). Essentially places both *Arabidopsis* DGAT1 (S205A) and oleosin under their own CaMV35s promoters and OCS terminators. Both DGA1 and oleosin clones contain a UBQ10 intron.

NetGene2 was used to predict the splicing pattern of Ole_5,6 and Ole_6,7. Both were predicted to have only one donor and acceptor site on the direct strand (both were predicted to have a very high probability of recognition) and no sites on the complementary strand.

The data indicates that the oleosins containing 1,3 or 3,1 cysteines do accumulate detectable levels of TAG but this is certainly less than the 3,3 cysteine oleosins (the 1,1 accumulated trace amounts while the 0, 0 did not). This suggests even more strongly that the 5,6 and 6,7 oleosins are likely to accumulate even more TAG than the 3,3 construct. The first data from the 5,6 and 6,7 constructs will be available soon.

Transformation of Oleosins Containing Engineered Cysteines and DGAT1 into Wild Type *Arabidopsis thaliana*

Five disulfide-oleosin/DGAT1 (S205A) gene constructs and one control (construct containing DGAT1 (S205A) but not oleosin) were been transferred to the plant binary vector pRSh1 (Winichayakul et al., 2008) and transformed into wild type *Arabidopsis thaliana* using *Agrobacterium*—mediated transformation.

A modification of the traditional floral dip method was followed since it has been reported that floral dipping tends to damage developing siliques due to the presence of detergent in the inoculums (Martinez-Trujillo et al., 2004). Therefore, a drop by drop inoculation to every flower was carried out using a micropipette. The inoculation was repeated after one week to introduce the inoculum to the newly developed flowers. Seeds were collected when the siliques have dried up, then cleaned and planted for screening of transformants.

Screening for transformants was performed by BASTA selection and homozygous transformants were selected using segregation ratio analysis for BASTA resistance.

Transformation of Oleosins Containing Engineered Cysteines and DGAT1 into Wild Type *Trifolium repens*

Transformation into *Trifolium repens* (white clover) was performed according to the procedure of Voisey et al., (1994).

Seeds were weighed to provide approximately 400-500 cotyledons (ie. 200-250 seeds) for dissection (0.06 gm=100 seeds). In a centrifuge tube, seeds were rinsed with 70% ethanol for 1 minute. Surface sterilised in bleach (5% available chlorine) by shaking on a circular mixer for 15 minutes followed by four washes in sterile water. Seeds were imbibed overnight at 4 degC.

The same constructs used to transform *Arabidopsis* (abover) were maintained in *Agrobacterium* strain GV3101 and inoculated into 25 mL of MGL broth (Table 4) containing spectinomycin at a concentration of 100 mg/L. Cultures were grown overnight (16 hours) on a rotary shaker (200 rpm) at 28° C. Bacterial cultures were harvested by centrifugation (3000×g, 10 minutes). The supernatant was removed and the cells resuspended in a 5 mL solution of 10 mM MgSO4.

Cotyledons were dissected from seeds using a dissecting microscope. First, the seed coat and endosperm were removed. Cotyledons were separated from the radical with the scalpel by placing the blade between the cotyledons and slicing through the remaining stalk. Cotyledonary explants were harvested onto a sterile filter disk on CR7 media.

For transformation, a 3 ul aliquot of *Agrobacterium* suspension was dispensed to each dissected cotyledon. Plates were sealed and cultured at 25 degC under a 16 hour photoperiod. Following a 72 hour period of co-cultivation, transformed cotyledons were transferred to plates containing CR7 medium supplemented with ammonium glufosinate (2.5 mg/L) and timentin (300 mg/L) and returned to the culture room.

Following the regeneration of shoots, explants were transferred to CR5 medium supplemented with ammonium glufosinate (2.5 mg/L) and timentin (300 mg/L). Regenerating shoots are subcultured three weekly to fresh CR5 media containing selection.

As root formation occurs, plantlets were transferred into tubs containing CR0 medium containing ammonium glufosinate selection. Large clumps of regenerants were divided to individual plantlets at this stage. Whole, rooted plants growing under selection were then potted into sterile peat plugs. Once established in peat plugs plants were then transfer to the greenhouse.

TABLE 4

Media compositions used for *Trifolium repens* transformation.

| | | |
|---|---|---|
| A. | CR#0 | |
| | MS salts | |
| | B5 vitamins | |
| | sucrose | 30 g/L |
| | pH 5.8 | (KOH) |
| | agar | 8.0 g/L |
| | CR#5 | |
| | MS salts | |
| | B5 vitamins | |
| | sucrose | 30 g/L |
| | BA | 0.1 mg/L |
| | NAA | 0.05 mg/L |
| | pH 5.8 | (KOH) |
| | agar | 8.0 g/L |
| B. | CR#7 | |
| | MS salts | |
| | B5 vitamins | |
| | sucrose | 30 g/L |
| | BA | 1.0 mg/L |
| | NAA | 0.05 mg/L |
| | pH 5.8 | (KOH) |
| | agar | 8.0 g/L |
| C. | MGL | |
| | Mannitol | 5.0 g/L |
| | L glutamic acid | 1.0 g/L |
| | KH2PO4 | 250 mg/L |
| | MgSO4 | 100 mg/L |
| | NaCl | 100 mg/L |
| | Biotin | 100 mg/L |
| | Bactotryptone | 5.0 g/L |
| | Yeast extract | 2.5 g/L |
| | pH 7.0 | (NaOH) |

Figure 17:
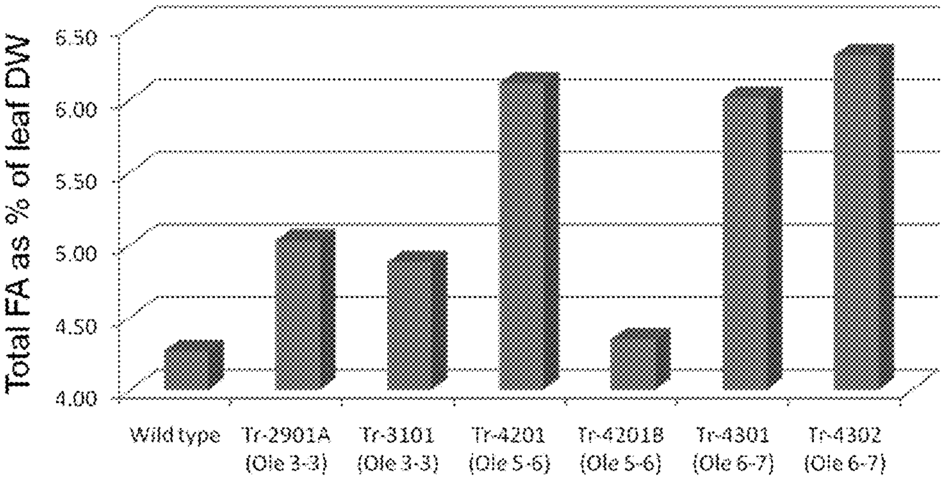
FIG. 17 shows FAMES GC/MS results showing total leaf lipid profiles of wild type and transgeneic *Trifolium repens* (containing DGAT1 (S205A) and Ole__3,3).

FAMES GC/MS results showed the transgeneic *Trifolium repens* (containing DGAT1 (S205A) and either Ole_3,3 or Ole_5,6 or Ole 6,7) had elevated total leaf lipid profiles compared to wild type (FIG. 17). There was a general correlation between the highest level of leaf lipid and the highest number of cysteines engineered into the oleosin.

Figure 18:
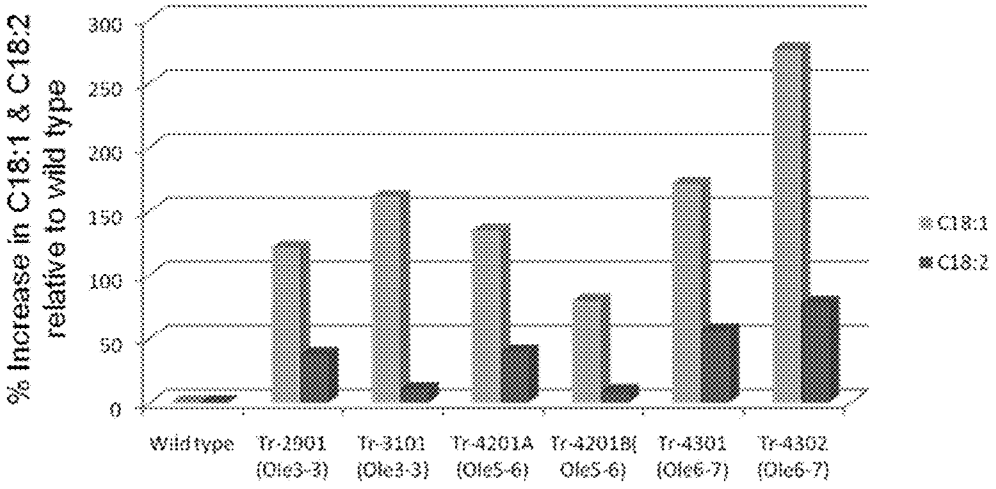
FIG. 18 shows FAMES GC/MS results showing C18:1 and C18:2 leaf lipid profiles of wild type and transgeneic *Trifolium repens* (containing DGAT1 (S205A) and Ole__3,3).

FAMES GC/MS results showed the transgeneic *Trifolium repens* (containing DGAT1 (S205A) and either Ole_3,3 or Ole_5,6 or Ole 6,7) had elevated C18:1 and C18:2 leaf lipid profiles compared to wild type as also seen in *Arabidopsis* (FIG. 18). The highest level of leaf C18:1 and C18:2 was found in plants transformed with the oleosin containing the highest number of engineered cysteines.

Determination of Oil Body Assembly in Leaves (and Seeds)

Further screening was conducted using immunoblot analysis (with an anti-sesame seed oleosin antibody, Scott et al., 2007) to determine the lines overexpressing the oleosin protein. Using this method, either oil bodies (OBs) were extracted from T2 seeds of putative transformants using sucrose density gradient or total protein was extracted from leaves in a denaturing/reducing buffer and proteins were separated in SDS-PAGE, transferred to nitrocellulose membrane, and challenged with an antibody raised against the sesame oleosin (Scott et al., 2007).

Crude oil body (OB) was extracted from 25 mg of seeds in 500 μL OB buffer (10 mM Sodium phosphate, pH 7.5 containing 600 mM sucrose). After centrifugation at 13,000×g, the aqueous layer was carefully suck out and the fat pad layer was resuspended in 200 μL of OB buffer without disturbing the pellet at the bottom. 20 μL of each OB extract was added with 4× loading dye and 10× reducing agent, heated up to 70° C. for 5 min and loaded onto 4-12% polyacrylamide gel for immunoblot analysis. The blot was incubated in α-sesame oleosin antibody (1° Ab) at 1:750 dilution for one hour, and another one hour in secondary antibody (1:10,000).

Oleosin is naturally expressed in seeds and not in the leaves. However, since we have co-expressed DGAT1 with oleosin both under the control of CaMV35S promoters it could be anticipated that this would enable detectable levels of oleosin to accumulate in the leaves. Leaves from transformed lines with high expression of recombinant oleosin in the seeds (identified by immunoblot analysis) were analyzed by immunoblot using antibodies raised against the sesame oleosin.

Table 5 below summarises the number of putative transformants generated and the number of plants expressing recombinant oleosin in the seed and leaf.

dard (C15:0 FA, 4 mg/mL dissolved in heptane) was added, To this mixture, 1 mL of the methanolic HCl reagent (1 mL of 3 M solution diluted to 1 M using dry methanol which had been treated with 5% 2,2-dimeethoxypropane as a water scavenger. The tube was then flushed with N2 gas then sealed immediately with Teflon-lined cap, and heated at 80° C. for 1 h. After the tubes had cooled to room temperature, 10 μL pre-methylated standard (4 mg/mL of C17:0 dissolved in heptane) was added. To this mixture, 0.6 mL heptane and 1.0 mL of 0.9% (w/v) NaCl was added, and mixed thoroughly by vortexing. Following centrifugation at 500 rpm for 1 min at room temperature, 100 μL of the top layer (containing heptanes) was collected and transferred to a flat-bottom glass insert fitted into a brown vial for GC/MS analysis.

FAMES GC/MS Analysis

The FAMES GC/MS was analysed using the SGE capillary column BPX70 (50m×0.22 mm×0.25 μm). The condition of GC-MS was as follows: the temperature was programmed from 80° C. to 150° C. at 15° C./min and then to 250° C. at 8° C./min and held isothermal for 10 min. Samples were injected in a split mode; total flow of 28.4 mL/min; column flow of 0.82 mL/min; and a purge flow of 3.0 mL/min. The pressure was kept at 150 kPa; ion source temperature was 200° C. and an interface temperature was kept at 260° C. The target compounds were acquired by mass spectrometry in a scan mode starting at 50 m/z and ending at 350 m/z.

TABLE 5

| Gene construct ID | Number of putative transformants (based on BASTA resistance) | Number of lines seeds were analysed by immunoblot (anti sesame seed oleosin antibody) | Number of lines with a positive immunoreactive band at the appropriate size in the seed extract | Number of lines with a positive immunoreactive band at the appropriate size in the leaf extract |
|---|---|---|---|---|
| pRSh1-DGAT1 (S205A) control | 8 | N/A | N/A | |
| pRSh1-DGAT1 (S205A)-Ole_0-0 | 14 | 8 | 7 | 3 |
| pRSh1-DGAT1 (S205A)-Ole_1-1 | 22 | 2 | 1 | 1 |
| pRSh1-DGAT1 (S205A)-Ole_1-3 | 20 | 0 | 0 | 1 |
| pRSh1-DGAT1 (S205A)-Ole_3-1 | 23 | 8 | 4 | 2 |
| pRSh1-DGAT1 (S205A)-Ole_3-3 | 54 | 22 | 16 | 5 |

It should be noted the level of recombinant oleosin that accumulated in the leaves was considerably lower than in the seeds. However, the proportion of individual lines accumulating detectable levels in both the leaves was much greater than when oleosin was expressed alone (Roberts Lab, unpublished data) indicating that the co-expression of both DGAT1 and oleosin in the leaf has lead to the accumulation of higher levels of oleosin.

Analysis of Leaves from Transgenic Plants Co-Expressing DGAT1 (S205A) and Disulfide Oleosins The seeds from homozygous lines over expressing the oleosin protein in the seeds were germinated to allow growth of 2, 3, 4 or 5 weeks. Sufficient leaf material was harvested for FAMES GC-MS, as well as by GC-MS using a RTX 65-TG Restek column which enable the separation and identification of free fatty acids, diacylglycerides, wax esters, sterol esters and triacylglycerides without derivatization.

Preparation of Material for FAMES-GC/MS Analysis 10 mg of freeze-dried leaf powder was placed in a 13×100 mm screw-cap tube, 10 μL of non methylated internal stan- TAG and Polar Lipid Extraction TAG was extracted using a modified method of Ruiz-López et al., (2003). Briefly, for each TAG analysis, betweeen 34-80 mg of freeze-dried leaf powder was placed into tared 13-mm screw cap tube and weighed, 2.4 mL of 0.17 M NaCl in MeOH was added and mixed by vortexing. Following the addition of 4.8 mL heptane and 10 μL of internal standard (C14:0, 10 μg.μL-1), the suspension was mixed gently and incubated without shaking in 80° C. water bath for 2 h. After cooling to room temperature, the upper phase (containing lipids) was transferred to fresh screw-cap tube and evaporated to dryness under stream of N gas. Finally, the dried powder were resuspended in 100 μL heptanes, mixed thoroughly then transferred to a flat-bottom glass insert fitted into a brown glass vial for TAG analysis.

TAG GC-MS Analysis

TAG analysis was performed on a Hewlett Packard (HP) GC and Shimadzu Scientific Instruments Inc. MS (QP2010). All analyses were performed with a RESTEK capillary column MXT-65TG (65% diphenyl-35% dimethyl polysiloxane, 30.0 m×0.10 μm thickness×0.25 mm diameter) in Electron Impact (EI) ionization mode. Helium was used as the carrier gas. All samples were injected in splitless mode, in 1.0 μl aliquots, and a column flow of 1.2 mL·min−1. The gas chromatograph was programmed from 200 to 370° C. at 15° C.·min−1 and kept isothermal at 370° C. for 15 min. The sample injector port temperature was maintained at 350° C., column oven temperature at 200° C., with a pressure of 131.1 kPa and a purge flow of 3.0 mL·min−1. The mass spectrometric conditions were as follows: ion source temperature was held at 260° C. during the GC-MS runs, the mass spectra were obtained at ionization voltage of 70 eV at an emission current of 60 μA and an interface temperature of 350° C. Acquisition mode was by scanning at a speed of 5000, 0.25 sec per scan. Chromatograph peaks with mass to charge ratio of 45 m/z to 1090 m/z were collected starting at 9 min and ending at 25 min.

Example 8

Further Oleosins, Caloleosins and Steroleosins Engineered to Contain Additional Cysteine Residues in the N- and C-Terminal Hydrophilic Arms The applicants have used the same strategy as for sesame seed oleosin, accession number AAD42942, (i,e., substituting charged residues predicted to be on the surface of OBs with cysteines) to engineer cysteines into the N- and C-terminal hydrophilic arms of oleosins caoleosins and steroleosins. In some cases it has been possible to substitute only negatively charged amino acids (Glutamic acid and Aspartic acid) that are relatively evenly spaced. In the case of the sesame oleosin AAD42942 it was necessary to sometimes compromise on the charge substitution. It should be noted in the examples below that two caleosins (AAB71227 and AAF13743) contain two endogenous cysteines in their C-terminal arm. These are left unaltered in the engineering.

To determine the position of the amino acid substitution each protein was aligned with the sesame oleosin (AAD42942) in the original form as well as the forms containing 1 or 3 cysteines per hydrophilic arm (i.e., ole__0,0; ole__1,1; ole__3,1; ole__1,3; ole__3,3). The potential glutamic acids and aspartic acids in N-terminus or C-terminus of each of the hydrophilic arms (determined by hydrophobicity plots) were then highlighted with grey boxes, as were the relevant lysine, arginine and glutamine residues (which were all successfully altered in the sesame oleosin (AAD42942). The mutation of these residues to cysteine were then considered along with their spacing with each other. The final substitutions are then shown with the original peptide sequence and the engineered sequence only. In this case only 3 cysteines were engineered into each arm, however, the number could have been greater or fewer. An alternative approach would have been to work with each protein in isolation and simply begin by identifying the hydrophilic regions by hydrophobicity plot then begin the process of substitution with the most appropriate charged amino acid.

Table 6 below shows additional oleosin and caoleosins that the applicants have modified to introduce cysteines in the hydrophilic portions.

TABLE 6

| Protein Type | Plant Source | Accession Number | SEQ ID NO |
|---|---|---|---|
| oleosin | *Brassica oleraceae* (pollen oleosin) | CAA65272.1 | 90 |
| oleosin | Maize | NP_001147032.1 | 91 |
| oleosin | Rice | AAL40177.1 | 92 |
| caoleosin | Sesame | AAF13743 | 93 |
| caoleosin | Soybean | AAB71227 | 94 |
| caoleosin | Maize | NP_001151906 | 95 |
| steroleosin | Sesame | AAL13315 | 96 |
| steroleosin | *Brassica napus* | ACG69522 | 97 |
| steroleosin | Maize | NP_001152614.1 | 98 |

Table 7 below references the SEQ ID NO in the modified oleosins

| Protein Type | Plant Source | Accession Number | SEQ ID NO |
|---|---|---|---|
| oleosin | *Brassica oleraceae* (pollen oleosin) | X96409 | 99 |
| oleosin | Maize | NP_001147032.1 | 100 |
| oleosin | Rice | AAL40177.1 | 101 |
| caoleosin | Sesame | AAF13743 | 102 |
| caoleosin | Soybean | AAB71227 | 103 |
| caoleosin | Maize | NP_001151906 | 104 |
| steroleosin | Sesame | AAL13315 | 105 |
| steroleosin | *Brassica napus* | ACG69522 | 106 |
| steroleosin | Maize | NP_001152614.1 | 107 |

The modified sequence can be expressed as described in the examples above to produce oil bodies, emulsions, transgenic host cells, plants etc, and to test the properties of each.

Example 9

Increased Biomass Production Through Elevation of Chloroplast $CO_2$ Concentration, Elevation of $CO_2$ Assimilation Rate and Elevation of Intrinsic Water use Efficiency in the Leaves The applicants have used the same strategy in Example 7 (by preventing the catabolism of TAG in the leaf which inturn ensures there is a continual recycling of $CO_2$ from pyruvate as it is used by the pyruvate dehydrogenase complex to generate Acetyl-CoA for lipid biosynthesis) to not only increase the $CO_2$ assimilation rate but also elevate intrinsic Water Use Efficiency. The net effect of this is to elevate the partial pressure of $CO_2$ compared to $O_2$ in the chloroplast. $CO_2$ assimilation rates in both air (containing rougly 79% $N_2$, 21% $O_2$ and 400 ppm $CO_2$) and in a calibrated gas mixture with reduced $O_2$ (containing 98% $N_2$, 2% $O_2$ and 400 ppm $CO_2$) were measured to demonstrate that the plants which had protected TAG (via the co-expression of DGAT and cysteine oleosin) had reduced levels of photorespiration IRGA Settings Rates of photosynthesis were measured for 6 wild type (WT) and 6 transgenic (T) plants (DGAT+Ole-3,3), at 200 μmol $m^{-2}$ $s^{-1}$ PAR (growing condition), between 11:00 and 16:00 on the 24th of May 2011 using a portable photosynthesis system (Li6400, LiCor Inc., Lincoln, Nebr., USA) fitted with standard 2×3 cm leaf chamber, leaf thermocouple and a blue-red LED light source. Intrinsic water-use efficiency was estimated from the ratio of photosynthesis/conductance (Osmond et al. 1980). Block temperature was held at 20° C., stomata ratio set at 1.6 and the vapour pressure deficit was between 0.6 and 0.9 kPa. For measurements under nonphotorespiratory conditions, a tank of 2% oxygen (certified) in nitrogen was connected to the Li-6400 inlet.

Statistical Analysis

A standard t-test statistic (R 2.12) was used in this study for comparison between treatments or between genotypes. The means of each genotype were obtained, together with the average standard error of the difference between two means (SED).

Net Photosynthesis and Intrinsic Water-Use Efficiency

Figure 30:
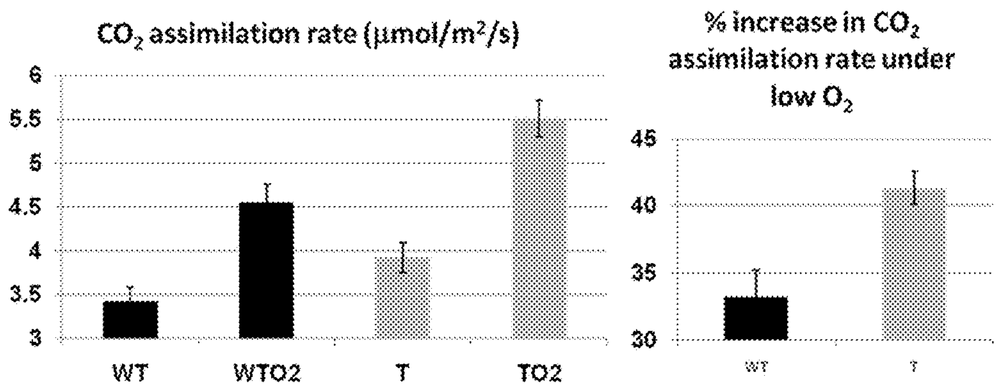
FIG. 30 left hand panel shows $CO_2$ fixation rate in air for wild type (WT) and plants transformed with DGAT1-Ole__3,3 (T) and in low $O_2$ for wild type (WTO2) and plants transformed with DGAT1-Ole__3,3 (TO2). Right hand panel shows % change of $CO_2$ fixation rate for wild type (WT) and plants transformed with DGAT1-Ole_3,3 (T) when placed in low $O_2$ environment.

Rates of photosynthesis were significantly greater (under photorespiratory conditions) in transgenic plants compared to wild type plants; similarly, rates of photosynthesis were significantly greater (under nonphotorespiratory conditions) in transgenic plants compared to wild type plants. (FIG. 30, left hand panel). The DGAT1-Ole_3,3 plants had greater increases in photosynthesis when photorespiration was completely removed using a low $O_2$ environment compared to wild type (FIG. 30, right hand panel). Thus showing that DGAT1-Ole_3,3 plants have elevated $CO_2$ assimilation rates compared to wild type plants.

Figure 31:
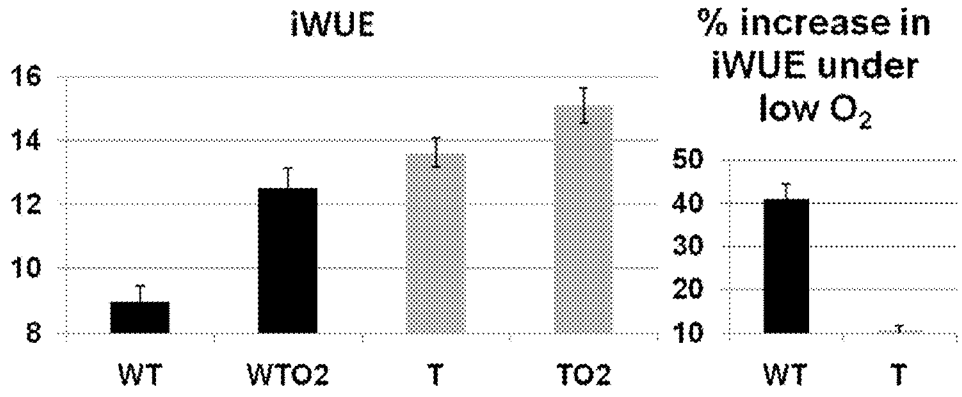
FIG. 31 left hand panel shows intrinsic Water Use Efficiency (iWUE) in air for wild type (WT) and plants transformed with DGAT1-Ole_3,3 (T) and in low $O_2$ for wild type (WTO2) and plants transformed with DGAT1-Ole_3,3 (TO2). Right hand panel shows % change in iWUE for wild type (WT) and plants transformed with DGAT1-Ole_3,3 (T) when placed in low $O_2$ environment.

Intrinsic water-use efficiency measurements were significantly greater under nonphotorespiratory conditions than under ambient oxygen concentration for both the WT and T genotypes (FIG. 31, left hand panel). At ambient $O_2$ levels the iWUE was consistently higher for plants transformed with DGAT1-Ole_3,3 than wild type plants; this was further demonstrated by the fact that the DGAT1-Ole_3,3 plants had smaller increases in iWUE when photorespiration was completely removed using a low $O_2$ environment (FIG. 31, right hand panel). Thus showing that DGAT1-Ole_3,3 plants have higher iWUE compared to wild type plants.

Figure 32:
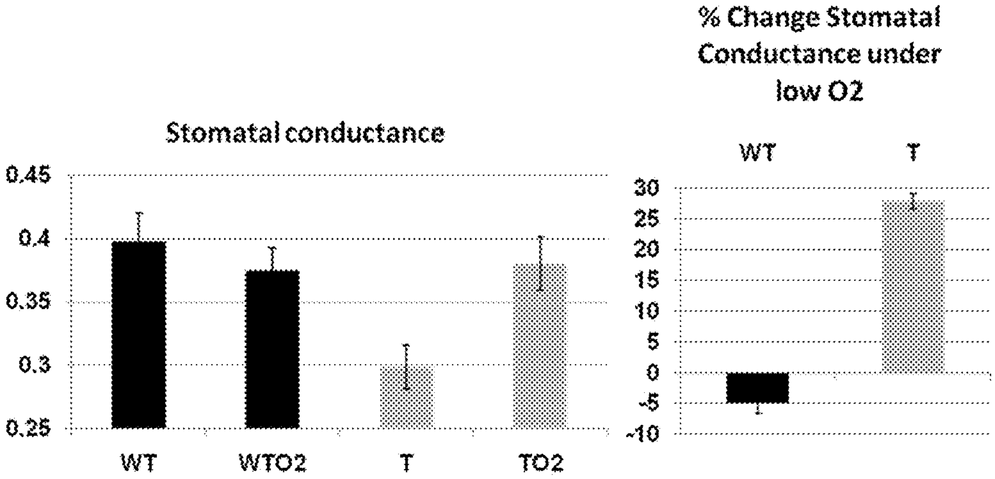
FIG. 32 left hand panel shows Stomatal Conductance in air for wild type (WT) and plants transformed with DGAT1-Ole_3,3 (T) and in low $O_2$ for wild type (WTO2) and plants transformed with DGAT1-Ole_3,3 (TO2). Right hand panel shows % change in Stomatal Conductance for wild type (WT) and plants transformed with DGAT1-Ole_3,3 (T) when placed in low $O_2$ environment.

Stomatal conductance was significantly higher in wild type plants than plants transformed with DGAT1-Ole_3,3 under ambient oxygen conditions (FIG. 32, left hand panel). In the wild typ plants, stomatal conductance was reduced slighlyt under nonphotorespiratory conditions where as in plants transformed with DGAT1-Ole_3,3 the stomatal conductance increased by over 25% compared to ambient conditions (FIG. 32, right hand panel). The stomatal conductance for both wild type and plants transformed with DGAT1-Ole_3,3 were approximately the same when photorespiration was eliminated by the low $O_2$ conditions (FIG. 32, left hand panel).

Figure 33:
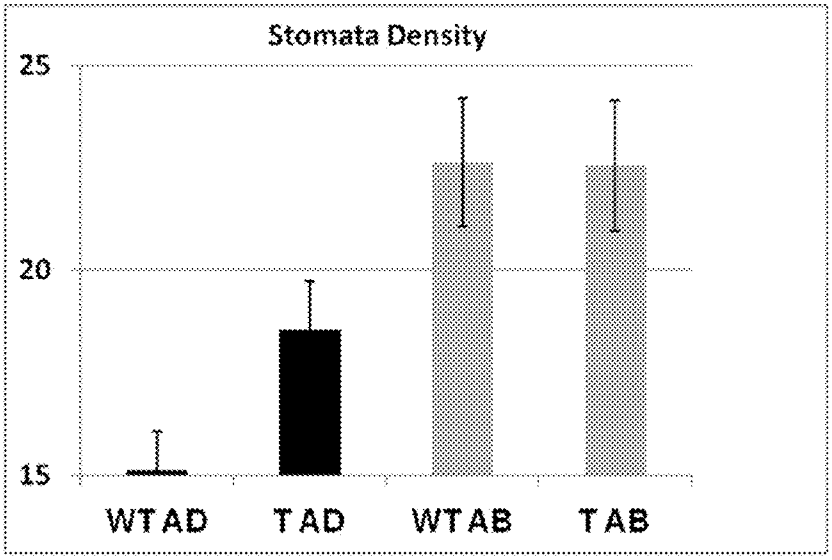
FIG. 33 shows Stomatal Density for wild type adaxial surface (WT AD), plants transformed with DGAT1-Ole_3,3 adaxial surface (T AD), wild type abaxial surface (WT AB), plants transformed with DGAT1-Ole_3,3 abaxial surface (T AB)

The stomatal density of the wild type plants and plants transformed with DGAT1-Ole_3,3 were similar (FIG. 33).

Figure 34:
FIG. 34 shows differences in plant size between wild type control plants and plants transformed with DGAT1-Ole_3,3 (DAG=Days After Germination).

The consequence of transforming plants with DGAT1-Ole_3,3 was an elevation in photosynthetic assimilation rates, increased water use efficiencies and decreased stomatal conductance leading to an increase in growth rate seen by higher biomass, shown in Table 8 below and FIG. 34.

TABLE 8

| | Average leaf DW/plant (mg) 20 Days after germination | Average leaf DW/plant (mg) 30 Days after germination |
|---|---|---|
| Wild Type | 30.9 ± 3.5 | 61.1 ± 3.3 |
| OLE1_3,3 | 47.6 ± 4.4 | 90.0 ± 6.1 |

Plants over expressing DGAT1(S205A) and OLE1_3,3 had approximately 50% more biomass than the wild type; this included at the onset of flower stalk emergence (~20 days after germination) as well as at mid to late floral stalk development (~35 days after germination).

Example 10

Production of TAG in the Roots of *Arabidopsis thaliana*

Figure 35:
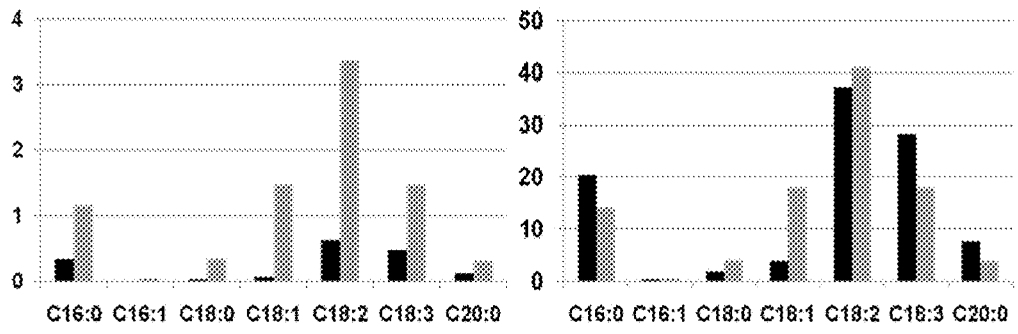
FIG. 35 left hand panel shows total quantity (as % of DW) for each major lipid species in roots of wild type (black bars) plants and in roots of plants transformed with DGAT1-Ole_3,3 (grey bars). Right hand panel shows each major lipid species as a % of total lipids in roots of wild type (black bars) plants and in roots of plants transformed with DGAT1-Ole_3,3 (grey bars).
Figure 36:
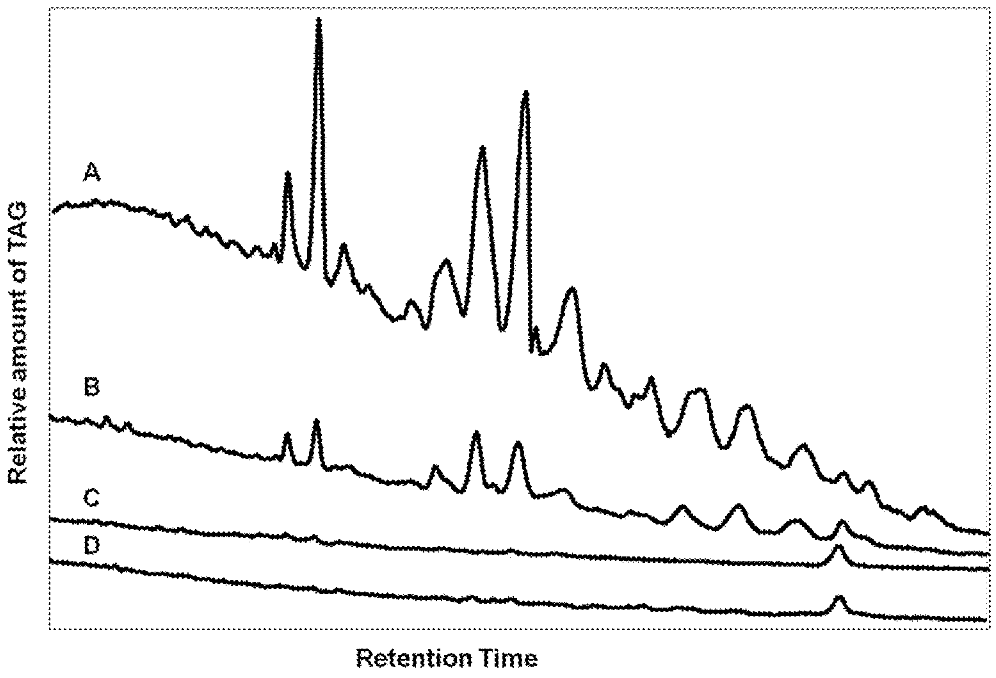
FIG. 36 shows four traces offset and over layed.

Roots from Ole_3,3 and wild type plants were extracted using the same procedures described in Example 7. Quantitative FAMES analysis (FIG. 35 left panel) showed that the total lipid content of the roots from Ole_3,3 was 8.2% of the DM while the total lipid content of the wild type roots was 1.7% of the DM. FAMES also showed that the lipid profile of the Ole_3,3 roots was not too different from the wild type (FIG. 34 right panel). The most noticeable change was the proportion of C18:1 was 4.0% in the wild type roots and rose over four fold to 18.1% of the total fatty acids in the roots of DGAT1-Ole_3,3 plants. Despite the similar total lipid content (~8%) of the leaves and roots from the DGAT1-Ole_3,3 plants the TAG analysis demonstrated that a higher portion of the total lipids in the roots was TAG when compared with the leaf material (FIG. 36). This was likely due to a much higher portion of the total lipid in the leaf being membrane lipid (predominantly thylakoid membrane).

It is not the intention to limit the scope of the invention to the abovementioned examples only. As would be appreciated by a skilled person in the art, many variations are possible without departing from the scope of the invention.

References

Abell et al., (2004). Plant J., 37: 461-70.

Altschul et al., (1997) Nucleic Acids Res. 25: 3389-3402,

Andrianov et al., (2010). Plant Biotechnol J. 8(3):277-87.

Ausubel et al., (1987) Current Protocols in Molecular Biology, Greene Publishing Bairoch and Bucher (1994), Nucleic Acids Res. 22, 3583

Bao et al, (2000) Plant J. 22(1):39-50.

Bari et al., (2009). J. Exp. Bot. 55:623-630.

Birch (1997) Ann Rev Plant Phys Plant Mol Biol, 48, 297

Bock & Khan (2004). Trends in Biotech. 22:311-318.

Bolton and McCarthy (1962) PNAS 84:1390

Bowie et al., (1990). Science 247, 1306

Bouvier-Nave et al., (2000) Eur. J. Biochem. 267, 85-96.

Bryan et al., (2007) Modification of fatty acid biosynthesis. United States Patent 20070118927.

Capuano et al., (2007). Biotechnol Adv. 25:203-206.

Chen et al., (1999). Plant Cell Physiol., 40:1079-1086 Chiang et al., (2005). J Agric Food Chem 53:4799-804.

Chiang et al., (2007). Protein Expr Purif. 52:14-8.

Chisti (2007). Biotech. Adv. 25:294-306.

Colman et al., (1974). Plant Phys, 53: 395-397.

Cookson et al., (2009). Improvements in and relating to oil production. PCT/NZ2008/000085 WO/2008/130248

Dahlqvist et al., (2000). Proc Natl Acad Sci USA. 97, 6487-6492.

Deckers et al., (2003). U.S. Pat. No. 6,582,710

Demeyer and Doreau, (1999). Proc Nutr Soc. 58(3):593-607.

Deutscher (1990) Ed, Methods in Enzymology, Vol. 182, Guide to Protein Purification Draper et al., 1988, Plant Genetic Transformation and Gene Expression. A Laboratory Manual. Blackwell Sci. Pub. Oxford, p. 365

Falquet et al., 2002, Nucleic Acids Res. 30, 235

Feng and Doolittle, 1987, J. Mol. Evol. 25, 351

Firkins et al., (2006). J Dairy Sci. 89 Suppl 1:E31-51. Review. Greenspan.

Frandsen et al., (2001). Physiologia Plantarum, 112:301-307.

Frohman (1993). Methods Enzymol. 218: 340-56

Galun and Breiman (1997). Transgenic Plants. Imperial College Press, London

Gelvin et al., 1993, Plant Molecular Biol. Manual. Kluwer Acad. Pub. Dordrecht

Giesen et al., Nucleic Acids Res. 1998 Nov. 1; 26(21):5004-6

Giordano et al., (2005). Ann. Rev. Pl. Biol. 56:99-131.

Halford & Hardie (1998). Plant Mol. Biol. 37:735-48. Review

Harada et al., (2002). OLEOSIN/PHOSPHOLIPID COMPLEX AND PROCESS FOR PRODUCING THE SAME. World Patent WO/2002/026788.
Hellens et al., (2000). Plant Mol Biol 42: 819-32
Hellens et al., (2005). Plant Meth 1: 13
Herrera-Estrella et al., (1993). Nature 303, 209
Hofmann et al., (1999). Nucleic Acids Res. 27, 215
Hou et al., (2003). J Dairy Sci; 86: 424-8.
Huang (1992). Ann. Rev. Plant Physiol. Plant Mol. Biol. 43:177-200.
Huang, X. (1994) Computer Applications in the Biosciences 10, 227-235
Jeanmougin et al., (1998) Trends Biochem. Sci. 23, 403-5.
Jenkins and Bridges (2007). Eur. J. Lipid Sci. Technol. 109: 778-789.
Jenkins and McGuire (2006). J Dairy Sci. 89(4):1302-10. Review.
Kaup et al., (2002) Plant Physiol. 129(4):1616-26.
Kebeish et al., (2007). Nature Biotech, 25:593-599.
Kozaki & Takeba (1996). Nature, 384:557-560.
Kyte and Doolitle (1982) J. Mol. Biol. 157:105-132
Lanfranco L. (2003). Riv Biol. 96(1):31-54.
Lardizabal et al., (2001). J.B.C. 276, 38862-38869.
Leprince et al., (1998). Planta 204 109-119.
Lin and Tzen. (2004). Plant Physiology and Biochemistry. 42:601-608.
Lock and Bauman (2004). Lipids. 39(12):1197-206. Review.
Loer and Herman (1993). Plant Physiol. 101(3):993-998.
Mayer and Fowler (1985). J. Cell Biol. 100(3):965-73.
Mekhedov et al., (2000). Plant Physiol. 122(2):389-402).
Mullis et al., Eds. 1994 The Polymerase Chain Reaction, Birkhauser
Murphy (1993). Prog. Lipid Res. 32:247-280.
Nakamura et al., (2005). Can. J. Bot. 83:820-833.
Needleman and Wunsch, (1970) J. Mol. Biol. 48, 443-453
Nielsen et al., Science. (1991) 254(5037):1497-500
Notredame et al., (2000). J. Mol. Biol. 302: 205-217
Ohlrogge and Jaworski (1997). Annu Rev Plant Physiol Plant Mol. Biol. 48:109-136.
Papapostolou and Howorka (2009). Mol. Biosyst. 5(7):723-32. Review.
Parry et al., (2003). J. Exp. Bot., 54:1321-1333.
Peng (2004). Development and applications of artificial sesame oil body. Ph.D. Dissertation. National ChunHsing University Graduate Institute of Biotechnology. Taichung, Taiwan.
Peng et al., (2006). Stability enhancement of native and artificial oil bodies by genipin crosslink. Taiwan patent 1250466.
Peng et al., (2004). J Biotechnol 2004; 111: 51-7.
Potrykus and Spangenburg (1995). Gene Transfer to Plants. Springer-Verlag, Berlin
Roberts et al., (2008). The Open Biotechnology Journal 2:13-21.
Roux et al., (2004). J Agric Food Chem. 52(16):5245-9.
Scott et al., (2007). Polyoleosins. WO2007045019.
Saha et al., (2006). Plant Physiol. 141(4):1533-43.
Sambrook et al., Eds, 1987, Molecular Cloning, A Laboratory Manual, 2nd Ed. Cold Spring Harbor Press
Sarmiento et al., (1997). Plant J. 11(4):783-96.
Schrott (1995) In: Gene Transfer to Plants (Potrykus, T., Spangenberg. Eds) Springer Verlag. Berline, pp. 325-336
Shimada et al., (2008). Plant J. 55(5):798-809.
Shockey et al., (2006). Plant Cell., 18, 2294-2313.
Siloto et al., (2006). Plant Cell. 18(8):1961-74.
Slack et al., (1980). Biochem J. 190(3):551-561.
Slocombe et al., (2009). Plant Biotechnol J. 7(7):694-703.
Stahl et al., (2004). Plant Physiology, 135: 1324-1335.
Stewart et al., (1969), In: Solid-Phase Peptide Synthesis, WH Freeman Co, San Francisco Calif.
Thompson et al., (1994) Nucleic Acids Research, 22:4673-4680
Ting et al., (1997). J Biol. Chem., 272: 3699-3706.
Tadege et al., (2005). Trends Plant Sci. 10(5):229-35.
Triglia et al., 1998, Nucleic Acids Res 16, 8186
Tolbert (1997). Ann. Rev. Pl. Phys. Pl. Molec. Biol. 48:1-25.
Tolbert et al., (1983). Pl. Physiol. 72:1075-1083.
Tzen et al., (1992). J. Biol. Chem. 267: 15626-34
Tzen et al., (2003). Adv Plant Physiol., 6: 93-104.
Tzen et al., (1997). J. Biochem. 121(4):762-8.
Voisey et al., (1994). Plant Cell Reports 13: 309 314.
Winichayakul et al., (2008). Proc. NZGA, 70:211-216
Xu et al., (2005). Plant Cell. 17(11):3094-110.
Zou et al., (1999). Plant J. 19, 645-653.
Zou et al., (2008). Plant Biotech. J. 6(8):799-818.

SUMMARY OF SEQUENCE LISTING

| SEQ ID NO: | Type | SPECIES | COMMENTS |
|---|---|---|---|
| 1 | polynucleotide | artificial | Oleosin disulfide 0,0 nucleotide sequence, as cloned into pET29b using NdeI and XhoI restriction sites (adds N-terminal S•tag thrombin cleavage site and C-terminal His tag). |
| 2 | polynucleotide | artificial | Oleosin disulfide 1,1 nucleotide sequence, as cloned into pET29b using NdeI and XhoI restriction sites (adds N-terminal S•tag thrombin cleavage site and C-terminal His tag). |
| 3 | polynucleotide | artificial | Oleosin disulfide 1,3 nucleotide sequence, as cloned into pET29b using NdeI and XhoI restriction sites (adds N-terminal S•tag thrombin cleavage site and C-terminal His tag). |
| 4 | polynucleotide | artificial | Oleosin disulfide 3,1 nucleotide sequence, as cloned into pET29b using NdeI and XhoI restriction sites (adds N-terminal S•tag thrombin cleavage site and C-terminal His tag). |
| 5 | polynucleotide | artificial | Oleosin disulfide 3,3 nucleotide sequence, as cloned into pET29b using NdeI and XhoI restriction sites (adds N-terminal S•tag thrombin cleavage site and C-terminal His tag). |
| 6 | Polypeptide | Artificial | Oleosin disulfide 0,0 peptide sequence, as cloned into pET29b using NdeI and XhoI |

-continued

SUMMARY OF SEQUENCE LISTING

| SEQ ID NO: | Type | SPECIES | COMMENTS |
|---|---|---|---|
| | | | restriction sites (adds N-terminal S•tag thrombin cleavage site and C-terminal His tag). |
| 7 | Polypeptide | Artificial | Oleosin disulfide 1,1 peptide sequence, as cloned into pET29b using NdeI and XhoI restriction sites (adds N-terminal S•tag thrombin cleavage site and C-terminal His tag). |
| 8 | Polypeptide | Artificial | Oleosin disulfide 1,3 peptide sequence, as cloned into pET29b using NdeI and XhoI restriction sites (adds N-terminal S•tag thrombin cleavage site and C-terminal His tag). |
| 9 | Polypeptide | Artificial | Oleosin disulfide 3,1 peptide sequence, as cloned into pET29b using NdeI and XhoI restriction sites (adds N-terminal S•tag thrombin cleavage site and C-terminal His tag). |
| 10 | Polypeptide | Artificial | Oleosin disulfide 3,3 peptide sequence, as cloned into pET29b using NdeI and XhoI restriction sites (adds N-terminal S•tag thrombin cleavage site and C-terminal His tag). |
| 11 | Polynucleotide | Artificial | (Nucleotide sequence of Oleosin disulfide 0,0 including Kozac sequence and UBQ10 intron, as transformed into *Arabidopsis thaliana* under the control of the CaMV35s promoter.) |
| 12 | Polynucleotide | Artificial | Nucleotide sequence of Oleosin disulfide 1,1 including Kozac sequence and UBQ10 intron, as transformed into *Arabidopsis thaliana* under the control of the CaMV35s promoter. |
| 13 | Polynucleotide | Artificial | (Nucleotide sequence of Oleosin disulfide 1,3 including Kozac sequence and UBQ10 intron, as transformed into *Arabidopsis thaliana* under the control of the CaMV35s promoter.) |
| 14 | Polynucleotide | Artificial | Nucleotide sequence of Oleosin disulfide 3,1 including Kozac sequence and UBQ10 intron, as transformed into *Arabidopsis thaliana* under the control of the CaMV35s promoter. |
| 15 | Polynucleotide | Artificial | Nucleotide sequence of Oleosin disulfide 3,3 including Kozac sequence and UBQ10 intron, as transformed into *Arabidopsis thaliana* under the control of the CaMV35s promoter. |
| 16 | Polypeptide | Artificial | Peptide sequence of Oleosin disulfide 0,0, as transformed into *Arabidopsis thaliana* under the control of the CaMV35s promoter. |
| 17 | Polypeptide | Artificial | Peptide sequence of Oleosin disulfide 1,1, as transformed into *Arabidopsis thaliana* under the control of the CaMV35s promoter.) |
| 18 | Polypeptide | Artificial | Peptide sequence of Oleosin disulfide 1,3, as transformed into *Arabidopsis thaliana* under the control of the CaMV35s promoter. |
| 19 | Polypeptide | Artificial | Peptide sequence of Oleosin disulfide 3,1, as transformed into *Arabidopsis thaliana* under the control of the CaMV35s promoter. |
| 20 | Polypeptide | Artificial | Peptide sequence of Oleosin disulfide 3,3, as transformed into *Arabidopsis thaliana* under the control of the CaMV35s promoter |
| 21 | Polynucleotide | Artificial | Nucleotide sequence of Oleosin disulfide 5,6 including Kozac sequence and UBQ10 intron, as transformed into *Arabidopsis thaliana* under the control of the CaMV35s promoter. |
| 22 | Polynucleotide | Artificial | Nucleotide sequence of Oleosin disulfide 6,7 including Kozac sequence and UBQ10 intron, as transformed into *Arabidopsis thaliana* under the control of the CaMV35s promoter. |
| 23 | Polypeptide | Artificial | Peptide sequence of Oleosin disulfide 5,6, as transformed into *Arabidopsis thaliana* under the control of the CaMV35s promoter |
| 24 | Polypeptide | Artificial | Peptide sequence of Oleosin disulfide 6,7, as transformed into *Arabidopsis thaliana* under the control of the CaMV35s promoter |

-continued

SUMMARY OF SEQUENCE LISTING

| SEQ ID NO: | Type | SPECIES | COMMENTS |
|---|---|---|---|
| 25 | Polynucleotide | Artificial | Oleoacceptor (contains OCS terminator, CAMV35S promoter, DGAT1 (S205A) from *Arabidopsis* and UBQ10 intron) |
| 26 | Polynucleotide | Artificial | Oleosin_0,0 and DGAT1 (S205A) in pRSH1 |
| 27 | Polynucleotide | Artificial | Oleosin_1,1 and DGAT1 (S205A) in pRSH1 |
| 28 | Polynucleotide | Artificial | Oleosin_1,3 and DGAT1 (S205A) in pRSH1 |
| 29 | Polynucleotide | Artificial | Oleosin_3,1 and DGAT1 (S205A) in pRSH1 |
| 30 | Polynucleotide | Artificial | Oleosin_3,3 and DGAT1 (S205A) in pRSH1 |
| 31 | Polynucleotide | Artificial | Oleosin_5,6 and DGAT1 (S205A) in pRSH1 |
| 32 | Polynucleotide | Artificial | Oleosin_6,7 and DGAT1 (S205A) in pRSH1 |
| 33 | Polypeptide | Artificial | DGAT1 (S205A) |
| 34 | Polynucleotide | *S. indicum* | Oleosin - AF302807 |
| 35 | Polypeptide | *S. indicum* | Oleosin - AAG23840 |
| 36 | Polynucleotide | *S. indicum* | Oleosin - U97700 |
| 37 | Polypeptide | *S. indicum* | Oleosin - AAB58402 |
| 38 | Polynucleotide | *A. thaliana* | Oleosin - X62353 |
| 39 | Polypeptide | *A. thaliana* | Oleosin - CAA44225 |
| 40 | Polynucleotide | *A. thaliana* | Oleosin - BT023738 |
| 41 | Polypeptide | *A. thaliana* | Oleosin - AAZ23930 |
| 42 | Polynucleotide | *H. annuus* | Oleosin - X62352.1 |
| 43 | Polypeptide | *H. annuus* | Oleosin - CAA44224.1 |
| 44 | Polynucleotide | *B. napus* | Oleosin - X82020.1 |
| 45 | Polypeptide | *B. napus* | Oleosin - CAA57545.1 |
| 46 | Polynucleotide | *Z. mays* | Oleosin - NM_001153560.1 |
| 47 | Polypeptide | *Z. mays* | Oleosin - NP_001147032.1 |
| 48 | Polynucleotide | *O. sativa* | Oleosin - L76464 |
| 49 | Polypeptide | *O. sativa* | Oleosin - AAL40177.1 |
| 50 | Polynucleotide | *B. oleracea* | Oleosin - AF117126.1 |
| 51 | Polypeptide | *B. oleracea* | Oleosin - AAD24547.1 |
| 52 | Polynucleotide | *C. arabica* | Oleosin - AY928084.1 |
| 53 | Polypeptide | *C. arabica* | Oleosin - AAY14574.1 |
| 54 | Polynucleotide | *S. indicum* | Steroleosin - AF421889 |
| 55 | Polypeptide | *S. indicum* | Steroleosin - AAL13315 |
| 56 | Polynucleotide | *B. napus* | Steroleosin - EU678274 |
| 57 | Polypeptide | *B. napus* | Steroleosin - ACG69522 |
| 58 | Polynucleotide | *Z. mays* | Steroleosin - NM_001159142.1 |
| 59 | Polypeptide | *Z. mays* | Steroleosin - NP_001152614.1 |
| 60 | Polynucleotide | *B. napus* | Steroleosin - EF143915.1 |
| 61 | Polypeptide | *B. napus* | Steroleosin - ABM30178.1 |
| 62 | Polynucleotide | *S. indicum* | Caleosin - AF109921 |
| 63 | Polypeptide | *S. indicum* | Caleosin - AAF13743 |
| 64 | Polynucleotide | *G. max* | Caleosin - AF004809 |
| 65 | Polypeptide | *G. max* | Caleosin - AAB71227 |
| 66 | Polynucleotide | *Z. mays* | Caleosin - NM_001158434.1 |
| 67 | Polypeptide | *Z. mays* | Caleosin - NP_001151906 |
| 68 | Polynucleotide | *B. napus* | Caleosin - AY966447.1 |
| 69 | Polypeptide | *B. napus* | Caleosin - AAY40837.1 |
| 70 | Polynucleotide | *C. revoluta* | Caleosin - FJ455154.1 |
| 71 | Polypeptide | *C. revoluta* | Caleosin - ACJ70083.1 |
| 72 | Polynucleotide | *C. sativus* | Caleosin - EU232173.1 |
| 73 | Polypeptide | *C. sativus* | Caleosin - ABY56103.1 |
| 74 | Polynucleotide | *A. thaliana* | DGAT1 - NM_127503 |
| 75 | Polypeptide | *A. thaliana* | DGAT1 - NP_179535 |
| 76 | Polynucleotide | *T. majus* | DGAT1 - AY084052 |
| 77 | Polypeptide | *T. majus* | DGAT1 - AAM03340 |
| 78 | Polynucleotide | *Z. mays* | DGAT1 - EU039830.1 |
| 79 | Polypeptide | *Z. mays* | DGAT1 - ABV91586.1 |
| 80 | Polynucleotide | *A. thaliana* | DGAT2 - NM_115011 |
| 81 | Polypeptide | *A. thaliana* | DGAT2 - NP_566952.1 |
| 82 | Polynucleotide | *B. napus* | DGAT2 - FJ858270 |
| 83 | Polypeptide | *B. napus* | DGAT2 - AC090187.1 |
| 84 | Polynucleotide | *A. hypogaea* | DGAT3 (soluble DGAT) - AY875644 |
| 85 | Polypeptide | *A. hypogaea* | DGAT3 (soluble DGAT) - AAX62735.1 |
| 86 | Polynucleotide | *A. thaliana* | PDAT - NM_121367 |
| 87 | Polypeptide | *A. thaliana* | PDAT - NP_196868.1 |
| 88 | Polynucleotide | *R. communis* | PDAT - XM_002521304 |
| 89 | Polypeptide | *R. communis* | PDAT - XP_002521350 |
| 90 | Polypeptide | *B. oleraceae* | Oleosin - CAA65272.1 |
| 91 | Polypeptide | *Z. mays* | Oleosin - NP_001147032.1 |
| 92 | Polypeptide | *O. sativa* | Oleosin - AAL40177.1 |
| 93 | Polypeptide | *S. indicum* | Caleosin - AAF13743 |
| 94 | Polypeptide | *G. Max* | Caleosin - AAB71227 |
| 95 | Polypeptide | *Z. mays* | Caleosin - NP_001151906 |
| 96 | Polypeptide | *S. indicum* | Steroleosin - AAL13315 |

-continued

SUMMARY OF SEQUENCE LISTING

Figure 2:
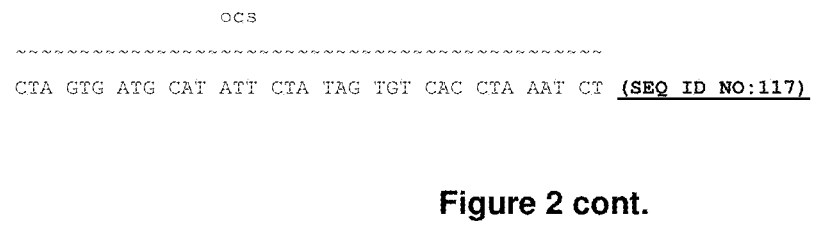
Figure 3:
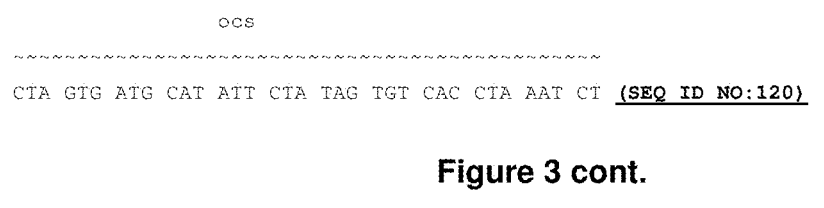
Figure 4:
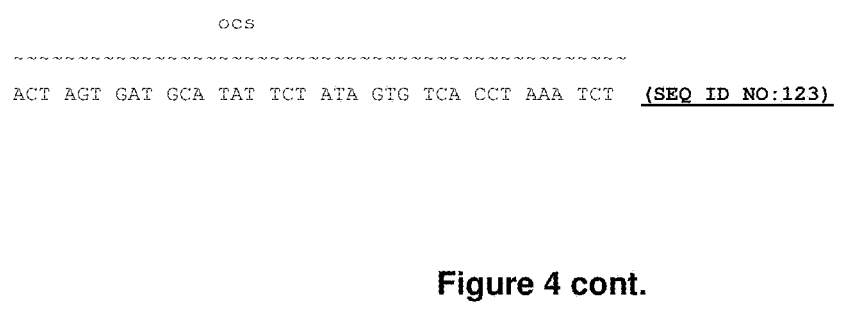
Figure 5:
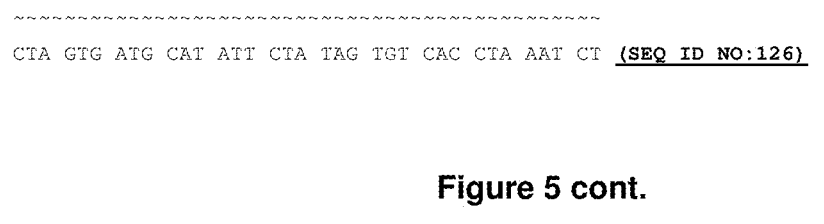

| SEQ ID NO: | Type | SPECIES | COMMENTS |
|---|---|---|---|
| 97 | Polypeptide | *Brassica napus* | steroleosin ACG69522 |
| 98 | Polypeptide | *Z. mays* | steroleosin NP_001152614.1 |
| 99 | Polypeptide | *Brassica oleraceae* | Modified pollen oleosin - CAA65272.1 |
| 100 | Polypeptide | *Zea mays* | Modified oleosin - NP_001147032.1 |
| 101 | Polypeptide | *Oryza sativa* | Modified oleosin - AAL40177.1 |
| 102 | Polypeptide | *S. indicum* | Modified caoleosin - AAF13743 |
| 103 | Polypeptide | *G. soja* | Modified caoleosin - AAB71227 |
| 104 | Polypeptide | *Z. mays* | Modified caoleosin - NP_001151906 |
| 105 | Polypeptide | *S. indicum* | Modified steroleosin - AAL13315 |
| 106 | Polypeptide | *Brassica napus* | Modified steroleosin - ACG69522 |
| 107 | Polypeptide | *Z. mays* | Modified steroleosin - NP_001152614.1 |
| 108 | Polypeptide | Artificial | Consensus in *Tropaeolum majus* (garden nasturtium) DGAT1 sequences |
| 109 | Polypeptide | Artificial | GlcF protein consensus sequence |
| 110 | Polynucleotide | Artificial | Example sequence |
| 111 | Polynucleotide | Artificial | Example sequence |
| 112 | Polynucleotide | Artificial | Sequence of construct in FIG. 1 |
| 113 | Polypeptide | Artificial | First portion of Oleosin 0-0 in FIG. 1 |
| 114 | Polypeptide | Artificial | Second portion of Oleosin 0-0 in FIG. 1 |
| 115 | Polypeptide | Artificial | First portion of DGAT1 (S205A) in FIGS. 1, 2, 3, 4 and 5 |
| 116 | Polypeptide | Artificial | Second portion of DGAT1 (S205A) in FIGS. 1, 2, 3, 4 and 5 |
| 117 | Polynucleotide | Artificial | Sequence of construct in FIG. 2 |
| 118 | Polypeptide | Artificial | First portion of Oleosin 1-1 in FIG. 2 |
| 119 | Polypeptide | Artificial | Second portion of Oleosin 1-1 in FIG. 2 |
| 120 | Polynucleotide | Artificial | Sequence of construct in FIG. 3 |
| 121 | Polypeptide | Artificial | First portion of Oleosin 1-3 in FIG. 3 |
| 122 | Polypeptide | Artificial | Second portion of Oleosin 1-3 in FIG. 3 |
| 123 | Polynucleotide | Artificial | Sequence of construct in FIG. 4 |
| 124 | Polypeptide | Artificial | First portion of Oleosin 3-1 in FIG. 4 |
| 125 | Polypeptide | Artificial | Second portion of Oleosin 3-1 in FIG. 4 |
| 126 | Polynucleotide | Artificial | Sequence of construct in FIG. 5 |
| 127 | Polypeptide | Artificial | First portion of Oleosin 3-3 in FIG. 5 |
| 128 | Polypeptide | Artificial | Second portion of Oleosin 3-3 in FIG. 5 |

The invention claimed is:

1. A polynucleotide encoding a modified oleosin including at least one artificially introduced cysteine, wherein the cysteine is introduced in at least one of:

a) in the N-terminal hydrophilic region of the oleosin, and b) in the C-terminal hydrophilic region of the oleosin.

2. The polynucleotide of claim 1 encoding a fusion protein including the modified oleosin fused to a protein of interest.

3. A genetic construct, or expression construct, comprising the polynucleotide of claim 1.

4. A host cell comprising a polynucleotide of claim 1.

5. The host cell of claim 4 that is also genetically modified to express a triacylglycerol (TAG) synthesising enzyme.

6. The host cell of claim 4 that is a plant cell.

7. A plant comprising a plant cell of claim 6.

8. The plant of claim 7 that is also genetically modified to express a triacylglycerol (TAG) synthesising enzyme.

9. A host cell genetically modified to express a polynucleotide of claim 1, or an expression product of the polynucleotide.

10. A method for producing an oil body in a host cell, the method comprising:

a) introducing into a host cell at least one polynucleotide of claim 1; and b) culturing the host cell in order to express the modified oleosin.

11. The method of claim 10 wherein the host cell is processed into an oil fraction.

12. A method for producing an oil body in a host cell, the method comprising:

a) introducing into a host cell at least one polynucleotide of claim 1 and a nucleic acid molecule encoding a TAG synthesizing enzyme; and b) culturing the host cell in order to express the modified oleosin and the TAG synthesizing enzyme.

13. A method for producing a photosynthetic cell with an increased rate of $CO_2$ assimilation, the method comprising:

transforming the photosynthetic cell with a polynucleotide of claim 1 encoding a modified oleosin including at least one artificially introduced cysteine.

14. The method of claim 13 wherein expression of the modified oleosin causes the increased rate of $CO_2$ assimilation.

15. The method of claim 13 wherein expression of the modified oleosin reduces or prevents lipid recycling in the photosynthetic cell.

16. The method of claim 15 wherein the reduced or prevented lipid recycling causes the increased $CO_2$ assimilation.

17. The method of claim 13 in which the cysteines are distributed substantially evenly between the N-terminal and C-terminal hydrophilic regions of the oleosin.

18. The method of claim 13 wherein, in addition to the increased rate of $CO_2$ assimilation the method produces a photosynthetic cell with at least one of:

a) an increased rate of photosynthesis, b) increased water use efficiency, c) an increased growth rate d) increased chloroplast $CO_2$ concentration, e) a decreased rate of photorespiration, f) increased high temperature tolerance, g) increased high oxygen concentration tolerance, h) increased nitrogen use efficiency, and i) decreased loss of fixed carbon.

19. The method of claim 13 wherein the polynucleotide is operably linked to a photosynthetic cell preferred promoter polynucleotide.

20. The method of claim 13 wherein the photosynthetic cell is also genetically modified to express a triacylglycerol (TAG) synthesising enzyme.

21. The method of claim 13 in which the photosynthetic cell is a plant cell.

22. The method of claim 21 in which the plant cell is part of a plant.

23. The method of claim 22 in which, in addition to the increased rate of $CO_2$ assimilation the plant also has at least one of:

a) an increased rate of photosynthesis, b) increased water use efficiency, c) an increased growth rate.

d) increased biomass, e) delayed flowering, f) increased chloroplast CO2 concentration, g) a decreased rate of photorespiration, h) increased seed, fruit or storage organ yield, i) increased drought tolerance, j) increased high temperature tolerance, k) increased high oxygen concentration tolerance, l) increased nitrogen use efficiency, and m) decreased loss of fixed carbon.

24. A method for producing oil, the method comprising the steps:

a) providing a plant comprising a polynucleotide of claim 1, b) cultivating the plant to express the modified oleosin and produce oil in its non-photosynthetic tissues/organs.

25. The method of claim 24 in which the plant accumulates more total lipid or oil in its non-photosynthetic tissues/organs than does a control plant.

26. The method of claim 24 in which the plant is also genetically modified to express a triacylglycerol (TAG) synthesising enzyme.

27. The method of claim 24 which comprises the additional step of processing the non-photosynthetic tissue/organ of the plant into an animal feedstock.

28. The method of claim 24 which comprises the additional step of processing the non-photosynthetic tissue/organ of the plant into a biofuel feedstock.

29. The method of claim 24 which comprises the additional step of extracting oil from the non-photosynthetic tissue/organ of the plant.

30. A non-photosynthetic tissue/organ of a plant produced by a method of claim 24.

31. An animal feed comprising the non-photosynthetic tissue/organ of claim 30.

32. A biofuel feedstock comprising the non-photosynthetic tissue/organ of claim 30.

33. A modified oleosin including at least one artificially introduced cysteine, wherein the cysteine is introduced in at least one of:

a) in the N-terminal hydrophilic region of the oleosin, and b) in the C-terminal hydrophilic region of the oleosin.

34. The modified oleosin of claim 33 that includes at least one cysteine in the N-terminal hydrophilic region, and at least one cysteine in the C-terminal hydrophilic region.

35. A fusion protein comprising the modified oleosin of claim 33 fused to protein of interest.

36. An oil body comprising the modified oleosin of claim 33.

37. The oil body of claim 36 that additionally comprises a fusion protein that includes an oleosin fused to a protein of interest.

38. The oil body of claim 37 in which the oleosin in the fusion protein includes an artificially introduced cysteine in its oleosin portion.

39. An emulsion comprising an oil body of claim 36.

40. A composition comprising an oil body of claim 36.

41. A plant, or part thereof, comprising the oil body of claim 36.

42. An animal feed comprising a plant, or part or tissue thereof, of claim 41.

43. An animal feed comprising the oil body of claim 36.

44. An emulsion comprising a modified oleosin of claim 33.

45. A composition comprising the modified oleosin of claim 33.

46. A method for producing an oil body, the method comprising the step of combining:

a) at least two of the modified oleosins of claim 33, b) triacylglycerol, and c) phospholipid.

47. The method of claim 46 in which the components of a), b) and c) are combined within a host cell.

48. The method of claim 47 in which the host cell is also genetically modified to express a triacylglycerol (TAG) synthesising enzyme.

49. The method of claim 47 in which the host cell forms part of an organism.

50. The method of claim 49 in which the organism is a plant.

51. The method of claim 47 including the additional step of purifying the oil bodies from the host cell.

52. A method of producing oil, the method comprising cultivating a host cell of claim 47 in conditions conducive to the production of oil.

53. The method of claim 46 in which the components of a), b) and c) are combined in vitro.

54. An oil body produced by the method of claim 46.

* * * * *